United States Patent
Babul

(10) Patent No.: US 10,624,887 B2
(45) Date of Patent: *Apr. 21, 2020

(54) COMPOSITIONS OF (-)-17-(CYCLOBUTYLMETHYL) MORPHINAN-3,14,-DIOL

(71) Applicant: Relmada Therapeutics, Inc., New York, NY (US)

(72) Inventor: Najib Babul, Blue Bell, PA (US)

(73) Assignee: Relmada Therapeutics, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/135,985

(22) Filed: Apr. 22, 2016

(65) Prior Publication Data

US 2016/0235740 A1 Aug. 18, 2016

Related U.S. Application Data

(63) Continuation of application No. 13/882,370, filed as application No. PCT/US2011/058690 on Oct. 31, 2011, now Pat. No. 9,364,430.

(60) Provisional application No. 61/408,544, filed on Oct. 29, 2010.

(51) Int. Cl.

| | | |
|---|---|---|
| *A61K 31/485* | (2006.01) |
| *A61K 9/50* | (2006.01) |
| *A61K 9/00* | (2006.01) |
| *A61K 9/16* | (2006.01) |
| *A61K 9/20* | (2006.01) |
| *A61K 9/28* | (2006.01) |
| *A61K 9/48* | (2006.01) |

(52) U.S. Cl.
CPC .......... *A61K 31/485* (2013.01); *A61K 9/006* (2013.01); *A61K 9/0053* (2013.01); *A61K 9/1635* (2013.01); *A61K 9/1676* (2013.01); *A61K 9/2054* (2013.01); *A61K 9/2866* (2013.01); *A61K 9/4858* (2013.01); *A61K 9/4891* (2013.01); *A61K 9/50* (2013.01)

(58) Field of Classification Search
CPC ........................... A61K 31/485; A61K 9/2054
USPC ........................................................ 514/282
See application file for complete search history.

(56) References Cited

U.S. PATENT DOCUMENTS 6,004,546 A * 12/1999 Sachetto .............. A61K 33/245
424/78.01
9,364,430 B2 * 6/2016 Babul .................. A61K 9/1635

* cited by examiner

*Primary Examiner* — Jennifer M Kim

(74) *Attorney, Agent, or Firm* — Wood Herron & Evans LLP

(57) ABSTRACT

The present invention is directed to oral, therapeutically effective modified release pharmaceutical compositions of (−)-17-(cyclobutylmethyl)morphinan-3,14-diol and it pharmaceutically acceptable salts and the use thereof, including delayed onset and extended release dosage forms. The present invention is also directed at modified release dosage forms of oral (−)-17-(cyclobutylmethyl)morphinan-3,14-dial which provide robust efficacy and reduced potential for abuse and misuse.

16 Claims, 10 Drawing Sheets

COMPOSITIONS OF (-)-17-(CYCLOBUTYLMETHYL)MORPHINAN-3,14,-DIOL

This application is a continuation of copending U.S. patent application Ser. No. 13/882,370 (allowed), which was a § 371 filing corresponding to international patent application PCT/US2011/058690, filed 31 Oct. 2011; the international application is entitled to priority to the applicant's U.S. provisional application No. 61/408,544, filed Oct. 29, 2010 which is herein incorporated in its entirety for all purposes.

FIELD OF THE INVENTION

The present invention is directed to oral, therapeutically effective modified release pharmaceutical compositions of (−)-17-(cyclobutylmethyl)morphinan-3,14-diol and it pharmaceutically acceptable salts and the use thereof, including delayed onset and extended release dosage forms. The present invention is also directed at modified release dosage forms of oral (−)-17-(cyclobutylmethyl)morphinan-3,14-diol which provide robust efficacy and reduced potential for abuse and misuse.

BACKGROUND TO THE INVENTION

While drugs are administered by a wide variety of routes and methods, including oral, oro-transmucosal, buccal, sublingual, via NG-tubes, rectal, intranasal, inhalational, topical, transdermal, intravenous, subcutaneous, intramuscular, epidural and intrathecal, the oral route is by far the most preferred route for most patients and medical settings.

The strong preference and universal acceptance of the oral route include simplicity of drug administration, patient convenience, lower drug costs, and reduced complexity of manufacturing, suitability for repeated and chronic administration and, in many cases, reliable therapeutic effect.

In some cases, drugs need to be administered by a non-oral route. Among the reasons for the use of non-oral routes are lack of therapeutic effect, lack of a consistent, reliable or robust effects, the need for rapid onset of effect, contraindications to oral drug administration, reduced safety by the oral route and the lack of availability of the oral route (for example due to GI obstruction, nausea, vomiting, GI obstruction, obtundation or coma).

Over the past several decades, there have been extensive research, development and commercialization efforts to advance alternatives to orally ingested drug administration, including oro-transmucosal, buccal, sublingual, intranasal, inhalational, topical, transdermal, intravenous, subcutaneous, intramuscular, epidural, intrathecal and transdermal routes. Although there have been remarkable advances in alternatives to orally ingested drugs, the oral route continues to be the preferred route of drug administration, particularly for chronic conditions which frequently require around the clock amelioration of symptoms.

In many cases, the prediction of absent or significantly poor therapeutic outcomes by the oral route has led to the abandonment of its evaluation through oral ingestion. Such drugs are frequently being used only by a non-oral route (e.g., parenteral route, intranasal or transdermal).

(−)17-(Cyclobutylmethyl)morphinan-3,14-diol (Butorphanol) acts as a partial agonist at opioid receptors and a pure agonist at κ-opioid receptors, with preponderantly antagonist activity at the δ-opioid receptor (Commiskey s, et al, J Pharmacol Sci 2005; 98; 109-116). Its synthesis was first reported in 1973 and has been commercially available in the USA as a parenteral formulation since 1978. It was introduced in the U.S. in parenteral form in 1978 and intranasal form in 1991 (Stadol®). Butorphanol is an infrequently utilized analgesic. Its use is widely relegated to the treatment of acute, self-limiting pain (e.g., migraine, post-surgical pain) where dosing may range from a single dose to a few days of therapy. Butorphanol is almost never used for the treatment of chronic pain for a variety of reasons, including the absence of an oral formulation, the occurrence of sedation, dizziness and psychotomimemtic reactions, the latter attributed to its kappa opioid receptor agonism. Misuse, abuse, addiction and diversion have been reported in humans. Side effects due to kappa opioid receptor agonism generally increase with repeated administration, particularly to individuals with comorbidities.

There are no orally available immediate release formulations of butorphanol for the prevention or treatment of any human ailments. Until now, butorphanol's high incidence of side effects has reduced any desire to develop an oral formulation, which is particularly suited to the treatment of chronic conditions (e.g., chronic pain). In addition, the development and commercialization of oral butorphanol has been impeded by the widely reported poor oral bioavailability. For this reason, pharmaceutical companies have made efforts to develop alternative non-invasive methods of delivering butorphanol into systemic circulation. Foremost among these methods is the intranasal delivery of butorphanol (Stadol®) for the treatment of pain.

Similarly, there are no orally available formulations of modified release or extended release butorphanol. To the applicant's knowledge, no local, state, national or international guidelines, professional society or expert guidelines recommend the use of butorphanol by the oral route in any form (e.g., immediate release form or modified release form), either as a single entity or in combination with other drugs. In addition, even when patients have a suboptimal safety or efficacy response to other opioids, there are no recommendations that butorphanol by the oral route should be among the list of alternatives to be considered (e.g., second or third line therapeutic options). Indeed, even with the commercially intranasal butorphanol, there are no local, state, national or international guidelines, professional society or expert guidelines recommending its use for the treatment of chronic pain There is a need for oral pharmaceutical compositions of butorphanol which are safe and therapeutically effective.

There is also a need for oral pharmaceutical compositions of butorphanol which have a reduced potential for abuse. Although butorphanol has lower risk of abuse, it does carry a real risk of drug addiction, drug diversion and drug abuse. Reinforcing properties and physical dependence has been demonstrated with butorphanol in experimental models. Unfortunately, when given orally to recreational drug users or addicts, all commercially available immediate release and extended release opioids produce measurable euphoric or psychic effects soon after administration, usually within 15 to 120 minutes. Importantly, recreational opioid users, opioid addicts and patients taking opioids for therapeutic purposes may report different psychic experiences from the same dose of an opioid. Patients taking opioids for therapeutic purposes usually desire the intended benefit (e.g., pain relief) but bemoan the mood altering effects, which may be dysphoric, while recreational opioid users and opioid addicts welcome such mood altering effects. The applicant has found a novel way to deter or minimize the abuse of oral butorphanol among recreational drug users and drug addicts by minimizing the euphoric or psychic effects of the dosage form.

To the applicant's knowledge, (i) the therapeutic benefit of orally ingested butorphanol in modified release release form has heretofore not been not been tested or established for any medical condition, including pain, cough, pruritus, dyspnea and other opioid responsive disorders; (ii) no orally ingested controlled release formulations of butorphanol have been has heretofore been developed or commercialized; and (iii) no orally ingested modified release, duodenal release, jejunal release, ileal release, ileo-colonic release, or colonic release formulations of butorphanol have been has heretofore been developed or commercialized.

The applicant has surprisingly discovered that that butorphanol deposited, delivered or made bioavailable distal to stomach, preferably distal to the duodenum, and more preferably, distal to the jejunum or ileum provides significantly more robust therapeutic effects than butorphanol deposited, delivered or made bioavailable proximal to the foregoing anatomic region (e.g., as applicable, proximal to the stomach, duodenum, jejunum or ileum).

The applicant has surprisingly discovered that that butorphanol deposited, delivered or made bioavailable distal to stomach, preferably distal to the duodenum, and more preferably, distal to the jejunum or ileum provides significantly reduced side effects than butorphanol deposited, delivered or made bioavailable proximal to the foregoing anatomic region (e.g., as applicable, proximal to the stomach, duodenum, jejunum or ileum).

The applicant has surprisingly discovered that that butorphanol deposited, delivered or made bioavailable distal to stomach, preferably distal to the duodenum, and more preferably, distal to the jejunum or ileum provides significantly reduced psychotomimetic side effects than butorphanol deposited, delivered or made bioavailable proximal to the foregoing anatomic region (e.g., as applicable, proximal to the stomach, duodenum, jejunum or ileum).

The applicant has surprisingly discovered that that butorphanol deposited, delivered or made bioavailable distal to stomach, preferably distal to the duodenum, and more preferably, distal to the jejunum or ileum reduces the likability and abuse potential of the dosage form than butorphanol deposited, delivered or made bioavailable proximal to the foregoing anatomic region (e.g., as applicable, proximal to the stomach, duodenum, jejunum or ileum).

Butorphanol may be given by the intranasal route. However, intranasal administration has a number of disadvantages, including: (i) the maximum volume and dose of drug that can be delivered by this route of administration, particularly with available formulations; (ii) patient resistance with intranasal administration for systemic therapy, particularly with repeated around the clock dosing; (iii) an increased risk of drug diversion and drug abuse, including intravenous use with liquid forms of abusable drugs; (iv) inability to readily provide prolonged duration of therapy, for example, in extended release dosage forms; (v) lack of dose proportional increases in bioavailability over a wide range of doses and particularly at high doses, thereby limiting clinical utility; (vi) a high peak concentration of butorphanol, which can produce various opioid side effects such as nausea, drowsiness, dizziness and (acute) cognitive impairment.

The dosage form of the invention also provides modified release pharmaceutical compositions and methods of use to improve treatment compliance and to deter episodic, occasional, or intermittent use in subjects requiring chronic butorphanol therapy around the clock or on a time contingent basis by rendering the dosage form therapeutically ineffective or suboptimally effective when taken episodically, intermittently, or occasionally.

The dosage form of the invention also provides pharmaceutical compositions and methods to deter the abuse and misuse of the dosage form by recreational drug users of opioids and opioid addicts by rendering the dosage form devoid of or substantially devoid of euphoria, pleasurable, drug liking or other mood alerting effects when taken on an as needed basis.

The oral route of administration is the most widely used and most widely preferred method of drug administration. It is simple, reliable and readily accessible. Under most conditions of use, particularly outside the hospital setting, it is the recommended method of drug administration. Even in settings of skilled nursing care, where there are resources to initiate and manage parenteral therapy, the goal is to rapidly transition patients from parenteral medications to oral medications. Some generally cited exceptions to the use of the oral route include: (i) drugs with poor oral bioavailability; (ii) drugs requiring a rapid onset of effect; (iii) where venous access already exists (e.g., in the peri-operative or intensive care setting); (iii) where the oral route provides unreliable or inconsistent clinical effects. Therapeutic administration of butorphanol in modified release (e.g., controlled release or delayed onset), duodenal release, jejunal release, ileal release, ileo-colonic release, and colonic release dosage forms has either not been practiced or has been dismissed as unreliable or clinically unacceptable for some of the reasons noted above.

There is a need oral formulations of butorphanol that are therapeutically efficient and that can provide modified release of the butorphanol (e.g., delayed onset, extended release; delayed onset, duodenal delivery; delayed onset, jejunal delivery; delayed onset, ileal delivery; delayed onset, ileo-colonic delivery and delayed onset, colonic delivery).

The applicant has demonstrated for the first time that oral administration of butorphanol in a dosage form that models extended release of butorphanol provides robust therapeutic effects.

The applicant has demonstrated for the first time that oral administration of butorphanol in a dosage form that that models delayed onset, ileo-colonic delivery provides robust therapeutic effects and that this therapeutic effect is more robust than following oral immediate release of butorphanol.

There is therefore a need for new modified release oral pharmaceutical compositions of butorphanol and methods for the treatment of pain, cough, pruritus, dyspnea and other butorphanol responsive medical conditions through targeted gastrointestinal delivery, availability, release, disintegration, dissolution.

Chronic butorphanol therapy can produce a variety of side effects, including drowsiness, dizziness, nausea, vomiting, constipation, psychic effects, mood alteration and cognitive impairment. In subjects under the care of physicians who are highly experienced in pain management in the controlled setting of a clinical trial (where treatment dropout rates should be low), approximately 20 to 40% of subjects discontinue treatment within a few days to a few weeks of initiation of opioid therapy due to side effects. Even after a single dose, intranasal butorphanol produces significant side effects. After intranasal administration of 1 mg or 2 mg butorphanol, side effects included nausea (38%; 46%), vomiting (17%; 17%), dizziness (46%; 58%) and headache (46%; 29%) and oxygen desaturation (3%; 3%). An additional frequently observed side effect of intranasal butorphanol is bad taste in the mouth or the back of throat, and an unpleasant taste immediately after taking the intranasal dose.

For the management of severe pain, the U.S. prescribing information for intranasal butorphanol (Stadol®) provides the option of a 2 mg initial dose (1 mg in each nostril), but requires that this be given only to subjects who "will be able to remain recumbent in the event drowsiness or dizziness occurs". Therefore, side effects are a substantial deterrent to initiating opioid therapy and they add to patient suffering and the cost of therapy (e.g., drugs to treat the side effects, additional physician visits, etc). There is a need for therapeutically effective formulations of butorphanol which have lower side effects.

Although butorphanol has a mean half-life of about 5 hours, it provides a surprisingly short duration of action following intranasal administration. In a randomized, controlled clinical trial in subjects with acute postsurgical pain receiving the recommended initial of 1 mg intranasal dose of butorphanol, the duration of analgesic effect (as measured by the median time to requesting rescue analgesia) was less than 2 hours. Surprisingly, the duration of analgesic effect in subjects receiving double this dose (2 mg) was also than 2 hours and not significantly different from the 1 mg dose. Even more surprising, about 90% of subjects receiving the usual 1 mg intranasal dose and about 80% of subjects receiving the 2 mg dose required rescue analgesia during the first 6 hours of observation.

There is therefore a need for new pharmaceutical compositions and methods for subjects in need of butorphanol which provide a prolonged duration of therapeutic effect (e.g., more than 6 or 8 hours, preferably more than 12 hours, most preferably at least about 14 hours, 16 hours, 18 hours, 20 hours or 24 hours) when given orally.

Another aspect of the invention provides for resistance of the oral dosage form of the invention to alcohol induced dose dumping. This problem has been documented with several extended release opioid analgesics and can have serious adverse consequences. (Sloan and Babul, Expert Opinion on Drug Delivery 2006; 3:489-97). There is therefore a need for extended release opioids which do not evidence dose dumping in relation to alcohol intake, which do not evidence clinically significant changes in rate or extent of absorption in relation to alcohol intake, which do not evidence clinically significant pharmacodynamic variability in relation to alcohol intake, and which do not evidence bio-inequivalence of the dosage form when given with or without alcohol.

Many commercialized extended release opioids have been shown to have a significant food effect. Another aspect of the invention provides for reduced fed fasted pharmacokinetic variability. An important issue with oral extended release products is its potential for "dose dumping" in relation to food, where the active drug, intended for slow release, is instead released rapidly, resulting in toxicity on the one hand and a decreased duration of effect on the other.

There is therefore a need for extended release opioids which do not evidence dose dumping in relation to food intake, which do not evidence clinically significant changes in rate or extent of absorption in relation to food intake, which do not evidence clinically significant pharmacodynamic variability in relation to food intake, and which do not evidence bio-inequivalence of the dosage form when given in a fed or fasted state.

A pharmaceutically acceptable dosage form of oral butorphanol for the treatment of butorphanol responsive conditions beyond its short duration of action at a controlled rate over an extended period of time appears to be lacking in the pharmaceutical and medical arts.

In view of the foregoing presentation, it is immediately apparent that a serious need exists for an improvement in the delivery of oral butorphanol for its therapeutic effect. The need exists to provide a novel therapeutic composition comprising oral butorphanol, the need exists to provide a novel dosage form comprising oral butorphanol, and the need to provide a novel method of administering butorphanol to a patient in need of butorphanol therapy. The invention provides an oral, relatively easy mode and manner of butorphanol administration in comparison with intranasal and parenteral administration.

To the applicants knowledge, no examples or working prototype formulations of any modified release oral butorphanol have been described in the prior art. Butorphanol is a challenging drug to develop orally due to its high intrinsic clearance and the potential for substantial pharmacokinetic variability.

To the applicant's knowledge, there are no data heretofore demonstrating the efficacy or safety of any oral pharmaceutical compositions of modified release butorphanol To the applicant's knowledge, there is no prior art on the manufacture, use, efficacy, safety or abuse liability of any delayed onset, duodenal delivery, jejunal delivery, ileal delivery, ileo-colonic delivery or colonic delivery dosage forms of oral butorphanol for the treatment of any butorphanol responsive medical conditions, including pain, cough, pruritus, and dyspnea.

There is a need for new pharmaceutical compositions and methods for the treatment of butorphanol or opioid responsive medical conditions that have high efficacy, good tolerability, are an alternative to the intranasal and parenteral routes, and provide consistent pharmacokinetics and pharmacodynamics.

DESCRIPTION OF THE INVENTION

The present invention is directed at modified release pharmaceutical compositions of oral butorphanol and methods for the treatment of patients with pain, dyspnea, cough, pruritus, urinary incontinence, and any other buprenorphine responsive medical condition.

The present invention is directed at modified release pharmaceutical compositions of oral butorphanol and methods for the treatment of patients with sickle cell disease, fibromyalgia, acute herpes zoster, diarrhea, irritable bowel syndrome, visceral pain, neuropathic pain, restless leg syndrome, opioid addiction disorders and opioid dependence.

The present invention is directed at modified release pharmaceutical compositions of oral butorphanol and methods for the treatment for patients in need of butorphanol.

The present invention is directed at modified release pharmaceutical compositions of oral butorphanol and methods for the treatment of butorphanol or opioid responsive medical conditions in a population of patients comprising at least some patients who are non-compliant with regular, scheduled or around the clock therapy with analgesics, particularly extended release analgesics.

The present invention is directed at modified release pharmaceutical compositions of oral butorphanol and methods for the treatment of butorphanol or opioid responsive medical conditions in a population of subjects comprising at least some subjects who take their opioid analgesic for its euphoric, pleasureable or other non-medical effects.

The present invention is directed at modified release pharmaceutical compositions of oral butorphanol and methods for the treatment of butorphanol or opioid responsive medical conditions in a population of subjects comprising at least some subjects who can be expected to divert their supply of opioid analgesic into the illicit on non-medical distribution channels or who will misuse, abuse, share or sell their opioid analgesic.

The present invention is directed at modified release pharmaceutical compositions of oral butorphanol and methods for the treatment of butorphanol or opioid responsive medical conditions in a population of subjects comprising at least some subjects who can be expected to take their dosage form concurrently or contemporaneously with alcohol, wherein the dosage form of the invention is resistant to alcohol associated dose dumping.

The present invention is directed at modified release pharmaceutical compositions of oral butorphanol and methods for the treatment of butorphanol or opioid responsive medical conditions in a population of subjects comprising at least some subjects who can be expected to take their dosage form on as needed (PRN) basis, wherein the delayed onset, extended release dosage forms of butorphanol is less effective than when taken on a scheduled (around the clock) basis.

The present invention is directed at modified release pharmaceutical compositions of oral butorphanol and methods for the treatment of butorphanol or opioid responsive medical conditions, where in the oral dosage form of the invention is resistant to dose dumping and pharmacokinetic variability in relation to the co-ingestion with or without food.

It is an object of certain embodiments of the present invention to provide modified release formulations which give a substantially improved dose range of dose proportional extent of absorption compared to intranasal or oral immediate release dosage forms of butorphanol.

It is an object of certain embodiments of the present invention to provide modified release formulations which give a substantially reduced psychotomimetic effects compared to intranasal or oral immediate release dosage forms of butorphanol.

It is an object of certain embodiments of the present invention to provide modified release formulations which give a substantially reduced euphoric, psychic, mood altering or pleasurable effect compared to intranasal oral immediate release dosage forms of butorphanol.

It is an object of certain embodiments of the present invention to provide modified release formulations of butorphanol which: (i) are abuse resistant or abuse deterrent; (ii) are resistant to alcohol associated dose dumping; (iii) are resistant to dose dumping and pharmacokinetic variability in relation to co-ingestion with or without food; (iv) in delayed onset, extended release dosage forms provide improved compliance with treatment; and/or (v) provide methods to achieve efficient dose titration and therapeutic effect with reduced side effects.

It is an object of certain embodiments of the present invention to provide modified release formulations which give a substantially improved safety for the treatment of chronic conditions (e.g., chronic pain) compared to intranasal or oral immediate release dosage forms of butorphanol.

It is an object of certain embodiments of the present invention to provide bioavailable formulations for modified release dosage forms of oral butorphanol suitable for up to three times-a-day, twice-day or up to once-a-day administration to subjects in need of butorphanol.

It is an object of certain embodiments of the present invention to provide bioavailable formulations for modified release dosage forms of oral butorphanol suitable for up to three times-a-day, twice-day or up to once-a-day administration which are a delayed onset and/or extended duration of therapeutic effect.

It is an object of certain preferred embodiments of the present invention to provide oral formulations which provide therapeutic effects for up to about 6, 8, 10, 12, 14, 16, 18, 20, 22, 24 or 30 hours.

In some preferred embodiments, the oral pharmaceutical compositions of the invention are modified release.

In some preferred embodiments, the modified release oral pharmaceutical compositions of the invention are delayed onset dosage forms of butorphanol.

In some preferred embodiments, the modified release oral pharmaceutical compositions of the invention are controlled release dosage forms of butorphanol.

In some preferred embodiments, the oral pharmaceutical compositions of the invention are modified release.

In some preferred embodiments, the oral pharmaceutical compositions of the invention are delayed onset, rapid release dosage forms of butorphanol.

In some preferred embodiments, the oral pharmaceutical compositions of the invention are delayed onset, extended release dosage forms of butorphanol.

In some preferred embodiments, the oral pharmaceutical compositions of the invention are delayed onset, pulsatile release dosage forms of butorphanol.

In some preferred embodiments, the oral pharmaceutical compositions of the invention are delayed duodenal release; or jejunal release; or ileal release; or ileo-colonic release; or colonic release.

In some embodiments, the modified release oral pharmaceutical compositions of the invention comprise some portion of the dose as immediate release butorphanol.

In some embodiments, the present invention is directed at oral pharmaceutical composition for the treatment of butorphanol responsive medical conditions comprising a therapeutically effective amount of butorphanol or a pharmaceutically acceptable salt of butorphanol, or a mixture thereof.

In some embodiments, the present invention relates to oral butorphanol pharmaceutical compositions and methods for the treatment of pain, sickle cell disease, dyspnea, fibromyalgia, acute herpes zoster, diarrhea, irritable bowel syndrome, visceral pain, neuropathic pain, pruritus (itch), urinary incontinence, acute or chronic cough, restless leg syndrome, opioid addiction disorders and opioid dependence.

It is an object of certain preferred embodiments of the present invention to provide bioavailable oral butorphanol formulations suitable for up to once-daily administration which improve the efficiency and quality of pain management.

It is an object of certain preferred embodiments of the present invention to substantially improve the efficiency and quality of pain management in human patients experiencing mild or moderate pain.

It is an object of some embodiments of the invention to provide modified release oral pharmaceutical compositions of butorphanol and methods for the treatment of pain, addiction disorders and other butorphanol responsive disorders, wherein the dosage form is administered at a prespecified dosing regimen. In some embodiments, said dosing regimen is associated with reduced side effects, improved tolerability, improved efficiency of therapeutic response, reduced breakthrough symptoms (e.g., breakthrough pain) and reduced treatment discontinuation due to side effects.

It is an object of certain preferred embodiments of the present invention to treat patients who are believed to be at increased risk of drug abuse, opioid abuse, continued opioid abuse and relapse.

It is an object of certain preferred embodiments of the present invention to treat pain and addiction disorders in patients who have a suboptimal efficacy or safety response to intranasal butorphanol.

It is an object of certain preferred embodiments of the present invention to treat pain in patients who have a suboptimal efficacy or safety response with other orally approved opioids (e.g., opioids described oral administration in the FDA's Orange Book. Goodman & Gilman's The Pharmacological Basis of Therapeutics (Brunton, Lazo and Parker, eds, 11 th ed., McGraw Hill (2005); Principles of Analgesic Use in the Treatment of Acute Pain and Cancer Pain, Fifth Ed., American, Pain Society (2003); Evidence Based Report of the U.S. Agency for Healthcare Research and Quality (AHRQ) on the Management of Cancer Pain, Report No. 35, AHRQ Publication No. 02-E002, October 2001; Carr et al. J Nat Cancer Inst Monograph 2004; 32:23-31; Agency for Health Care Policy and Research Clinical Practice Guidelines for Cancer Pain Management, Guideline No. 9, AHCPR Publication No. 94-0592, March 1994; Agency for Health Care Policy and Research Clinical Practice Guideline for Acute Pain Management, Guideline No. 1, AHCPR Publication No. 92-0032, February, 1992; Guideline for the Management of Cancer Pain in Adults, American Pain Society, 2005; Guideline for the Management of Pain in Osteoarthritis, Rheumatoid Arthritis, and Juvenile Chronic Arthritis, $2^{nd}$ Ed., American Pain Society, 2002), e.g., morphine, codeine, oxycodone, oxymorphone, hydromorphone, methadone, hydrocodone.

It is an object of certain preferred embodiments of the present invention to treat pain in patients who have a suboptimal efficacy or safety response with other orally approved extended release opioids (e.g., MS Contin®, Kadian®, Avinza®, Ultram® ER, Opana® ER, Palladone®, Jurnista®).

It is an object of certain preferred embodiments of the present invention to substantially improve the efficiency and quality of pain management in human patients experiencing pain which is unresponsive or suboptimally responsive to mu-receptor agonists.

It is an object of certain preferred embodiments of the present invention to substantially improve the efficiency and quality of pain management in human patients experiencing pain which is unresponsive or suboptimally responsive to strong opioids.

It is an object of certain preferred embodiments of the present invention to substantially improve the efficiency and quality of pain management in human patients experiencing pain which is unresponsive or suboptimally responsive to opioids classified as Schedule II (C-II) or Schedule III (C-III) opioids under the United States Controlled Substance Act and regulations (as amended).

It is an object of some preferred embodiments to provide an oral pharmaceutical composition comprising a therapeutically effective amount of butorphanol which produces less drowsiness, nausea, dizziness, vomiting than after an equal amount (or dose) or lower amount (or dose) of intranasal butorphanol or immediate release oral butorphanol.

It is an object of some preferred embodiments to provide an oral pharmaceutical composition comprising a therapeutically effective amount of butorphanol which produces less abuse or abuse potential (e.g., produces lower abuse scores for "drug effects", "drug liking", "coasting", "take again", as defined herein) than after an equal amount (or dose) or lower amount (or dose) of intranasal butorphanol or immediate release oral butorphanol.

It is an object of some preferred embodiments to provide an oral pharmaceutical composition comprising a therapeutically effective amount of butorphanol which produces less neurologic, cognitive, motor and psychomotor impairment (e.g., solution, suspension, tablet or capsule) given orally (e.g., produces lower impairment scores for "critical tracking task", "stop signal task" and "Tower of London" (TOL), as defined herein) than after an equal amount (or dose) or lower amount (or dose) of intranasal butorphanol or immediate release oral butorphanol.

It is an object of certain preferred embodiments of the present invention to provide bioavailable oral butorphanol formulations which provide a substantially increased duration of effect as compared to intranasal butorphanol and oral immediate release butorphanol formulations.

It is an object of certain preferred embodiments of the invention to provide an oral butorphanol formulation which are delayed onset, extended release dosage forms.

It is an object of certain preferred embodiments of the invention to provide an oral butorphanol formulation which are delayed onset, rapid release dosage forms.

It is an object of certain preferred embodiments of the invention to provide an oral butorphanol formulation which are delayed onset, pulsatile release dosage forms.

It is an object of certain preferred embodiments of the present invention to provide bioavailable formulations oral administration which provide a therapeutic effect for up to for up to about 8, 10, 12, or 16, 18 or 24 hours after administration.

It is an object of certain preferred embodiments of the present invention to provide bioavailable formulations oral administration suitable for up to every 6, 8, 12, or 24 hour administration.

It is an object of certain preferred embodiments of the invention to provide a method and formulations of oral butorphanol intended as therapeutic substitutes for unprescribed, illicit, or medically unsanctioned pharmaceutical grade or street grade opioids.

It is an object of certain preferred embodiments of the invention to provide a method and formulations of oral butorphanol intended as part of an opioid substitution or opioid maintenance therapy in patients with an opioid addiction disorder or a polysubstance abuse disorder.

It is an object of certain preferred embodiments of the invention to provide a method and formulations of oral butorphanol, said formulations having a reduced potential for drug abuse and drug diversion.

It is an object of certain preferred embodiments of the invention to provide a method and formulations of oral butorphanol, said formulations having a reduced intrasubject or intersubject pharmacokinetic variability compared with intranasal butorphanol and immediate release oral butorphanol.

In some preferred embodiments, the invention comprises pharmaceutical composition comprising a therapeutically effective amount of butorphanol or a pharmaceutically acceptable salt of butorphanol or a mixture thereof wherein the specifications of the invention applicable to the treatment of pain are also applicable to the treatment of medical conditions other than pain in subjects in need of butorphanol.

In some preferred embodiments, the invention provides oral butorphanol formulations which when evaluated versus other butorphanol dosage forms (e.g., intranasal butorphanol and immediate release oral butorphanol) provide a relative mean $C_{max}$, $AUC_{0-t}$, and/or $AUC_{0-inf}$ whose 90% confidence interval is outside the 80.00% to 125.00, under single-dose fasted test conditions in healthy subjects.

It is an object of certain preferred embodiments of the invention to provide a method and formulations of oral butorphanol for the treatment of pain in opioid tolerant patients (e.g., tolerant to morphine, oxymorphone, buprenorphine, oxycodone, hydromorphone, hydrocodone, etc).

It is an object of certain preferred embodiments of the invention to provide a method and formulations of oral butorphanol for the treatment of pain in patients with opioid hyperalgesia from the use of other opioids.

The present invention also provides advantages in that equivalent, or higher doses of butorphanol may be used with better efficacy and/or fewer side effects observed than with intranasal formulation or oral immediate release formulations. For example, oral butorphanol formulations of the present invention may include the same amount or up to 5-fold higher daily maximum doses of intranasal butorphanol. However, even with these higher doses, formulations of the present invention achieve better efficacy and fewer side effects.

Oral administration of butorphanol in modified release can produce robust, dose dependent therapeutic effects.

Surprisingly, oral administration of butorphanol delivered to the ileum or colon produces a robust therapeutic effect; said effect greater that oral immediate release butorphanol delivered to the stomach.

In some preferred embodiments, the oral pharmaceutical compositions of the invention provide greater dose proportional bioavailability over a 2, 3, 4, 5, 6, 7, 8, 9, 10, 12 and 15-fold dose range than the nasal formulations of butorphanol.

As used herein, "dose proportionality", "dose-proportional" and "dose proportional bioavailability" means that change in dose by a particular percentage changes the drug exposure by a similar percentage, as assessed by the area under the plasma concentration time curve and maximum plasma concentration ($C_{max}$). For example, if a dosage form provides dose proportional bioavailability, doubling the dose approximately doubles the AUC and $C_{max}$. Some drugs or dosage forms may be dose proportional bioavailability over a narrow range of doses (e.g., 2 fold, or 3 fold), but may not be dose proportional over a wider range of doses (e.g., 4, 5, 6, or 7 fold). Dose proportionality may be assessed by methods well known in the art. A particularly preferred method is described by Smith B P et al, Pharm Res 17:1278-1283, which is hereby incorporated in its entirety by reference.

In some embodiments, the invention provides an oral dosage form for the treatment of butorphanol responsive conditions requiring chronic butorphanol therapy which is designed to improve treatment compliance and deter episodic, occasional, intermittent, periodic, as needed, or PRN use of the dosage form by rendering the dosage form therapeutically ineffective or suboptimally effective when taken episodically, intermittently, occasionally, periodically, on an as needed basis, or PRN, said dosage form comprising: (i) a therapeutically effective amount of butorphanol, a pharmaceutically acceptable salt thereof, or a mixture thereof, and (ii) controlled release material to render said dosage form suitable for modified release, said dosage form providing oral butorphanol release distal to the stomach, duodenum, jejunum or ileum.

In some embodiments, the invention provides an oral dosage form for the treatment of butorphanol responsive conditions requiring around the clock or time contingent butorphanol therapy which is designed to improve treatment compliance and deter episodic, occasional, intermittent, periodic, as needed, or PRN use of the dosage form by rendering the dosage form therapeutically ineffective or suboptimally effective when taken episodically, intermittently, occasionally, periodically, on an as needed basis, or PRN, said dosage form comprising: (i) a therapeutically effective amount of butorphanol, a pharmaceutically acceptable salt thereof, or a mixture thereof, and (ii) controlled release material to render said dosage form suitable for modified release, said dosage form providing oral butorphanol release distal to the stomach, duodenum, jejunum or ileum.

In some embodiments, the invention provides an oral dosage form of butorphanol which is therapeutically effective but which deters the abuse and misuse of the dosage form by rendering the dosage devoid of or substantially devoid of euphoria, pleasurable effects, drug liking, psychic and mood alerting effects when taken episodically, intermittently, occasionally, periodically, on an as needed basis, or PRN, said dosage form comprising: (i) a therapeutically effective amount of butorphanol, a pharmaceutically acceptable salt thereof, or a mixture thereof, and (ii) controlled release material to render said dosage form suitable for modified release, said dosage form providing oral butorphanol release distal to the stomach, duodenum, jejunum or ileum.

In some embodiments, the invention provides an oral dosage form of butorphanol which is therapeutically effective but which deters the abuse and misuse of the dosage form by delaying or substantially delaying euphoria, pleasurable effects, drug liking, psychic and mood alerting effects when taken regularly or when taken episodically, intermittently, occasionally, periodically, on an as needed basis, or PRN, said dosage form comprising: (i) a therapeutically effective amount of butorphanol, a pharmaceutically acceptable salt thereof, or a mixture thereof, and (ii) controlled release material to render said dosage form suitable for modified release, said dosage form providing oral butorphanol release distal to the stomach, duodenum, jejunum or ileum.

Another aspect of the invention provides for improved compliance with treatment. A major issue with pharmacologic management of chronic conditions is compliance with therapy. While extended release dosage forms assist this effort, compliance with extended releases dosage forms is still not adequate, which defeats the now widely accepted concept of continuous suppression of pain. Many erroneously assume that medication compliance is not a problem in chronic pain (unlike, an asymptomatic condition such as hypertension), since the patient will be reminded when to take their medication by the recurrence of pain. We have previously demonstrated that patients given unlimited access to PRN or as needed opioids consume lower doses of opioids but have worse analgesic outcomes than patients who are placed on schedule around the clock therapy (Arkinstall et al, Pain, 2005; 62:169-78). The present invention provides a novel method to improve compliance by making the dosage form substantially ineffective when taken on a PRN basis but effective when taken regularly.

In some embodiments, the invention provides a method of improving treatment compliance and deterring episodic, occasional, intermittent, periodic, as needed, or PRN use of the dosage form in subjects requiring around the clock, scheduled or time contingent oral butorphanol therapy by rendering the dosage form therapeutically ineffective or suboptimally effective when taken episodically, intermittently, occasionally, periodically, on an as needed basis, or PRN, said dosage form therapeutically effective in a substantial number of subjects when taken around the clock, on scheduled basis or on time contingent basis, comprising: (i) a therapeutically effective amount of butorphanol, a pharmaceutically acceptable salt thereof, or a mixture thereof, and (ii) controlled release material to render said dosage form suitable for modified release, said dosage form providing oral butorphanol release distal to the stomach, duodenum, jejunum or ileum.

In some embodiments, the invention provides a method of improving treatment compliance and deterring episodic, occasional, intermittent, periodic, as needed, or PRN use of the dosage form in subjects requiring chronic or prolonged oral butorphanol therapy by rendering the dosage form therapeutically ineffective or suboptimally effective when taken episodically, intermittently, occasionally, periodically, on an as needed basis, or PRN, said dosage form therapeutically effective in a substantial number of subjects when taken around the clock, on scheduled basis or on time contingent basis, comprising: (i) a therapeutically effective amount of butorphanol, a pharmaceutically acceptable salt thereof, or a mixture thereof, and (ii) controlled release material to render said dosage form suitable for modified release, said dosage form providing oral butorphanol release distal to the stomach, duodenum, jejunum or ileum.

In some embodiments, the invention provides a method of deterring abuse and misuse of oral butorphanol by rendering the dosage form devoid of or substantially devoid of euphoria, pleasurable effects, drug liking, psychic and mood alerting effects when taken episodically, intermittently, occasionally, periodically, on an as needed basis, or PRN, said dosage form comprising: (i) a therapeutically effective amount of butorphanol, a pharmaceutically acceptable salt thereof, or a mixture thereof, and (ii) controlled release material to render said dosage form suitable for modified release, said dosage form providing oral butorphanol release distal to the stomach, duodenum, jejunum or ileum.

In some embodiments, the invention provides a method of deterring abuse and misuse of oral butorphanol by delaying or substantially delaying or reducing euphoria, pleasurable effects, drug liking, psychic and mood alerting effects when taken regularly or when taken episodically, intermittently, occasionally, periodically, on an as needed basis, or PRN, said dosage form comprising: (i) a therapeutically effective amount of butorphanol, a pharmaceutically acceptable salt thereof, or a mixture thereof, and (ii) controlled release material to render said dosage form suitable for modified release, said dosage form providing oral butorphanol release distal to the stomach, duodenum, jejunum or ileum.

As used herein, when referring to use or administration of the oral butorphanol dosage form of the invention in some embodiments to provide or confer improved treatment compliance and deterrence to episodic, occasional, intermittent, periodic, as needed, or PRN use of the dosage form, the term "episodic", "occasional", "intermittent", "periodic", "as needed", "PRN" and "PRN basis" refer to use or administration which is non-consecutive, i.e., one oral butorphanol dose, given at its usual dosing interval (i) is not followed by a second administration or use at the end of the usual dosing interval doses; or (ii) is separated from the second administration by at least one dose interval of non-use or non-administration of the dosage form.

As used herein, when referring to use or administration of the oral butorphanol dosage form of the invention in some embodiments to deter the abuse and misuse of the dosage form by rendering the dosage devoid of or substantially devoid of euphoria, pleasurable effects, drug liking, psychic and mood alerting effects, the term "episodic", "occasional", "intermittent", "periodic", "as needed", "PRN" and "PRN basis" refer to use or administration which is non-consecutive, i.e., one oral butorphanol dose, given at its usual dosing interval (i) is not followed by a second administration or use at the end of the usual dosing interval doses; or (ii) is separated from the second administration by at least one dose interval of non-use or non-administration of the dosage form.

As used herein, when referring to use or administration of the oral butorphanol dosage form of the invention in some embodiments to deter the abuse and misuse of the dosage form by rendering the dosage devoid of or substantially devoid of euphoria, pleasurable effects, drug liking, psychic and mood alerting effects, the term "devoid of" or "substantially devoid of" means at least about 15%, or 20%, or 25%, or 30%, or 35%, or 40%, or 50%, or 60%, or 70%, or 80% less euphoria, pleasurable effects, drug liking, psychic and mood alerting effects compared with (i) an oral immediate release dosage form of butorphanol; or (ii) an oral controlled release dosage form which provides onset or substantial onset of release proximal to the duodenum, jejunum or ileum; or (iii) an intranasal dosage form of butorphanol.

In some embodiments, the invention provides an oral dosage form comprising: (i) a therapeutically effective amount of butorphanol, a pharmaceutically acceptable salt thereof, or a mixture thereof, and (ii) controlled release material to render said dosage form suitable for modified release, said dosage form providing butorphanol release distal to the stomach, duodenum, jejunum or ileum, said dosage form providing less side effects than intranasal butorphanol or oral immediate release butorphanol, said side effects measured after single dose administration to opioid naïve subjects.

In some embodiments, the invention provides a method for reducing side effects, comprising administering an oral dosage form comprising: (i) a therapeutically effective amount of butorphanol, a pharmaceutically acceptable salt thereof, or a mixture thereof, and (ii) controlled release material to render said dosage form suitable for modified release, said dosage form providing butorphanol release distal to the stomach, duodenum, jejunum or ileum, said dosage form providing less side effects than intranasal butorphanol or oral immediate release butorphanol, said side effects measured after single dose administration to opioid naïve subjects.

In some embodiments, the present invention is directed to modified release oral pharmaceutical compositions of butorphanol which provide one or more of the following, when compared with intransal butorphanol: (i) efficacy or improved efficacy; (ii) improved safety; (iii) improved efficiency of the dosage form; (iv) improved dose proportional extent of absorption; (v) reduced variability in absorption; and (vi) reduced potential for misuse, abuse, addiction and drug diversion. Without being hound by theory, in some embodiments, the pharmaceutical compositions and methods of the invention achieve their objectives at least in part through delivery of some, most, substantially all or all of the drug into the lower segments of the gastrointestinal tract (e.g., duodenal release; or jejunal release; or ileal release; or ileo-colonic release; or colonic release, or delayed onset, extended release).

In some embodiments, the modified release oral pharmaceutical compositions of butorphanol of the present invention improve the clinical efficacy, safety, tolerability, abuse resistance, dose proportional extent of absorption, predictability of clinical response, reproducibility of clinical response, therapeutic efficiency, and/or pharmacokinetics, said effect achieved through targeted gastrointestinal delivery, availability, release, disintegration, dissolution, metabolism and/or absorption, said targeted delivery achieved at least in part through delivery of some, most, substantially all or all of the drug in lower segments of the gastrointestinal tract (e.g., duodenal release; or jejunal release; or ileal release; or ileo-colonic release; or colonic release, or delayed onset, extended release) said targeted gastrointestinal delivery achieved in some embodiments by incorporation of materials into the dosage form to provide time-controlled, diffusion-controlled pH-controlled, pressure-controlled, osmotic pressure controlled, microbially controlled and/or enzyme controlled delivery or release.

In some embodiments, the oral controlled release; or delayed onset, rapid release; or delayed onset, extended release; or delayed onset, pulsatile release; or duodenal release pharmaceutical compositions of butorphanol result in one or more or all of the following benefits or characteristics when given at equal doses compared with immediate release oral dosage forms of butorphanol: increased dose proportional extent of absorption; increased time to peak concentration ($t_{max}$); reduced variability in extent of absorption (% coefficient of variation for $AUC_{0-inf}$ or $AUC_{0-t}$); reduced apparent oral clearance; lower hydroxybutorphanol to butorphanol $AUC_{0-inf}$ ratio; improved clinical efficacy; improved safety; reduced side effects 0.5, 1, 2, 3, 4 5, 6, 7 and/or 8 hours after oral ingestion of the dose; reduced abuse potential in drug abusers and recreational drug users; reduced abuse potential in subjects using the drug in accordance with the instructions of the medical practitioner, manufacturer, approved prescribing information or package insert; reduced risk of drug diversion, addiction or iatrogenic addiction; more predictable or reproducible clinical response; more efficient clinical response; more predictable or reproducible analgesic; and more efficient analgesic response.

In some embodiments, the modified release pharmaceutical compositions of butorphanol liberate or deliver some, a lot, most, substantially all or all of the butorphanol in the dosage form upon reaching the duodenum, jejunum, terminal ileum, ileo-cecal junction, ascending colon, transverse colon or descending colon.

An important drawback with the use of opioids is the risk of drug addiction, drug diversion and drug abuse. Although the use of opioids for non-medical purposes has existed throughout recorded human history, their abuse has increased significantly in the past few decades.

Pharmaceutical dosage forms containing butorphanol have been abused in a variety of settings, including patients with an addiction disorder who obtain it from illicit sources, patients with pain who have a pre-existing addiction disorder, patients with pain who have developed an addiction disorder following initiation of butorphanol or opioid therapy and recreational drug users.

Another aspect of the invention provides for extended release dosage forms of butorphanol which resist abuse by patients, recreational drug users and individuals with an addition disorder. Extended release opioids which do not require the incorporation of aversive and potentially unsafe excipients into the formulation, which do not require the incorporation of sequestered or unsequestered opioid antagonists, which involve multiple mechanism of abuse deterrence and/or complement other safe and effective methods of abuse deterrence provide a significant therapeutic advantage. The abuse deterrent pharmaceutical dosage forms of the invention are achieved in part through delayed onset, extended release dosage forms which provide duodenal release, jejunal release, ileal release, ileo-colonic release or colonic release of the extended release butorphanol from the dosage form.

Preferably, the dosage forms of the invention release drug distal to the stomach, more preferably, distal to the duodenum, and most preferably distal to the jejunum or ileum.

An important drawback with the use of opioid analgesics is the risk of addiction, diversion and abuse. Tampering extended release opioid formulations can deliver a significant dose in immediate release form and produce a variety of potentially serious or life threatening side effects. The focus of virtually all abuse resistant technology for extended release opioid formulations has been predicated on abuse through tampering of the extended release dosage form by the recreational drug user or drug addicts. Such technologies purport to (i) frustrate attempts at dosage form tampering to extract the drug; (ii) nullify the effects of the drug if tampered, and/or (iii) produce an unpleasant or unwanted effect when consumed in tampered form.

In the applicants view, the foregoing technologies are not an adequate solution to the problem of opioid abuse and fail to take into account the full spectrum of misuse, overuse and abuse of opioids. Such technologies show an over-reliance on the experience of addiction disorder clinics and emergency rooms which treat a very small minority of non-medical opioid users, primarily "hard core" abusers who consume the dosage form after tampering to maximize the delivered dose. In contrast to this skewed observation derived from a minority of non-medical "hard core" opioid abusers, in a vast majority of cases, the abuse of opioid analgesics is with the intact dosage form (i.e., the dosage form has not been physically manipulated or tampered with to alter its absorption profile) and the opioid is taken by the usual (oral) route of administration. For example, a vast majority of recreational drug users and patients with an addiction disorder, including iatrogenic addiction disorders will seldom or never use an opioid intended to be taken orally by any other route (e.g., intravenously after extraction and filtration, or by inhalation), nor will they physically manipulate or tamper the dosage form prior to oral ingestion. This population has a different self-image of their non-medical opioid use and attempts to distinguish or differentiate themselves and their use (abuse) from what they sometimes perceive as "reckless" and "irresponsible" use by "junkies", "addicts", "hard core addicts" or "real addicts". In addition, a considerable amount of abuse of opioids is the intact ingestion at a dose which is simply higher that the medically prescribed dose. A majority of technologies described in the art donot deal with the abuse of intact dosage forms of opioids.

In many cases, opioid abuse by the oral route involves immediate release or controlled release opioids. Such immediate release opioids generally an onset of euphoric or psychic within about 15 to about 180 minutes or within about 15 to about 120 minutes or within about 15 to about 90 minutes.

In some embodiments, the dosage forms of the invention reduces the intensity, frequency, duration, peak and/or total euphoric or psychic effects when compared with oral, immediate release and oral, controlled release dosage forms containing the same drug. Consequently, in some embodiments, the dosage form of the invention will have a lower propensity for abuse and misuse.

In some embodiments, the butorphanol dosage forms of the invention have a reduced potential for abuse and misuse, including: (a) drug abuse in individuals with a history of drug abuse or recreational drug use; (b) drug abuse in individuals with no prior history of drug abuse or recreational drug use; (c) iatrogenic addiction, euphoria, or pleasurable effects in individuals who take the dosage form in accordance with the approved prescribing information; (d) drug diversion; (e) pharmaceutical company liability; (f) pharmacy break-ins, prescription forgeries, doctor shopping; (g) illicit (street) availability and price; and/or (g) mood altering effects, said reduced potential abuse and misuse resulting in some embodiments at least in part dosage froms that release all or substantially all of the active drug distal to the duodenum, jejunum or ileum.

In some embodiments, the present invention is directed to oral dosage forms of butorphanol for the treatment of butorphanol responsive conditions requiring chronic butorphanol therapy where the dosage form is designed to improve treatment compliance and deter episodic, occasional, intermittent, periodic, as needed, or PRN use, for example and without being bound by theory, by rendering the dosage form therapeutically ineffective or suboptimally effective when taken episodically, intermittently, occasionally, periodically, on an as needed basis, or PRN, said dosage form comprising: (i) a therapeutically effective amount of butorphanol, a pharmaceutically acceptable salt thereof, or a mixture thereof, and (ii) controlled release material to render said dosage form suitable for modified release, said dosage form providing butorphanol release distal to the duodenum, jejunum or ileum. In some embodiments, said dosage form improves compliance or deters episodic, occasional, intermittent, periodic, as needed, or PRN use by more than about 1%, or 2%, or 3%, or 5%, or 7%, or 10%, or 12%, or 15%, or 18%, or 20%, or 25%, or 30%, or 35%, or 40%, or 50%, or 60%, or 70%, or 100%.

In some embodiments, the present invention is directed to oral dosage forms of butorphanol for the treatment of butorphanol responsive conditions around the clock or time contingent butorphanol therapy where the dosage form is designed to improve treatment compliance and deter episodic, occasional, intermittent, periodic, as needed, or PRN use, for example and without being bound by theory, by rendering the dosage form therapeutically ineffective or suboptimally effective when taken episodically, intermittently, occasionally, periodically, on an as needed basis, or PRN, said dosage form comprising: (i) a therapeutically effective amount of butorphanol, a pharmaceutically acceptable salt thereof, or a mixture thereof, and (ii) controlled release material to render said dosage form suitable for modified release, said dosage form providing butorphanol release distal to the duodenum, jejunum or ileum. In some embodiments, said dosage form improves compliance or deters episodic, occasional, intermittent, periodic, as needed, or PRN use by more than about 1%, or 2%, or 3%, or 5%, or 7%, or 10%, or 12%, or 15%, or 18%, or 20%, or 25%, or 30%, or 35%, or 40%, or 50%, or 60%, or 70%, or 100%.

In some embodiments, the present invention is directed at oral butorphanol dosage forms which are therapeutically effective but which deter the abuse and misuse of the dosage form by recreational drug users of opioids and opioid addicts by rendering the dosage devoid of or substantially devoid of euphoria, pleasurable, drug liking or other mood alerting effects when taken episodically, intermittently, occasionally, periodically, on an as needed basis, or PRN, said dosage form comprising: (i) a therapeutically effective amount of butorphanol, a pharmaceutically acceptable salt thereof, or a mixture thereof, and (ii) controlled release material to render said dosage form suitable for modified release, said dosage form providing butorphanol release distal to the duodenum, jejunum or ileum. In some embodiments, said dosage form reduces euphoria, pleasurable, drug liking or other mood alerting effects by more than about 1%, or 2%, or 3%, or 5%, or 7%, or 10%, or 12%, or 15%, or 18%, or 20%, or 25%, or 30%, or 35%, or 40%, or 50%, or 60%, or 70%, or 100%.

In some embodiments, the present invention is directed at oral butorphanol dosage forms which are therapeutically effective but which deter the abuse and misuse of the dosage form by recreational drug users of opioids and opioid addicts, for example and without being bound by theory, by rendering the dosage devoid of or substantially devoid of the instant gratification from euphoria, pleasurable, drug liking or other mood alerting effects sought by recreational drug users of opioids and opioid addicts, said dosage form comprising: (i) a therapeutically effective amount of butorphanol, a pharmaceutically acceptable salt thereof, or a mixture thereof, and (ii) controlled release material to render said dosage form suitable for modified release, said dosage form providing butorphanol release distal to the duodenum, jejunum or ileum. In some embodiments, said dosage form reduces the instant gratification from euphoria, pleasurable, drug liking or other mood alerting effects by more than about 1%, or 2%, or 3%, or 5%, or 7%, or 10%, or 12%, or 15%, or 18%, or 20%, or 25%, or 30%, or 35%, or 40%, or 50%, or 60%, or 70%, or 100%.

In some embodiments, the orally administered butorphanol dosage forms of the invention have a reduced potential for abuse and misuse, including frequency, duration or magnitude of euphoria, sedation, drug liking, fatigue, cognitive impairment, motor impairment and CNS impairment.

In some embodiments, the present invention is directed at oral butorphanol dosage forms which are therapeutically effective but which have reduced nausea, vomiting/retching, sedation, cognitive impairment and fatigue, said dosage form comprising: (i) a therapeutically effective amount of butorphanol, a pharmaceutically acceptable salt thereof, or a mixture thereof, and (ii) controlled release material to render said dosage form suitable for modified release, said dosage form providing butorphanol release distal to the duodenum, jejunum or ileum. In some embodiments, said dosage form reduces nausea, vomiting/retching, sedation, cognitive impairment and/or fatigue by more than about 1%, or 2%, or 3%, or 5%, or 7%, or 10%, or 12%, or 15%, or 18%, or 20%, or 25%, or 30%, or 35%, or 40%, or 50%, or 60%, or 70%, or 100%. In some other embodiments, said dosage form reduces nausea, vomiting/retching, sedation, cognitive impairment and/or fatigue by more than about 1%, or 2%, or 3%, or 5%, or 7%, or 10%, or 12%, or 15%, or 18%, or 20%, or 25%, or 30%, or 35%, or 40%, or 50%, or 60%, or 70%, or 100%, when measured at up to 1, 2, 3, 4, 5, or 6 hours after dosing.

In some embodiments, the orally administered butorphanol dosage forms of the invention have a reduced street value, or a reduced frequency, duration or magnitude of sedation, drug liking fatigue, cognitive impairment, motor impairment and CNS impairment when assessed 0.5, or 1, or 1.5, or 2, or 2.5 or 3, or 4, or 5 or 6, or 7 or 8 hours after ingestion of the initial dose, or a subsequent dose by recreational drug users, drug addicts, or opioid naïve healthy subjects.

In some embodiments, the orally administered butorphanol dosage forms of the invention have a reduced street value, or a reduced frequency, duration or magnitude of nausea, vomiting, sedation, drug liking fatigue, cognitive impairment, motor impairment, CNS impairment and other side effects, when assessed 0.5, or 1, or 1.5, or 2, or 2.5 or 3, or 4, or 5 or 6, or 7 or 8 hours after ingestion of the initial dose, or a subsequent dose by recreational drug users, drug addicts, or opioid naïve healthy subjects, when compared with the an oral immediate release solid or solution dosage form of butorphanol, or an intranasal dosage form, or extended release dosage form which is not duodenal release, jejunal release, ileal release or colonic release. In some embodiments, said oral immediate release solid or solution dosage form or said intranasal dosage form of butorphanol is administered at about the same dose, or at ≤about 90%, or ≤about 80%, or ≤about 75%, at ≤about 70%, or ≤about 60%, or ≤about 50%, or ≤about 45%, or ≤about 40%, or ≤about 35%, at ≤about 30%, or ≤about 25%, or ≤about 20%, or ≤about 15% of the dose of orally administered butorphanol of the invention.

In some embodiments, the present invention discloses that the dose range required to control pain with oral butorphanol dosage forms of the invention in about 90% of subjects is less than or substantially less than the 8-fold dose range required with morphine, thereby providing several potential benefits, including more efficient titration process (adjusting the subject's dosage to provide acceptable pain relief without unacceptable side effects), more therapeutically and cost efficient control of symptoms, faster control of symptoms, reduced cost of goods, reduced need for dose titration, reduced need for additional visits to the clinician, reduced need for a wider range of dosage strengths and reduced pharmacy inventory. In some embodiments, the close range of modified release oral butorphanol dosage forms of the invention is at least about 5%, 7%, 10%, 12%, 15%, 17%, 20%, 25%, 30%, 35%, 40%, 45%, 50%, 60%, 70% or 75% less than oral morphine.

In some embodiments, the present invention discloses that the dose range required to control pain with oral butorphanol dosage forms of the invention in about 90% of subjects is less than or substantially less than the 4-fold dose range required with oxycodone, thereby providing several potential benefits, including more efficient titration process (adjusting the subject's dosage to provide acceptable pain relief without unacceptable side effects), more therapeutically and cost efficient control of symptoms, faster control of symptoms, reduced cost of goods, reduced need for dose titration, reduced need for additional visits to the clinician, reduced need for a wider range of dosage strengths and reduced pharmacy inventory. In some embodiments, the dose range of modified release oral butorphanol dosage forms of the invention is at least about 5%, 7%, 10%, 12%, 15%, 17%, 20%, 25%, 30%, 35%, 40%, 45%, or 50% less than oral oxycodone.

In some preferred embodiments, the dose range of modified release oral butorphanol required to control pain in about 90% of subjects with oral butorphanol dosage forms of the invention is less than about 3 fold, 3.5 fold or 4 fold, or not more than about 3 fold, 3.5 fold, 4 fold, 4.5 fold, 5 fold, 5.5 fold or 6 fold.

In some preferred embodiments where the dosage form is a delayed onset oral butorphanol which releases most, substantially all or all the active drug after an initial delay, said delayed onset dosage form is limited to compositions that deliver or release drug distal to the jejunum (i.e., ileal release, ileo-colonic release or colonic release).

In some preferred embodiments, the daily dose range of modified release oral butorphanol required to control pain in about 90% of subjects is 5 mg to 60 mg, or 10 mg to 60 mg, or 10 mg to 50 mg, or 10 mg to 40 mg, or 10 mg to 30 mg.

It should be noted that while the oral butorphanol daily dose range required to control pain in about 90% of subjects in some embodiments of the invention is less than or substantially less than the 8-fold dose range seen with morphine which is the prototype opioid agonist, some patients will require doses that exceed or far exceed the dose range required to control pain in a substantial majority of subjects (e.g., 5, 10, 15 or 20 fold higher than the dose range required to control pain in about 90% of subjects said dosage form providing controlled release or delayed onset, extended release, or duodenal release, or jejunal release or ileal release or colonic release), due to a variety of pharmacokinetic and pharmacodynamic factors known in the art.

In some preferred embodiments, the dosage form provides a method for reducing the range in daily dosages required to control pain in substantially all human patients, comprising administering a modified release oral butorphanol comprising from about 5 mg to about 60 mg of butorphanol, which provides a mean a systemic exposure of butorphanol as assessed by the mean butorphanol area under the plasma concentration time curve over two consecutive dosing intervals ($AUC_{0-24}$) from about 1 ng·hr/mL to about 160 ng·hr/mL, and a mean maximum plasma concentration of butorphanol from the first of the two consecutive doses from about 0.1 ng/mL to about 6 ng/mL after repeated oral administration about every 12 hours to steady-state conditions, said dosage form providing controlled release or delayed onset, extended release or duodenal release, or jejunal release or ileal release or colonic release.

In some preferred embodiments, the dosage form provides a method for reducing the range in daily dosages required to control pain in substantially all human patients, comprising administering a modified release oral butorphanol comprising from about 5 mg to about 60 mg of butorphanol, a pharmaceutically acceptable salt thereof, or a mixture thereof, which provides a mean maximum plasma concentration of butorphanol from about 0.1 ng/mL to about 6 ng/mL from the first of the two consecutive doses from a mean of about 2 hours to about 7 hours, and a mean minimum plasma concentration of butorphanol of about 0.05 ng/mL to about 4.5 ng/mL, said minimum concentration measured from a mean of about 8 to about 15 hours after repeated oral administration about every 12 hours to steady-state conditions, said dosage form providing controlled release or delayed onset, extended release, or duodenal release, or jejunal release or ileal release or colonic release.

In some preferred embodiments, the dosage form provides a method for reducing the range in daily dosages required to control pain in substantially all human patients, comprising administering a modified release oral butorphanol comprising from about 5 mg to about 60 mg of butorphanol, a pharmaceutically acceptable salt thereof, or a mixture thereof, which provides a mean a systemic exposure of butorphanol as assessed by the mean butorphanol area under the plasma concentration time curve over two consecutive dosing intervals ($AUC_{0-24}$) from about 1 ng·hr/mL to about 160 ng·hr/mL, and a mean maximum plasma concentration of butorphanol from the first of the two consecutive doses from about 0.1 ng/mL to about 6 ng/mL from a mean of about 2 hours to about 7 hours after repeated oral administration about every 12 hours to steady-state conditions, said dosage form providing controlled release or delayed onset, extended release or duodenal release, or jejunal release or ileal release or colonic release.

In some preferred embodiments, the dosage form provides a method for reducing the range in daily dosages required to control pain in substantially all human patients, comprising administering a modified release oral butorphanol comprising from about 5 mg to about 60 mg of butorphanol, a pharmaceutically acceptable salt thereof, or a mixture thereof, which provides a mean a systemic exposure of butorphanol as assessed by the mean butorphanol area under the plasma concentration time curve over two consecutive dosing intervals ($AUC_{0-24}$) from about 1 ng·hr/mL to about 160 ng·hr/mL, a mean maximum plasma concentration of butorphanol from the first of the two consecutive doses from about 0.1 ng/mL to about 6 ng/mL from a mean of about 2 hours to about 7 hours, and a mean minimum plasma concentration of butorphanol of about 0.05 ng/mL to about 4.5 ng/mL, said minimum concentration measured from a mean of about 8 to about 15 hours after repeated oral administration about every 12 hours to steady-state conditions, said dosage form providing controlled release or delayed onset, extended release, or duodenal release, or jejunal release or ileal release or colonic release.

In some preferred embodiments, the dosage form provides a method for reducing the range in daily dosages required to control pain in substantially all human patients, comprising administering a modified release oral butorphanol comprising from about 10 mg to about 120 mg of butorphanol, which provides a mean a systemic exposure of butorphanol as assessed by the mean butorphanol area under the plasma concentration time curve over a single dosing interval ($AUC_{0-24}$) from about 1 ng·hr/mL to about 160 ng·hr/mL, and a mean maximum plasma concentration of butorphanol from about 0.1 ng/mL to about 6 ng/mL after repeated oral administration about every 24 hours to steady-state conditions, said dosage form providing controlled release or delayed onset, extended release, or duodenal release, or jejunal release or ileal release or colonic release.

In some preferred embodiments, the dosage form provides a method for reducing the range in daily dosages required to control pain in substantially all human patients, comprising administering a modified release oral butorphanol comprising from about 10 mg to about 120 mg of butorphanol, a pharmaceutically acceptable salt thereof, or a mixture thereof, which provides a mean maximum plasma concentration of butorphanol from about 0.1 ng/mL to about 6 ng/mL from a mean of about 3 hours to about 18 hours, and a mean minimum plasma concentration of butorphanol of about 0.05 ng/mL to about 4.5 ng/mL, said minimum concentration measured from a mean of about 20 to about 28 hours after repeated oral administration about every 24 hours to steady-state conditions, said dosage form providing controlled release or delayed onset, extended release, or duodenal release, or jejunal release or ileal release or colonic release.

In some preferred embodiments, the dosage form provides a method for reducing the range in daily dosages required to control pain in substantially all human patients, comprising administering a modified release oral butorphanol comprising from about 10 mg to about 120 mg of butorphanol, a pharmaceutically acceptable salt thereof, or a mixture thereof, which provides a mean a systemic exposure of butorphanol as assessed by the mean butorphanol area under the plasma concentration time curve over a single dosing interval ($AUC_{0-24}$) from about 1 ng·hr/mL to about 160 ng·hr/mL, and a mean maximum plasma concentration of butorphanol from about 0.1 ng/mL to about 6 ng/mL from a mean of about 3 hours to about 18 hours after repeated oral administration about every 24 hours to steady-state conditions, said dosage form providing controlled release or delayed onset, extended release, or duodenal release, or jejunal release or ileal release or colonic release.

In some preferred embodiments, the dosage form provides a method for reducing the range in daily dosages required to control pain in substantially all human patients, comprising administering a modified release oral butorphanol comprising from about 10 mg to about 120 mg of butorphanol, a pharmaceutically acceptable salt thereof, or a mixture thereof, which provides a mean a systemic exposure of butorphanol as assessed by the mean butorphanol area under the plasma concentration time curve over a single dosing interval ($AUC_{0-24}$) from about 1 ng·hr/mL to about 160 ng·hr/mL, and a mean maximum plasma concentration of butorphanol from about 0.1 ng/mL to about 6 ng/mL from a mean of about 3 hours to about 18 hours, and a mean minimum plasma concentration of butorphanol of about 0.05 ng/mL to about 4.5 ng/mL, said minimum concentration measured from a mean of about 20 to about 28 hours after repeated oral administration every 24 hours to steady-state conditions, said dosage form providing controlled release or delayed onset, extended release, or duodenal release, or jejunal release or ileal release or colonic release.

In some preferred embodiments, the dosage form provides a method for reducing the range in daily dosages required to control pain in substantially all human patients, comprising administering a modified release oral butorphanol comprising from about 10 mg to about 40 mg of butorphanol, which provides a mean a systemic exposure of butorphanol as assessed by the mean butorphanol area under the plasma concentration time curve over two consecutive dosing intervals ($AUC_{0-24}$) from about 2 ng·hr/mL to about 110 ng·hr/mL, and a mean maximum plasma concentration of butorphanol from the first of the two consecutive doses from about 0.2 ng/mL to about 4 ng/mL after repeated oral administration about every 12 hours to steady-state conditions, said dosage form providing controlled release or delayed onset, extended release, or duodenal release, or jejunal release or ileal release or colonic release.

In some preferred embodiments, the dosage form provides a method for reducing the range in daily dosages required to control pain in substantially all human patients, comprising administering a modified release oral butorphanol comprising from about 10 mg to about 40 mg of butorphanol, a pharmaceutically acceptable salt thereof, or a mixture thereof, which provides a mean maximum plasma concentration of butorphanol from about 0.2 ng/mL to about 4 ng/mL from the first of the two consecutive doses from a mean of about 2 hours to about 7 hours, and a mean minimum plasma concentration of butorphanol of about 0.1 ng/mL, to about 3 ng/mL, said minimum concentration measured from a mean of about 8 to about 15 hours after repeated oral administration about every 12 hours to steady-state conditions, said dosage form providing controlled release or delayed onset, extended release, or duodenal release, or jejunal release or ileal release or colonic release.

In some preferred embodiments, the dosage form provides a method for reducing the range in daily dosages required to control pain in substantially all human patients, comprising administering a modified release oral butorphanol comprising from about 10 mg to about 40 mg of butorphanol, a pharmaceutically acceptable salt thereof, or a mixture thereof, which provides a mean a systemic exposure of butorphanol as assessed by the mean butorphanol area under the plasma concentration time curve over two consecutive dosing intervals ($AUC_{0-24}$) from about 2 ng·hr/mL to about 110 ng·hr/mL, and a mean maximum plasma concentration of butorphanol from the first of the two consecutive doses from about 0.2 ng/mL to about 4 ng/mL from a mean of about 2 hours to about 7 hours after repeated oral administration about every 12 hours to steady-state conditions, said dosage form providing controlled release or delayed onset, extended release, or duodenal release, or jejunal release or ileal release or colonic release.

In some preferred embodiments, the dosage form provides a method for reducing the range in daily dosages required to control pain in substantially all human patients, comprising administering a modified release oral butorphanol comprising from about 10 mg to about 40 mg of butorphanol, a pharmaceutically acceptable salt thereof, or a mixture thereof, which provides a mean a systemic exposure of butorphanol as assessed by the mean butorphanol area under the plasma concentration time curve over two consecutive dosing intervals ($AUC_{0-24}$) from about 2 ng·hr/mL to about 110 ng·hr/mL, a mean maximum plasma concentration of butorphanol from the first of the two consecutive doses from about 0.2 ng/mL to about 4 ng/mL from a mean of about 2 hours to about 7 hours, and a mean minimum plasma concentration of butorphanol of about 0.1 ng/mL to about 3 ng/mL, said minimum concentration measured from a mean of about 8 to about 15 hours after repeated oral administration about every 12 hours to steady-state conditions, said dosage form providing controlled release or delayed onset, extended release, or duodenal release, or jejunal release or ileal release or colonic release.

In some preferred embodiments, the dosage form provides a method for reducing the range in daily dosages required to control pain in substantially all human patients, comprising administering a modified release oral butorphanol comprising from about 20 mg to about 80 mg of butorphanol, which provides a mean a systemic exposure of butorphanol as assessed by the mean butorphanol area under the plasma concentration time curve over a single dosing interval ($AUC_{0-24}$) from about 2 ng·hr/mL to about 110 ng·hr/mL, and a mean maximum plasma concentration of butorphanol from about 0.2 ng/mL to about 4 ng/mL after repeated oral administration about every 24 hours to steady-state conditions, said dosage form providing controlled release or delayed onset, extended release, or duodenal release, or jejunal release or ileal release or colonic release.

In some preferred embodiments, the dosage form provides a method for reducing the range in daily dosages required to control pain in substantially all human patients, comprising administering a modified release oral butorphanol comprising from about 20 mg to about 80 mg of butorphanol, a pharmaceutically acceptable salt thereof, or a mixture thereof, which provides a mean maximum plasma concentration of butorphanol from about 0.2 ng/mL to about 4 ng/mL from a mean of about 3 hours to about 18 hours, and a mean minimum plasma concentration of butorphanol of about 0.1 ng/mL to about 3 ng/mL, said minimum concentration measured from a mean of about 20 to about 28 hours after repeated oral administration about every 24 hours to steady-state conditions, said dosage form providing controlled release or delayed onset, extended release, or duodenal release, or jejunal release or ileal release or colonic release.

In some preferred embodiments, the dosage form provides a method for reducing the range in daily dosages required to control pain in substantially all human patients, comprising administering a modified release oral butorphanol comprising from about 20 mg to about 80 mg of butorphanol, a pharmaceutically acceptable salt thereof, or a mixture thereof, which provides a mean a systemic exposure of butorphanol as assessed by the mean butorphanol area under the plasma concentration time curve over a single dosing interval ($AUC_{0-24}$) from about 2 ng·hr/mL to about 110 ng·hr/mL, and a mean maximum plasma concentration of butorphanol from about 0.2 ng/mL to about 4 ng/mL from a mean of about 3 hours to about 18 hours after repeated oral administration about every 24 hours to steady-state conditions, said dosage form providing controlled release or delayed onset, extended release, or duodenal release, or jejunal release or ileal release or colonic release.

In some preferred embodiments, the dosage form provides a method for reducing the range in daily dosages required to control pain in substantially all human patients, comprising administering a modified release oral butorphanol comprising from about 20 mg to about 80 mg of butorphanol, a pharmaceutically acceptable salt thereof, or a mixture thereof, which provides a mean a systemic exposure of butorphanol as assessed by the mean butorphanol area under the plasma concentration time curve over a single dosing interval ($AUC_{0-24}$) from about 2 ng·hr/mL to about 110 ng·hr/mL, and a mean maximum plasma concentration of butorphanol from about 0.2 ng/mL to about 4 ng/mL from a mean of about 3 hours to about 18 hours, and a mean minimum plasma concentration of butorphanol of about 0.1 ng/mL to about 3 ng/mL, said minimum concentration measured from a mean of about 20 to about 28 hours after repeated oral administration every 24 hours to steady-state conditions, said dosage form providing controlled release or delayed onset, extended release, or duodenal release, or jejunal release or ileal release or colonic release.

In some preferred embodiments, the dosage form provides a method for reducing the range in daily dosages required to control pain in substantially all human patients, comprising administering a modified release oral butorphanol comprising from about 5 mg to about 80 mg of butorphanol, which provides a mean a systemic exposure of butorphanol as assessed by the mean butorphanol area under the plasma concentration time curve over two consecutive dosing intervals ($AUC_{0-24}$) from about 1 ng·hr/mL to about 220 ng·hr/mL, and a mean maximum plasma concentration of butorphanol from the first of the two consecutive doses from about 0.1 ng/mL to about 8 ng/mL after repeated oral administration about every 12 hours to steady-state conditions, said dosage form providing controlled release or delayed onset, extended release, or duodenal release, or jejunal release or ileal release or colonic release.

In some preferred embodiments, the dosage form provides a method for reducing the range in daily dosages required to control pain in substantially all human patients, comprising administering a modified release oral butorphanol comprising from about 5 mg to about 80 mg of butorphanol, a pharmaceutically acceptable salt thereof, or a mixture thereof, which provides a mean maximum plasma concentration of butorphanol from about 0.1 ng/mL to about 8 ng/mL from the first of the two consecutive doses from a mean of about 2 hours to about 7 hours, and a mean minimum plasma concentration of butorphanol of about 0.05 ng/mL to about 6 ng/mL, said minimum concentration measured from a mean of about 8 to about 15 hours after repeated oral administration about every 12 hours to steady-state conditions, said dosage form providing controlled release or delayed onset, extended release, or duodenal release, or jejunal release or ileal release or colonic release.

In some preferred embodiments, the dosage form provides a method for reducing the range in daily dosages required to control pain in substantially all human patients, comprising administering a modified release oral butorphanol comprising from about 5 mg to about 80 mg of butorphanol, a pharmaceutically acceptable salt thereof, or a mixture thereof, which provides a mean a systemic exposure of butorphanol as assessed by the mean butorphanol area under the plasma concentration time curve over two consecutive dosing intervals ($AUC_{0-24}$) from about 1 ng·hr/mL to about 220 ng·hr/mL, and a mean maximum plasma concentration of butorphanol from the first of the two consecutive doses from about 0.1 ng/mL to about 8 ng/mL from a mean of about 2 hours to about 7 hours after repeated oral administration about every 12 hours to steady-state conditions, said dosage form providing controlled release or delayed onset, extended release, or duodenal release, or jejunal release or ileal release or colonic release.

In some preferred embodiments, the dosage form provides a method for reducing the range in daily dosages required to control pain in substantially all human patients, comprising administering a modified release oral butorphanol comprising from about 5 mg to about 80 mg of butorphanol, a pharmaceutically acceptable salt thereof, or a mixture thereof, which provides a mean a systemic exposure of butorphanol as assessed by the mean butorphanol area under the plasma concentration time curve over two consecutive dosing intervals ($AUC_{0-24}$) from about 1 ng·hr/mL to about 220 ng·hr/mL, a mean maximum plasma concentration of butorphanol from the first of the two consecutive doses from about 0.1 ng/mL to about 8 ng/mL from a mean of about 2 hours to about 7 hours, and a mean minimum plasma concentration of butorphanol of about 0.05 ng/mL to about 6 ng/mL, said minimum concentration measured from a mean of about 8 to about 15 hours after repeated oral administration about every 12 hours to steady-state conditions, said dosage form providing controlled release or delayed onset, extended release, or duodenal release, or jejunal release or ileal release or colonic release.

In some preferred embodiments, the dosage form provides a method for reducing the range in daily dosages required to control pain in substantially all human patients, comprising administering a modified release oral butorphanol comprising from about 10 mg to about 120 mg of butorphanol, which provides a mean a systemic exposure of butorphanol as assessed by the mean butorphanol area under the plasma concentration time curve over a single dosing interval ($AUC_{0-24}$) from about 1 ng·hr/mL to about 220 ng·hr/mL, and a mean maximum plasma concentration of butorphanol from about 0.1 ng/mL to about 8 ng/mL after repeated oral administration about every 24 hours to steady-state conditions, said dosage form providing controlled release or delayed onset, extended release, or duodenal release, or jejunal release or ileal release or colonic release.

In some preferred embodiments, the dosage form provides a method for reducing the range in daily dosages required to control pain in substantially all human patients, comprising administering a modified release oral butorphanol comprising from about 10 mg to about 120 mg of butorphanol, a pharmaceutically acceptable salt thereof, or a mixture thereof, which provides a mean maximum plasma concentration of butorphanol from about 0.1 ng/mL to about 8 ng/mL from a mean of about 3 hours to about 18 hours, and a mean minimum plasma concentration of butorphanol of about 0.05 ng/mL to about 6 ng/mL, said minimum concentration measured from a mean of about 20 to about 28 hours after repeated oral administration about every 24 hours to steady-state conditions, said dosage form providing controlled release or delayed onset, extended release, or duodenal release, or jejunal release or ileal release or colonic release.

In some preferred embodiments, the dosage form provides a method for reducing the range in daily dosages required to control pain in substantially all human patients, comprising administering a modified release oral butorphanol comprising from about 10 mg to about 120 mg of butorphanol, a pharmaceutically acceptable salt thereof, or a mixture thereof, which provides a mean a systemic exposure of butorphanol as assessed by the mean butorphanol area under the plasma concentration time curve over a single dosing interval ($AUC_{0-24}$) from about 1 ng·hr/mL to about 220 ng·hr/mL, and a mean maximum plasma concentration of butorphanol from about 0.1 ng/mL to about 8 ng/mL from a mean of about 3 hours to about 18 hours after repeated oral administration about every 24 hours to steady-state conditions, said dosage form providing controlled release or delayed onset, extended release, or duodenal release, or jejunal release or ileal release or colonic release.

In some preferred embodiments, the dosage form provides a method for reducing the range in daily dosages required to control pain in substantially all human patients, comprising administering a modified release oral butorphanol comprising from about 10 mg to about 120 mg of butorphanol, a pharmaceutically acceptable salt thereof, or a mixture thereof, which provides a mean a systemic exposure of butorphanol as assessed by the mean butorphanol area under the plasma concentration time curve over a single dosing interval ($AUC_{0-24}$) from about 1 ng·hr/mL to about 220 ng·hr/mL, and a mean maximum plasma concentration of butorphanol from about 0.1 ng/mL to about 8 ng/mL from a mean of about 3 hours to about 18 hours, and a mean minimum plasma concentration of butorphanol of about 0.05 ng/mL to about 6 ng/mL, said minimum concentration measured from a mean of about 20 to about 28 hours after repeated oral administration every 24 hours to steady-state conditions, said dosage form providing controlled release or delayed onset, extended release, or duodenal release, or jejunal release or ileal release or colonic release.

In some preferred embodiments, the dosage form provides a method for reducing the number of dose adjustments or dose titrations required to control pain over the first month of treatment in substantially all human patients, comprising administering a modified release oral butorphanol comprising from about 5 mg to about 60 mg of butorphanol, which provides a mean a systemic exposure of butorphanol as assessed by the mean butorphanol area under the plasma concentration time curve over two consecutive dosing intervals ($AUC_{0-24}$) from about 1 ng·hr/mL to about 160 ng·hr/mL, and a mean maximum plasma concentration of butorphanol from the first of the two consecutive doses from about 0.1 ng/mL to about 6 ng/mL after repeated oral administration about every 12 hours to steady-state conditions, said dosage form providing controlled release or delayed onset, extended release, or duodenal release, or jejunal release or ileal release or colonic release.

In some preferred embodiments, the dosage form provides a method for reducing the number of dose adjustments or dose titrations required to control pain over the first month of treatment in substantially all human patients, comprising administering a modified release oral butorphanol comprising from about 5 mg to about 60 mg of butorphanol, a pharmaceutically acceptable salt thereof, or a mixture thereof, which provides a mean maximum plasma concentration of butorphanol from about 0.1 ng/mL to about 6 ng/mL from the first of the two consecutive doses from a mean of about 2 hours to about 7 hours, and a mean minimum plasma concentration of butorphanol of about 0.05 ng/mL to about 4.5 ng/mL, said minimum concentration measured from a mean of about 8 to about 15 hours after repeated oral administration about every 12 hours to steady-state conditions, said dosage form providing controlled release or delayed onset, extended release, or duodenal release, or jejunal release or ileal release or colonic release.

In some preferred embodiments, the dosage form provides a method for reducing the number of dose adjustments or dose titrations required to control pain over the first month of treatment in substantially all human patients, comprising administering a modified release oral butorphanol comprising from about 5 mg to about 60 mg of butorphanol, a pharmaceutically acceptable salt thereof, or a mixture thereof, which provides a mean a systemic exposure of butorphanol as assessed by the mean butorphanol area under the plasma concentration time curve over two consecutive dosing intervals ($AUC_{0-24}$) from about 1 ng·hr/mL to about 160 ng·hr/mL, and a mean maximum plasma concentration of butorphanol from the first of the two consecutive doses from about 0.1 ng/mL to about 6 ng/mL from a mean of about 2 hours to about 7 hours after repeated oral administration about every 12 hours to steady-state conditions, said dosage form providing controlled release or delayed onset, extended release, or duodenal release, or jejunal release or ileal release or colonic release.

In some preferred embodiments, the dosage form provides a method for reducing the number of dose adjustments or dose titrations required to control pain over the first month of treatment in substantially all human patients, comprising administering a modified release oral butorphanol comprising from about 5 mg to about 60 mg of butorphanol, a pharmaceutically acceptable salt thereof, or a mixture thereof, which provides a mean a systemic exposure of butorphanol as assessed by the mean butorphanol area under the plasma concentration time curve over two consecutive dosing intervals ($AUC_{0-24}$) from about 1 ng·hr/mL to about 160 ng·hr/mL, a mean maximum plasma concentration of butorphanol from the first of the two consecutive doses from about 0.1 ng/mL to about 6 ng/mL from a mean of about 2 hours to about 7 hours, and a mean minimum plasma concentration of butorphanol of about 0.05 ng/mL to about 4.5 ng/mL, said minimum concentration measured from a mean of about 8 to about 15 hours after repeated oral administration about every 12 hours to steady-state conditions, said dosage form providing controlled release or delayed onset, extended release, or duodenal release, or jejunal release or ileal release or colonic release.

In some preferred embodiments, the dosage form provides a method for reducing the number of dose adjustments or dose titrations required to control pain over the first month of treatment in substantially all human patients, comprising administering a modified release oral butorphanol comprising from about 10 mg to about 120 mg of butorphanol, which provides a mean a systemic exposure of butorphanol as assessed by the mean butorphanol area under the plasma concentration time curve over a single dosing interval ($AUC_{0-24}$) from about 1 ng·hr/mL to about 160 ng·hr/mL, and a mean maximum plasma concentration of butorphanol from about 0.1 ng/mL to about 6 ng/mL after repeated oral administration about every 24 hours to steady-state conditions, said dosage form providing controlled release or delayed onset, extended release, or duodenal release, or jejunal release or ileal release or colonic release.

In some preferred embodiments, the dosage form provides a method for reducing the number of dose adjustments or dose titrations required to control pain over the first month of treatment in substantially all human patients, comprising administering a modified release oral butorphanol comprising from about 10 mg to about 120 mg of butorphanol, a pharmaceutically acceptable salt thereof, or a mixture thereof, which provides a mean maximum plasma concentration of butorphanol from about 0.1 ng/mL to about 6 ng/mL from a mean of about 3 hours to about 18 hours, and a mean minimum plasma concentration of butorphanol of about 0.05 ng/mL to about 4.5 ng/mL, said minimum concentration measured from a mean of about 20 to about 28 hours after repeated oral administration about every 24 hours to steady-state conditions, said dosage form providing controlled release or delayed onset, extended release, or duodenal release, or jejunal release or ileal release or colonic release.

In some preferred embodiments, the dosage form provides a method for reducing the number of dose adjustments or dose titrations required to control pain over the first month of treatment in substantially all human patients, comprising administering a modified release oral butorphanol comprising from about 10 mg to about 120 mg of butorphanol, a pharmaceutically acceptable salt thereof, or a mixture thereof, which provides a mean a systemic exposure of butorphanol as assessed by the mean butorphanol area under the plasma concentration time curve over a single dosing interval ($AUC_{0-24}$) from about 1 ng·hr/mL to about 160 ng·hr/mL, and a mean maximum plasma concentration of butorphanol from about 0.1 ng/mL to about 6 ng/mL from a mean of about 3 hours to about 18 hours after repeated oral administration about every 24 hours to steady-state conditions, said dosage form providing controlled release or delayed onset, extended release, or duodenal release, or jejunal release or ileal release or colonic release.

In some preferred embodiments, the dosage form provides a method for reducing the number of dose adjustments or dose titrations required to control pain over the first month of treatment in substantially all human patients, comprising administering a modified release oral butorphanol comprising from about 10 mg to about 120 mg of butorphanol, a pharmaceutically acceptable salt thereof, or a mixture thereof, which provides a mean a systemic exposure of butorphanol as assessed by the mean butorphanol area under the plasma concentration time curve over a single dosing interval ($AUC_{0-24}$) from about 1 ng·hr/mL to about 160 ng·hr/mL, and a mean maximum plasma concentration of butorphanol from about 0.1 ng/mL to about 6 ng/mL from a mean of about 3 hours to about 18 hours, and a mean minimum plasma concentration of butorphanol of about 0.05 ng/mL to about 4.5 ng/mL, said minimum concentration measured from a mean of about 20 to about 28 hours after repeated oral administration every 24 hours to steady-state conditions, said dosage form providing controlled release or delayed onset, extended release, or duodenal release, or jejunal release or ileal release or colonic release.

In some preferred embodiments, the dosage form provides a method for reducing the number of dose adjustments or dose titrations required to control pain over the first month of treatment in substantially all human patients, comprising administering a modified release oral butorphanol comprising from about 10 mg to about 40 mg of butorphanol, which provides a mean a systemic exposure of butorphanol as assessed by the mean butorphanol area under the plasma concentration time curve over two consecutive dosing intervals ($AUC_{0-24}$) from about 2 ng·hr/mL to about 110 ng·hr/mL, and a mean maximum plasma concentration of butorphanol from the first of the two consecutive doses from about 0.2 ng/mL to about 4 ng/mL after repeated oral administration about every 12 hours to steady-state conditions, said dosage form providing controlled release or delayed onset, extended release, or duodenal release, or jejunal release or ileal release or colonic release.

In some preferred embodiments, the dosage form provides a method for reducing the number of dose adjustments or dose titrations required to control pain over the first month of treatment in substantially all human patients, comprising administering a modified release oral butorphanol comprising from about 10 mg to about 40 mg of butorphanol, a pharmaceutically acceptable salt thereof, or a mixture thereof, which provides a mean maximum plasma concentration of butorphanol from about 0.2 ng/mL to about 4 ng/mL from the first of the two consecutive doses from a mean of about 2 hours to about 7 hours, and a mean minimum plasma concentration of butorphanol of about 0.1 ng/mL to about 3 ng/mL, said minimum concentration measured from a mean of about 8 to about 15 hours after repeated oral administration about every 12 hours to steady-state conditions, said dosage form providing controlled release or delayed onset, extended release, or duodenal release, or jejunal release or ileal release or colonic release.

In some preferred embodiments, the dosage form provides a method for reducing the number of dose adjustments or dose titrations required to control pain over the first month of treatment in substantially all human patients, comprising administering a modified release oral butorphanol comprising from about 10 mg to about 40 mg of butorphanol, a pharmaceutically acceptable salt thereof, or a mixture thereof, which provides a mean a systemic exposure of butorphanol as assessed by the mean butorphanol area under the plasma concentration time curve over two consecutive dosing intervals ($AUC_{0-24}$) from about 2 ng·hr/mL to about 110 ng·hr/mL, and a mean maximum plasma concentration of butorphanol from the first of the two consecutive doses from about 0.2 ng/mL to about 4 ng/mL from a mean of about 2 hours to about 7 hours after repeated oral administration about every 12 hours to steady-state conditions, said dosage form providing controlled release or delayed onset, extended release, or duodenal release, or jejunal release or ileal release or colonic release.

In some preferred embodiments, the dosage form provides a method for reducing the number of dose adjustments or dose titrations required to control pain over the first month of treatment in substantially all human patients, comprising administering a modified release oral butorphanol comprising from about 10 mg to about 40 mg of butorphanol, a pharmaceutically acceptable salt thereof, or a mixture thereof, which provides a mean a systemic exposure of butorphanol as assessed by the mean butorphanol area under the plasma concentration time curve over two consecutive dosing intervals ($AUC_{0-24}$) from about 2 ng·hr/mL to about 110 ng·hr/mL, a mean maximum plasma concentration of butorphanol from the first of the two consecutive doses from about 0.2 ng/mL to about 4 ng/mL from a mean of about 2 hours to about 7 hours, and a mean minimum plasma concentration of butorphanol of about 0.1 ng/mL to about 3 ng/mL, said minimum concentration measured from a mean of about 8 to about 15 hours after repeated oral administration about every 12 hours to steady-state conditions, said dosage form providing controlled release or delayed onset, extended release, or duodenal release, or jejunal release or ileal release or colonic release.

In some preferred embodiments, the dosage form provides a method for reducing the number of dose adjustments or dose titrations required to control pain over the first month of treatment in substantially all human patients, comprising administering a modified release oral butorphanol comprising from about 20 mg to about 80 mg of butorphanol, which provides a mean a systemic exposure of butorphanol as assessed by the mean butorphanol area under the plasma concentration time curve over a single dosing interval ($AUC_{0-24}$) from about 2 ng·hr/mL to about 110 ng·hr/mL, and a mean maximum plasma concentration of butorphanol from about 0.2 ng/mL to about 4 ng/mL after repeated oral administration about every 24 hours to steady-state conditions, said dosage form providing controlled release or delayed onset, extended release, or duodenal release, or jejunal release or ileal release or colonic release.

In some preferred embodiments, the dosage form provides a method for reducing the number of dose adjustments or dose titrations required to control pain over the first month of treatment in substantially all human patients, comprising administering a modified release oral butorphanol comprising from about 20 mg to about 80 mg of butorphanol, a pharmaceutically acceptable salt thereof, or a mixture thereof, which provides a mean maximum plasma concentration of butorphanol from about 0.2 ng/mL to about 4 ng/mL from a mean of about 3 hours to about 18 hours, and a mean minimum plasma concentration of butorphanol of about 0.1 ng/mL to about 3 ng/mL, said minimum concentration measured from a mean of about 20 to about 28 hours after repeated oral administration about every 24 hours to steady-state conditions, said dosage form providing controlled release or delayed onset, extended release, or duodenal release, or jejunal release or ileal release or colonic release.

In some preferred embodiments, the dosage form provides a method for reducing the number of dose adjustments or dose titrations required to control pain over the first month of treatment in substantially all human patients, comprising administering a modified release oral butorphanol comprising from about 20 mg to about 80 mg of butorphanol, a pharmaceutically acceptable salt thereof, or a mixture thereof, which provides a mean a systemic exposure of butorphanol as assessed by the mean butorphanol area under the plasma concentration time curve over a single dosing interval ($AUC_{0-24}$) from about 2 ng·hr/mL to about 110 ng·hr/mL, and a mean maximum plasma concentration of butorphanol from about 0.2 ng/mL to about 4 ng/mL from a mean of about 3 hours to about 18 hours after repeated oral administration about every 24 hours to steady-state conditions, said dosage form providing controlled release or delayed onset, extended release, or duodenal release, or jejunal release or ileal release or colonic release.

In some preferred embodiments, the dosage form provides a method for reducing the number of dose adjustments or dose titrations required to control pain over the first month of treatment in substantially all human patients, comprising administering a modified release oral butorphanol comprising from about 20 mg to about 80 mg of butorphanol, a pharmaceutically acceptable salt thereof, or a mixture thereof, which provides a mean a systemic exposure of butorphanol as assessed by the mean butorphanol area under the plasma concentration time curve over a single dosing interval ($AUC_{0-24}$) from about 2 ng·hr/mL to about 110 ng·hr/mL, and a mean maximum plasma concentration of butorphanol from about 0.2 ng/mL to about 4 ng/mL from a mean of about 3 hours to about 18 hours, and a mean minimum plasma concentration of butorphanol of about 0.1 ng/mL to about 3 ng/mL, said minimum concentration measured from a mean of about 20 to about 28 hours after repeated oral administration every 24 hours to steady-state conditions, said dosage form providing controlled release or delayed onset, extended release, or duodenal release, or jejunal release or ileal release or colonic release.

In some preferred embodiments, the dosage form provides a method for reducing the number of dose adjustments or dose titrations required to control pain over the first month of treatment in substantially all human patients, comprising administering a modified release oral butorphanol comprising from about 5 mg to about 80 mg of butorphanol, which provides a mean a systemic exposure of butorphanol as assessed by the mean butorphanol area under the plasma concentration time curve over two consecutive dosing intervals ($AUC_{0-24}$) from about 1 ng·hr/mL to about 220 ng·hr/mL, and a mean maximum plasma concentration of butorphanol from the first of the two consecutive doses from about 0.1 ng/mL to about 8 ng/mL after repeated oral administration about every 12 hours to steady-state conditions, said dosage form providing controlled release or delayed onset, extended release, or duodenal release, or jejunal release or ileal release or colonic release.

In some preferred embodiments, the dosage form provides a method for reducing the number of dose adjustments or dose titrations required to control pain over the first month of treatment in substantially all human patients, comprising administering a modified release oral butorphanol comprising from about 5 mg to about 80 mg of butorphanol, a pharmaceutically acceptable salt thereof, or a mixture thereof, which provides a mean maximum plasma concentration of butorphanol from about 0.1 ng/mL to about 8 ng/mL from the first of the two consecutive doses from a mean of about 2 hours to about 7 hours, and a mean minimum plasma concentration of butorphanol of about 0.05 ng/mL to about 6 ng/mL, said minimum concentration measured from a mean of about 8 to about 15 hours after repeated oral administration about every 12 hours to steady-state conditions, said dosage form providing controlled release or delayed onset, extended release, or duodenal release, or jejunal release or ileal release or colonic release.

In some preferred embodiments, the dosage form provides a method for reducing the number of dose adjustments or dose titrations required to control pain over the first month of treatment in substantially all human patients, comprising administering a modified release oral butorphanol comprising from about 5 mg to about 80 mg of butorphanol, a pharmaceutically acceptable salt thereof, or a mixture thereof, which provides a mean a systemic exposure of butorphanol as assessed by the mean butorphanol area under the plasma concentration time curve over two consecutive dosing intervals ($AUC_{0-24}$) from about 1 ng·hr/mL to about 220 ng·hr/mL, and a mean maximum plasma concentration of butorphanol from the first of the two consecutive doses from about 0.1 ng/mL to about 8 ng/mL from a mean of about 2 hours to about 7 hours after repeated oral administration about every 12 hours to steady-state conditions, said dosage form providing controlled release or delayed onset, extended release, or duodenal release, or jejunal release or ileal release or colonic release.

In some preferred embodiments, the dosage form provides a method for reducing the number of dose adjustments or dose titrations required to control pain over the first month of treatment in substantially all human patients, comprising administering a modified release oral butorphanol comprising from about 5 mg to about 80 mg of butorphanol, a pharmaceutically acceptable salt thereof, or a mixture thereof, which provides a mean a systemic exposure of butorphanol as assessed by the mean butorphanol area under the plasma concentration time curve over two consecutive dosing intervals ($AUC_{0-24}$) from about 1 ng·hr/mL to about 220 ng·hr/mL, a mean maximum plasma concentration of butorphanol from the first of the two consecutive doses from about 0.1 ng/mL to about 8 ng/mL from a mean of about 2 hours to about 7 hours, and a mean minimum plasma concentration of butorphanol of about 0.05 ng/mL to about 6 ng/mL, said minimum concentration measured from a mean of about 8 to about 15 hours after repeated oral administration about every 12 hours to steady-state conditions, said dosage form providing controlled release or delayed onset, extended release, or duodenal release, or jejunal release or ileal release or colonic release.

In some preferred embodiments, the dosage form provides a method for reducing the number of dose adjustments or dose titrations required to control pain over the first month of treatment in substantially all human patients, comprising administering a modified release oral butorphanol comprising from about 10 mg to about 120 mg of butorphanol, which provides a mean a systemic exposure of butorphanol as assessed by the mean butorphanol area under the plasma concentration time curve over a single dosing interval ($AUC_{0-24}$) from about 1 ng·hr/mL to about 220 ng·hr/mL, and a mean maximum plasma concentration of butorphanol from about 0.1 ng/mL to about 8 ng/mL after repeated oral administration about every 24 hours to steady-state conditions, said dosage form providing controlled release or delayed onset, extended release, or duodenal release, or jejunal release or ileal release or colonic release.

In some preferred embodiments, the dosage form provides a method for reducing the number of dose adjustments or dose titrations required to control pain over the first month of treatment in substantially all human patients, comprising administering a modified release oral butorphanol comprising from about 10 mg to about 120 mg of butorphanol, a pharmaceutically acceptable salt thereof, or a mixture thereof, which provides a mean maximum plasma concentration of butorphanol from about 0.1 ng/mL to about 8 ng/mL from a mean of about 3 hours to about 18 hours, and a mean minimum plasma concentration of butorphanol of about 0.05 ng/mL to about 6 ng/mL, said minimum concentration measured from a mean of about 20 to about 28 hours after repeated oral administration about every 24 hours to steady-state conditions, said dosage form providing controlled release or delayed onset, extended release, or duodenal release, or jejunal release or ileal release or colonic release.

In some preferred embodiments, the dosage form provides a method for reducing the number of dose adjustments or dose titrations required to control pain over the first month of treatment in substantially all human patients, comprising administering a modified release oral butorphanol comprising from about 10 mg to about 120 mg of butorphanol, a pharmaceutically acceptable salt thereof, or a mixture thereof, which provides a mean a systemic exposure of butorphanol as assessed by the mean butorphanol area under the plasma concentration time curve over a single dosing interval ($AUC_{0-24}$) from about 1 ng·hr/mL to about 220 ng·hr/mL, and a mean maximum plasma concentration of butorphanol from about 0.1 ng/mL to about 8 ng/mL from a mean of about 3 hours to about 18 hours after repeated oral administration about every 24 hours to steady-state conditions, said dosage form providing controlled release or delayed onset, extended release, or duodenal release, or jejunal release or ileal release or colonic release.

In some preferred embodiments, the dosage form provides a method for reducing the number of dose adjustments or dose titrations required to control pain over the first month of treatment in substantially all human patients, comprising administering a modified release oral butorphanol comprising from about 10 mg to about 120 mg of butorphanol, a pharmaceutically acceptable salt thereof, or a mixture thereof, which provides a mean a systemic exposure of butorphanol as assessed by the mean butorphanol area under the plasma concentration time curve over a single dosing interval ($AUC_{0-24}$) from about 1 ng·hr/mL to about 220 ng·hr/mL, and a mean maximum plasma concentration of butorphanol from about 0.1 ng/mL to about 8 ng/mL from a mean of about 3 hours to about 18 hours, and a mean minimum plasma concentration of butorphanol of about 0.05 ng/mL to about 6 ng/mL, said minimum concentration measured from a mean of about 20 to about 28 hours after repeated oral administration every 24 hours to steady-state conditions, said dosage form providing controlled release or delayed onset, extended release, or duodenal release, or jejunal release or ileal release or colonic release.

A major challenge with the administration of more than one drug concurrently or in close proximity to each other is the occurrence of increased adverse effects from the combined and simultaneous high plasma concentrations of more than one drug producing the same or similar side effects through additive, super-additive or synergistic effects. For example, butorphanol may be used in conjunction with other drugs for the treatment of the same or different condition or side effect. Such other drugs can produce similar or the same side effects as butorphanol, including sedation, nausea, vomiting, and fatigue. Unfortunately, in many cases, using an alternative concomitant drug is not a practical option. In some embodiments, the present invention provides oral pharmaceutical compositions and methods to reduce the frequency, duration or magnitude of side effects from such concurrent, allowing for the advantageous use of drugs with similar or the same side effects as butorphanol.

Butorphanol is widely believed to be inappropriate to give orally, resulting in the need to: (i) administer the opioid by the parenteral route, with all of its sterility, cost, route accessibility to patients, and technical challenges; (ii) administer an intranasal dosage form with its limited duration of action, high incidence of side effects, limited dosage range, limited dose range showing dose proportional bioavailability, low patient acceptance and higher potential for tampering and abuse.

In some embodiments of the present invention the oral dosage from delivers most, substantially all or all of the butorphanol into the lower segments of the gastrointestinal tract (e.g., delayed onset, rapid release; or delayed onset, extended release; or delayed onset, pulsatile release; or duodenal release; or jejunal release; or ileal release; or ileo-colonic release; or colonic release) and the dosage form is best suited under certain circumstances (e.g., when the dosage form is a delayed onset form) for the treatment of signs and symptoms which do not require a rapid onset of effect from "one of", intermittent or episodic use of the dosage form or which are not administered as a single dose, or an intermittent dose or for episodic use. For example, if an individual has a new onset muscle tension headache or a new onset migraine, in some embodiments of the invention where the dosage form of the present invention delivers most, substantially all or all of the butorphanol into the lower segments of the gastrointestinal tract, it would usually be impractical to use the dosage form to produce a meaningful pharmacologic response due to the unacceptably long time the onset of effect would take. In some embodiments, this delay in onset of effect with single-dose, intermittent doses or episodic use contributes to providing a butorphanol dosage form with lower abuse potential.

Without being bound by theory, at first glance, a major potential concern with some embodiments of the present invention (e.g., delayed onset, rapid release; or delayed onset, extended release; or delayed onset, pulsatile release; or duodenal release; or jejunal release; or ileal release; or ileo-colonic release; or colonic release) would be whether such compositions would provide continuous or around the clock plasma concentration and therapeutic effect, in view of the delayed release of drug following ingestion. In some embodiments, the invention deals with this issue in the following way: (i) oral butorphanol formulations whose release is delayed but subsequently immediate upon arriving at the target site in the lower segments of the gastrointestinal tract, the current dose would provide a therapeutic effect until the next dose of the invention reaches the target site; (ii) oral butorphanol formulations whose release is delayed but when initiated it is subsequently further retarded at the target site(s) in the lower segments of the gastrointestinal tract (e.g., controlled release, extended release or sustained release), the current dose would provide a therapeutic effect until the next dose of the invention reaches the target site. Thus, in some embodiments of the invention, the only potential "therapeutic gap" of relates to the delay with therapeutic effect with the initial or first dose of the drug. This may be dealt with by using the dosage form of the drug in conventional or immediate release form on a one time basis, or by use of an alternate drug with the same or similar therapeutic effect or by limiting such dosage forms to individuals requiring repeated or multiple dose therapy, time contingent therapy, treatment lasting more than a few days, or chronic therapy, or by excluding individuals requiring single doses, rapid onset of effect with the initial dose, intermittent dosing, episodic dosing. This potential "therapeutic gap" also provides for some of the abuse deterrent properties of the invention.

In some embodiments, the dosage form of the invention is a modified release oral formulation which, after an initial in vivo lag period lasting at least about 1 hour, more preferably 1.5 hours, even more preferably 2 hours, and most preferably 2.5 to 4 hours during which there is little or no release of butorphanol, rapidly releases (e.g., over a period of less than about 1, 2 or 3 hours), most, substantially all or all of the butorphanol in vivo.

In some embodiments, the dosage form of the invention is a modified release oral formulation which, after an initial in vivo lag period lasting at least about 1 hour, more preferably 1.5 hours, even more preferably 2 hours, and most preferably 2.5 to 4 hours during which there is little or no release of butorphanol, gradually or slowly releases (e.g., over a period of not less than about 5, 7, 10, 12, 14, 16, 18, 20, 21, 22, 23, 24, 28 or 30 hours), most, substantially all or all of the butorphanol in vivo.

In some embodiments, the dosage form of the invention is a modified release oral formulation which, after ingestion is characterized by little or no release of the butorphanol in the stomach, said dosage form releases most, substantially all or all of the butorphanol from the dosage form in the duodenum, jejunum, ileum and/or colon, over a period of less than about 1, 2 or 3 hours.

In some embodiments, the dosage form of the invention is a modified release oral formulation which, after ingestion is characterized by little or no release of the butorphanol in the stomach or duodenum, said dosage form releases most, substantially all or all of the butorphanol from the dosage form upon arrival in the jejunum, ileum and/or colon, over a period of less than about 1, 2 or 3 hours.

In some embodiments, the dosage form of the invention is a modified release oral formulation which, after ingestion is characterized by little or no release of the butorphanol in the stomach, duodenum or jejunum, said dosage form releases most, substantially all or all of the butorphanol from the dosage form upon arrival in the ileum and/or colon, over a period of less than about 1, 2 or 3 hours.

In some embodiments, the dosage form of the invention is a modified release oral formulation which, after ingestion is characterized by little or no release of the butorphanol in the stomach, duodenum, jejunum or ileum, said dosage form releases most, substantially all or all of the butorphanol from the dosage form upon arrival in the colon, over a period of less than about 1, 2 or 3 hours.

In some embodiments, the dosage form of the invention is a modified release oral formulation which, after ingestion is characterized by little or no release of the butorphanol in the stomach, said dosage form releases most, substantially all or all of the butorphanol from the dosage form in the duodenum, jejunum, ileum and/or colon gradually over a period of not less than about 5, 7, 10, 12, 14, 16, 18, 20, 21, 22, 23, 24, 28 or 30 hours.

In some embodiments, the dosage form of the invention is a modified release oral formulation which, after ingestion is characterized by little or no release of the butorphanol in the stomach or duodenum, said dosage form releases most, substantially all or all of the butorphanol from the dosage form upon arrival in the jejunum, ileum and/or colon gradually over a period of not less than about 5, 7, 10, 12, 14, 16, 18, 20, 21, 22, 23, 24, 28 or 30 hours.

In some embodiments, the dosage form of the invention is a modified release oral formulation which, after ingestion is characterized by little or no release of the butorphanol in the stomach, duodenum or jejunum, said dosage form releases most, substantially all or all of the butorphanol from the dosage form upon arrival in the ileum and/or colon gradually over a period of not less than about 5, 7, 10, 12, 14, 16, 18, 20, 21, 22, 23, 24, 28 or 30 hours.

In some embodiments, the dosage form of the invention is a modified release oral formulation which, after ingestion is characterized by little or no release of the butorphanol in the stomach, duodenum, jejunum or ileum, said dosage form releases most, substantially all or all of the butorphanol from the dosage form upon arrival in the colon gradually over a period of not less than about 5, 7, 10, 12, 14, 16, 18, 20, 21, 22, 23, 24, 28 or 30 hours.

In some embodiments, the described in vitro or in vivo (including gastrointestinal tract and systemic) release characteristics, specifications and claims of the dosage forms of the invention are observed after some, or most, or substantially all, or all administered or ingested doses.

In some embodiments, the described pharmacokinetic and pharmacodynamic characteristics, specifications and claims of the dosage forms of the invention are observed after some, or most, or substantially all, or all administered or ingested doses.

In some embodiments, the described in vitro or in vivo (including gastrointestinal tract and systemic) release characteristics, specifications and claims of the dosage forms of the invention are observed after first administration.

In some embodiments, the described pharmacokinetic and pharmacodynamic characteristics, specifications and claims of the dosage forms of the invention are observed after first administration.

In some embodiments, the described in vitro or in vivo (including gastrointestinal tract and systemic) release characteristics, specifications and claims of the dosage forms of the invention are observed after repeated or multiple administration.

In some embodiments, the described pharmacokinetic and pharmacodynamic characteristics, specifications and claims of the dosage forms of the invention are observed after repeated or multiple administrations.

In some embodiments, the oral modified release butorphanol dosage form is coated, or sequestered so as to release little or no butorphanol in the stomach, or stomach and duodenum, or stomach, duodenum and jejunum, or stomach, duodenum, jejunum and ileum, or stomach, duodenum, jejunum, ileum and ileo-cecal junction.

In some embodiments, the oral modified release butorphanol dosage form provides an oral pharmaceutical composition and method of treating a butorphanol responsive medical condition, said treatment (i) achieving the same therapeutic objectives with a reduced dose of butorphanol; (ii) providing improved dose proportional extent of absorption; (iii) a more consistent clinical effect; (iv) a more consistent pharmacokinetic effect; (v) more consistent extent of oral absorption; (vi) greater efficacy; (vii) reduced frequency, duration and/or magnitude of side effects; (viii) reduced frequency, duration and/or magnitude of side effects at or for up to 0.5, 1, 2, 3, 4, 5, 6, 7 or 8 hours after the first dose; (ix) reduced frequency, duration and/or magnitude of nausea, vomiting and/or drowsiness; (x) reduced potential for drug abuse, drug diversion, drug liking, and mood altering effects; (xi) reduced potential for euphoria, drug liking, and mood altering effects; (xii) more efficient clinical management; (xiii) reduced metabolite accumulation (reduced metabolite to parent drug ratio), including in subjects with renal impairment; (xiv) reduced metabolite related side effects, e.g., neurotoxicity and myoclonus.

In some embodiments, the oral modified release butorphanol dosage form demonstrate increased efficacy of at least about 1%, 2%, 3%, 4%, 5%, 6%, or 8%, 10%, 12%, 15%, 20%, 30%, or 40%, when compared with oral immediate release dosage forms.

In some embodiments, the oral modified release butorphanol dosage form demonstrate reduced euphoria, drug liking, mood altering effects, nausea, vomiting, blurred vision, fatigue and/or drowsiness of at least about 1%, 2%, 3%, 4%, 5%, 6%, or 8%, 10%, 12%, 15%, 20%, 30%, or 40%, when compared with oral immediate release dosage forms.

In some embodiments, the oral modified release butorphanol dosage form demonstrate reduced euphoria, drug liking, mood altering effects, nausea, vomiting, blurred vision, fatigue and/or drowsiness of at least about 1%, 2%, 3%, 4%, 5%, 6%, or 8%, 10%, 12%, 15%, 20%, 30%, or 40%, when compared with intranasal dosage forms.

In some embodiments, the dosage form of the invention is an oral dosage form comprising: (i) a therapeutically effective amount of butorphanol, a pharmaceutically acceptable salt thereof, or a mixture thereof, and (ii) controlled release material to render said dosage form suitable for modified release, said dosage form providing butorphanol release distal to the duodenum, jejunum or ileum.

In some embodiments, the dosage form of the invention is an oral dosage form comprising: (i) a therapeutically effective amount of butorphanol, a pharmaceutically acceptable salt thereof, or a mixture thereof, and (ii) controlled release material to render said dosage form suitable for modified release, said dosage form providing butorphanol release distal to the stomach, duodenum, jejunum or ileum. said delayed release rendering said dosage form abuse resistant.

In some embodiments, the dosage form of the invention is an oral dosage form comprising: (i) a therapeutically effective amount of butorphanol, a pharmaceutically acceptable salt thereof, or a mixture thereof, and (ii) controlled release material to render said dosage form suitable for modified release, said dosage form providing butorphanol release distal to the stomach, duodenum, jejunum or ileum, said dosage form having reduced drug liking compared with oral dosage forms of butorphanol suitable for modified release but without delayed release. In some embodiments, said modified release dose with delayed onset has at least about 10%, 20%, or 30%, or 40%, or 50%, or 60%, or 75%, or 100%, or 150%, or 200%, or 250%, or 300% less drug liking than said comparator dose of modified release without delayed onset.

In some preferred embodiments, the controlled release material of the oral dosage form of the invention further comprises material to render said composition resistant or substantially resistant to dissolution in the stomach, or in the duodenum, or in the jejunum, or in the ileum, or in the small intestine, or in the stomach and duodenum, or in the stomach, duodenum and jejunum, or in the stomach, duodenum, jejunum and terminal ileum, in the stomach and small intestine, or before it reaches the ileo-cecal junction, or until it crosses the ileo-cecal junction or until it reaches the colon.

In some preferred embodiments, the controlled release material of the oral dosage form of the invention further comprises an overcoat material or an embedded material to render said composition resistant or substantially resistant to dissolution in the stomach, or in the duodenum, or in the jejunum, or in the ileum, or in the small intestine, or in the stomach and duodenum, or in the stomach, duodenum and jejunum, or in the stomach, duodenum, jejunum and terminal ileum, in the stomach and small intestine, or before it reaches the ileo-cecal junction, or until it crosses the ileo-cecal junction or until it reaches the colon. In some preferred embodiments, said overcoat is additionally incorporated into or applied over immediate release dosage forms, and controlled release matrix dosage forms, including controlled porosity osmotic dosage forms, push pull osmotic dosage forms.

As used herein with respect to the butorphanol dosage form of the invention, the term "oral", "oral dosage form", "oral pharmaceutical dosage form", "oral administration", "oral compositions" "oral pharmaceutical compositions", "oral tablets", "oral capsules", "orally ingested", "orally", "oral route" and the like all refer to any method of administration through the mouth. The oral dosage form of the invention is usually ingested intact, although it may be ingested un-intact or tampered (e.g., crushed) and usually with the aid of water or a beverage to hasten passage through the mouth. As used herein, "controlled release material", "controlled release means", and "material to provide controlled release" means an in vitro or in vivo release rate controlling excipient or material incorporated in the dosage form whose function or primary function is to modify release (e.g., onset of release, rate of release, duration of release) of an active drug (e.g., butorphanol) from a dosage form or a portion (i.e., cause the dosage form to release in other than an immediate release fashion). In preferred embodiments of the invention, the controlled release material functions to provide one or more of the following: (1) delay in the onset of release; (2) delay in the rate of release; (3) increase in the duration of release; (4) prolonged or extended duration of release; (5) pulsatile release; (6) delay in the onset of therapeutic effect; (7) delay in onset of side effects; (8) delay in the onset of psychic or mood altering effects; (9) reduced abuse liability; (10) prolonged or extended duration of therapeutic effect; (11) more robust therapeutic effect; (12) a pharmacokinetic profile consistent with dosage forms which are controlled release, extended release, sustained release, delayed onset, rapid release or delayed onset, extended release, or delayed onset, pulsatile release, or modified release, or slow release or prolonged release; (13) a pharmacodynamic profile consistent with dosage forms which are controlled release, extended release, sustained release, delayed onset, rapid release or delayed onset, extended release, or delayed onset, pulsatile release, or modified release, or slow release or prolonged release (14) efficacy or improved efficacy by the oral route; (15) improved safety by the oral route; (16) improved efficiency of the dosage form; (17) improved dose proportional extent of absorption; (18) reduced variability in absorption; (19) provide pulsatile release of the active drug; (20) provide delayed onset, rapid release of the dosage form; (21) provide delayed onset, extended release of the dosage form; (22) improved efficacy through delayed onset, rapid release or delayed onset, extended release compared with immediate release oral dosage forms; and (23) reduced potential for misuse, abuse, addiction and drug diversion.

In particularly preferred embodiments of the invention, the controlled release material functions to provide one or more of the following: (1) delay in the onset of release; (2) delay in the rate of release; (3) prolonged or extended duration of release; (4) delay in the onset of therapeutic effect; (5) delay in onset of side effects; (6) delay in the onset of psychic or mood altering effects; (7) reduced abuse liability; (8) prolonged or extended duration of therapeutic effect; (9) improved safety by the oral route compared with the same dose intranasally; (10) improved dose proportional extent of absorption, compared with the intranasal butorphanol; (11) reduced variability in absorption; and (12) jejunal, ileal, ileo-colonic or colonic release In some preferred nonlimiting examples, incorporation of controlled release material into the dosage form can provide for one or more of the following: (1) delay in release for at least about 1 hour, more preferably 1.5 hours, even more preferably 2 hours, and most preferably 2.5 to 4 hours, where the onset of first release or first substantial release is delayed but after start of said release, most, substantially all, or all of the active drug is rapidly released or liberated from the dosage form; (2) delay in release for at least about 1 hour, more preferably 1.5 hours, even more preferably 2 hours, and most preferably 2.5 to 4 hours, where the onset of first release or first substantial release is delayed but after start of said release, the active drug is rapidly released or liberated from the dosage form; (3) a delay in release, where, (a) the onset of first release or first substantial release is delayed until a specified or preferred time after oral ingestion, preferably for at least about 1 hour, more preferably 1.5 hours, even more preferably 2 hours, and most preferably 2.5 to 4 hours, or until the dosage form reaches a specified or preferred anatomic location in the GI lumen (preferably the duodenum, more preferably the jejunum and most preferably, the ileum or colon), or until the dosage form is in contact or prolonged contact with a preferred or specified in vitro or in vivo (GI) environment (such pH, GI luminal osmotic pressure, dosage form osmotic pressure, hydration, microbial environment, level of GI peristalsis or agitation), and (b) after the start of said release, most, substantially all, or all of the active drug is rapidly released or liberated from the dosage form (e.g., over a period of less than about 1, 2 or 3 hours); (4) a delay in release, where, (a) the onset of first release or first substantial release is delayed until a specified or preferred time after oral ingestion (preferably a delay in release for at least about 1 hour, more preferably 1.5 hours, even more preferably 2 hours, and most preferably 2.5 to 4 hours), and/or until the dosage form is in contact or prolonged contact with a particular in vitro or in vivo (GI) pH, or until the dosage form is in contact or prolonged contact with a preferred or specified in vitro or in vivo (GI) environment (such pH, GI luminal osmotic pressure, dosage form osmotic pressure, hydration, microbial environment, level of GI peristalsis or agitation), and (b) after the start of said release, the active drug is rapidly released or liberated from the dosage form (preferably over a period of less than about 1, 2 or 3 hours); (5) delay in release, where the onset of first release or first substantial release is delayed (preferably a delay in release for at least about 1 hour, more preferably 1.5 hours, even more preferably 2 hours, and most preferably 2.5 to 4 hours) but after start of said release, most, substantially all, or all of the active drug is slowly released or liberated from the dosage form; (6) delay in release, where the onset of first release or first substantial release is delayed (preferably over a period of less than about 1, 2 or 3 hours) but after start of said release, the active drug is slowly released or liberated from the dosage form, over a period of not less than about 5, 7, 10, 12, 14, 16, 18, 20, 21, 22, 23, 24, 28 or 30 hours; (7) delayed onset, extended release, where, (a) the onset of first release or first substantial release is delayed until a specified or preferred time after oral ingestion (preferably a delay in release for at least about 1 hour, more preferably 1.5 hours, even more preferably 2 hours, and most preferably 2.5 to 4 hours), or until the dosage form reaches a specified or preferred anatomic location in the GI lumen, or until the dosage form is in contact or prolonged contact with a preferred or specified in vitro or in vivo (GI) environment (such pH, GI luminal osmotic pressure, dosage form osmotic pressure, hydration, microbial environment, level of GI peristalsis or agitation), and (b) after the start of said release, most, substantially all, or all of the active drug is slowly released or liberated from the dosage form (e.g., prolonged release, or extended release, or sustained release, or slow release, or release over a period of not less than about 5, 7, 10, 12, 14, 16, 18, 20, 21, 22, 23, 24, 28 or 30 hours); (8) delayed onset, rapid release, where, (a) the onset of first release or first substantial release is delayed until a specified or preferred time after oral ingestion (preferably a delay in release for at least about 1 hour, more preferably 1.5 hours, even more preferably 2 hours, and most preferably 2.5 to 4 hours), or until the dosage form reaches a specified or preferred anatomic location in the GI lumen, or until the dosage form is in contact or prolonged contact with a preferred or specified in vitro or in vivo (G1) environment (such pH, GI luminal osmotic pressure, dosage form osmotic pressure, hydration, microbial environment, level of GI peristalsis or agitation), and (b) after the start of said release, the active drug is rapidly released or liberated from the dosage form (preferably over a period of less than about 1, 2 or 3 hours); (8b) "delayed onset, pulsatile release", where, (a) the onset of first release or first substantial release is delayed until a specified or preferred time after oral ingestion (preferably a delay in release for at least about 1 hour, more preferably 1.5 hours, even more preferably 2 hours, and most preferably 2.5 to 4 hours), or until the dosage form reaches a specified or preferred anatomic location in the GI lumen, or until the dosage form is in contact or prolonged contact with a preferred or specified in vitro or in vivo (GI) environment (such pH, GI luminal osmotic pressure, dosage form osmotic pressure, hydration, microbial environment, level of GI peristalsis or agitation), and (b) after the start of said release, rapidly release the active drug from the dosage form in "pulses" at their desired time intervals (e.g., about every 2, 3, 4, 5, 6, 8 or 12 hours), each pulse releasing a portion of the active drug rapidly (e.g., over about 0.125, 0.25, 0.5, 0.75, 1, 1.5, 2, 2.5, 3, 3.5 hours from the desired time); (9) rapid onset of first release or first substantial release, with continued slow release or liberation of the active drug from the dosage form; (10) slow onset of first release or first substantial release, with continued slow release or liberation of the active drug from the dosage form; (11) slow onset of first release or first substantial release (preferably over a period of less than about 1, 2 or 3 hours), with continued slow release or liberation of the active drug from the dosage form over a period of not less than about 5, 7, 10, 12, 14, 16, 18, 20, 21, 22, 23, 24, 28 or 30 hours; (12) no release or substantially no release in the stomach, followed by first release or first substantial release of the active drug from the dosage form in the duodenum or distal to the duodenum, where, after start of said first release, the active drug is rapidly released or liberated from the dosage form; (13) no release or substantially no release in the stomach, followed by first release or first substantial release of the active drug from the dosage form in the duodenum or distal to the duodenum, where, after start of said first release, the active drug is slowly released or liberated from the dosage form; (14) no release or substantially no release in the stomach, followed by first release or first substantial release of the active drug from the dosage form in the duodenum or distal to the duodenum, where, after start of said first release, the active drug is slowly released or liberated from the dosage form over a period of not less than about 5, 7, 10, 12, 14, 16, 18, 20, 21, 22, 23, 24, 28 or 30 hours; (15) no release or substantially no release in the duodenum or proximal to the duodenum, followed by first release or first substantial release of the active drug from the dosage form in the jejunum or distal to the jejunum, where, after start of said first release, the active drug is rapidly released or liberated from the dosage form; (16) no release or substantially no release in the duodenum or proximal to the duodenum, followed by first release or first substantial release of the active drug from the dosage form in the jejunum or distal to the jejunum, where, after start of said first release, the active drug is slowly released or liberated from the dosage form over a period of not less than about 5, 7, 10, 12, 14, 16, 18, 20, 21, 22, 23, 24, 28 or 30 hours; (17) no release or substantially no release in the jejunum or proximal to the jejunum, followed by first release or first substantial release of the active drug from the dosage form in the ileum and/or colon, where, after start of said first release, the active drug is rapidly released or liberated from the dosage form; (18) no release or substantially no release in the jejunum or proximal to the jejunum, followed by first release or first substantial release of the active drug from the dosage form in the ileum and/or colon, where, after start of said first release, the active drug is slowly released or liberated from the dosage form over a period of not less than about 5, 7, 10, 12, 14, 16, 18, 20, 21, 22, 23, 24, 28 or 30 hours; (19) no release or substantially no release in the ileum or proximal to the ileum, followed by first release or first substantial release of the active drug from the dosage form in the colon, where, after start of said first release, the active drug is rapidly released or liberated from the dosage form; (20) no release or substantially no release in the ileum or proximal to the ileum, followed by first release or first substantial release of the active drug from the dosage form in the colon, where, after start of said first release, the active drug is rapidly released or liberated from the dosage form, over a period of not less than about 5, 7, 10, 12, 14, 16, 18, 20, 21, 22, 23, 24, 28 or 30 hours.

As used herein, the term "modified release" dosage forms mean pharmaceutical preparations which release an active ingredient from a dosage form or a portion thereof in other than an immediate release fashion. Modified release pharmaceutical compositions are usually made by incorporating a controlled release material in the dosage form. Modified release pharmaceutical compositions are sometimes made also by direct compression, wherein the compression force excdees the usual compression force for immediate release tablets. Modified release dosage forms are sometimes designed to accomplish pharmaceutical, pharmacokinetic, pharmacodynamic, therapeutic or convenience objectives not offered by conventional dosage forms such as a solution or an immediate release dosage form.

As used herein, the term "modified release" includes "delayed onset" (or "delayed release") and "controlled release".

As used herein, the term "modified release" also includes dosage forms that provide "duodenal release", "duodenal delivery", "jejunal release", "jejunal delivery", "ileal release", "ileal delivery", "colonic release", "colonic delivery", "ileo-colonic release" and "ileo-colonic delivery".

As used herein, "controlled release" dosage forms mean pharmaceutical preparations which release an active ingredient from a dosage form or a portion thereof over an extended period of time (over a period of time greater than 4 or 6 hours, preferably over for period of up to about 8 hours, and most preferably for periods of up to about 12 hours or up to about 24 hours, or longer, either with an initial delay in release (e.g., a delay of 0.5, 1, 1.5, 2, 2.5, 3, 3.5, 4, 4.5, 5, 5.5, 6, 6.5, 7, 7.5 or 8 hours; preferably lasting at least about 1 hour, more preferably 1.5 hours, even more preferably 2 hours, and most preferably 2.5 to 4 hours) or without an initial delay in release.

As used herein, "controlled release" is used interchangeably with "prolonged release", "slow release", "sustained release", "extended release", "retarded release", "long acting" and the like.

As used herein, "delayed onset" and "delayed release" dosage forms mean pharmaceutical preparations which release begin the first release of an active ingredient from a dosage form or a portion thereof (i) at time other than immediately following oral administration; and/or (ii) after a lag period lasting from minutes to hours (e.g., 0.5, 1, 1.5, 2, 2.5, 3, 3.5, 4, 4.5, 5, 5.5, 6, 6.5, 7, 7.5 or 8 hours; preferably lasting at least about 1 hour, more preferably 1.5 hours, even more preferably 2 hours, and most preferably 2.5 to 4 hours); and/or (iii) upon reaching the desired or target GI anatomic location distal to the stomach (e.g., distal to the stomach, duodenum, jejunum, ileum, ileo-cecal junction or colon; preferably distal to the stomach, more preferably distal to the duodenum, and most preferably distal to the jejunum or ileum) or GI environment distal to the stomach (e.g., pH at the point of release, osmotic pressure at the point of release, hydration, microbial flora). Delayed onset formulations of the invention may be delayed onset, rapid release; delayed onset, pulsatile release; or delayed onset, extended release.

As used herein, "delayed onset, rapid release" means dosage forms which after a desired lag period post-ingestion (e.g., 0.5, 1, 1.5, 2, 2.5, 3, 3.5, 4, 4.5, 5, 5.5, 6, 6.5, 7, 7.5 or 8 hours; preferably lasting at least about 1 hour, more preferably 1.5 hours, even more preferably 2 hours, and most preferably 2.5 to 4 hours), rapidly releases (i.e., over about 0.05, 0.1, 0.125, 0.25, 0.5, 0.75, 1, 1.5, 2, 2.5, 3, 3.5 hours; preferably over a period of less than about 1, 2 or 3 hours) substantially all or all the active drug from the dosage form.

As used herein, "delayed onset, pulsatile release" means dosage forms which after a desired lag period post-ingestion (e.g., 0.5, 1, 1.5, 2, 2.5, 3, 3.5, 4, 4.5, 5, 5.5, 6, 6.5, 7, 7.5 or 8 hours; preferably lasting at least about 1 hour, more preferably 1.5 hours, even more preferably 2 hours, and most preferably 2.5 to 4 hours), rapidly releases (i.e., over about 0.05, 0.1, 0.125, 0.25, 0.5, 0.75, 1, 1.5, 2, 2.5, 3, 3.5 hours; preferably over a period of less than about 1, 2 or 3 hours) some of the active drug from the dosage form in "pulses" at the desired time intervals (e.g., about every 1, 2, 3, 4, 5, 8, or 12 hours), each pulse releasing a portion of the active drug in the dosage form.

As used herein, "delayed onset, extended release" means dosage forms which after a desired lag period post-ingestion (e.g., 0.5, 1, 1.5, 2, 2.5, 3, 3.5, 4, 4.5, 5, 5.5, 6, 6.5, 7, 7.5 or 8 hours; preferably lasting at least about 1 hour, more preferably 1.5 hours, even more preferably 2 hours, and most preferably 2.5 to 4 hours), slowly release the active drug from the dosage form over an extended period of time, over a period of not less than about 5, 7, 10, 12, 14, 16, 18, 20, 21, 22, 23, 24, 28 or 30 hours.

As used herein, "delayed release" and "delayed onset" include dosage forms which are delayed onset, rapid release; delayed onset, pulsatile release; and delayed onset.

In some embodiments, one or more, or substantially all, or all of the embodiments and specifications showing benefit or a difference for modified release delayed onset dosage forms of oral butorphanol (e.g., delayed onset, rapid release; delayed onset, pulsatile release; delayed onset, extended release) over immediate release oral butorphanol, the phrase "immediate release" may be substituted with "controlled release", "extended release", "sustained release" or "pulsatile release", provided said controlled release, extended release or pulsatile release dosage forms are not delayed onset dosage forms.

In some embodiments, one or more, or substantially all, or all of the embodiments and specifications showing benefit or a difference for delayed onset dosage forms of oral butorphanol (e.g., delayed onset, rapid release; delayed onset, pulsatile release; delayed onset, extended release) over intranasal butorphanol, "intranasal" dosage forms of butorphanol may be substituted with oral "immediate release" dosage forms of butorphanol.

In some embodiments, one or more, or substantially all, or all of the embodiments and specifications showing benefit or a difference for delayed onset dosage forms of oral butorphanol (e.g., delayed onset, rapid release; delayed onset, pulsatile release; delayed onset, extended release) over intranasal butorphanol, "intranasal" dosage forms of butorphanol may be substituted with oral "immediate release" dosage forms of butorphanol.

In some embodiments, controlled release dosage forms of the present invention releases butorphanol from the oral dosage form at a slower rate than immediate release formulations. In some preferred embodiments, extended release dosage forms and delayed onset, extended release dosage forms release butorphanol at such a rate that plasma concentrations and/or therapeutic effects are maintained within the therapeutic range (above the minimum effective therapeutic concentration) but below toxic levels for intended duration (e.g., over a period of about 6 to about 30 hours, preferably over a period of time indicative of a Q8H, Q8H PRN, Q12H, Q12H PRN, Q24H or Q24H PRN administration, more preferably over a period of time indicative of a Q12H, Q12H PRN, Q24H or Q24H PRN administration). In some preferred embodiments, the extended release formulations of the present invention provide therapeutic effects for a duration that is longer or substantially longer than the duration of meaningful or detectable plasma concentrations of butorphanol.

When applied to the present invention, present invention, the term "immediate release", "immediate release dosage forms", "immediate release composition", "immediate release tablet", "immediate release capsule", "immediate release formulation", immediate release forms" and the like is a dosage form which is formulated to release the active drug from the dosage form immediately (i.e., without an attempt to delay or prolong the release of the active drug from the dosage form as is the case, for example, with extended release dosage forms) or a dosage form which allows the drug to dissolve in the gastrointestinal contents, with no intention of delaying or prolonging the dissolution or absorption of the drug) Immediate release dosage forms may be in any form, including tablet, capsule, solution, suspension, powder, micronized, granulated etc. When applied to butorphanol dosage forms of the invention, unless further modified to alter the meaning, "immediate release" refers to oral dosage forms. In the absence of a commercially available oral immediate release butorphanol product, an available parenteral or intranasal formulation of butorphanol or a salt thereof may be used orally, or a solution of butorphanol or a salt thereof may be prepared or an immediate release tablet may be prepared for the purpose of in vivo testing requiring immediate release butorphanol. Alternatively, an immediate release formulation of butorphanol may be prepared by encapsulating liquid or uncompressed solid butorphanol, or by compressing butorphanol into tablet form without excipients or material that impart a delay or retardation to its release. Immediate release dosage forms generally disintegrate in ≤about 0.5 hours or ≤about 1 hour, and generally substantially or completely dissolve in ≤about 0.25, or ≤about 0.5, or about 0.75, or ≤about 1 or ≤about 1.25, or ≤about 1.5, or ≤about 1.75, or ≤about 2 hours, when measured by the recommended or appropriate USP compendial methods (for example some dosage forms may be tested by USP Basket Method or USP Paddle Method at 100 rpm in 900 mL of water at 37° C.).

As used herein, "intranasal" dosage forms of butorphanol refer to a commercially available intranasal formulation of butorphanol listed in FDA's Orange Book, preferably the reference listed product, and in its absence, a listed A/B generic product. In the absence of such a product, alternative intranasal formulations may be substituted (for example, commercially available intranasal formulations are listed non-A/B generic products in the USA, formulation approved by the EMEA or available in the European Union, or formulations listed in Martindale: The Complete Drug Reference, 35th Edition [or more recent], Pharmaceutical Press), or in the absence of a suitable alternative, an extemporaneously compounded solution suitable for intranasal administration may be prepared.

When commercially available immediate release oral dosage forms of butorphanol are not available, they may be made or extemporaneously compounded in the forms of powder, solution, suspension, tablets, uncompressed capsules or tablets, each devoid of controlled release material.

For purposes of the invention, the oral modified release and oral immediate release formulations are dose proportional. In such formulations, the pharmacokinetic parameters (e.g., AUC and $C_{max}$) generally increase linearly from one dosage strength to another. Therefore the pharmacokinetic parameters of a particular dose can be inferred from the parameters of a different dose of the same formulation.

As used herein with respect to the butorphanol dosage form of the invention, "duodenal release" and "duodenal delivery" are interchangeable and refer to in vivo release of all, substantially all or most butorphanol from the dosage form into the portion of gastrointestinal tract distal to the stomach. In some embodiments, duodenal release or duodenal delivery dosage forms of the invention provide in vivo release of all, substantially all or most butorphanol from the dosage form rapidly upon reaching the portion of gastrointestinal tract distal to the stomach. In other embodiments, duodenal release and duodenal delivery dosage forms of the invention provide in vivo release of all, substantially all or most butorphanol from the dosage form slowly (e.g., sustained release or extended release) upon reaching the portion of gastrointestinal tract distal to the stomach.

As used herein with respect to the butorphanol dosage form of the invention, "jejunal release" and "jejunal delivery" are interchangeable, and refers to in vivo release of all, substantially all or most butorphanol from the dosage form into the portion of gastrointestinal tract distal to the duodenum. In some embodiments, jejunal release" or "jejunal delivery dosage forms of the invention provide in vivo release of all, substantially all or most butorphanol from the dosage form rapidly upon reaching the portion of gastrointestinal tract distal to the duodenum. In other embodiments, duodenal release and duodenal delivery dosage forms of the invention provide in vivo release of all, substantially all or most butorphanol from the dosage form slowly (e.g., sustained release or extended release) upon reaching the portion of gastrointestinal tract distal to the duodenum.

As used herein with respect to the butorphanol dosage form of the invention, "ileal release" and "ileal delivery" are interchangeable and refers to in vivo release of all, substantially all or most butorphanol from the dosage form into the portion of gastrointestinal tract distal to the jejunum. In some embodiments, ileal release or ileal delivery dosage forms of the invention provide in vivo release of all, substantially all or most butorphanol from the dosage form rapidly upon reaching the portion of gastrointestinal tract distal to the jejunum. In other embodiments, ileal release and ileal delivery dosage forms of the invention provide in vivo release of all, substantially all or most butorphanol from the dosage form slowly (e.g., sustained release or extended release) upon reaching the portion of gastrointestinal tract distal to the jejunum.

As used herein with respect to the butorphanol dosage form of the invention, "ileo-colonic release" and "ileo-colonic delivery" are interchangeable and are interchangeable and refer to in vivo release of all, substantially all or most butorphanol from the dosage form into the portion of gastrointestinal tract distal to the jejunum and/or distal to the ileum. In some embodiments, ileo-colonic release or ileo-colonic delivery dosage forms of the invention provide in vivo release of all, substantially all or most butorphanol from the dosage form rapidly upon reaching the portion of gastrointestinal tract distal to the jejunum or distal to the ileum. In other embodiments, ileo-colonic release and ileo-colonic delivery dosage forms of the invention provide in vivo release of all, substantially all or most butorphanol from the dosage form slowly (e.g., sustained release or extended release) upon reaching the portion of gastrointestinal tract distal to the jejunum or distal to the ileum.

As used herein with respect to the butorphanol dosage form of the invention, "colonic release" and "colonic delivery" are interchangeable and refer to in vivo release of all, substantially all or most butorphanol from the dosage form into the portion of gastrointestinal tract distal to the ileum. In some embodiments, colonic release and colonic delivery dosage forms of the invention provide in vivo release of all, substantially all or most butorphanol from the dosage form rapidly upon reaching the portion of gastrointestinal tract distal to the ileum. In other embodiments, colonic release and colonic delivery dosage forms of the invention provide in vivo release of all, substantially all or most butorphanol from the dosage form slowly (e.g., sustained release or extended release) upon reaching the portion of gastrointestinal tract distal to the ileum.

Duodenal delivery, jejunal delivery, ileal delivery, ileocolonic delivery or colonic delivery dosage forms may be in the form of delayed onset, rapid release; delayed onset, pulsatile release; or delayed onset extended release dosage forms The term "optionally a controlled release material" means that the dosage may or may not be require one or more controlled release material to achieve some, most, substantially all or all of the objectives, specifications or claims of the invention.

In some preferred embodiments, the dosage form provides an oral pharmaceutical composition for the treatment of a butorphanol responsive medical condition comprising a therapeutically effective amount of butorphanol or pharmaceutically acceptable salts thereof or mixture thereof, and optionally a controlled release material, said butorphanol given alone or in combination with another drug in the same dosage form or in a different dosage form to treat the same or a different condition or to treat side effects of butorphanol or to deter abuse of the butorphanol.

In some preferred embodiments, the dosage form provides a pharmaceutical dosage form for the treatment of a butorphanol responsive medical condition comprising a therapeutically effective amount of butorphanol or pharmaceutically acceptable salts thereof or mixture thereof, said dosage form resistant or substantially resistant to dissolution and/or absorption in the stomach, and/or in the duodenum, and/or in the jejunum, and/or in the ileum, or in the small intestine, or in the stomach and duodenum, or in the stomach, duodenum and jejunum, or in the stomach, duodenum, jejunum and terminal ileum, or in the stomach and small intestine, or before it reaches the ileo-cecal junction, or until it crosses the ileo-cecal junction, or until it reaches the colon; said butorphanol in the dosage form released rapidly or slowly upon reaching a the desired anatomic region of the GI tract (e.g., ileum or colon) or upon reaching the desired gastrointestinal conditions conducive to release from the dosage form (e.g., osmotic pressure, pH, time after ingestion, microbial flora); said dosage form in some embodiments providing immediate release of butorphanol following the expected lag time; said dosage form in some other embodiments providing sustained release of butorphanol following the expected lag time.

In some embodiments, the oral butorphanol dosage form is substantially non-releasable in the stomach and small intestine, or substantially non-releasable in the stomach and duodenum, or substantially non-releasable in the stomach, duodenum and jejunum, or substantially non-releasable in the stomach, duodenum, jejunum and terminal ileum, or substantially non-releasable until it reaches the ileum, or substantially non-releasable until it reaches the colon.

In some embodiments, the oral butorphanol dosage form is substantially non-releasable until up to about 1, or 1.5, 2, or 2.25, or 2.5, or 2.75, or 3, or 3.25, or 3.5, or 3.75, or 4, or 4.25, or 4.5, or 4.75, or 5, or 5.25, or 5.5, or 5.75, or 6, or 6.25, or 6.5, or 7.75, or 7, or 7.25, or 7.5, or 7.75, or 8, or 8.25, or 8.5, or 8.75, or 9, or 9.25, or 9.5, or 9.75, or 10, or 10.25, or 10.5, or 10.75, or 11, or 11.25, or 1.5, or 11.75, or 12, or 14, or 16, or 18, or 20 hours after oral ingestion of the oral dosage form. In some particularly preferred embodiments, said dosage form is substantially non-releasable until up to about 2.5, or 2.75, or 3, or 3.25, or 3.5, or 3.75, or 4, or 4.25, or 4.5, or 4.75, or 5, or 5.25, or 5.5, or 5.75, or 6, or 6.25, or 6.5, or 7.75, or 7 hours after oral ingestion of the oral dosage form.

In some preferred embodiments, the oral butorphanol dosage form includes a coated capsule or tablet wherein the coating comprises material which dissolves at a pH ≥5, or ≥5.5, or ≥5.7, or ≥6, or 6.2, or ≥6.4, or ≥6.6, or ≥6.8, ≥7, or ≥7.2. In some other preferred embodiments, the oral butorphanol dosage form includes material incorporated in dosage form, wherein the material substantially resists dissolution for at least about 1, or 1.5, or 2, or 2.5, or 3, or 3.25, or 3.5, or 3.75, or 4, or 4.25, or 4.5, or 4.75, or 5, or 5.25, or 5.5, or 5.75, or 6, or 6.25, or 6.5, or 7.75, or 7.31 hours at a pH of about ≤5, or ≤5.5, or ≤5.7, or ≤6, or ≤6.2, or ≤6.4, or ≤6.6, or ≤6.8, ≤7, or ≤7.2.

In some embodiments, the oral butorphanol dosage form is coated with or includes incorporated one or more of the following: (i) cellulose acetate trimellitate (CAT); (ii) hydroxypropylmethyl cellulose phthalate (HPMCP); (iii) polyvinyl acetate phthalate (PVAP); (iv) shellac; (v) a copolymer of methacrylic acid and methylmethacrylate; (vi) a material which is redox-sensitive; (vii) an azopolymer or a disulphide polymer; (viii) a material which is degraded by enzymes or bacteria present in the colon; (ix) a copolymer of methacrylic acid and methylmethacrylate to which has been added during polymerization the monomer methyl acrylate; (x) a cellulose ester; (xi) polyvinyl acetate phthalate.

In some embodiments, the dosage form consists of a coated capsule wherein the coating is applied separately to empty capsule body and cap. In some embodiments, the dosage form consists of a coated capsule filled with a caplet or tablet.

In some embodiments, the oral butorphanol dosage form is non-releasing or substantially non-releasing for up to about 2, 2.5, 3, 3.5, 4, 4.5, or 5 hours following ingestion.

In some embodiments, the oral butorphanol dosage form comprises material which is non-dissolving or substantially non-dissolving at a particular pH or range of pH and is dissolving or substantially dissolving at another pH or another range of pH, said material commingled with the butorphanol API or with the granulation containing butorphanol API.

In some embodiments, the oral butorphanol dosage form comprises material which is non-dissolving or substantially non-dissolving at a particular pH or range of pH and is dissolving or substantially dissolving at another pH or another range of pH, said material commingled with the butorphanol API or with the granulation containing butorphanol API, in addition to being coated on the dosage form.

In some embodiments, the specifications regarding coating of the dosage form of the invention with controlled release material or pH sensitive material are also applicable to dosage forms where said material is commingled with the butorphanol API or with the granulation containing butorphanol API, instead of or in addition to coating the dosage form.

In some embodiments, the specifications regarding coating of the dosage form of the invention with controlled release material or pH sensitive material are also applicable to dosage forms where is the coating is applied to multiparticulate matrices or to subunits of the dosage form e.g., beads incorporating drug), instead of or in addition to coating the dosage form.

In some embodiments, the dosage form consists of a coated capsule wherein the coating is applied to capsules having a sealing on the gap between capsule body and cap.

In some embodiments, the dosage form consists of a coated capsule containing a butorphanol, wherein the capsule is coated with a material selected from the group comprising cellulose acetate trimellitate, hydroxypropylmethyl cellulose phthalate, polyvinyl acetate phthalate, shellac, and a copolymer of methacrylic acid and ethyl acrylate, azopolymers, disulphide polymers and amylose.

In some preferred embodiments, the oral butorphanol dosage form has a butorphanol Tmax that exceeds its dosing frequency.

In some preferred embodiments, the butorphanol Tmax ratio of the oral butorphanol dosage form of the invention to butorphanol given orally as a conventional solution, suspension, immediate release tablet or capsule or given intranasally is ≥1.25, or ≥1.5, or ≥1.75, or ≥2, or ≥2.5, or ≥3, or ≥3.5, or ≥4, or ≥4.5, or ≥5, or ≥5.5, or ≥6, or ≥6.5, or ≥7, or ≥7.5, or ≥8, or ≥8.5, or ≥9, or ≥9.5, or ≥10, or ≥10.5, or ≥12, or ≥14, or ≥16, or ≥18, or ≥20.

In some preferred embodiments, the hydroxybutorphanol Tmax ratio of the oral butorphanol dosage form of the invention to butorphanol given orally as a conventional solution, suspension, immediate release tablet or capsule or given intranasally is ≥1.25, or ≥1.5, or ≥1.75, or ≥2, or ≥2.5, or ≥3, or ≥3.5, or ≥4, or ≥4.5, or ≥5, or ≥5.5, or ≥6, or ≥6.5, or ≥7, or ≥7.5, or ≥8, or ≥8.5, or ≥9, or ≥9.5, or ≥10, or ≥10.5, or ≥12, or ≥14, or ≥16, or ≥18, or ≥20.

In some preferred embodiments, the butorphanol Cmax ratio after butorphanol given orally as a conventional solution, suspension, immediate release tablet or capsule, or given intranasally, to the oral butorphanol dosage form of the invention given orally is ≥1.1, or ≥1.2, or ≥1.3, or ≥1.5, or ≥1.5, or ≥1.6, or ≥1.7, or ≥1.8, or ≥1.9, or ≥2, or ≥2.2, or ≥2.5, or ≥3, or ≥3.5, or ≥4, or ≥4.5, or ≥5, or ≥5.5, or ≥6, or ≥6.5, or ≥7, or ≥7.5, or ≥8, or ≥8.5, or ≥9, or ≥9.5, or ≥10, or ≥10.5, or ≥12, or ≥14, or ≥16, or ≥18, or ≥20.

In some preferred embodiments, the hydroxybutorphanol Cmax ratio of butorphanol given orally as a conventional solution, suspension, immediate release tablet or capsule, or given intranasally, to the oral butorphanol dosage form of the invention given orally is ≥1.1, or ≥1.2, or ≥1.3, or ≥1.5, or ≥1.5, or ≥1.6, or ≥1.7, or ≥1.8, or ≥1.9, or ≥2, or ≥2.2, or ≥2.5, or ≥3, or ≥3.5, or ≥4, or ≥4.5, or ≥5, or ≥5.5, or ≥6, or ≥6.5, or ≥7, or ≥7.5, or ≥8, or ≥8.5, or ≥9, or ≥9.5, or ≥10, or ≥10.5, or ≥12, or ≥14, or ≥16, or ≥18, or ≥20.

In some preferred embodiments, the butorphanol $AUC_{0-24}$ ratio of the oral butorphanol dosage form of the invention to butorphanol given orally as a conventional solution, suspension, immediate release tablet or capsule is ≥1.1, or ≥1.2, or ≥1.3, or ≥1.5, or ≥1.5, or ≥1.6, or ≥1.7, or ≥1.8, or ≥1.9, or ≥2, or ≥2.2, or ≥2.5, or ≥3.

In some preferred embodiments, the butorphanol $AUC_{0-inf}$ ratio of the oral butorphanol dosage form of the invention to butorphanol given orally as a conventional solution, suspension, immediate release tablet or capsule is ≥1.1, or ≥1.2, or ≥1.3, or ≥1.5, or ≥1.5, or ≥1.6, or ≥1.7, or ≥1.8, or ≥1.9, or ≥2, or ≥2.2, or ≥2.5, or ≥3.

In some preferred embodiments, the hydroxybutorphanol $AUC_{0-24}$ ratio of the oral butorphanol dosage form of the invention to butorphanol given orally as a conventional solution, suspension, immediate release tablet or capsule is ≥1.1, or ≥1.2, or ≥1.3, or ≥1.5, or ≥1.5, or ≥1.6, or ≥1.7, or ≥1.8, or ≥1.9, or ≥2, or ≥2.2, or ≥2.5, or ≥3.

In some preferred embodiments, the hydroxybutorphanol $AUC_{0-inf}$ ratio of the oral butorphanol dosage form of the invention to butorphanol given orally as a conventional solution, suspension, immediate release tablet or capsule is ≥1.1, or ≥1.2, or ≥1.3, or ≥1.5, or ≥1.5, or ≥1.6, or ≥1.7, or ≥1.8, or ≥1.9, or ≥2, or ≥2.2, or ≥2.5, or ≥3.

In some preferred embodiments, the apparent oral clearance ratio of butorphanol given orally as a conventional solution, suspension, immediate release tablet or capsule, to the oral butorphanol dosage form of the invention given orally is ≥1.1, or ≥1.2, or ≥1.3, or ≥1.4, or ≥1.5.

In some embodiments, the oral modified release butorphanol dosage form releases 0%, or less than about 0.1%, or 0.5%, or 1%, or 1.5%, or 2%, or 2.5%, or 3%, or 3.5%, or 4%, or 4.5%, or 5%, or 6%, or 7%, or 8%, or 9%, or 10%, or 12%, or 14%, or 15%, or 16%, or 17%, or 18%, or 20% or 25% or 28% or 30% or 35% of butorphanol in vivo from the dosage form prior to reaching the duodenum, or jejunum, or ileum, or terminal ileum, or ileo-cecal junction, or ascending colon, or transverse colon, or descending colon, or colon In some embodiments, the oral modified release butorphanol dosage form releases 0%, or less than about 0.1%, or 0.5%, or 1%, or 1.5%, or 2%, or 2.5%, or 3%, or 3.5%, or 4%, or 4.5%, or 5%, or 6%, or 7%, or 8%, or 9%, or 10%, or 12%, or 14%, or 15%, or 16%, or 17%, or 18%, or 20% or 25% or 28% or 30% or 35% of butorphanol in vivo from the dosage form for at least about 1 hour, or at least about 1.5 hours, or at least about 2 hours, or at least about 2.5 hours, or at least about 3 hours, or at least about 3.25 hours, or at least about 3.5 hours, or at least about 3.75 hours, or at least about 4 hours, or at least about 4.25 hours, or at least about 4.5 hours, or at least about 4.75 hours, or at least about 5 hours, or at least about 5.25 hours, or at least about 5.5 hours, or at least about 5.75 hours, or at least about 6 hours, or at least about 6.25 hours, or at least about 6.5 hours, or at least about 6.75 hours, or at least about 7 hours, or at least about 7.25 hours, or at least about 7.5 hours, or at least about 7.75 hours, or at least about 8 hours, or at least about 8.25 hours, or at least about 8.5 hours, or at least about 8.75 hours, or at least about 9 hours, or at least about 9.25 hours, or at least about 9.5 hours, or at least about 9.75 hours, or at least about 10 hours, or at least about 10.25 hours, or at least about 10.5 hours, or at least about 10.75 hours, or at least about 11 hours, or at least about 11.5 hours, or at least about 12 hours after oral ingestion, said in vivo release from the dosage form measured by appearance of butorphanol in plasma, using $AUC_{0-n}/AUC_{0-inf}$ or $AUC_{0-n}/AUC_{0-\tau}$, where "n" is the time after oral ingestion. Most preferably, the time after oral ingestion is at least about 2 hours, or at least about 2.5 hours, or at least about 3 hours, or at least about 3.5 hours, or at least about 4 hours, or at least about 4.5 hours, or at least about 5 hours, or at least about 5.5 hours, or at least about 6 hours, or at least about 6.5 hours, or at least about 7 hours.

In some embodiments, the oral modified release butorphanol dosage form releases 0%, or less than about 0.1%, or 0.5%, or 1%, or 1.5%, or 2%, or 2.5%, or 3%, or 3.5%, or 4%, or 4.5%, or 5%, or 6%, or 7%, or 8%, or 9%, or 10%, or 12%, or 14%, or 15%, or 16%, or 17%, or 18%, or 20% or 25% or 28% or 30% or 35% of butorphanol in vivo from the dosage form when the average measured or expected gastrointestinal pH is less than about 3.5, or is less than about 4, or is less than about 4.5, or is less than about 5, or less than about 5.2, or less than about 5.4, or less than about 5.6, or less than about 5.8, or less than about 6, or less than about 6.2, or less than about 6.4, or less than about 6.5, or less than about 6.6, or less than about 6.7, or less than about 6.8, or less than about 6.9, or less than about 7, or less than about 7.1, or less than about 7.2, when measured up to about 1 hour, or up to about 1.5 hours, or up to about 2 hours, or up to about 2.5 hours, or up to about 2.75 hours, or up to about 3 hours, or up to about 3.25 hours, or up to about 3.5 hours, or up to about 3.75 hours, or up to about 4 hours, or up to about 4.25 hours, or up to about 4.5 hours, after oral ingestion. More preferably, the dosage form releases 0%, or less than about 0.1%, or 0.5%, or 1%, or 1.5%, or 2%, or 2.5%, or 3%, or 3.5%, or 4%, or 4.5%, or 5%, or 6%, or 7%, or 8%, or 9%, or 10%, or 12%, or 14%, or 15%, or 16%, or 17%, or 18%, or 20% or 25% or 28% or 30% or 35% of butorphanol in vivo when the measured or expected gastrointestinal pH is less than about 5, or less than about 5.5, or less than about 6, or less than about 6.5, or less than about 6.8. More preferably, said release is measured at about 2 hours, or about 2.5 hours, or about 3 hours, or 4 hours.

In some embodiments, the targeted gastrointestinal delivery of the butorphanol from the oral modified release butorphanol dosage form into the lower segments of the gastrointestinal tract can be achieved through a variety of approaches, including but limited to incorporation of material or processes to achieve one or more of the following: time-controlled, pH-controlled, pressure-controlled, enzyme-controlled and hydration-controlled. Since the gastrointestinal tract is a complex, variable and highly dynamic environment and further complicated by the volume, content and location of food and beverages, in some embodiments, incorporation of material to achieve more than one of the above approaches is preferred.

In some embodiments, the targeted gastrointestinal delivery of the butorphanol from the oral modified release butorphanol dosage form into the lower segments of the gastrointestinal tract can be achieved through encapsulation of the butorphanol, preferably with excipients or functional excipients, said capsule incorporating, coated with or overcoated with material or processes to achieve targeted gastrointestinal delivery.

In some embodiments, the oral modified release butorphanol dosage form is non-bioavailable or substantially non-bioavailable for up to about 0.5, 1, 1.5, 2, 2.5, 3, 3.5, 4, 4.5, or 5 hours after oral ingestion (e.g., the dosage form releases 0%, or less than about 0.1%, or 0.5%, or 1%, or 1.5%, or 2%, or 2.5%, or 3%, or 3.5%, or 4%, or 4.5%, or 5%, or 6%, or 7%, or 8%, or 9%, or 10%, or 12%, or 14%, or 15%, or 16%, or 17%, or 18%, or 20% or 25% or 28% or 30% or 35% of butorphanol in vivo when assessed up to the specified time). In some embodiments, the oral modified release butorphanol dosage form is coated with a material or incorporates material which renders the dosage form non-bioavailable or substantially non-bioavailable for up to about 0.5, 1, 1.5, 2, 2.5, 3, 3.5, 4, 4.5, 5, 5.5, 6, 6.5, 7, 7.5 or 8 hours; preferably at least about 1 hour, more preferably 1.5 hours, even more preferably 2 hours, and most preferably 2.5 to 4 hours.

Some or all of the above objects and others are achieved by embodiments of the present invention, which is directed in part to a dosage form of orally administered butorphanol.

In some preferred embodiments, the invention comprises an oral pharmaceutical composition for the treatment of diseases and disorders comprising a therapeutically effective amount of a butorphanol or a pharmaceutically acceptable salt thereof or a mixture thereof.

In some embodiments, the invention provides modified release oral pharmaceutical compositions of butorphanol for the treatment of diseases and disorders, said compositions in modified release form, said dosage form releasing 0%, or less than about 0.1%, or 0.5%, or 1%, or 1.5%, or 2%, or 2.5%, or 3%, or 3.5%, or 4%, or 4.5%, or 5%, or 6%, or 7%, or 8%, or 9%, or 10%, or 12%, or 14%, or 15%, or 16%, or 17%, or 18%, or 20% or 25% or 28% or 30% or 35% of butorphanol in vivo from the dosage form prior to reaching the duodenum, or jejunum, or ileum, or terminal ileum, or ileo-cecal junction, or ascending colon, or transverse colon, or descending colon, or colon.

In some embodiments, the invention provides modified release oral pharmaceutical compositions of butorphanol for the treatment of diseases and disorders, said compositions in modified release form, said dosage form releasing most, substantially all or all of the releasable butorphanol in the lower segment of the gastrointestinal tract (e.g., distal to the duodenum, or jejunum, or ileum, or terminal ileum, or ileo-cecal junction, ascending colon, or transverse colon), said release occurring over about 4, 5, 6, 7, 8, 9, 10, 12, 14, 15, 16, 17, 18, 19, 20, 21, 22, 23, 24, 25, 26, 30, 32, 36 or 40 hours.

In some embodiments, the invention provides modified release oral pharmaceutical compositions of butorphanol for the treatment of diseases and disorders, said compositions in modified release form, said dosage form releasing most, substantially all or all of the releasable butorphanol in the lower segment of the gastrointestinal tract (e.g., distal to the duodenum, or jejunum, or ileum, or terminal ileum, or ileo-cecal junction, ascending colon, or transverse colon), said release occurring over about 0.25, 0.5, 0.75, 1, 1.5, 2, 2.5, 3, 3.5 or 4 hours.

In some embodiments, the invention provides modified release oral pharmaceutical compositions of butorphanol for the treatment of diseases and disorders, said composition in modified, controlled, sustained or extended release form, said dosage form releasing 0%, or less than about 0.1%, or 0.5%, or 1%, or 1.5%, or 2%, or 2.5%, or 3%, or 3.5%, or 4%, or 4.5%, or 5%, or 6%, or 7%, or 8%, or 9%, or 10%, or 12%, or 14%, or 15%, or 16%, or 17%, or 18%, or 20% or 25% or 28% or 30% or 35% of butorphanol proximal to the duodenum, or jejunum, or ileum, or terminal ileum, or ileo-cecal junction.

In some embodiments, the invention provides modified release oral pharmaceutical compositions of butorphanol for the treatment of diseases and disorders, said composition in modified, controlled, sustained or extended release form, or for delivery distal to the duodenum, or jejunum, or ileum, or terminal ileum, or ileo-cecal junction, said dosage form containing up to about 50%, or up to about 45%, or up to about 40%, or up to about 35%, or up to about 30%, or up to about 25%, or up to about 20%, or up to about 15%, or up to about 10%, or up to about 5% of the butorphanol dose in immediate release form, said immediate release form released and/or available for absorption in the stomach, duodenum, jejunum and/or ileum, and said immediate release form released and/or available for absorption at a pH of less than about 1, or less than about 1.5, or less than about 2, or less than about 2.5, or less than about 3, or less than about 3.5, or less than about 4, or less than about 4.5, or less than about 5, or less than about 5.5, or less than about 6, or less than about 7.

It is an object of certain preferred embodiments of the present invention to provide oral extended release pharmaceutical compositions of butorphanol that have greater bioavailability (AUC) than oral immediate release formulations.

It is an object of certain preferred embodiments of the present invention to provide oral immediate release and oral extended release pharmaceutical compositions of butorphanol that provide a greater plasma AUC ratio of hydroxybutorphanol (a major metabolite of butorphanol) to butorphanol than is attained by intranasally administered dosage forms.

It is an object of certain preferred embodiments of the present invention to provide oral immediate release and oral extended release pharmaceutical compositions of butorphanol that provide a greater plasma AUC ratio of hydroxybutorphanol to butorphanol than is attained by intranasally administered dosage forms.

Some or all of the above objects and others are achieved by embodiments of the present invention, which is directed in part to a dosage form of oral butorphanol.

In certain preferred embodiments the oral dosage form of the present invention comprises a matrix which includes a sustained release material and butorphanol or a pharmaceutically acceptable salt thereof. In certain preferred embodiments, the matrix is compressed into a tablet and may be optionally overcoated with a coating that in addition to the sustained release material of the matrix may control the release of the butorphanol or pharmaceutically acceptable salt thereof from the formulation, such that blood levels of active ingredient are maintained within the therapeutic range over an extended period of time. In certain alternate embodiments, the matrix is encapsulated.

In certain preferred embodiments, the sustained release oral dosage form of the present invention comprises a plurality of pharmaceutically acceptable sustained release matrices comprising butorphanol, the dosage form maintaining the blood plasma levels of butorphanol within the therapeutic range over an extended period of time when administered to patients.

In some preferred embodiments, the dosage form of the invention comprises oral butorphanol formulated to release the butorphanol from the dosage form or to initiate the release of the butorphanol from the dosage form after a certain specific amount of time post-oral ingestion, or at an approximately specific anatomic location in the gastrointestinal tract, or when the dosage form is in contact with specific gastrointestinal conditions (e.g., pH range, osmolarity, electrolyte content, food content, pressure, time since first ingestion, osmotic pressure in the dosage form, osmotic pressure in the gastrointestinal tract, hydration, etc), said dosage form suitable for providing an orally effective therapeutic for a short, intermediate or extended duration of effect, said dosage form providing a rapid or delayed onset of clinical effect.

In certain preferred embodiments the sustained release oral dosage form of the present invention is an osmotic dosage form which comprises a single layer or bilayer core comprising butorphanol; an expandable polymer; a semipermeable membrane surrounding the core; and a passageway disposed in the semipermeable membrane for sustained release of the butorphanol or pharmaceutically acceptable salt thereof, such that blood levels of active ingredient are maintained within the therapeutic range over an extended period of time when administered to patients.

Other oral osmotic delivery systems may be used for the oral administration of butorphanol.

In some preferred embodiments of the invention, the oral butorphanol is interdispersed and are not isolated from each other in two distinct layers.

In some preferred embodiments of the invention, the oral butorphanol is in the form of multiparticulates.

In some preferred embodiments of the invention, the oral butorphanol is dispersed in a matrix In some preferred embodiments of the invention, the oral butorphanol is in the form of multiparticulates can be dispersed in a matrix or contained in a capsule.

In some preferred embodiments of the invention, the oral butorphanol is in the form of multiparticulates can be dispersed in a matrix and compressed into a tablet.

In some preferred embodiments of the invention, the oral butorphanol is in a matrix that is in the form of pellets.

In some preferred embodiments of the invention, the oral butorphanol is in coated beads.

In some preferred embodiments, the dosage form of the invention comprises a compressed tablet, compressed capsule or uncompressed capsule. In other embodiments, the dosage form comprises a liquid fill capsule.

In some preferred embodiments, the oral dosage in immediate or sustained release form provides therapeutic effects that persist despite the low or undetectable butorphanol concentrations.

In some preferred embodiments, the dosage form of the invention comprises an oral formulation (e.g., tablet or capsule) which is coated to prevent substantial direct contact of butorphanol with oral cavity (e.g. tongue, oral mucosa), oropharyngeal mucosal surface, esophagus or stomach.

In some preferred embodiments, the dosage form of the invention comprises an oral formulation which is coated with a film or polymer. In some preferred embodiments, the dosage form of the invention comprises butorphanol in an enteric coating.

In some preferred embodiments, the dosage form provides an oral pharmaceutical composition comprising a therapeutically effective amount of butorphanol; said therapeutically effective amount in a reservoir comprising: (i) butorphanol or a pharmaceutically acceptable salt of butorphanol, or a mixture thereof; (ii) a membrane layer, said membrane being substantially permeable to butorphanol; wherein the dosage form substantially releases the butorphanol from the dosage form to render said dosage form suitable for extended release to a human patient.

In some preferred embodiments, the dosage form provides an oral pharmaceutical composition comprising a plurality of pharmaceutically acceptable beads coated with a therapeutically effective amount of butorphanol or a pharmaceutically acceptable salt of butorphanol, or a mixture thereof; and overcoated with controlled release material to render said dosage form suitable for extended release oral administration to a human patient.

In some preferred embodiments, the dosage form provides an oral pharmaceutical composition comprising (i) a drug layer comprising a therapeutically effective amount of butorphanol; and (ii) a displacement layer comprising an osmopolymer; and (b) a semipermeable wall surrounding the bilayer core having a passageway disposed therein for the release of said butorphanol or a pharmaceutically acceptable salt thereof; said dosage form suitable for extended release oral administration to a human patient.

In some preferred embodiments, the oral dosage form is a controlled release material suitable for extended release in a human patient of the dosage form comprises a matrix. In some preferred embodiments, the said matrix is a plurality of multiparticulate matrices. In some preferred embodiments, the multiparticulates are compressed into a tablet. In some preferred embodiments, the multiparticulates are disposed in a pharmaceutically acceptable capsule.

In some preferred embodiments, the controlled release material of the oral dosage form of the invention is selected from the group consisting of hydrophobic polymers, hydrophilic polymers, gums, protein derived materials, waxes, shellac, oils, fats and mixtures thereof.

In some preferred embodiments, the controlled release material of the oral dosage form of the invention is selected from the group consisting of polyethylene oxide, polyvinyl alcohol, hydroxypropyl methyl cellulose, a carbomer and mixtures thereof.

In some preferred embodiments, the dosage form provides an oral pharmaceutical composition comprising a therapeutically effective amount of butorphanol or a pharmaceutically acceptable salt of butorphanol, or a mixture thereof; and material which imparts abuse deterrence, abuse resistance, tamper resistance, tamper deterrence qualities or which otherwise deters the abuse, misuse, diversion or recreational use or abuse of the drug.

In some preferred embodiments, the controlled release material of the oral dosage form of the invention is selected from the group consisting of hydrogenated Type I or Type II vegetable oils, polyoxyethylene stearates and distearates, glycerol monostearate, and non-polymeric, non-water soluble liquids carbohydrate-based substances or poorly water soluble, high melting point (mp=40 to 100° C.) waxes and mixtures thereof.

In some preferred embodiments, the oral dosage form comprises a plurality of pharmaceutically acceptable beads coated with drug and overcoated with controlled release material.

In some preferred embodiments, the oral dosage form comprises (i) a drug layer; and (ii) a displacement layer comprising an osmopolymer; and (b) a semipermeable wall surrounding the bilayer core having a passageway disposed therein for the release of said drug.

In some preferred embodiments, the oral dosage form comprises a compressed tablet, compressed capsule or uncompressed capsule. In some preferred embodiments, the oral dosage form comprises a liquid fill capsule.

In some preferred embodiments, the in vivo pharmacokinetic parameters of the specifications, embodiments and claims are derived or determined under fed conditions. In other preferred embodiments, the in vivo pharmacokinetic parameters are derived or determined under fasted conditions.

In some preferred embodiments, the present invention excludes immediate release dosage forms.

In some preferred embodiments, the present invention excludes dosage forms devoid of controlled release material to render the dosage form as modified release, delayed release, extended release or controlled release.

In some preferred embodiments, the present invention excludes dosage forms devoid of material to render the dosage form as modified release.

In some embodiments of the invention, the oral dosage form of the invention exclude oral immediate release forms of butorphanol. In some embodiments of the invention, the oral dosage form of the invention excludes oral immediate release dosage forms of butorphanol which have been modified to enhance the solubility or bioavailability of the butorphanol in the upper GI tract (e.g., by use of certain excipients or by physical manipulation of the butorphanol or granulation), using methods well know in the art, including complexation (e.g., with cyclodextrins), or particle size reduction (e.g., micronization), or lipid suspensions, solutions, emulsions, microemulsions, or mixed micelles, or self-emulsifying drug delivery systems (SEDDS), or self-microemulsifying drug delivery systems (SMEDDS), or thixotropic vehicles, or surfactants, or solid dispersions, or liposomes, or co-solvents, or solvation.

In some embodiments of the invention, the oral dosage form of the invention excludes oral dosage forms of butorphanol which have been modified to enhance the bioavailability of the butorphanol in the upper GI tract.

In some embodiments of the invention, the oral dosage forms of butorphanol are limited to controlled release butorphanol. In some embodiments of the invention, the oral dosage forms of butorphanol are limited to controlled release butorphanol which are matrix or monolithic matrix formulations. In some embodiments of the invention, the oral dosage forms of butorphanol exclude osmotic delivery dosage forms. In some embodiments of the invention, the oral dosage forms of butorphanol exclude osmotic delivery dosage forms which are push-pull osmotic pumps (PPOP). In some embodiments of the invention, the oral dosage forms of butorphanol exclude osmotic delivery dosage forms which are controlled porosity osmotic pumps. In some embodiments of the invention, the oral dosage forms of butorphanol exclude multiparticulate matrix controlled release butorphanol formulations.

In some embodiments of the invention, the oral dosage forms of butorphanol are limited to controlled release butorphanol which provide first release or first therapeutically beneficial release of butorphanol not until about 2, 2.5, 3, 3.5, 4, 4.5, 5, 5.5, 6, 6.5, 7, 7.5, or 8 hours after first oral ingestion, preferably at least about 2, 2.5, 3, 3.5, or 4 hours after first oral ingestion. In some embodiments of the invention, the oral dosage forms of butorphanol are limited to controlled release butorphanol which are overcoated with a pH sensitive material which dissolve at a pH <4, or pH <4.5, or pH, <5, or pH <5.5, or pH <6, or pH <6.5, or pH <6.8, or pH <7, or pH <7.2.

In some embodiments of the invention, the oral dosage form of the invention excludes oral controlled release dosage forms of butorphanol which have been modified to enhance the solubility or bioavailability of the butorphanol in the upper GI tract through complexation (e.g., with cyclodextrins), or particle size reduction (e.g., micronization), or lipid suspensions, solutions, emulsions, microemulsions, mixed micelles, or self-emulsifying drug delivery systems (SEDDS), or self-microemulsifying drug delivery systems (SMEDDS), or thixotropic vehicles, or surfactants, or solid dispersions, or liposomes, or co-solvents, or solvation. In some embodiments of the invention, the oral dosage forms of butorphanol are limited to modified release butorphanol which provides an onset of therapeutic effect not before about 1, 1.5, 2, 2.5 3, 3.5, 4, 4.5, 5, 5.5 or 6 hours following first ingestion.

In some embodiments of the invention, the oral dosage forms of butorphanol are limited to modified release butorphanol which provides quantifiable or therapeutic or substantial plasma concentrations not before about 1, 1.5, 2, 2.5 3, 3.5, 4, 4.5, 5, 5.5 or 6 hours following first ingestion. In some embodiments of the invention, the oral dosage forms of butorphanol are limited to modified release butorphanol which provide quantifiable, or substantial plasma concentrations or therapeutic plasma concentrations not before about 1, 1.5, 2, 2.5 3, 3.5, 4, 4.5, 5, 5.5 or 6 hours following first ingestion. In some embodiments of the invention, the oral dosage forms of butorphanol are limited to modified release butorphanol which are osmotic delivery dosage forms (e.g., push pull osmotic pumps, monolithic osmotic delivery systems and controlled porosity osmotic pumps).

In some embodiments of the invention, the oral dosage forms of butorphanol are limited to modified release butorphanol which are osmotic delivery dosage forms, overcoated with a pH sensitive material which dissolve at a pH <4, or pH <4.5, or pH, <5, or pH <5.5, or pH <6, or pH <6.5, or pH <6.8, or pH <7, or pH <7.2. In some embodiments of the invention, the oral dosage forms of butorphanol are limited to modified release butorphanol which provide release of all, substantially all, or most of the butorphanol only at pH >4, or pH >4.5, or pH, >5, or pH >5.5, or pH >6, or pH >6.5, or pH >7, or pH >7.5, or pH >7.8 upon dissolution using the USP Paddle Method for 2 hours at 37° C. at 100 rpm in 900 mL distilled water adjusted for pH.

In some embodiments of the invention, the oral dosage forms of butorphanol are limited to modified release butorphanol which provide release of all, substantially all, or most of the butorphanol distal to the stomach, distal to the duodenum, distal to the jejunum, distal to the ileum, or distal to the ileo-cecal junction. In some embodiments of the invention, the oral dosage forms of butorphanol are limited to modified release butorphanol which provide release of all, substantially all, or most of the butorphanol at least about 1, 1.5, 2, 2.5, 3, 3.5, 4, 4.5, 5, 5.5, 6, 6.5, 7, 7.5, or 8 hours after first oral ingestion, preferably at least about 2, 2.5, 3, 3.5, or 4 hours after first oral ingestion. In some embodiments of the invention, the oral dosage forms of butorphanol are limited to modified release butorphanol which begin the release of all, substantially all, most, or some of the butorphanol at least about 1, 1.5, 2, 2.5, 3, 3.5, 4, 4.5, 5, 5.5, 6, 6.5, 7, 7.5, or 8 hours after first oral ingestion, preferably at least about 2, 2.5, 3, 3.5, or 4 hours after first oral ingestion.

In some embodiments of the invention, the oral dosage forms of butorphanol are limited to modified release butorphanol which provide the intended therapeutic effect not until about 1, 1.5, 2, 2.5, 3, 3.5, 4, 4.5, 5, 5.5, 6, 6.5, 7, 7.5, or 8 hours after first oral ingestion, preferably at least about 2, 2.5, 3, 3.5, or 4 hours after first oral ingestion. In some embodiments of the invention, the oral dosage forms of butorphanol are limited to modified release butorphanol which provide all, substantially all, most, or some of the intended therapeutic effect not until about 1, 1.5, 2, 2.5, 3, 3.5, 4, 4.5, 5, 5.5, 6, 6.5, 7, 7.5, or 8 hours after first oral ingestion, preferably at least about 2, 2.5, 3, 3.5, or 4 hours after first oral ingestion. In some embodiments of the invention, the oral dosage forms of butorphanol are limited to modified release butorphanol which begin to provide all, substantially all, most, or some of the intended therapeutic effect not until about 1, 1.5, 2, 2.5, 3, 3.5, 4, 4.5, 5, 5.5, 6, 6.5, 7, 7.5, or 8 hours after first oral ingestion, preferably at least about 2, 2.5, 3, 3.5, or 4 hours after first oral ingestion.

In some embodiments of the invention, the oral dosage forms of butorphanol are limited to modified release butorphanol which provide a psychic effect in recreational drug or opioid users and drug or opioid abusers not until about 1, 1.5, 2, 2.5, 3, 3.5, 4, 4.5, 5, 5.5, 6, 6.5, 7, 7.5, or 8 hours after first oral ingestion, preferably at least about 2, 2.5, 3, 3.5, or 4 hours after first oral ingestion. In some embodiments of the invention, the oral dosage forms of butorphanol are limited to modified release butorphanol provide a psychic effect in recreational drug or opioid users and drug or opioid abusers not until about 1, 1.5, 2, 2.5, 3, 3.5, 4, 4.5, 5, 5.5, 6, 6.5, 7, 7.5, or 8 hours after first oral ingestion, preferably at least about 2, 2.5, 3, 3.5, or 4 hours after first oral ingestion. In some embodiments of the invention, the oral dosage forms of butorphanol are limited to modified release butorphanol which begin to provide a psychic effect in recreational drug or opioid users and drug or opioid abusers not until about 1, 1.5, 2, 2.5, 3, 3.5, 4, 4.5, 5, 5.5, 6, 6.5, 7, 7.5, or 8 hours after first oral ingestion, preferably at least about 2, 2.5, 3, 3.5, or 4 hours after first oral ingestion.

In some embodiments of the invention, the oral dosage forms of butorphanol are limited to modified release butorphanol which result in little or no nausea, or little or no sedation until about 1, 1.5, 2, 2.5, 3, 3.5, 4, 4.5, 5, 5.5, 6, 6.5, 7, 7.5, or 8 hours after first oral ingestion, preferably at least about 2, 2.5, 3, 3.5, or 4 hours after first oral ingestion. In some embodiments of the invention, the oral dosage forms of butorphanol are limited to modified release butorphanol which result in little or no nausea, or little or no sedation until about 1, 1.5, 2, 2.5, 3, 3.5, 4, 4.5, 5, 5.5, 6, 6.5, 7, 7.5, or 8 hours after first oral ingestion, preferably at least about 2, 2.5, 3, 3.5, or 4 hours after first oral ingestion. In some embodiments of the invention, the oral dosage forms of butorphanol are limited to modified release butorphanol which result in little or no nausea, or little or no sedation until about 1, 1.5, 2, 2.5, 3, 3.5, 4, 4.5, 5, 5.5, 6, 6.5, 7, 7.5, or 8 hours after first oral ingestion, preferably at least about 2, 2.5, 3, 3.5, or 4 hours after first oral ingestion.

In some embodiments of the invention, the oral dosage forms of butorphanol are limited to modified release butorphanol which provide all, substantially all, most, or some of the release of butorphanol from the dosage form distal to the stomach, or distal to the duodenum, or distal to the jejunum, or distal to the ileum, or distal to the ileo-cecal junction, or in the colon.

In some embodiments of the invention, the oral dosage forms of butorphanol are limited to butorphanol without an additional therapeutic agent (e.g., acetaminophen, COX-2 inhibitor, NSAID, methadone) incorporated in the dosage form or given concurrently with the dosage form of the invention. In some embodiments of the invention, the oral dosage forms of butorphanol are limited to butorphanol without an additional therapeutic agent to treat the same medical condition or to enhance the effect of the butorphanol which is incorporated in the dosage form or given concurrently with the dosage form of the invention.

In some embodiments, the invention excludes oral butorphanol pharmaceutical compositions which provide a more rapid onset of action of butorphanol compared with intranasal butorphanol, orally ingested butorphanol active pharmaceutical ingredient (API), oral immediate release butorphanol.

In some embodiments, the invention excludes oral butorphanol pharmaceutical compositions for the treatment of acute pain. In some embodiments, the invention excludes oral butorphanol pharmaceutical compositions for the treatment of addiction disorders. In some embodiments, the invention is limited to oral butorphanol pharmaceutical compositions for the treatment of chronic pain.

In some embodiments of the invention, the invention excludes oral butorphanol pharmaceutical compositions which provide more rapid (or "improved") dissolution of the butorphanol when oral immediate release butorphanol made using conventional excipients. In some embodiments, the invention excludes oral butorphanol pharmaceutical compositions which provide greater than 65%, or greater than 75%, or greater than 85% release of butorphanol form the dosage form when measured by USP Paddle Method at 50 or 100 rpm in 900 mL of 0.1 N HCl buffer (at any pH between 1.6 and 3) at 37° C. after 45 minutes. In some embodiments, the invention excludes oral butorphanol pharmaceutical compositions which provide greater than about 50%, or about 60% or about 70% or about 80% release of butorphanol form the dosage form when measured by USP Paddle Method at 50 or 100 rpm in 900 mL of pH 6.8 buffer at 37° C. after 60 minutes.

Some or all of the objects and others are achieved by embodiments of the present invention, which is directed in part to a dosage form of oral butorphanol in modified release dosage form.

In some preferred embodiments, the dosage form provides an oral pharmaceutical composition comprising a therapeutically effective amount of butorphanol or a pharmaceutically acceptable salt of butorphanol or a mixture thereof; said dosage form intended solely for the treatment of pain.

In some preferred embodiments, the dosage form provides an oral pharmaceutical composition comprising a therapeutically effective amount of butorphanol or a pharmaceutically acceptable salt of butorphanol or a mixture thereof; said dosage form intended solely for the treatment of chronic pain.

In some preferred embodiments, the dosage form provides an oral pharmaceutical composition comprising a therapeutically effective amount of butorphanol or a pharmaceutically acceptable salt of butorphanol or a mixture thereof; said dosage form intended solely for the treatment of neuropathic pain.

In some preferred embodiments, the dosage form provides an oral pharmaceutical composition comprising a therapeutically effective amount of butorphanol or a pharmaceutically acceptable salt of butorphanol or a mixture thereof; said dosage form intended solely for the treatment of cancer pain.

In some preferred embodiments, the dosage form provides an oral pharmaceutical composition comprising a therapeutically effective amount of butorphanol or a pharmaceutically acceptable salt of butorphanol or a mixture thereof; said dosage form intended solely for the treatment of pain, excluding acute pain.

In some preferred embodiments, the dosage form provides an oral pharmaceutical composition comprising a therapeutically effective amount of butorphanol or a pharmaceutically acceptable salt of butorphanol or a mixture thereof; said dosage form intended solely for the treatment of pain, excluding acute postsurgical pain.

In some preferred embodiments, the dosage form provides an oral pharmaceutical composition comprising a therapeutically effective amount of butorphanol or a pharmaceutically acceptable salt of butorphanol or a mixture thereof; said dosage form intended solely for the treatment of pain which is unresponsive to other oral formulations of opioid analgesics, particularly full or pure mu opioid agonists.

In some preferred embodiments, the dosage form provides an oral pharmaceutical composition comprising a therapeutically effective amount of butorphanol or a pharmaceutically acceptable salt of butorphanol or a mixture thereof; said dosage form intended solely for the treatment of pain which is unresponsive to other oral formulations of pure or full mu-opioid receptor agonists.

In some preferred embodiments, the dosage form provides an oral pharmaceutical composition comprising a therapeutically effective amount of butorphanol or a pharmaceutically acceptable salt of butorphanol or a mixture thereof; said dosage form intended for the treatment of pain which is unresponsive to intranasal butorphanol.

In some preferred embodiments, the dosage form provides an oral pharmaceutical composition comprising a therapeutically effective amount of butorphanol or a pharmaceutically acceptable salt of butorphanol or a mixture thereof; said dosage form intended solely for the treatment of pain in patients with an addiction disorder or at significant risk of an addiction disorder.

In some preferred embodiments, the dosage form provides an oral pharmaceutical composition comprising a therapeutically effective amount of butorphanol or a pharmaceutically acceptable salt of butorphanol or a mixture thereof; said dosage form intended solely for the treatment of addiction disorders.

In some preferred embodiments, the dosage form provides an oral pharmaceutical composition comprising a therapeutically effective amount of butorphanol or a pharmaceutically acceptable salt of butorphanol or a mixture thereof; said dosage form intended solely for the treatment of opioid addiction disorders.

In some preferred embodiments, the dosage form provides an oral pharmaceutical composition comprising a therapeutically effective amount of butorphanol or a pharmaceutically acceptable salt of butorphanol or a mixture thereof; said dosage form intended solely for the treatment of addiction disorders unresponsive to methadone.

In some preferred embodiments, the dosage form provides an oral pharmaceutical composition comprising a therapeutically effective amount of butorphanol or a pharmaceutically acceptable salt of butorphanol or a mixture thereof; said dosage form intended solely for treatment unresponsive to intranasal butorphanol.

In some preferred embodiments, the dosage form provides an oral extended release pharmaceutical composition comprising a therapeutically effective amount of butorphanol or a pharmaceutically acceptable salt of butorphanol or a mixture thereof; said dosage form intended solely for treatment unresponsive to oral immediate release butorphanol.

In some preferred embodiments, the dosage form provides an oral pharmaceutical composition comprising a therapeutically effective amount of butorphanol or a pharmaceutically acceptable salt of butorphanol or a mixture thereof; said dosage form intended solely for the treatment of pruritus, or cough, or fibromyalgia, or restless leg syndrome or urinary incontinence, or a condition other than pain.

The invention is also directed to kits of the dosage forms, including kits for titration disclosed herein.

In another aspect, the invention relates to a method for prevention or treatment of pain, cough, dyspnea, opioid addiction disorders, restless leg syndrome, acute herpes zoster, visceral pain, breakthrough pain, opioid dependence and urinary incontinence, comprising oral administration of a dosage form containing butorphanol or a pharmaceutically acceptable salt of butorphanol or a mixture thereof.

In another aspect, the invention relates to a method for prevention or treatment of butorphanol responsive or opioid responsive medical conditions, comprising oral administration of a dosage form containing butorphanol or a pharmaceutically acceptable salt of butorphanol or a mixture thereof.

In some preferred embodiments, the dosage form provides an oral pharmaceutical composition comprising a therapeutically effective amount of butorphanol; an oral controlled release material to render said dosage form suitable for extended release, or delayed onset, extended release or delayed onset, rapid release or delayed onset, pulsatile release in a human patient; said dosage form administered at a prespecified dosing regimen; said dosing regimen associated with reduced side effects, improved tolerability, improved efficiency of therapeutic response, reduced breakthrough symptoms (e.g., breakthrough pain) and reduced treatment discontinuation due to side effects.

In some preferred embodiments, the dosage form provides an oral pharmaceutical composition comprising a therapeutically effective amount of butorphanol; optionally, an oral controlled release material to render said dosage form suitable for extended release, or delayed onset, extended release or delayed onset, rapid release or delayed onset, pulsatile release in a human patient; said dosage form administered at a prespecified dosing regimen; said dosing regimen associated with reduced side effects, improved tolerability, improved efficiency of therapeutic response, reduced breakthrough symptoms (e.g., breakthrough pain) and reduced treatment discontinuation due to side effects.

In some preferred embodiments, the dosage form provides an oral pharmaceutical composition comprising a therapeutically effective amount of butorphanol; said dosage form suitable oral immediate release in a human patient; said dosage form administered at a prespecified dosing regimen; said dosing regimen associated with reduced side effects, improved tolerability, improved efficiency of therapeutic response, reduced breakthrough symptoms (e.g., breakthrough pain) and reduced treatment discontinuation due to side effects.

In some preferred embodiments, the dosage form provides an oral pharmaceutical composition comprising a therapeutically effective amount of butorphanol; optionally; said dosage form intended to treat pediatric patients; said dosage form administered at a prespecified dosing regimen; said dosing regimen as provided herein, except that the dose or total daily dose (as applicable) is multiplied by the ratio obtained from the child's weight in kilograms divided by 70 kilograms.

As used herein, "plasma $T_{lag}$" refers to a time period from first administration (or first dosing) of butorphanol to the occurrence of first of two consecutive plasma butorphanol concentrations of not less than 0.75 ng/mL per mg of administered butorphanol base, provided that the second consecutive butorphanol plasma concentration is obtained not less than 10 minutes and not more than 20 minutes after the first plasma butorphanol concentration.

In some embodiments, the plasma $T_{lag}$ of the oral butorphanol dosage form is more than about 0.25, 0.5, 0.75, 1, 1.25, 1.5, 1.75, 2, 2.25, 2.5, 2.75, 3, 3.5, 4, 4.5, or 5 hours. Preferably, the $T_{lag}$ is at least 1 hour, more preferably, at least 1.5 hours and most preferably at least 2 to 4 hours.

As used herein, "$T_{lag(x)}$" refers to the time from the start of dissolution testing to the first attainment of an in-vitro release of about 5% by weight of the active drug from the dosage form rate when measured by the USP Basket or Paddle Method at 100 rpm in 900 mL of dissolution media at 37° C., where "$_{(x)}$" is the pH of the dissolution media.

In some embodiments, the $T_{lag(5.0)}$, $T_{lag(5.5)}$, $T_{lag(6.8)}$ $T_{lag(7.0)}$, and $T_{lag(7.2)}$ of the oral butorphanol dosage form is more than about 0.25, 0.5, 0.75, 1, 1.25, 1.5, 1.75, 2, 2.25, 2.5, 2.75, 3, 3.5, 4 or 5 hours, preferably more than about 2, 2.25, 2.5, 2.75, or 3 hours.

In some embodiments, where the oral dosage form of the invention incorporates controlled release material, the $T_{lag(5.0)}$, $T_{lag(5.5)}$, $T_{lag(6.8)}$ $T_{lag(7.0)}$, and $T_{lag(7.2)}$ of the oral butorphanol dosage form is more than about 0.25, 0.5, 0.75, 1, 1.25, 1.5, 1.75, 2, 2.25, 2.5, 2.75, 3, 3.5, or 4 hours, preferably more than about 2, 2.25, 2.5, 2.75, or 3 hours.

In some embodiments, where the oral dosage form of the invention incorporates controlled release material, the $T_{lag(7.2)}$ of the oral butorphanol dosage form is more than about 0.25, 0.5, 0.75, 1, 1.25, 1.5, 1.75, 2, 2.25, 2.5, 2.75, 3, 3.5, or 4 hours, preferably more than about 2, 2.25, 2.5, 2.75, or 3 hours.

In some preferred embodiments, the dosage form provides an oral pharmaceutical composition comprising a therapeutically effective amount of butorphanol and controlled release material to render said dosage form suitable for delayed onset, rapid release or delayed onset, pulsatile release, said dosage form releasing or delivering butorphanol at a rate of about 0.05 mg/hr, or 0.1 mg/hr, or 0.2 mg/hr, or 0.3 mg/hr, or 0.4 mg/hr, or 0.5 mg/hr, or 0.6 mg/hr, or 0.7 mg/hr, or 0.8 mg/hr, or 0.9 mg/hr, or 1 mg/hr, or 1.1 mg/hr, or 1.2 mg/hr, or 1.3 mg/hr, or 1.4 mg/hr, or 1.5 mg/hr, or 1.6 mg/hr, or 1.7 mg/hr, or 1.8 mg/hr, or 2 mg/hr, or 2.2 mg/hr, or 2.3 mg/hr, or 2.4 mg/hr, or 2.5 mg/hr, or 2.6 mg/hr, or 2.7 mg/hr, or 2.8 mg/hr, or 2.9 mg/hr, or 3 mg/hr, or 3.4 mg/hr, or 3.5 mg/hr, or 3.6 mg/hr, or 3.7 mg/hr, or 3.8 mg/hr, or 3.9 mg/hr, or 4 mg/hr, or 4.2 mg/hr, or 4.4 mg/hr, or 4.6 mg/hr, or 4.8 mg/hr, or 5 mg/hr, or 5.5 mg/hr, or 6 mg/hr, or 6.5 mg/hr, or 7 mg/hr, or 7.5 mg/hr, or 8 mg/hr, or 8.5 mg/hr, or 9 mg/hr, or 9.5 mg/hr, or 10 mg/hr, or 11 mg/hr, or 12 mg/hr, or 14 mg/hr, or 16 mg/hr, or 18 mg/hr, or 20 mg/hr, or 25 mg/hr, or 30 mg/hr, or 35 mg/hr, or 40 mg/hr, or 50 mg/hr.

In some preferred embodiments, the dosage form provides an oral pharmaceutical composition comprising a therapeutically effective amount of butorphanol and controlled release material to render said dosage form suitable for controlled release or delayed onset, extended release, said dosage form releasing or delivering butorphanol at a controlled rate of release of about 0.1 mg/hr, or 0.2 mg/hr, or 0.3 mg/hr, or 0.4 mg/hr, or 0.5 mg/hr, or 0.6 mg/hr, or 0.7 mg/hr, or 0.8 mg/hr, or 0.9 mg/hr, or 1 mg/hr, or 1.1 mg/hr, or 1.2 mg/hr, or 1.3 mg/hr, or 1.4 mg/hr, or 1.5 mg/hr, or 1.6 mg/hr, or 1.7 mg/hr, or 1.8 mg/hr, or 2 mg/hr, or 2.2 mg/hr, or 2.3 mg/hr, or 2.4 mg/hr, or 2.5 mg/hr, or 2.6 mg/hr, or 2.7 mg/hr, or 2.8 mg/hr, or 2.9 mg/hr, or 3 mg/hr, or 3.4 mg/hr, or 3.5 mg/hr, or 3.6 mg/hr, or 3.7 mg/hr, or 3.8 mg/hr, or 3.9 mg/hr, or 4 mg/hr, or 4.2 mg/hr, or 4.4 mg/hr, or 4.6 mg/hr, or 4.8 mg/hr, or 5 mg/hr, or 6 mg/hr, or 7 mg/hr, or 8 mg/hr, or 9 mg/hr, or 10 mg/hr, more preferably at a rate of about 0.2 mg/hr, or 0.3 mg/hr, or 0.4 mg/hr, or 0.5 mg/hr, or 0.6 mg/hr, or 0.7 mg/hr, or 0.8 mg/hr, or 0.9 mg/hr, or 1 mg/hr, or 1.1 mg/hr, or 1.2 mg/hr, or 1.3 mg/hr, or 1.4 mg/hr, or 1.5 mg/hr, or 1.6 mg/hr, or 1.7 mg/hr, or 1.8 mg/hr, or 2 mg/hr, or 2.2 mg/hr, or 2.3 mg/hr, or 2.4 mg/hr, or 2.5 mg/hr, or 2.6 mg/hr, or 2.7 mg/hr, or 2.8 mg/hr, or 2.9 mg/hr, or 3 mg/hr, or 3.4 mg/hr, or 3.5 mg/hr, or 3.6 mg/hr, or 3.7 mg/hr, or 3.8 mg/hr, or 3.9 mg/hr, or 4 mg/hr, or 4.2 mg/hr, or 4.4 mg/hr, or 4.6 mg/hr, or 4.8 mg/hr, or 5 mg/hr, or 5.5 mg/hr, or 6 mg/hr, or 6.5 mg/hr, or 7 mg/hr, or 7.5 mg/hr, or 8 mg/hr.

In some preferred embodiments where the oral butorphanol dosage form incorporates a controlled release material to render said dosage form suitable for controlled release or delayed onset, extended release in a human patient, said dosage form releases or delivers butorphanol at a controlled rate of release of 0.2 mg/hr to 8 mg/hr, more preferably 0.4 mg/hr to 6 mg/hr, or 0.4 mg/hr to 4 mg/hr.

In some preferred embodiments, the dosage form provides an oral pharmaceutical composition comprising a therapeutically effective amount of butorphanol, said dosage form a modified release form, said dosage form releasing or delivering butorphanol at a controlled rate of release of about 0.1 mg/hr to about 8 mg/hr, or about 0.2 mg/hr to about 8 mg/hr, or about 0.3 mg/hr to about 8 mg/hr, or about 0.4 mg/hr to about 8 mg/hr, or 0.5 mg/hr to about 8 mg/hr, or 0.6 mg/hr to about 8 mg/hr, or about 0.7 mg/hr to about 8 mg/hr, or about 0.8 mg/hr to about 8 mg/hr, or about 0.9 mg/hr to about 8 mg/hr, or about 1 mg/hr to about 8 mg/hr, or about 0.4 mg/hr to about 7 mg/hr, or about 0.4 mg/hr to about 6 mg/hr, or 0.4 mg/hr to about 5 mg/hr, or 0.4 mg/hr to about 3 mg/hr, or about 0.4 mg/hr to about 3 mg/hr, or about 0.2 mg/hr to about 5 mg/hr.

In some preferred embodiments, the dosage form provides an oral pharmaceutical composition comprising a therapeutically effective amount of butorphanol and controlled release material to render said dosage form suitable for controlled release or delayed onset, extended release in a human patient, said dosage form releasing or delivering butorphanol at a controlled rate of release of about 0.1 mg/hr to about 4 mg/hr, or about 0.2 mg/hr to about 4 mg/hr, or about 0.3 mg/hr to about 4 mg/hr, or about 0.4 mg/hr to about 4 mg/hr, or 0.5 mg/hr to about 4 mg/hr, or 0.6 mg/hr to about 4 mg/hr, or about 0.7 mg/hr to about 4 mg/hr, or about 0.8 mg/hr to about 4 mg/hr, or about 0.9 mg/hr to about 4 mg/hr, or about 1 mg/hr to about 4 mg/hr, or about 1.2 mg/hr to about 4 mg/hr, or about 1.4 mg/hr to about 4 mg/hr, or 1.5 mg/hr to about 4 mg/hr, or 1.6 mg/hr to about 4 mg/hr, or about 1.8 mg/hr to about 4 mg/hr, or about 2 mg/hr to about 4 mg/hr.

In some preferred embodiments, the dosage form provides an oral pharmaceutical composition comprising a therapeutically effective amount of butorphanol and controlled release material to render said dosage form suitable for controlled release or delayed onset, extended release in a human patient, said dosage form releasing or delivering butorphanol at a controlled rate of release of about 0.1 mg/hr to about 3 mg/hr, or about 0.2 mg/hr to about 3 mg/hr, or about 0.3 mg/hr to about 3 mg/hr, or about 0.4 mg/hr to about 3 mg/hr, or 0.5 mg/hr to about 3 mg/hr, or 0.6 mg/hr to about 3 mg/hr, or about 0.7 mg/hr to about 3 mg/hr, or about 0.8 mg/hr to about 3 mg/hr, or about 0.9 mg/hr to about 3 mg/hr, or about 1 mg/hr to about 3 mg/hr, or about 1.2 mg/hr to about 3 mg/hr, or about 1.4 mg/hr to about 3 mg/hr, or 1.5 mg/hr to about 3 mg/hr, or 1.6 mg/hr to about 3 mg/hr, or about 1.8 mg/hr to about 3 mg/hr, or about 2 mg/hr to about 3 mg/hr.

In some preferred embodiments where the oral butorphanol dosage form incorporates a controlled release material to render it controlled release or delayed onset suitable for dosing every 6 hours, said dosage form releases or delivers butorphanol at a controlled rate of release for a period of about 2, 3, 4, 5, 6, 7, 8, 9, or 10 hours.

In some preferred embodiments where the oral butorphanol dosage form incorporates a controlled release material to render it controlled release or delayed onset suitable for dosing every 8 hours, said dosage form releases or delivers butorphanol at a controlled rate of release for a period of about 4, 5, 6, 7, 8, 9, 10 or 12 hours.

In some preferred embodiments where the oral butorphanol dosage form incorporates a controlled release material to render it controlled release or delayed onset suitable for dosing every 12 hours, said dosage form releases or delivers butorphanol at a controlled rate of release for a period of about 7, 8, 9, 10, 11, 12, 14, 16 or 18 hours.

In some preferred embodiments where the oral butorphanol dosage form incorporates a controlled release material to render it controlled release or delayed onset suitable for dosing every 24 hours, said dosage form releases or delivers butorphanol at a controlled rate of release for a period of about 12, 14, 16, 18, 20, 22, 24, 26 or 30 hours.

In some preferred embodiments where the oral butorphanol dosage form incorporates a controlled release material to render it delayed onset (e.g., release or delivery of drug distal to the stomach, duodenum, or ileum) and where said delayed onset dosage form is intended to provide rapid release or burst release upon reaching the target GI anatomic location or GI environment, or at a desired time after oral ingestion (e.g., 2 to 6 hours), the dosage form releases or delivers butorphanol in less than about 15, 30, 60, 90, 120, 160, 180 or 240 minutes, preferably in less than about 15, 30, 60, 90, or 120 minutes.

As used herein, "controlled rate of release" refers to the release or delivery of the active drug from the oral dosage form of the invention at rate per unit time over an extended period of time, or any time period over thirty-minutes up to thirty hours.

In some more preferred embodiments, the dosage form provides an oral pharmaceutical composition comprising a therapeutically effective amount of butorphanol; an oral controlled release material to render said dosage form extended release and suitable for duodenal, jejunal or ileal delivery or release; said dosage form administered at a prespecified dosing regimen; said regimen comprising administering a dose of about 5 mg to about 10 mg for about 1 to about 16 days, then about 15 mg to about 80 mg for at least 1 day and optionally thereafter; or a dose of about 10 mg to about 20 mg for about 1 to about 16 days, then about 21 mg to about 80 mg for at least 1 day and optionally thereafter. In some embodiments, the foregoing doses and dose ranges of said prespecified dosing regimens are the total daily dose (e.g., "about 5 mg to about 10 mg for about 3 to about 10 days" is a total daily dose of about 5 mg to about 10 mg taken for about 3 to about 10 days). In some other embodiments, the foregoing doses and dose ranges of said prespecified dosing regimens are the doses (or unit doses) at individual drug administration times (e.g., "about 5 mg to about 10 mg for about 1 to about 16 days" is about 5 mg to about 10 mg at each dosing time [e.g., Q8H, or Q12H or Q24H], taken for about 1 to about 16 days). In other embodiments, the foregoing doses and dose ranges of said prespecified dosing regimens are the daily dose (e.g., "about 5 mg to about 10 mg for about 1 to about 16 days" is about 5 mg to about 10 mg total daily dose, taken for about 1 to about 16 days).

In some preferred embodiments, the dosage form provides an oral pharmaceutical composition comprising a therapeutically effective amount of butorphanol; optionally; said dosage form intended to treat pediatric patients; said dosage form administered at a prespecified dosing regimen; said dosing regimen providing a mean butorphanol area under the plasma concentration time curve (AUC) as provided herein, except that the AUC is multiplied by the ratio obtained from the child's weight in kilograms divided by 70 kilograms.

In some more preferred embodiments, the dosage form provides an oral pharmaceutical composition comprising a therapeutically effective amount of butorphanol; an oral controlled release material to render said dosage form extended release and suitable for duodenal, jejunal or ileal delivery or release; said regimen comprising administering a dose which provides a mean butorphanol area under the plasma concentration time curve to 24 hours post-dose ($AUC_{0-24}$) of about 1 ng·hr/mL to about 27 ng·hr/mL for about for about 1 to about 16 days, then about then about 3 ng·hr/mL to about 214 ng·hr/mL for at least 1 day and optionally thereafter; or a dose of about then about 2 ng·hr/mL to about 4 ng·hr/mL for about 1 to about 16 days, then about then about 2.1 ng·hr/mL to about 214 ng·hr/mL for at least 1 day and optionally thereafter. In some embodiments, the foregoing mean butorphanol area under the plasma concentration time curve is calculated from time of administration to infinity ($AUC_{0-inf}$). In other embodiments, the foregoing mean butorphanol area under the plasma concentration time curve is calculated from time of administration to 24 hours ($AUC_{0-24}$).

In some more preferred embodiments, the dosage form provides an oral pharmaceutical composition comprising a therapeutically effective amount of butorphanol; an oral controlled release material to render said dosage form extended release and suitable for duodenal, jejunal or ileal delivery or release; said regimen comprising administering a total daily dose which provides a mean butorphanol area under the plasma concentration time curve to 24 hours post-dose ($AUC_{0-24}$) of about 1 ng·hr/mL to about 27 ng·hr/mL for about for about 1 to about 16 days, then about then about 3 ng·hr/mL to about 214 ng·hr/mL for at least 1 day and optionally thereafter; or a dose of about then about 2 ng·hr/mL to about 4 ng·hr/mL for about 1 to about 16 days, then about then about 2.1 ng·hr/mL to about 214 ng·hr/mL for at least 1 day and optionally thereafter. In some embodiments, the foregoing mean butorphanol area under the plasma concentration time curve is calculated from time of administration to infinity ($AUC_{0-inf}$). In other embodiments, the foregoing mean butorphanol area under the plasma concentration time curve is calculated from time of administration to 24 hours ($AUC_{0-24}$).

In some more preferred embodiments, the dosage form provides an oral pharmaceutical composition comprising a therapeutically effective amount of butorphanol; an oral controlled release material to render said dosage form extended release and suitable for duodenal, jejunal or ileal delivery or release; said regimen comprising administering a dose which provides a mean peak plasma concentration of about 0.1 ng/mL to about 0.2 ng·hr/mL for about for about 1 to about 16 days, then about then about 0.3 ng·hr/mL to about 8 ng·hr/mL for at least 1 clay and optionally thereafter; or a close of about then about 0.2 ng·hr/mL to about 0.44 ng·hr/mL for about 1 to about 16 days, then about then about 0.21 ng·hr/mL to about 8 ng·hr/mL for at least 1 day and optionally thereafter.

In a preferred embodiment, the dosage form containing butorphanol or a pharmaceutically acceptable salt of butorphanol or a mixture thereof is an extended release form. Oral, extended release butorphanol has several distinct advantages over oral immediate release opioids and over intranasal opioids, including fewer interruptions in sleep, reduced dependence on caregivers, improved compliance, enhanced quality of life outcomes, and increased control over the management of their malady (e.g., pain). In addition, such formulations can provide more constant plasma concentrations and clinical effects, less frequent peak to trough fluctuations and fewer side effects.

In some preferred embodiments, the dosage form provides an oral pharmaceutical composition comprising a therapeutically effective amount of butorphanol or a pharmaceutically acceptable salt of butorphanol or a mixture thereof; optionally, a controlled release material to render said dosage form suitable for up to every 24 hour (once-a-day) administration to a human patient; said dosage form providing at least 10% of the steady state concentration of butorphanol after administration of one dose at its intended dosing frequency. In other preferred embodiments, the dosage form provides at least about 15%, or at least about 20%, or at least about 30%, or at least about 40%, or at least about 50%, or at least about 60%, or at least about 70%, or at least about 75%, or at least about 80%, or at least about 85%, or at least about 90% of the steady state therapeutic concentration of butorphanol after administration of one dose or two doses at their intended dosing frequency.

In some preferred embodiments, the invention provides a method of providing relief in a human patient suffering from pain comprising a therapeutically effective amount of oral butorphanol or a pharmaceutically acceptable salt of butorphanol or a mixture thereof.

In some preferred embodiments, the invention provides a method of providing relief in a human patient suffering from cough, dyspnea, opioid addiction disorders, restless leg syndrome, fibromyalgia, diarrhea, irritable bowel syndrome, pruritus, acute herpes zoster, visceral pain, breakthrough pain, opioid dependence and urinary incontinence comprising a therapeutically effective amount of oral butorphanol or a pharmaceutically acceptable salt of butorphanol or a mixture thereof.

In some preferred embodiments, the invention provides a method of providing relief in a human patient suffering from a butorphanol responsive medical condition comprising a therapeutically effective amount of oral butorphanol or a pharmaceutically acceptable salt of butorphanol or a mixture thereof.

In some preferred embodiments, the oral pharmaceutical composition is used on a time contingent basis.

In some preferred embodiments, the oral pharmaceutical composition is used on a pain contingent basis.

In some preferred embodiments, the Q4H or Q4H PRN oral pharmaceutical composition provides a therapeutic effect for about 4 hours.

In some preferred embodiments, the QID, Q6H or Q6H PRN oral pharmaceutical composition provides a therapeutic effect for about 6 hours.

In some preferred embodiments, the TID, Q8H or Q8H PRN oral pharmaceutical composition provides a therapeutic effect for about 8 hours.

In some preferred embodiments, the Q4H or Q4H PRN oral pharmaceutical composition provides a $C_{max}$ of butorphanol at about 1 to about 4 hours.

In some preferred embodiments, the Q4H or Q4H PRN oral pharmaceutical composition provides a $C_{min}$ of butorphanol at about 3 to 6 hours.

In some preferred embodiments, the Q4H or Q4H PRN oral pharmaceutical composition provides a mean butorphanol $AUC_{0-inf}$ after first administration or $AUC_{0-4}$ at steady state of about 0.5 ng·hr/mL to about 100 ng·hr/mL, or about 0.5 ng·hr/mL to about 75 ng·hr/mL or about 0.5 ng·hr/mL to about 40 ng·hr/mL, or about 0.5 ng·hr/mL to about 30 ng·hr/mL, or about 0.5 ng·hr/mL to about 20 ng·hr/mL or about 0.5 ng·hr/mL to about 10 ng·hr/mL, about 0.5 ng·hr/mL to about 5 ng·hr/mL, or about 0.5 ng·hr/mL to about 3 ng·hr/mL or about 0.5 ng·hr/mL to about 2 ng·hr/mL.

In some preferred embodiments, the Q4H or Q4H PRN oral pharmaceutical composition provides a mean of butorphanol $C_4/Cmax$ ratio of 0.05 to about 1.25.

In some preferred embodiments, the Q4H or Q4H PRN oral pharmaceutical composition provides a butorphanol percent fluctuation of less than 400%.

In some preferred embodiments, the Q4H or Q4H PRN oral pharmaceutical composition provides of butorphanol $W_{50}$ of 0.5 to about 3.5 hours.

In some preferred embodiments, the Q4H or Q4H PRN oral pharmaceutical composition provides a HVD of butorphanol of 0.75 to about 3.75 hours.

In some preferred embodiments, the Q4H or Q4H PRN oral pharmaceutical composition provides an AI of butorphanol of not more than 4.0.

In some preferred embodiments, the Q6H or Q6H PRN oral pharmaceutical composition provides a $C_{max}$ of butorphanol at about 1 to about 6 hours.

In some preferred embodiments, the Q6H or Q6H PRN oral pharmaceutical composition provides a $C_{min}$ of butorphanol at about 3 to 8 hours.

In some preferred embodiments, the Q6H or Q6H PRN oral pharmaceutical composition provides a mean butorphanol $AUC_{0-inf}$ after first administration or $AUC_{0-6}$ at steady state of about 0.5 ng·hr/mL to about 100 ng·hr/mL, or about 0.5 ng·hr/mL to about 75 ng·hr/mL or about 0.5 ng·hr/mL to about 40 ng·hr/mL, or about 0.5 ng·hr/mL to about 30 ng·hr/mL, or about 0.5 ng·hr/mL to about 20 ng·hr/mL or about 0.5 ng·hr/mL to about 10 ng·hr/mL, about 0.5 ng·hr/mL to about 5 ng·hr/mL, or about 0.5 ng·hr/mL to about 3 ng·hr/mL or about 0.5 ng·hr/mL to about 2 ng·hr/mL.

In some preferred embodiments, the Q6H or Q6H PRN oral pharmaceutical composition provides a mean of butorphanol $C_4$/Cmax ratio of 0.05 to about 1.25.

In some preferred embodiments, the Q6H or Q6H PRN oral pharmaceutical composition provides a butorphanol percent fluctuation of less than 400%.

In some preferred embodiments, the Q6H or Q6H PRN oral pharmaceutical composition provides of butorphanol $W_{50}$ of 1.0 to about 5 hours.

In some preferred embodiments, the Q6H or Q6H PRN oral pharmaceutical composition provides a HVD of butorphanol of 1.25 to about 5.5 hours.

In some preferred embodiments, the Q6H or Q6H PRN oral pharmaceutical composition provides an AI of butorphanol of not more than 4.0.

In some preferred embodiments, the TID or Q8H oral pharmaceutical composition provides a $C_{max}$ of butorphanol at about 1 to about 6 hours.

In some preferred embodiments, the TID or Q8H oral pharmaceutical composition provides a $C_{min}$ of butorphanol at about 6 to 10 hours.

In some preferred embodiments, the TID or Q8H oral pharmaceutical composition provides a mean butorphanol $AUC_{0-inf}$ after first administration or $AUC_{0-8}$ at steady state of about 0.5 ng·hr/mL to about 200 ng·hr/mL, or about 0.5 ng·hr/mL to about 150 ng·hr/mL, or about 0.5 ng·hr/mL to about 100 ng·hr/mL, or about 0.5 ng·hr/mL to about 75 ng·hr/mL or about 0.5 ng·hr/mL to about 40 ng·hr/mL, or about 0.5 ng·hr/mL to about 30 ng·hr/mL, or about 0.5 ng·hr/mL to about 20 ng·hr/mL or about 0.5 ng·hr/mL to about 10 ng·hr/mL, about 0.5 ng·hr/mL to about 5 ng·hr/mL, or about 0.5 ng·hr/mL to about 3 ng·hr/mL or about 0.5 ng·hr/mL to about 2 ng·hr/mL.

In some preferred embodiments, the TID or Q8H oral pharmaceutical composition provides a mean of butorphanol $C_8$/Cmax ratio of 0.05 to about 1.25.

In some preferred embodiments, the TID or Q8H oral pharmaceutical composition provides a butorphanol percent fluctuation of less than 400%.

In some preferred embodiments, the TID or Q8H oral pharmaceutical composition provides of butorphanol $W_{50}$ of 1.5 to about 6.5 hours.

In some preferred embodiments, the TID or Q8H oral pharmaceutical composition provides a HVD of butorphanol of 2 to about 7 hours.

In some preferred embodiments, the TID or Q8H oral pharmaceutical composition provides an AI of butorphanol of not more than 4.0.

In some preferred embodiments, the invention comprises an oral modified release pharmaceutical composition comprising a therapeutically effective amount of butorphanol or a pharmaceutically acceptable salt of butorphanol, or a mixture thereof; said dosage from providing a $C_{max}$ of butorphanol from about 0.025 ng/mL to about 30 ng/mL. In other preferred embodiments, the dosage form provides a $C_{max}$ of butorphanol of about 0.05 ng/mL to about 30 ng/mL, or about 0.75 ng/mL to about 30 ng/mL, or about 0.1 ng/mL to about 30 ng/mL, or about 0.2 ng/mL to about 30 ng/mL, or about 0.3 ng/mL to about 30 ng/mL, or about 0.4 ng/mL to about 30 ng/mL, or about 0.05 ng/mL to about 25 ng/mL, or about 0.05 ng/mL to about 20 ng/mL, or about 0.05 ng/mL to about 18 ng/mL, or about 0.05 ng/mL to about 15 ng/mL, or about 0.05 ng/mL to about 12 ng/mL, or about 0.05 ng/mL to about 10 ng/mL, or about 0.05 ng/mL to about 8 ng/mL, or about 0.05 ng/mL to about 7 ng/mL, or about 0.05 ng/mL to about 6 ng/mL, or about 0.05 ng/mL to about 5 ng/mL, or about 0.05 ng/mL to about 4 ng/mL, or about 0.05 ng/mL to about 3 ng/mL, or about 0.1 ng/mL to about 7 ng/mL, or about 0.1 ng/mL to about 6 ng/mL, or about 0.1 ng/mL to about 5 ng/mL, or about 0.1 ng/mL to about 4 ng/mL, or about 0.1 ng/mL to about 3 ng/mL.

In some preferred embodiments, the invention comprises an oral pharmaceutical composition comprising a therapeutically effective amount of butorphanol; said dosage from providing a $C_{max}$ of butorphanol occurring from a mean of about 0.25 to about 30 hours. In other preferred embodiments, the dosage form provides a $C_{max}$ of butorphanol occurring from a mean of about 0.5 to about 30 hours, or from a mean of about 1 to about 30 hours, or about 1 to about 26 hours, or about 1 to about 24 hours, or about 1 to about 20 hours, or about 1 to about 18 hours, or about 1 to about 16 hours, or about 1 to about 14 hours, or about 1 to about 12 hours, or about 1 to about 10 hours, or about 1 to about 8 hours, or about 1 to about 6 hours, or about 1 to about 4 hours, or about 1 to about 3 hours, or about 2 to about 30 hours, or about 4 to about 30 hours, or about 4 to about 24 hours, or about 6 to about 24 hours, or about 8 to about 24 hours, or about 10 to about 20 hours, or about 12 to about 24 hours, or about 18 to about 24 hours, or about 2 to about 12 hours, or about 3 to about 12 hours, or about 3 to about 8 hours, or about 4 to about 10 hours, or about 4 to about 12 hours, or about 4 to about 9 hours, or about 5 to about 8 hours In some preferred embodiments, the invention comprises an oral pharmaceutical composition comprising a therapeutically effective amount of butorphanol; a controlled release material to render said dosage form suitable for extended release in a human patient.

In some preferred embodiments, the invention comprises an oral modified release pharmaceutical composition and method for the treatment of butorphanol responsive disorders comprising a therapeutically effective amount of butorphanol or a pharmaceutically acceptable salt of butorphanol, or a mixture thereof; a controlled release material to render said dosage form suitable for extended release in a human patient; said dosage form administered at a prespecified dosing regimen; said dosing regimen associated with reduced side effects, improved tolerability and reduced treatment discontinuation due to side effects; said regimen comprising administering a dose of about 2 to 4 mg for 1 to 7 days, followed by about 3 to 6 mg for a subsequent period of 1 to 7 days, followed by >about 7 mg for duration of treatment; or about 4 to 6 mg for 1 to 7 days, followed by about 5 to 8 mg for a subsequent period of 1 to 7 days, followed by >about 8 mg for duration of treatment; or about 6 to 8 mg for 1 to 7 days, followed by about 9 to 12 mg for a subsequent period of 1 to 7 days, followed by >about 9 mg for duration of treatment; or about 4 to 8 mg for 1 to 7 days, followed by about 9 to 12 mg for a subsequent period of 1 to 7 days, followed by >about 9 mg for duration of treatment; or about 8 mg for 1 to 7 days, followed by about 9 to 12 mg for a subsequent period of 1 to 7 days, followed by >about 9 mg for duration of treatment; or about 8 mg for 1 to 7 days, followed by about 9 to 16 mg for a subsequent period of 1 to 7 days, followed by >about 9 mg for duration of treatment; or about 2.5 to 5 mg for 1 to 7 days, followed by about 3 to 10 mg for a subsequent period of 1 to 7 days, followed by >about 3 mg for duration of treatment; or about 4 mg for 1 to 7 days, followed by about 6 mg for a subsequent period of 1 to 7 days, followed by >about 6 mg for duration of treatment; or about 4 for 1 to 7 days, followed by about 6 to 8 mg for a subsequent period of 1 to 7 days, followed by >about 6 mg for duration of treatment; or about 4 mg for 1 to 7 days, followed by about 8 mg for a subsequent period of 1 to 7 days, followed by >about 9 mg for duration of treatment; or about 8 mg for 1 to 7 days, followed by >about 9 mg for duration of treatment; or about 2 to 4 mg for 4 days, followed by about 3 to 8 mg for a subsequent period of 4 days, followed by >about 4 mg for duration of treatment; or about 8 mg for 4 to 7 days, followed by about 9 to 16 mg for a subsequent period of 4 to 7 days, followed by >about 9 mg for duration of treatment; or about 5 mg for 4 to 7 days, followed by about 10 to 15 mg for a subsequent period of 1 to 7 days, followed by >about 10 mg for duration of treatment.

In some preferred embodiments, the invention comprises an oral modified release pharmaceutical composition and method for the treatment of butorphanol responsive disorders comprising a therapeutically effective amount of butorphanol or a pharmaceutically acceptable salt of butorphanol, or a mixture thereof; a controlled release material to render said dosage form suitable for extended release in a human patient; said dosage form administered at a prespecified dosing regimen; said dosing regimen associated with reduced side effects, improved tolerability and reduced treatment discontinuation due to side effects; said regimen comprising administering a total daily dose of about 4 to 10 mg for 1 to 7 days, followed by about 5 to 15 mg for a subsequent period of 1 to 7 days, followed by >about 10 mg for duration of treatment; or about 5 to 20 mg for 1 to 7 clays, followed by about 5 to 30 mg for a subsequent period of 1 to 7 days, followed by >about 10 mg for duration of treatment; or about 10 to 20 mg for 1 to 7 days, followed by about 10 to 30 mg for a subsequent period of 1 to 7 days, followed by >about 15 mg for duration of treatment; or about 10 to 20 mg for 1 to 7 days, followed by about 10 to 40 mg for a subsequent period of 1 to 7 days, followed by >about 15 mg for duration of treatment; or about 10 to 20 mg for 1 to 7 days, followed by about 10 to 40 mg for a subsequent period of 1 to 7 days, followed by >about 20 mg for duration of treatment; or about 15 to 30 mg for 1 to 7 days, followed by about 15 to 40 mg for a subsequent period of 1 to 7 days, followed by >about 20 mg for duration of treatment; or about 15 to 30 mg for 1 to 7 days, followed by about 15 to 40 mg for a subsequent period of 1 to 7 days, followed by >about 30 mg for duration of treatment;
or about 15 to 40 mg for 1 to 7 days, followed by about 20 to 40 mg for a subsequent period of 1 to 7 days, followed by >about 25 mg for duration of treatment; or about 15 to 40 mg for 1 to 7 days, followed by about 20 to 50 mg for a subsequent period of 1 to 7 days, followed by >about 30 mg for duration of treatment; or about 15 to 40 mg for 1 to 7 clays, followed by about 20 to 60 mg for a subsequent period of 1 to 7 days, followed by >about 30 mg for duration of treatment; or about 20 to 60 mg for 1 to 7 days, followed by about 20 to 80 mg for a subsequent period of 1 to 7 days, followed by >about 30 mg for duration of treatment; or about 20 to 60 mg for 1 to 7 days, followed by about 30 to 80 mg for a subsequent period of 1 to 7 days, followed by >about 30 mg for duration of treatment; or about 20 to 60 mg for 1 to 7 days, followed by about 30 to 80 mg for a subsequent period of 1 to 7 days, followed by >about 40 mg for duration of treatment; or about 25 to 50 mg for 1 to 7 days, followed by about 25 to 100 mg for a subsequent period of 1 to 7 days, followed by >about 30 mg for duration of treatment; or about 25 to 50 mg for 1 to 7 days, followed by about 25 to 100 mg for a subsequent period of 1 to 7 days, followed by >about 40 mg for duration of treatment; or about 25 to 50 mg for 1 to 7 days, followed by about 50 to 100 mg for a subsequent period of 1 to 7 days, followed by >about 50 mg for duration of treatment; or about 10 to 40 mg for 1 to 7 days, followed by about 20 to 40 mg for a subsequent period of 1 to 7 days, followed by >about 30 mg for duration of treatment; or about 10 to 40 mg for 1 to 7 days, followed by about 20 to 60 mg for a subsequent period of 1 to 7 days, followed by >about 30 mg for duration of treatment; or about 10 to 40 mg for 1 to 7 days, followed by about 20 to 60 mg for a subsequent period of 1 to 7 days, followed by >about 40 mg for duration of treatment; or about 10 to 40 mg for 1 to 7 days, followed by >about 20 mg for duration of treatment; or about 10 to 40 mg for 1 to 7 days, followed by >about 30 mg for duration of treatment; or about 10 to 50 mg for 1 to 7 days, followed by >about 20 mg for duration of treatment; or about 10 to 50 mg for 1 to 7 days, followed by >about 30 mg for duration of treatment; or about 15 to 40 mg for 1 to 7 days, followed by >about 30 mg for duration of treatment; or about 15 to 50 mg for 1 to 7 days, followed by >about 30 mg for duration of treatment; or about 20 to 60 mg for 1 to 7 days, followed by >about 25 mg for duration of treatment; or about 20 to 60 mg for 1 to 7 days, followed by >about 30 mg for duration of treatment; or about 20 to 60 mg for 1 to 7 days, followed by >about 40 mg for duration of treatment; or about 20 to 60 mg for 1 to 7 days, followed by >about 25 mg for duration of treatment; or about 5 to 60 mg for the duration of treatment; or about 5 to 80 mg for the duration of treatment; or about 5 to 120 mg for the duration of treatment; or about 5 to 160 mg for the duration of treatment; or about 10 to 60 mg for the duration of treatment; or about 10 to 80 mg for the duration of treatment; or about 10 to 120 mg for the duration of treatment; or about 10 to 160 mg for the duration of treatment; or about 10 to 200 mg for the duration of treatment;
or about 20 to 60 mg for the duration of treatment; or about 20 to 80 mg for the duration of treatment; or about 20 to 120 mg for the duration of treatment; or about 20 to 160 mg for the duration of treatment; or about 20 to 200 mg for the duration of treatment; or about 25 to 100 mg for the duration of treatment; or about 25 to 150 mg for the duration of treatment; or about 25 to 200 mg for the duration of treatment.

In some preferred embodiments, the invention comprises an oral modified release pharmaceutical composition comprising a therapeutically effective amount of butorphanol or a pharmaceutically acceptable salt of butorphanol, or a mixture thereof; said dosage from providing a $C_{min}$ of butorphanol of about 0 ng/mL to about 20 ng/mL or 0.01 ng/mL to about 20 ng/mL In other preferred embodiments, the dosage form provides a $C_{min}$ of butorphanol of less than about 18 ng/mL, or less than about 15 ng/mL, or less than about 14 ng/mL, or less than about 12 ng/mL, or less than about 10 ng/mL, or less than about 8 ng/mL, or less than about 7 ng/mL, or less than about 6 ng/mL, or less than about 5 ng/mL, or less than about 4 ng/mL, or less than about 3 ng/mL, or less than about 2 ng/mL, or less than about 1.5 ng/mL, or less than about 1 ng/mL, or less than about 0.7 ng/mL, or less than about 0.6 ng/mL, or less than about 0.5 ng/mL, or less than about 0.4 ng/mL, or less than about 0.3 ng/mL, or less than about 0.2 ng/mL, or less than about 0.1 ng/mL, or less than about 0.05 ng/mL.

In some preferred embodiments, the invention comprises an oral pharmaceutical composition comprising a therapeutically effective amount of butorphanol; said dosage from providing a $C_{min}$ of butorphanol measured from a mean of about 0.5 to about 30 hours. In other preferred embodiments, the dosage form provides a $C_{min}$ of butorphanol measured from a mean of about 0.5 to about 28 hours, or about 1 to about 28 hours, or about 1 to 24 hours, or about 1 to about 20 hours, or about 1 to about 18 hours, or about 1 to about 16 hours, or about 1 to about 12 hours, or about 1 to 10 hours, or about 1 to about 8 hours, or about 1 to about 6 hours, or about 1 to about 4 hours, about 2 to about 24 hours, or about 3 to 24 hours, or about 4 to about 24 hours, or about 6 to about 24 hours, or about 8 to about 24 hours, about 2 to about 12 hours, or about 3 to 10 hours, or about 3 to about 8 hours, or about 4 to about 8 hours, or about 6 to about 10 hours. In some preferred embodiments, the aforementioned $C_{min}$ being achieved with oral pharmaceutical compositions comprising a controlled release material to render said dosage form extended release, or delayed onset, extended release, or delayed onset, rapid release, or delayed onset, pulsatile release.

In some preferred embodiments, the invention comprises an oral modified release pharmaceutical composition comprising a therapeutically effective amount of butorphanol or a pharmaceutically acceptable salt of butorphanol, or a mixture thereof; said dosage form providing a systemic exposure as assessed by the mean of butorphanol area under the plasma concentration time curves to 24 hours post-dose ($AUC_{0-24}$) of about 0.1 ng·hr/mL to about 600 ng·hr/mL In other preferred embodiments, the dosage form provides an $AUC_{0-24}$ of butorphanol of about 0.2 ng·hr/mL to about 600 ng·hr/mL, or about 0.3 ng·hr/mL to about 600 ng·hr/mL, or about 0.5 ng·hr/mL to about 600 ng·hr/mL, or about 0.7 ng·hr/mL to about 600 ng·hr/mL, or about 1 ng·hr/mL to about 600 ng·hr/mL, or about 2 ng·hr/mL to about 600 ng·hr/mL, or about 3 ng·hr/mL to about 600 ng·hr/mL, or about 4 ng·hr/mL to about 600 ng·hr/mL, or about 5 ng·hr/mL to about 600 ng·hr/mL, or about 6 ng·hr/mL to about 600 ng·hr/mL, or about 7 ng·hr/mL to about 600 ng·hr/mL, or about 8 ng·hr/mL to about 600 ng·hr/mL, or about 9 ng·hr/mL to about 600 ng·hr/mL, or about 10 ng·hr/mL to about 600 ng·hr/mL, or about 12 ng·hr/mL to about 600 ng·hr/mL, or about 14 ng·hr/mL to about 600 ng·hr/mL, or about 15 ng·hr/mL to about 600 ng·hr/mL, or about 17 ng·hr/mL to about 600 ng·hr/mL, or about 20 ng·hr/mL to about 600 ng·hr/mL, or about 0.1 ng·hr/mL to about 550 ng·hr/mL, or about 0.1 ng·hr/mL to about 500 ng·hr/mL, or about 0.1 ng·hr/mL to about 450 ng·hr/mL, or about 0.1 ng·hr/mL to about 400 ng·hr/mL, or about 0.1 ng·hr/mL to about 350 ng·hr/mL, or about 0.1 ng·hr/mL to about 300 ng·hr/mL, or about 0.1 ng·hr/mL to about 250 ng·hr/mL, or about 0.1 ng·hr/mL to about 200 ng·hr/mL, or about 0.1 ng·hr/mL to about 175 ng·hr/mL, or about 0.1 ng·hr/mL to about 150 ng·hr/mL, or about 0.1 ng·hr/mL to about 125 ng·hr/mL, or about 0.1 ng·hr/mL to about 100 ng·hr/mL, or about 0.1 ng·hr/mL to about 90 ng·hr/mL, or about 0.1 ng·hr/mL to about 80 ng·hr/mL, or about 0.1 ng·hr/mL to about 70 ng·hr/mL, or about 0.1 ng·hr/mL to about 60 ng·hr/mL, or about 0.1 ng·hr/mL to about 55 ng·hr/mL, or about 0.1 ng·hr/mL to about 50 ng·hr/mL, or about 0.1 ng·hr/mL to about 45 ng·hr/mL, or about 0.1 ng·hr/mL to about 40 ng·hr/mL, or about 0.1 ng·hr/mL to about 35 ng·hr/mL, or about 0.1 ng·hr/mL to about 30 ng·hr/mL, or about 0.1 ng·hr/mL to about 28 ng·hr/mL, or about 0.1 ng·hr/mL to about 25 ng·hr/mL, or about 0.1 ng·hr/mL to about 22 ng·hr/mL, or about 0.1 ng·hr/mL to about 20 ng·hr/mL, or about 0.1 ng·hr/mL to about 18 ng·hr/mL, or about 0.1 ng·hr/mL to about 15 ng·hr/mL, or about 0.1 ng·hr/mL to about 12 ng·hr/mL, or about 0.1 ng·hr/mL to about 10 ng·hr/mL, or about 1 ng·hr/mL to about 100 ng·hr/mL, or about 1 ng·hr/mL to about 75 ng·hr/mL, or about 1 ng·hr/mL to about 50 ng·hr/mL, or about 2 ng·hr/mL to about 100 ng·hr/mL, or about 2 ng·hr/mL to about 75 ng·hr/mL, or about 2 ng·hr/mL to about 50 ng·hr/mL, or about 4 ng·hr/mL to about 100 ng·hr/mL, or about 4 ng·hr/mL to about 75 ng·hr/mL, or about 4 ng·hr/mL to about 50 ng·hr/mL, or about 1 ng·hr/mL to about 30 ng·hr/mL, or about 2 ng·hr/mL to about 30 ng·hr/mL, or about 3 ng·hr/mL to about 30 ng·hr/mL, or about 1 ng·hr/mL to about 20 ng·hr/mL, or about 1 ng·hr/mL to about 15 ng·hr/mL, or about 5 ng·hr/mL to about 40 ng·hr/mL, or about 8 ng·hr/mL to about 40 ng·hr/mL, or about 10 ng·hr/mL to about 40 ng·hr/mL, or about 10 ng·hr/mL to about 300 ng·hr/mL, or about 12 ng·hr/mL to about 300 ng·hr/mL, or about 14 ng·hr/mL to about 300 ng·hr/mL, or about 15 ng·hr/mL to about 300 ng·hr/mL, or about 16 ng·hr/mL to about 300 ng·hr/mL, or about 17 ng·hr/mL to about 300 ng·hr/mL, or about 18 ng·hr/mL to about 300 ng·hr/mL, or about 19 ng·hr/mL to about 300 ng·hr/mL, or about 20 ng·hr/mL to about 300 ng·hr/mL, or about 22 ng·hr/mL to about 300 ng·hr/mL, or about 24 ng·hr/mL to about 300 ng·hr/mL, or about 26 ng·hr/mL to about 300 ng·hr/mL, or about 28 ng·hr/mL to about 300 ng·hr/mL, or about 30 ng·hr/mL to about 300 ng·hr/mL. In other preferred embodiments, the dosage form provides an $AUC_{0-24}$ of butorphanol of about 2 ng·hr/mL to about 60 ng·hr/mL, or about 2 ng·hr/mL to about 120 ng·hr/mL, or about 2 ng·hr/mL to about 180 ng·hr/mL, or about 4 ng·hr/mL to about 60 ng·hr/mL, or about 4 ng·hr/mL to about 120 ng·hr/mL, or about 4 ng·hr/mL to about 180 ng·hr/mL. In particularly preferred embodiments, the dosage form provides an $AUC_{0-24}$ of butorphanol of about 8 ng·hr/mL to about 60 ng·hr/mL, or about 12 ng·hr/mL to about 60 ng·hr/mL, or about 16 ng·hr/mL to about 60 ng·hr/mL, or about 8 ng·hr/mL to about 100 ng·hr/mL, or about 12 ng·hr/mL to about 100 ng·hr/mL, or about 20 ng·hr/mL to about 100 ng·hr/mL.

In some preferred embodiments, the invention comprises an oral modified release pharmaceutical composition comprising a therapeutically effective amount of butorphanol or a pharmaceutically acceptable salt of butorphanol, or a mixture thereof; said dosage form providing a systemic exposure as assessed by the mean butorphanol area under the plasma concentration time curve to infinity ($AUC_{0-inf}$) of about 0.1 ng·hr/mL to about 600 ng·hr/mL In other preferred embodiments, the dosage form provides an $AUC_{0-inf}$ of butorphanol of about 0.2 ng·hr/mL to about 600 ng·hr/mL, or about 0.3 ng·hr/mL to about 600 ng·hr/mL, or about 0.5 ng·hr/mL to about 600 ng·hr/mL, or about 0.7 ng·hr/mL to about 600 ng·hr/mL, or about 1 ng·hr/mL to about 600 ng·hr/mL, or about 2 ng·hr/mL to about 600 ng·hr/mL, or about 3 ng·hr/mL to about 600 ng·hr/mL, or about 4 ng·hr/mL to about 600 ng·hr/mL, or about 5 ng·hr/mL to about 600 ng·hr/mL, or about 6 ng·hr/mL to about 600 ng·hr/mL, or about 7 ng·hr/mL to about 600 ng·hr/mL, or about 8 ng·hr/mL to about 600 ng·hr/mL, or about 9 ng·hr/mL to about 600 ng·hr/mL, or about 10 ng·hr/mL to about 600 ng·hr/mL, or about 12 ng·hr/mL to about 600 ng·hr/mL, or about 14 ng·hr/mL to about 600 ng·hr/mL, or about 15 ng·hr/mL to about 600 ng·hr/mL, or about 17 ng·hr/mL to about 600 ng·hr/mL, or about 20 ng·hr/mL to about 600 ng·hr/mL, or about 0.1 ng·hr/mL to about 550 ng·hr/mL, or about 0.1 ng·hr/mL to about 500 ng·hr/mL, or about 0.1 ng·hr/mL to about 450 ng·hr/mL, or about 0.1 ng·hr/mL to about 400 ng·hr/mL, or about 0.1 ng·hr/mL to about 350 ng·hr/mL, or about 0.1 ng·hr/mL to about 300 ng·hr/mL, or about 0.1 ng·hr/mL to about 250 ng·hr/mL, or about 0.1 ng·hr/mL to about 200 ng·hr/mL, or about 0.1 ng·hr/mL to about 175 ng·hr/mL, or about 0.1 ng·hr/mL to about 150 ng·hr/mL, or about 0.1 ng·hr/mL to about 125 ng·hr/mL, or about 0.1 ng·hr/mL to about 100 ng·hr/mL, or about 0.1 ng·hr/mL to about 90 ng·hr/mL, or about 0.1 ng·hr/mL to about 80 ng·hr/mL, or about 0.1 ng·hr/mL to about 70 ng·hr/mL, or about 0.1 ng·hr/mL to about 60 ng·hr/mL, or about 0.1 ng·hr/mL to about 55 ng·hr/mL, or about 0.1 ng·hr/mL to about 50 ng·hr/mL, or about 0.1 ng·hr/mL to about 45 ng·hr/mL, or about 0.1 ng·hr/mL to about 40 ng·hr/mL, or about 0.1 ng·hr/mL to about 35 ng·hr/mL, or about 0.1 ng·hr/mL to about 30 ng·hr/mL, or about 0.1 ng·hr/mL to about 28 ng·hr/mL, or about 0.1 ng·hr/mL to about 25 ng·hr/mL, or about 0.1 ng·hr/mL to about 22 ng·hr/mL, or about 0.1 ng·hr/mL to about 20 ng·hr/mL, or about 0.1 ng·hr/mL to about 18 ng·hr/mL, or about 0.1 ng·hr/mL to about 15 ng·hr/mL, or about 0.1 ng·hr/mL to about 12 ng·hr/mL, or about 0.1 ng·hr/mL to about 10 ng·hr/mL, or about 1 ng·hr/mL to about 100 ng·hr/mL, or about 1 ng·hr/mL to about 75 ng·hr/mL, or about 1 ng·hr/mL to about 50 ng·hr/mL, or about 2 ng·hr/mL to about 100 ng·hr/mL, or about 2 ng·hr/mL to about 75 ng·hr/mL, or about 2 ng·hr/mL to about 50 ng·hr/mL, or about 4 ng·hr/mL to about 100 ng·hr/mL, or about 4 ng·hr/mL to about 75 ng·hr/mL, or about 4 ng·hr/mL to about 50 ng·hr/mL, or about 1 ng·hr/mL to about 30 ng·hr/mL, or about 2 ng·hr/mL to about 30 ng·hr/mL, or about 3 ng·hr/mL to about 30 ng·hr/mL, or about 1 ng·hr/mL to about 20 ng·hr/mL, or about 1 ng·hr/mL to about 15 ng·hr/mL, or about 5 ng·hr/mL to about 40 ng·hr/mL, or about 8 ng·hr/mL to about 40 ng·hr/mL, or about 10 ng·hr/mL to about 40 ng·hr/mL, or about 10 ng·hr/mL to about 300 ng·hr/mL, or about 12 ng·hr/mL to about 300 ng·hr/mL, or about 14 ng·hr/mL to about 300 ng·hr/mL, or about 15 ng·hr/mL to about 300 ng·hr/mL, or about 16 ng·hr/mL to about 300 ng·hr/mL, or about 17 ng·hr/mL to about 300 ng·hr/mL, or about 18 ng·hr/mL to about 300 ng·hr/mL, or about 19 ng·hr/mL to about 300 ng·hr/mL, or about 20 ng·hr/mL to about 300 ng·hr/mL, or about 22 ng·hr/mL to about 300 ng·hr/mL, or about 24 ng·hr/mL to about 300 ng·hr/mL, or about 26 ng·hr/mL to about 300 ng·hr/mL, or about 28 ng·hr/mL to about 300 ng·hr/mL, or about 30 ng·hr/mL to about 300 ng·hr/mL. In other preferred embodiments, the dosage form provides an $AUC_{0-inf}$ of butorphanol of about 2 ng·hr/mL to about 60 ng·hr/mL, or about 2 ng·hr/mL to about 120 ng·hr/mL, or about 2 ng·hr/mL to about 180 ng·hr/mL, or about 4 ng·hr/mL to about 60 ng·hr/mL, or about 4 ng·hr/mL to about 120 ng·hr/mL, or about 4 ng·hr/mL to about 180 ng·hr/mL. In particularly preferred embodiments, the dosage form provides an $AUC_{0-inf}$ of butorphanol of about 8 ng·hr/mL to about 60 ng·hr/mL, or about 12 ng·hr/mL to about 60 ng·hr/mL, or about 16 ng·hr/mL to about 60 ng·hr/mL, or about 8 ng·hr/mL to about 100 ng·hr/mL, or about 12 ng·hr/mL to about 100 ng·hr/mL, or about 20 ng·hr/mL to about 100 ng·hr/mL.

In some preferred embodiments, the invention comprises an oral modified release pharmaceutical composition comprising a therapeutically effective amount of butorphanol or a pharmaceutically acceptable salt of butorphanol, or a mixture thereof; said dosage form providing a systemic exposure as assessed by the mean butorphanol area under the plasma concentration time curve ($AUC_{0-24}$) of up to 600 ng·hr/mL, or up to 500 ng·hr/mL, or up to 400 ng·hr/mL, or up to 350 ng·hr/mL, or up to 300 ng·hr/mL, or up to 250 ng·hr/mL, or up to 200 ng·hr/mL, or up to 175 ng·hr/mL, or up to 150 ng·hr/mL, or up to 125 ng·hr/mL, or up to 100 ng·hr/mL, or up to 90 ng·hr/mL, or up to 80 ng·hr/mL, or up to 70 ng·hr/mL, up to 60 ng·hr/mL, or up to 50 ng·hr/mL, or up to 45 ng·hr/mL, or up to 40 ng·hr/mL, or up to 35 ng·hr/mL, or up to 30 ng·hr/mL, or up to 25 ng·hr/mL, or up to 20 ng·hr/mL, or up to 18 ng·hr/mL, or up to 16 ng·hr/mL, or up to 15 ng·hr/mL, up to 60 ng·hr/mL, or up to 14 ng·hr/mL, or up to 12 ng·hr/mL, or up to 10 ng·hr/mL In other preferred embodiments, the dosage form provides an $AUC_{0-24}$ of butorphanol of up to 40 ng·hr/mL, or up to 50 ng·hr/mL, or up to 60 ng·hr/mL, or up to 80 ng·hr/mL, or up to 100 ng·hr/mL, up to 120 ng·hr/mL, or up to 140 ng·hr/mL, or up to 160 ng·hr/mL, or up to 200 ng·hr/mL In particularly preferred embodiments, the dosage form provides an $AUC_{0-24}$ of butorphanol of up to 40 ng·hr/mL, or up to 60 ng·hr/mL, or up to 80 ng·hr/mL, or up to 100 ng·hr/mL, up to 120 ng·hr/mL, or up to 140 ng·hr/mL, or up to 180 ng·hr/mL.

In some preferred embodiments, the invention comprises an oral modified release pharmaceutical composition comprising a therapeutically effective amount of butorphanol or a pharmaceutically acceptable salt of butorphanol, or a mixture thereof; said dosage form providing a systemic exposure as assessed by the mean butorphanol area under the plasma concentration time curve ($AUC_{0-24}$) of not less than about 60 ng·hr/mL, or not less than about 50 ng·hr/mL, or not less than about 45 ng·hr/mL, or not less than about 40 ng·hr/mL, or not less than about 35 ng·hr/mL, or not less than about 30 ng·hr/mL, or not less than about 25 ng·hr/mL, or not less than about 20 ng·hr/mL, or not less than about 18 ng·hr/mL, or not less than about 16 ng·hr/mL, or not less than about 15 ng·hr/mL, or not less than about 14 ng·hr/mL, or not less than about 12 ng·hr/mL, or not less than about 11 ng·hr/mL, or not less than about 10 ng·hr/mL, or not less than about 8 ng·hr/mL, or not less than about 7 ng·hr/mL, or not less than about 6 ng·hr/mL, or not less than about 5 ng·hr/mL, or not less than about 4 ng·hr/mL.

In some preferred embodiments, the invention comprises an oral modified release pharmaceutical composition comprising a therapeutically effective amount of butorphanol or a pharmaceutically acceptable salt of butorphanol, or a mixture thereof; said dosage form providing a systemic exposure as assessed by the mean butorphanol area under the plasma concentration time curve ($AUC_{0-inf}$) of up to 600 ng·hr/mL, or up to 500 ng·hr/mL, or up to 400 ng·hr/mL, or up to 350 ng·hr/mL, or up to 300 ng·hr/mL, or up to 250 ng·hr/mL, or up to 200 ng·hr/mL, or up to 175 ng·hr/mL, or up to 150 ng·hr/mL, or up to 125 ng·hr/mL, or up to 100 ng·hr/mL, or up to 90 ng·hr/mL, or up to 80 ng·hr/mL, or up to 70 ng·hr/mL, up to 60 ng·hr/mL, or up to 50 ng·hr/mL, or up to 45 ng·hr/mL, or up to 40 ng·hr/mL, or up to 35 ng·hr/mL, or up to 30 ng·hr/mL, or up to 25 ng·hr/mL, or up to 20 ng·hr/mL, or up to 18 ng·hr/mL, or up to 16 ng·hr/mL, or up to 15 ng·hr/mL, up to 60 ng·hr/mL, or up to 14 ng·hr/mL, or up to 12 ng·hr/mL, or up to 10 ng·hr/mL In other preferred embodiments, the dosage form provides an $AUC_{0-inf}$ of butorphanol of up to 40 ng·hr/mL, or up to 50 ng·hr/mL, or up to 60 ng·hr/mL, or up to 80 ng·hr/mL, or up to 100 ng·hr/mL, up to 120 ng·hr/mL, or up to 140 ng·hr/mL, or up to 160 ng·hr/mL, or up to 200 ng·hr/mL In particularly preferred embodiments, the dosage form provides an $AUC_{0-inf}$ of butorphanol of up to 40 ng·hr/mL, or up to 60 ng·hr/mL, or up to 80 ng·hr/mL, or up to 100 ng·hr/mL, up to 120 ng·hr/mL, or up to 140 ng·hr/mL, or up to 120 ng·hr/mL.

In some preferred embodiments, the invention comprises an oral modified release pharmaceutical composition comprising a therapeutically effective amount of butorphanol or a pharmaceutically acceptable salt of butorphanol, or a mixture thereof; said dosage form providing a systemic exposure as assessed by the mean butorphanol area under the plasma concentration time curve ($AUC_{0-inf}$) of not less than about 60 ng·hr/mL, or not less than about 50 ng·hr/mL, or not less than about 45 ng·hr/mL, or not less than about 40 ng·hr/mL, or not less than about 35 ng·hr/mL, or not less than about 30 ng·hr/mL, or not less than about 25 ng·hr/mL, or not less than about 20 ng·hr/mL, or not less than about 18 ng·hr/mL, or not less than about 16 ng·hr/mL, or not less than about 15 ng·hr/mL, or not less than about 14 ng·hr/mL, or not less than about 12 ng·hr/mL, or not less than about 11 ng·hr/mL, or not less than about 10 ng·hr/mL.

In some preferred embodiments, the dosage form provides an oral pharmaceutical composition comprising a therapeutically effective amount of butorphanol; said dosage form providing at least 80% of the steady state therapeutic concentration of butorphanol after administration of ≤3, or ≤4, or ≤5, or ≤6 doses at their intended dosing frequency.

In some preferred embodiments, the dosage form provides an oral pharmaceutical composition comprising a therapeutically effective amount of butorphanol; said dosage form after administration to a human patient providing a $C_{min}/C_{max}$ ratio of butorphanol of 0.1 to about 1.25. In other preferred embodiments, the dosage form provides a $C_{min}/C_{max}$ ratio of butorphanol of about 0.1 to about 1.15, about 0.1 to about 1.19, about 0.1 to about 1, about 0.1 to about 0.9, about 0.1 to about 0.85, or about 0.1 to about 0.8, or about 0.1 to about 0.7, or about 0.1 to about 0.6, or about 0.1 to about 0.5, or about 0.1 to about 0.4, or about 0.1 to about 0.3, or about 0.2 to about 1.0, or about 0.25 to about 1.25, or about 0.25 to about 1.25, or about 0.4 to about 1.25, or about 0.5 to about 1.25, or about 0.65 to about 1.25, or about 0.75 to about 1.25, or about 0.2 to about 0.9, or about 0.3 to about 0.9, or about 0.3 to about 0.8, or about 0.4 to about 0.8, or about 0.4 to about 0.7, or about 0.4 to about 0.6.

In some preferred embodiments, the dosage form provides an oral pharmaceutical composition comprising a therapeutically effective amount of butorphanol; said dosage form after administration to a human patient providing a percent fluctuation of butorphanol of less than 400%. In other preferred embodiments, the dosage form provides a percent fluctuation of butorphanol of less than 350%, or less than 300%, or less than 250%, or less than 200%, or less than 150%, or less than 100%, or less than 75%, or less than 50%, or less than 25%.

In some preferred embodiments, the dosage form provides an oral pharmaceutical composition comprising a therapeutically effective amount of butorphanol; said dosage form after administration to a human patient providing a $W_{50}$ of butorphanol of about 1 to about 6 hours for each 6 hour time period of intended dosing frequency and intended duration of action. In other preferred embodiments, the dosage form provides a $W_{50}$ of butorphanol for each 6 hour time period of intended dosing frequency and intended duration of action of about 1 to about 5 hours, or about 1 to about 4 hours, or about 1 to about 3 hours, or about 1 to about 2 hours, or 2 to about 6 hours, or about 3 to about 6 hours, or about 4 to about 6 hours, or about 2 to about 4 hours.

In some preferred embodiments, the dosage form provides an oral pharmaceutical composition comprising a therapeutically effective amount of butorphanol; said dosage form after administration to a human patient providing a HVD of butorphanol of about 1.5 to about 6 hours for each 6 hour time period of intended dosing frequency and intended duration of action. In other preferred embodiments, the dosage form provides a HVD of butorphanol for each 6 hour time period of intended dosing frequency and intended duration of action of about 1.5 to about 5 hours, or about 1.5 to about 4 hours, or about 1.5 to about 3 hours, or about 1.5 to about 2 hours, or 2 to about 6 hours, or about 3 to about 6 hours, or about 4 to about 6 hours, or about 2 to about 4 hours.

In some preferred embodiments, the dosage form provides an oral pharmaceutical composition comprising a therapeutically effective amount of butorphanol; said dosage form after administration to a human patient providing an AI of butorphanol of not more than 4.0. In other preferred embodiments, the dosage form provides an AI of butorphanol of not more than about 3.5, or not more than about 3.0, or not more than about 2.5, or not more than about 2, or not more than about 1.75, or not more than about 1.5, or not more than about 1.25, or not more than about 1, or not more than about 0.75, or not more than about 0.5, or not more than about 0.25.

In some preferred embodiments, the in vivo pharmacokinetic parameters of the specifications, embodiments and claims are achieved with oral pharmaceutical compositions comprising a controlled release material to render said dosage form suitable for extended release.

In some preferred embodiments, the specifications and claims are achieved with oral pharmaceutical compositions comprising a controlled release material to render said dosage form suitable for extended release.

In some preferred embodiments, the dosage form provides an oral pharmaceutical composition comprising a therapeutically effective amount of butorphanol; and a controlled release material with gastroretentive properties to render said dosage form suitable for extended release oral administration to a human patient.

In some preferred embodiments, the dosage form provides an oral pharmaceutical composition comprising a therapeutically effective amount of butorphanol; and a controlled release material with osmotic release to render said dosage form suitable for extended release oral administration to a human patient.

In some preferred embodiments, the dosage form provides an oral pharmaceutical composition comprising a therapeutically effective amount of butorphanol; and a controlled release material with zero-order or pseudo-zero-order release to render said dosage form suitable for extended release oral administration to a human patient.

In some preferred embodiments, the dosage form provides an oral pharmaceutical composition comprising a therapeutically effective amount of butorphanol and a controlled release material to render said dosage form suitable for four times-a-day (Q6H or Q6H PRN), three times-a-day (Q8H or Q8H PRN), twice-a-day (Q12H or Q12H PRN) or once-a-day (QD, Q24H or Q24H PRN) administration to a human patient, said dosage form after administration to a human patient providing a percent fluctuation of butorphanol of less than 400%. In other preferred embodiments, the dosage form provides a percent fluctuation of butorphanol of less than about 375%, or less than about 350%, or less than about 325%, or less than about 300%, or less than about 275%, or less than about 250%, or less than about 225%, or less than about 200%, or less than about 175%, or less than about 150%, or less than about 125%, or less than about 100%, or less than about 75%, or less than about 50%, or less than about 25%.

In some preferred embodiments, the dosage form provides an oral pharmaceutical composition comprising a therapeutically effective amount of butorphanol and controlled release material to render said dosage form suitable for four times-a-day (Q6H or Q6H PRN), three times-a-day (Q8H or Q8H PRN), twice-a-day (Q12H or Q12H PRN) or once-a-day (QD, Q24H or Q24H PRN) administration to a human patient, said dosage form after administration to a human patient, providing an AI of butorphanol of not more than 4.0. In other preferred embodiments, the dosage form provides an AI of butorphanol of not more than about 3.75, or not more than about 3.5, or not more than about 3.25, or not more than about 3, or not more than about 2.75, or not more than about 2.5, or not more than about 2, or not more than about 1.5, not more than about 1.25, or not more than about 1, or not more than about 0.75.

In some preferred embodiments, the dosage form comprises an oral modified release pharmaceutical composition comprising a therapeutically effective amount of butorphanol or a pharmaceutically acceptable salt of butorphanol, or a mixture thereof and controlled release material to render said dosage form suitable for three times-a-day (Q8H or Q8H PRN), twice-a-day (Q12H or Q12H PRN) or once-a-day (QD, Q24H or Q24H PRN) administration to a human patient, said dosage form after administration to a human patient providing a mean butorphanol $C_{max}$ of about 0.025 ng/mL to about 30 ng/mL In other preferred embodiments, the dosage form provides a $C_{max}$ of butorphanol of about 0.05 ng/mL to about 30 ng/mL, or about 0.75 ng/mL to about 30 ng/mL, or about 0.1 ng/mL to about 30 ng/mL, or about 0.2 ng/mL to about 30 ng/mL, or about 0.3 ng/mL to about 30 ng/mL, or about 0.4 ng/mL to about 30 ng/mL, or about 0.05 ng/mL to about 25 ng/mL, or about 0.05 ng/mL to about 20 ng/mL, or about 0.05 ng/mL to about 18 ng/mL, or about 0.05 ng/mL to about 15 ng/mL, or about 0.05 ng/mL to about 12 ng/mL, or about 0.05 ng/mL to about 10 ng/mL, or about 0.05 ng/mL to about 8 ng/mL, or about 0.05 ng/mL to about 7 ng/mL, or about 0.05 ng/mL to about 6 ng/mL, or about 0.05 ng/mL to about 5 ng/mL, or about 0.05 ng/mL to about 4 ng/mL, or about 0.05 ng/mL to about 3 ng/mL, or about 0.1 ng/mL to about 7 ng/mL, or about 0.1 ng/mL to about 6 ng/mL, or about 0.1 ng/mL to about 5 ng/mL, or about 0.1 ng/mL to about 4 ng/mL, or about 0.1 ng/mL to about 3 ng/mL.

In some preferred embodiments, the dosage form comprises an oral modified release pharmaceutical composition comprising a therapeutically effective amount of butorphanol or a pharmaceutically acceptable salt of butorphanol, or a mixture thereof and controlled release material to render said dosage form suitable for three times-a-day (Q8H or Q8H PRN), twice-a-day (Q12H or Q12H PRN) or once-a-day (QD, Q24H or Q24H PRN) administration to a human patient, said dosage form after administration to a human patient providing a mean butorphanol $C_{max}$ of less than about 30 ng/mL In other preferred embodiments, the dosage form provides a $C_{max}$ of butorphanol of less than about 28 ng/mL, or less than about 25 ng/mL, or of less than about 28 ng/mL, or less than about 25 ng/mL, or less than about 23 ng/mL, or less than about 21 ng/mL, or less than about 20 ng/mL, or less than about 18 ng/mL, or less than about 15 ng/mL, or less than about 12 ng/mL, or less than about 10 ng/mL, or less than about 9 ng/mL, or less than about 8 ng/mL, or less than about 7 ng/mL, or less than about 6 ng/mL, or less than about 5 ng/mL, or less than about 4 ng/mL, or less than about 3 ng/mL, or less than about 2 ng/mL, or less than about 1.5 ng/mL, or less than about 1.25 ng/mL, or less than about 1 ng/mL, or less than about 0.9 ng/mL, or less than about 0.8 ng/mL, or less than about 0.5 ng/mL, or less than about 0.4 ng/mL, or less than about 0.2 ng/mL, or less than about 0.1 ng/mL.

In some preferred embodiments, the dosage form comprises an oral modified release pharmaceutical composition comprising a therapeutically effective amount of butorphanol or a pharmaceutically acceptable salt of butorphanol, or a mixture thereof and controlled release material to render said dosage form suitable for three times-a-day (Q8H or Q8H PRN), twice-a-day (Q12H or Q12H PRN) or once-a-day (QD, Q24H or Q24H PRN) administration to a human patient, said dosage form after administration to a human patient providing a mean butorphanol $C_{max}$ of more than about 0.7 ng/mL. In other preferred embodiments, the dosage form provides a $C_{max}$ of butorphanol of more than about 0.8 ng/mL, or more than about 0.9 ng/mL, or more than about 1 ng/mL, or more than about 1.1 ng/mL, or more than about 1.2 ng/mL, or more than about 1.3 ng/mL, or more than about 1.4 ng/mL, or more than about 1.5 ng/mL, or more than about 1.6 ng/mL, or more than about 1.7 ng/mL, or more than about 1.8 ng/mL, or more than about 1.9 ng/mL, or more than about 2 ng/mL, or more than about 2.1 ng/mL, or more than about 2.2 ng/mL, or more than about 2.3 ng/mL, or more than about 2.4 ng/mL, or more than about 2.5 ng/mL, or more than about 2.6 ng/mL, or more than about 2.7 ng/mL, or more than about 2.8 ng/mL, or more than about 3 ng/mL, or more than about 3.25 ng/mL, or more than about 3.5 ng/mL, or more than about 3.75 ng/mL, or more than about 4 ng/mL, or more than about 4.25 ng/mL, or more than about 4.5.

In some preferred embodiments, the dosage form comprises an oral modified release pharmaceutical composition comprising a therapeutically effective amount of butorphanol or a pharmaceutically acceptable salt of butorphanol, or a mixture thereof and controlled release material to render said dosage form suitable for three times-a-day (Q8H or Q8H PRN), twice-a-day (Q12H or Q12H PRN) or once-a-day (QD, Q24H or Q24H PRN) administration to a human patient, said dosage form after administration to a human patient providing a mean butorphanol $C_{min}$ of about 0 ng/mL to about 20 ng/mL or 0.01 ng/mL to about 20 ng/mL. In other preferred embodiments, the dosage form provides a $C_{min}$ of butorphanol of less than about 18 ng/mL, or less than about 15 ng/mL, or less than about 14 ng/mL, or less than about 12 ng/mL, or less than about 10 ng/mL, or less than about 8 ng/mL, or less than about 7 ng/mL, or less than about 6 ng/mL, or less than about 5 ng/mL, or less than about 4 ng/mL, or less than about 3 ng/mL, or less than about 2 ng/mL, or less than about 1.5 ng/mL, or less than about 1 ng/mL, or less than about 0.7 ng/mL, or less than about 0.6 ng/mL, or less than about 0.5 ng/mL, or less than about 0.4 ng/mL, or less than about 0.3 ng/mL, or less than about 0.2 ng/mL, or less than about 0.1 ng/mL, or less than about 0.05 ng/mL.

In some preferred embodiments, the dosage form comprises an oral modified release pharmaceutical composition comprising a therapeutically effective amount of butorphanol or a pharmaceutically acceptable salt of butorphanol, or a mixture thereof and controlled release material to render said dosage form suitable for three times-a-day (Q8H or Q8H PRN), twice-a-day (Q12H or Q12H PRN) or once-a-day (QD, Q24H or Q24H PRN) administration to a human patient, said dosage form after administration to a human patient providing a mean butorphanol $C_{min}$ of less than about 20 ng/mL. In other preferred embodiments, the dosage form provides a mean butorphanol $C_{min}$ of less than about 18 ng/mL, or less than about 15 ng/mL, or less than about 12 ng/mL, or less than about 10 ng/mL, or less than about 9 ng/mL, or less than about 8 ng/mL, or less than about 7 ng/mL, or less than about 5 ng/mL, or less than about 4 ng/mL, or less than about 3 ng/mL, or less than about 2 ng/mL, or less than about 1 ng/mL, or less than about 0.8 ng/mL, or less than about 0.7 ng/mL, or less than about 0.5 ng/mL, or less than about 0.4 ng/mL, or less than about 0.3 ng/mL, or less than about 0.2 ng/mL, or less than about 0.1 ng/mL, or less than about 0.05 ng/mL.

In some preferred embodiments, the dosage form comprises an oral modified release pharmaceutical composition comprising a therapeutically effective amount of butorphanol or a pharmaceutically acceptable salt of butorphanol, or a mixture thereof and controlled release material to render said dosage form suitable for three times-a-day (Q8H or Q8H PRN), twice-a-day (Q12H or Q12H PRN) or once-a-day (QD, Q24H or Q24H PRN) administration to a human patient, said dosage form after administration to a human patient providing a mean butorphanol $C_{min}$ of greater than about 0.1 ng/mL, or greater than about 0.2 ng/mL, or greater than about 0.4 ng/mL, or greater than about 0.5 ng/mL, or greater than about 0.6 ng/mL, or greater than about 0.7 ng/mL, or greater than about 0.8 ng/mL, or greater than about 0.9 ng/mL, or greater than about 1 ng/mL, or greater than about 1.1 ng/mL, or greater than about 1.2 ng/mL, or greater than about 1.3 ng/mL, or greater than about 1.4 ng/mL, or greater than about 1.5 ng/mL, or greater than about 1.6 ng/mL, or greater than about 1.7 ng/mL, or greater than about 1.8 ng/mL.

In some preferred embodiments, the dosage form comprises an oral modified release pharmaceutical composition comprising a therapeutically effective amount of butorphanol and, optionally, controlled release material to render said dosage form suitable for four times-a-day (Q6H or Q6H PRN), three times-a-day (Q8H or Q8H PRN), twice-a-day (Q12H or Q12H PRN) or once-a-day (QD, Q24H or Q24H PRN) administration to a human patient, said dosage form after administration to a human patient providing a greater than about 60%, 65%, 70%, 75%, 80%, 85%, 90%, 95%, or 100% of the total absorbed dose into systemic circulation (as measured by bioavailability) during the first half of the intended dosing frequency.

In some preferred embodiments, the dosage form comprises an oral modified release pharmaceutical composition comprising a therapeutically effective amount of butorphanol and, optionally, controlled release material to render said dosage form suitable for four times-a-day (Q6H or Q6H PRN), three times-a-day (Q8H or Q8H PRN), twice-a-day (Q12H or Q12H PRN) or once-a-day (QD, Q24H or Q24H PRN) administration to a human patient, said dosage form after administration to a human patient providing a greater than about 60%, 65%, 70%, 75%, 80%, 85%, 90%, 95%, or 100% of the total absorbed dose into systemic circulation (as measured by bioavailability) during the second half of the intended dosing frequency.

In some preferred embodiments, the dosage form comprises an oral modified release pharmaceutical composition comprising a therapeutically effective amount of butorphanol and, optionally, controlled release material to render said dosage form suitable for four times-a-day (Q6H or Q6H PRN), three times-a-day (Q8H or Q8H PRN), twice-a-day (Q12H or Q12H PRN) or once-a-day (QD, Q24H or Q24H PRN) administration to a human patient, said dosage form after administration to a human patient providing a greater than about 50%, 55%, 60%, 65%, 70%, 75%, 80%, 85%, 90%, 95%, or 100% of the total absorbed dose into systemic circulation (as measured by bioavailability) during the first one-third of the intended dosing frequency.

In some preferred embodiments, the dosage form comprises an oral modified release pharmaceutical composition comprising a therapeutically effective amount of butorphanol and, optionally, controlled release material to render said dosage form suitable for four times-a-day (Q6H or Q6H PRN), three times-a-day (Q8H or Q8H PRN), twice-a-day (Q12H or Q12H PRN) or once-a-day (QD, Q24H or Q24H PRN) administration to a human patient, said dosage form after administration to a human patient providing a greater than about 50%, 55%, 60%, 65%, 70%, 75%, 80%, 85%, 90%, 95%, or 100% of the total absorbed dose into systemic circulation (as measured by bioavailability) during the last one-third of the intended dosing frequency.

In some preferred embodiments, the dosage form comprises an oral modified release pharmaceutical composition comprising a therapeutically effective amount of butorphanol and, optionally, controlled release material to render said dosage form suitable for four times-a-day (Q6H or Q6H PRN), three times-a-day (Q8H or Q8H PRN), twice-a-day (Q12H or Q12H PRN) or once-a-day (QD, Q24H or Q24H PRN) administration to a human patient, said dosage form after administration to a human patient providing a greater than about 50%, 55%, 60%, 65%, 70%, 75%, 80%, 85%, 90%, 95%, or 100% of the total absorbed dose into systemic circulation (as measured by bioavailability) during the first one-quarter of the intended dosing frequency.

In some preferred embodiments, the dosage form comprises an oral modified release pharmaceutical composition comprising a therapeutically effective amount of butorphanol and, optionally, controlled release material to render said dosage form suitable for four times-a-day (Q6H or Q6H PRN), three times-a-day (Q8H or Q8H PRN), twice-a-day (Q12H or Q12H PRN) or once-a-day (QD, Q24H or Q24H PRN) administration to a human patient, said dosage form after administration to a human patient providing a greater than about 50%, 55%, 60%, 65%, 70%, 75%, 80%, 85%, 90%, 95%, or 100% of the total absorbed dose into systemic circulation (as measured by bioavailability) during the last one-quarter of the intended dosing frequency.

In some preferred embodiments, in order to attain the specifications and claims of the invention, it is necessary or critical to incorporate a controlled release material in the dosage form.

In some preferred embodiments, the aforementioned embodiments which provide a greater amount of the total absorbed dose into systemic circulation (as measured by bioavailability) during the first half, first one-third or first one quarter of the intended dosing frequency result in reduced frequency or duration of butorphanol related side effects.

In some preferred embodiments, the aforementioned embodiments which provide a greater amount of the total absorbed dose into systemic circulation (as measured by bioavailability) during the second half, last one-third or last one quarter of the intended dosing frequency result in reduced frequency or duration of butorphanol related side effects.

In some preferred embodiments, the dosage form comprises a therapeutically effective amount of oral butorphanol or a pharmaceutically acceptable salt of butorphanol, or a mixture thereof, said dosage form suitable for four times-a-clay (Q6H or Q6H PRN), three times-a-clay (Q8H or Q8H PRN), twice-a-day (Q12H or Q12H PRN) or once-a-day (QD, Q24H or Q24H PRN) administration to a human patient, wherein the in vivo specifications, including pharmacokinetic specifications achieved with oral pharmaceutical compositions which are devoid of a controlled release material to render said dosage form extended release.

In some preferred embodiments, the dosage form comprises a therapeutically effective amount of oral butorphanol or a pharmaceutically acceptable salt of butorphanol, or a mixture thereof, said dosage form suitable for four times-a-day (Q6H or Q6H PRN), three times-a-day (Q8H or Q8H PRN), twice-a-day (Q12H or Q12H PRN) or once-a-day (QD, Q24H or Q24H PRN) administration to a human patient, wherein the in vitro specifications, including dissolution rate specifications achieved with oral pharmaceutical compositions which are devoid of a controlled release material to render said dosage form extended release.

In some embodiments, the pharmacokinetic parameters in the specifications (e.g., AUC, Cmax) referring to "butorphanol" are also applicable to hydroxybutorphanol alone.

In some preferred embodiments, the dosage form comprises an oral modified release pharmaceutical composition comprising a therapeutically effective amount of butorphanol, said dosage form suitable for four times-a-day (Q6H or Q6H PRN), three times-a-day (Q8H or Q8H PRN), twice-a-day (Q12H or Q12H PRN) or once-a-day (QD, Q24H or Q24H PRN) administration to a human patient, wherein the butorphanol $C_{max}$ is substantially independent of food intake in that a difference, at any given time, between the $C_{max}$ of butorphanol administered in fasted state and the $C_{max}$ of butorphanol administered in fed state (using a standardized meal) is no greater than about 30%. In other preferred embodiments, said difference is no greater than about 25%, or 20%, or 18%, or 15%, or 12%, or 10%, or 8%, or 5%.

In some preferred embodiments, the dosage form comprises an oral modified release pharmaceutical composition comprising a therapeutically effective amount of butorphanol, said dosage form suitable for four times-a-day (Q6H or Q6H PRN), three times-a-day (Q8H or Q8H PRN), twice-a-day (Q12H or Q12H PRN) or once-a-day (QD, Q24H or Q24H PRN) administration to a human patient, wherein the butorphanol $C_{max}$ is substantially independent of food intake in that a difference, at any given time, between the $C_{max}$ of butorphanol administered in fasted state and the $C_{max}$ of butorphanol administered after a standardized high fat meal is no greater than about 30%. In other preferred embodiments, said difference is no greater than about 25%, or 20%, or 18%, or 15%, or 12%, or 10%, or 8%, or 5%.

In some preferred embodiments, the dosage form comprises an oral modified release pharmaceutical composition comprising a therapeutically effective amount of butorphanol, said dosage form suitable for four times-a-day (Q6H or Q6H PRN), three times-a-day (Q8H or Q8H PRN), twice-a-day (Q12H or Q12H PRN) or once-a-day (QD, Q24H or Q24H PRN) administration to a human patient, wherein the butorphanol $C_{max}$ is substantially independent of alcohol intake in that a difference, at any given time, between the $C_{max}$ of butorphanol administered with about 30 to about 240 mL of a 40% ethanol solution and the $C_{max}$ of butorphanol administered without concurrent alcohol (i.e., in an alcohol free state) is no greater than about 30%. In other preferred embodiments, said difference is no greater than about 25%, or 20%, or 18%, or 15%, or 12%, or 10%, or 8%, or 5%.

In some preferred embodiments, the dosage form comprises an oral modified release pharmaceutical composition comprising a therapeutically effective amount of butorphanol, said dosage form suitable for four times-a-day (Q6H or Q6H PRN), three times-a-day (Q8H or Q8H PRN), twice-a-day (Q12H or Q12H PRN) or once-a-day (QD, Q24H or Q24H PRN) administration to a human patient, wherein the $AUC_{0-12}$, $AUC_{0-24}$ and $AUC_{0-inf}$ after single-dose administration are substantially independent of food intake in that a difference, at any given time, between the said AUC of butorphanol when the dosage form administered in fasted state and the said AUC of butorphanol when the dosage form is administered in fed state (using a standardized meal) is no greater than about 30%. In other preferred embodiments, said difference is no greater than about 25%, or 20%, or 18%, or 15%, or 12%, or 10%, or 8%, or 5%.

In some preferred embodiments, the dosage form comprises an oral modified release pharmaceutical composition comprising a therapeutically effective amount of butorphanol, said dosage form suitable for four times-a-day (Q6H or Q6H PRN), three times-a-day (Q8H or Q8H PRN), twice-a-day (Q12H or Q12H PRN) or once-a-day (QD, Q24H or Q24H PRN) administration to a human patient, wherein the butorphanol $AUC_{0-12}$, $AUC_{0-24}$ and $AUC_{0-inf}$ is substantially independent of food intake in that a difference, at any given time, between the said AUC when administered in fasted state and the AUC when administered after a standardized high fat meal is no greater than about 30%. In other preferred embodiments, said difference is no greater than about 25%, or 20%, or 18%, or 15%, or 12%, or 10%, or 8%, or 5%.

In some preferred embodiments, the dosage form comprises an oral modified release pharmaceutical composition comprising a therapeutically effective amount of butorphanol, said dosage form suitable for four times-a-day (Q6H or Q6H PRN), three times-a-day (Q8H or Q8H PRN), twice-a-day (Q12H or Q12H PRN) or once-a-day (QD, Q24H or Q24H PRN) administration to a human patient, wherein the butorphanol $AUC_{0-1}$, $AUC_{0-2}$, and $AUC_{0-4}$ is substantially independent of alcohol intake in that a difference, at any given time, between the said AUC when administered with about 30 to about 240 mL of a 40% ethanol solution and the said AUC when administered without concurrent alcohol (i.e., in an alcohol free state) is no greater than about 30%. In other preferred embodiments, said difference is no greater than about 25%, or 20%, or 18%, or 15%, or 12%, or 10%, or 8%, or 5%.

In some preferred embodiments, the dosage form comprises an oral modified release pharmaceutical composition comprising a therapeutically effective amount of butorphanol and, optionally, controlled release material to render said dosage form suitable for three times-a-day (Q8H or Q8H PRN) administration to a human patient, said dosage form after administration to a human patient providing a $C_{max}$ of butorphanol at 0.75 to about 7 hours; and said dosage form providing a therapeutic effect for at least about 8 hours. In other preferred embodiments, the dosage form provides a $C_{max}$ of butorphanol at about 0.75 to about 6.5 hours or about 0.75 to about 6 hours, or about 0.75 to about 5 hours, or about 0.75 to about 4 hours, or about 0.75 to about 3.5 hours, or about 0.75 to about 3 hours, or 0.75 to about 2.5 hours, or about 0.75 to about 2 hours, or about 0.75 to about 1.5 hours, or about 1 to about 7 hours, or about 1.5 to about 7 hours, or about 2 to about 7 hours, or about 2.5 to about 7 hours, or 3 to about 7 hours, or about 3.5 to about 7 hours, or about 4 to about 7 hours, or about 4.5 to about 7 hours, or about 5 to about 6 hours, or about 5.5 to about 7 hours, or about 2 to about 6, or about 2.5 to about 5.5 hours, or about 3 to about 5 hours, or about 3 to about 6. In some preferred embodiments, the aforementioned $C_{max}$ being achieved with oral pharmaceutical compositions devoid of a controlled release material to render said dosage form extended release.

In some preferred embodiments, the dosage form comprises an oral modified release pharmaceutical composition comprising a therapeutically effective amount of butorphanol and, optionally, controlled release material to render said dosage form suitable for three times-a-day (Q8H or Q8H PRN) administration to a human patient, said dosage form after administration to a human patient providing a $C_{min}$ of butorphanol at about 6 to about 10 hours; and said dosage form providing a therapeutic effect for at least about 8 hours. In other preferred embodiments, the dosage form provides a $C_{min}$ of butorphanol at about 6 to about 9 hours, or about 6 to about 8.5 hours, or about 6 to about 8 hours, or about 6 to about 7.5 hours, or about 6 to about 7 hours, or about 6.5 to about 10 hours, or about 7 to about 10 hours, or about 8 to about 10 hours, or about 8 hours. In some preferred embodiments, the aforementioned $C_{min}$ being achieved with oral pharmaceutical compositions devoid of a controlled release material to render said dosage form extended release.

In some preferred embodiments, the dosage form provides an oral modified release pharmaceutical composition comprising a therapeutically effective amount of butorphanol or a pharmaceutically acceptable salt of butorphanol, or a mixture thereof and controlled release material to render said dosage form suitable for three times-a-day (Q8H or Q8H PRN) administration to a human patient, said dosage form after administration to a human patient providing a mean butorphanol $AUC_{0-inf}$ after first administration or $AUC_{0-8}$ at steady state of about 2 ng·hr/mL to about 200 ng·hr/mL; and said dosage form providing a therapeutic effect for at least about 8 hours. In other preferred embodiments, the dosage form provides a mean butorphanol $AUC_{0-inf}$ after first administration or $AUC_{0-8}$ at steady state of about 2 ng·hr/mL to about 175 ng·hr/mL, or about 2 ng·hr/mL to about 150 ng·hr/mL, or about 2 ng·hr/mL to about 125 ng·hr/mL, or about 2 ng·hr/mL to about 110 ng·hr/mL, or about 2 ng·hr/mL to about 90 ng·hr/mL, or about 2 ng·hr/mL to about 8 ng·hr/mL, or about 2 ng·hr/mL to about 70 ng·hr/mL, or about 2 ng·hr/mL to about 60 ng·hr/mL, or about 2 ng·hr/mL to about 50 ng·hr/mL, or about 2 ng·hr/mL to about 45 ng·hr/mL, or about 2 ng·hr/mL to about 40 ng·hr/mL, or about 2 ng·hr/mL to about 35 ng·hr/mL, or about 2 ng·hr/mL to about 30 ng·hr/mL, or about 2 ng·hr/mL to about 28 ng·hr/mL, or about 2 ng·hr/mL to about 25 ng·hr/mL, or about 2 ng·hr/mL to about 22 ng·hr/mL, or about 2 ng·hr/mL to about 20 ng·hr/mL, or about 2 ng·hr/mL to about 18 ng·hr/mL, or about 2 ng·hr/mL to about 16 ng·hr/mL, or about 2 ng·hr/mL to about 15 ng·hr/mL, or about 2 ng·hr/mL to about 14 ng·hr/mL, or about 2 ng·hr/mL to about 12 ng·hr/mL, or about 2 ng·hr/mL to about 10 ng·hr/mL, or about 2 ng·hr/mL to about 9 ng·hr/mL, or about 2 ng·hr/mL to about 8 ng·hr/mL, or about 2 ng·hr/mL to about 7 ng·hr/mL, or about 2 ng·hr/mL to about 6 ng·hr/mL, or about 2 ng·hr/mL to about 5 ng·hr/mL, or about 2 ng·hr/mL to about 4 ng·hr/mL, or about 1 ng·hr/mL to about 60 ng·hr/mL, or about 1 ng·hr/mL to about 50 ng·hr/mL, or about 1 ng·hr/mL to about 40 ng·hr/mL, or about 3 ng·hr/mL to about 40 ng·hr/mL, or about 4 ng·hr/mL to about 50 ng·hr/mL, or about 5 ng·hr/mL to about 30 ng·hr/mL.

In some preferred embodiments, the dosage form provides an oral modified release pharmaceutical composition comprising a therapeutically effective amount of butorphanol or a pharmaceutically acceptable salt of butorphanol, or a mixture thereof and controlled release material to render said dosage form suitable for three times-a-day (Q8H or Q8H PRN) administration to a human patient, said dosage form after administration to a human patient providing a mean butorphanol $AUC_{0-inf}$ after first administration or $AUC_{0-8}$ at steady state of not more than about 200 ng·hr/mL; and said dosage form providing a therapeutic effect for at least about 8 hours. In other preferred embodiments, the dosage form provides a mean butorphanol $AUC_{0-inf}$ after first administration or $AUC_{0-8}$ at steady state of not more than about 175 ng·hr/mL, or not more than about 150 ng·hr/mL, or not more than about 125 ng·hr/mL, or not more than about 100 ng·hr/mL, or not more than about 75 ng·hr/mL, or not more than about 50 ng·hr/mL, or not more than about 40 ng·hr/mL, or not more than about 30 ng·hr/mL, or not more than about 20 ng·hr/mL, or not more than about 10 ng·hr/mL, or not more than about 5 ng·hr/mL.

In some preferred embodiments, the dosage form provides an oral modified release pharmaceutical composition comprising a therapeutically effective amount of butorphanol or a pharmaceutically acceptable salt of butorphanol, or a mixture thereof and controlled release material to render said dosage form suitable for three times-a-day (Q8H or Q8H PRN) administration to a human patient, said dosage form after administration to a human patient providing a mean butorphanol $AUC_{0-inf}$ after first administration or $AUC_{0-8}$ at steady state of not less than about 200 ng·hr/mL; and said dosage form providing a therapeutic effect for at least about 8 hours. In other preferred embodiments, the dosage form provides a mean butorphanol $AUC_{0-inf}$ after first administration or $AUC_{0-8}$ at steady state of not less than about 30 ng·hr/mL, or not less than about 20 ng·hr/mL, or not less than about 10 ng·hr/mL, or not less than about 8 ng·hr/mL, or not less than about 6 ng·hr/mL, or not less than about 5 ng·hr/mL, or not less than about 4 ng·hr/mL, or not less than about 2 ng·hr/mL, or not less than about 1 ng·hr/mL.

In some preferred embodiments, the dosage form comprises an oral modified release pharmaceutical composition comprising a therapeutically effective amount of butorphanol and controlled release material to render said dosage form suitable for three times-a-day (Q8H or Q8H PRN) administration to a human patient, said dosage form after administration to a human patient providing a $C_8/C_{max}$ ratio of butorphanol 0.1 to about 1.25; and said dosage form providing a therapeutic effect for at least about 8 hours. In other preferred embodiments, the dosage form provides a $C_8/C_{max}$ ratio of butorphanol of about 0.1 to about 1, or about 0.1 to about 0.8, or about 0.1 to about 0.75, or about 0.1 to about 0.6, or 0.1 to about 0.5, or about 0.1 to about 0.4, or about 0.1 to about 0.35, or about 0.25 to about 0.95, or about 0.4 to about 0.95, or about 0.5 to about 0.95, or about 0.65 to about 0.95, or about 0.75 to about 0.95, or about 0.3 to about 0.8, or about 0.4 to about 0.75, or about 0.5 to about 0.75. In some preferred embodiments, the aforementioned $C_8/C_{max}$ ratio being achieved with oral pharmaceutical compositions devoid of a controlled release material to render said dosage form extended release.

In some preferred embodiments, the dosage form comprises an oral modified release pharmaceutical composition comprising a therapeutically effective amount of butorphanol and controlled release material to render said dosage form suitable for three times-a-day (Q8H or Q8H PRN)

administration to a human patient, said dosage form after administration to a human patient, providing a $W_{50}$ of butorphanol of 1 to about 7 hours; and said dosage form providing a therapeutic effect for at least about 8 hours. In other preferred embodiments, the dosage form provides a $W_{50}$ of butorphanol of about 1 to about 6 hours, or about 1 to about 5 hours, or about 1 to about 5.5 hours, or about 1 to about 5 hours, or 1 to about 4.5 hours, or about 1 to about 4 hours, or about 1 to about 3.5 hours, or about 1 to about 3 hours, or about 1 to about 2.5 hours, or about 1 to about 2 hours, or about 1.5 to about 7 hours, or about 2 to about 6 hours, or 2 to about 5.5 hours, or about 2 to about 5 hours, or about 2 to about 4.5 hours, or about 2 to about 4 hours, or about 2 to about 3.5 hours, or about 2.5 to about 6.5 hours, or about 2.5 to about 6 hours, or about 2.5 to about 5 hours, or about 2.5 to about 4.5 hours, or 3 to about 6.5 hours, or about 3 to about 6 hours, or about 3 to about 5 hours, or about 3 to about 6.5 hours. In some preferred embodiments, the aforementioned $W_{50}$ ratio being achieved with oral pharmaceutical compositions devoid of a controlled release material to render said dosage form extended release.

In some preferred embodiments, the dosage form comprises an oral modified release pharmaceutical composition comprising a therapeutically effective amount of butorphanol and controlled release material to render said dosage form suitable for three times-a-day (Q8H or Q8H PRN) administration to a human patient, said dosage form after administration to a human patient, providing a HVD of butorphanol of 1.5 to about 7 hours; and said dosage form providing a therapeutic effect for at least about 8 hours. In other preferred embodiments, the dosage form provides a HVD of butorphanol of about 1.5 to about 6 hours, or about 1.5 to about 5 hours, or about 1.5 to about 5.5 hours, or about 1.5 to about 5 hours, or 1.5 to about 4.5 hours, or about 1.5 to about 4 hours, or about 1.5 to about 3.5 hours, or about 1.5 to about 3 hours, or about 1.5 to about 2.5 hours, or about 1.5 to about 2 hours, or about 1.5 to about 7 hours, or about 2 to about 6 hours, or 2 to about 5.5 hours, or about 2 to about 5 hours, or about 2 to about 4.5 hours, or about 2 to about 4 hours, or about 2 to about 3.5 hours, or about 2.5 to about 6.5 hours, or about 2.5 to about 6 hours, or about 2.5 to about 5 hours, or about 2.5 to about 4.5 hours, or 3 to about 6.5 hours, or about 3 to about 6 hours, or about 3 to about 5 hours, or about 3 to about 6.5 hours. In some preferred embodiments, the aforementioned HVD ratio being achieved with oral pharmaceutical compositions devoid of a controlled release material to render said dosage form extended release.

In some preferred embodiments, the dosage form provides an oral pharmaceutical composition comprising a therapeutically effective amount of butorphanol and controlled release material to render said dosage form suitable for twice-a-day administration to a human patient, said dosage form after administration to a human patient providing a $C_{max}$ of butorphanol at 2 to about 10 hours; and said dosage form providing a therapeutic effect for at least about 12 hours. In other preferred embodiments, the dosage form provides a $C_{max}$ of butorphanol at about 2 to about 8 hour or about 2 to about 6 hours, or about 2 to about 5 hours, or about 2 to about 7 hours, or about 2 to about 4.5 hours, or about 2 to about 4 hours, or 2 to about 3.5 hours, or about 2 to about 3 hours, or about 3 to about 10 hours, or about 3.5 to about 10 hours, or about 4 to about 10 hours, or about 4.5 to about 10 hours, or about 5 to about 10 hours, or 5 to about 10 hours, or 6 to about 10 hours, or about 3 to about 8 hours, or about 3 to about 7 hours, or about 3 to about 6 hours, or about 4 to about 8 hours, or about 4 to about 6. In some preferred embodiments, the aforementioned $C_{max}$ being achieved with oral pharmaceutical compositions devoid of a controlled release material to render said dosage form extended release.

In some preferred embodiments, the dosage form provides an oral pharmaceutical composition comprising a therapeutically effective amount of butorphanol and controlled release material to render said dosage form suitable for twice-a-day administration to a human patient, said dosage form after administration to a human patient providing a $C_{min}$ of butorphanol at about 10 to about 14 hours; and said dosage form providing a therapeutic effect for at least about 12 hours. In other preferred embodiments, the dosage form provides a $C_{min}$ of butorphanol at about 10 to about 13 hours, or about 10 to about 12.5 hours, or about 10 to about 12 hours, or about 10 to about 11.5 hours, or about 10 to about 11 hours, or about 10.5 to about 14 hours, or about 11 to about 14 hours, or about 12 to about 14 hours. In some preferred embodiments, the aforementioned $C_{min}$ being achieved with oral pharmaceutical compositions devoid of a controlled release material to render said dosage form extended release.

In some preferred embodiments, the dosage form provides an oral modified release pharmaceutical composition comprising a therapeutically effective amount of butorphanol or a pharmaceutically acceptable salt of butorphanol, or a mixture thereof and controlled release material to render said dosage form suitable for twice-a-day (Q12H or Q12H PRN) administration to a human patient, said dosage form after administration to a human patient providing a mean butorphanol $AUC_{0-inf}$ after first administration or $AUC_{0-12}$ at steady state of about 2 ng·hr/mL to about 300 ng·hr/mL; and said dosage form providing a therapeutic effect for at least about 12 hours. In other preferred embodiments, the dosage form provides a mean butorphanol $AUC_{0-inf}$ after first administration or $AUC_{0-12}$ at steady state of about 2 ng·hr/mL to about 275 ng·hr/mL, or about 2 ng·hr/mL to about 250 ng·hr/mL, or about 2 ng·hr/mL to about 225 ng·hr/mL, about 2 ng·hr/mL to about 200 ng·hr/mL, or about 2 ng·hr/mL to about 175 ng·hr/mL, or about 2 ng·hr/mL to about 150 ng·hr/mL, or about 2 ng·hr/mL to about 125 ng·hr/mL, or about 2 ng·hr/mL to about 110 ng·hr/mL, or about 2 ng·hr/mL to about 90 ng·hr/mL, or about 2 ng·hr/mL to about 8 ng·hr/mL, or about 2 ng·hr/mL to about 70 ng·hr/mL, or about 2 ng·hr/mL to about 60 ng·hr/mL, or about 2 ng·hr/mL to about 50 ng·hr/mL, or about 2 ng·hr/mL to about 45 ng·hr/mL, or about 2 ng·hr/mL to about 40 ng·hr/mL, or about 2 ng·hr/mL to about 35 ng·hr/mL, or about 2 ng·hr/mL to about 30 ng·hr/mL, or about 2 ng·hr/mL to about 28 ng·hr/mL, or about 2 ng·hr/mL to about 25 ng·hr/mL, or about 2 ng·hr/mL to about 22 ng·hr/mL, or about 2 ng·hr/mL to about 20 ng·hr/mL, or about 2 ng·hr/mL to about 18 ng·hr/mL, or about 2 ng·hr/mL to about 16 ng·hr/mL, or about 2 ng·hr/mL to about 15 ng·hr/mL, or about 2 ng·hr/mL to about 14 ng·hr/mL, or about 2 ng·hr/mL to about 12 ng·hr/mL, or about 2 ng·hr/mL to about 10 ng·hr/mL, or about 2 ng·hr/mL to about 9 ng·hr/mL, or about 2 ng·hr/mL to about 8 ng·hr/mL, or about 2 ng·hr/mL to about 7 ng·hr/mL, or about 2 ng·hr/mL to about 6 ng·hr/mL, or about 1 ng·hr/mL to about 300 ng·hr/mL, or about 3 ng·hr/mL to about 300 ng·hr/mL, or about 4 ng·hr/mL to about 300 ng·hr/mL, or about 5 ng·hr/mL to about 300 ng·hr/mL, or about 6 ng·hr/mL to about 300 ng·hr/mL, or about 7 ng·hr/mL to about 300 ng·hr/mL, or about 8 ng·hr/mL to about 300 ng·hr/mL, or about 9 ng·hr/mL to about 300 ng·hr/mL, or about 10 ng·hr/mL to about 300 ng·hr/mL, or about 11 ng·hr/mL to about 300 ng·hr/mL, or about 12 ng·hr/mL to about 300 ng·hr/mL, or about 14 ng·hr/mL to about 300 ng·hr/mL, or about 15 ng·hr/mL to about 300 ng·hr/mL, or about 1 ng·hr/mL to about 100 ng·hr/mL, or about 1 ng·hr/mL to about 50 ng·hr/mL, or about 3 ng·hr/mL to about 100 ng·hr/mL, or about 4 ng·hr/mL to about 100 ng·hr/mL, or about 5 ng·hr/mL to about 100 ng·hr/mL.

In some preferred embodiments, the dosage form provides an oral modified release pharmaceutical composition comprising a therapeutically effective amount of butorphanol or a pharmaceutically acceptable salt of butorphanol, or a mixture thereof and controlled release material to render said dosage form suitable for twice-a-day (Q12H or Q12H PRN) administration to a human patient, said dosage form after administration to a human patient providing a mean butorphanol $AUC_{0\text{-}inf}$ after first administration or $AUC_{0\text{-}12}$ at steady state of not more than about 300 ng·hr/mL; and said dosage form providing a therapeutic effect for at least about 12 hours. In other preferred embodiments, the dosage form provides a mean butorphanol $AUC_{0\text{-}inf}$ after first administration or $AUC_{0\text{-}12}$ at steady state of not more than about 275 ng·hr/mL, or not more than about 250 ng·hr/mL, or not more than about 225 ng·hr/mL, or not more than about 200 ng·hr/mL, or not more than about 175 ng·hr/mL, or not more than about 150 ng·hr/mL, or not more than about 125 ng·hr/mL, or not more than about 100 ng·hr/mL, or not more than about 75 ng·hr/mL, or not more than about 50 ng·hr/mL, or not more than about 40 ng·hr/mL, or not more than about 30 ng·hr/mL, or not more than about 20 ng·hr/mL, or not more than about 10 ng·hr/mL, or not more than about 5 ng·hr/mL.

In some preferred embodiments, the dosage form provides an oral modified release pharmaceutical composition comprising a therapeutically effective amount of butorphanol or a pharmaceutically acceptable salt of butorphanol, or a mixture thereof and controlled release material to render said dosage form suitable for twice-a-day (Q12H or Q12H PRN) administration to a human patient, said dosage form after administration to a human patient providing a mean butorphanol $AUC_{0\text{-}inf}$ after first administration or $AUC_{0\text{-}12}$ at steady state of not less than about 300 ng·hr/mL; and said dosage form providing a therapeutic effect for at least about 12 hours. In other preferred embodiments, the dosage form provides a mean butorphanol $AUC_{0\text{-}inf}$ after first administration or $AUC_{0\text{-}12}$ at steady state of not less than about 275 ng·hr/mL, or not less than about 250 ng·hr/mL, or not less than about 225 ng·hr/mL, or not less than about 200 ng·hr/mL, or not less than about 175 ng·hr/mL, or not less than about 150 ng·hr/mL, or not less than about 125 ng·hr/mL, or not less than about 100 ng·hr/mL, or not less than about 75 ng·hr/mL, or not less than about 50 ng·hr/mL, or not less than about 40 ng·hr/mL, or not less than about 30 ng·hr/mL, or not less than about 20 ng·hr/mL, or not less than about 10 ng·hr/mL, or not less than about 5 ng·hr/mL.

In some preferred embodiments, the dosage form provides an oral pharmaceutical composition comprising a therapeutically effective amount of butorphanol and controlled release material to render said dosage form suitable for twice-a-day administration to a human patient, said dosage form after administration to a human patient providing a $C_{12}/C_{max}$ ratio of butorphanol 0.1 to about 1.25; and said dosage form providing a therapeutic effect for at least about 12 hours. In other preferred embodiments, the dosage form provides a $C_{12}/C_{max}$ ratio of butorphanol of about 0.1 to about 1, or about 0.1 to about 0.8, or about 0.1 to about 0.75, or about 0.1 to about 0.6, or about 0.1 to about 0.5, or about 0.1 to about 0.4, or about 0.1 to about 0.35, or about 0.25 to about 0.95, or about 0.4 to about 0.95, or about 0.5 to about 0.95, or about 0.65 to about 0.95, or about 0.75 to about 0.95, or about 0.3 to about 0.8, or about 0.4 to about 0.75, or about 0.5 to about 0.75. In some preferred embodiments, the aforementioned $C_{12}/C_{max}$ ratio being achieved with oral pharmaceutical compositions devoid of a controlled release material to render said dosage form extended release.

In some preferred embodiments, the dosage form provides an oral pharmaceutical composition comprising a therapeutically effective amount of butorphanol and, optionally, controlled release material to render said dosage form suitable for twice-a-day administration to a human patient, said dosage form after administration to a human patient, providing a $W_{50}$ of butorphanol of 2 to about 11 hours; and said dosage form providing a therapeutic effect for at least about 12 hours. In other preferred embodiments, the dosage form provides a $W_{50}$ of butorphanol of about 2 to about 10 hours, or about 2 to about 9 hours, or about 2 to about 9 hours, or about 2 to about 8 hours, or 2 to about 7 hours, or about 2 to about 6 hours, or about 2 to about 5 hours, or about 2 to about 4 hours, or about 3 to about 10 hours, or about 4 to about 10 hours, or about 5 to about 10 hours, or about 6 to about 10 hours, or 7 to about 10 hours, or about 3 to about 8 hours, or about 4 to about 8 hours, or about 4 to about 7 hours, or about 3 to about 6 hours.

In some preferred embodiments, the dosage form provides an oral pharmaceutical composition comprising a therapeutically effective amount of butorphanol and, optionally, controlled release material to render said dosage form suitable for twice-a-day administration to a human patient, said dosage form after administration to a human patient, providing a HVD of butorphanol of 1.5 to about 10 hours; and said dosage form providing a therapeutic effect for at least about 12 hours. In other preferred embodiments, the dosage form provides an HVD of butorphanol of about 1.5 to about 9 hours, or about 1.5 to 8 hours, or about 1.5 to about 7 hours, or about 1.5 to 6 hours, or about 1.5 to about 5 hours, or about 1.5 to about 4 hours, or about 2 to about 10 hours, or about 3 to 10 hours, or about 4 to about 10 hours, or about 5 to 10 hours, or about 6 to about 10 hours, or about 8 to 10 hours, about 3 to about 8 hours, or about 4 to 8 hours, or about 5 to about 7 hours, or about 3 to 6 hours, or about 3 to about 8 hours, or about 5 to about 8 hours.

In some preferred embodiments, the dosage form provides an oral pharmaceutical composition comprising a therapeutically effective amount of butorphanol and, optionally, controlled release material to render said dosage form suitable for once-a-day administration to a human patient, said dosage form after administration to a human patient providing a $C_{max}$ of butorphanol at about 3 to about 20 hours; and said dosage form providing a therapeutic effect for at least about 24 hours. In some preferred embodiments, the dosage form provides a $C_{max}$ at about 3 to about 18 hours, or about 3 to about 15 hours, or about 3 to about 12 hours, or at about 3 to about 10 hours, or at about 3 to about 8 hours, or at about 3 to about 7 hours, or at about 3 to about 7 hours, or about 4 to about 20 hours, or about 5 to about 20 hours, or about 6 to about 20 hours, or at about 8 to about 20 hours, or at about 10 to about 20 hours, or at about 12 to about 20 hours, or at about 14 to about 20 hours, or about 18 to about 20 hours, or about 4 to about 18 hours, or about 4 to about 16 hours, or at about 4 to about 12 hours, or at about 4 to about 8 hours, or at about 4 to about 10 hours, or at about 3 to about 6 hours.

In some preferred embodiments, the dosage form provides an oral pharmaceutical composition comprising a therapeutically effective amount of butorphanol and, optionally, controlled release material to render said dosage form suitable for once-a-day administration to a human patient, said dosage form after administration to a human patient providing a $C_{min}$ of butorphanol at about 20 to about 28 hours; and said dosage form providing a therapeutic effect for at least about 24 hours. In some preferred embodiments, the dosage form provides a $C_{min}$ at about 20 to about 26 hours, or about 20 to about 27 hours, or about 20 to about 25 hours, or about 20 to about 24 hours, or about 20 to about 23 hours, or about 21 to about 28 hours, or about 22 to about 28 hours, or about 23 to about 28 hours, or about 23.5 to about 28 hours, or about 22 to 26 hours.

In some preferred embodiments, the dosage form provides an oral pharmaceutical composition comprising a therapeutically effective amount of butorphanol; said dosage form providing a therapeutic effect longer than would be expected based on the prevailing plasma concentrations. For example, under normal circumstances, many drugs provide duration of effect that is at least partly correlated with or dependent on the prevailing plasma concentrations of drug. In some preferred embodiments of the invention, the dosage form provides persistent therapeutic effects despite short lived, low or negligible prevailing plasma concentrations.

In some preferred embodiments of the invention, the dosage form provides sustained therapeutic effects of up to about 4, or about 6, or about 8, or about 12, or about 18 or about 20 or about 24 hours despite being administered in immediate release form.

In some preferred embodiments, the dosage form provides an oral pharmaceutical composition comprising a therapeutically effective amount of butorphanol; said dosage from providing a Cmax of butorphanol from about 0.25 hours to about 30 hours.

In some preferred embodiments, the dosage form provides an oral pharmaceutical composition comprising a therapeutically effective amount of butorphanol; said dosage from providing a of butorphanol from about 1 hour to about 30 hours.

In some preferred embodiments, the dosage form provides an oral modified release pharmaceutical composition comprising a therapeutically effective amount of butorphanol or a pharmaceutically acceptable salt of butorphanol, or a mixture thereof and controlled release material to render said dosage form suitable for once-a-day (Q24H OR Q24H PRN) administration to a human patient, said dosage form after administration to a human patient providing a butorphanol mean $AUC_{0-inf}$ after first administration or $AUC_{0-24}$ at steady state of about 4 ng·hr/mL to about 60 ng·hr/mL; and said dosage form providing a therapeutic effect for at least about 24 hours. In other preferred embodiments, the dosage form provides a mean butorphanol $AUC_{0-inf}$ after first administration or $AUC_{0-24}$ at steady state of about 4 ng·hr/mL to about 550 ng·hr/mL, or about 4 ng·hr/mL to about 500 ng·hr/mL, or about 4 ng·hr/mL to about 450 ng·hr/mL, or about 4 ng·hr/mL to about 400 ng·hr/mL, or about 4 ng·hr/mL to about 375 ng·hr/mL, or about 4 ng·hr/mL to about 350 ng·hr/mL, or about 4 ng·hr/mL to about 325 ng·hr/mL, or about 4 ng·hr/mL to about 300 ng·hr/mL, or about 4 ng·hr/mL to about 275 ng·hr/mL, or about 4 ng·hr/mL to about 250 ng·hr/mL, or about 4 ng·hr/mL to about 225 ng·hr/mL, about 4 ng·hr/mL to about 200 ng·hr/mL, or about 4 ng·hr/mL to about 175 ng·hr/mL, or about 4 ng·hr/mL to about 150 ng·hr/mL, or about 4 ng·hr/mL to about 125 ng·hr/mL, or about 4 ng·hr/mL to about 110 ng·hr/mL, or about 4 ng·hr/mL to about 90 ng·hr/mL, or about 4 ng·hr/mL to about 8 ng·hr/mL, or about 4 ng·hr/mL to about 70 ng·hr/mL, or about 4 ng·hr/mL to about 60 ng·hr/mL, or about 4 ng·hr/mL to about 50 ng·hr/mL, or about 4 ng·hr/mL to about 45 ng·hr/mL, or about 4 ng·hr/mL to about 40 ng·hr/mL, or about 4 ng·hr/mL to about 35 ng·hr/mL, or about 4 ng·hr/mL to about 30 ng·hr/mL, or about 4 ng·hr/mL to about 28 ng·hr/mL, or about 4 ng·hr/mL to about 25 ng·hr/mL, or about 4 ng·hr/mL to about 24 ng·hr/mL, or about 4 ng·hr/mL to about 20 ng·hr/mL, or about 4 ng·hr/mL to about 18 ng·hr/mL, or about 4 ng·hr/mL to about 16 ng·hr/mL, or about 4 ng·hr/mL to about 15 ng·hr/mL, or about 4 ng·hr/mL to about 14 ng·hr/mL, or about 4 ng·hr/mL to about 14 ng·hr/mL, or about 4 ng·hr/mL to about 10 ng·hr/mL, or about 4 ng·hr/mL to about 9 ng·hr/mL, or about 4 ng·hr/mL to about 8 ng·hr/mL, or about 4 ng·hr/mL to about 7 ng·hr/mL, or about 1 ng·hr/mL to about 600 ng·hr/mL, or about 3 ng·hr/mL to about 600 ng·hr/mL, or about 4 ng·hr/mL to about 600 ng·hr/mL, or about 5 ng·hr/mL to about 600 ng·hr/mL, or about 6 ng·hr/mL to about 600 ng·hr/mL, or about 7 ng·hr/mL to about 600 ng·hr/mL, or about 10 ng·hr/mL to about 600 ng·hr/mL, or about 12 ng·hr/mL to about 600 ng·hr/mL, or about 15 ng·hr/mL to about 600 ng·hr/mL, or about 10 ng·hr/mL to about 400 ng·hr/mL, or about 15 ng·hr/mL to about 300 ng·hr/mL, or about 15 ng·hr/mL to about 200 ng·hr/mL, or about 15 ng·hr/mL to about 100 ng·hr/mL, or about 1 ng·hr/mL to about 100 ng·hr/mL, or about 1 ng·hr/mL to about 50 ng·hr/mL, or about 3 ng·hr/mL to about 100 ng·hr/mL, or about 4 ng·hr/mL to about 100 ng·hr/mL, or about 5 ng·hr/mL to about 100 ng·hr/mL. In some preferred embodiments, the aforementioned $AUC_{0-inf}$ being achieved with oral pharmaceutical compositions comprising a controlled release material to render said dosage form suitable for extended release.

In some preferred embodiments, the dosage form provides an oral modified release pharmaceutical composition comprising a therapeutically effective amount of butorphanol or a pharmaceutically acceptable salt of butorphanol, or a mixture thereof and controlled release material to render said dosage form suitable for once-a-day (Q24H OR Q24H PRN) administration to a human patient, said dosage form after administration to a human patient providing a butorphanol mean $AUC_{0-inf}$ after first administration or $AUC_{0-24}$ at steady state of not more than about 600 ng·hr/mL; and said dosage form providing a therapeutic effect for at least about 24 hours. In other preferred embodiments, the dosage form provides a mean butorphanol $AUC_{0-inf}$ after first administration or $AUC_{0-24}$ at steady state of not more than about 550 ng·hr/mL, or not more than about 500 ng·hr/mL, or not more than about 450 ng·hr/mL, or not more than about 400 ng·hr/mL, or not more than about 350 ng·hr/mL, or not more than about 300 ng·hr/mL, or not more than about 275 ng·hr/mL, or not more than about 250 ng·hr/mL, or not more than about 225 ng·hr/mL, or not more than about 200 ng·hr/mL, or not more than about 175 ng·hr/mL, or not more than about 150 ng·hr/mL, or not more than about 125 ng·hr/mL, or not more than about 100 ng·hr/mL, or not more than about 75 ng·hr/mL, or not more than about 50 ng·hr/mL, or not more than about 40 ng·hr/mL, or not more than about 30 ng·hr/mL, or not more than about 20 ng·hr/mL, or not more than about 10 ng·hr/mL, or not more than about 5 ng·hr/mL.

In some preferred embodiments, the dosage form provides an oral modified release pharmaceutical composition comprising a therapeutically effective amount of butorphanol or a pharmaceutically acceptable salt of butorphanol, or a mixture thereof and controlled release material to render said dosage form suitable for once-a-day (Q24H OR Q24H PRN) administration to a human patient, said dosage form after administration to a human patient providing a butorphanol mean $AUC_{0-inf}$ after first administration or $AUC_{0-24}$ at steady state of not less than about 600 ng·hr/mL; and said dosage form providing a therapeutic effect for at least about 24 hours. In other preferred embodiments, the dosage form provides a mean butorphanol $AUC_{0-inf}$ after first administration or $AUC_{0-24}$ at steady state of not less than about 550 ng·hr/mL, or not less than about 500 ng·hr/mL, or not less than about 450 ng·hr/mL, or not less than about 400 ng·hr/mL, or not less than about 350 ng·hr/mL, or not less than about 300 ng·hr/mL, or not less than about 275 ng·hr/mL, or not less than about 250 ng·hr/mL, or not less than about 225 ng·hr/mL, or not less than about 200 ng·hr/mL, or not less than about 175 ng·hr/mL, or not less than about 150 ng·hr/mL, or not less than about 125 ng·hr/mL, or not less than about 100 ng·hr/mL, or not less than about 75 ng·hr/mL, or not less than about 50 ng·hr/mL, or not less than about 40 ng·hr/mL, or not less than about 30 ng·hr/mL, or not less than about 20 ng·hr/mL, or not less than about 10 ng·hr/mL, or not less than about 5 ng·hr/mL.

In some preferred embodiments, the oral dosage form of the invention provides at least about 5%, or 10%, or 15%, or 20%, or 30% or 40%, or 50% or 60%, or 70%, or 80%, or 100% lower variability in butorphanol $C_{max}$ (as defined by the coefficient of variation or C.V.) than after the intranasal dosage form of butorphanol, each given according to its intended route and method of administration.

In some preferred embodiments, the oral dosage form of the invention provides at least about 5%, or 10%, or 15%, or 20%, or 30% or 40%, or 50% or 60%, or 70%, or 80%, or 100% lower variability in butorphanol $T_{max}$ (as defined by the coefficient of variation or C.V.) than after the intranasal dosage form of butorphanol, each given according to its intended route and method of administration.

In some preferred embodiments, the oral dosage form of the invention provides at least about 5%, or 10%, or 15%, or 20%, or 30% or 40%, or 50% or 60%, or 70%, or 80%, or 100% lower variability in the butorphanol $AUC_{0-24}$, or $AUC_{0-36}$, or $AUC_{0-48}$, or $AUC_{0-72}$ (as defined by the coefficient of variation or C.V.) than after the intranasal dosage form of butorphanol, each given according to its intended route and method of administration.

In some preferred embodiments, the oral dosage form of the invention provides a ratio of mean $AUC_{0-48}$ of hydroxybutorphanol to butorphanol after the first dose which is at least about 5%, or 10%, or 15%, or 20%, or 30% or 40%, or 50% or 60%, or 70%, or 80%, or 100%, or 120%, or 140%, or 150%, or 170%, or 200%, or 230%, or 250%, or 270%, or 300% greater than said ratio after the same amount of intranasal dosage form of butorphanol, each given according to its intended route and method of administration.

In some preferred embodiments, the oral dosage form of the invention provides a time to 75% mean $C_{max}$ of butorphanol after the first dose which is at least about 5%, or 10%, or 15%, or 20%, or 30% or 40%, or 50% or 60%, or 70%, or 80%, or 100%, or 120%, or 140%, or 150%, or 170%, or 200%, or 230%, or 250%, or 270%, or 300% or 400%, or 500%, or 600%, or 700%, or 1000% longer than said time to mean $C_{max}$ after the same amount of intranasal dosage form of butorphanol, each given according to its intended route and method of administration.

In some preferred embodiments, the oral dosage form of the invention provides a mean $T_{max}$ of butorphanol after the first dose which is at least about 5%, or 10%, or 15%, or 20%, or 30% or 40%, or 50% or 60%, or 70%, or 80%, or 100%, or 120%, or 140%, or 150%, or 170%, or 200%, or 230%, or 250%, or 270%, or 300% or 400%, or 500%, or 600%, or 700%, or 1000% longer than said $T_{max}$ after the same amount of intranasal dosage form of butorphanol, each given according to its intended route and method of administration.

In some preferred embodiments, the oral dosage form of the invention provides a mean $C_{max}$ of butorphanol which is at least about 5%, or 10%, or 15%, or 20%, or 30% or 40%, or 50% or 60%, or 70%, or 80%, or 100%, or 120%, or 140%, or 150%, or 170%, or 200%, or 230%, or 250%, or 270%, or 300% less than said $C_{max}$ after the same amount of intranasal dosage form of butorphanol, each given according to its intended route and method of administration.

In some preferred embodiments, the oral dosage form of the invention provides a mean $C_{max}$ ratio of hydroxybutorphanol to butorphanol which is at least about 5%, or 10%, or 15%, or 20%, or 30% or 40%, or 50% or 60%, or 70%, or 80%, or 100%, or 120%, or 140%, or 150%, or 170%, or 200%, or 230%, or 250%, or 270%, or 300% greater than said $C_{max}$ ratio after the same amount of intranasal dosage form of butorphanol, each given according to its intended route and method of administration.

In some preferred embodiments, a controlled release dosage form of the invention provides a time to mean $C_{max}$ of butorphanol which is at least about 1.25, 1.5, 2, 3, 4, 5, 6, 7, 8, 9, 10 or 12 fold greater than the time to mean $C_{max}$ after the same amount of an oral immediate release butorphanol solution.

In some preferred embodiments, the oral dosage form of the invention provides a time to mean $C_{max}$ of butorphanol which is at least about 1.25, 1.5, 2, 3, 4, 5, 6, 7, 8, 9, 10 or 12 fold greater than the time to mean $C_{max}$ after the same amount of an intranasal formulation of butorphanol or an immediate release dosage form given orally.

In some preferred embodiments, the oral dosage form of the invention provides a mean $C_{max}$ of butorphanol which is at least about 5%, 10%, 15%, 20%, 30%, 40%, 50%, 60%, 70%, 80%, 90%, 100%, 120%, 140%, 150%, 180%, 200%, 230%, 260%, or 300% lower than the mean $C_{max}$ after the same amount of an intranasal formulation of butorphanol or an immediate release dosage form given orally.

In some preferred embodiments, the oral dosage form of the invention provides a ratio of mean $AUC_{0-14}$ of hydroxybutorphanol to butorphanol after the first dose which is at least about 5%, 10%, 15%, 20%, 30%, 40%, 50%, 60%, 70%, 80%, 90%, 100%, 120%, 140%, 150%, 180%, 200%, 230%, 260%, or 300% greater than the said ratio after the same amount of an intranasal formulation of butorphanol, each given according to its intended route of administration.

In some preferred embodiments, the oral dosage form of the invention provides a ratio of mean $AUC_{0-24}$ of hydroxybutorphanol to butorphanol after the first dose which is at least about 5%, 10%, 15%, 20%, 30%, 40%, 50%, 60%, 70%, 80%, 90%, 100%, 120%, 140%, 150%, 180%, 200%, 230%, 260%, or 300% greater than the said ratio after the same amount of an intranasal formulation of butorphanol, each given according to its intended route of administration.

In some preferred embodiments, the oral dosage form of the invention provides a ratio of mean $AUC_{0-36}$ of hydroxybutorphanol to butorphanol after the first dose which is at least about 5%, 10%, 15%, 20%, 30%, 40%, 50%, 60%, 70%, 80%, 90%, 100%, 120%, 140%, 150%, 180%, 200%, 230%, 260%, or 300% greater than the said ratio after the same amount of an intranasal formulation of butorphanol, each given according to its intended route of administration.

In some preferred embodiments, the oral dosage form of the invention provides a ratio of mean $AUC_{0-48}$ of hydroxybutorphanol to butorphanol after the first dose which is at least about 5%, 10%, 15%, 20%, 30%, 40%, 50%, 60%, 70%, 80%, 90%, 100%, 120%, 140%, 150%, 180%, 200%, 230%, 260%, or 300% greater than the said ratio after the same amount of an intranasal formulation of butorphanol, each given according to its intended route of administration.

In some preferred embodiments, the oral dosage form of the invention provides a ratio of mean $AUC_{0-60}$ of hydroxybutorphanol to butorphanol after the first dose which is at least about 5%, 10%, 15%, 20%, 30%, 40%, 50%, 60%, 70%, 80%, 90%, 100%, 120%, 140%, 150%, 180%, 200%, 230%, 260%, or 300% greater than the said ratio after the same amount of an intranasal formulation of butorphanol, each given according to its intended route of administration.

In some preferred embodiments, the oral immediate release and oral extended release dosage forms provide a ratio of mean $AUC_{0-12}$, or $AUC_{0-24}$, or $AUC_{0-48}$ of hydroxybutorphanol to butorphanol after the first dose which is at least about 5%, 10%, 15%, 20%, 30%, 40%, 50%, 60%, 70%, 80%, 90%, 100%, 120%, 140%, 150%, 180%, 200%, 230%, 260%, or 300% greater than the said ratio after intranasal butorphanol, each given according to its intended route and method of administration.

In some preferred embodiments, the oral immediate release and oral extended release dosage forms provides a ratio of mean $AUC_{0-24}$, or $AUC_{0-36}$, or $AUC_{0-48}$, or $AUC_{0-72}$ of hydroxybutorphanol to butorphanol after the first dose which is at least about 5%, 10%, 15%, 20%, 30%, 40%, 50%, 60%, 70%, 80%, 90%, 100%, 120%, 140%, 150%, 180%, 200%, 230%, 260%, or 300% greater than the said ratio after a intranasal formulation of butorphanol, each given according to its intended route and method of administration.

In some preferred embodiments, the oral extended release dosage form provides a ratio of mean $AUC_{0-24}$, or $AUC_{0-36}$, or $AUC_{0-48}$, or $AUC_{0-72}$ of hydroxybutorphanol to butorphanol after the first dose which is at least about 5%, 10%, 15%, 20%, 30%, 40%, 50%, 60%, 70%, 80%, 90%, 100%, 120%, 140%, 150%, 180%, 200%, 230%, 260%, or 300% less than the said ratio after the same amount of an oral immediate release formulation of butorphanol.

In some preferred embodiments, the oral extended release dosage form provides a mean extent of absorption (as measured by $AUC_{0-24}$, or $AUC_{0-36}$, or $AUC_{0-48}$, or $AUC_{0-72}$) of butorphanol after the first dose which is at least about 5%, 10%, 15%, 20%, 30%, or 40% greater than the said ratio after the same amount of an oral immediate release formulation of butorphanol.

In some preferred embodiments, the ratio of the mean ratio of the extent of absorption (as measured by $AUC_{0-24}$, or $AUC_{0-36}$, or $AUC_{0-48}$, or $AUC_{0-72}$) of hydroxybutorphanol to butorphanol oral extended release butorphanol after the first dose is at least about 5%, 10%, 15%, 20%, 30%, 40%, 50%, 60%, 70%, 80%, 90%, 100%, 120%, 140%, 150%, 180%, 200%, 230%, 260%, or 300% less than the said ratio after the first dose of the same amount of an oral immediate release formulation of butorphanol.

In some preferred embodiments, the oral dosage form of the invention provides a mean drowsiness score in butorphanol and opioid naïve subjects which is at least about 5%, 10%, 15%, 20%, 30%, 40%, 50%, 60%, 70%, 80%, 90%, 100%, 120%, 140%, 150%, 180%, 200%, 230%, 260%, or 300% lower than the mean drowsiness score after the same amount of an intranasal formulation of butorphanol or an immediate release dosage form given orally.

In some preferred embodiments, the oral dosage form of the invention provides a mean dizziness score in butorphanol and opioid naïve subjects which is at least about 5%, 10%, 15%, 20%, 30%, 40%, 50%, 60%, 70%, 80%, 90%, 100%, 120%, 140%, 150%, 180%, 200%, 230%, 260%, or 300% lower than the mean drowsiness score after the same amount of an intranasal formulation of butorphanol or an immediate release dosage form given orally.

In some preferred embodiments, the oral dosage form of the invention provides a mean nausea score which is at least about 5%, 10%, 15%, 20%, 30%, 40%, 50%, 60%, 70%, 80%, 90%, 100%, 120%, 140%, 150%, 180%, 200%, 230%, 260%, or 300% lower than the mean nausea score after the same amount of an intranasal formulation of butorphanol or an immediate release dosage form given orally.

In some preferred embodiments, the oral dosage form of the invention provides a mean dizziness score in butorphanol and opioid naïve subjects which is at least about 5%, 10%, 15%, 20%, 30%, 40%, 50%, 60%, 70%, 80%, 90%, 100%, 120%, 140%, 150%, 180%, 200%, 230%, 260%, or 300% lower than the mean vomiting score after the same amount of an intranasal formulation of butorphanol or an immediate release dosage form given orally.

In some preferred embodiments, the oral dosage form of the invention provides a mean driving simulation impairment score in butorphanol and opioid naïve subjects which is at least about 5%, 10%, 15%, 20%, 30%, 40%, 50%, 60%, 70%, 80%, 90%, 100%, 120%, 140%, 150%, 180%, 200%, 230%, 260%, or 300% lower than the mean driving simulation impairment score after the same amount of an intranasal formulation of butorphanol or an immediate release dosage form given orally.

In some preferred embodiments, the oral dosage form of the invention provides a mean number needed to harm (NNH) due to moderate to severe sedation or drowsiness in opioid naïve subjects which is at least about 5%, 10%, 15%, 20%, 30%, 40%, 50%, 60%, 70%, 80%, 90%, 100%, 120%, 140%, 150%, 180%, 200%, 230%, 260%, or 300% lower than said score after an equal amount (or dose) or lower amount (or dose) of intranasal formulation of butorphanol or an immediate release dosage form given orally.

In some preferred embodiments, the oral dosage form of the invention provides a mean number needed to harm (NNH) due to moderate or severe nausea in opioid naïve subjects which is at least about 5%, 10%, 15%, 20%, 30%, 40%, 50%, 60%, 70%, 80%, 90%, 100%, 120%, 140%, 150%, 180%, 200%, 230%, 260%, or 300% lower than said score after an equal amount (or dose) or lower amount (or dose) of intranasal formulation of butorphanol or an immediate release dosage form given orally.

In some preferred embodiments, the oral dosage form of the invention provides a mean number needed to harm (NNH) due to dizziness in opioid naïve subjects which is at least about 5%, 10%, 15%, 20%, 30%, 40%, 50%, 60%, 70%, 80%, 90%, 100%, 120%, 140%, 150%, 180%, 200%, 230%, 260%, or 300% lower than said score after an equal amount (or dose) or lower amount (or dose) of intranasal formulation of butorphanol or an immediate release dosage form given orally.

In some preferred embodiments, the oral dosage form of the invention provides a mean "drug effects" score in opioid abusers or recreational opioid users which is at least about 5%, 10%, 15%, 20%, 30%, 40%, 50%, 60%, 70%, 80%, 90%, 100%, 120%, 140%, 150%, 180%, 200%, 230%, 260%, or 300% lower than said score after an equal amount (or dose) or lower amount (or dose) of intranasal formulation of butorphanol or an immediate release dosage form given orally.

In some preferred embodiments, the oral dosage form of the invention provides a mean "drug liking" score in opioid abusers or recreational opioid users which is at least about 5%, 10%, 15%, 20%, 30%, 40%, 50%, 60%, 70%, 80%, 90%, 100%, 120%, 140%, 150%, 180%, 200%, 230%, 260%, or 300% lower than said score after an equal amount (or dose) or lower amount (or dose) of intranasal formulation of butorphanol or an immediate release dosage form given orally.

In some preferred embodiments, the oral dosage form of the invention provides a mean "take again" score in opioid abusers or recreational opioid users which is at least about 5%, 10%, 15%, 20%, 30%, 40%, 50%, 60%, 70%, 80%, 90%, 100%, 120%, 140%, 150%, 180%, 200%, 230%, 260%, or 300% lower than said score after an equal amount (or dose) or lower amount (or dose) of intranasal formulation of butorphanol or an immediate release dosage form given orally.

In some preferred embodiments, the oral dosage form of the invention provides a mean "coasting" score in opioid abusers or recreational opioid users which is at least about 5%, 10%, 15%, 20%, 30%, 40%, 50%, 60%, 70%, 80%, 90%, 100%, 120%, 140%, 150%, 180%, 200%, 230%, 260%, or 300% lower than said score after an equal amount (or dose) or lower amount (or dose) of intranasal formulation of butorphanol or an immediate release dosage form given orally.

In some preferred embodiments, the oral dosage form of the invention provides a mean "critical tracking task" impairment score in opioid naïve subjects which is at least about 5%, 10%, 15%, 20%, 30%, 40%, 50%, 60%, 70%, 80%, 90%, 100%, 120%, 140%, 150%, 180%, 200%, 230%, 260%, or 300% lower than said score after an equal amount (or dose) or lower amount (or dose) of intranasal formulation of butorphanol or an immediate release dosage form given orally.

In some preferred embodiments, the oral dosage form of the invention provides a mean "stop signal task" impairment score in opioid naïve subjects which is at least about 5%, 10%, 15%, 20%, 30%, 40%, 50%, 60%, 70%, 80%, 90%, 100%, 120%, 140%, 150%, 180%, 200%, 230%, 260%, or 300% lower than said score after an equal amount (or dose) or lower amount (or dose) of intranasal formulation of butorphanol or an immediate release dosage form given orally.

In some preferred embodiments, the oral dosage form of the invention provides a mean "Tower of London" (TOL) impairment score in opioid naïve subjects which is at least about 5%, 10%, 15%, 20%, 30%, 40%, 50%, 60%, 70%, 80%, 90%, 100%, 120%, 140%, 150%, 180%, 200%, 230%, 260%, or 300% lower than said score after an equal amount (or dose) or lower amount (or dose) of intranasal formulation of butorphanol or an immediate release dosage form given orally.

In some preferred embodiments, the oral dosage form of the invention provides a mean ratio of street price at about 1, or 2, or 3, or 4 or 5, or 6 hours post-dose, after administration of an equal amount or dose of intranasal formulation of butorphanol or an immediate release dosage form given orally to the dosage form of the invention is $\geq 1.10$, $\geq 1.15$, or $\geq 1.25$, or $\geq 1.5$, or $\geq 1.75$, or $\geq 2$, or $\geq 2.5$, or $\geq 3$, or $\geq 3.5$, or $\geq 4$, or $\geq 4.5$, or $\geq 5$, or $\geq 5.5$, or $\geq 6$, or $\geq 6.5$, or $\geq 7$, or $\geq 7.5$, or $\geq 8$, or $\geq 8.5$, or $\geq 9$, or $\geq 9.5$, or $\geq 10$, where "street price" is based the price recreational drug users or drug addicts would be prepared to pay after consuming said butorphanol by the intended method of use or by any method of use.

In some preferred embodiments, the oral dosage form of the invention provides a mean ratio of street price at about 1, or 2, or 3, or 4 or 5, or 6 hours post-dose, after administration of an equal amount or dose of intranasal formulation of butorphanol or an immediate release dosage form given orally to the dosage form of the invention is $\geq 1.10$, $\geq 1.15$, or $\geq 1.25$, or $\geq 1.5$, or $\geq 1.75$, or $\geq 2$, or $\geq 2.5$, or $\geq 3$, or $\geq 3.5$, or $\geq 4$, or $\geq 4.5$, or $\geq 5$, or $\geq 5.5$, or $\geq 6$, or $\geq 6.5$, or $\geq 7$, or $\geq 7.5$, or $\geq 8$, or $\geq 8.5$, or $\geq 9$, or $\geq 9.5$, or $\geq 10$, where "street price" is based the price recreational drug users or drug addicts would be prepared to pay after consuming said butorphanol by the intended method of use or by any method of use, and where said butorphanol use is followed about 0.5 to 1.5 hours later by alcohol (ethanol) administration sufficient to maintain a blood alcohol concentration of 0.04% to 0.08%.

In some preferred embodiments, the delayed onset, extended release butorphanol dosage form provides a mean drowsiness score in opioid naïve or opioid inexperienced subjects which is at least about 5%, 10%, 15%, 20%, 30%, 40%, 50%, 60%, 70%, 80%, 90%, 100%, 120%, 140%, 150%, 180%, 200%, 230%, 260%, or 300% lower than the mean drowsiness score after an equal amount (or dose) or lower amount (or dose) of an oral extended release dosage form of butorphanol which is not delayed onset, extended release.

In some preferred embodiments, the delayed onset, extended release butorphanol dosage form provides a mean nausea score in opioid naïve or opioid inexperienced subjects which is at least about 5%, 10%, 15%, 20%, 30%, 40%, 50%, 60%, 70%, 80%, 90%, 100%, 120%, 140%, 150%, 180%, 200%, 230%, 260%, or 300% lower than the mean nausea score after an equal amount (or dose) or lower amount (or dose) of an oral extended release dosage form of butorphanol which is not delayed onset, extended release.

In some preferred embodiments, the delayed onset, extended release butorphanol dosage form provides a mean driving simulation impairment score in opioid naïve or opioid inexperienced subjects which is at least about 5%, 10%, 15%, 20%, 30%, 40%, 50%, 60%, 70%, 80%, 90%, 100%, 120%, 140%, 150%, 180%, 200%, 230%, 260%, or 300% lower than the mean driving simulation impairment score after an equal amount (or dose) or lower amount (or dose) of an oral extended release dosage form of butorphanol which is not delayed onset, extended release.

In some preferred embodiments, the delayed onset, extended release butorphanol dosage form provides a mean "drug effects" score in opioid abusers or recreational opioid users which is at least about 5%, 10%, 15%, 20%, 30%, 40%, 50%, 60%, 70%, 80%, 90%, 100%, 120%, 140%, 150%, 180%, 200%, 230%, 260%, or 300% lower than said score after an equal amount (or dose) or lower amount (or dose) of an oral extended release dosage form of butorphanol which is not delayed onset, extended release.

In some preferred embodiments, the delayed onset, extended release butorphanol dosage form provides a mean "drug liking" score in opioid abusers or recreational opioid users which is at least about 5%, 10%, 15%, 20%, 30%, 40%, 50%, 60%, 70%, 80%, 90%, 100%, 120%, 140%, 150%, 180%, 200%, 230%, 260%, or 300% lower than said score after an equal amount (or dose) or lower amount (or dose) of an oral extended release dosage form of butorphanol which is not delayed onset, extended release.

In some preferred embodiments, the delayed onset, extended release butorphanol dosage form provides a mean "take again" score in opioid abusers or recreational opioid users which is at least about 5%, 10%, 15%, 20%, 30%, 40%, 50%, 60%, 70%, 80%, 90%, 100%, 120%, 140%, 150%, 180%, 200%, 230%, 260%, or 300% lower than said score after an equal amount (or lower amount (or dose) of an oral extended release dosage form of butorphanol which is not delayed onset, extended release.

In some preferred embodiments, the delayed onset, extended release butorphanol dosage form provides a mean "coasting" score in opioid abusers or recreational opioid users which is at least about 5%, 10%, 15%, 20%, 30%, 40%, 50%, 60%, 70%, 80%, 90%, 100%, 120%, 140%, 150%, 180%, 200%, 230%, 260%, or 300% lower than said score after an equal amount (or dose) or lower amount (or dose) of an oral extended release dosage form of butorphanol which is not delayed onset, extended release.

In some preferred embodiments, the delayed onset, extended release butorphanol dosage form provides a mean "critical tracking task" impairment score in opioid naïve or opioid inexperienced subjects which is at least about 5%, 10%, 15%, 20%, 30%, 40%, 50%, 60%, 70%, 80%, 90%, 100%, 120%, 140%, 150%, 180%, 200%, 230%, 260%, or 300% lower than said score after an equal amount (or dose) or lower amount (or dose) of an oral extended release dosage form of butorphanol which is not delayed onset, extended release.

In some preferred embodiments, the delayed onset, extended release butorphanol dosage form provides a mean "stop signal task" impairment score in opioid naïve or opioid inexperienced subjects which is at least about 5%, 10%, 15%, 20%, 30%, 40%, 50%, 60%, 70%, 80%, 90%, 100%, 120%, 140%, 150%, 180%, 200%, 230%, 260%, or 300% lower than said score after an equal amount (or dose) or lower amount (or dose) of an oral extended release dosage form of butorphanol which is not delayed onset, extended release.

In some preferred embodiments, the delayed onset, extended release butorphanol dosage form provides a mean "Tower of London" (TOL) impairment score in opioid naïve or opioid inexperienced subjects which is at least about 5%, 10%, 15%, 20%, 30%, 40%, 50%, 60%, 70%, 80%, 90%, 100%, 120%, 140%, 150%, 180%, 200%, 230%, 260%, or 300% lower than said score after an equal amount (or dose) or lower amount (or dose) of an oral extended release dosage form of butorphanol which is not delayed onset, extended release.

In some preferred embodiments, the ratio of the foregoing mean scores for drowsiness, dizziness score, nausea, driving simulation impairment, "drug effects", "drug liking", "take again", "coasting", "critical tracking task" impairment, "stop signal task" impairment and "Tower of London" (TOL) impairment after extended release dosage form of butorphanol given orally, to the delayed onset, extended release butorphanol dosage form, is at least about 10:1, or 8:1, or 6:1, or 5:1, or 4:1, or 3:1, or 2.5:1, or 2:1, or 1.75:1, or 1.5:1, or 1.25:1, or 1.15:1, wherein the extended release dosage form is given at an equal amount or lower amount.

In some preferred embodiments, the foregoing mean scores for drowsiness, dizziness score, nausea, driving simulation impairment, "drug effects", "drug liking", "take again", "coasting", "critical tracking task" impairment, "stop signal task" impairment and "Tower of London" (TOL) impairment are measured after single administration or first administration. In some other preferred embodiments, the foregoing mean scores for drowsiness, dizziness score, nausea, driving simulation impairment, "drug effects", "drug liking", "take again", "coasting", "critical tracking task" impairment and "Tower of London" (TOL) impairment are measured after repeated dose administration. In some preferred embodiments, the foregoing mean scores for drowsiness, dizziness score, nausea, driving simulation impairment, "drug effects", "drug liking", "take again", "coasting", "critical tracking task" impairment, "stop signal task" impairment and "Tower of London" (TOL) impairment are measured after administration to patients in need of treatment with butorphanol. Most preferably, the foregoing mean scores for drowsiness, dizziness score, nausea, driving simulation impairment, "drug effects", "drug liking", "take again", "coasting", "critical tracking task" impairment, "stop signal task" impairment and "Tower of London" (TOL) impairment are measured after first administration to opioid naïve subjects, between 0.5 to 6 hours after administration of the dosage form.

In some preferred embodiments, the foregoing drowsiness, dizziness score, nausea, driving simulation impairment, "drug effects", "drug liking", "take again", "coasting", "critical tracking task" impairment, "stop signal task" impairment and "Tower of London" (TOL) impairment is assessed at a time 2.5 to 6 hours after administration of the dosage form, following alcohol (ethanol) administration sufficient to maintain a blood alcohol concentration of 0.04% to 0.08%, said ethanol administration 1.5 hours after said dosage form administration, said subjects only occasional or light consumers of alcohol.

In some preferred embodiments, the delayed onset, extended release butorphanol dosage form provides a mean number needed to harm (NNH) due to drowsiness in opioid naïve or opioid inexperienced subjects which is at least about 5%, 10%, 15%, 20%, 30%, 40%, 50%, 60%, 70%, 80%, 90%, 100%, 120%, 140%, 150%, 180%, 200%, 230%, 260%, or 300% lower than said score after an equal amount (or dose) or lower amount (or dose) of an oral extended release dosage form of butorphanol which is not delayed onset, extended release.

In some preferred embodiments, the delayed onset, extended release butorphanol dosage form provides a mean number needed to harm (NNH) due to moderate to severe nausea in opioid naïve or opioid inexperienced subjects which is at least about 5%, 10%, 15%, 20%, 30%, 40%, 50%, 60%, 70%, 80%, 90%, 100%, 120%, 140%, 150%, 180%, 200%, 230%, 260%, or 300% lower than said score after an equal amount (or dose) or lower amount (or dose) of an oral extended release dosage form of butorphanol which is not delayed onset, extended release.

In some preferred embodiments, the delayed onset, extended release butorphanol dosage form provides a mean number needed to harm (NNH) due to dizziness in opioid naïve or opioid inexperienced subjects which is at least about 5%, 10%, 15%, 20%, 30%, 40%, 50%, 60%, 70%, 80%, 90%, 100%, 120%, 140%, 150%, 180%, 200%, 230%, 260%, or 300% lower than said score after an equal amount (or dose) or lower amount (or dose) of an oral extended release dosage form of butorphanol which is not delayed onset, extended release.

In some preferred embodiments, the ratio of the foregoing NNH for drowsiness, nausea and dizziness after extended release dosage form of butorphanol given orally, to the delayed onset, extended release butorphanol dosage form, is at least about 10:1, or 8:1, or 6:1, or 5:1, or 4:1, or 3:1, or 2.5:1, or 2:1, or 1.75:1, or 1.5:1, or 1.25:1, or 1.15:1, wherein the extended release dosage form is given at an equal amount or lower amount.

In some preferred embodiments, the foregoing NNH for drowsiness, nausea and dizziness is assessed at a time 2.5 to 6 hours after administration of the dosage form, following alcohol (ethanol) administration sufficient to maintain a blood alcohol concentration of 0.04% to 0.08%, said ethanol administration 1.5 hours after said dosage form administration, said subjects only occasional or light consumers of alcohol.

In some preferred embodiments, the foregoing NNH for drowsiness, nausea and dizziness are measured after single administration or first administration. In some other preferred embodiments, the foregoing NNH for drowsiness, nausea and dizziness are measured after repeated dose administration. In some preferred embodiments, the foregoing NNH for drowsiness, nausea and dizziness are measured after administration to patients in need of treatment with butorphanol. Most preferably, the foregoing NNH for drowsiness, nausea and dizziness are measured after first administration to opioid naïve subjects, between 0.5 to 6 hours after administration of the dosage form.

As used herein, the phrase "after an equal amount or lower amount of an immediate release dosage form of butorphanol given orally" means an amount of oral immediate release butorphanol which is the equal to or at least up to about 5%, 10%, 15%, 20%, 25%, 30%, 35%, 40%, 45%, 50%, 55%, 60%, 65%, 70%, 75% or 80% less than the dose or amount of extended release butorphanol in the dosage form of the invention, when said amounts are expressed in mass units of unsalified butorphanol.

In some preferred embodiments, the delayed onset, extended release butorphanol dosage form provides a mean ratio of street price at about 1, or 2, or 3, or 4 or 5, or 6 hours post-dose, after administration of an equal amount of an oral extended release dosage form of butorphanol which is not delayed onset, extended release to the dosage form of the invention is ≥1.10, ≥1.15, or ≥1.25, or ≥1.5, or ≥1.75, or ≥2, or ≥2.5, or ≥3, or ≥3.5, or ≥4, or ≥4.5, or ≥5, or ≥5.5, or ≥6, or ≥6.5, or ≥7, or ≥7.5, or ≥8, or ≥8.5, or ≥9, or ≥9.5, or ≥10, where "street price" is based the price recreational drug users or drug addicts would be prepared to pay after consuming said butorphanol by the intended method of use or by any method of use.

In some preferred embodiments, the delayed onset, extended release butorphanol dosage form provides a mean ratio of street price at about 1, or 2, or 3, or 4 or 5, or 6 hours post-dose, after administration of an equal amount of an oral immediate release dosage form or an oral extended release dosage form of butorphanol which is not delayed onset, extended release to the dosage form of the invention is ≥1.10, ≥1.15, or ≥1.25, or ≥1.5, or ≥1.75, or ≥2, or ≥2.5, or ≥3, or ≥3.5, or ≥4, or ≥4.5, or ≥5, or ≥5.5, or ≥6, or ≥6.5, or ≥7, or ≥7.5, or ≥8, or ≥8.5, or ≥9, or ≥9.5, or ≥10, where "street price" is based the price recreational drug users or drug addicts would be prepared to pay after consuming said butorphanol by the intended method of use or by any method of use, and where said butorphanol use is followed about 0.5 to 1.5 hours later by alcohol (ethanol) administration sufficient to maintain a blood alcohol concentration of 0.04% to 0.08%.

In some preferred embodiments, the oral dosage form of the invention provides a relative mean $C_{max}$ whose 90% confidence interval is outside the 80.00% to 125.00, under single-dose fasted test conditions in healthy subjects, when compared with intranasal butorphanol, each given to according to its intended route of administration.

In some preferred embodiments, the oral dosage form of the invention provides a relative mean $C_{max}$ whose 90% confidence interval is outside the 80.00% to 125.00, under single-dose fasted test conditions in healthy subjects, when compared with other available butorphanol dosage forms.

In some preferred embodiments, the oral dosage form of the invention provides a relative mean $C_{max}$ under single-dose fasted test conditions in healthy subjects which is statistically significantly different, when compared with intranasal butorphanol, each given to according to its intended route of administration.

In some preferred embodiments, the oral dosage form of the invention provides a relative mean $C_{max}$ under single-dose fasted test conditions in healthy subjects which is statistically significantly different, when compared with oral ingestion of a conventional solution, suspension, immediate release tablet or capsule.

In some preferred embodiments, the oral dosage form of the invention provides a relative mean $C_{max}$ whose 90% confidence interval is outside the 80.00% to 125.00, under single-dose fasted test conditions in healthy subjects, when compared with intranasal dosage forms of butorphanol dosage forms.

In some preferred embodiments, the oral dosage form of the invention provides a relative mean $C_{max}$ whose 90% confidence interval is outside the 80.00% to 125.00, under single-dose fasted test conditions in healthy subjects, when compared with immediate release oral butorphanol.

In some preferred embodiments, the oral dosage form of the invention provides a relative mean $C_{max}$ whose 90% confidence interval is outside the 80.00% to 125.00, under single-dose fasted test conditions in healthy subjects, when compared with immediate release oral butorphanol solution.

In some preferred embodiments, the oral dosage form of the invention provides a relative mean $AUC_{0-6}$, or $AUC_{0-8}$, or $AUC_{0-12}$, or $AUC_{0-24}$, or $AUC_{0-\tau}$, or $AUC_{0-inf}$ under single-dose fasted test conditions in healthy subjects which is statistically significantly different, when compared with intranasal butorphanol, each given to according to its intended route of administration.

In some preferred embodiments, the oral dosage form of the invention provides a relative mean $AUC_{0-6}$, or $AUC_{0-8}$, or $AUC_{0-12}$, or $AUC_{0-24}$, or $AUC_{0-\tau}$, or $AUC_{0-inf}$ under single-dose fasted test conditions in healthy subjects which is statistically significantly different, when compared with oral ingestion of a conventional solution, suspension, immediate release tablet or capsule.

In some preferred embodiments, the oral dosage form of the invention provides a relative mean $AUC_{0-\tau}$ whose 90% confidence interval is outside the 80.00% to 125.00, under single-dose fasted test conditions in healthy subjects, when compared with intranasal butorphanol.

In some preferred embodiments, the oral dosage form of the invention provides a relative mean $AUC_{0-\tau}$ whose 90% confidence interval is outside the 80.00% to 125.00, under single-dose fasted test conditions in healthy subjects, when compared with intranasal butorphanol, each given to according to its intended route of administration.

In some preferred embodiments, the oral dosage form of the invention provides a relative mean $AUC_{0-\tau}$ whose 90% confidence interval is outside the 80.00% to 125.00, under single-dose fasted test conditions in healthy subjects, when compared with other available butorphanol dosage forms.

In some preferred embodiments, the oral dosage form of the invention provides a relative mean $AUC_{0-\tau}$ whose 90% confidence interval is outside the 80.00% to 125.00, under single-dose fasted test conditions in healthy subjects, when compared with intranasal dosage forms of butorphanol dosage forms.

In some preferred embodiments, the oral dosage form of the invention provides a relative mean $AUC_{0-\tau}$ whose 90% confidence interval is outside the 80.00% to 125.00, under single-dose fasted test conditions in healthy subjects, when compared with immediate release oral butorphanol.

In some preferred embodiments, the oral dosage form of the invention provides a relative mean $AUC_{0-\tau}$ whose 90% confidence interval is outside the 80.00% to 125.00, under single-dose fasted test conditions in healthy subjects, when compared with immediate release oral butorphanol solution.

In some preferred embodiments, the oral dosage form of the invention provides a relative mean $AUC_{0-inf}$ whose 90% confidence interval is outside the 80.00% to 125.00, under single-dose fasted test conditions in healthy subjects, when compared with intranasal butorphanol.

In some preferred embodiments, the oral dosage form of the invention provides a relative mean $AUC_{0-inf}$ whose 90% confidence interval is outside the 80.00% to 125.00, under single-dose fasted test conditions in healthy subjects, when compared with intranasal butorphanol, each given to according to its intended route of administration.

In some preferred embodiments, the oral dosage form of the invention provides a relative mean $AUC_{0-inf}$ whose 90% confidence interval is outside the 80.00% to 125.00, under single-dose fasted test conditions in healthy subjects, when compared with other available butorphanol dosage forms.

In some preferred embodiments, the oral dosage form of the invention provides a relative mean $AUC_{0-inf}$ whose 90% confidence interval is outside the 80.00% to 125.00, under single-dose fasted test conditions in healthy subjects, when compared with intranasal dosage forms of butorphanol dosage forms.

In some preferred embodiments, the oral dosage form of the invention provides a relative mean $AUC_{0-inf}$ whose 90% confidence interval is outside the 80.00% to 125.00, under single-dose fasted test conditions in healthy subjects, when compared with immediate release oral butorphanol.

In some preferred embodiments, the oral dosage form of the invention provides a relative mean $AUC_{0-inf}$ whose 90% confidence interval is outside the 80.00% to 125.00, under single-dose fasted test conditions in healthy subjects, when compared with immediate release oral butorphanol solution.

In some preferred embodiments, the dosage from maintains a plasma butorphanol concentration within 50% of $C_{max}$ for about 1 to about 9 hours, or about 2 to about 9 hours, or about 3 to about 9 hours, or about 4 to about 9 hours, or about 5 to about 9 hours, or about 6 to about 9 hours, or about 1 to about 8 hours, or about 2 to about 8 hours, or about 3 to about 8 hours, or about 4 to about 8 hours, or about 5 to about 8 hours, or about 6 to about 8 hours, or about 2 to about 7 hours, or about 2 to about 6 hours, or about 2 to about 5 hours, or about 2 to about 4 hours, or about 1 to about 4 hours, or about 1 to about 3 hours, or about 2 to about 6 hours, or about 3 to about 5 hours.

In some preferred embodiments, the dosage from maintains a plasma butorphanol concentration within 50% of $C_{max}$ for about 1 to about 9 hours, or about 2 to about 9 hours, or about 3 to about 9 hours, or about 4 to about 9 hours, or about 5 to about 9 hours, or about 6 to about 9 hours, or about 1 to about 8 hours, or about 2 to about 8 hours, or about 3 to about 8 hours, or about 4 to about 8 hours, or about 5 to about 8 hours, or about 6 to about 8 hours, or about 2 to about 7 hours, or about 2 to about 6 hours, or about 2 to about 5 hours, or about 2 to about 4 hours, or about 1 to about 4 hours, or about 1 to about 3 hours, or about 2 to about 6 hours, or about 3 to about 5 hours during a 12 hour dosing interval.

In some preferred embodiments, the dosage from maintains a plasma butorphanol concentration within 50% of $C_{max}$ for about 1 to about 20 hours, or about 1 to about 18 hours or about 1 to about 16 hours, or about 1 to about 14 hours or about 1 to about 10 hours, or about 1 to about 8 hours or about 1 to about 6 hours, or about 1 to about 5 hours or about 2 to about 20 hours, or about 4 to about 20 hours or about 4 to about 18 hours, or about 5 to about 18 hours or about 6 to about 18 hours, or about 7 to about 18 hours or about 8 to about 18 hours, or about 10 to about 18 hours or about 12 to about 18 hours, or about 14 to about 18 hours or about 4 to about 16 hours, or about 4 to about 12 hours or about 4 to about 10 hours, or about 4 to about 8 hours or about 5 to about 15 hours, or about 5 to about 10 hours or about 6 to about 18 hours, or about 6 to about 12 hours or about 6 to about 10 hours, or about 8 to about 18 hours or about 8 to about 16 hours, or about 10 to about 18 hours.

In some preferred embodiments, the dosage from maintains a plasma butorphanol concentration within 50% of $C_{max}$ for about 1 to about 20 hours, or about 1 to about 18 hours or about 1 to about 16 hours, or about 1 to about 14 hours or about 1 to about 10 hours, or about 1 to about 8 hours or about 1 to about 6 hours, or about 1 to about 5 hours or about 2 to about 20 hours, or about 4 to about 20 hours or about 4 to about 18 hours, or about 5 to about 18 hours or about 6 to about 18 hours, or about 7 to about 18 hours or about 8 to about 18 hours, or about 10 to about 18 hours or about 12 to about 18 hours, or about 14 to about 18 hours or about 4 to about 16 hours, or about 4 to about 12 hours or about 4 to about 10 hours, or about 4 to about 8 hours or about 5 to about 15 hours, or about 5 to about 10 hours or about 6 to about 18 hours, or about 6 to about 12 hours or about 6 to about 10 hours, or about 8 to about 18 hours or about 8 to about 16 hours, or about 10 to about 18 hours, during a 24 hour dosing interval.

In some preferred embodiments, the oral pharmaceutical composition of butorphanol or a pharmaceutically dosage from provides a butorphanol $T_{max}$ greater than about 0.25 hours, or greater than about 0.5 hours, or greater than about 0.75 hours, or greater than about 1 hour, or greater than about 1.5 hours, or greater than about 2 hours, or greater than about 2.5 hours, or greater than about 3 hours, or greater than about 3.5 hours, or greater than about 4 hours, or greater than about 4.5 hours, or greater than about 5 hours, or greater than about 6 hours, or greater than about 8 hours, or greater than about 10 hours, or greater than about 12 hours, or greater than about 14 hours, or greater than about 16 hours, or greater than about 17 hours, or greater than about 18 hours, or greater than about 20 hours, or greater than about 22 hours, or greater than about 24 hours.

In some preferred embodiments, the oral pharmaceutical composition of butorphanol or a pharmaceutically dosage from provides a butorphanol $T_{max}$ of about 0.25 to about 8 hours, about 0.5 to about 30 hours, or about 0.5 to about 26 hours, or about 0.5 to about 22 hours, or about 0.5 to about 20 hours, or about 0.5 to about 18 hours, or about 0.5 to about 16 hours, or about 0.5 to about 14 hours, or about 0.5 to about 12 hours, or about 0.5 to about 10 hours, or about 0.5 to about 9 hours, or about 0.5 to about 8 hours, or about 0.5 to about 7 hours, or about 0.5 to about 6 hours, or about 0.5 to about 5 hours, or about 0.5 to about 4 hours, or about 0.5 to about 3 hours, or about 0.5 to about 2 hours, or about 0.5 to about 1 hour, or about 1 to about 30 hours, or about 2 to about 30 hours, or about 3 to about 30 hours, or about 4 to about 30 hours, or about 5 to about 30 hours, or about 6 to about 30 hours, or about 1 to about 24 hours, or about 2 to about 24 hours, or about 3 to about 24 hours, or about 4 to about 24 hours, or about 5 to about 24 hours, or about 6 to about 24 hours, or about 8 to about 24 hours, or about 10 to about 24 hours, or about 12 to about 24 hours, or about 14 to about 24 hours, or about 1.5 to about 16 hours, or about 2 to about 16 hours, or about 2.5 to about 16 hours, or about 3 to about 16 hours, or about 3.5 to about 16 hours, or about 4 to about 16 hours, or about 5 to about 16 hours, or about 6 to about 16 hours, or about 7 to about 16 hours, or about 8 to about 16 hours, or about 10 to about 16 hours, or about 12 to about 16 hours, or about 2 to about 10 hours, or about 2.5 to about 10 hours, or about 3 to about 10 hours, or about 3.5 to about 10 hours, or about 4 to about 10 hours, or about 4.5 to about 10 hours, or about 5 to about 10 hours, or about 6 to about 10 hours, or about 7 to about 10 hours, or about 7.5 to about 10 hours.

In some preferred embodiments, the oral pharmaceutical composition of butorphanol or a pharmaceutically dosage from provides a hydroxybutorphanol $T_{max}$ greater than about 0.25 hours, or greater than about 0.5 hours, or greater than about 0.75 hours, or greater than about 1 hour, or greater than about 1.5 hours, or greater than about 2 hours, or greater than about 2.5 hours, or greater than about 3 hours, or greater than about 3.5 hours, or greater than about 4 hours, or greater than about 4.5 hours, or greater than about 5 hours, or greater than about 6 hours, or greater than about 8 hours, or greater than about 10 hours, or greater than about 12 hours, or greater than about 14 hours, or greater than about 16 hours, or greater than about 17 hours, or greater than about 18 hours, or greater than about 20 hours, or greater than about 22 hours, or greater than about 24 hours.

In some preferred embodiments, the oral pharmaceutical composition of butorphanol or a pharmaceutically dosage from provides a hydroxybutorphanol $T_{max}$ of about 0.25 to about 8 hours, about 0.5 to about 30 hours, or about 0.5 to about 26 hours, or about 0.5 to about 22 hours, or about 0.5 to about 20 hours, or about 0.5 to about 18 hours, or about 0.5 to about 16 hours, or about 0.5 to about 14 hours, or about 0.5 to about 12 hours, or about 0.5 to about 10 hours, or about 0.5 to about 9 hours, or about 0.5 to about 8 hours, or about 0.5 to about 7 hours, or about 0.5 to about 6 hours, or about 0.5 to about 5 hours, or about 0.5 to about 4 hours, or about 0.5 to about 3 hours, or about 0.5 to about 2 hours, or about 0.5 to about 1 hour, or about 1 to about 30 hours, or about 2 to about 30 hours, or about 3 to about 30 hours, or about 4 to about 30 hours, or about 5 to about 30 hours, or about 6 to about 30 hours, or about 1 to about 24 hours, or about 2 to about 24 hours, or about 3 to about 24 hours, or about 4 to about 24 hours, or about 5 to about 24 hours, or about 6 to about 24 hours, or about 8 to about 24 hours, or about 10 to about 24 hours, or about 12 to about 24 hours, or about 14 to about 24 hours, or about 1.5 to about 16 hours, or about 2 to about 16 hours, or about 2.5 to about 16 hours, or about 3 to about 16 hours, or about 3.5 to about 16 hours, or about 4 to about 16 hours, or about 5 to about 16 hours, or about 6 to about 16 hours, or about 7 to about 16 hours, or about 8 to about 16 hours, or about 10 to about 16 hours, or about 12 to about 16 hours, or about 2 to about 10 hours, or about 2.5 to about 10 hours, or about 3 to about 10 hours, or about 3.5 to about 10 hours, or about 4 to about 10 hours, or about 4.5 to about 10 hours, or about 5 to about 10 hours, or about 6 to about 10 hours, or about 7 to about 10 hours, or about 7.5 to about 10 hours.

In some preferred embodiments, the oral dosage form of the invention provides a mean in vivo extent of absorption of butorphanol from 0 to 4 hours which is at least 20% of the mean in vivo extent of absorption from to 0 to 12 hours, wherein the mean in vivo extent of absorption is the area under the plasma or serum butorphanol concentration time curve from the time of drug administration to the specified time point.

In some preferred embodiments, the oral dosage form of the invention provides a mean in vivo extent of absorption of butorphanol from 0 to 8 hours which is at least 20% of the mean in vivo extent of absorption from to 0 to 24 hours, wherein the mean in vivo extent of absorption is the area under the plasma or serum butorphanol concentration time curve from the time of drug administration to the specified time point.

In some preferred embodiments, the oral dosage form of the invention provides a mean in vivo extent of absorption of butorphanol over the dosing interval (e.g., from 0 to 12 hours or from 0 to 24 hours) which is at least 40% of the mean in vivo extent of absorption from to 0 to infinity, wherein the mean in vivo extent of absorption is the area under the plasma or serum butorphanol concentration time curves (AUC) from the time of drug administration to the specified time point and where AUC infinity is the sum of AUC from time "0" to time "t" (the last quantifiable time point which has been sampled) plus the extrapolated AUC from the last quantifiable sampling time point to infinity.

In some preferred embodiments, the oral butorphanol dosage form provides a mean in vivo extent of absorption of butorphanol from about 0 to about 2 hours, or about 0 to about 3 hours, or about 0 to about 4 hours, or about 0 to about 5 hours, or about 0 to about 6 hours, which is ≤about 1% of the mean in vivo extent of absorption from to 0 to 12 hours, wherein the mean in vivo extent of absorption is the area under the plasma or serum butorphanol concentration time curve from the time of drug administration to the specified time point. In other embodiments, said in vivo extent of absorption from about 0 to about 2 hours, or about 0 to about 3 hours, or about 0 to about 4 hours, or about 0 to about 5 hours, or about 0 to about 6 hours is ≤about 2%, or ≤about 3%, or ≤about 4%, or ≤about 5%, or ≤about 6%, or ≤about 7%, or ≤about 8%, or ≤about 9%, or ≤about 10%, or ≤about 12%, or ≤about 14%, or ≤about 15%, or ≤about 16%, or ≤about 18%, or ≤about 20%, or ≤about 25%, or ≤about 30%, or ≤about 35% of the mean in vivo extent of absorption from to 0 to 12 hours.

In some preferred embodiments, the oral butorphanol dosage form provides a mean in vivo extent of absorption of butorphanol from about 0 to about 2 hours, or about 0 to about 3 hours, or about 0 to about 4 hours, or about 0 to about 5 hours, or about 0 to about 6 hours, which is ≤about 1% of the mean in vivo extent of absorption from to 0 to 24 hours, wherein the mean in vivo extent of absorption is the area under the plasma or serum butorphanol concentration time curve from the time of drug administration to the specified time point. In other embodiments, said in vivo extent of absorption from about 0 to about 2 hours, or about 0 to about 3 hours, or about 0 to about 4 hours, or about 0 to about 5 hours, or about 0 to about 6 hours is ≤about 2%, or ≤about 3%, or ≤about 4%, or ≤about 5%, or ≤about 6%, or ≤about 7%, or ≤about 8%, or ≤about 9%, or ≤about 10%, or ≤about 12%, or ≤about 14%, or ≤about 15%, or ≤about 16%, or ≤about 18%, or ≤about 20%, or ≤about 25%, or ≤about 30%, or ≤about 35% of the mean in vivo extent of absorption from to 0 to 24 hours.

In some preferred embodiments, the oral butorphanol dosage form provides a mean in vivo extent of absorption of butorphanol from about 0 to about 7 hours, or about 0 to about 8 hours, or about 0 to about 9 hours, or about 0 to about 10 hours, which is ≤about 1% of the mean in vivo extent of absorption from to 0 to 24 hours, wherein the mean in vivo extent of absorption is the area under the plasma or serum butorphanol concentration time curve from the time of drug administration to the specified time point. In other embodiments, said in vivo extent of absorption from about 0 to about 7 hours, or about 0 to about 8 hours, or about 0 to about 9 hours, or about 0 to about 10 hours is ≤about 2%, or ≤about 3%, or ≤about 4%, or ≤about 5%, or ≤about 6%, or ≤about 7%, or ≤about 8%, or ≤about 9%, or ≤about 10%, or ≤about 12%, or ≤about 14%, or ≤about 15%, or ≤about 16%, or ≤about 18%, or ≤about 20%, or ≤about 25% or ≤about 30% or ≤about 35%, or ≤about 40%, or ≤about 45%, or ≤about 50% of the mean in vivo extent of absorption from to 0 to 24 hours.

In some preferred embodiments, the oral butorphanol dosage form provides a mean in vivo extent of absorption of butorphanol from about 0 to about 2 hours, or about 0 to about 3 hours, or about 0 to about 4 hours, or about 0 to about 5 hours, or about 0 to about 6 hours, or about 0 to about 7 hours, or about 0 to about 8 hours, or about 0 to about 9 hours, or about 0 to about 10 hours, which is ≤about 1% of the mean in vivo extent of absorption from to 0 to 36 hours, wherein the mean in vivo extent of absorption is the area under the plasma or serum butorphanol concentration time curve from the time of drug administration to the specified time point. In other embodiments, said in vivo extent of absorption from about 0 to about 2 hours, or about 0 to about 3 hours, or about 0 to about 4 hours, or about 0 to about 5 hours, or about 0 to about 6 hours, or about 0 to about 7 hours, or about 0 to about 8 hours, or about 0 to about 9 hours, or about 0 to about 10 hours is ≤about 2%, or ≤about 3%, or ≤about 4%, or ≤about 5%, or ≤about 6%, or ≤about 7%, or ≤about 8%, or ≤about 9%, or ≤about 10%, or ≤about 12%, or ≤about 14%, or ≤about 15%, or ≤about 16%, or ≤about 18%, or ≤about 20%, or ≤about 25% or ≤about 30% or ≤about 35%, or ≤about 35%, or ≤about 40% or ≤about 45%, or ≤about 50%, or ≤about 60% of the mean in vivo extent of absorption from to 0 to 36 hours.

Resistance to Alcohol Associated Dose Dumping

Another aspect of the invention provides for dosage forms of extended release butorphanol which are resistant to alcohol induced dose dumping. Extended release opioids which do not evidence dose dumping in relation to alcohol intake, which do not evidence clinically significant changes in rate or extent of absorption in relation to alcohol intake, which do not evidence clinically significant pharmacodynamic variability in relation to alcohol intake, and which do not evidence bio-inequivalence of the dosage form when given with or without alcohol provide a significant therapeutic advantage.

In 2005, a serious new clinical problem arose with the therapeutic use of extended release opioids, particularly extended release multiparticulate capsule dosage forms, when co-ingested with alcohol. Although subjects with chronic pain are discouraged from using opioids with alcohol, such co-ingestion in the setting of intractable pain is rather widespread. In addition, when used for non-medical purposes (e.g., to obtain a euphoric effect by recreational drug users), opioids are often used concomitantly with alcohol. This co-ingestion provides additional mood altering effects desired by the non-medical user. Regardless of whether the concomitant use of opioids and alcohol is for medical or non-medical purposes, any impact of alcohol on the integrity of an extended release dosage form of an opioid can produce additional toxicity from alcohol induced dose dumping.

The problem of alcohol induced dose dumping for extended release opioids was discovered with a once-a-day extended release multiparticulate formulation of hydromorphone HCL (Palladone™ capsules). Palladone™ was introduced in the United States and Canada in 2004. In 2005, Palladone™ was withdrawn from the market in both countries due to dose-dumping when co-ingested with alcohol. Patients consuming Palladone™ with 240 mL of 40% ethanol had a 6-fold mean increase in peak plasma hydromorphone concentration compared with co-ingestion with water. One subject experienced a 16-fold increase. Patients consuming 240 mL of 20% ethanol had a 2-fold mean increase in peak plasma hydromorphone concentration. One subject experienced a 6-fold increase. In some subjects, 8 ounces of 4% alcohol (equivalent to ⅔ of a typical serving of beer) resulted in almost twice the peak plasma hydromorphone concentration. In requesting the withdrawal of Palladone™, FDA noted that the manufacturer of "drinking alcohol while taking Palladone™ capsules may cause rapid release of hydromorphone, leading to high drug levels in the body, with potentially fatal effects. High drug levels of hydromorphone may depress or stop breathing, cause coma, and even cause death. The Agency has concluded that the overall risk versus benefit profile of Palladone™ is unfavorable due to a potentially fatal interaction with alcohol. Pharmacokinetic data indicate that the co-ingestion of Palladone™ and alcohol results in dangerous increases in the peak plasma concentrations of hydromorphone. These elevated levels may be lethal, even in opioid tolerant patients." (Sloan and Babul, Expert Opinion on Drug Delivery 2006; 3:489-97)

FDA has since noted that a number of other controlled release opioids may be similarly vulnerable to dose dumping when co-ingested with alcohol. In vitro studies of alcohol dose dumping studies performed by the FDA demonstrated that Avinza™ (once-daily extended release morphine) release was alcohol concentration-dependent, leading to a more rapid release of morphine. FDA the mandated a "Black Box" warning which states "consumption of alcohol while taking Avinza may result in the rapid release and absorption of a potentially fatal dose of morphine" (Sloan and Babul, Expert Opinion on Drug Delivery 2006; 3:489-97; Avinza U.S. Prescribing Information, April, 2008). Similarly, when evaluated with alcohol, Opana™ ER (twice-daily extended release oxymorphone) demonstrates significant dose dumping. The mean oxymorphone peak plasma concentration increase was 70% and 31%, after concomitant administration of 240 mL of 40% and 20% ethanol, respectively. In individual subjects, oxymorphone peak plasma concentrations increased by up to about 260%. Similarly, the mean extent of absorption was numerically higher by 13% after co-administration of 240 mL of 40% alcohol (U.S. Prescribing Information for Opana™ ER).

In some preferred embodiments, the invention provides a method of protecting from ethanol induced dose-dumping in a population which includes subjects that can be expected to at least occasionally co-ingest the dosage form with ethanol comprising administering a therapeutically effective amount of oral butorphanol and a controlled release material to render said dosage form delayed onset, extended release.

In some preferred embodiments, the invention provides a method of protecting from ethanol induced dose-dumping in a population which includes subjects that can be expected to at least occasionally co-ingest the dosage form with ethanol comprising administering a therapeutically effective amount of oral butorphanol and a controlled release material to render said dosage form extended release suitable for twice-a-day (Q12H or Q12H PRN) or once-a-day (QD, Q24H or Q24H PRN) administration to a human patient, wherein, upon co-ingestion with 120 mL of a 40% solution of ethanol, said dosage form provides a mean $C_{max}$ difference of less than about 90% when compared with the same dose of said dosage given with 120 mL of water. In other embodiments, the foregoing volume of ethanol and water is 180 mL or 240 mL. In other embodiments, the foregoing mean $C_{max}$ difference is less than about 80%, or less than about 70%, or less than about 60%, or less than about 50%, or less than about 45%, or less than about 40%, or less than about 35%, or less than about 30%, or less than about 25%, or less than about 20%, or less than about 15%.

In some preferred embodiments, the invention provides a method of protecting from ethanol induced dose-dumping in a population which includes subjects that can be expected to at least occasionally co-ingest the dosage form with ethanol comprising administering a therapeutically effective amount of oral butorphanol and a controlled release material to render said dosage form extended release suitable for twice-a-day (Q12H or Q12H PRN) or once-a-day (QD, Q24H or Q24H PRN) administration to a human patient, wherein, upon co-ingestion with 120 mL of a 40% solution of ethanol, said dosage form provides a mean area under the plasma butorphanol concentration time curve from 0 to one hour after dosing ($AUC_{0-1\ hour}$) difference of less than about 90% when compared with the same dose of said dosage given with 120 mL of water. In other embodiments, the foregoing volume of ethanol and water is 180 mL or 240 mL. In other embodiments, the foregoing mean $AUC_{0-1\ hour}$ difference is less than about 80%, or less than about 70%, or less than about 60%, or less than about 50%, or less than about 45%, or less than about 40%, or less than about 35%, or less than about 30%, or less than about 25%, or less than about 20%, or less than about 15%. In other embodiments, the foregoing area under the plasma concentration time curve is from zero to two hours after dosing ($AUC_{0-2\ hour}$). In other embodiments, the foregoing area under the plasma concentration time curve is from zero to three hours after dosing ($AUC_{0-3\ hour}$).

In some preferred embodiments, the dosage form comprises an oral pharmaceutical composition comprising a therapeutically effective amount of butorphanol and a controlled release material to render said dosage form extended release administration wherein the butorphanol $C_{max}$ is substantially independent of alcohol intake in that a difference, at any given time, between the mean $C_{max}$ of butorphanol administered with about 30 mL to about 240 mL of a 40% ethanol solution and the mean $C_{max}$ of butorphanol administered without concurrent alcohol (i.e., in an alcohol free state) is less than about 90%. In other preferred embodiments, said difference in mean $C_{max}$ of butorphanol is less than about 80%, or less than about 70%, or less than about 60%, or less than about 50%, or less than about 45%, or less than about 40%, or less than about 35%, or less than about 30%, or less than about 25%, or less than about 20%, or less than about 15%.

In some preferred embodiments, the dosage form comprises an oral pharmaceutical composition comprising a therapeutically effective amount of butorphanol and a controlled release material to render said dosage form extended release administration wherein the difference in mean area under the plasma butorphanol concentration time curve from 0 to one hour after dosing ($AUC_{0-1\ hour}$) is substantially independent of alcohol intake in that a difference between the mean butorphanol $AUC_{0-1\ hour}$ with about 30 mL to about 240 mL of a 40% ethanol solution and with an equal amount of water (i.e., in an alcohol free state) is less than about 90%. In other preferred embodiments, said difference in mean $AUC_{0-1\ hour}$ of butorphanol is less than about 80%, or less than about 70%, or less than about 60%, or less than about 50%, or less than about 45%, or less than about 40%, or less than about 35%, or less than about 30%, or less than about 25%, or less than about 20%, or less than about 15%. In other embodiments, the foregoing area under the plasma concentration time curve is from zero to two hours after dosing ($AUC_{0-2\ hour}$). In other embodiments, the foregoing area under the plasma concentration time curve is from zero to three hours after dosing ($AUC_{0-3\ hour}$).

Resistance to Food Associated Dose Dumping

Another aspect of the invention provides for dosage forms of extended release butorphanol which are resistant to fed fasted pharmacokinetic variability. Extended release opioids which do not evidence dose dumping in relation to food intake, which do not evidence clinically significant changes in rate or extent of absorption in relation to food intake, which do not evidence clinically significant pharmacodynamic variability in relation to food intake, and which do not evidence bio-inequivalence of the dosage form when given in a fed or fasted state provide a significant therapeutic advantage.

An important issue with oral extended release products is its potential for "dose dumping" in relation to food, where the active drug, intended for slow release, is instead released rapidly, resulting in toxicity on the one hand and a decreased duration of effect on the other. Concurrent intake of food may increase, decrease or have no effect on the bioavailability of pharmaceutical products. The ability to resist food related changes in bioavailability is both a therapeutic benefit and a competitive marketing advantage.

Many commercialized extended release opioids have been shown to have a significant food effect. For example, the U.S. prescribing information for OxyContin™ (oxycodone ER) states "Food has no significant effect on the extent of absorption of oxycodone from OxyContin. However, the peak plasma concentration of oxycodone increased by 25% when an OxyContin 160 mg Tablet was administered with a high-fat meal".

The U.S. prescribing information for Avinza (morphine ER) states "When a 60 mg dose of AVINZA was administered immediately following a high fat meal, peak morphine concentrations and AUC values were similar to those observed when the dose of AVINZA was administered in a fasting state, although achievement of initial concentrations was delayed by approximately 1 hour under fed conditions."

According to the FDA "food caused a 16.9% increase in Cmax shifting $t_{max}$ from 21.06 hour to 8.54 hour" with Palladone™ (hydromorphone ER), (Palladone™ New Drug Application No. 21-044, FDA Summary Basis for Approval).

The U.S. prescribing information for Kadian™ (morphine ER) states "While concurrent administration of food slows the rate of absorption of KADIAN™, the extent of absorption is not affected and KADIAN™ can be administered without regard to meals".

The U.S. prescribing information for Opana™ ER (oxymorphone ER) states "two studies examined the effect of food on the bioavailability of single doses of 20 and 40 mg of OPANA ER in healthy volunteers. In both studies, after the administration of OPANA ER, the $C_{max}$ was increased by approximately 50% in fed subjects compared to fasted subjects. A similar increase in $C_{max}$ was also observed with oxymorphone solution."

Fed-fasted effects on oral bioavailability of extended release opioids are not limited to dose dumping in the presence of food or a high fat meal. For example, an extended release abuse deterrent dosage form of oxycodone (Remoxy™) which is currently under FDA review for marketing authorization purportedly has adequate bioavailability when taken with food but also purportedly has reduced bioavailability in the fasted state. The manufacturer of Remoxy™ states that "a food effect study indicated that administration with food has a significant effect on the rate and extent of absorption of oxycodone. The rate of absorption is slower and the extent of absorption is higher; REMOXY should therefore be taken with food" (NDA 22-324, REMOXY XRT™, FDA Advisory Committee Briefing Materials for the Anesthetic Life Support Drugs Advisory Committee Meeting of Nov. 13, 2008). A poster presentation on Remoxy™ at scientific meeting suggests more than a doubling of its extent of absorption ($AUC_{0-48}$) in relation to food status (Friedmann et al, Remoxy™, A Novel Drug Candidate, Deters Oxycodone Abuse in Humans, World Institute of Pain Meeting, Barcelona, 2004).

In some preferred embodiments, the invention provides a method of protecting from food induced dose-dumping and food associated variability in bioavailability comprising administering a therapeutically effective amount of oral butorphanol and a controlled release material to render said dosage form delayed onset, extended release.

In some preferred embodiments, the invention provides a method of reducing the variability in bioavailability when taken with food, compared with the fasted state, comprising administering a therapeutically effective amount of oral butorphanol and a controlled release material to render said dosage form extended release suitable for twice-a-day (Q12H or Q12H PRN) or once-a-day (QD, Q24H or Q24H PRN) administration to a human patient, wherein the mean butorphanol $C_{max}$ is substantially independent of food intake in that a difference, at any given time, between the $C_{max}$ of butorphanol administered in fasted state and the mean $C_{max}$ of butorphanol administered in fed state (using a standardized meal) is less than about 90%. In other preferred embodiments, said difference in the mean $C_{max}$ of butorphanol is less than about 80%, or less than about 70%, or less than about 60%, or less than about 50%, or less than about 45%, or less than about 40%, or less than about 35%, or less than about 30%, or less than about 25%, or less than about 20%, or less than about 15%.

In some preferred embodiments, the invention provides a method of reducing the variability in bioavailability when taken with food, compared with the fasted state, comprising administering a therapeutically effective amount of oral butorphanol and a controlled release material to render said dosage form extended release suitable for twice-a-day (Q12H or Q12H PRN) or once-a-day (QD, Q24H or Q24H PRN) administration to a human patient, mean area under the plasma butorphanol concentration time curve from 0 to one hour after dosing ($AUC_{0-1\ hour}$) is substantially independent of food intake in that a difference, at any given time, between the $AUC_{0-1\ hour}$ of butorphanol administered in fasted state and the mean $AUC_{0-1\ hour}$ of butorphanol administered in fed state (using a standardized meal) is less than about 90%. In other preferred embodiments, said difference in the mean $AUC_{0-1\ hour}$ of butorphanol is less than about 80%, or less than about 70%, or less than about 60%, or less than about 50%, or less than about 45%, or less than about 40%, or less than about 35%, or less than about 30%, or less than about 25%, or less than about 20%, or less than about 15%. In other embodiments, the foregoing area under the plasma concentration time curve is from zero to two hours after dosing ($AUC_{0-2\ hour}$). In other embodiments, the foregoing area under the plasma concentration time curve is from zero to three hours after dosing ($AUC_{0-3\ hour}$).

In some preferred embodiments, the invention provides a method of reducing the variability in bioavailability when taken with food, compared with the fasted state, comprising administering a therapeutically effective amount of oral butorphanol and a controlled release material to render said dosage form extended release suitable for twice-a-day (Q12H or Q12H PRN) or once-a-day (QD, Q24H or Q24H PRN) administration to a human patient, mean area under the plasma butorphanol concentration time ($AUC_{0-12}$) is substantially independent of food intake in that a difference, at any given time, between the $AUC_{0-12}$ of butorphanol administered in fasted state and the mean $AUC_{0-12}$ of butorphanol administered in fed state (using a standardized meal) is less than about 90%. In other preferred embodiments, said difference in the mean $AUC_{0-12}$ of butorphanol is less than about 80%, or less than about 70%, or less than about 60%, or less than about 50%, or less than about 45%, or less than about 40%, or less than about 35%, or less than about 30%, or less than about 25%, or less than about 20%, or less than about 15%. In other embodiments, the foregoing area under the plasma concentration time curve is $AUC_{0-24\ hours}$. In other embodiments, the foregoing area under the plasma concentration time curve is $AUC_{0-inf}$.

In some preferred embodiments, the dosage form comprises an oral pharmaceutical composition comprising a therapeutically effective amount of butorphanol and a controlled release material to render said dosage form extended release administration wherein the mean butorphanol $C_{max}$ is substantially independent of food intake in that a difference, at any given time, between the $C_{max}$ of butorphanol administered in fasted state and the mean $C_{max}$ of butorphanol administered in fed state (using a standardized meal) is less than about 90%. In other preferred embodiments, said difference in the mean $C_{max}$ of butorphanol is less than about 80%, or less than about 70%, or less than about 60%, or less than about 50%, or less than about 45%, or less than about 40%, or less than about 35%, or less than about 30%, or less than about 25%, or less than about 20%, or less than about 15%.

In some preferred embodiments, the dosage form comprises an oral pharmaceutical composition comprising a therapeutically effective amount of butorphanol and a controlled release material to render said dosage form extended release administration wherein the mean area under the plasma butorphanol concentration time curve from 0 to one hour after dosing ($AUC_{0-1\ hour}$) is substantially independent wherein the mean butorphanol $AUC_{0-hour}$ is substantially independent of food intake in that a difference, at any given time, between the $AUC_{0-1\ hour}$ of butorphanol administered in fasted state and the mean $AUC_{0-1\ hour}$ of butorphanol administered in fed state (using a standardized meal) is less than about 90%. In other preferred embodiments, said difference in the mean $AUC_{0-1\ hour}$ of butorphanol is less than about 80%, or less than about 70%, or less than about 60%, or less than about 50%, or less than about 45%, or less than about 40%, or less than about 35%, or less than about 30%, or less than about 25%, or less than about 20%, or less than about 15%. In other embodiments, the foregoing area under the plasma concentration time curve is from zero to two hours after dosing ($AUC_{0-2\ hour}$). In other embodiments, the foregoing area under the plasma concentration time curve is from zero to three hours after dosing ($AUC_{0-3\ hour}$).

In some preferred embodiments, the dosage form comprises an oral pharmaceutical composition comprising a therapeutically effective amount of butorphanol and a controlled release material to render said dosage form extended release administration wherein the mean area under the plasma butorphanol concentration time curve ($AUC_{0-12}$) is substantially independent of food intake in that a difference, at any given time, between the $AUC_{0-12}$ of butorphanol administered in fasted state and the mean $AUC_{0-12}$ of butorphanol administered in fed state (using a standardized meal) is less than about 90%. In other preferred embodiments, said difference in the mean $AUC_{0-12}$ of butorphanol is less than about 80%, or less than about 70%, or less than about 60%, or less than about 50%, or less than about 45%, or less than about 40%, or less than about 35%, or less than about 30%, or less than about 25%, or less than about 20%, or less than about 15%. In other embodiments, the foregoing area under the plasma concentration time curve is $AUC_{0-24\ hours}$. In other embodiments, the foregoing area under the plasma concentration time curve is $AUC_{0-inf}$.

Dissolution

In some preferred embodiments, the dosage form is coated with a film or incorporates material which makes the dosage form: (i) is non-dissolving at pH<3 to 4 and dissolving at pH>5; or (ii) non-dissolving at pH<3 to 4 and dissolving at pH>5.5; or (iii) non-dissolving at pH<3 to 4 and dissolving at pH>6; or (iv) non-dissolving at pH<3 to 4.5 and dissolving at pH>6; or (v) non-dissolving at pH<3 to 4 and dissolving at pH>6.5; or (vi) non-dissolving at pH<3 to 4.5, and dissolving at pH>6.5; or (vii) non-dissolving at pH<3 to 4 and dissolving at pH>7; or (viii) non-dissolving at pH<3 to 4.5 and dissolving at pH>7; or (ix) is non-dissolving at pH<3 to 5 and dissolving at pH>7; or (x) non-dissolving at pH<3 to 5.5 and dissolving at pH>7.

In some preferred embodiments, the oral butorphanol dosage form is non-dissolving or substantially non-dissolving at pH <5.5, or at pH <6.0, or at pH <6.2, or at pH <6.5, or at pH <6.8, or at pH <7.0, when measured by USP Basket Method or USP Paddle Method at 100 rpm in 900 mL of water at 37° C. (adjusted to the required pH with hydrochloric acid or sodium hydroxide) for up to about 2, 2.5, 3, 3.5, 4, 4.5, or 5.

In some preferred embodiments, the oral butorphanol dosage form is non-releasing or substantially non-releasing at pH <5.5, or at pH <6.0, or at pH <6.2, or at pH <6.5, or at pH <6.8, or at pH <7.0, when measured by USP Basket Method or USP Paddle Method at 100 rpm in 900 mL of water at 37° C. (adjusted to the required pH with hydrochloric acid or sodium hydroxide) for up to about 2, 2.5, 3, 3.5, 4, 4.5, or 5.

In some preferred embodiments, the oral modified release butorphanol dosage form releases less than about 0.1%, or 0.5%, or 1%, or 1.5%, or 2%, or 2.5%, or 3%, or 3.5%, or 4%, or 4.5%, or 5%, or 6%, or 7%, or 8%, or 9%, or 10%, or 12%, or 14%, or 15%, or 16%, or 17%, or 18%, or 20% of butorphanol in vitro from the dosage form when measured at about 1, 1.5, 2, 2.5, 3, 3.25, 3.5, 3.75, 4, 4.25, 4.5, 4.75, or 5 hours, said in vitro release measured by the USP Basket or Paddle Method at 100 rpm in 100 to 900 mL in one or more of the following: (a) water at 37° C. at a pH of 4.5, adjusted with HCl; (b) water at 37° C. at a pH of 5, adjusted with HCl; (c) water at 37° C. at a pH of 5.5, adjusted with HCl; (d) simulated gastric fluid at 37° C.; (e) simulated intestinal fluid at 37° C.; (f) simulated gastric fluid at 37° C. for one hour followed by a switch to simulated intestinal fluid; (g) Phosphate buffer 0.067M (pH 7.0) at 37° C.; and (h) Phosphate buffer 0.067M (pH 7.0) containing Tween 80 at 37° C. In some embodiments, said in vitro dissolution is measured by the USP Apparatus III (Reciprocating Cylinder) Method instead of the Basket or Paddle Method. In some embodiments, most preferably, the dosage form releases less than about 0.1%, or 0.5%, or 1%, or 1.5%, or 2%, or 2.5%, or 3%, or 3.5%, or 4%, or 4.5%, or 5%, or 6%, or 7%, or 8%, or 9%, or 10 of butorphanol in vitro from the dosage form when measured at about 1.5, 2, 2.5, 3, 3.5, 4, 4.5, 5, 5.5, 6, 6.5, or 7 hours.

In some preferred embodiments, the oral modified release butorphanol dosage form is coated with a material or incorporates material which is non-dissolving or substantially resistant to dissolution, each when measured by USP Basket Method or USP Paddle Method at 100 rpm in 900 mL of water at 37° C. (adjusted to the required pH with hydrochloric acid or sodium hydroxide) at about pH 2, pH 2.2, pH 2.4, pH 2.6, pH 2.8, pH 3, pH 3.2, pH 3.4, pH 3.6, pH 3.8, pH 4, pH 4.2, pH 4.4, pH 4.6, pH 4.8, pH 5, pH 5.2, pH 5.4, pH 5.6, pH 5.8, pH 6, pH 6.2, pH 6.4, pH 6.6, pH 6.8, pH 7, most preferably at a pH between 5 and 6.2, for at least up to about 0.5, 1, 1.5, 2, 2.5, 3, 3.5, 4, 4.5, or 5 hours.

In some preferred embodiments, the oral modified release butorphanol dosage form is coated with a material or incorporates material which is non-releasing or substantially non-releasing, each when measured by USP Basket Method or USP Paddle Method at 100 rpm in 900 mL of water at 37° C. (adjusted to the required pH with hydrochloric acid or sodium hydroxide) at about pH 2, pH 2.2, pH 2.4, pH 2.6, pH 2.8, pH 3, pH 3.2, pH 3.4, pH 3.6, pH 3.8, pH 4, pH 4.2, pH 4.4, pH 4.6, pH 4.8, pH 5, pH 5.2, pH 5.4, pH 5.6, pH 5.8, pH 6, pH 6.2, pH 6.4, pH 6.6, pH 6.8, pH 7, pH 7.2, pH 7.4, most preferably at a pH between 5 and 6.2, for at least up to about 0.5, 1, 1.5, 2, 2.5, 3, 3.5, 4, 4.5, or 5 hours.

In some preferred embodiments, the oral modified release butorphanol dosage form is coated with a material or incorporates material which is non-dissolving or substantially non-dissolving at one pH but dissolving or substantially dissolving at another pH for up to at least about 0.5, 1, 1.5, 2, 2.5, 3, 3.5, 4, 4.5, and 5 hours; said one pH being ≤2, or ≤2.1, or ≤2.2, or ≤2.3, or ≤2.4, or ≤2.5, or ≤2.6, or ≤2.7, or ≤2.8, or ≤2.9, or ≤3, or ≤3.1, or ≤3.2, or ≤3.3, or ≤3.4, or ≤3.5, or ≤3.6, or ≤3.7, or ≤3.8, or ≤3.9, or ≤4, or ≤4.1, or ≤4.2, or ≤4.3, or ≤4.4, or ≤4.5, or ≤4.6, or ≤4.7, or ≤4.8, or ≤4.9, or ≤5; said another pH being ≥5.2, or ≥5.3, or ≥5.4, or ≥5.5, or ≥5.6, or ≥5.7, or ≥5.8, or ≥5.9, or ≥6, or ≥6.1, or ≥6.2, or ≥6.3, or ≥6.4, or ≥6.5, or ≥6.6, or ≥6.7, or ≥6.8, or ≥6.9, or ≥7, or ≥7.1, or ≥7.2, or ≥7.3, or ≥7.4, or ≥7.5, or ≥7.6, or ≥7.7, or ≥7.8, or ≥7.9, or ≥8.0, or ≥8.1, or ≥8.2, or ≥8.3, or ≥8.4, or ≥8.5, or ≥8.6, or ≥8.7, or ≥8.8, or ≥8.9, or ≥9.0, each when measured by USP Basket Method or USP Paddle Method at 100 rpm in 900 mL of water at 37° C. (adjusted to the required pH with hydrochloric acid or sodium hydroxide). Preferably, said one pH is ≤4 and said another pH is ≥6.5; most preferably, said one pH is ≤5 and said another pH is ≥6.

In some preferred embodiments, the oral modified release butorphanol dosage form is coated with a material or incorporates material which is non-releasing or substantially non-releasing at one pH but releasing or substantially releasing at another pH for at least up to about 0.5, 1, 1.5, 2, 2.5, 3, 3.5, 4, 4.5, or 5 hours; said one pH being ≤2, or ≤2.1, or ≤2.2, or ≤2.3, or ≤2.4, or ≤2.5, or ≤2.6, or ≤2.7, or ≤2.8, or ≤2.9, or ≤3, or ≤3.1, or ≤3.2, or ≤3.3, or ≤3.4, or ≤3.5, or ≤3.6, or ≤3.7, or ≤3.8, or ≤3.9, or ≤4, or ≤4.1, or ≤4.2, or ≤4.3, or ≤4.4, or ≤4.5, or ≤4.6, or ≤4.7, or ≤4.8, or ≤4.9, or ≤5; said another pH being ≥5.2, or ≥5.3, or ≥5.4, or ≥5.5, or ≥5.6, or ≥5.7, or ≥5.8, or ≥5.9, or ≥6, or ≥6.1, or ≥6.2, or ≥6.3, or ≥6.4, or ≥6.5, or ≥6.6, or ≥6.7, or ≥6.8, or ≥6.9, or ≥7, or ≥7.1, or ≥7.2, or ≥7.3, or ≥7.4, or ≥7.5, or ≥7.6, or ≥7.7, or ≥7.8, or ≥7.9, or ≥8.0, or ≥8.1, or ≥8.2, or ≥8.3, or ≥8.4, or ≥8.5, or ≥8.6, or ≥8.7, or ≥8.8, or ≥8.9, or ≥9.0, each when measured when by USP Basket Method or USP Paddle Method at 100 rpm in 900 mL of water at 37° C. (adjusted to the required pH with hydrochloric acid or sodium hydroxide). Preferably, said one pH is ≤4 and said another pH is ≥6.5; most preferably, said one pH is ≤5 and said another pH is ≥6.

In some preferred embodiments, the dosage form provides an oral pharmaceutical composition comprising a therapeutically effective amount of butorphanol, and a controlled release material to render said dosage form suitable for three times-a-day (Q8H or Q8H PRN) administration to a human patient; said dosage form providing an in-vitro release rate by weight of butorphanol, when measured by the USP Basket or Paddle Method at 100 rpm in 900 mL aqueous buffer at a pH of between 1.6 and 7.2 at 37° C. of from 0% to about 47.5% at 1 hour, from about 10% to about 65% at 2 hours, from about 10% to about 90% at 4 hours, from about 15% to about 95% at 6 hours, and greater than about 65% at 8 hours. In other preferred embodiments, the dosage form provides said an in-vitro release rate of from 0% to about 40% at 1 hour, from about 5% to about 60% at 2 hours, from about 10% to about 70% at 4 hours, from about 15% to about 90% at 6 hours, and greater than about 50% at 8 hours.

In some embodiments, some of the dissolution rate specifications of butorphanol referred to herein are obtained following pretreatment of the dosage form using the USP Basket or Paddle Method at 100 rpm in 900 mL distilled water at a pH of ≤4.5, ≤5, or ≤5.5 for two hours at 37° C. before a switch to an aqueous buffer at 37° C. at a pH ≥6, or ≥6.8 or a pH ≥7 (instead of the aqueous buffer at a pH of between 1.6 and 7.2), whereupon the clock is reset to time equal to 0.

In some preferred embodiments, the dosage form provides an oral pharmaceutical composition comprising a therapeutically effective amount of butorphanol, and a controlled release material to render said dosage form suitable for three times-a-day (Q8H or Q8H PRN) administration to a human patient; said dosage form providing an in-vitro release rate by weight of butorphanol, when measured by the USP Basket or Paddle Method at 100 rpm in 900 mL aqueous buffer at a pH of between 1.6 and 7.2 at 37° C. of from 0% to about 47.5% at 1 hour, from about 10% to about 65% at 2 hours, from about 15% to about 70% at 4 hours, from about 25% to about 80% at 6 hours, and greater than about 65% at 8 hours; said in-vitro release rate being substantially independent of pH in that a difference, at any given time, between an amount of butorphanol released at one pH and an amount released at any other pH, when measured in-vitro using the USP Basket or Paddle Method of USP Drug Release test of U.S. Pharmacopeia (2003) at 100 rpm in 900 ml aqueous buffer, is no greater than 30%. In other preferred embodiments, said pH independent in-vitro release rate is from 0% to about 47.5% at 1 hour, from about 10% to about 65% at 2 hours, from about 10% to about 90% at 4 hours, from about 15% to about 95% at 6 hours, and greater than about 65% at 8 hours or from 0% to about 40% at 1 hour, from about 5% to about 60% at 2 hours, from about 10% to about 70% at 4 hours, from about 15% to about 90% at 6 hours, and greater than about 50% at 8 hours.

In some preferred embodiments, the dosage form provides an oral pharmaceutical composition for the treatment of a butorphanol responsive medical condition comprising a therapeutically effective amount of butorphanol or pharmaceutically acceptable salts thereof or mixture thereof; and a controlled release material; said dosage form providing an in-vitro butorphanol release rate, when measured by the USP Basket or Paddle Method at 100 rpm in 900 mL of distilled water at 37° C. which is substantially pH dependent in that a difference, at 1, or 1.5, or 2, or 2.5, or 3 hours, between the amount of butorphanol released at a pH of ≤0.5, or ≤1, or ≤1.5, or ≤2, or ≤2.5, or ≤3, or ≤3.5, or ≤4, or ≤4.5, or ≤5, or ≤5.5 and an amount released at a pH of or ≥5.8, or ≥6, or ≥6.2, or ≥6.4, or ≥6.6, or ≥6.8, or ≥7, or ≥7.1, or ≥7.2, or ≥7.3, or ≥7.4, or ≥7.5, or ≥7.6, or ≥7.7, or ≥7.8, or ≥7.9, or ≥8, is greater than about 20%, 25%, 35%, 50%, 60%, 75%, 80%, 90%, 100%, 125%, 150%, 175%, 200%, 225%, 250%, 275%, 300%, 350%, 400%, 450%, 500%, 600%, 700%, 800%, 900%, 1000%, or 1200%, 1500%, 2000%, 3000%, 4000%%, 5000%, or 6000%.

In some preferred embodiments, the dosage form provides an oral pharmaceutical composition for the treatment of a butorphanol responsive medical condition comprising a therapeutically effective amount of butorphanol or pharmaceutically acceptable salts thereof or mixture thereof; and a controlled release material; said dosage form providing duodenal delivery, jejunal delivery, ileal delivery, ileo-colonic delivery or colonic delivery; said dosage form providing an in-vitro butorphanol release rate, when measured by the USP Basket or Paddle Method at 100 rpm in 900 mL of distilled water at 37° C. which is substantially pH dependent in that a difference, at 1, or 1.5, or 2, or 2.5, or 3 hours, between the amount of butorphanol released at a pH of ≤0.5, or ≤1, or ≤1.5, or ≤2, or ≤2.5, or ≤3, or ≤3.5, or ≤4, or ≤4.5, or ≤5, or ≤5.5 and an amount released at a pH of ≥5.8, or ≥6, or ≥6.2, or ≥6.4, or ≥6.6, or ≥6.8, or ≥7, or ≥7.1, or ≥7.2, or ≥7.3, or ≥7.4, or ≥7.5, or ≥7.6, or ≥7.7, or ≥7.8, or ≥7.9, or ≥8, is greater than about 20%, 25%, 35%, 50%, 60%, 75%, 80%, 90%, 100%, 125%, 150%, 175%, 200%, 225%, 250%, 275%, 300%, 350%, 400%, 450%, 500%, 600%, 700%, 800%, 900%, 1000%, or 1200%, 1500%, 2000%, 3000%, 4000%%, 5000%, or 6000%.

In some preferred embodiments, the dosage form provides an oral pharmaceutical composition for the treatment of a butorphanol responsive medical condition comprising a therapeutically effective amount of butorphanol or pharmaceutically acceptable salts thereof or mixture thereof, and a controlled release material; said dosage form, following dissolution (pretreatment) with USP Basket or Paddle Method at 100 rpm in 900 mL of 0.1N HCl for two hours at 37° C., providing an in-vitro release rate of butorphanol by weight, when measured at about 5, 10, 15, 20, 25, 30, 40, 50, or 60 minutes, 1, 1.5, 2, 2.5, 3, 4, 5 6, 7, 8, 10, 12, 14, 16, 18, 20, 24 or 30 hours by the USP Basket or Paddle Method at 100 rpm in 900 mL distilled water (time=0 hour begins here) at 37° C. at a pH between 4.5 and 8: (i) of less than about 1%, 2%, 3%, 4%, 5%, 10%, 15%, 20%, 25%, 30%, 40%, 50%, 60%, 70% 80%, 90% or 100%; or (ii) of less than about 1% to about 20% or less than about 2% to about 20% or less than about 5% to about 20% or less than about 8% to about 20% or less than about 10% to about 20% or less than about 12% to about 20% or less than about 15% to about 20% or less than about 1% to about 50% or less than about 2% to about 50% or less than about 5% to about 50% or less than about 10% to about 50% or less than about 15% to about 50% or less than about 20% to about 50% or less than about 30% to about 50% or less than about 40% to about 50% or less than about 1% to about 60% or less than about 2% to about 60% or less than about 5% to about 60% or less than about 10% to about 60% or less than about 15% to about 60% or less than about 20% to about 60% or less than about 30% to about 60% or less than about 40% to about 60% or less than about 1% to about 70% or less than about 2% to about 70% or less than about 5% to about 70% or less than about 10% to about 70% or less than about 15% to about 70% or less than about 20% to about 70% or less than about 30% to about 70% or less than about 50% to about 70% or less than about 1% to about 80% or less than about 2% to about 80% or less than about 5% to about 80% or less than about 10% to about 80% or less than about 15% to about 80% or less than about 20% to about 80% or less than about 30% to about 80% or less than about 40% to about 80% or less than about 1% to about 90% or less than about 2% to about 90% or less than about 5% to about 90% or less than about 10% to about 90% or less than about 15% to about 90% or less than about 20% to about 90% or less than about 30% to about 90% or less than about 40% to about 90% or about 60% to about 90% or less than about 70% to about 90% or less than about 80% to about 90%, or more than about 1%, or more than about 5%, or more than about 10%, or more than about 15%, or more than about 20%, or more than about 30%, or more than about 40%, or more than about 50%, or more than about 55%, or more than about 60%, or more than about 70%, or more than about 80%, or more than about 85%, or more than about 90%, or more than about 95%, or more than 99%; or (iii) of ≥0.1%, or ≥0.5%, or ≥1%, or ≥5%, ≥10%, or ≥20%, or ≥30%, or ≥40%, or ≥50%, or ≥60%, or ≥70%, or ≥80%, or ≥90%, or about 100%.

In some preferred embodiments, the dosage form provides an oral pharmaceutical composition for the treatment of a butorphanol responsive medical condition comprising a therapeutically effective amount of butorphanol or pharmaceutically acceptable salts thereof or mixture thereof, and a controlled release material; said dosage form providing duodenal release, jejunal release, ileal release, ileo-colonic release or colonic release; said dosage form, following dissolution (pretreatment) with USP Basket or Paddle Method at 100 rpm in 900 mL of 0.1N HCl for two hours at 37° C., providing an in-vitro release rate of butorphanol by weight, when measured at about 5, 10, 15, 20, 25, 30, 40, 50, or 60 minutes, 1, 1.5, 2, 2.5, 3, 4, 5 6, 7, 8, 10, 12, 14, 16, 18, 20, 24 or 30 hours by the USP Basket or Paddle Method at 100 rpm in 900 mL distilled water (time=0 hour begins here) at 37° C. at a pH between 4.5 and 8: (i) of less than about 1%, 2%, 3%, 4%, 5%, 10%, 15%, 20%, 25%, 30%, 40%, 50%, 60%, 70% 80%, 90% or 100%; or (ii) of less than about 1% to about 20% or less than about 2% to about 20% or less than about 5% to about 20% or less than about 8% to about 20% or less than about 10% to about 20% or less than about 12% to about 20% or less than about 15% to about 20% or less than about 1% to about 50% or less than about 2% to about 50% or less than about 5% to about 50% or less than about 10% to about 50% or less than about 15% to about 50% or less than about 20% to about 50% or less than about 30% to about 50% or less than about 40% to about 50% or less than about 1% to about 60% or less than about 2% to about 60% or less than about 5% to about 60% or less than about 10% to about 60% or less than about 15% to about 60% or less than about 20% to about 60% or less than about 30% to about 60% or less than about 40% to about 60% or less than about 1% to about 70% or less than about 2% to about 70% or less than about 5% to about 70% or less than about 10% to about 70% or less than about 15% to about 70% or less than about 20% to about 70% or less than about 30% to about 70% or less than about 50% to about 70% or less than about 1% to about 80% or less than about 2% to about 80% or less than about 5% to about 80% or less than about 10% to about 80% or less than about 15% to about 80% or less than about 20% to about 80% or less than about 30% to about 80% or less than about 40% to about 80% or less than about 1% to about 90% or less than about 2% to about 90% or less than about 5% to about 90% or less than about 10% to about 90% or less than about 15% to about 90% or less than about 20% to about 90% or less than about 30% to about 90% or less than about 40% to about 90% or about 60% to about 90% or less than about 70% to about 90% or less than about 80% to about 90%, or more than about 1%, or more than about 5%, or more than about 10%, or more than about 15%, or more than about 20%, or more than about 30%, or more than about 40%, or more than about 50%, or more than about 55%, or more than about 60%, or more than about 70%, or more than about 80%, or more than about 85%, or more than about 90%, or more than about 95%, or more than 99%; or (iii) of ≥0.1%, or ≥0.5%, or ≥1%, or ≥5%, ≥10%, or ≥20%, or ≥30%, or ≥40%, or ≥50%, or ≥60%, or ≥70%, or ≥80%, or ≥90%, or about 100%.

In some embodiments of the invention, pH adjustments of the dissolution media may be achieved by adjustment as required with hydrochloric acid or sodium hydroxide. In some embodiments of the invention, pH adjustments of the dissolution media may be achieved with other pharmaceutical excipients, including acids, bases and buffers known in the art.

In some preferred embodiments, the dosage form provides an oral pharmaceutical composition for the treatment of a butorphanol responsive medical condition comprising a therapeutically effective amount of butorphanol or pharmaceutically acceptable salts thereof or mixture thereof, and a controlled release material; said dosage form, following dissolution (pretreatment) with USP Basket or Paddle Method at 100 rpm in 900 mL of 0.1N HCl for two hours at 37° C., and then following further dissolution (pretreatment) with USP Basket or Paddle Method at 100 rpm in 900 mL distilled water at any pH of between 2 and 4 for a further time of up to two hours at 37° C., providing an in-vitro release rate by weight of butorphanol, when measured by the USP Basket or Paddle Method at 100 rpm in 900 mL distilled water (time=0 hour begins here) at 37° C. at any pH between 4.5 and 8 at 37° C. (measured at about 5, about 10, about 15, about 20, about 25, about 30, about 35, about 40, about 45, about 50, about 55 or about 60 minutes, or about 2 hours, or about 3 hours, or about 4 hours, or about 5 hours, or about 6 hours, or about 7 hours, or about 8 hours, or about 10 hours, or about 12 hours, or about 14 hours, or about 16 hours, or about 18 hours, or about 20 hours, or about 24 hours, or about 30 hours): (i) of less than about 1% to about 20% or less than about 2% to about 20% or less than about 5% to about 20% or less than about 8% to about 20% or less than about 10% to about 20% or less than about 12% to about 20% or less than about 15% to about 20% or less than about 1% to about 50% or less than about 2% to about 50% or less than about 5% to about 50% or less than about 10% to about 50% or less than about 15% to about 50% or less than about 20% to about 50% or less than about 30% to about 50% or less than about 40% to about 50% or less than about 1% to about 60% or less than about 2% to about 60% or less than about 5% to about 60% or less than about 10% to about 60% or less than about 15% to about 60% or less than about 20% to about 60% or less than about 30% to about 60% or less than about 40% to about 60% or less than about 1% to about 70% or less than about 2% to about 70% or less than about 5% to about 70% or less than about 10% to about 70% or less than about 15% to about 70% or less than about 20% to about 70% or less than about 30% to about 70% or less than about 50% to about 70% or less than about 1% to about 80% or less than about 2% to about 80% or less than about 5% to about 80% or less than about 10% to about 80% or less than about 15% to about 80% or less than about 20% to about 80% or less than about 30% to about 80% or less than about 40% to about 80% or less than about 1% to about 90% or less than about 2% to about 90% or less than about 5% to about 90% or less than about 10% to about 90% or less than about 15% to about 90% or less than about 20% to about 90% or less than about 30% to about 90% or less than about 40% to about 90% or about 60% to about 90% or less than about 70% to about 90% or less than about 80% to about 90%, or more than about 1%, or more than about 5%, or more than about 10%, or more than about 15%, or more than about 20%, or more than about 30%, or more than about 40%, or more than about 50%, or more than about 55%, or more than about 60%, or more than about 70%, or more than about 80%, or more than about 85%, or more than about 90%, or more than about 95%, or more than 99%, or about 100%; or (ii) of ≥0.1%, or ≥0.5%, or ≥1%, or ≥5%, ≥10%, or ≥20%, or ≥30%, or ≥40%, or ≥50%, or ≥60%, or ≥70%, or ≥80%, or ≥90%, or about 100. In some embodiments, the foregoing dosage form provides duodenal delivery, jejunal delivery, ileal delivery, ileo-colonic delivery or colonic delivery.

In some preferred embodiments, the dosage form provides an oral pharmaceutical composition for the treatment of a butorphanol responsive medical condition comprising a therapeutically effective amount of butorphanol or pharmaceutically acceptable salts thereof or mixture thereof, and a controlled release material; said dosage form, following dissolution (pretreatment) with USP Basket or Paddle Method at 100 rpm in 900 mL of 0.1N HCl for two hours at 37° C., and then following further dissolution (pretreatment) with USP Basket or Paddle Method at 100 rpm in 900 mL distilled water at any pH of between 2 and 4 for a further time of up to two hours at 37° C., providing an in-vitro release rate by weight of butorphanol, when measured by the USP Basket or Paddle Method at 100 rpm in 900 mL distilled water (time=0 hour begins here) at 37° C. at any pH between 4.5 and 8 at 37° C.: (i) from 0% to about 47.5% at 1 hour, from about 10% to about 65% at 2 hours, from about 15% to about 70% at 4 hours, from about 25% to about 77.5% at 6 hours, from about 35% to about 87.5% at 9 hours, and greater than about 65% at 12 hours; or (ii) from 0% to about 40% at 1 hour, from about 5% to about 55% at 2 hours, from about 10% to about 60% at 4 hours, from about 15% to about 70% at 6 hours, from about 25% to about 80% at 9 hours, and greater than about 50% at 12 hours. In some embodiments, the foregoing dosage form provides duodenal delivery, jejunal delivery, ileal delivery, ileo-colonic delivery or colonic delivery.

In some preferred embodiments, the dosage form provides an oral pharmaceutical composition for the treatment of a butorphanol responsive medical condition comprising a therapeutically effective amount of butorphanol or pharmaceutically acceptable salts thereof or mixture thereof; said dosage form, following dissolution (pretreatment) with USP Basket or Paddle Method at 100 rpm in 900 mL of 0.1N HCl for two hours at 37° C., providing an in-vitro release rate by weight of butorphanol, when measured by the USP Basket or Paddle Method at 100 rpm in 900 mL distilled water (time=0 hour begins here) at 37° C. at any pH between 4.5 and 8 at 37° C.: (1) between 0% to about 47.5% at 1 hour, between about 10% to about 65% at 2 hours, between about 15% to about 70% at 4 hours, between about 25% to about 77.5% at 6 hours, between about 35% to about 87.5% at 9 hours, and greater than about 65% at 12 hours; or (2) between about 10% to about 65% at 4 hours, between about 20% to about 70% at 8 hours, between about 25% to about 80% at 12 hours, between about 35% to about 95% at 18 hours, and greater than about 65% at 24 hours; or (3) between 0% to about 60% at 1 hour, between about 0% and about 80% at 2 hours, between about 3% and about 95% at 4 hours and between about 10% and about 100% at 8 hours; or (4) between about 10% and about 65% at 1 hour, between about 20% and about 75% at 2 hours, between about 30% and about 95% at 4 hours and between about 40% and about 100% at 8 hours; or (5) between about 10% to about 65% at 2 hours, between about 15% to about 70% at 4 hours, between about 25% to about 77.5% at 6 hours, between about 35% to about 87.5% at 9 hours, and greater than about 65% at 12 hours; or (6) between about 5% and about 50% at 1 hour, between about 10% and about 75% at 2 hours, between about 20% and about 95% at 4 hours, between about 40% and about 100% at 8 hours, greater than about 50% at 12 hours, greater than about 70% at 18 hours, and greater than about 80% at 24 hours; or (7) between about 5% and about 50% at 1 hour, between about 10% and about 75% at 2 hours, between about 20% and about 95% at 4 hours, between about 40% and about 100% at 8 hours, greater than about 50% at 12 hours, greater than about 70% at 18 hours, and greater than about 80% at 24 hours; or (8) between 0% to about 30% at 1 hour, between about 10% to about 65% at 4 hours, between about 20% to about 70% at 8 hours, between about 25% to about 80% at 12 hours, between about 35% to about 95% at 18 hours, and greater than about 65% at 24 hours; or (9) between 0% to about 50% at 1 hour, between about 0% and about 75% at 2 hours, between about 3% and about 95% at 4 hours, between about 10% and about 100% at 8 hours, between about 25% and about 100% at 12 hours, between about 30% and about 100% at 16 hours, between about 50% and about 100% at 24 hours, and greater than about 80% at 36 hours; or (10) between about 20% and about 50% at 1 hour, between about 40% and about 75% at 2 hours, between about 60% and about 95% at 4 hours, between about 80% and about 100% at 8 hours and between about 90% and about 100% at 12 hours; or (11) between 0% to about 50% at 1 hour, between about 0% and about 75% at 2 hours, between about 10% and about 95% at 4 hours, between about 35% and about 100% at 8 hours, between about 55% and about 100% at 12 hours, between about 70% to about 100% at 16 hours, and greater than about 90% at 24 hours; or (12) between 0% to about 30% at 1 hour, between about 0% and about 45% at 2 hours, between about 3% and about 55% at 4 hours, between about 10% and about 65% at 8 hours, between about 20% and about 75% at 12 hours, between about 30% to about 88% at 16 hours, between about 50% and about 100% hours at 24 hours and greater than 80% at 36 hours; or (13) between 0% to about 50% at 1 hour, between about 0% and about 75% at 2 hours, between about 3% and about 95% at 4 hours, between about 10% and about 100% at 8 hours, between about 20% and about 100% at 12 hours, between about 30% to about 100% at 16 hours, between about 50% and about 100% hours at 24 hours and greater than about 80% at 36 hours; or (14) between about 15% and about 25% at 1 hour, between about 25% and about 35% at 2 hours, between about 30% and about 45% at 4 hours, between about 40% and about 60% at 8 hours, between about 55% and about 70% at 12 hours and between about 60% to about 75% at 16 hours; or (15) between 0% to about 60% at 1 hour, between about 0% and about 80% at 2 hours, between about 3% and about 95% at 4 hours and between about 10% and about 100% at 8 hours; or (16) between 0% and about 10% at 1 hour, between about 0% and about 20% at 2 hours, between about 2% and about 80% at 4 hours and between about 5% and about 100% at 8 hours; or (17) between 0% and about 20% at 1 hour, between about 0% and about 40% at 2 hours, between about 0% and about 80% at 4 hours and between about 2% and about 100% at 8 hours; or (18) between 0% and about 40% at 1 hour, between about 0% and about 60% at 2 hours, between about 5% and about 85% at 4 hours and between about 5% and about 90% at 8 hours and greater than 20% at 12 hours; or (19) between 0% and about 50% at 1 hour, between about 0% and about 50% at 2 hours, between about 10% and about 90% at 4 hours and between about 15% and about 90% at 8 hours and greater than 30% at 12 hours; or (20) between 0% and about 70% at 1 hour, between about 0% and about 70% at 2 hours, between about 10% and about 75% at 4 hours and between about 15% and about 90% at 8 hours and greater than 30% at 12 hours; or (21) between about 10% and about 65% at 1 hour, between about 20% and about 75% at 2 hours, between about 30% and about 95% at 4 hours and between about 40% and about 100% at 8 hours; or (22) between 2% and about 70% at 1 hour, between about 5% and about 80% at 2 hours, between about 10% and about 90% at 4 hours and between about 20% and about 100% at 8 hours; or (23) between 5% and about 60% at 1 hour, between about 10% and about 75% at 2 hours, between about 15% and about 85% at 4 hours and between about 30% and about 100% at 8 hours; or (24) between 20% and about 70% at 1 hour, between about 20% and about 75% at 2 hours, between about 20% and about 90% at 4 hours and between about 40% and about 100% at 8 hours; or (25) between 30% and about 80% at 1 hour, between about 40% and about 85% at 2 hours, between about 40% and about 90% at 4 hours and between about 60% and about 100% at 8 hours; or (26) between 1% and about 20% at 1 hour, between about 5% and about 20% at 2 hours, between about 10% and about 40% at 4 hours and between about 20% and about 40% at 8 hours and greater than 40% at 12 hours; or (27) between 0% to about 47.5% at 1 hour, between about 10% to about 65% at 2 hours, between about 15% to about 70% at 4 hours, between about 25% to about 77.5% at 6 hours, between about 35% to about 87.5% at 9 hours, and greater than about 65% at 12 hours; or (28) between 0% to about 30% at 1 hour, between about 5% to about 45% at 2 hours, between about 10% to about 60% at 4 hours, between about 15% to about 70% at 6 hours, between about 25% to about 80% at 9 hours, and greater than about 50% at 12 hours; or (29) between 0% to about 20% at 1 hour, between about 2% to about 35% at 2 hours, between about 5% to about 50% at 4 hours, between about 10% to about 60% at 6 hours, between about 15% to about 70% at 9 hours, and greater than about 40% at 12 hours; or (30) between 0% to about 10% at 1 hour, between about 1% to about 30% at 2 hours, between about 5% to about 40% at 4 hours, between about 10% to about 60% at 6 hours, between about 15% to about 70% at 9 hours, and greater than about 40% at 12 hours; or (31) between 0% to about 5% at 1 hour, between about 0% to about 10% at 2 hours, between about 2% to about 20% at 4 hours, between about 5% to about 30% at 6 hours, between about 10% to about 40% at 9 hours, and greater than about 30% at 12 hours; or (32) between 0% to about 50% at 1 hour, between about 15% to about 70% at 2 hours, between about 20% to about 75% at 4 hours, between about 30% to about 80% at 6 hours, between about 30% to about 90% at 9 hours, and greater than about 70% at 12 hours; or (33) between 0% to about 60% at 1 hour, between about 15% to about 80% at 2 hours, between about 25% to about 85% at 4 hours, between about 35% to about 90% at 6 hours, between about 40% to about 90% at 9 hours, and greater than about 80% at 12 hours; (34) between 0% to about 70% at 1 hour, between about 20% to about 80% at 2 hours, between about 25% to about 80% at 4 hours, between about 35% to about 80% at 6 hours, between about 40% to about 80% at 9 hours, and greater than about 60% at 12 hours; or (35) between 0% to about 75% at 1 hour, between about 30% to about 80% at 2 hours, between about 35% to about 90% at 4 hours, between about 50% to about 90% at 6 hours, between about 55% to about 95% at 9 hours, and greater than about 70% at 12 hours; or (36) between about 5% and about 50% at 1 hour, between about 10% and about 75% at 2 hours, between about 20% and about 95% at 4 hours, between about 40% and about 100% at 8 hours, greater than about 50% at 12 hours, greater than about 70% at 18 hours, and greater than about 80% at 24 hours; or (37) between 2% and about 50% at 1 hour, between about 5% and about 75% at 2 hours, between about 15% and about 75% at 4 hours, between about 30% and about 90% at 8 hours, greater than about 40% at 12 hours, greater than about 60% at 18 hours, and greater than about 70% at 24 hours; or (38) between 1% and about 40% at 1 hour, between about 2% and about 60% at 2 hours, between about 10% and about 65% at 4 hours, between about 20% and about 80% at 8 hours, greater than about 30% at 12 hours, greater than about 40% at 18 hours, and greater than about 60% at 24 hours; or (39) between 5% and about 60% at 1 hour, between about 15% and about 80% at 2 hours, between about 25% and about 95% at 4 hours, between about 45% and about 100% at 8 hours, greater than about 60% at 12 hours, greater than about 80% at 18 hours, and greater than about 90% at 24 hours; or (40) between 10% and about 65% at 1 hour, between about 20% and about 85% at 2 hours, between about 30% and about 100% at 4 hours, between about 60% and about 100% at 8 hours, greater than about 70% at 12 hours, greater than about 90% at 18 hours, and greater than about 95% at 24 hours; or (41) between 0% to about 30% at 1 hour, between about 10% to about 65% at 4 hours, between about 20% to about 70% at 8 hours, between about 25% to about 80% at 12 hours, between about 35% to about 95% at 18 hours, and greater than about 65% at 24 hours; or (42) between 0% to about 20% at 1 hour, between about 5% to about 50% at 4 hours, between about 10% to about 60% at 8 hours, between about 15% to about 70% at 12 hours, between about 25% to about 90% at 18 hours, and greater than about 55% at 24 hours; or (43) between 0% to about 10% at 1 hour, between about 5% to about 40% at 4 hours, between about 8% to about 50% at 8 hours, between about 10% to about 60% at 12 hours, between about 22% to about 80% at 18 hours, and greater than about 45% at 24 hours; or (44) between 0% to about 35% at 1 hour, between about 15% to about 70% at 4 hours, between about 25% to about 75% at 8 hours, between about 30% to about 85% at 12 hours, between about 40% to about 100% at 18 hours, and greater than about 75% at 24 hours; or (45) between 0% to about 40% at 1 hour, between about 20% to about 70% at 4 hours, between about 30% to about 80% at 8 hours, between about 35% to about 90% at 12 hours, between about 45% to about 100% at 18 hours, and greater than about 80% at 24 hours; or (46) between 0% to about 45% at 1 hour, between about 25% to about 75% at 4 hours, between about 35% to about 85% at 8 hours, between about 40% to about 90% at 12 hours, between about 50% to about 100% at 18 hours, and greater than about 90% at 24 hours; or (47) between 0% to about 50% at 1 hour, between about 30% to about 80% at 4 hours, between about 40% to about 90% at 8 hours, between about 45% to about 95% at 12 hours, between about 60% to about 100% at 18 hours, and greater than about 95% at 24 hours; or (48) between 0% to about 60% at 1 hour, between about 40% to about 80% at 4 hours, between about 45% to about 90% at 8 hours, between about 50% to about 100% at 12 hours, between about 70% to about 100% at 18 hours, and greater than about 80% at 24 hours; or (49) between 0% and about 50% at 1 hour, between about 0% and about 75% at 2 hours, between about 3% and about 95% at 4 hours, between about 10% and about 100% at 8 hours, between about 25% and about 100% at 12 hours, between about 30% and about 100% at 16 hours, between about 50% and about 100% at 24 hours, and greater than about 80% at 36 hours; or (50) between 0% and about 40% at 1 hour, between about 0% and about 65% at 2 hours, between about 2% and about 85% at 4 hours, between about 8% and about 90% at 8 hours, between about 20% and about 95% at 12 hours, between about 25% and about 95% at 16 hours, between about 40% and about 90% at 24 hours, and greater than about 70% at 36 hours; or (51) between 0% and about 30% at 1 hour, between about 0% and about 50% at 2 hours, between about 1% and about 75% at 4 hours, between about 5% and about 80% at 8 hours, between about 10% and about 85% at 12 hours, between about 15% and about 90% at 16 hours, between about 30% and about 80% at 24 hours, and greater than about 70% at 36 hours; or (52) between 0% and about 60% at 1 hour, between about 0% and about 80% at 2 hours, between about 5% and about 100% at 4 hours, between about 15% and about 100% at 8 hours, between about 35% and about 100% at 12 hours, between about 40% and about 100% at 16 hours, between about 60% and about 100% at 24 hours, and greater than about 85% at 36 hours; or (53) between 0% and about 65% at 1 hour, between about 0% and about 85% at 2 hours, between about 10% and about 100% at 4 hours, between about 20% and about 100% at 8 hours, between about 40% and about 100% at 12 hours, between about 50% and about 100% at 16 hours, between about 70% and about 100% at 24 hours, and greater than about 90% at 36 hours; or (54) between 0% and about 70% at 1 hour, between about 0% and about 90% at 2 hours, between about 20% and about 100% at 4 hours, between about 30% and about 100% at 8 hours, between about 50% and about 100% at 12 hours, between about 60% and about 100% at 16 hours, between about 80% and about 100% at 24 hours, and greater than about 95% at 36 hours; or (55) between 20% and about 50% at 1 hour, between about 40% and about 75% at 2 hours, between about 60% and about 95% at 4 hours, between about 80% and about 100% at 8 hours and between about 90% and about 100% at 12 hours; or (56) between 15% and about 45% at 1 hour, between about 35% and about 70% at 2 hours, between about 55% and about 90% at 4 hours, between about 75% and about 90% at 8 hours and between about 80% and about 95% at 12 hours; or (57) between 10% and about 40% at 1 hour, between about 30% and about 65% at 2 hours, between about 50% and about 85% at 4 hours, between about 70% and about 85% at 8 hours and between about 75% and about 90% at 12 hours; or (58) between 5% and about 35% at 1 hour, between about 25% and about 60% at 2 hours, between about 45% and about 80% at 4 hours, between about 65% and about 80% at 8 hours and between about 70% and about 85% at 12 hours; or (59) between 25% and about 55% at 1 hour, between about 45% and about 80% at 2 hours, between about 65% and about 95% at 4 hours, between about 85% and about 100% at 8 hours and between about 95% and about 100% at 12 hours; or (60) between 30% and about 60% at 1 hour, between about 50% and about 80% at 2 hours, between about 70% and about 95% at 4 hours, between about 90% and about 100% at 8 hours and between about 95% and about 100% at 12 hours; or (61) between 35% and about 60% at 1 hour, between about 50% and about 80% at 2 hours, between about 80% and about 95% at 4 hours, between about 90% and about 100% at 8 hours and between about 95% and about 100% at 12 hours; or (62) between 20% and about 40% at 1 hour, between about 40% and about 65% at 2 hours, between about 60% and about 85% at 4 hours, between about 70% and about 90% at 8 hours and between about 80% and about 100% at 12 hours; or (63) between 0% and about 50% at 1 hour, between about 0% and about 75% at 2 hours, between about 10% and about 95% at 4 hours, between about 35% and about 100% at 8 hours, between about 55% and about 100% at 12 hours, between about 70% to about 100% at 16 hours, and greater than about 90% at 24 hours; or (64) between 0% and about 40% at 1 hour, between about 0% and about 65% at 2 hours, between about 8% and about 85% at 4 hours, between about 30% and about 90% at 8 hours, between about 45% and about 100% at 12 hours, between about 60% to about 100% at 16 hours, and greater than about 80% at 24 hours; or (66) between 0% and about 30% at 1 hour, between about 0% and about 55% at 2 hours, between about 5% and about 75% at 4 hours, between about 20% and about 80% at 8 hours, between about 35% and about 100% at 12 hours, between about 50% to about 100% at 16 hours, and greater than about 70% at 24 hours; or (67) between 0% and about 20% at 1 hour, between about 0% and about 45% at 2 hours, between about 5% and about 65% at 4 hours, between about 10% and about 70% at 8 hours, between about 25% and about 80% at 12 hours, between about 40% to about 100% at 16 hours, and greater than about 60% at 24 hours; or (68) between 0% and about 60% at 1 hour, between about 0% and about 80% at 2 hours, between about 15% and about 95% at 4 hours, between about 40% and about 100% at 8 hours, between about 60% and about 100% at 12 hours, between about 75% to about 100% at 16 hours, and greater than about 90% at 24 hours; or (69) between 0% and about 65% at 1 hour, between about 0% and about 85% at 2 hours, between about 20% and about 90% at 4 hours, between about 45% and about 100% at 8 hours, between about 65% and about 100% at 12 hours, between about 80% to about 100% at 16 hours, and greater than about 90% at 24 hours; or (70) between 0% and about 40% at 1 hour, between about 0% and about 50% at 2 hours, between about 10% and about 80% at 4 hours, between about 25% and about 70% at 8 hours, between about 40% and about 80% at 12 hours, between about 60% to about 100% at 16 hours, and greater than about 90% at 24 hours; or (71) between 0% and about 30% at 1 hour, between about 0% and about 45% at 2 hours, between about 3% and about 55% at 4 hours, between about 10% and about 65% at 8 hours, between about 20% and about 75% at 12 hours, between about 30% to about 88% at 16 hours, between about 50% and about 100% hours at 24 hours and greater than 80% at 36 hours; or (72) between 0% and about 25% at 1 hour, between about 0% and about 40% at 2 hours, between about 2% and about 50% at 4 hours, between about 8% and about 60% at 8 hours, between about 10% and about 70% at 12 hours, between about 25% to about 80% at 16 hours, between about 45% and about 100% hours at 24 hours and greater than 75% at 36 hours; or (73) between 0% and about 20% at 1 hour, between about 0% and about 35% at 2 hours, between about 1% and about 45% at 4 hours, between about 5% and about 55% at 8 hours, between about 8% and about 65% at 12 hours, between about 20% to about 75% at 16 hours, between about 40% and about 100% hours at 24 hours and greater than 70% at 36 hours; or (74) between 0% and about 15% at 1 hour, between about 0% and about 30% at 2 hours, between about 0% and about 40% at 4 hours, between about 5% and about 50% at 8 hours, between about 8% and about 60% at 12 hours, between about 15% to about 70% at 16 hours, between about 35% and about 100% hours at 24 hours and greater than 60% at 36 hours; or (75) between 0% and about 10% at 1 hour, between about 0% and about 25% at 2 hours, between about 0% and about 35% at 4 hours, between about 5% and about 45% at 8 hours, between about 10% and about 50% at 12 hours, between about 10% to about 60% at 16 hours, between about 30% and about 90% hours at 24 hours and greater than 70% at 36 hours; or (76) between 0% and about 35% at 1 hour, between about 0% and about 50% at 2 hours, between about 5% and about 60% at 4 hours, between about 15% and about 70% at 8 hours, between about 25% and about 80% at 12 hours, between about 35% to about 90% at 16 hours, between about 55% and about 100% hours at 24 hours and greater than 85% at 36 hours; or (77) between 0% and about 40% at 1 hour, between about 0% and about 55% at 2 hours, between about 10% and about 65% at 4 hours, between about 20% and about 75% at 8 hours, between about 30% and about 85% at 12 hours, between about 40% to about 100% at 16 hours, between about 55% and about 100% hours at 24 hours and greater than 90% at 36 hours; or (78) between 0% and about 45% at 1 hour, between about 0% and about 60% at 2 hours, between about 15% and about 70% at 4 hours, between about 25% and about 80% at 8 hours, between about 35% and about 90% at 12 hours, between about 45% to about 100% at 16 hours, between about 60% and about 100% hours at 24 hours and greater than 60% at 36 hours; or (79) between 0% and about 50% at 1 hour, between about 5% and about 65% at 2 hours, between about 20% and about 75% at 4 hours, between about 30% and about 85% at 8 hours, between about 40% and about 95% at 12 hours, between about 50% to about 100% at 16 hours, between about 70% and about 100% hours at 24 hours and greater than 70% at 36 hours; or (80) between 0% and about 30% at 1 hour, between about 5% and about 40% at 2 hours, between about 10% and about 60% at 4 hours, between about 20% and about 70% at 8 hours, between about 30% and about 100% at 12 hours, between about 40% to about 100% at 16 hours, between about 60% and about 100% hours at 24 hours and greater than 90% at 36 hours; or (81) between 0% and about 30% at 1 hour, between about 0% and about 30% at 2 hours, between about 0% and about 30% at 4 hours, between about 5% and about 70% at 8 hours, between about 10% and about 80% at 12 hours, between about 20% to about 100% at 16 hours, between about 40% and about 100% hours at 24 hours and greater than 50% at 36 hours; or (82) between 0% and about 20% at 1 hour, between about 0% and about 20% at 2 hours, between about 0% and about 20% at 4 hours, between about 0% and about 20% at 8 hours, between about 5% and about 40% at 12 hours, between about 10% to about 80% at 16 hours, between about 40% and about 100% hours at 24 hours and greater than 60% at 36 hours; or (83) between 0% and about 10% at 1 hour, between about 0% and about 20% at 2 hours, between about 0% and about 40% at 4 hours, between about 5% and about 60% at 8 hours, between about 10% and about 80% at 12 hours, between about 20% to about 100% at 16 hours, between about 40% and about 100% hours at 24 hours and greater than 50% at 36 hours; or (84) between 0% and about 50% at 1 hour, between about 0% and about 75% at 2 hours, between about 3% and about 95% at 4 hours, between about 10% and about 100% at 8 hours, between about 20% and about 100% at 12 hours, between about 30% to about 100% at 16 hours, between about 50% and about 100% hours at 24 hours and greater than 80% at 36 hours; or (85) between 0% and about 45% at 1 hour, between about 0% and about 70% at 2 hours, between about 3% and about 90% at 4 hours, between about 8% and about 100% at 8 hours, between about 15% and about 100% at 12 hours, between about 25% to about 100% at 16 hours, between about 45% and about 100% hours at 24 hours and greater than 80% at 36 hours; or (86) between 0% and about 40% at 1 hour, between about 0% and about 65% at 2 hours, between about 0% and about 80% at 4 hours, between about 5% and about 80% at 8 hours, between about 10% and about 90% at 12 hours, between about 20% to about 100% at 16 hours, between about 40% and about 100% hours at 24 hours and greater than 70% at 36 hours; or (87) between 0% and about 35% at 1 hour, between about 0% and about 60% at 2 hours, between about 0% and about 70% at 4 hours, between about 3% and about 70% at 8 hours, between about 5% and about 80% at 12 hours, between about 15% to about 100% at 16 hours, between about 30% and about 100% hours at 24 hours and greater than 40% at 36 hours; or (88) between 0% and about 60% at 1 hour, between about 0% and about 80% at 2 hours, between about 5% and about 100% at 4 hours, between about 15% and about 100% at 8 hours, between about 30% and about 100% at 12 hours, between about 40% to about 100% at 16 hours, between about 60% and about 100% hours at 24 hours and greater than 70% at 36 hours; or (89) between 0% and about 50% at 1 hour, between about 0% and about 75% at 2 hours, between about 5% and about 95% at 4 hours, between about 25% and about 80% at 8 hours, between about 30% and about 100% at 12 hours, between about 40% to about 100% at 16 hours, between about 60% and about 100% hours at 24 hours and greater than 60% at 36 hours; or (90) between 0% and about 60% at 1 hour, between about 0% and about 85% at 2 hours, between about 5% and about 100% at 4 hours, between about 10% and about 100% at 8 hours, between about 20% and about 100% at 12 hours, between about 30% to about 100% at 16 hours, between about 50% and about 100% hours at 24 hours and greater than 80% at 36 hours; or (91) between 15% and about 25% at 1 hour, between about 25% and about 35% at 2 hours, between about 30% and about 45% at 4 hours, between about 40% and about 60% at 8 hours, between about 55% and about 70% at 12 hours and between about 60% to about 75% at 16 hours; or (92) between 10% and about 20% at 1 hour, between about 20% and about 30% at 2 hours, between about 25% and about 40% at 4 hours, between about 30% and about 50% at 8 hours, between about 50% and about 65% at 12 hours and between about 55% to about 65% at 16 hours; or (93) between 5% and about 15% at 1 hour, between about 15% and about 25% at 2 hours, between about 20% and about 35% at 4 hours, between about 25% and about 45% at 8 hours, between about 45% and about 60% at 12 hours and between about 50% to about 60% at 16 hours; or (94) between 15% and about 30% at 1 hour, between about 20% and about 40% at 2 hours, between about 20% and about 50% at 4 hours, between about 30% and about 70% at 8 hours, between about 60% and about 80% at 12 hours and between about 70% to about 90% at 16 hours; or (95) between 0% and about 50% at 1 hour, between about 5% and about 50% at 2 hours, between about 5% and about 70% at 4 hours, between about 10% and about 80% at 8 hours, between about 20% and about 100% at 12 hours and between about 40% to about 100% at 16 hours; or (96) between 15% and about 40% at 1 hour, between about 15% and about 45% at 2 hours, between about 20% and about 60% at 4 hours, between about 20% and about 80% at 8 hours, between about 30% and about 90% at 12 hours and between about 40% to about 100% at 16 hours; or (97) between 0% to about 80% at 0.5 hours, and greater than about 40% at 1 hour; or (98) between 0% to about 40% at 0.5 hours, and greater than about 60% at 1 hour; or (98a)

between 0% to about 20% at 0.5 hours, and greater than about 40% at 1 hour; or (99) between 0% to about 20% at 0.5 hours, and greater than about 20% at 1 hour; or (100) between 0% to about 90% at 0.5 hours, and greater than about 60% at 1 hour; or (101) between 0% to about 100% at 0.5 hours, and greater than about 60% at 1 hour; or (102) between 0% to about 90% at 1 hour, and greater than about 40% at 2 hours; or (103) between 0% to about 100% at 1 hour, and greater than about 60% at 2 hours; or (104) between 0% to about 60% at 1 hour, and greater than about 40% at 2 hours; or (105) between 0% to about 40% at 1 hour, and greater than about 30% at 2 hours; or (106) between 0% to about 50% at 1 hour, and greater than about 40% at 2 hours; or (107) between 0% to about 30% at 1 hour, and greater than about 20% at 2 hours; or (108) between 0% and about 50% at 1 hour, between about 0% and about 80% at 2 hours, between about 5% and about 100% at 4 hours and between about 10% and about 100% at 8 hours; or (109) between 10% and about 60% at 1 hour, between about 15% and about 75% at 2 hours, between about 20% and about 95% at 4 hours and between about 30% and about 100% at 8 hours; or (110) between 0% to about 80% at 0.25 hours, and greater than about 90% at 1 hour; or (111) between 0% to about 100% at 0.25 hours, and greater than about 60% at 1 hour. In some preferred embodiments, the foregoing in-vitro release rate of butorphanol is achieved when measured by the USP Basket or Paddle Method at 100 rpm in 900 mL distilled water (time=0 hour begins here) at 37° C. at any pH between 4.5 and 8 at 37° C., said release rate measured following dissolution (pretreatment) with USP Basket or Paddle Method at 100 rpm in 900 mL of 0.1N HCl for two hours at 37° C., and then following further dissolution (pretreatment) with USP Basket or Paddle Method at 100 rpm in 900 mL distilled water at any pH of between 2 and 4 for a further time of up to two hours at 37° C. In some preferred embodiments, the foregoing dosage forms in (1) to (111) also incorporate a controlled release material and/or provide duodenal delivery, jejunal delivery, ileal delivery, ileo-colonic delivery or colonic delivery. In some preferred embodiments, the foregoing in-vitro release rate of butorphanol in (1) to (111) are achieved when measured by the USP Basket or Paddle Method at 100 rpm in 900 mL distilled water (time=0 hour begins here) at 37° C. at a pH of between 4.5 and 8 at 37° C., said release rate measured following dissolution (pretreatment) with USP Basket or Paddle Method at 100 rpm in 900 mL of 0.1N HCl for about 1, 1.5 or 2 hours at 37° C. In some preferred embodiments, the foregoing in-vitro release rate of butorphanol in (1) to (111) are achieved when measured by the USP Basket or Paddle Method at 100 rpm in 900 mL distilled water (time=0 hour begins here) at 37° C. at a pH of between 4.5 and 8 at 37° C., said release rate measured following dissolution (pretreatment) with USP Basket or Paddle Method at 100 rpm in 900 mL of 0.1N HCl for about 1, 1.5 or 2 hours at 37° C., and then following further dissolution (pretreatment) with USP Basket or Paddle Method at 100 rpm in 900 mL distilled water at a pH of between 2 and 4 for a further time of up to two hours at 37° C. In some preferred embodiments, the foregoing in-vitro release rate of butorphanol in (1) to (111) are achieved when measured by the USP Basket or Paddle Method at 100 rpm in 900 mL distilled water at 37° C. at a pH of between 4.5 and 8 at 37° C.

In some more preferred embodiments, the dosage form for once-a-day or Q24H administration provides an oral modified release pharmaceutical composition for the treatment of a butorphanol responsive medical condition comprising a therapeutically effective amount of butorphanol or pharmaceutically acceptable salts thereof or mixture thereof; and controlled release material to provide duodenal, jejunal or ileal release over an extended period of time, following dissolution (pretreatment) with USP Basket or Paddle Method at 100 rpm in 900 mL of 0.1N HCl for two hours at 37° C., providing an in-vitro release rate by weight of butorphanol, when measured by the USP Basket or Paddle Method at 100 rpm in 900 mL distilled water (time=0 hour begins here) at 37° C. at any pH between 4.5 and 8 at 37° C.: (1) between 0% to about 40% over 0 to 4 hours, between about 10% to about 70% over 4 to 8 hours, between about 40% to about 95% over 8 to 12 hours and more than 95% at 24 hours; (2) in some even more preferred embodiments, between 0% to about 30% over 0 to 4 hours, between about 15% to about 60% over 4 to 8 hours, between about 45% to about 90% over 8 to 12 hours and more than 70% at 24 hours; (3) in some especially preferred embodiments, between 0% to about 20% over 0 to 4 hours, between about 20% to about 50% over 4 to 8 hours, between about 55% to about 85% over 8 to 12 hours and more than 80% at 24 hours.

In some more preferred embodiments, the dosage form for once-a-day or Q24H administration provides an oral modified release pharmaceutical composition for the treatment of a butorphanol responsive medical condition comprising a therapeutically effective amount of butorphanol or pharmaceutically acceptable salts thereof or mixture thereof; and controlled release material to provide duodenal, jejunal or ileal release over an extended period of time, following dissolution (pretreatment) with USP Basket or Paddle Method at 100 rpm in 900 mL of 0.1N HCl for two hours at 37° C., providing an in-vitro release rate by weight of butorphanol, when measured by the USP Basket or Paddle Method at 100 rpm in 900 mL distilled water (time=0 hour begins here) at 37° C. at any pH between 4.5 and 8 at 37° C.: (1) between 5% to about 20% at 1 hour, between about 5% to about 40% at 4 hours, between about 20% to about 70% at 9 hours, between about 30% to about 85% at 12 hours and more than 60% at 24 hours; (2) in some even more preferred embodiments, between 10% to about 20% at 1 hour, between about 10% to about 40% at 4 hours, between about 25% to about 65% at 9 hours, between about 35% to about 75% at 12 hours and more than 70% at 24 hours; (3) in some especially preferred embodiments, between 10% to about 15% at 1 hour, between about 15% to about 30% at 4 hours, between about 35% to about 50% at 9 hours, between about 45% to about 65% at 12 hours and more than 80% at 24 hours.

In some more preferred embodiments, the dosage form for once-a-day or Q24H administration provides an oral modified release pharmaceutical composition for the treatment of a butorphanol responsive medical condition comprising a therapeutically effective amount of butorphanol or pharmaceutically acceptable salts thereof or mixture thereof; and controlled release material to provide duodenal, jejunal or ileal release over an extended period of time, providing an in-vitro release rate by weight of butorphanol, when measured by the USP Basket or Paddle Method at 100 rpm in 900 mL pH 6.8 phosphate buffer at 37° C. at 37° C.: (1) between 0% to about 40% over 0 to 4 hours, between about 10% to about 70% over 4 to 8 hours, between about 40% to about 95% over 8 to 12 hours and more than 95% at 24 hours; (2) in some even more preferred embodiments, between 0% to about 30% over 0 to 4 hours, between about 15% to about 60% over 4 to 8 hours, between about 45% to about 90% over 8 to 12 hours and more than 70% at 24 hours; (3) in some especially preferred embodiments, between 0% to about 20% over 0 to 4 hours, between about 20% to about 50% over 4 to 8 hours, between about 55% to about 85% over 8 to 12 hours and more than 80% at 24 hours.

In some more preferred embodiments, the dosage form for once-a-day or Q24H administration provides an oral modified release pharmaceutical composition for the treatment of a butorphanol responsive medical condition comprising a therapeutically effective amount of butorphanol or pharmaceutically acceptable salts thereof or mixture thereof; and controlled release material to provide duodenal, jejunal or ileal release over an extended period of time, providing an in-vitro release rate by weight of butorphanol, when measured by the USP Basket or Paddle Method at 100 rpm in 900 mL pH 6.8 phosphate buffer at 37° C. at 37° C.: (1) between 5% to about 20% at 1 hour, between about 5% to about 40% at 4 hours, between about 20% to about 70% at 9 hours, between about 30% to about 85% at 12 hours and more than 60% at 24 hours; (2) in some even more preferred embodiments, between 10% to about 20% at 1 hour, between about 10% to about 40% at 4 hours, between about 25% to about 65% at 9 hours, between about 35% to about 75% at 12 hours and more than 70% at 24 hours; (3) in some especially preferred embodiments, between 10% to about 15% at 1 hour, between about 15% to about 30% at 4 hours, between about 35% to about 50% at 9 hours, between about 45% to about 65% at 12 hours and more than 80% at 24 hours.

In some more preferred embodiments, the dosage form for twice-a-day or Q12H administration provides an oral modified release pharmaceutical composition for the treatment of a butorphanol responsive medical condition comprising a therapeutically effective amount of butorphanol or pharmaceutically acceptable salts thereof or mixture thereof; and controlled release material to provide duodenal, jejunal or ileal release over an extended period of time, following dissolution (pretreatment) with USP Basket or Paddle Method at 100 rpm in 900 mL of 0.1N HCl for two hours at 37° C., providing an in-vitro release rate by weight of butorphanol, when measured by the USP Basket or Paddle Method at 100 rpm in 900 mL distilled water (time=0 hour begins here) at 37° C. at any pH between 4.5 and 8 at 37° C.: (1) between 0% to about 60% over 0 to 4 hours, between about 20% to about 90% over 4 to 8 hours, between about 30% to about 100% over 8 to 12 hours and more than 50% at 24 hours; (2) in some even more preferred embodiments, between 0% to about 50% over 0 to 4 hours, between about 30% to about 100% over 4 to 8 hours, between about 40% to about 100% over 8 to 12 hours and more than 60% at 24 hours; (3) in some especially preferred embodiments, between 0% to about 40% over 0 to 4 hours, between about 40% to about 100% over 4 to 8 hours, between about 50% to about 100% over 8 to 12 hours and more than 90% at 24 hours.

In some more preferred embodiments, the dosage form for twice-a-day or Q12H administration provides an oral modified release pharmaceutical composition for the treatment of a butorphanol responsive medical condition comprising a therapeutically effective amount of butorphanol or pharmaceutically acceptable salts thereof or mixture thereof; and controlled release material to provide duodenal, jejunal or ileal release over an extended period of time, following dissolution (pretreatment) with USP Basket or Paddle Method at 100 rpm in 900 mL of 0.1N HCl for two hours at 37° C., providing an in-vitro release rate by weight of butorphanol, when measured by the USP Basket or Paddle Method at 100 rpm in 900 mL distilled water (time=0 hour begins here) at 37° C. at any pH between 4.5 and 8 at 37° C.: (1) between 5% to about 50% at 1 hour, between about 10% to about 80% at 4 hours, between about 20% to about 100% at 9 hours, and more than about 40% at 12 hours; (2) in some even more preferred embodiments, between 10% to about 40% at 1 hour, between about 15% to about 70% at 4 hours, between about 30% to about 100% at 9 hours, and more than about 50% at 12 hours; (3) in some especially preferred embodiments, between 15% to about 30% at 1 hour, between about 25% to about 60% at 4 hours, between about 65% to about 100% at 9 hours, and more than about 80% at 12 hours.

In some more preferred embodiments, the dosage form for twice-a-day or Q12H administration provides an oral modified release pharmaceutical composition for the treatment of a butorphanol responsive medical condition comprising a therapeutically effective amount of butorphanol or pharmaceutically acceptable salts thereof or mixture thereof; and controlled release material to provide duodenal, jejunal or ileal release over an extended period of time, providing an in-vitro release rate by weight of butorphanol, when measured by the USP Basket or Paddle Method at 100 rpm in 900 mL pH 6.8 phosphate buffer at 37° C. at 37° C.: (1) between 0% to about 60% over 0 to 4 hours, between about 20% to about 90% over 4 to 8 hours, between about 30% to about 100% over 8 to 12 hours and more than 50% at 24 hours; (2) in some even more preferred embodiments, between 0% to about 50% over 0 to 4 hours, between about 30% to about 100% over 4 to 8 hours, between about 40% to about 100% over 8 to 12 hours and more than 60% at 24 hours; (3) in some especially preferred embodiments, between 0% to about 40% over 0 to 4 hours, between about 40% to about 100% over 4 to 8 hours, between about 50% to about 100% over 8 to 12 hours and more than 90% at 24 hours.

In some more preferred embodiments, the dosage form for twice-a-day or Q12H administration provides an oral modified release pharmaceutical composition for the treatment of a butorphanol responsive medical condition comprising a therapeutically effective amount of butorphanol or pharmaceutically acceptable salts thereof or mixture thereof; and controlled release material to provide duodenal, jejunal or ileal release over an extended period of time, providing an in-vitro release rate by weight of butorphanol, when measured by the USP Basket or Paddle Method at 100 rpm in 900 mL pH 6.8 phosphate buffer at 37° C. at 37° C.: (1) between 5% to about 50% at 1 hour, between about 10% to about 80% at 4 hours, between about 20% to about 100% at 9 hours, and more than about 40% at 12 hours; (2) in some even more preferred embodiments, between 10% to about 40% at 1 hour, between about 15% to about 70% at 4 hours, between about 30% to about 100% at 9 hours, and more than about 50% at 12 hours; (3) in some especially preferred embodiments, between 15% to about 30% at 1 hour, between about 25% to about 60% at 4 hours, between 65% to about 100% at 9 hours, and more than about 80% at 12 hours.

Although dosage forms that provide pH independent in vitro dissolution and in vivo release are frequently sought after and viewed favorably, particularly many controlled release or extended release forms, in some embodiments, pH independent dissolution and release can work against the objectives of the some oral dosage forms of butorphanol (delayed onset, rapid release or delayed onset, extended release, or delayed onset, pulsatile release) which are intended to provide delivery or release of the dosage form in the proximal to the stomach, duodenum, or ileum (i.e., duodenal release, jejunal release, ileal release, ileo-colonic release or colonic release). Indeed, certain controlled release material used to achieve delayed onset, duodenal release, jejunal release, ileal release, ilco-colonic release or colonic release exploit the pH difference in the GI tract to achieve some or all of its objectives.

Therefore, in some preferred embodiments, where the oral butorphanol pharmaceutical composition is intended to provide delayed onset, rapid release or delayed onset, extended release, or delayed onset, pulsatile release through use of a pH sensitive controlled release material, the in-vitro release rate is substantially dependent on pH in that the amount of butorphanol released at an undesirable pH (e.g., pH 1.2) and the amount released at a desirable pH (e.g., depending on the controlled release material and delivery and release objectives, pH 5.5, 6, 6.5, 7, 7.2, 7.4), when measured in-vitro at 1.5 or 2 hours using the USP Basket or Paddle Method of USP Drug Release test of U.S. Pharmacopeia (2003) at 100 rpm in 900 ml aqueous buffer is significantly different. For example, in some preferred embodiments, the in-vitro release rate difference is greater than about 35%, or 40%, or 45%, or 50%, or 55%, or 60% or 70%, or 80%, with the release rate higher at the desirable pH compared with the undesirable pH.

In certain embodiments, the dosage forms of the invention contains one or more substances in sufficient quantity to render said dosage form controlled release, such that: (i) in-vitro release rate of butorphanol by weight immediate release oral butorphanol compared with in-vitro release rate by weight of butorphanol from the dosage form of the invention is at least about 10%, or at least about 15%, or at least about 20%, or at least about 30%, or at least about 40%, or at least about 50%, or at least about 60%, or at least about 70%, or at least about 80%, or at least about 90% faster, or at least 100% faster, or at least 200% faster, or at least 300% faster, or at least 400% faster, or at least 500% faster, or at least 600% faster, or at least 700% faster, or at least 800% faster, or at least 1000% faster, at 0.25 hour, or at 0.5 hours, or at 1 hour, or at 2 hours, or at 1 to 2 hours, when measured by the USP Basket or Paddle Methods at 100 rpm in 900 mL aqueous buffer at a pH of between 1.6 and 7.2 at 37° C.; and/or (ii) in-vivo release rate of butorphanol by weight of any immediate release oral butorphanol compared with the in-vivo release rate of butorphanol from the dosage form of the invention is at least about 10%, or at least about 15%, or at least about 20%, or at least about 30%, or at least about 40%, or at least about 50%, or at least about 60%, or at least about 70%, or at least about 80%, or at least about 90% faster, or at least about 100% faster, or at least 200% faster, or at least 300% faster, or at least 400% faster, or at least 500% faster, or at least 600% faster, or at least 700% faster, or at least 800% faster, or at least 1000% faster, said in-vivo release rate quantified by the $C_{max}$ of butorphanol after single dose administration to human subjects, each dosage form administered according to its approved route of administration.

In some preferred embodiments, the oral dosage form is a controlled release material suitable for extended release oral administration to a human patient of the dosage form comprises a matrix. In some preferred embodiments, the said matrix is a plurality of multiparticulate matrices. In some preferred embodiments, the multiparticulates are compressed into a tablet. In some preferred embodiments, the multiparticulates are disposed in a pharmaceutically acceptable capsule.

In some preferred embodiments, the in vivo pharmacokinetic parameters of the specifications and claims are derived or determined from first administration. In other preferred embodiments, the in vivo pharmacokinetic parameters are derived or determined from steady state administration.

In some preferred embodiments, the in vivo pharmacokinetic parameters of the specifications and claims are derived or determined under fed conditions. In other preferred embodiments, the in vivo pharmacokinetic parameters are derived or determined under fasted conditions.

In some preferred embodiments, the in vivo pharmacokinetic parameters of the specifications and claims are derived or determined from an individual subject. In other preferred embodiments, the in vivo pharmacokinetic parameters are derived or determined from a population of subjects.

In some preferred embodiments, the in vivo specifications and claims of the invention are measured, reported, observed or achieved after administration of some or most doses of the invention. In other preferred embodiments, the in vivo specifications and claims of the invention are measured, reported, observed or achieved after administration of substantially all or all doses of the invention.

In some preferred embodiments, the in vivo pharmacokinetic parameters of the specifications and claims are derived or determined in subjects having a Body Mass Index (BMI) between 18 and 26 kg/$m^2$, inclusive (BMI=[weight in kg/height in $m^2$]×10,000). In some preferred embodiments, the in vivo pharmacokinetic parameters of the specifications and claims are derived or determined in subjects having a Body Mass Index (BMI) ≥38 kg/$m^2$.

Also disclosed are methods for the targeted release of butorphanol from the dosage form into the duodenum, jejunum, ileum and colon to provide a therapeutic effect comprising administering a therapeutically effective amount of oral butorphanol or a pharmaceutically acceptable salt of butorphanol or a mixture thereof.

Also disclosed are methods for the treatment of opioid dependence or addiction disorders in a human patient suffering comprising administering a therapeutically effective amount of oral butorphanol or a pharmaceutically acceptable salt of butorphanol or a mixture thereof. Preferably, the addiction disorder is an opioid addiction disorder or a poly-substance abuse disorder.

Also disclosed are methods for resisting, deterring, minimizing or preventing drug abuse, drug diversion and drug addiction in a human patient comprising administering a therapeutically effective amount of oral butorphanol or a pharmaceutically acceptable salt of butorphanol or a mixture thereof.

Also disclosed are methods for the treatment of medical conditions amenable to treatment with butorphanol in patients who are at higher risk for nausea, vomiting, sedation or other opioid agonist side effects or who have a prior history of said side effects on other opioids comprising administering a therapeutically effective amount of oral butorphanol or a pharmaceutically acceptable salt of butorphanol or a mixture thereof.

Also disclosed are methods for the treatment of medical conditions amenable to treatment with butorphanol in patients who are at higher risk for nausea, vomiting, sedation or other side effects with intranasal butorphanol oral immediate release butorphanol comprising administering a therapeutically effective amount of oral butorphanol or a pharmaceutically acceptable salt of butorphanol or a mixture thereof.

Also disclosed are methods for the treatment of dyspnea, cough and COPD comprising administering a therapeutically effective amount of oral butorphanol or a pharmaceutically acceptable salt of butorphanol or a mixture thereof.

Also disclosed are methods for the treatment of medical conditions amenable to treatment with butorphanol or opioid agonists in a human patient who also suffers from an addiction disorder, who is at risk or increased risk for addiction or who may be prone to drug diversion into illicit channels comprising administering a therapeutically effective amount of oral butorphanol or a pharmaceutically acceptable salt of butorphanol or a mixture thereof.

Also disclosed are methods for the treatment of medical conditions amenable to treatment with butorphanol or opioid agonists in a human patient suffering comprising administering a therapeutically effective amount of oral butorphanol or a pharmaceutically acceptable salt of butorphanol or a mixture thereof.

Also disclosed are methods for preventing and treating pain in a human patient comprising administering a therapeutically effective amount of oral butorphanol or a pharmaceutically acceptable salt of butorphanol or a mixture thereof.

All pain states are contemplated by this invention, regardless of etiology, mechanisms, duration, prior treatment response and anatomic location, including acute pain, inflammatory pain, chronic pain, cancer pain, visceral pain and neuropathic pain.

Also disclosed are methods of providing relief in a human patient suffering from neuropathic and chronic pain comprising a therapeutically effective amount of oral butorphanol or a pharmaceutically acceptable salt butorphanol or a mixture thereof. In some preferred embodiments, the dosage form of the invention is intended for the treatment of neuropathic pain, peripheral neuropathic pain, central neuropathic pain, chronic pain, osteoarthritis, back pain, cancer pain, and chronic inflammatory pain.

Also disclosed are methods of providing relief in a human patient suffering from acute pain comprising a therapeutically effective amount of oral butorphanol or a pharmaceutically acceptable salt butorphanol or a mixture thereof.

Also disclosed are methods of providing relief in a human patient suffering from an addiction disorder comprising a therapeutically effective amount of oral butorphanol or a pharmaceutically acceptable salt butorphanol or a mixture thereof.

All kinds of kits of the present invention are contemplated. In some preferred embodiments, also provided are kits for use in treating or preventing the pain with the oral administration of butorphanol or a pharmaceutically acceptable salt of butorphanol, or a mixture thereof for a subject in need of such treatment, comprising: (i) a dosage form of the invention; (ii) a container for the dosage form; and optionally, any of (iii) to (vi): (iii) a container for individual units of the dosage form (e.g., individual tablets or capsules in blisters); (iv) educational instructions in any media about various medical conditions, their etiology, pathophysiology, consequences and treatment, including information on the potential for abuse and diversion and methods for prevention of same and information on the proper use and disposal of the medication; (v) containers or bags for the safe disposal of any used or remaining unused dosage form, preferably child proof and flushable; (vi) tamper evident and child proof packaging for the kit and its contents.

The amount of butorphanol in the oral dosage form will vary depending on variety of physiologic, pharmacologic, pharmacokinetic, pharmaceutical and physicochemical factors, including: (i) the choice of butorphanol as the base, pharmaceutically acceptable salt or mixtures thereof; (ii) the nature of the oral dosage form (e.g., immediate release or extended release); (iii) the anatomical location of the pain relieving target; (iv) the intensity and intractability of the pain; (v) the contribution of different mechanism to the initiation, propagation, summation and maintenance of the pain; (vi) the absorption, metabolism, distribution and excretion of orally administered butorphanol in healthy subjects and in patients with various diseases and disorders, including renal and hepatic impairment; (vii) the presence of comorbid pathology; (viii) the patient's risk of iatrogenic side effects; (ix) the tolerability of the dose, including the patient's propensity for butorphanol associated CNS and gastrointestinal side effects; (x) use of concurrent analgesics; (xi) the efficiency of the dosage form.

In certain embodiments, the amount of butorphanol in the dosage form is about 0.001 mg to 1500 mg. In other embodiments, the amount of butorphanol in the dosage form is about 0.1 mg to 1000 mg. In other embodiments, the amount of butorphanol in the dosage form is about 0.5 mg to about 500 mg or about 1 mg to about 200 mg, or 2 mg to about 100 mg or 1 mg to about 60 mg. In certain embodiments, the maximum dose of oral butorphanol exceeds the maximum approved dose of intranasal butorphanol by at least about 5%, or 10%, or 15%, or 20%, or 30%, or 40%, or 50%, or 60%, or 70%, or 80%, or 90%, or 100%, or 120%, or 140%, or 160%, or 180%, or 200%, or 220%, or 240%, or 260%, or 280%, or 300%, or 320%, or 340%, or 360%, or 380%, or 400%, or 450%, or 500%, or 550%, or 600%, or 650%, or 700%. In certain embodiments, the minimum dose of oral butorphanol exceeds the minimum approved dose of intranasal butorphanol by at least about 5%, or 10%, or 15%, or 20%, or 30%, or 40%, or 50%, or 60%, or 70%, or 80%, or 90%, or 100%, or 120%, or 140%, or 160%, or 180%, or 200%, or 220%, or 240%, or 260%, or 280%, or 300%, or 320%, or 340%, or 360%, or 380%, or 400%, or 450%, or 500%, or 550%, or 600%, or 650%, or 700%. In certain embodiments, the average dose of oral butorphanol exceeds the average dose of intranasal butorphanol by at least about 5%, or 10%, or 15%, or 20%, or 30%, or 40%, or 50%, or 60%, or 70%, or 80%, or 90%, or 100%, or 120%, or 140%, or 160%, or 180%, or 200%, or 220%, or 240%, or 260%, or 280%, or 300%, or 320%, or 340%, or 360%, or 380%, or 400%, or 450%, or 500%, or 550%, or 600%, or 650%, or 700%. In certain embodiments, the induction (where appropriate) or maintenance dose of oral butorphanol exceeds the approved induction (where appropriate) or maintenance dose of intranasal butorphanol by at least about 5%, or 10%, or 15%, or 20%, or 30%, or 40%, or 50%, or 60%, or 70%, or 80%, or 90%, or 100%, or 120%, or 140%, or 160%, or 180%, or 200%, or 220%, or 240%, or 260%, or 280%, or 300%, or 320%, or 340%, or 360%, or 380%, or 400%, or 450%, or 500%, or 550%, or 600%, or 650%, or 700%. In certain embodiments, the induction (where appropriate) dose, maintenance dose, minimum dose, average doe and/or maximum dose of oral butorphanol exceeds the corresponding dose intranasal butorphanol by at least about 5%, or 10%, or 15%, or 20%, or 30%, or 40%, or 50%, or 60%, or 70%, or 80%, or 90%, or 100%, or 120%, or 140%, or 160%, or 180%, or 200%, or 220%, or 240%, or 260%, or 280%, or 300%, or 320%, or 340%, or 360%, or 380%, or 400%, or 450%, or 500%, or 550%, or 600%, or 650%, or 700%. In certain embodiments, the dose of oral butorphanol is at least about 2 mg, or 3 mg, or 4 mg, or 5 mg, or 6 mg, or 7 mg, or 8 mg, or 9 mg, or 10 mg or 11 mg, or 12 mg, or 13 mg, or 14 mg, or 15 mg, or 16 mg, or 17 mg, or 18 mg, or 19 mg, or 20 mg, or 21 mg, or 22 mg, or 23 mg, or 24 mg, or 25 mg, or 26 mg, or 27 mg, or 28 mg, or 29 mg, or 30 mg, or 32 mg, or 34 mg, or 35 mg, or 36 mg, or 38 mg, or 40 mg, or 45 mg, or 50 mg, or 55 mg, or 60 mg, or 65 mg, or 70 mg. In certain embodiments, the amount of butorphanol base in the dosage form is not less than 10 mg, or not less than about 10 mg, or 11 mg, or 12 mg, or 13 mg or 14 mg, or 15 mg, or 16 mg, or 17 mg, or 18 mg, or 19 mg, or 20 mg, or 21 mg, or 22 mg, or 23 mg, or 24 mg, or 25 mg, or 26 mg, or 27 mg, or 28 mg, or 29 mg, or 30 mg. In certain embodiments, the amount of butorphanol hydrochloride in the dosage form is not less than 10 mg, or not less than about 10 mg, or 11 mg, or 12 mg, or 13 mg or 14 mg, or 15 mg, or 16 mg, or 17 mg, or 18 mg, or 19 mg, or 20 mg, or 21 mg, or 22 mg, or 23 mg, or 24 mg, or 25 mg, or 26 mg, or 27 mg, or 28 mg, or 29 mg, or 30 mg. In certain embodiments, the amount of any pharmaceutically acceptable salt of butorphanol in the dosage form is not less than 10 mg, or not less than about 10 mg, or 11 mg, or 12 mg, or 13 mg or 14 mg, or 15 mg, or 16 mg, or 17 mg, or 18 mg, or 19 mg, or 20 mg, or 21 mg, or 22 mg, or 23 mg, or 24 mg, or 25 mg, or 26 mg, or 27 mg, or 28 mg, or 29 mg, or 30 mg. In certain embodiments, the daily dose of butorphanol or its pharmaceutically acceptable salt in the dosage form is not less than 40 mg, or 50 mg or 60 mg or 65 mg.

The invention is also directed to methods of preparing the dosage forms disclosed herein.

The invention is also directed to a process for the preparation and manufacture of the dosage form.

The invention is also directed to methods of treating butorphanol responsive medical conditions comprising administering a therapeutically effective amount of oral butorphanol in a dosage form of the invention, or pharmaceutically acceptable salts thereof or mixtures thereof.

The invention is also directed to methods of treating pain, chronic pain, neuropathic pain, opioid dependence, dyspnea, cough and addiction disorders comprising administering a therapeutically effective amount of oral butorphanol in a dosage form of the invention, or pharmaceutically acceptable salts thereof or mixtures thereof.

The invention is also directed to methods of treating butorphanol responsive medical conditions with reduced risk of drug abuse, drug misuse, and drug diversion comprising administering a therapeutically effective amount of oral butorphanol in a dosage form of the invention, or pharmaceutically acceptable salts thereof or mixtures thereof.

The invention is also directed to methods of improving treatment compliance and deter episodic, occasional, intermittent, periodic, as needed, or PRN use of the dosage form when treating butorphanol responsive medical conditions requiring more than few days of therapy to more than a few weeks of therapy or chronic therapy comprising administering a therapeutically effective amount of oral butorphanol in a dosage form of the invention, or pharmaceutically acceptable salts thereof or mixtures thereof.

In certain preferred embodiments, the butorphanol in the dosage form is combined with one or more other drugs for the treatment of the same medical condition as the butorphanol or for the treatment of a different medical condition. All modes of co-administration are contemplated, including via an oral, subcutaneous, direct intravenous, slow intravenous infusion, continuous intravenous infusion, intravenous or epidural patient controlled analgesia (PCA and PCEA), intramuscular, intrathecal, epidural, intracisternal, intramuscular, intraperitoneal, transdermal, topical, transmucosal, buccal, sublingual, inhalation, intranasal, epidural, intra-atricular, intranasal, rectal or ocular routes.

The term "first administration" means administration of a dose of the present invention at the initiation of therapy to an individual patient or a patient population.

The term "steady state" means that the amount of the drug reaching the system is approximately the same as the amount of the drug leaving the system. Thus, at "steady-state", the patient's body eliminates the drug at approximately the same rate that the drug becomes available to the patient's system through absorption into the blood stream.

As used herein the terms: (i) "$AUC_{0-t}$", and "$AUC_{0-\tau}$" (or "$AUC_{0-Tau}$") mean the area under the plasma drug concentration-time curve from time zero to the intended dosing frequency of the dosage form after a single administration (e.g., 8 hours, 12 hours or 24 hours) and to the end of the dosing interval after repeated dosing or at steady-state, respectively; (ii) "$AUC_{0-inf}$" (means area under the plasma drug concentration-time curve from time zero to infinity; (iii) "$AUC_{0-6}$" means area under the plasma drug concentration-time curve from time zero to 6 hours after dosing; (iv) "$AUC_{0-8}$" means area under the plasma drug concentration-time curve from time zero to 8 hours after dosing; (v) "$AUC_{0-12}$" means area under the plasma drug concentration-time curve from time zero to 12 hours after dosing; (vi) "$AUC_{0-24}$" means area under the plasma drug concentration-time curve from time zero to 24 hours after dosing; (vii) "$C_{max}$" means the maximum observed plasma drug concentration; (viii) "$C_6$" means the plasma drug concentration at 6 hours after dosing; (ix) "$C_8$" means the plasma drug concentration at 8 hours after dosing; (x) "$C_{12}$" means the plasma drug concentration at 12 hours after dosing; (xi) "$C_{24}$" means the plasma drug concentration at 24 hours after dosing; (xii) "$t_{max}$" or "$T_{max}$" means the time of the observed maximum drug concentration (also known as time to achieve $C_{max}$); (xiii) "$C_{min}$" means the minimum observed drug concentration following the maximum plasma concentration or the concentration at the end of the intended dosing interval; (xiv) "half value duration" or "HVD" means the duration over the dosing interval during which plasma concentration of drug are greater than or equal to one-half of $C_{max}$, obtained by calculating the time interval beginning when the interpolated concentration first equals or exceeds one-half of $C_{max}$ and ending at the first time point for which the interpolated concentration falls below one-half of $C_{max}$; (xv) "$W_{50}$" for purposes of the present invention means the width of the plasma concentration time curve at 50% of the height of the $C_{max}$ over the dosing interval; (xvi) "steady state" is a state of equilibrium wherein the amount of the drug reaching the system is approximately the same as the amount of the drug leaving the system or put another way, the patient's body eliminates the drug at approximately the same rate that the drug becomes available to the patient's system through absorption into the blood stream, said "time to steady state" measured by calculating the $C_{min}$ after each sequential dosing of drug administered at the intended dosing frequency until two consecutive $C_{min}$'s are not statistically different at a 10% significance level (p=0.10); (xvii) "percent fluctuation" means the variation in plasma concentrations of the drug computed as: (a) $(C_{max}-C_{min})/C_{min} \times 100$ (for an individual patient) and (mean $C_{max}$-mean $C_{min}$)/mean $C_{min} \times 100$ (for a population); or (b) $(C_{max}-C_{min})/C_{av} \times 100$ (for an individual patient) and (mean $C_{max}$-mean $C_{min}$)/mean $C_{av} \times 100$ (for a population); (xviii) "accumulation index" or "AI" means the ratio of the plasma concentration of the drug at the end of the intended dosing interval (i.e., 8 hours for a Q8H dosage form, 12 hours for a Q12H dosage form, and 24 hours for a Q24H dosage form) after administration, determined at steady-state ($C_{ssmin}$) to the plasma concentration of the drug at the end of the intended dosing interval determined at first administration (i.e., after the first dose); (xix) "$AUC_{0-n}$" means the area under the plasma drug concentration-time curve from time zero to the specified time point ("n").

Pharmacokinetic parameters of the invention are be computed from single dose (i.e., first administration) and steady state pharmacokinetic studies conducted in an individual subject or in a population of subjects in the fasted or fed states. The AI and percent of steady state computations requires both single dose (i.e., first administration) and steady state pharmacokinetic assessment.

In certain preferred embodiments of the present invention, an effective amount of butorphanol in immediate release form is included in the controlled release unit dose butorphanol formulation to be administered. The immediate release form of the butorphanol is preferably included in an amount which is effective to shorten the time to $C_{max}$ of the butorphanol in the blood (e.g., plasma). In such embodiments, an effective amount of the butorphanol in immediate release form may be coated onto the substrates of the present invention. For example, where the extended release butorphanol from the formulation is due to a controlled release coating, the immediate release layer would be overcoated on top of the controlled release coating. On the other hand, the immediate release layer maybe coated onto the surface of substrates wherein the butorphanol is incorporated in a controlled release matrix. Where a plurality of the sustained release substrates comprising an effective unit dose of the butorphanol (e.g., multiparticulate systems including pellets, spheres, beads and the like) are incorporated into a hard gelatin capsule, the immediate release portion of the butorphanol dose may be incorporated into the gelatin capsule via inclusion of the sufficient amount of immediate release butorphanol as a powder or granulate within the capsule. Alternatively, the gelatin capsule itself may be coated with an immediate release layer of the butorphanol. One skilled in the art would recognize still other alternative manners of incorporating the immediate release butorphanol into the unit dose. Such alternatives are deemed to be encompassed by the appended claims. By including such an effective amount of immediate release butorphanol in the unit dose, the experience of relatively higher levels of pain in patients may be significantly reduced.

For purposes of the invention, the term "a patient" in reference to pharmacokinetic parameters means that the discussion (or claim) is directed to the pharmacokinetic parameters of an individual patient or subject.

The term "population of patients" or "patient population" means that the discussion (or claim) is directed to the mean pharmacokinetic parameters of at least two patients or subjects.

In certain preferred embodiments, any one or all of the above in-vivo parameters are achieved after a first administration (often referred to as "single dose administration") of the dosage form to a human patient or a population of human patients.

In certain alternative embodiments, any one or all of the above in-vivo parameters are achieved after steady state administration of the dosage form to a human patient or a population of human patients.

The term "USP Paddle or Basket Method" is the Paddle and Basket Method described, e.g., in specified in the United States Pharmacopeia, USP-28 NF-23 (2005), published by the United States Pharmacopeial Convention, Inc, herein incorporated by reference.

The term "pH-dependent" for purposes of the present invention is defined as having characteristics (e.g., dissolution) which vary according to environmental pH.

The term "pH-independent" for purposes of the present invention is defined as having characteristics (e.g., dissolution) which are substantially unaffected by pH.

The term "pH-dependent" for purposes of the present invention is defined as having characteristics (e.g., dissolution) which are substantially affected by pH.

The term "bioavailability" is defined for purposes of the present invention as the extent to which the drug (e.g., butorphanol) is absorbed from the unit dosage forms.

All oral pharmaceutical dosage forms of the invention are contemplated, including oral suspensions, tablets, capsules, effervescent tablets, effervescent powders, powders, solutions, powders for reconstitution, oral gastroretentive tablets and capsules, administered as immediate release, modified release, enteric coated, sustained release, controlled release, pulsatile release and extended release dosage form.

In some preferred embodiments of the invention, the dosage form comprises one or more of the following: modified release or enteric coated or sustained release or controlled release or pulsatile release or extended release. In some preferred embodiments of the invention, the dosage form comprises only one of the following: modified release or enteric coated or sustained release or controlled release or pulsatile release or extended release. In some preferred embodiments of the invention, the dosage form specifically excludes delayed onset, rapid release dosage forms. In some preferred embodiments of the invention, the dosage form specifically excludes delayed onset, extended release dosage forms In some embodiments, the invention specifically excludes oral immediate release dosage forms.

In some preferred embodiments of the invention, the dosage form of the invention is controlled release, extended release, sustained release, modified release, or delayed onset.

In some preferred embodiments of the invention, the dosage form of the invention is delayed onset, rapid release or delayed onset, extended release, or delayed onset, pulsatile release.

In some preferred embodiments of the invention, the dosage form of the invention is delayed onset, duodenal delivery, jejunal delivery, ileal delivery, ileo-colonic delivery, colonic delivery In some embodiments, the controlled release material of the dosage form may function to provide duodenal delivery, jejunal delivery, ileal delivery, ileo-colonic delivery or colonic delivery.

In some embodiments, the controlled release material of the dosage form may function to provide delayed onset, rapid release or delayed onset, extended release, or delayed onset, pulsatile release In some preferred dosage forms of the invention, the dosage form includes taste aversive agents (e.g., bittering agents) in sequestered or unsequestered form to deter sublingual, oromucosal, buccal or intranasal use of the dosage form. In some embodiments, the taste aversive agents (bittering agent) is coated on the oral dosage form and then overcoated with material which prevents or minimizes the bitter sensation upon normal oral ingestion but which does not protect against an aversive taste upon prolonged residence in the oral cavity (e.g., upon sublingual, oromucosal or buccal use) or upon intranasal use. In this manner the taste aversive agent is not sequestered in the sense that it is readily released in the GI tract upon oral ingestion, where it is devoid of taste aversive effects. A wide variety of pharmaceutical excipients known in the art may be used to provide the desired outer coating to the dosage form. In some embodiments, the taste aversive agents (e.g., bittering agent) is incorporated in the oral dosage form which prevents or minimizes the bitter sensation upon normal oral ingestion but which does not protect against an aversive taste upon prolonged residence in the oral cavity (e.g., upon sublingual, oromucosal or buccal use). In this manner the taste aversive agent may be sequestered or unsequestered. In some embodiments, the taste aversive agents (e.g., bittering agent) is incorporated into the inside walls of the capsule shell which prevents or minimizes the bitter sensation upon normal oral ingestion but which does not protect against an aversive taste upon prolonged residence in the oral cavity (e.g., upon sublingual, oromucosal or buccal use).

In some preferred embodiments, the dosage form is non-releasable or substantially non-releasable until (i) after a particular time following oral ingestion, when the dosage form can be anticipated to have reached the duodenum, jejunum, ileum, ileo-cecal junction, cecum, or colon; (ii) the dosage form has come in contact or substantial contact or sustained contact with a desired gastrointestinal pH environment (e.g., pH >3, or pH >3.5, or pH >4, or pH >4.5, or pH, >5, or pH >5.5, or pH >6, or pH >7, or pH >7.5, or pH >7.8); (iii) the dosage form has come in contact with desired microbial flora (e.g., colonic microbial flora).

In certain situations involving pharmacokinetic evaluations, it may not be possible to provide the same amount of drug by different routes of administration due to the lack of commercially available dosage strengths or because such administration would require testing outside the approved method of administration (e.g., simultaneous intranasal administration of more than one or two doses into each nostril of oral administration of high doses of immediate release butorphanol). Under such circumstances, the term "after the same amount of an oral immediate release formulation of butorphanol" and after the same amount of an intranasal formulation of butorphanol" may be waived and different amounts of drug may be evaluated, provided the data are dose normalized using pharmacokinetic approaches well known in the art.

The term "agonist" means a ligand that binds to a receptor and alters the receptor state resulting in a biological response. Conventional agonists increase receptor activity, whereas inverse agonists reduce it (See Neubig et al, IUPHAR Committee on Receptor Nomenclature and Classification, Pharmacol Rev, 2003; Howlett et al., Mol Pharmacol, 1988).

The term "opioid agonist" means a molecule that causes a specific physiologic, pathophysiologic or pharmacologic effect after binding to an opioid receptor.

An "antagonist" is a drug or ligand that reduces the action of another drug or ligand, generally an agonist. Many antagonists act at the same receptor macromolecule as the agonist. (See Neubig et al, IUPHAR Committee on Receptor Nomenclature and Classification, Pharmacol Rev, 2003; Howlett et al., Mol Pharmacol, 1988).

The term "receptor" means a molecule within a cell, on a cell surface, on a membrane, in tissue, in fluid or otherwise found in humans that serve as a recognition or binding site to cause specific physiologic, pathophysiologic or pharmacologic effects. The term "receptor" also means a cellular macromolecule, or an assembly of macromolecules, that is concerned directly and specifically in chemical signaling between and within cells. Combination of a hormone, neurotransmitter, drug, ligand, or intracellular messenger with its receptor(s) initiates a change in cell function (Neubig et al, IUPHAR Committee on Receptor Nomenclature and Classification, Pharmacol Rev, 2003).

The term "opioid receptor" includes mu ($\mu$), delta ($\delta$) and kappa ($\kappa$) opioid receptors, their subtypes and splice variants such as $mu_1$, $mu_2$, $delta_1$, $delta_2$, $kappa_1$, $kappa_2$ and $kappa_3$, etc.

Opioid antagonists are known or readily determined by individuals who practice the art. Preferably, the opioid antagonists useful for the present invention may be selected from the group consisting of naltrexone, methylnaltrexone, nalbuphine, naloxone, nalmefene, cyclazocine, cyclorphan, oxilorphan nalorphine, nalorphine dinicotinate, nalmefene, nadide and levallorphan.

In certain preferred embodiments of the present invention, the invention allows for the use of lower doses of butorphanol by virtue of the inclusion or co-administration of an additional drug for the prevention or treatment of pain. By using lower amounts of either or both drugs, the side effects associated with treatment in humans are reduced.

The term "(−)17-(cyclobutylmethyl)morphinan-3,14-diol" is used interchangeably with "butorphanol", (−)-17-(cyclobutylmethyl) morphinan-3, and 14-diol, 17-cyclobutylmethylmorphinan-3,14-diol and means butorphanol base (CAS number 42408-82-2), as well as their pharmaceutically acceptable salts, prodrugs, esters, analogs, derivatives, solvates, complexes, polymorphs, and hydrates, as racemates or an individual diastereoisomers or enantiomeric isomers thereof or mixtures thereof. In some preferred embodiments, the pharmaceutically acceptable salt is the tartrate (butorphanol tartrate CAS number 58786-99-5). In other preferred embodiments, the dosage form comprises butorphanol base. In some even more preferred embodiments, the dosage form comprises butorphanol tartrate or butorphanol, or mixtures thereof.

The phrase "comprising a therapeutically effective amount of butorphanol" means "comprising a therapeutically effective amount of butorphanol or a pharmaceutically acceptable salt of butorphanol, or prodrugs, esters, analogs, derivatives, solvates, complexes, polymorphs and hydrates thereof, as racemates or an individual diastereoisomers or enantiomeric isomers thereof or mixtures thereof.

When the dosage form includes a pharmaceutically acceptable salt, any salt may be use. Preferably, the salt is the hydrochloride salt of butorphanol.

The singular forms "a", "an" and "the" include plural referents unless the context clearly dictates otherwise. Thus, for example, reference to "a polymer" includes a single polymer as well as a mixture of two or more different polymers, reference to "a permeation enhancer" includes a single permeation enhancer as well as two or more different permeation enhancer in combination, and the like.

Some of the drugs disclosed herein may contain one or more asymmetric centers and may thus give rise to enantiomers, diastereomers, and other stereoisomeric forms. The present invention is also meant to encompass all such possible forms as well as their racemic and resolved forms and mixtures thereof. When the compounds described herein contain olefinic double bonds or other centers of geometric asymmetry, and unless specified otherwise, it is intended to include both E and Z geometric isomers. All tautomers are intended to be encompassed by the present invention as well.

As used herein, the term "stereoisomers" is a general term for all isomers of individual molecules that differ only in the orientation of their atoms is space. It includes enantiomers and isomers of compounds with more than one chiral center that are not mirror images of one another (diastereomers).

The term "chiral center" refers to a carbon atom to which four different groups are attached.

The term "enantiomer" or "enantiomeric" refers to a molecule that is nonsuperimposable on its mirror image and hence optically active wherein the enantiomer rotates the plane of polarized light in one direction and its mirror image rotates the plane of polarized light in the opposite direction.

The term "racemic" refers to a mixture of equal parts of enantiomers and which is optically inactive.

The term "resolution" refers to the separation or concentration or depletion of one of the two enantiomeric forms of a molecule.

The mean drowsiness score is the score in mm on a 100 mm VAS scale bounded on the left by "no drowsiness" and on the right by "extreme drowsiness".

The mean nausea score is the score in mm on a 100 mm VAS scale bounded on the left by "no nausea" and on the right by "extreme nausea".

The mean dizziness score is the score in mm on a 100 mm VAS scale bounded on the left by "no dizziness" and on the right by "extreme dizziness".

The mean vomiting score is the number of episodes of vomiting or retching.

The "NNH" or "number needed to harm" is a measure that indicates how many patients would require a specific treatment to cause harm in one patient. As used herein, the "NNH or "number needed to harm" is a measure that includes: (i) how many opioid naive healthy subjects would require treatment to cause moderate or severe sedation (or drowsiness) in one subject, where moderate to severe sedation or drowsiness is defined as a VAS score of ≥50 mm on a 100 mm scale bounded on the left by "no sedation or drowsiness" and on the right by "extreme sedation or drowsiness"; (ii) how many opioid naive healthy subjects would require treatment to cause moderate or severe nausea in one subject, where moderate to severe nausea is defined as a VAS score of ≥50 mm on a 100 mm scale bounded on the left by "no nausea" and on the right by "extreme nausea"; (iii) how many opioid naive healthy subjects would require treatment to cause dizziness in one subject, where dizziness is defined as unsteadiness, imbalance, lightheadedness, spinning sensation or sensation that one is falling.

The "drug effects" questionnaire assesses the extent to which subjects currently felt a drug effect, on a scale of 1 to 5 (1="I feel no effect from it at all"; 2="I think I feel a mild effect, but I'm not sure"; 3="I feel an effect, but it is not real strong"; 4="I feel a strong effect"; 5="I feel a very strong effect"). This questionnaire can be used to examine the overall drug effects, preferably in drug abusers and recreational drug users.

The "drug liking" questionnaire assesses the extent to which subjects currently like the effects of the drug on a 100-mm VAS, bounded on the left by "0=dislike a lot", bounded on the right by "100=like a lot". This questionnaire can be used to examine the overall drug liking of, preferably in drug abusers and recreational drug users.

The "take again" questionnaire assesses whether subjects would take the drug again if given the opportunity. The patient is asked "If given an opportunity, would you take this drug again? (circle one: YES or NO). This questionnaire can be used to examine the overall desirability of the drug experience, preferably in drug abusers and recreational drug users.

On the "coasting" questionnaire the patient is asked to put a mark on a horizontal line that best describes their response to the question: "Do you feel like you are coasting or spaced out? The horizontal line is a visual analog scale (VAS) bounded on the left by "not at all" and on the right by "extremely". This questionnaire can be used to examine the degree to which subjects feel like they are coasting or spaced out, preferably in drug abusers and recreational drug users.

Three performance tasks may be employed for measuring skills related to driving.

The "critical tracking task" measures the patient's ability to control a displayed error signal in a first-order compensatory tracking task. The error is displayed as a horizontal deviation of a cursor from the midpoint on a horizontal, linear scale. Compensatory joystick movements correct the error by returning the cursor to the midpoint. The frequency at which the patient loses the control is the critical frequency. The critical tracking task measures the psychomotor control during a closed loop operation. It is a laboratory analog to on-the-road tracking performance.

The "stop signal task" measures motor impulsivity, which is defined as the inability to inhibit an activated or pre-cued response leading to errors of commission. The task requires patients to make quick key responses to visual go signals, i.e. the letters ARCD presented one at a time in the middle of the screen, and to inhibit any response when a visual stop signal, i.e. "*" in one of the four corners of the screen, is presented at predefined delays. The main dependent variable is the stop reaction time on stop signal trials that represents the estimated mean time required to inhibit a response.

The "Tower of London" (TOL) is a decision-making task that measures executive function and planning. The task consists of computer generated images of begin- and end-arrangements of three colored balls on three sticks. The subject's task is to determine as quickly as possible, whether the end-arrangement can be accomplished by "moving" the balls in two to five steps from the beginning arrangement by pushing the corresponding number coded button. The total number of correct decisions is the main performance measure.

In some embodiments, the dosage form of the invention, one or more or all of the specifications and claims applicable to the prevention and treatment of pain or addiction disorders is also applicable to the prevention or treatment of any other disease or disorder that responds to opioid agonists or to butorphanol.

The prevention and treatment of all diseases and disorders is contemplated by the use of this invention, including without limitation, (i) pain; (ii) addiction disorders; (iii) opioid substitution and opioid maintenance therapy; (iv) restless leg syndrome; (v) cough; (vi) urinary incontinence; (vii) cough; (viii) pain associated with sickle cell disease, including vaso-occlusive crisis; (ix) peripheral and central neuropathic pain; (x) cancer pain; (xi) breakthrough pain; (xii) visceral pain; (xiii) dyspnea and respiratory distress; (xiv) infectious, immunologic, cardiovascular, pulmonary, gastrointestinal, hepatic, biliary, nutritional, metabolic, endocrine, hematologic, oncologic, musculoskeletal, rheumatic, neurologic, psychiatric, genitourinary, gynecologic, obstetric, pediatric, otolaryngogologic, ophthalmic, dermatologic, dental, oral, and genetic disorders, diseases and maladies and signs and symptoms thereof; (xv) depression, schizophrenia, influenza, common colds, anxiety, panic attacks, agoraphobia, ADHD, insomnia, sleep disorders, nasal congestion, headaches, migraine, urinary incontinence, constipation, allergies, cough, pneumonia, COPD, asthma, fluid retention, acid reflux, peptic ulcers, hypertension, cardiac arrhythmias, hypercholesterolemia, CHF, fever, diarrhea, back pain, myofascial pain, osteoarthritis, neuropathic pain, cancer pain, acute pain, diabetes, muscle spasms, and rheumatoid arthritis, and signs and symptoms thereof; and (xvi) disorders, diseases and maladies, and signs and symptoms thereof referred to in Harrison's Principles of Internal Medicine, 16th Edition, 2004, Kasper D L, Braunwald W, Fauci A, Hauser S, Longo D, and Jameson J L (eds)], which is hereby incorporated in its entirety by reference; said disorders, diseases and maladies, and signs and symptoms thereof comprising butorphanol responsive medical conditions.

In some preferred embodiments, the oral pharmaceutical dosage forms of butorphanol are used to treat pain, sickle cell disease pain, cough, dyspnea, opioid addiction disorders, restless leg syndrome, fibromyalgia, acute herpes zoster, visceral pain, breakthrough pain, opioid dependence and urinary incontinence.

As used herein, "pruritus" means an unpleasant sensation that evokes the desire or reflex to scratch the skin. Pruritus includes, but is not limited to idiopathic itch, iatrogenic itch (e.g., cutaneous manifestations of drug reactions), neurogenic itch secondary to skin disorders (e.g., inflammation, dryness, atopic dermatitis, scabies, urticaria, and insect bite reactions), itch secondary to systemic disorders (e.g., chronic liver disease or chronic renal failure), neuropathic itch (e.g., herpes zoster, post-herpetic neuropathy, notalgia paresthetica, multiple sclerosis and brain tumors) and psychogenic itch (e.g., parasitophobia and obsessive compulsive disorder).

As used herein, "cough" includes acute cough, chronic cough, iatrogenic cough, post-infectious cough, and cough secondary to asthma, COPD, lung cancer, gastroesophageal reflux disease, respiratory bacterial and viral infections, and upper airway cough syndrome.

As used herein, "urinary incontinence" includes stress incontinence, urge incontinence, total incontinence, and overflow incontinence.

As used herein, "diarrhea" includes acute diarrhea (e.g., acute in onset and persisting for less than 2 weeks) secondary to viral, bacterial or protozoal infectious agents, bacterial toxins or drugs, and chronic diarrhea secondary to medications, osmotic diarrhea, secretory conditions, inflammatory conditions, malabsorptive conditions, motility disorders, chronic infections, and factitious diarrhea.

As used herein, the term "pain" includes: (i) peripheral neuropathic pain, e.g., acute and chronic inflammatory demeyelinating polyradiculopathy, alcoholic polyneuropathy, chemotherapy-induced polyneuropathy, complex regional pain syndrome (CRPS) Type I and Type II, entrapment neuropathies (e.g., carpal tunnel syndrome), HIV sensory neuropathy, iatrogenic neuralgias (e.g., postthoracotomy pain, postmastectomy pain), idiopathic sensory neuropathy, painful diabetic neuropathy, phantom limb pain, postherpetic neuralgia, trigeminal neuralgia, radiculopathy (e.g., cervical thoracic, lumbosacral), sciatica, acute herpes zoster pain, temporomandibular joint disorder pain and postradiation plexopathy; and (ii) central neuropathic pain, e.g., compressive myelopathy from spinal stenosis, HIV myelopathy, multiple sclerosis pain, Parkinson's disease pain, postischemic myelopathy, post postradiation myelopathy, poststroke pain, posttraumatic spinal cord injury and syringomyelia; and (iii) cancer associated neuropathic pain, e.g., chemotherapy induced polyneuropathy, neuropathy secondary to tumor infiltration or nerve compression, phantom breast pain, postmastectomy pain, postradiation plexopathy and myelopathy; (iv) chronic pain, e.g., back pain, rheumatoid arthritis, osteoarthritis, inflammatory pain, non-inflammatory pain, myofascial pain, cancer pain, visceral pain, somatic pain, pelvic pain, musculoskeletal pain, posttraumatic pain, bone pain and idiopathic pain; (v) acute pain, e.g., acute postsurgical pain (including laparoscopic, laparatomy, gynecologic, urologic, cardiothoracic, arthroscopic, gastrointestinal, neurologic, orthopedic, oncologic, maxillofacial, ophthalmic, otolaryngologic, soft tissue, plastic, cosmetic, vascular and podiatric surgery, including abdominal surgery, abdominoplasty, adenoidectomy, amputation, angioplasty, appendectomy, arthrodesis, arthroplasty, arthroscopy, bilateral cingulotomy, biopsy, brain surgery, breast biopsy, cauterization, cesarean section, cholecystectomy, circumcision, commissurotomy, cordotomy, corneal transplantation, cricothoracotomy, discectomy, diverticulectomy, episiotomy, endarterectomy, endoscopic thoracic sympathectomy, foreskin restoration, fistulotomy, frenectomy, frontalis lift, fundectomy, gastrectomy, grafting, heart transplantation, hemicorporectomy, hemorrhoidectomy, hepatectomy, hernia repair, hypnosurgery, hysterectomy, kidney transplantation, laminectomy, laparoscopy, laparotomy, laryngectomy, lithotripsy, lobotomy, lumpectomy, lung transplantation, mammectomy, mammoplasty, mastectomy, mastoidectomy, mentoplasty, myotomy, mryingotomy, nephrectomy, nissen fundoplication, oophorectomy, orchidectomy, parathyroidectomy, penectomy, phalloplasty, pneumotomy, pneumonectomy, prostatectomy, psychosurgery, radiosurgery, ritidoplasty, rotationplasty, sigmoidostomy, sphincterotomy, splenectomy, stapedectomy, thoracotomy, thrombectomy, thymectomy, thyroidectomy, tonsillectomy, tracheotomy, tracheostomy, tubal ligation, ulnar collateral ligament reconstruction, ureterosigmoidostomy, vaginectomy, vasectomy, vulvectomy; renal colic; incisional pain; inflammatory incisional pain; nociceptive incisional pain; acute neuropathic incisional pain following surgery), renal colic, trauma, acute back pain, burn pain, burn dressing change pain, migraine pain, tension headache pain, acute musculoskeletal pain, acute exacerbation or flare of chronic hack pain, acute exacerbation or flare of osteoarthritis, acute exacerbation or flare of chronic pain, breakthrough chronic non-cancer pain, breakthrough cancer pain, acute exacerbation or flare of rheumatoid arthritis, acute exacerbation or flare of myofascial pain, acute exacerbation or flare of chronic idiopathic pain, acute exacerbation or flare of neuropathic pain, procedure related pain (e.g., arthroscopy, laparoscopy, endoscopy, intubation, bone marrow biopsy, soft tissue biopsy, catheterization), and other self-limiting pain states.

As used herein, the term "acute pain" refers to self-limiting pain that subsides over time and usually lasting less that about 30 days and more preferably lasting less than about 21 days. Acute pain does not include chronic conditions such as chronic neuropathy, chronic neuropathic pain and chronic cancer and non-cancer pain.

As used herein, "neuropathic pain" is pain initiated or caused by a primary lesion or dysfunction of the nervous system and includes (i) peripheral neuropathic pain and (ii) central neuropathic pain.

As used herein, the term "chronic pain" includes all non-neuropathic pain usually lasting more than 30 days, including inflammatory pain, non-inflammatory pain, muscle pain, joint pain, fascia pain, visceral pain, bone pain and idiopathic pain.

The term "analgesic effectiveness" is defined for purposes of the present invention as a satisfactory prevention, reduction in or elimination of pain, along with a tolerable level of side effects, as determined by the human patient.

According to the American Academy of Pain Medicine, the American Pain Society and the American Society of Addiction Medicine "addiction" and "addiction disorder" is a primary, chronic, neurobiologic disease, with genetic, psychosocial, and environmental factors influencing its development and manifestations. It is characterized by behaviors that include one or more of the following: impaired control over medication use, compulsive use, continued use despite harm, and craving (Sloan and Babul, Expert Opinion on Drug Delivery 2006; 3:489-97). The pharmaceutical composition of the present invention is in some embodiments intended to treat addiction disorder, particularly opioid addiction disorder and poly-substance abuse involving opioids. In some embodiments, the dosage form of the invention is intended to reduce or eliminate the craving or desire for opioids and the antisocial, medically harmful and potentially criminal behavior of the patient with the addiction disorder. The term "therapeutic effectiveness" is defined for purposes of the present invention as a satisfactory prevention, reduction in or elimination of signs and symptoms of the medical disorder, disease or syndrome (e.g., pain, addiction disorder), along with a tolerable level of side effects, as determined by the human patient.

As used herein, the "Orange Book" as it is commonly known is the database of Approved Drug Products with Therapeutic Equivalence Evaluations maintained by or on behalf of the US Food and Drug Administration, (http://www.fda.gov/cder/ob/default.htm, accessed Feb. 15, 2008), the content of which is hereby incorporated by reference.

"Drug", "drug substance", "substance", "therapeutic", "therapeutic agent", "pharmacological agent", "pharmaceutical agent", "active agent", "active ingredient", "agent" "active pharmaceutical ingredient" or "API" are used interchangeably and are intended to have their broadest interpretation as to any therapeutically active substance which is delivered to a living organism to furnish pharmacological activity or other direct effect in the diagnosis, cure, mitigation, treatment, or prevention of a disease, or to affect the structure or any function of the human body. In general, this includes therapeutic agents in all of the major therapeutic areas.

As used herein, "dosage forms" is interchangeable with "formulations", "compositions", "pharmaceutical compositions" or "formulations". Dosage forms of the invention are modified release dosage forms, which may be controlled release or delayed release as further defined herein.

The term "subject" for purposes of treatment is used interchangeably with "patient", "male", "female" and "human", and includes any human subject or other mammal. A most preferred mammal is a human subject of any age. It will be obvious to any practitioner of the art that some of the embodiments, specifications and claims of the invention are not applicable to non-human mammals or need to be modified. For example, the dose of invention may vary depending on the species, its weight, metabolism and GI transit time. Similarly, certain behaviors (e.g., drug abuse, drug diversion) and pharmacodynamic effects (e.g., assessment of mood altering effects or cognitive impairment) are not usually directly assessed in or applicable to many non-human species. Preferred non-human mammals are mammals whose medical care is provided by veterinarians, veterinary technicians, paraveterenarians, animal agriculture industry personnel, and game and wildlife personnel. Preferred non-human mammals include domesticated farm animals, pets, livestock and wild game.

"Pharmaceutically or therapeutically acceptable excipient or carrier" or "excipient" refers to a substance which does not interfere with the effectiveness or the biological activity of the active ingredients and which is not toxic to the subject. In some embodiments of the present invention, pharmaceutically or therapeutically acceptable excipients or carriers may play a role in imparting or optimizing the rate and extent of absorption or butorphanol or additional drugs in the pharmaceutical composition. In some embodiments of the present invention, pharmaceutically or therapeutically acceptable excipients or carriers may play a role in stabilizing the butorphanol or additional drugs in the pharmaceutical composition. Excipients are widely known in the art (see, for example, FDA EAFUS database; FDA Food Additives Status List; FDA GRAS list and database; FDA Color Additive Status List; FDA Inactive Ingredients Database; Rowe, Sheskey and Owen, Handbook of Pharmaceutical Excipients, APhA Publications; 5th edition (2006); Goodman & Gilman's The Pharmacological Basis of Therapeutics (Brunton, Lazo and Parker, eds, 11th ed., McGraw Hill (2005); Remington: The Science and Practice of Pharmacy, 21st ed, Lippincott Williams & Wilkins (2005); Martindale: The Complete Drug Reference, 35th Edition, Pharmaceutical Press (2007); United States Pharmacopeia-National Formulary (USP-NF), (USP 30-NF 25, 2007), the International Programme on Chemical Safety and Health Canada's List of Acceptable Non-medicinal Ingredients).

Any pharmaceutically acceptable excipient, including functional excipients may be included in the dosage form, in any molecular weight, particle size, viscosity or amount. In some embodiments, the total amount of pharmaceutically acceptable excipient is about 0.0001% to about 99.9 percent, preferably about 0.1% to 98 percent and more preferably about 1% to about 90% on a dry weight basis of the composition. In some embodiments, the total amount of individual pharmaceutically acceptable excipient is about 0.001% to about 99 percent, preferably about 0.1% to 97 percent and more preferably about 1% to about 95% on a dry weight basis of the composition.

In some embodiments, the amount of individual pharmaceutically acceptable excipient, including functional excipient in the dosage form is about 0.0001 mg to about 600 mg, more preferably, from about 0.001 mg to about 500 mg, even more preferably from about 0.001 mg to about 400 mg, and most preferably from 0.01 mg to about 300 mg.

In certain preferred embodiments of the present invention, an effective amount of butorphanol in immediate release form is included in the controlled release unit dose butorphanol formulation to be administered. The immediate release form of the butorphanol is preferably included in an amount which is effective to shorten the time to $C_{max}$ of the butorphanol in the blood (e.g., plasma). One skilled in the art would recognize various means of incorporating the immediate release butorphanol into the unit dose. By including such an effective amount of immediate release butorphanol in the unit dose, patients may experience superior relief of pain and neuropathy symptoms.

In certain preferred embodiments of the present invention, the dosage form may include, in addition to the butorphanol, substances, process or technologies that impart abuse deterrent, abuse resistant or tamper resistant properties to the dosage form, including aversive agents; said dosage form reducing or preventing opioid abuse, drug abuse, drug misuse, recreational drug use, drug diversion and toxicity from intentional or accidental overdose.

As used herein, the term "aversive", "aversive agents", "aversion producing agents" and "aversive compounds" means to compounds contained within the dosage form that produce an aversive, undesirable, repugnant, distasteful, unpleasant, unacceptable physiologic effect, unacceptable psychic effect, or that pharmacologically block or reduce physiologic effects sought by recreational drug users, addicts and drug abusers, including one or more of the following effects: mood alterations; euphoria, pleasure; a feeling of high; a feeling of drug liking; anxiolysis; sedation; calmness; a state of relaxation; psychotomimesis; hallucinations; alterations in perception, cognition and mental focus; drowsiness; and psychological reinforcement.

In certain preferred embodiments of the present invention, the dosage form may include, in addition to butorphanol or a pharmaceutically acceptable salt thereof, abuse deterrent or abuse resistant substances, process or technologies known in the art, including one or more aversive agents. All kinds of aversive agents are contemplated, including, without limitation, antagonists of abusable drugs, laxatives, cutaneous vasodilators, headache producing agents, emetics, emetogenic compound, nausea producing compounds, bittering agents, drugs that cause burning on irritation when in contact with tissue or mucous membranes (e.g., naso-mucosal irritants, oro-mucosal irritants, respiratory irritants), tissue irritants, gastrointestinal irritants, drugs that precipitate withdrawal effects, tissue dyes, lakes and colorants, beverage dyes, lakes and colorants, non-tissue staining beverage dyes, lakes and colorants (i.e., that do not stain or discolor the skin upon ingestion), fecal discolorants, urine discolorants, malodorous agents, opioid antagonists, benzodiazepine antagonists (e.g., flumazenil), cannabinoid antagonists and pharmacologic antagonists to co-abused drugs not contained in the dosage form. Such aversive agents may be in the dosage form in a releasable, partially releasable or a non-releasable form (i.e., sequestered), the latter being released on tampering the dosage form (e.g., mechanical, thermal, chemical, solvent tampering, ingestion in ways not recommended, and the like). Further, in some embodiments, such aversive agents may be in the dosage form in an amount that does not produce an aversive effect or aversion in any, many or substantially all patients when taken in accordance with the prescribing information or the manufacturer's instructions (for example, in small quantities), but which produce an aversive effect when taken in excess (e.g., higher dose or more frequently). In other embodiments, said aversive agent pharmacologically blocks the effects of the butorphanol and/or the effects of a co-abused drug, said co-abused drug in the same dosage form or in a different dosage form or not an approved or conventional pharmaceutical product.

The term "tampering" or "tamper" means any manipulation by mechanical, thermal, chemical and/or pharmacologic means which changes the physical or chemical properties of the dosage form, e.g., to liberate the abusable drugs for immediate release if it is in sustained release form, or to make the abusable drugs available for inappropriate use such as administration by an alternate route, e.g., parenterally. The tampering can be, e.g., by means of crushing, shearing, grinding, mechanical extraction, solvent extraction, solvent immersion, combustion, heating or any combination thereof.

The term "abuse", "drug abuse", "opioid abuse", "recreational drug use" and "drug misuse" in the context of the present invention means, use: (i) in quantities or by methods and routes of administration that do not conform to standard medical practice; (ii) outside the scope of specific instructions for use provided by a qualified medical professional; (iii) outside the supervision of a qualified medical professional; (iv) outside the approved instructions on proper use provided by the drug's legal manufacturer; (v) which is not in specifically approved dosage forms for medical use as pharmaceutical agents; (vi) where there is an intense desire for and efforts to procure same; (vii) compulsive use; (viii) through acquisition by manipulation of the medical system, including falsification of medical history, symptom intensity, disease severity, patient identity, doctor shopping, prescription forgeries; (ix) where there is impaired control over use; (x) despite harm; (xi) by procurement from non-medical sources; (xii) by others through sale or diversion by the individual into the non-medical supply chain; (xiii) for medically unapproved or mood altering purposes.

The term "mood altering" is defined for purposes of the present invention to mean that the "high", "liking", pleasurable, euphoric, alerting, calming, anxiolytic, auditory and visual perception altering, relaxing, psychotomimetic, rewarding and reinforcing, of the abusable drug.

The term "abuse resistant", "abuse deterrent", "tamper resistant", "deter abuse" and "resist abuse" (as well of the words "resist" or "deter" when applied to abusable drugs of the invention) are used interchangeably in the context of the present invention and include pharmaceutical compositions and methods that resist, deter, discourage, diminish, delay and/or frustrate: (i) the physical, chemical, thermal or pharmacologic manipulation or tampering of the dosage form (e.g., crushing, shearing, grinding, chewing, dissolving, melting, needle aspiration, inhalation, insufflation, extraction by mechanical, thermal and chemical means, and/or filtration); (ii) use or misuse of the dosage form outside the scope of specific instructions for use provided by a qualified medical professional; (iii) use outside the supervision of a qualified medical professional; (iv) use outside the approved instructions on proper use provided by the drug's legal manufacturer (e.g., intravenous use, intranasal use, inhalational use and oral ingestion to provide high peak concentrations, use in excess quantities, etc.); (v) the conversion of an extended release dosage form of the invention into a more immediate release form; (vi) the intentional and iatrogenic increase in physical and psychic effects sought by recreational drug users, addicts, and patients with pain who have an addiction disorder; (vii) attempts to procure the dosage form by manipulation of the medical system and from non-medical sources; (viii) the sale or diversion of the dosage form into the non-medical supply chain and for medically unapproved or unintended mood altering purposes; (ix) the intentional, unintentional or accidental attempts at otherwise changing the physical, pharmaceutical, pharmacological and/or medical properties of the dosage form from what was intended by the manufacturer; (x) the psychic, pleasurable, reinforcing or rewarding effects of the dosage form when used as directed or when used outside the approved instructions on proper use provided by the drug's legal manufacturer.

All kinds of abuse deterrent agents, excipients, dosage forms and technologies are contemplated, including, without limitation, excipients that deter or resist extraction of drug with the application of mechanical, chemical, or thermal energy, use of solvents, use of sequestered or unsequestered (releasable) antagonists to the drug or to a co-abused drug, use of sequestered or unsequestered (releasable) aversive agents, and use covalently bound moieties that modulate release of the butorphanol in vitro, in the GI tract and in the liver.

In some embodiments, one or more aversive agents may be added to the formulation in an amount of less than about 80% by weight, preferably less than about 60% by weight, more preferably less than about 40% by weight of the dosage form, even more preferably less than about 20% by weight of the dosage form, and most preferably less than about 10 by weight of the dosage form (e.g., 0.000000000000001% to 1%, or 0.000000001% to 3%, or 0.0001% to 10%, or 0.001% to 5%, or 1% to 10%, or 0.001% to 2%, or 1% or 10%, or 2% to 7%) depending on the particular aversive agent used.

In some embodiments, the aversive agent in the dosage form may be about 0.00000000001 mg to about 2000 mg, or about 0.0000001 mg to about 1500 mg, or about 0.000001 mg to about 1000 mg, or about 0.0001 mg to about 1000 mg, or about 0.001 mg to about 1000 mg, or about 0.01 mg to about 1000 mg, or about 0.1 mg to about 1500 mg, or 1 mg to about 800 mg, or about 1 mg to about 500 mg, or about 1 mg to about 300 mg, or about 1 mg to about 150 mg, or about 5 mg to about 400 mg, or about 5 mg to about 200 mg, or about 0.00000000001 mg to about 200 mg, or about 0.00000000001 mg to about 100 mg, or about 0.00000000001 mg to about 50 mg, or about 0.0000001 mg to about 200 mg, or about 0.0000001 mg to about 100 mg, or about 0.00001 mg to about 400 mg, or about 0.0001 mg to about 300 mg.

In some embodiments, the amount of aversive agent in the dosage form of the present invention can be a fixed ratio in relation to the amount of abusable drug in the dosage form. By appropriately selecting the quantity of the aversive agent in the dosage form, aversive effects can be avoided under conditions of proper medical use (e.g., manufacturers prescribing directions). However, under some conditions of abuse, for example excessive intake of the dosage form of the invention, the quantity of aversive agent consumed will exceed the "no effect" or "minimum effect" threshold, thereby producing one or more aversive effects, for example, e.g., nausea, emesis, diarrhea, laxation, cutaneous vasodilation, headache, bitter taste, naso-mucosal irritation, oromucosal irritation, precipitation of abstinence from the abusable drug of the dosage form, precipitation of abstinence from a co-abused drug which is not part of the dosage form, reduction of the pleasurable, mood altering, rewarding, reinforcing, stimulant, depressant or other psychic and physiologic effects of the abusable drug or a co-abused drug, etc.).

In some embodiments, the "no effect" or "minimum effect" threshold amount of aversive agent can be exceeded when the dosage form of the invention is taken in excess of the manufacturer's recommendation by a factor of about 1.5, or about 2, or about 2.5, or about 3, or about 4, or about 5, or about 6, or about 7, or about 8, or about 10, or more than 10. In some embodiments, the production of an aversive effect can reduce or stop further abuse of the dosage form, thereby reducing the harm or toxicity of the drug in the subject who is tampering, misusing or abusing the dosage form, e.g., addicts, drug abusers and recreational drug users.

In some embodiments, the aversive agent in the dosage form may be an opioid antagonist. Opioid antagonists are well known in the art and include naltrexone, methylnaltrexone, naloxone, nalmefene, cyclazocine, cyclorphan, oxilorphan nalorphine and levallorphan or pharmaceutically acceptable salt thereof or mixture thereof. In a preferred embodiment, said antagonist is naltrexone or naloxone. In a most preferred embodiment, said antagonist is naloxone. In some embodiments, the aversive agent in the dosage form may be an opioid antagonist in the amount of about 0.00001 mg to about 800 mg, or about 0.001 mg to about 400 mg, or about 0.01 mg to about 200 mg, or about 0.2 mg to about 100 mg, or about 0.2 mg to about 50 mg, or 0.2 to 8 mg.

In some embodiments, the ratio of butorphanol base to naloxone base is more than about: 3:1; 4:1, 5:1, 3:1, 4:1, 5:1, 6:1, 7:1, 8:1, 9:1, 10:1, 12:1, 14:1, 16:1, 18:1, 20:1, 22:1, 24:1, 26:1, 28:1, 30:1, 35:1, 40:1, 45:1 50:1; 55:1, 60:1, 65:1, 70:1, 75:1, 80:1, 85:1 or 90:1.

In some embodiments, the ratio of naloxone may be replaced with naltrexone, and the butorphanol base to naltrexone base ratio is more than about: 3:1, 4:1, 5:1, 6:1, 7:1, 8:1, 9:1, 10:1, 12:1, 14:1, 16:1, 18:1, 20:1, 22:1, 24:1, 26:1, 28:1, 30:1; 35:1; 40:1; 45:1 50:1; 55:1, 60:1, 65:1, 70:1, 75:1, 80:1, 85:1 or 90:1.

In some embodiments, the present invention is directed to oral pharmaceutical compositions of butorphanol comprising naloxone, where the systemic exposure to naloxone as measured by the area under the plasma naloxone concentration-time curve from time 0 to 48 hours or 0 to infinity ($AUC_{0-48}$ or $AUC_{0-inf}$) after single dose oral administration of the untampered or intact dosage form is less than about: 20 ng·hr/mL, 18 ng·hr/mL, 15 ng·hr/mL, 12 ng·hr/mL, 10 ng·hr/mL, 8 ng·hr/mL, 7 ng·hr/mL, or 6 ng·hr/mL, or 5 ng·hr/mL, 4 ng·hr/mL, or 3 ng·hr/mL, or 2 ng·hr/mL, or 1.5 ng·hr/mL, or 1 ng·hr/mL, or 0.8 ng·hr/mL, or 0.7 ng·hr/mL, or 0.6 ng·hr/mL, or 0.55 ng·hr/mL, or 0.5 ng·hr/mL, or 0.45 ng·hr/mL, or 0.4 ng·hr/mL, 0.35 ng·hr/mL, or 0.3 ng·hr/mL, or 0.25 ng·hr/mL, or 0.2 ng·hr/mL. In some embodiments, said AUC is after single dose oral administration of the tampered or crushed dosage form.

In some embodiments, the present invention is directed to oral pharmaceutical compositions of butorphanol comprising naltrexone, where the systemic exposure to naltrexone as measured by the area under the plasma naltrexone concentration-time curve from time 0 to 48 hours or 0 to infinity ($AUC_{0-48}$ or $AUC_{0-inf}$) after single dose oral administration of the untampered or intact dosage form is less than about: 20 ng·hr/mL, 18 ng·hr/mL, 15 ng·hr/mL, 12 ng·hr/mL, 10 ng·hr/mL, 8 ng·hr/mL, 7 ng·hr/mL, or 6 ng·hr/mL, or 5 ng·hr/mL, 4 ng·hr/mL, or 3 ng·hr/mL, or 2 ng·hr/mL, or 1.5 ng·hr/mL, or 1 ng·hr/mL, or 0.8 ng·hr/mL, or 0.7 ng·hr/mL, or 0.6 ng·hr/mL, or 0.55 ng·hr/mL, or 0.5 ng·hr/mL, or 0.45 ng·hr/mL, or 0.4 ng·hr/mL, 0.35 ng·hr/mL, or 0.3 ng·hr/mL, or 0.25 ng·hr/mL, or 0.2 ng·hr/mL. In some embodiments, said AUC is after single dose oral administration of the tampered or crushed dosage form.

In some embodiments, the present invention is directed to oral pharmaceutical compositions of butorphanol comprising naloxone, where the peak plasma naloxone concentration ($C_{max}$) after single dose oral administration of the untampered or intact dosage form is less than about: 4 ng/mL, 3 ng/mL, 2 ng/mL, 1.5 ng/mL, 1.25 ng/mL, or 1 ng/mL, or 0.8 ng/mL, or 0.7 ng/mL, or 0.6 ng/mL, or 0.5 ng/mL, or 0.4 ng/mL, or 0.3 ng/mL, or 0.2 ng/mL, or 0.1 ng/mL. In some embodiments, said $C_{max}$ is after single dose oral administration of the tampered or crushed dosage form.

In some embodiments, the present invention is directed to oral pharmaceutical compositions of butorphanol comprising naltrexone, where the peak plasma naltrexone concentration ($C_{max}$) after single dose oral administration of the untampered or intact dosage form is less than about: 4 ng/mL, 3 ng/mL, 2 ng/mL, 1.5 ng/mL, 1.25 ng/mL, or 1 ng/mL, or 0.8 ng/mL, or 0.7 ng/mL, or 0.6 ng/mL, or 0.5 ng/mL, or 0.4 ng/mL, or 0.3 ng/mL, or 0.2 ng/mL, or 0.1 ng/mL. In some embodiments, said $C_{max}$ is after single dose oral administration of the tampered or crushed dosage form.

In some embodiments, the oral butorphanol dosage forms of the invention comprising naloxone or naltrexone in the amounts, ratios or exposure level in the specifications are abuse deterrent in some, most, substantially all or all recreational opioid users and opioid abusers when the dosage form is tampered with and the contents (butorphanol plus naloxone or butorphanol plus naltrexone) are injected.

In some embodiments, the oral butorphanol dosage forms of the invention comprising naloxone or naltrexone in the amounts, ratios or exposure level in the specifications are abuse deterrent in some, most, substantially all or all recreational opioid users and opioid abusers when the dosage form is tampered with and the contents (butorphanol plus naloxone or butorphanol plus naltrexone) are taken orally.

In some embodiments, the dosage form comprises butorphanol, optionally material to render said dosage form controlled release and one or more opioid antagonists, preferably selected from the group comprising naloxone, naltrexone and nalmefene; said opioid antagonist having an in vitro release rate provided herein. In some embodiments, the butorphanol and the opioid antagonist share the same in vitro release rate (dissolution rate) specifications. In other embodiments, the butorphanol and the opioid antagonist have different in vitro release rate (dissolution rate) specifications referred to herein. In yet other embodiments, the in vitro release rate (dissolution rate) specifications referred to herein are applicable only to the butorphanol.

In some embodiments, the dosage form comprises butorphanol, optionally material to render said dosage form controlled release and one or more aversive agents; said aversive agent having an in vitro release rate provided herein. In some embodiments, butorphanol and the aversive agent share the same in vitro release rate (dissolution rate) specifications. In other embodiments, butorphanol and the aversive agent have different in vitro release rate (dissolution rate) specifications referred to herein. In yet other embodiments, the in vitro release rate (dissolution rate) specifications referred to herein are applicable only to the butorphanol.

It should be noted that the above mentioned aversive agents may, in some embodiments be used in the dosage form of the invention for purposes other than as aversive agents, or for both aversive and non-aversive purposes. Such non-aversive uses can include, without limitation, pharmaceutical purposes and pharmacologic purposes. For example, in some embodiments, the laxative agent may be used to counteract the constipating effects of the abusable dosage form of the invention. In some embodiments, zinc and pharmaceutically acceptable salts of zinc and niacin may be used for pharmaceutical purposes (e.g., pharmaceutical optimization, drug release and drug stability).

In some embodiments, an aversive agent incorporated into the oral dosage form shares one, or more dissolution rate specifications, GI delivery and release specifications and pharmacokinetic parameter specifications (limited to $T_{max}$, HVD and $W_{50}$) with the oral butorphanol in the dosage form.

In some embodiments, an aversive agent incorporated into the oral dosage form has different dissolution rate specifications, GI delivery and release specifications and pharmacokinetic parameter specifications from the oral butorphanol in the dosage form.

In one embodiment of the invention, the dosage form includes both an immediate release and extended release component.

In one embodiment of the invention, the dosage form includes a capsule within a capsule, each capsule containing a different drug or the same drug intended for treating the same or a different malady. In some preferred embodiments, the outer capsule may be an enteric coated capsule or a capsule containing an immediate release formulation to provide rapid plasma concentrations or a rapid onset of effect or a loading dose and the inner capsule contains an extended release formulation. In some preferred embodiments, up to 3 capsules within a capsule are contemplated as part of the invention. In one embodiment of the invention, the dosage form involves one or more tablets within a capsule, wherein the butorphanol is either in the tablet and/or in one of the capsules.

In one embodiment of the invention, the formulation is ingested orally as a tablet or capsule, preferably as a capsule. In another embodiment of the invention, the formulation is administered bucally.

"Therapeutically effective amount" or "therapeutically-effective" refers to the amount of an active agent sufficient to induce a desired biological result. That result may be alleviation of the signs, symptoms, or causes of a disease, or any other desired alteration of a biological system.

"Therapeutically effective amount of butorphanol" refers to the amount of oral butorphanol sufficient to prevent, to cure, or at least partially arrest a medical disorder, disease, sign or symptom for which the butorphanol has been prescribed to a subject.

The term "effective amount" means the quantity of a compound according to the invention necessary to prevent, to cure, or at least partially arrest a medical disorder, disease, sign or symptom for which the butorphanol has been prescribed to a subject.

The term "pharmaceutically acceptable salt" as used herein refers to a salt which is toxicologically safe for human and animal administration. Nonlimiting examples of salts include hydrochlorides, hydrobromides, hydroiodides, sulfates, bisulfates, nitrates, citrates, tartrates, bitartrates, phosphates, malates, maleates, napsylates, fumarates, succinates, acetates, terephthalates, pamoates and pectinates. In some embodiments, the pharmaceutical composition is a salt or complex of inorganic cation salts, organic salts such primary, secondary, tertiary and quaternary amines include substituted amines It is contemplated that the present invention may be used alone or in combination with other drugs to provide additive, complementary, or synergistic therapeutic effects or for the treatment of entirely different medical conditions.

Other pharmaceutically active ingredients from various therapeutic classes may also be used in combination with the present invention. In some embodiment, co-administered may be used to provide additive, complementary, superadditive or synergistic therapeutic effects. In some embodiment, co-administered may be used to provide a different therapeutic effects from the present invention or to treat the side effects of the present invention. They include, but are not limited to decongestants, analgesics, analgesic adjuvants, antihistamines, expectorants, antitussives, diuretics, anti-inflammatory agents, antipyretics, antirheumatics, antioxidants, laxatives, proton pump inhibitors, motility modifying agents, vasodilators, inotropes, beta blockers, beta adrenergic agonists, drugs to treat asthma and COPD, antiinfectives, antihypertensives, antianginal agents, anticoagulants, lipid and cholesterol lowering drugs, anti-diabetic drugs, hormones, smooth muscle relaxants, skeletal muscle relaxants, bronchodilators, vitamins, trace minerals, amino acids, biological peptides, and drugs to treat disorders, diseases and maladies, and signs and symptoms thereof referred to in Harrison's Principles of Internal Medicine, 16th Edition, 2004, Kasper D L, Braunwald W, Fauci A, Hauser S, Longo D, and Jameson J L (eds)], which is hereby incorporated in its entirety by reference The drug being used in combination therapy with the present invention can be administered by any route, including parenterally, orally, topically, transdermally, sublingually, and the like.

As used herein, "butorphanol responsive conditions", butorphanol responsive medical conditions", "opioid responsive conditions", "opioid responsive medical conditions", "butorphanol or opioid responsive medical conditions", "in need to butorphanol", and the like refer to any medical condition in which butorphanol can be employed for a therapeutically beneficial outcome.

The terms "medical condition", "malady", "disease", "disorder" and "pathological states" are used interchangeably and are intended to have their broadest interpretation to refer to any physiologic, pathologic or pathophysiologic state in a human or other mammal that can be prevented, treated, managed or altered to produce a desired, usually beneficial effect.

In some embodiments, the oral butorphanol is intended to prevent or treat pain. A co-administered drug (in the same or different dosage form, by any route of administration) may be used to provide additive, complementary, superadditive or synergistic therapeutic analgesic effects, including other NSAIDs, NO-NSAIDs, COX-2 selective inhibitors, acetaminophen, tramadol, local anesthetics, antidepressants, beta adrenergic agonists, alpha-2 agonists, selective prostanoid receptor antagonists, cannabinoid agonists, other opioid receptor agonists, NMDA receptor antagonists, gabapentin, pregabalin, gabapentinoids, neuronal nicotinic receptor agonists, calcium channel antagonists, sodium channel blockers, superoxide dismutase mimetics, p38 MAP kinase inhibitors, TRPV1 agonists, dextromethorphan, dextrorphan, ket amine, glycine receptor antagonists, antiepileptics, and any other drugs that can be shown by a person proficient in the art to prevent or treat pain.

In other embodiments, particularly preferred combinations include butorphanol with acetaminophen, NSAID, COX-2 inhibitors, NMDA antagonists, antiepileptics, antidepressants, calcium channel blockers, sodium channel modulators, cannabinoid agonists, muscle relaxants, including cyclobenzaprine and drugs selected from the class of benzodiazepine agonists, and other opioids agonists In certain preferred embodiments of the present invention, an effective amount of another drug to treat the butorphanol responsive condition, a butorphanol related side effect (e.g., laxative, CNS stimulant or anti-emetic) or a co-existing medical condition may be incorporated into the dosage form. Such a coadministered drug may be in any form, including immediate release, controlled release and delayed release. The co-administered drug may be incorporated at a therapeutic dose or a subtherapeutic dose. If included in immediate release form, it may be coated onto the substrates of the present invention. For example, where the extended release butorphanol from the formulation is due to a controlled release coating, the immediate release layer of another drug may be overcoated on top of the controlled release coating. On the other hand, the immediate release layer maybe coated onto the surface of substrates wherein the butorphanol is incorporated in a controlled release matrix. Where a plurality of the sustained release substrates comprising an effective unit dose of the butorphanol (e.g., multiparticulate systems including pellets, spheres, beads and the like) are incorporated into a capsule, the immediate release drug may be incorporated into the capsule via inclusion of the sufficient amount of immediate release drug as a powder or granulate within the capsule. Alternatively, the capsule itself may be coated with an immediate release layer of the drug. One skilled in the art would recognize still other alternative manners of incorporating the immediate release butorphanol into the unit dose. Such alternatives are deemed to be encompassed by the appended claims. By including such an effective amount of immediate release drug to treat the same condition as the butorphanol, it may be possible to reduce the dose of butorphanol in the dosage form.

In certain preferred embodiments of the present invention where the dosage form is delayed onset (e.g., delayed onset, rapid release; delayed onset, extended release; or delayed onset, pulsatile release), an effective amount of another drug to treat the butorphanol responsive condition in immediate release form may be particularly advantageous. In certain preferred embodiments, an NSAID, acetaminophen or a COX-2 inhibitor in immediate release form may be advantageously incorporated into the dosage form.

In some embodiments, another drug to treat the same condition as the oral butorphanol or to treat a different condition may be incorporated into the oral dosage form, where the other drug shares one, or more, or all the dissolution rate specifications, GI delivery and release specifications and pharmacokinetic parameter specifications (limited to $T_{max}$, HVD and $W_{50}$) as the oral butorphanol in the dosage form.

In some embodiments, another drug to treat the same condition as the oral butorphanol or to treat a different condition may be incorporated into the oral dosage form, where the other drug has different dissolution rate specifications, GI delivery and release specifications and pharmacokinetic parameter specifications from the oral butorphanol in the dosage form, one or more or all said different specifications contained herein.

In some embodiments, another drug to treat the same condition as the oral butorphanol or to treat a different condition may be incorporated into the oral dosage form, where the other drug has different dissolution rate specifications, GI delivery and release specifications and pharmacokinetic parameter specifications from the oral butorphanol in the dosage form.

BRIEF DESCRIPTION OF THE DRAWINGS

The included drawings are illustrative but not limiting of the methods and composition of the present invention. Other suitable modifications and adaptations of the variety of conditions and parameters normally encountered and obvious to those skilled in the art are within the spirit and scope of the invention.

METHODS OF CARRYING OUT THE INVENTION

Dosage Forms

Figure 1:
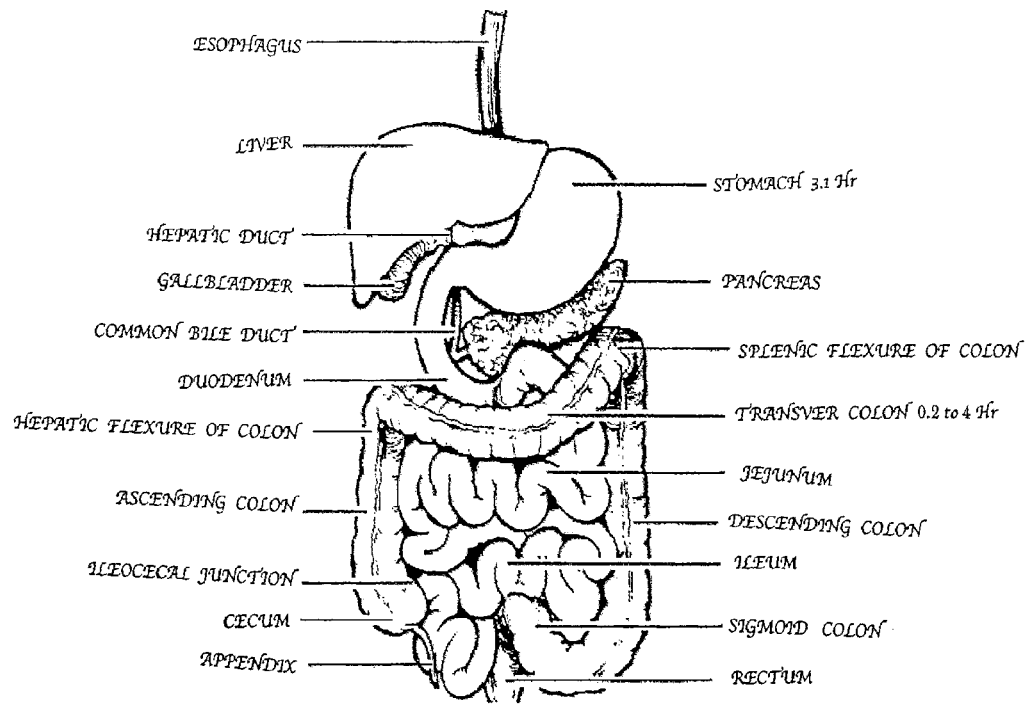
FIG. 1: Illustrates the gastrointestinal tract of a human subject, including the stomach, the small intestine (duodenum, jejunum and ileum), and the colon.
Figure 2:
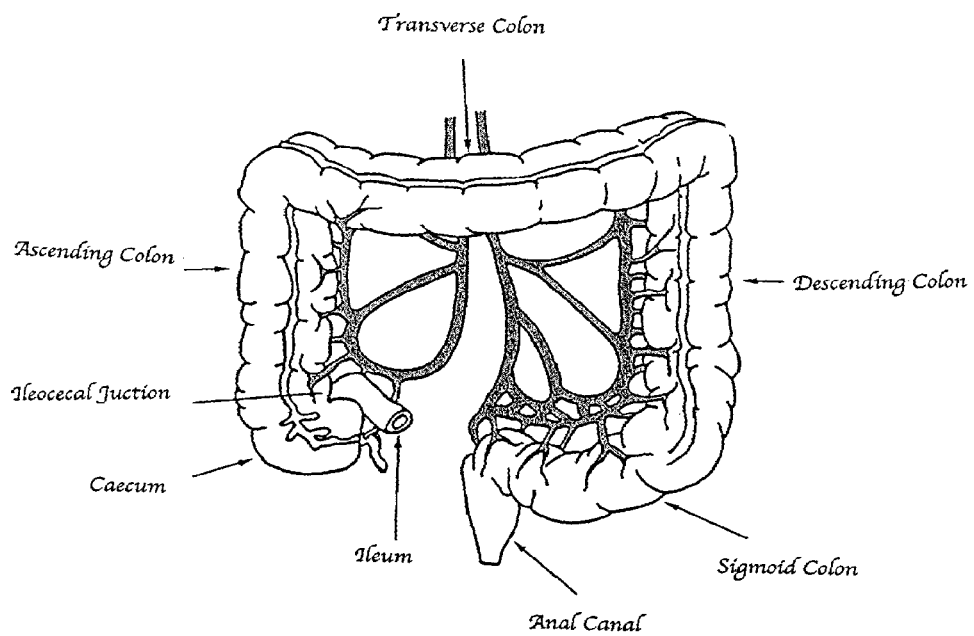
FIG. 2: Provides an expanded view of the anatomy of the colon.
Figure 3:
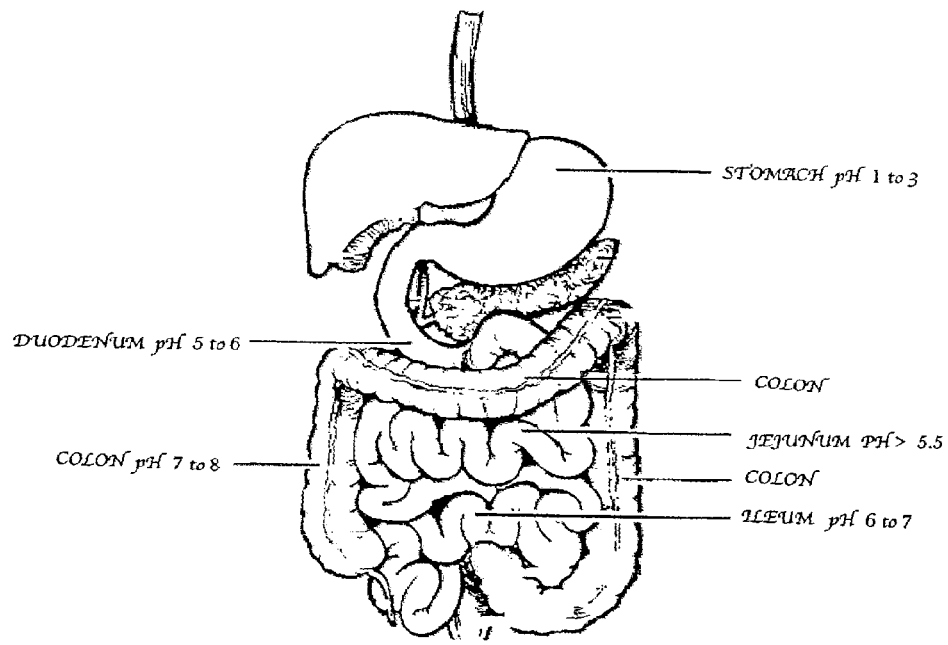
FIG. 3: Illustrates the average pH of various segments of the gastrointestinal tract.

Pharmaceutical composition and methods of the present invention comprise butorphanol base or pharmaceutically acceptable salts in racemic or enantiomeric form, or mixtures thereof, or prodrugs thereof intended oral administration as modified release dosage forms.

Preferred modified release dosage forms of the invention include delayed onset formulations (e.g., delayed onset, rapid release; delayed onset, pulsatile release; or delayed onset, extended release) and controlled release formulations (also sometimes referred to as prolonged release, slow release, sustained release, extended release, retarded release, and long acting).

All oral pharmaceutical dosage forms of the invention are contemplated, including oral suspensions, tablets, chewable tablets, capsules, lozenges, effervescent tablets, effervescent powders, powders, solutions, powders for reconstitution, gastroretentive tablets and capsules, orally disintegrating tablets, oral fast dissolving tablets, oral fast dispersing tablets, oral fast disintegrating dosage forms.

The formulation may optionally comprise excipients, including release controlling excipients and non-release controlling excipient. Non-limiting examples of these auxiliary materials (or pharmaceutically acceptable excipients) are (i) Binders such as acacia, alginic acid and salts thereof, cellulose derivatives, methylcellulose, hydroxyethyl cellulose, hydroxypropyl cellulose, magnesium aluminum silicate, polyethylene glycol, gums, polysaccharide acids, bentonites, hydroxypropyl methylcellulose, gelatin, polyvinylpyrrolidone, polyvinylpyrrolidone/vinyl acetate copolymer, crospovidone, povidone, polymethacrylates, hydroxypropylmethylcellulose, hydroxypropylcellulose, starch, pregelatinized starch, ethylcellulose, tragacanth, dextrin, microcrystalline cellulose, sucrose, or glucose, and the like; (ii) Disintegrants such as starches, pregelatinized corn starch, pregelatinized starch, celluloses, cross-linked carboxymethylcellulose, crospovidone, cross-linked polyvinylpyrrolidone, a calcium or a sodium alginate complex, clays, alginates, gums, or sodium starch glycolate, and any disintegration agents used in tablet preparations; (iii) Filling agents such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like; (iv) Stabilizers such as any antioxidation agents, buffers, or acids, and the like; (v) Lubricants such as magnesium stearate, calcium hydroxide, talc, colloidal silicon dioxide, sodium stearyl fumarate, hydrogenated vegetable oil, stearic acid, glyceryl behenate, magnesium, calcium and sodium stearates, stearic acid, talc, waxes, Stearowet, boric acid, sodium benzoate, sodium acetate, sodium chloride, DL-leucine, polyethylene glycols, sodium oleate, or sodium lauryl sulfate, and the like; (vi) Wetting agents such as oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, or sodium lauryl sulfate, and the like; (vii) Diluents such lactose, starch, mannitol, sorbitol, dextrose, microcrystalline cellulose, dibasic calcium phosphate, sucrose-based diluents, confectioner's sugar, monobasic calcium sulfate monohydrate, calcium sulfate dihydrate, calcium lactate trihydrate, dextrates, inositol, hydrolyzed cereal solids, amylose, powdered cellulose, calcium carbonate, glycine, or bentonite, and the like; (viii) Anti-adherents or glidants such as talc, corn starch, DL-leucine, sodium lauryl sulfate, and magnesium, calcium, or sodium stearates, and the like; (ix) Pharmaceutically compatible carriers such as acacia, gelatin, colloidal silicon dioxide, calcium glycerophosphate, calcium lactate, maltodextrin, glycerin, magnesium silicate, sodium caseinate, soy lecithin, sodium chloride, tricalcium phosphate, dipotassium phosphate, sodium stearoyl lactylate, carrageenan, monoglyceride, diglyceride, or pregelatinized starch, and the like; and (x) excipients referred to herein.

Targeted Gastrointestinal Delivery

Targeted delivery of the butorphanol dosage form of the present invention for release and subsequent absorption can be achieved to provide delayed onset, rapid release dosage forms; delayed onset, pulsatile release dosage forms; delayed onset, extended release dosage forms; and other modified release dosage forms. In addition, conventional extended release products which release the active drug rapidly on ingestion may be coated or embedded with further controlled release material designed to provide a lag time before release of drug upon ingestion.

A wide variety of methods for the preparation of delayed onset dosage form are known in the art. These methods may be employed for the preparation of delayed onset dosage forms of the invention, including but not limited to: (i) Prodrug Approach: in some embodiments such products control the rate of release of active drug by azo-bond conjugates, glycoside conjugates, glucuronide conjugates, cyclodextrin conjugates, dextran conjugates, polypeptide conjugates; (ii) Polymeric Coating: in some embodiments, such products control the release of active drug by coating with pH sensitive polymers and coating with biodegradable polymers; (iii) Embedding in Matrices: in some embodiments, such products control the release of active drug by embedding in pH sensitive matrices, embedding in biodegradable hydrogels and matrices (e.g., amylose, chondroitin sulfate, chitosan, inulin, dextran, guar gum, pectin). Other approaches include the use of time dependent systems, Pulsincap®, CODDES® and intestinal pressure controlled delivery systems.

In some embodiments, the need for a rapid initial dose may require that a portion of the dose (e.g., up to about 1%, or 3%, or 5%, or 7%, or 10%, or 12%, or 15%, or 17%, or 20%, or 22%, or 25%, or 30%) is provided without delay as an immediate release dosage form (e.g., without limitation, a capsule within a capsule, a tablet within a capsule, an immediate release overcoat on a tablet or a capsule) in order to achieve, for example, immediate symptom relief An immediate or controlled release tablet or capsule formulation may be overcoated with one or more polymers to provide butorphanol release in the appropriate gastrointestinal environment (defined, in some embodiments by location in the GI tract, pH at the point of release, osmotic pressure at the point of release, hydration, microbial flora, and/or the time after ingestion at the point of release).

In some embodiments, the dosage form of the invention is in the form of a compressed tablet, or a capsule, said tablet or capsule coated with a polymer to retard or delay its release to achieve the objectives of the invention, said polymers including polymethacrylates (copolymerisate of methacrylic acid and either methylmethacrylate or ethyl acrylate (Eudragit®), cellulose based polymers e.g. cellulose acetate phthalate (Aquateric®) or polyvinyl derivatives e.g. polyvinyl acetate phthalate (Coateric®).

In some embodiments, the dosage form of the invention is in the form of a compressed tablet or a capsule, said tablet or capsule coated with one or more anionic polymers with methacrylic acid as a functional group (Eudragit™ polymer, Evonik Degussa, Darmstadt, Germany) to retard or delay its release to achieve the objectives of the invention, said polymers including Eudragit™ L 30 D-55 or Eudragit™ L 100-55 which dissolve in the duodenum or at about pH >5.5, or Eudragit™ L 100 which dissolves in the jejunum or at a pH of about 6, or Eudragit™ S100, which dissolves in the ileum or at a pH o >7.0, or Eudragit™ FS 30D, which dissolves in the colon or at a pH of about 6, which dissolve at a pH>7.0.

In some embodiments, the dosage form of the invention can provide delayed and subsequently ileo-colonic or colonic release over an extended period of time (an extended release) by use of multiple polymers. In one embodiment, at the center of the dosage form is a core containing the butorphanol. The butorphanol is then coated with one or more layers of polymers that permit the drug to pass through the stomach, duodenum and jejunum (and optionally the ileum) without substantial absorption. As the dosage form reaches the alkaline pH of the ileum and colon (or optionally, upon arrival near or in the colon, for example upon traversing the ileo-cecal junction), the polymer allows permeability to water and thereby allows drug to diffuse from the dosage form and be available for systemic absorption in the terminal ileum and/or in the colon.

In some embodiments, the dosage form of the invention can provide delayed and subsequently rapid ileo-colonic or colonic release (an immediate pulsed release) by use of materials such as polymers. In this manner, after a defined lag time, rapid (pulsed) drug release is provided. For example, a layer composed of drug and organic acid is applied to the dosage form core. The core is then coated with material such a poly(meth)acrylate with basic groups such as quaternary ammonium groups, which become permeable in the presence of water. During gastrointestinal transit, water penetrates the coating into the core and dissolves the organic acid. Following the desired lag time, the drug is released as an immediate release or pulsed release.

In some embodiments, the dosage form of the invention is in the form of a capsule, said capsule made from materials known in the art, including gelatin, plasticizers, starch, hydroxypropylmethyl cellulose (HPMC), pullulan capsule.

In some embodiments of the invention, the butorphanol if formulated as an immediate release or controlled release tablet or capsule formulation. If used as prepared, the dosage form would usually release some of the butorphanol from the dosage form in the stomach, duodenum, jejunum and ileum. Some suitable coatings include U.S. Pat. Nos. 4,311, 833; 4,377,568; 4,385,078; 4,457,907; 4,462,839; 4,518, 433; 4,556,552; 4,606,909; 4,615,885; 4,670,287; 5,536, 507; 5,567,423; 5,591,433; 5,597,564; 5,609,871; 5,614, 222; 5,626,875; 5,629,001; and 6,608,075, all of which are incorporated herein in their entirety by reference.

In some embodiments of the invention, preferred coating compositions include alkyl and hydroxyalkyl celluloses and their aliphatic esters, e.g., methylcellulose, ethylcellulose, hydroxyethylcellulose, hydroxypropylcellulose, hydroxybutylcellulose, hydroxyethylmethylcellulose, hydroxypropymethylcellulose, hydroxybutylmethylcellulose, hydroxypropylcellulose phthalate, hydroxypropylmethylcellulose phthalate and hydroxypropylmethylcellulose acetate e succinate; carboxyalkylcelluloses and their salts, e.g., carboxymethylethylcellulose; cellulose acetate phthalate; cellulose acetate trimellitate, polycarboxymethylene and its salts and derivatives; polyvinyl alcohol and its esters: polyvinyl acetate phthalate; polycarboxymethylene copolymer with sodium formaldehyde carboxylate; acrylic polymers and copolymers, e.g., methacrylic acid-methyl methacrylic acid copolymer and methacrylic acid-methyl acrylate copolymer; edible oils such as peanut oil, palm oil, olive oil and hydrogenated vegetable oils; polyvinylpyrrolidone; polyethylene glycol and its esters: natural products such as shellac, and zein.

In some embodiments of the invention, other preferred coatings include polyvinylacetate esters, e.g., polyvinyl acetate phthalate; alkyleneglycolether esters of copolymers such as partial ethylene glycol monomethylether ester of ethylacrylate-maleic anhydride copolymer or diethyleneglycol monomethylether ester of methylacrylate-maleic anhydride copolymer, N-butylacrylate-maleic anhydride copolymer, isobutylacrylate-maleic anhydride copolymer or ethylacrylate-maleic anhydride copolymer; and polypeptides resistant to degradation in the gastric environment, e.g., polyarginine and polylysine. Other suitable coatings and methods to make and use delayed onset, rapid release and delayed onset, extended release, and delayed onset, pulsatile release, and controlled release, and modified release, and extended release, and pulsatile release, and slow release, and duodenal release, and jejunal release, and deal release, and ileo colonic release and colonic release pharmaceutical compositions and dosage forms of oral butorphanol are well known to those skilled in the art, including, Colonic Drug Delivery (page 287-294), Wilson C G, In: Modified-Release Drug Delivery Technology, Second Edition, Vol. 1, Rathbone M J, Hadgraft J, Roberts M S, Lane M E (eds), Informa Healthcare USA Inc. 2008; Biopolymers and Colonic Delivery, Wilson C G, Mukherji G, Shah H K (pages 295-309), In: Modified-Release Drug Delivery Technology, Second Edition, Vol. 1, Rathbone M J, Hadgraft J, Roberts M S, Lane M E (eds), Informa Healthcare USA Inc. 2008; Enteric Coating for Colonic Delivery, Shah H K, Mukherji G, Brogmann B, Wilson C G (pages 311-324), In: Modified-Release Drug Delivery Technology, Second Edition, Vol. 1, Rathbone M J, Hadgraft J, Roberts M S, Lane M E (eds), Informa Healthcare USA Inc. 2008; Programmed Drug Delivery Systems and the Colon, Wilson C G, Shah H K, Lee W W, Brogmann B, Mukherji G (pages 325-335), In: Modified-Release Drug Delivery Technology, Second Edition, Vol. 1, Rathbone M J, Hadgraft J, Roberts M S, Lane M E (eds), Informa Healthcare USA Inc. 2008; Targeting the Colon Using COLAL™: A Novel Bacteria-Sensitive Drug Delivery System, McConnell E L, Basit A W (pages 343-348), In: Modified-Release Drug Delivery Technology, Second Edition, Vol. 1, Rathbone M J, Hadgraft J, Roberts M S, Lane M E (eds), Informa Healthcare USA Inc. 2008; Remington: the science of Pharmacy Practice, 21$^{st}$ Edition, 2006, Lippincott, Williams & Wilkins, Baltimore, Md.; Pharmaceutical Preformulation and Formulation: A Practical Guide from Candidate Drug Selection to Commercial Dosage Form. Gibson, M (ed). CRC Press, 2001; Niazi, S. Handbook of Pharmaceutical Manufacturing Formulations: Compressed Solid Products (Volume 1 of 6), CRC Press, 2004; Niazi, S. Mollet, H, Grubenmann A, Payne H. Formulation Technology: Emulsions, Suspensions, Solid Forms, Wiley-VCH, 2001; FDA list and database; FDA Color Additive Status List; FDA Inactive Ingredients Database; Rowe, Sheskey and Owen, Handbook of Pharmaceutical Excipients, APhA Publications; 5th edition (2006); Rowe, Sheskey and Quinn, Handbook of Pharmaceutical Excipients, 6 edition, Pharmaceutical Press; APhA Publications; 2009; Pharmaceutical Additives Electronic Handbook, Third Edition, Michael Ash (compiler), Synapse Information Resources, Inc.; 3 Cdr edition (Feb. 19, 2007); and Health Canada's List of Acceptable Non-medicinal Ingredients; Patel et al. Therapeutic Opportunities in Colon-Specific Drug-Delivery System, Therapeutic Drug carrier Systems, 24(2), 147-202 (2007); Van den Mooter, Colon Drug Delivery, Expert Opin Drug Deliv (2006) 3(1):111-125; Singh. Modified-Release Solid Formulation for Colonic Delivery, Drug Deliv & Formulation 2007, 1, 53-56; Kumar et al. Colon Targeted Drug System—An Overview, Current Drug Deliv, 2008, 5, 186-198; Jain et al. Target-Specific Drug Release to the Colon, Expert Opin Drug Deliv (2008) 5(5): 483-498; Wei et al. Selective Drug Delivery to the Colon Using Pectin-Coated Pellets, PDA J Pharm Sci Tech Vol. 62, No. 4, 2008; Schellekens et al. Pulsatile Drug Delivery to Ileo-Colonic Segments by Structured Incorporation of Disintegrants in pH-Responsive Polymer Coatings, J Controlled Release 132 (2008) 91-98; Coviello et al. Polysaccharide Hydrogels for Modified Release Formulations, J Controlled Release 119 (2007) 5-24; McConnell et al. An in Vivo Comparison of Intestinal pH & Bacteria as Physiological Trigger Mechanisms for Colonic Targeting in Man, J Controlled Release 130 (2008) 154-160; Wei et al. Chitosan/Kollicoat SR 30D film-coated pellets of aminosalicylates for colonic drug delivery J Pharm Sci, 2009 Aug. 4; Yassin et al. New targeted-colon delivery system: in vitro and in vivo evaluation using X-ray imaging. J Drug Target, 2009 Aug. 5; Fan et al. Studies of chitosan/Kollicoat SR 30D film-coated tablets for colonic drug delivery. Int J Pharm, 2009 Jun. 22; 375(1-2):8-15; Yehia et al. Optimization of budesonide compression-coated tablets for colonic delivery. AAPS PharmSciTech, 2009; 10(1):147-57; Chandran et al. Microspheres with pH modulated release: Design and characterization of formulation variables for colonic delivery J Microencapsul, 2008 Sep. 22:1-11; Gohel et al. Design of a potential colonic drug delivery system of mesalamine Pharm Dev Technol 2008; 13(5):447-56; Maestrelli et al. Microspheres for colonic delivery of ketoprofen-hydroxypropyl-beta-cyclodextrin complex. Eur J Pharm Sci 2008 May 10; 34(1):1-11; Maestrelli et al. Development of enteric-coated calcium pectinate microspheres intended for colonic drug delivery. Eur J Pharm Biopharm 2008 June; 69(2):508-18; Fude et al. Preparation and in vitro evaluation of pH, time-based and enzyme-degradable pellets for colonic drug delivery. Drug Dev Ind Pharm 2007 September; 33(9):999-1007; Oosegi et al. Novel preparation of enteric-coated chitosan-prednisolone conjugate microspheres and in vitro evaluation of their potential as a colonic delivery system. Eur J Pharm Biopharm, 2008 February; 68(2):260-6; Nunthanid et al. Development of time-, pH-, and enzyme-controlled colonic drug delivery using spray-dried chitosan acetate and hydroxypropyl methylcellulose. Eur J Pharm Biopharm, 2008 February; 68(2):253-9; Singh Characterization and relevance of physicochemical interactions among components of a novel multiparticulate formulation for colonic delivery. Int J Pharm, 2007 Aug. 16; 341(1-2):143-51; Gazzaniga et al. Oral Colon Delivery: Rationale & Time-based Drug Design Strategy. Discov Med, 2006 December; 6(36):223-8; Singh Modified-release solid formulations for colonic delivery. Recent Pat Drug Deliv Formul, 2007; 1(1):53-63; Akhgari et al. Combination of time-dependent & pH-dependent polymethacrylates as a single coating formulation for colonic delivery of indomethacin pellets. Int J Pharm, 2006 Aug. 31; 320(1-2):137-42; Ibekwe et al. A comparative in vitro assessment of the drug release performance of pH-responsive polymers for ileo-colonic delivery. Int J Pharm. 2006 Feb. 3; 308(1-2): 52-60; Al-Saidan et al. In vitro and in vivo evaluation of guar gum-based matrix tablets of rofecoxib for colonic drug delivery. Curr Drug Deliv, 2005 April; 2(2):155-63; Basit. Advances in colonic drug delivery. Drugs. 2005; 65(14): 1991-2007; Bott et al. In vivo evaluation of a novel pH- & time-based multiunit colonic drug delivery system. Aliment Pharmacol Ther. 2004 Aug. 1; 20(3):347-53; Qi et al. A novel pH- and time-dependent system for colonic drug delivery. Drug Dev Ind Pharm. 2003 July; 29(6):661-7; 21: Shareef et al. Colonic drug delivery: an updated review. AAPS PharmSci. 2003; 5(2):E17. Review. PubMed PMID: 12866944; Tuleu et al. Colonic delivery of sodium butyrate via oral route: acrylic coating design of pellets and in vivo evaluation in rats. Methods Find Exp Clin Pharmacol. 2001 June; 23(5):245-53; Gupta et al. A novel pH- & time-based multi-unit potential colonic drug delivery system. II. Optimization of multiple response variables. Int J Pharm. 2001 Feb. 1; 213(1-2):93-102; Gupta et al. A novel pH- and time-based multi-unit potential colonic drug delivery system. I. Development. Int J Pharm. 2001 Feb. 1; 213(1-2): 83-91; Muraoka et al. Evaluation of intestinal pressure-controlled colon delivery capsule containing caffeine as a model drug in human volunteers. J Control Release. 1998 Mar. 2; 52(1-2):119-29; Niwa et al. Preparation & evaluation of a time-controlled release capsule made of ethylcellulose for colon delivery of drugs. J Drug Target. 1995; 3(2):83-9. Erratum in: J Drug Target 96; 3(6):478; Ashford et al. Targeting drugs to the colon: delivery systems oral administration. J Drug Target. 1994; 2(3):241-57, all hereby incorporated by reference in their entirety.

In some embodiments of the invention, the coating material may be mixed with various excipients including plasticizers such as triethyl citrate, acetyl triethyl citrate, diethyl phthalate, dibutyl phthalate, dibutyl subacute, dibutyl tartrate, dibutyl maleate, dibutyl succinate and diethyl succinate and inert fillers such as chalk or pigments.

The composition and thickness of the coating may be selected to dissolve immediately upon contact with the digestive juice of the intestine. Alternatively, the composition and thickness of the external coating may be selected to be a time-release coating which dissolves over a selected period of time, as is well known in the art.

The amount of enteric coating depends on the particular coating composition used and is preferably sufficient to substantially prevent the absorption of in the stomach, duodenum, jejunum and, in some embodiments, the ileum as well.

In some embodiments of the invention, hydroxyalkyl celluloses and their aliphatic esters, carboxyalkyl celluloses and their salts, polycarboxymethylene and its salts and derivatives, polyvinyl alcohol and its esters, polycarboxymethylene copolymer with sodium formaldehyde carboxylates, poly-vinylpyrrolidone, and polyethylene glycol and its esters can be applied as coatings by first dissolving the compound in a minimum amount of water. Alcohol is then added to the point of incipient cloudiness. The mixture can then be applied by conventional techniques.

In some embodiments, application of cellulose acetate phthalate may be accomplished by simply dissolving the cellulose acetate phthalate in a minimum amount of alcohol and then applying by conventional techniques. Hydrogenated vegetable oils may be applied by first dissolving the oil in a minimal amount of a non-polymer solvent, such as methylene chloride, chloroform or carbon tetrachloride, then adding alcohol to the point of incipient cloudiness and then applying by conventional techniques.

In some embodiments, the dosage form of is a capsule or tablet, said dosage form pre-coated with an excipient, prior to coating with a polymer.

In some embodiments, the capsule dosage form is sealed after filling in the overlapping region of capsule body and cap by commonly known sealing techniques like banding or applying a sealing liquid and/or heat to the gap between capsule body and cap. Preferred is a sealing process, in which a sealing liquid which may include a solvent applied individually and uniformly to the external edge of the gap of a capsule to be sealed to form a liquid ring around the circumference of the capsule, removing excess sealing liquid from the exterior of the capsule and drying the capsule by applying thermal energy from outside. Such a sealing before coating can prevent problems e.g. with non-uniformity of the coating at the gap or development of fissures during storage under stressing conditions, which can lead to early leaking of the capsule content into the stomach. In some embodiments, the banding is achieved through the application of a ring of liquid gelatin or hypromellose on the external surface of the capsule. In some embodiments, a double-band sealing technique is used to ensure ensures that if an air bubble or unevenness occurs in the first band, it will be eliminated by the second application. Capsule banding can provide tamper evidence, deter counterfeiting, improve mechanical strength, provide color brand differentiation, improve product stability and reduce oxygen diffusion.

For rapid release of the drug from the dosage form in some embodiments, the composition of the coating will usually provide substantial or complete disintegration of the coating in the preferred anatomic location and/or at the preferred time after oral ingestion and/or in the preferred gastrointestinal environment, including preferred pH, preferred osmotic pressure in the lumen, preferred osmotic pressure in the dosage form, preferred hydration level, preferred microbial environment, preferred level of GI peristalsis or agitation.

For controlled or slow release of the drug from the dosage form in some embodiments, the composition of the pH sensitive coating will dissolve, but other controlled release mechanisms will provide for slow release of the drug in the preferred anatomic location and/or at the preferred time after oral ingestion and/or in the preferred gastrointestinal environment, including preferred pH, preferred osmotic pressure in the lumen, preferred osmotic pressure in the dosage form, preferred hydration level, preferred microbial environment, preferred level of GI peristalsis or agitation.

In some embodiments, for rapid release in the small intestine any coating can be used which ensures that the dosage form does not disintegrate until it is emptied from the stomach. The coating may be one which is pH sensitive and which completely dissolves in the small intestine. Typical coating thicknesses will be in the range 2 to 30 mg polymer per $cm^2$ of capsule surface, preferably 5 to 15 mg polymer per $cm^2$ of capsule surface, but this will vary greatly depending on the choice of coating. For a capsule of size 1 with a surface area of approximately 4 $cm^2$ this represents a weight gain of 20 mg to 60 mg per capsule (50 to 150 μm).

In some embodiments, preferred coating materials are those which dissolve at a pH between 5 and 7.6, for example, >about 5, or >about 5.2, or >about 5.5, or >about 5.7, or >about 6, or >about 6.1, or >about 6.2, or >about 6.3, or >about 6.4, or >about 6.5, or >about 6.6, or >about 6.7, or >about 6.8, or >about 6.9, or >about 7, or >about 7.2, or >about 7.4, or >about 7.6.

In some embodiments, preferred coating materials include polymers such as cellulose acetate trimellitate (CAT), hydroxypropylmethyl cellulose phthalate (HPMCP), polyvinyl acetate phthalate (PVAP), cellulose acetate phthalate (CAP) and shellac. In some embodiments, especially preferred materials for aqueous film coating are copolymers of methacrylic acid and ethyl acrylate, Eudragit® L30D-55 (Evonik Degussa, Darmstadt, Germany).

In some embodiments, for release in the terminal ileum or colon any coating can be used which ensures that the dosage form does not disintegrate until it is reaches the desired location. In some embodiments, the coating may be one which is pH-sensitive, redox-sensitive or sensitive to particular enzymes or bacteria, such that the coating only dissolves or finishes dissolving in the colon. Thus the capsules will not release the drug until it is in the terminal ileum or colon.

In some embodiments, preferred coating materials are those which dissolve at a pH of 7 or above. Generally, such coatings only start to dissolve when they have left the stomach and passed through the duodenum and in cases the jejunum and/or terminal ileum. Generally, by the time the dosage form has reached the terminal ileum or colon the coating will have completely dissolved. Such a coating can be made from a variety of polymers including, without limitation, cellulose acetate trimellitate (CAT) hydroxypropylmethyl cellulose phthalate (HPMCP), polyvinyl acetate phthalate (PVAP), cellulose acetate phthalate (CAP), shellac and copolymers of methacrylic acid and ethyl acrylate. In some embodiments, especially preferred materials for aqueous film coating are copolymers of methacrylic acid and ethyl acrylate to which a monomer of methylacrylate has been added during polymerization. (Eudragit™ FS 30 D, Evonik Degussa, Darmstadt, Germany). Due to the free carboxylic acid group the polymer dissolves at pH 7 or above making it particularly suitable for delivery into the colon.

It should be noted that when delayed but (subsequently) sustained release of butorphanol is desired, upon dissolution or disintegration of the pH sensitive coating or material, a variety of mechanisms can provide extended release of the drug, including diffusion from matrix, membranes or pores, osmotic pressure, hydration, etc)

Using preparation Eudragit™ FS 30D a coating thickness of 5 to 15 mg polymer per $cm^2$ of capsule surface is preferred in some embodiments.

The colonic region is rich in microbial anaerobic organisms providing reducing conditions. Thus the coating may suitably comprise a material which is redox-sensitive. Such coatings may comprise azopolymers which can for example consist of a random copolymer of styrene and hydroxyethyl methacrylate, cross-linked with divinylazobenzene synthesized by free radical polymerization, the azopolymer being broken down enzymatically and specifically in the colon or may consist of disulphide polymers.

Other materials providing release in the colon are amylose, for example a coating composition can be prepared by mixing amylose-butan-1-ol complex (glassy amylose) with an aqueous dispersion of Ethocel or a coating formulation comprising an inner coating of glassy amylose and an outer coating of cellulose or acrylic polymer material, calcium pectinate, pectin, a polysaccharide which is totally degraded by colonic bacterial enzymes, chondroitin sulfate and resistant starches, dextran hydrogels, modified guar gum such as borax modified guar gum, cyclodextrins, beta.-cyclodextrin, saccharide containing polymers, which can include a polymeric construct comprising a synthetic oligosaccharides-containing biopolymer including methacrylic polymers covalently couples to oligosaccharides such as cellobiose, lactalose, raffinose, and stachyose, or saccharide-containing natural polymers including modified mucopolysaccharides such as cross-linked chondroitin sulfate and metal pectin salts, for example calcium pectate, methacrylate-galactomannan and pH sensitive hydrogels.

Pharmaceutical compositions of the present invention can be prepared using methods described in the art. There is a wide body of literature and other prior art on the delivery, release and absorption of drug from oral dosage forms wherein said delivery, release and absorption is "targeted", i.e., where said delivery, release and absorption is: (i) achieved at the desired anatomic location of the GI tract; (ii) substantially avoided at certain anatomic locations of the GI tract; (iii) achieved after a particular amount of time has elapsed post-ingestion; (iv) achieved when the GI environment meets certain conditions (e.g., pH, electrolyte concentration, enzymes, hydration, bacterial flora, and the like).

Pharmaceutical compositions of the present invention can be prepared using methods described, referenced or disclosed in U.S. Pat. Nos. 7,196,059, 7,189,414, 7,163,696, 7,157,444, 7,119,079, 7,112,578, 7,109,239, 7,094,425, 7,041,651, 7,030,082, 7,022,683, 6,930,093, 6,919,348, 6,916,791, 6,897,205, 6,893,662, 6,867,183, 6,852,693, 6,824,790, 6,777,000, 6,770,625, 6,761,901, 6,747,014, 6,743,445, 6,734,170, 6,727,287, 6,699,848, 6,692,766, 6,677,321, 6,669,951, 6,632,454, 6,632,451, 6,630,453, 6,555,136, 6,552,072, 6,531,152, 6,525,078, 6,432,967, 6,428,968, 6,346,547, 6,340,476, 6,326,364, 6,277,411, 6,238,689, 6,231,888, 6,228,396, 6,217,904, 6,200,605, 6,200,602, 6,197,763, 6,166,044, 6,166,024, 6,106,864, 6,074,689, 6,063,402, 6,039,975, 5,948,407, 5,914,132, 5,905,081, 5,889,028, 5,866,619, 5,849,327, 5,846,983, 5,843,479, 5,840,332, 5,814,336, 5,811,388, 5,744,166, 5,691,343, 5,686,106, 5,686,105, 5,681,584, 5,672,359, 5,670,158, 5,656,294, 5,656,290, 5,651,983, 5,631,022, 5,554,388, 5,525,634, 5,514,663, 5,482,718, 5,183,802, 5,122,376, 4,904,474, 4,705,515 and 4,627,851, and in US Patent Application No. 20070167416, 20070112075, 20070087939, 20070072828, 20070071820, 20070071806, 20070060580, 20070059366, 20070054945, 20070026067, 20070020254, 20070020197, 20070003626, 20060280795, 20060251720, 20060223787, 20060189635, 20060177507, 20060121091, 20060105045, 20060099243, 20060083718, 20060045865, 20060041109, 20060003995, 20050287276, 20050281781, 20050260262, 20050249716, 20050222040, 20050220861, 20050209271, 20050208132, 20050186267, 20050182134, 20050181053, 20050169996, 20050158408, 20050153908, 20050153907, 20050152978, 20050118326, 20050112201, 20050107334, 20050101611, 20050090473, 20050090451, 20050069550, 20050058701, 20050043298, 20050009848, 20050009768, 20050009767, 20050009766, 20050008702, 20050008688, 20040267240, 20040258754, 20040253304, 20040241173, 20040229831, 20040224898, 20040219216, 20040186045, 20040185107, 20040176319, 20040162263, 20040162259, 20040161459, 20040147445, 20040142880, 20040126422, 20040121967, 20040110837, 20040109894, 20040062778, 20040052846, 20040038866, 20040017387, 20040013687, 20030207851, 20030194439, 20030181380, 20030170181, 20030162717, 20030152617, 20030133978, 20030083232, 20030077326, 20030069170, 20030040497, 20030022843, 20030008914, 20020147156, 20020127198, 20020110593, 20020110590, 20020098235, 20020058061, 20020035139, 20020015729, 20010052137, 20010039262, 20010036473, 20010031748 and 20010026807.

Pharmaceutical compositions of the present invention can be prepared to provide targeted delivery of butorphanol, wherein the targeted delivery of the immediate or controlled release dosage forms can advantageously provide, among other things, (i) improved efficacy; (ii) improved safety; (iii) reduced appeal to drug addicts, drug abusers and recreational drug users; (iv) reduced nausea; (v) reduced drowsiness; (vi) reduced psychic effects desired by drug addicts, drug abusers and recreational drug users; (vii) reduced desirability for co-abuse with alcohol or other drugs of abuse; and (viii) reduced risk of diversion.

Pharmaceutical compositions of the present invention can be prepared using methods described in the art achieve delivery, release and absorption of drug from oral dosage forms, wherein said delivery, release and absorption is "targeted", e.g., by way of non-limiting examples, where said delivery, release and absorption is: (i) achieved at the desired anatomic location of the GI tract (e.g., upon arrival in the duodenum, or jejum, or ileum, or ileo-cecal junction, or cecum, or ascending colon, or transverse colon, or descending colon); (ii) substantially avoided at certain anatomic locations of the GI tract (e.g., stomach, or stomach and duodenum, or stomach, duodenum and jejunum, or stomach, duodenum, jejunum and ileum); (iii) achieved after a particular amount of time has elapsed post-ingestion (e.g., ≥1.5 hours or ≥2 hours, or ≥2.5 hours, or ≥3 hours, or ≥3.5 hours, or ≥4 hours, or ≥4.5 hours, or ≥5 hours, or ≥5.5 hours, or ≥6 hours, or ≥6.5 hours, or ≥7 hours, or ≥7.5 hours); (iv) achieved when the dosage form has come in contact or substantial contact or sustained contact with a desired gastrointestinal pH environment (e.g., pH ≥3, or pH ≥3.5, or pH ≥4, or pH ≥4.5, or pH, ≥5, or pH ≥5.5, or pH ≥6, or pH ≥7, or pH ≥7.5, or pH ≥7.8); (v) achieved when the dosage form has come in contact with desired microbial flora (e.g., colonic microbial flora); (vi) achieved when the GI environment meets certain other conditions (e.g., electrolyte concentration, enzymes, hydration, and the like); (vii) a combination of two or more of the foregoing.

Pharmaceutical compositions of the present invention can be prepared using methods described, referenced or disclosed in U.S. Pat. Nos. 7,196,059, 7,189,414, 7,163,696, 7,157,444, 7,119,079, 7,112,578, 7,109,239, 7,094,425, 7,041,651, 7,030,082, 7,022,683, 6,930,093, 6,919,348, 6,916,791, 6,897,205, 6,893,662, 6,867,183, 6,852,693, 6,824,790, 6,777,000, 6,770,625, 6,761,901, 6,747,014, 6,743,445, 6,734,170, 6,727,287, 6,699,848, 6,692,766, 6,677,321, 6,669,951, 6,632,454, 6,632,451, 6,630,453, 6,555,136, 6,552,072, 6,531,152, 6,525,078, 6,432,967, 6,428,968, 6,346,547, 6,340,476, 6,326,364, 6,277,411, 6,238,689, 6,231,888, 6,228,396, 6,217,904, 6,200,605, 6,200,602, 6,197,763, 6,166,044, 6,166,024, 6,106,864, 6,074,689, 6,063,402, 6,039,975, 5,948,407, 5,914,132, 5,905,081, 5,889,028, 5,866,619, 5,849,327, 5,846,983, 5,843,479, 5,840,332, 5,814,336, 5,811,388, 5,744,166, 5,691,343, 5,686,106, 5,686,105, 5,681,584, 5,672,359, 5,670,158, 5,656,294, 5,656,290, 5,651,983, 5,631,022, 5,554,388, 5,525,634, 5,514,663, 5,482,718, 5,183,802, 5,122,376, 4,904,474, 4,705,515 and 4,627,851, and in US Patent Application No. 20070167416, 20070112075, 20070087939, 20070072828, 20070071820, 20070071806, 20070060580, 20070059366, 20070054945, 20070026067, 20070020254, 20070020197, 20070003626, 20060280795, 20060251720, 20060223787, 20060189635, 20060177507, 20060121091, 20060105045, 20060099243, 20060083718, 20060045865, 20060041109, 20060003995, 20050287276, 20050281781, 20050260262, 20050249716, 20050222040, 20050220861, 20050209271, 20050208132, 20050186267, 20050182134, 20050181053, 20050169996, 20050158408, 20050153908, 20050153907, 20050152978, 20050118326, 20050112201, 20050107334, 20050101611, 20050090473, 20050090451, 20050069550, 20050058701, 20050043298, 20050009848, 20050009768, 20050009767, 20050009766, 20050008702, 20050008688, 20040267240, 20040258754, 20040253304, 20040241173, 20040229831, 20040224898, 20040219216, 20040186045, 20040185107, 20040176319, 20040162263, 20040162259, 20040161459, 20040147445, 20040142880, 20040126422, 20040121967, 20040110837, 20040109894, 20040062778, 20040052846, 20040038866, 20040017387, 20040013687, 20030207851, 20030194439, 20030181380, 20030170181, 20030162717, 20030152617, 20030133978, 20030083232, 20030077326, 20030069170, 20030040497, 20030022843, 20030008914, 20020147156, 20020127198, 20020110593, 20020110590, 20020098235, 20020058061, 20020035139, 20020015729, 20010052137, 20010039262, 20010036473, 20010031748 and 20010026807, which are hereby fully incorporated by reference herein in their entirety.

Pharmaceutical compositions of the present invention can be prepared using methods described, referenced or disclosed in Singh and Kim, Int J Pharm. 2007; 341:143-51; Jain et al., Crit Rev Ther Drug Carrier Syst. 2006; 23:349-400; Ugurlu et al., Eur J Pharm Biopharm. 2007; 67:202-10; Sinha et al., J Pharm Pharmacol. 2007; 59:359-65; Gazzaniga et al., Discov Med. 2006; 6:223-8; Rhaman et al., AAPS PharmSciTech. 2006; 7:E47; Akhgari et al., Int J Pharm. 2006; 320:137-42; Bourgeois et al., J Drug Target. 2005; 13:277-84; Curini et al., Bioorg Med Chem Lett. 2005; 15:5049-52; Lamprecht et al., J Control Release. 2005; 104:337-46; Verbeke et al., Aliment Pharmacol Ther. 2005; 21:187-94; Bruce et al., Eur J Pharm Biopharm. 2005; 59:85-97; Lamprecht et al., Eur J Pharm Biopharm. 2004; 58:37-43; Mura et al., J Drug Target. 2003; 11:365-71; Lamprecht et al., J Control Release. 2003; 90:313-22; Wiwattanapatapee et al., J Control Release. 2003; 88:1-9; Waterman et al., J Control Release. 2003; 86:293-304; Park et al., Arch Pharm Res. 2002; 25:964-8; Tuleu et al., Aliment Pharmacol Ther. 2002; 16:1771-9; Gupta et al., Drug Dev Ind Pharm. 2002; 28:207-15; Turkoglu et al., Eur J Pharm Biopharm. 2002; 53:65-73; Tuleu et al., Methods Find Exp Clin Pharmacol. 2001; 23:245-53; Stubbe et al., J Control Release. 2001; 75:103-14; Shibata et al., J Pharm Pharmacol. 2001; 53:441-7; Jeong et al., J Control Release. 2001; 71:175-82; Hu et al., J Pharm Pharmacol. 2000; 52:1187-93; Hu et al., Pharm Res. 2000; 17:160-7; Ahrabi et al., Eur J Pharm Sci. 2000; 10:43-52; Yoshikawa et al., J Pharm Pharmacol. 1999; 51:979-89; Ahrabi et al., Drug Dev Ind Pharm. 1999; 25:453-62; Hu et al., J Control Release. 1998; 56:293-302; Kakoulides et al., J Control Release. 1998; 52:291-300; Kakoulides et al., J Control Release. 1998; 54:95-109; Muraoka et al., J Control Release. 1998; 52:119-29; Takaya et al., J Control Release. 1998; 50:111-22; Muraoka et al., Nippon Rinsho. 1998; 56:788-94; Kenyon et al, Aliment Pharmacol Ther. 1997; 11:205-13; Takaya et al., J Drug Target. 1997; 4:271-6; Matsuda et al., J Drug Target. 1996; 4:59-67; Jones S P, J Drug Target. 1996; 3:477-8; Fedorak et al., Gastroenterology. 1995; 108:1688-99; Takaya et al., J Pharm Pharmacol. 1995; 47:474-8; Niwa et al., J Drug Target. 1995; 3:83-9; Ashford and Fell, J Drug Target. 1994; 2:241-57, Colonic Drug Delivery (page 287-294), Wilson C G, In: Modified-Release Drug Delivery Technology, Second Edition, Vol. 1, Rathbone M J, Hadgraft J, Roberts M S, Lane M E (eds), Informa Healthcare USA Inc. 2008; Biopolymers and Colonic Delivery, Wilson C C, Mukherji C, Shah I I K (pages 295-309), In: Modified- Release Drug Delivery Technology, Second Edition, Vol. 1, Rathbone M J, Hadgraft J, Roberts M S, Lane M E (eds), Informa Healthcare USA Inc. 2008; Enteric Coating for Colonic Delivery, Shah H K, Mukherji G, Brogmann B, Wilson C G (pages 311-324), In: Modified-Release Drug Delivery Technology, Second Edition, Vol. 1, Rathbone M J, Hadgraft J, Roberts M S, Lane M E (eds), Informa Healthcare USA Inc. 2008; Programmed Drug Delivery Systems and the Colon, Wilson C G, Shah H K, Lee W W, Brogmann B, Mukherji G (pages 325-335), In: Modified-Release Drug Delivery Technology, Second Edition, Vol. 1, Rathbone M J, Hadgraft J, Roberts M S, Lane M E (eds), Informa Healthcare USA Inc. 2008; Targeting the Colon Using COLAL™: A Novel Bacteria-Sensitive Drug Delivery System, McConnell E L, Basit A W (pages 343-348), In: Modified-Release Drug Delivery Technology, Second Edition, Vol. 1, Rathbone M J, Hadgraft J, Roberts M S, Lane M E (eds), Informa Healthcare USA Inc. 2008, Niazi, S. Handbook of Pharmaceutical Manufacturing Formulations: Compressed Solid Products (Volume 1 of 6), CRC Press, 2004, which are hereby fully incorporated by reference herein in their entirety.

Controlled-Release Dosage Forms

All oral extended release pharmaceutical dosage forms of the invention are contemplated. The preparation of oral extended release pharmaceutical dosage forms has been described in the art—see—$^{se}$e for example, (i) Remington: the science of Pharmacy Practice, $21^{st}$ Edition, 2006, Lippincott, Williams & Wilkins, Baltimore, Md.; and (ii) Pharmaceutical Preformulation and Formulation: A Practical Guide from Candidate Drug Selection to Commercial Dosage Form. Gibson, M (ed). CRC Press, 2001; and (iii) Niazi, S. Handbook of Pharmaceutical Manufacturing Formulations: Compressed Solid Products (Volume 1 of 6), CRC Press, 2004 (iiib) Niazi, S. Handbook of Pharmaceutical Manufacturing Formulations: Uncompressed Solid Products (Volume 2 of 6), CRC Press, 2004; and (iv) Mollet, H, Grubenmann A, Payne H. Formulation Technology: Emulsions, Suspensions, Solid Forms, Wiley-VCH, 2001; (v) Donald Wise, Handbook of Pharmaceutical Controlled Release Technology, CRC; 1st edition (Aug. 15, 2000); (vi) Cherng-ju Kim, Controlled Release Dosage Form Design, Informa Healthcare (Oct. 25, 1999); (vii) Xiaoling Li, Design of Controlled Release Drug Delivery Systems, McGraw-Hill Professional; 1 edition (Nov. 3, 2005); (viii) Jean-Maurice Vergnaud, Controlled Drug Release Of Oral Dosage Forms, CRC (Jul. 31, 1993); (ix) L. T. Fan and S. K. Singh. Controlled Release: A Quantitative Treatment, Springer-Verlag (July 1989); (x) Tapash K. Ghosh and Bhaskara R. Jasti (eds). Theory and Practice of Contemporary Pharmaceutics, CRC; 2Rev Ed edition (Nov. 23, 2004); (xi) Xiaoling Li and Bhaskara R. Jasti (eds). Design of Controlled release Drug Delivery Systems; (xii) Anya M. Hillery, Andrew W. Lloyd and James Swarbrick (eds). Drug Delivery and Targeting: For Pharmacists and Pharmaceutical Scientists, CRC (Sep. 27, 2001); (xiii) Ram I. Mahato. Pharmaceutical Dosage Forms and Drug Delivery, CRC; 1 edition (Jun. 7, 2007); (xiv) Vasant V. Ranade and Mannfred A. Hollinger. Drug Delivery Systems, Second Edition, CRC; 2 edition (Aug. 26, 2003); (xv) Ashok Katdare and Mahesh Chaubal (eds). Excipient Development for Pharmaceutical, Biotechnology, and Drug Delivery Systems, Informa Healthcare; 1 edition (Jul. 28, 2006); and (xvi) Binghe Wang, Teruna J. Siahaan and Richard A. Soltero. Drug Delivery: Principles and Applications, Wiley-Interscience (Mar. 28, 2005), all of which are hereby incorporated in their entirety by reference.

A wide variety of methods for the preparation of controlled release dosage form are known in the art. These methods may be employed for the preparation of controlled release dosage forms of the invention, including but not limited to: (i) Diffusion-controlled Products: in some embodiments such products employ a water-insoluble polymer to control the flow of water and the subsequent egress of dissolved drug from the dosage form. Both diffusion and dissolution processes are involved. In "reservoir" systems, a core of drug is coated with the polymer and, in "matrix" systems, the drug is dispensed throughout the matrix. Cellulose derivatives are commonly used in the reservoir systems, while the matrix systems may use methylacrylate-methyl methacrylate, polyvinyl chloride, hydrophilic polymers such as cellulose derivatives or fatty compounds including carnauba wax; (ii) Dissolution-Controlled Products: in some embodiments such products control the rate of dissolution of the drug (and therefore absorption) by slowly soluble polymers or by microencapsulation. Once the coating is dissolved, the active drug becomes available for dissolution. By varying the thicknesses or amount of coating and its composition, the rate of active drug release can be controlled. Some dosage forms contain a portion of the total dose as in immediate release form to provide an early "pulse dose". Spheroid (pellet) dosage forms of diffusion or dissolution-controlled products can be encapsulated or prepared as a tablet. One potential advantage of encapsulated spheroid products is that the onset of absorption is less sensitive to gastric emptying, since the entry of the spheroids into the duodenum tends to be more uniform than with non-disintegrating extended-release tablet formulations; (iii) Erosion Products: in some embodiments, such products control the release of active drug by the erosion rate of a carrier matrix. The release rate is determined by the rate of erosion; (iv) Osmotic Pump Systems: in some embodiments such products control the rate of release of active drug by the constant inflow of water across a semipermeable membrane into a reservoir which contains an osmotic agent. The drug is either mixed with the agent or is located in a reservoir. The dosage form contains one or more small passageways, or through pores within a membrane through which drug in suspension or solution is pumped at a rate determined by the rate of entry of water due through osmotic pressure. The rate of release is can be kept relatively constant; (v) Ion Exchange Resins: in some embodiments, such products control the release of active drug bound to an ion exchange resin by release of drug in the ionic environment within the GI tract.

The preparation of oral extended release pharmaceutical dosage forms has also been described in the art. Nonlimiting examples are provided in U.S. Pat. Nos. 7,427,414; 7,422,758; 7,413,750; 7,413,749; 7,387,793; 7,316,821; 7,229,642; 7,198,803; 7,189,414; 7,125,567; 7,074,430; 7,070,806; 7,052,706; 6,979,463; 6,936,275; 6,932,981; 6,905,709; 6,902,742; 6,793,936; 6,733,783; 6,730,325; 6,726,931; 6,716,449; 6,709,677; 6,699,508; 6,699,506; 6,692,769; 6,692,766; 6,682,759; 6,667,060; 6,645,527; 6,599,529; 6,579,536; 6,517,868; 6,440,458; 6,387,404; 6,344,215; 6,342,250; 6,326,027; 6,319,520; 6,306,438; 6,274,599; 6,254,887; 6,245,356; 6,245,351; 6,228,398; 6,221,399; 6,210,714; 6,162,463; 6,159,501; 6,156,342; 6,153,623; 6,143,353; 6,143,322; 6,132,772; 6,103,261; 6,074,674; 6,048,548; 6,039,980; 6,034,085; 6,030,642; 6,024,982; 5,952,005; 5,885,616; 5,869,100; 5,858,408; 5,795,882; 5,773,025; 5,681,585; 5,674,533; 5,656,295; 5,656,291; 5,639,476; 5,614,218; 5,591,452; 5,589,190; 5,582,837; 5,580,578; 5,549,912; 5,520,931; 5,512,293; 5,508,042; 5,500,227; 5,484,607; 5,472,712; 5,451,409; 5,399, 358; 5,378,474; 5,334,392; 5,330,766; 5,314,697; 5,281,415; 5,262,164; 5,242,910; 5,229,135; 5,202,128; 5,198,220; 5,202,202; 5,186,930; 5,173,299; 5,128,144; 5,114,718; 5,084,267; 5,077,051; 5,047,248; and 5,043,165, and in U.S. Patent application No. 20090060994; 20090017127; 20090017126; 20080318910; 20080312309; 20080305160; 20080299196; 20080299189; 20080274181; 20080274177; 20080268057; 20080234352; 20080226713; 20080221174; 20080206335; 20080138411; 20080124399; 20080124398; 20080118556; 20080113025; 20080102121; 20080095853; 20080075785; 20080075781; 20080070972; 20080069888; 20080069873; 20080063711; 20080057123; 20080026052; 20080020039; 20080003281; 20070298101; 20070275065; 20070275062; 20070264325; 20070219175; 20070207214; 20070196500; 20070196396; 20070185218; 20070166375; 20070160663; 20070149590; 20070148153; 20070128276; 20070122481; 20070077297; 20070071819; 20070048377; 20070003617; 20060269603; 20060269601; 20060251721; 20060240105; 20060233880; 20060228413; 20060210631; 20060210630; 20060204578; 20060193912; 20060193911; 20060165808; 20060165807; 20060165792; 20060165791; 20060147527; 20060128806; 20060110463; 20060099262; 20060099261; 20060073204; 20060068009; 20060057203; 20060024366; 20050244498; 20050106247; 20040213844; 20040197405; 20040132826; 20040122104; 20040076665; 20040052851; 20030170304; 20030129237 and 20020054907, all of which are hereby incorporated in their entirety by reference.

In certain preferred embodiments of the present invention, the dosage form may comprise, in addition to butorphanol or a pharmaceutically acceptable salt thereof, POLYOX WSR 301, Hypromellose K4M, Microcrystalline Cellulose 102, Talc, Magnesium Stearate, Silicone dioxide.

In certain preferred embodiments of the present invention, the dosage form may comprise, in addition to butorphanol or a pharmaceutically acceptable salt thereof, POLYOX WSR 301, Hypromellose K4M, Microcrystalline Cellulose 102, Talc, Magnesium Stearate, Silicone dioxide.

In certain preferred embodiments of the present invention, the dosage form may comprise, in addition to butorphanol or a pharmaceutically acceptable salt thereof, Microcrystalline cellulose 101, Hypromellose K100M, Ethyl cellulose N7, Talc, Aerosil 200, Carbopol 710.

In certain preferred embodiments of the present invention, the dosage form may comprise, in addition to butorphanol or a pharmaceutically acceptable salt thereof, POLYOX WSR 301, Hypromellose K4M, Microcrystalline cellulose 101, Talc, Magnesium Stearate, Silicone dioxide.

In certain preferred embodiments of the present invention, the dosage form may comprise, in addition to butorphanol or a pharmaceutically acceptable salt thereof, POLYOX WSR 301, Hypromellose K4M, Microcrystalline cellulose 101, Talc, Magnesium Stearate, Silicone dioxide.

In certain preferred embodiments of the present invention, the dosage form may comprise, in addition to butorphanol or a pharmaceutically acceptable salt thereof, POLYOX WSR 301, Hypromellose K4M, Microcrystalline cellulose 101, BTH EP, Talc, Magnesium Stearate, Silicone dioxide.

In certain preferred embodiments of the present invention, the dosage form may comprise, in addition to butorphanol or a pharmaceutically acceptable salt thereof, Glyceryl Behenate (Melted), Cetyl Alcohol (Melted), Avicel PH 101, Talc, Mg. Stearate, Avicel PH 101.

In certain preferred embodiments of the present invention, the dosage form may comprise, in addition to butorphanol or a pharmaceutically acceptable salt thereof, Polyox WSR 301, MCC 101, Talc, Mg. Stearate, SiO2.

In certain preferred embodiments of the present invention, the dosage form may comprise, in addition to butorphanol or a pharmaceutically acceptable salt thereof, Polyox WSR 301, MCC 101, Talc, Mg. Stearate, SiO2.

In certain preferred embodiments of the present invention, the dosage form may comprise, in addition to butorphanol or a pharmaceutically acceptable salt thereof, Polyox WSR 301, HPMC K100 M CR, MCC 102, Talc, Mg. Stearate, SiO2.

In certain preferred embodiments of the present invention, the dosage form may comprise, in addition to butorphanol or a pharmaceutically acceptable salt thereof, Polyox WSR 301, HPMC K4 M, MCC 102, Talc, Mg. Stearate, SiO2.

In certain preferred embodiments of the present invention, the dosage form may comprise, in addition to butorphanol or a pharmaceutically acceptable salt thereof, Polyox WSR 301, HPMC K100 M, HPMC K4 M, MCC 102, Talc, Mg. Stearate, and SiO2.

In certain preferred embodiments of the present invention, the dosage form may comprise, in addition to butorphanol or a pharmaceutically acceptable salt thereof, Mannitol, Lactose, and PVP K 30 in IPA 3 ml, Mg. Stearate, Talc, and Aerosil 200.

In certain preferred embodiments of the present invention, the dosage form may comprise, in addition to butorphanol or a pharmaceutically acceptable salt thereof, Sodium Chloride, Lactose, and PVP K 30 in IPA 3 ml, Mg. Stearate, Talc, and Aerosil 200.

In certain preferred embodiments of the present invention, the dosage form may comprise, in addition to butorphanol or a pharmaceutically acceptable salt thereof and a pH sensitive polymer overcoat described herein, POLYOX WSR 301, Hypromellose K4M, Microcrystalline Cellulose 102, Talc, Magnesium Stearate, Silicone dioxide.

In certain preferred embodiments of the present invention, the dosage form may comprise, in addition to butorphanol or a pharmaceutically acceptable salt thereof and a pH sensitive polymer overcoat described herein, POLYOX WSR 301, Hypromellose K4M, Microcrystalline Cellulose 102, Talc, Magnesium Stearate, Silicone dioxide.

In certain preferred embodiments of the present invention, the dosage form may comprise, in addition to butorphanol or a pharmaceutically acceptable salt thereof and a pH sensitive polymer overcoat described herein, Microcrystalline cellulose 101, Hypromellose K100M, Ethyl cellulose N7, Talc, Aerosil 200, Carbopol 71G.

In certain preferred embodiments of the present invention, the dosage form may comprise, in addition to butorphanol or a pharmaceutically acceptable salt thereof and a pH sensitive polymer overcoat described herein, POLYOX WSR 301, Hypromellose K4M, Microcrystalline cellulose 101, Talc, Magnesium Stearate, Silicone dioxide.

In certain preferred embodiments of the present invention, the dosage form may comprise, in addition to butorphanol or a pharmaceutically acceptable salt thereof and a pH sensitive polymer overcoat described herein, POLYOX WSR 301, Hypromellose K4M, Microcrystalline cellulose 101, Talc, Magnesium Stearate, Silicone dioxide.

In certain preferred embodiments of the present invention, the dosage form may comprise, in addition to butorphanol or a pharmaceutically acceptable salt thereof and a pH sensitive polymer overcoat described herein, POLYOX WSR 301, Hypromellose K4M, Microcrystalline cellulose 101, BTH EP, Talc, Magnesium Stearate, Silicone dioxide.

In certain preferred embodiments of the present invention, the dosage form may comprise, in addition to butorphanol or a pharmaceutically acceptable salt thereof and a pH sensitive polymer overcoat described herein, Glyceryl Behenate (Melted), Cetyl Alcohol (Melted), Avicel PH 101, Talc, Mg. Stearate, Avicel PH 101.

In certain preferred embodiments of the present invention, the dosage form may comprise, in addition to butorphanol or a pharmaceutically acceptable salt thereof and a pH sensitive polymer overcoat described herein, Polyox WSR 301, MCC 101, Talc, Mg. Stearate, and SiO2.

In certain preferred embodiments of the present invention, the dosage form may comprise, in addition to butorphanol or a pharmaceutically acceptable salt thereof and a pH sensitive polymer overcoat described herein, Polyox WSR 301, MCC 101, Talc, Mg. Stearate, and SiO2.

In certain preferred embodiments of the present invention, the dosage form may comprise, in addition to butorphanol or a pharmaceutically acceptable salt thereof and a pH sensitive polymer overcoat described herein, Polyox WSR 301, HPMC K100 M CR, MCC 102, Talc, Mg. Stearate, and SiO2.

In certain preferred embodiments of the present invention, the dosage form may comprise, in addition to butorphanol or a pharmaceutically acceptable salt thereof and a pH sensitive polymer overcoat described herein, Polyox WSR 301, HPMC K4 M, MCC 102, Talc, Mg. Stearate, and SiO2.

In certain preferred embodiments of the present invention, the dosage form may comprise, in addition to butorphanol or a pharmaceutically acceptable salt thereof and a pH sensitive polymer overcoat described herein, Polyox WSR 301, HPMC K100 M, HPMC K4 M, MCC 102, Talc, Mg. Stearate, and SiO2.

In certain preferred embodiments of the present invention, the dosage form may comprise, in addition to butorphanol or a pharmaceutically acceptable salt thereof and a pH sensitive polymer overcoat described herein, Mannitol, Lactose, PVP K 30 in IPA 3 ml, Mg. Stearate, Talc, and Aerosil 200.

In certain preferred embodiments of the present invention, the dosage form may comprise, in addition to butorphanol or a pharmaceutically acceptable salt thereof and a pH sensitive polymer overcoat described herein, Sodium Chloride, Lactose, PVP K 30 in IPA 3 ml, Mg. Stearate, Talc, and Aerosil 200.

Matrix-Based Dosage Forms

In some embodiments, the modified release formulations of the present invention are provided as matrix-based dosage forms. Matrix formulations according to the invention may include hydrophilic, e.g., water-soluble, and/or hydrophobic, e.g., water-insoluble, polymers. The matrix formulations of the present invention may optionally be prepared with functional coatings, which may be enteric, e.g., exhibiting a pH-dependent solubility, or non-enteric, e.g., exhibiting a pH-independent solubility.

Matrix formulations of the present invention may be prepared by using, for example, direct compression or wet granulation. A functional coating, as noted above, may then be applied in accordance with the invention. Additionally, a barrier or sealant coat may be applied over a matrix tablet core prior to application of a functional coating. The barrier or sealant coat may serve the purpose of separating an active ingredient from a functional coating, which may interact with the active ingredient, or it may prevent moisture from contacting the active ingredient.

In a matrix-based dosage form in accordance with the present invention, the butorphanol and optional pharmaceutically acceptable excipient(s) are dispersed within a polymeric matrix, which typically comprises one or more water-soluble polymers and/or one or more water-insoluble polymers. The drug may be released from the dosage form by diffusion and/or erosion.

In one embodiment, a matrix-based dosage form comprises butorphanol, a filler such as starch, lactose, or microcrystalline cellulose; a controlled-release polymer, such as hydroxypropyl methylcellulose or polyvinyl pyrrolidone; a disintegrant, such crospovidone, or starch; a lubricant, such as magnesium stearate or stearic acid; a surfactant, such as sodium lauryl sulfate or polysorbates; and a glidant, such as colloidal silicon dioxide or talc. The amounts and types of polymers, and the ratio of water-soluble polymers to water-insoluble polymers in the inventive formulations are generally selected to achieve a desired release profile of butorphanol. For example, by increasing the amount of water insoluble-polymer relative to the amount of water soluble-polymer, the release of the drug may, in some embodiments, be delayed or slowed. This is due, in part, to an increased impermeability of the polymeric matrix, and, in some cases, to a decreased rate of erosion during transit through the GI tract.

The controlled-release dosage form may optionally include a controlled release material which is incorporated into a matrix along with the butorphanol, or which is applied as a sustained release coating over a substrate comprising the drug (the term "substrate" encompassing beads, pellets, spheroids, tablets, tablet cores, etc). The controlled release material may be hydrophobic or hydrophilic as desired. The oral dosage form according to the invention may be provided as, for example, granules, spheroids, pellets or other multiparticulate formulations. An amount of the multiparticulates which is effective to provide the desired dose of butorphanol over time may be placed in a capsule or may be incorporated in any other suitable oral solid form, e.g., compressed into a tablet. On the other hand, the oral dosage form according to the present invention may be prepared as a tablet core coated with a controlled-release coating, or as a tablet comprising a matrix of drug and controlled release material, and optionally other pharmaceutically desirable ingredients (e.g., diluents, binders, colorants, lubricants, etc.). The controlled release dosage form of the present invention may also be prepared as a bead formulation or an osmotic dosage formulation.

In certain preferred embodiments of the present invention, the controlled-release formulation is achieved via a matrix (e.g. a matrix tablet) which includes a controlled-release material as set forth below. A dosage form including a controlled-release matrix provides in-vitro dissolution rates of butorphanol within the preferred ranges and that releases the butorphanol in a pH-dependent or pH-independent manner. The materials suitable for inclusion in a controlled-release matrix will depend on the method used to form the matrix. The oral dosage form may contain between 1% and 99% (by weight) of at least one hydrophilic or hydrophobic controlled release material.

A non-limiting list of suitable controlled-release materials which may be included in a controlled-release matrix according to the invention include hydrophilic and/or hydrophobic materials, such as gums, cellulose ethers, acrylic resins, protein derived materials, waxes, shellac, and oils such as hydrogenated castor oil, hydrogenated vegetable oil hydrogenated Type I or Type II vegetable oils, polyoxyethylene stearates and distearates, glycerol monostearate, and non-polymeric, non-water soluble liquids carbohydrate-based substances or poorly water soluble, high melting point (mp=40 to 100° C.) waxes and mixtures thereof.

Hydrogenated vegetable oils of the present invention may include hydrogenated cottonseed oil (e.g., Akofine®; Lubritab®; Sterotex® NF), hydrogenated palm oil (Dynasan® P60; Softisan® 154), hydrogenated soybean oil (Hydrocote®; Lipovol HS-K®; Sterotex® HM) and hydrogenated palm kernel oil (e.g., Hydrokote® 112).

Polyoxyethylene stearates and distearates of the present invention include Polyoxyl 2, 4, 6, 8, 12, 20, 30, 40, 50, 100 and 150 stearates (e.g., Hodag® DGS; PEG-2 stearate; Acconon® 200-MS; Hodag® 20-S; PEG-4 stearate; Cerasynt® 616; Kessco® PEG 300 Monostearate; Acconon® 400-MS; Cerasynt® 660; Cithrol® 4MS; Hodag® 60-S; Kessco® PEG 600 Monostearate; Cerasynt® 840; Hodag 100-S; Myrj® 51; PEG-30 stearate; polyoxyethylene (30) stearate; Crodet® S40; E431; Emerest® 2672; Atlas G-2153; Crodet® S50) and polyoxyl 4, 8, 12, 32 and 150 distearates (e.g., Lipo-PEG® 100-S; Myrj® 59; Hodag® 600-S; Ritox® 59; Hodag® 22-S; PEG-4 distearate; Hodag® 42-S; Kessco® PEG 400 DS; Hodag® 62-S; Kessco® PEG 600 Distearate; Hodag® 154-S; Kessco® PEG 1540 Distearate; Lipo-PEG® 6000-DS; Protamatc® 6000-DS).

In one embodiment of the present invention, the butorphanol is combined with beeswax, hydroxypropyl methyl cellulose (e.g., HPMC K15M), silicon dioxide (alone or in combination with $Al_2O_3$; e.g., Aerosil®, Aerosil® 200, Aerosil® COK84).

In one embodiment of the present invention, the butorphanol is combined with hydrogenated cottonseed oil (e.g., Sterotex® NF), hydroxypropyl methyl cellulose (e.g., HPMC K15M), coconut oil and silicon dioxide (alone or in combination with $Al_2O_3$; e.g., Aerosil®, Aerosil® 200, Aerosil® COK84).

In another embodiment of the present invention, the butorphanol is combined with glycerol monostearate (e.g., Cithrol® GMS), hydroxypropyl methyl cellulose (e.g., HPMC K100M) and silicon dioxide (alone or in combination with $Al_2O_3$; e.g., Aerosil®, Aerosil® 200, Aerosil® COK84).

In yet another embodiment of the present invention, the butorphanol is combined with hydrogenated palm kernel oil (e.g., Hydrokote® 112), hydroxypropyl methyl cellulose (e.g., HPMC K15M) and silicon dioxide (alone or in combination with $Al_2O_3$; e.g., Aerosil®, Aerosil® 200, Aerosil® COK84).

In one embodiment of the present invention, release rate modifiers, including hydroxypropyl methyl cellulose (e.g., HPMC K15M) may incorporated. Release rate modifiers can also have additional useful properties that optimize the formulation.

A variety of agents may be incorporated into the invention as thixotropes (e.g., fumed silicon dioxides, Aerosil®, Aerosil® COK84, Aerosil® 200, etc.). Thixotropes enhance the pharmaceutical formulations of the invention by increasing the viscosity of solutions complementing the action of HPMCs.

Any pharmaceutically acceptable hydrophobic or hydrophilic controlled-release material which is capable of imparting controlled-release of the butorphanol may be used in accordance with the present invention. Preferred controlled-release polymers include alkylcelluloses such as ethylcellulose, acrylic and methacrylic acid polymers and copolymers, and cellulose ethers, especially hydroxyalkylcelluloses (e.g., hydroxypropylmethylcellulose) and carboxyalkylcelluloses. Preferred acrylic and methacrylic acid polymers and copolymers include methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer, poly(methyl methacrylate), poly(methacrylic acid)(anhydride), polymethacrylate, polyacrylamide, poly(methacrylic acid anhydride), glycidyl methacrylate copolymers, ethylcellulose, cellulose acetate cellulose propionate, cellulose acetate propionate, cellulose acetate butyrate, cellulose acetate phthalate, cellulose triacetate, poly (methyl methacrylate), poly (ethyl methacrylate), poly (butyl methacrylate), poly (isobutyl methacrylate), and poly (hexyl methacrylate), poly (isodecyl methacrylate), poly (lauryl methacrylate), poly (phenyl methacrylate), poly (methyl acrylate), poly (isopropyl acrylate), poly (isobutyl acrylate), poly (octadecyl acrylate), poly (ethylene), poly (ethylene) low density, poly (ethylene) high density, poly (ethylene oxide), poly (ethylene terephthalate), poly (vinyl isobutyl ether), poly (vinyl acetate), poly (vinyl chloride) or polyurethane, and/or mixtures thereof. Certain preferred embodiments utilize mixtures of any of the foregoing controlled-release materials in the matrices of the invention.

The matrix also may include a binder. In such embodiments, the binder preferably contributes to the controlled-release of the butorphanol from the controlled-release matrix.

Preferred hydrophobic binder materials are water-insoluble with more or less pronounced hydrophilic and/or hydrophobic trends. Preferred hydrophobic binder materials which may be used in accordance with the present invention include digestible, long chain ($C_8$-$C_{50}$, especially $C_{12}$-$C_{40}$), substituted or unsubstituted hydrocarbons, such as fatty acids, fatty alcohols, glyceryl esters of fatty acids, mineral and vegetable oils, natural and synthetic waxes and polyalkylene glycols. Preferably, the hydrophobic hinder materials useful in the invention have a melting point from about 30 to about 200° C., preferably from about 45 to about 90° C. When the hydrophobic material is a hydrocarbon, the hydrocarbon preferably has a melting point of between 25 and 90° C. Of the long chain ($C_8$-$C_{50}$) hydrocarbon materials, fatty (aliphatic) alcohols are preferred. The oral dosage form may contain up to 98% (by weight) of at least one digestible, long chain hydrocarbon.

The oral dosage form contains up to 98% (by weight) of at least one polyalkylene glycol. The hydrophobic binder material may comprise natural or synthetic waxes, fatty alcohols (such as lauryl, myristyl, stearyl, cetyl or preferably cetostearyl alcohol), fatty acids, including but not limited to fatty acid esters, fatty acid glycerides (mono-, di-, and tri-glycerides), hydrogenated fats, hydrocarbons, normal waxes, stearic acid, stearyl alcohol and hydrophobic and hydrophilic materials having hydrocarbon backbones. Suitable waxes include, for example, beeswax, glycowax, castor wax and carnauba wax. For purposes of the present invention, a wax-like substance is defined as any material which is normally solid at room temperature and has a melting point of from about 30 to about 100° C.

In certain preferred embodiments, a combination of two or more hydrophobic binder materials are included in the matrix formulations. If an additional hydrophobic binder material is included, it is preferably selected from natural and synthetic waxes, fatty acids, fatty alcohols, and mixtures of the same. Examples include beeswax, carnauba wax, stearic acid and stearyl alcohol. This list is not meant to be exclusive.

One particular suitable controlled-release matrix comprises at least one water soluble hydroxyalkyl cellulose, at least one $C_{12}$-$C_{36}$, preferably $C_{14}$-$C_{22}$, aliphatic alcohol and, optionally, at least one polyalkylene glycol. The hydroxyalkyl cellulose is preferably a hydroxy ($C_1$ to $C_6$) alkyl cellulose, such as hydroxypropylcellulose, hydroxypropylmethylcellulose and, especially, hydroxyethyl cellulose. The amount of the at least one hydroxyalkyl cellulose in the present oral dosage form will be determined, inter alia, by the precise rate of the butorphanol release required. The aliphatic alcohol may be, for example, lauryl alcohol, myristyl alcohol or stearyl alcohol. In particularly preferred embodiments of the present oral dosage form, however, the at least one aliphatic alcohol is cetyl alcohol or cetostearyl alcohol. The amount of aliphatic alcohol in the present oral dosage form will be determined, as above, by the precise rate of the butorphanol release required. It will also depend on whether at least one polyalkylene glycol is present in or absent from the oral dosage form. In the absence of at least one polyalkylene glycol, the oral dosage form preferably contains between 20% and 50% (by wt) of the aliphatic alcohol. When a polyalkylene glycol is present in the oral dosage form, then the combined weight of the aliphatic alcohol and the polyalkylene glycol preferably constitutes between 20% and 50% (by wt) of the total dosage.

In one preferred embodiment, the ratio of, e.g., the at least one hydroxyalkyl cellulose or acrylic resin to the at least one aliphatic alcohol/polyalkylene glycol determines, to a considerable extent, the release rate of the butorphanol from the formulation. A ratio of the hydroxyalkyl cellulose to the aliphatic alcohol/polyalkylene glycol of between 1:2 and 1:4 is preferred, with a ratio of between 1:3 and 1:4 being particularly preferred.

The polyalkylene glycol maybe, for example, polypropylene glycol or, which is preferred, polyethylene glycol. The number average molecular weight of the at least one polyalkylene glycol is preferred between 1,000 and 15,000 especially between 1,500 and 12,000.

Another suitable controlled-release matrix comprises an alkylcellulose (especially ethylcellulose), a $C_{12}$ to $C_{36}$ aliphatic alcohol and, optionally, a polyalkylene glycol.

Another method of producing the dosage form of the invention involves liquid fill compositions, including hydrogenated Type I or Type II vegetable oils (e.g., Hydrokote® 112), polyoxyethylene stearates and distearates, glycerol monostearate (e.g., Cithrol® GMS), non-polymeric, non-water soluble liquids carbohydrate-based substances, poorly water soluble, high melting point (mp=40 to 100° C.) waxes.

Hydrogenated vegetable oils may include hydrogenated cottonseed oil (e.g., Akofine®; Lubritab®; Sterotex® NF), hydrogenated palm oil (Dynasan® P60; Softisan® 154), hydrogenated soybean oil (Hydrocote®; Lipovol HS-K®; Sterotex® HM) and hydrogenated palm kernel oil (e.g., Hydrokote® 112).

Polyoxyethylene stearates and distearates may include Polyoxyl 2, 4, 6, 8, 12, 20, 30, 40, 50, 100 and 150 stearates (e.g., Hodag® DGS; PEG-2 stearate; Acconon® 200-MS; Hodag® 20-S; PEG-4 stearate; Cerasynt® 616; Kessco® PEG 300 Monostearate; Acconon® 400-MS; Cerasynt® 660; Cithrol® 4MS; Hodag® 60-S; Kessco® PEG 600 Monostearate; Cerasynt® 840; Hodag 100-S; Myrj® 51; PEG-30 stearate; polyoxyethylene (30) stearate; Crodet® S40; E431; Emerest® 2672; Atlas G-2153; Crodet® S50) and polyoxyl 4, 8, 12, 32 and 150 distearates (e.g., Lipo-PEG® 100-S; Myrj® 59; Hodag® 600-S; Ritox® 59; Ilodag® 22-S; PEG-4 distearate; Ilodag® 42-S; Kessco® PEG 400 DS; Ilodag® 62-S; Kessco® PEG 600 Distearate; Hodag® 154-S; Kessco® PEG 1540 Distearate; Lipo-PEG® 6000-DS; Protamate® 6000-DS).

In one embodiment of the present invention, release rate modifiers, including hydroxypropyl methyl cellulose (e.g., HPMC K15M) may be incorporated. Release rate modifiers can also have additional useful properties that optimize the formulation.

A variety of agents may be incorporated into the invention as thixotropes (e.g., fumed silicon dioxides, Aerosil®, Aerosil® COK84, Aerosil® 200, etc.). Thixotropes enhance the pharmaceutical formulations of the invention by increasing the viscosity of solutions during attempted extraction, complementing the action of HPMCs. They may also provide a tamper resistance by helping to retain the structure of dosage units that have been heated to temperatures greater than the melting point of the base excipient (Aerosils are unaffected by heat).

In addition to the above ingredients, a controlled-release matrix may also contain suitable quantities of other materials, e.g., diluents, lubricants, binders, granulating aids, colorants, flavorants and glidants that are conventional in the pharmaceutical art.

In order to facilitate the preparation of a solid, controlled-release oral dosage form according to the invention there is provided, in a further aspect of the present invention, a process for the preparation of a solid, controlled-release oral dosage form according to the present invention comprising incorporating the butorphanol or a salt thereof in a controlled-release matrix. Incorporation in the matrix may be effected, for example, by (a) forming granules comprising at least one hydrophobic and/or hydrophilic material as set forth above (e.g., a water soluble hydroxyalkyl cellulose) together with the butorphanol; (b) mixing the at least one hydrophobic and/or hydrophilic material-containing granules with at least one $C_{12}$-$C_{36}$ aliphatic alcohol, and (c) optionally, compressing and shaping the granules.

The granules may be formed by any of the procedures well-known to those skilled in the art of pharmaceutical formulation. For example, in one preferred method, the granules may be formed by wet granulating hydroxyalkyl cellulose/butorphanol with water. In a particular preferred embodiment of this process, the amount of water added during the wet granulation step is preferably between 1.5 and 5 times, especially between 135 and 3.5 times, the dry weight of the butorphanol.

In certain embodiments, the dosage form comprises a plurality of matrices described above.

The matrices of the present invention may also be prepared via a melt pelletization technique. In such circumstance, the butorphanol in finely divided form is combined with a binder (also in particulate form) and other optional inert ingredients, and thereafter the mixture is pelletized, e.g., by mechanically working the mixture in a high shear mixer to form the pellets (granules, spheres). Thereafter, the pellets (granules, spheres) may be sieved in order to obtain pellets of the requisite size. The binder material is preferably in particulate form and has a melting point above about 40° C. Suitable binder substances include, for example, hydrogenated castor oil, hydrogenated vegetable oil, other hydrogenated fats, fatty alcohols, fatty acid esters, fatty acid glycerides, and the like.

Controlled-release matrices can also be prepared by, e.g., melt-granulation or melt-extrusion techniques. Generally, melt-granulation techniques involve melting a normally solid hydrophobic binder material, e.g. a wax, and incorporating a powdered drug therein. To obtain a controlled release dosage form, it may be necessary to incorporate a hydrophobic controlled release material, e.g. ethylcellulose or a water-insoluble acrylic polymer, into the molten wax hydrophobic binder material.

The hydrophobic binder material may comprise one or more water-insoluble wax-like thermoplastic substances possibly mixed with one or more wax-like thermoplastic substances being less hydrophobic than said one or more water-insoluble wax-like substances. In order to achieve controlled release, the individual wax-like substances in the formulation should be substantially non-degradable and insoluble in gastrointestinal fluids during the initial release phases. Useful water-insoluble wax-like binder substances may be those with a water-solubility that is lower than about 1:5,000 (w/w).

In addition to the above ingredients, a controlled release matrix may also contain suitable quantities of other materials, e.g., diluents, lubricants, binders, granulating aids, colorants, flavorants and glidants that are conventional in the pharmaceutical art in amounts up to about 50% by weight of the particulate if desired. The quantities of these additional materials will be sufficient to provide the desired effect to the desired formulation.

The preparation of a suitable melt-extruded matrix according to the present invention may, for example, include the steps of blending the butorphanol, together with a controlled release material and preferably a binder material to obtain a homogeneous mixture. The homogeneous mixture is then heated to a temperature sufficient to at least soften the mixture sufficiently to extrude the same. The resulting homogeneous mixture is then extruded, e.g., using a twin-screw extruder, to form strands. The extrudate is preferably cooled and cut into multiparticulates by any means known in the art. The strands are cooled and cut into multiparticulates. The multiparticulates are then divided into unit doses. The extrudate preferably has a diameter of from about 0.1 to about 5 mm and provides controlled release of the therapeutically active agent for a time period of from about 6 to at least about 24 hours.

An optional process for preparing the melt extrusioned formulations of the present invention includes directly metering into an extruder a hydrophobic controlled release material, a therapeutically active agent, and an optional hinder material; heating the homogenous mixture; extruding the homogenous mixture to thereby form strands; cooling the strands containing the homogenous mixture; cutting the strands into particles having a size from about 0.1 mm to about 12 mm; and dividing said particles into unit doses. In this aspect of the invention, a relatively continuous manufacturing procedure is realized.

Plasticizers, such as those described herein, may be included in melt-extruded matrices. The plasticizer is preferably included as from about 0.1 to about 30% by weight of the matrix. Other pharmaceutical excipients, e.g., talc, mono or poly saccharides, colorants, flavorants, lubricants and the like may be included in the controlled release matrices of the present invention as desired. The amounts included will depend upon the desired characteristic to be achieved.

The diameter of the extruder aperture or exit port can be adjusted to vary the thickness of the extruded strands. Furthermore, the exit part of the extruder need not be round; it can be oblong, rectangular, etc. The exiting strands can be reduced to particles using a hot wire cutter, guillotine, etc.

A melt extruded multiparticulate system can be, for example, in the form of granules, spheroids or pellets depending upon the extruder exit orifice. For purposes of the present invention, the terms "melt-extruded multiparticulate (s)" and "melt-extruded multiparticulate system(s)" and "melt-extruded particles" shall refer to a plurality of units, preferably within a range of similar size and/or shape and containing one or more active agents and one or more excipients, preferably including a hydrophobic controlled release material as described herein. Preferably the melt-extruded multiparticulates will be of a range of from about 0.1 to about 12 mm in length and have a diameter of from about 0.1 to about 5 mm. In addition, it is to be understood that the melt-extruded multiparticulates can be any geometrical shape within this size range. Alternatively, the extrudate may simply be cut into desired lengths and divided into unit doses of the therapeutically active agent without the need of a spheronization step.

In one preferred embodiment, oral dosage forms are prepared that include an effective amount of melt-extruded multiparticulates within a capsule. For example, a plurality of the melt-extruded multiparticulates may be placed in a gelatin capsule in an amount sufficient to provide an effective controlled release dose when ingested and contacted by gastric fluid.

In another preferred embodiment, a suitable amount of the multiparticulate extrudate is compressed into an oral tablet using conventional tableting equipment using standard techniques. Techniques and compositions for making tablets (compressed and molded), capsules (hard and soft gelatin) and pills are also described in Remington's Pharmaceutical Sciences, $21^{st}$ ed., 2005 incorporated by reference herein.

In yet another preferred embodiment, the extrudate can be shaped into tablets as set forth in U.S. Pat. No. 4,957,681, hereby incorporated by reference.

Optionally, the controlled-release matrix multiparticulate systems or tablets can be coated, or the gelatin capsule can be further coated, with a controlled release coating such as the controlled release coatings described above. Such coatings preferably include a sufficient amount of hydrophobic and/or hydrophilic controlled-release material to obtain a weight gain level from about 2 to about 25 percent, although the overcoat may be greater depending upon, e.g., the physical properties of the drug and the desired release rate, among other things.

The dosage forms of the present invention may further include combinations of melt-extruded multiparticulates containing one or more drugs. Furthermore, the dosage forms can also include an amount of an immediate release therapeutically active agent for prompt therapeutic effect. The immediate release therapeutically active agent may be incorporated, e.g., as separate pellets within a gelatin capsule, or may be coated on the surface of, e.g., melt extruded multiparticulates. The unit dosage forms of the present invention may also contain a combination of, e.g., controlled release beads and matrix multiparticulates to achieve a desired effect.

The controlled-release formulations of the present invention preferably slowly release the therapeutically active agent, e.g., when ingested and exposed to gastric fluids, and then to intestinal fluids. The controlled-release profile of the melt-extruded formulations of the invention can be altered, for example, by varying the amount of controlled-release material, by varying the amount of plasticizer relative to other matrix constituents, hydrophobic material, by the inclusion of additional ingredients or excipients, by altering the method of manufacture, etc.

In other embodiments of the invention, melt-extruded formulations are prepared without the inclusion of the therapeutically active agent, which is added thereafter to the extrudate. Such formulations typically will have the therapeutically active agent blended together with the extruded matrix material, and then the mixture would be tableted in order to provide a slow release formulation. Such formulations may be advantageous, for example, when the therapeutically active agent included in the formulation is sensitive to temperatures needed for softening the hydrophobic material and/or the retardant material.

Typical melt-extrusion production systems suitable for use in accordance with the present invention include a suitable extruder drive motor having variable speed and constant torque control, start-stop controls, and ammeter. In addition, the production system will include a temperature control console which includes temperature sensors, cooling means and temperature indicators throughout the length of the extruder. In addition, the production system will include an extruder such as twin-screw extruder which consists of two counter-rotating intermeshing screws enclosed within a cylinder or barrel having an aperture or die at the exit thereof. The feed materials enter through a feed hopper and are moved through the barrel by the screws and are forced through the die into strands which are thereafter conveyed such as by a continuous movable belt to allow for cooling and being directed to a pelletizer or other suitable device to render the extruded ropes into the multiparticulate system. The pelletizer can consist of rollers, fixed knife, rotating cutter and the like. Suitable instruments and systems will be apparent to those of ordinary skill in the art.

A further aspect of the invention is related to the preparation of melt-extruded multiparticulates as set forth above in a manner which controls the amount of air included in the extruded product. By controlling the amount of air included in the extrudate, the release rate of the therapeutically active agent from the, e.g., multiparticulate extrudate, can be altered significantly. In certain embodiments, the pH dependency of the extruded product can be altered as well.

Thus, in a further aspect of the invention, the melt-extruded product is prepared in a manner which substantially excludes air during the extrusion phase of the process. This may be accomplished, for example, by using a Leistritz extruder having a vacuum attachment. In certain preferred embodiments the extruded multiparticulates prepared according to the invention using the Leistritz extruder under vacuum provides a melt-extruded product having different physical characteristics. In particular, the extrudate is substantially non-porous when magnified, e.g., using a scanning electron microscope which provides an SEM (scanning electron micrograph). Such substantially non-porous formulations provide a faster release of the therapeutically active agent, relative to the same formulation prepared without vacuum. SEMs of the multiparticulates prepared using an extruder under vacuum appear very smooth, and the multiparticulates tend to be more robust than those multiparticulates prepared without vacuum. In certain formulations, the use of extrusion under vacuum provides an extruded multiparticulate product which is more pH-dependent than its counterpart formulation prepared without vacuum. Alternatively, the melt-extruded product is prepared using a Werner-Pfleiderer twin screw extruder.

In certain embodiments, a spheronizing agent is added to a granulate or multiparticulates of the present invention and then spheronized to produce controlled release spheroids. The spheroids are then optionally overcoated with a controlled release coating by methods such as those described herein.

Spheronizing agents which may be used to prepare the multiparticulate formulations of the present invention include any art-known spheronizing agent. Cellulose derivatives are preferred, and microcrystalline cellulose is especially preferred. A suitable microcrystalline cellulose is, for example, the material sold as Avicel® PH 101. The spheronizing agent is preferably included as about 1 to about 99% of the multiparticulate by weight.

In addition to the active ingredient and spheronizing agent, the spheroids may also contain a binder. Suitable binders, such as low viscosity, water soluble polymers, will be well known to those skilled in the pharmaceutical art. However, water soluble hydroxy lower alkylcellulose, such as hydroxypropylcellulose, are preferred.

In addition to the butorphanol and spheronizing agent, the multiparticulate formulations of the present invention may include a controlled release material such as those described hereinabove. Preferred controlled-release materials for inclusion in the multiparticulate formulations include acrylic and methacrylic acid polymers or copolymers, and ethylcellulose. When present in the formulation, the controlled-release material will be included in amounts of from about 1 to about 80% of the multiparticulate, by weight. The controlled-release material is preferably included in the multiparticulate formulation in an amount effective to provide controlled release of the butorphanol from the multiparticulate.

Pharmaceutical processing aids such as binders, diluents, and the like may be included in the multiparticulate formulations. Amounts of these agents included in the formulations will vary with the desired effect to be exhibited by the formulation.

Specific examples of pharmaceutically acceptable carriers and excipients that may be used to formulate oral dosage forms of the present invention are described in the Handbook of Pharmaceutical Excipients, APhA Publications; 5 edition (Jan. 5, 2006) incorporated by reference herein.

The multiparticulates may be overcoated with a controlled-release coating including a controlled-release material such as those described hereinabove. The controlled-release coating is applied to a weight gain of from about 5 to about 30%. The amount of the controlled-release coating to be applied will vary according to a variety of factors, e.g., the composition of the multiparticulate and the chemical and/or physical properties of the drug.

Matrix multiparticulates may also be prepared by granulating the spheronizing agent together with the butorphanol, e.g. by wet granulation. The granulate is then spheronized to produce the matrix multiparticulates. The matrix multiparticulates are then optionally overcoated with the controlled release coating by methods such as those described hereinabove.

Another method for preparing matrix multiparticulates, for example, by (a) forming granules comprising at least one water soluble hydroxyalkyl cellulose and the butorphanol or the butorphanol salt; (b) mixing the hydroxyalkyl cellulose containing granules with at least one $C_{12}$-$C_{36}$ aliphatic alcohol; and (c) optionally, compressing and shaping the granules. Preferably, the granules are formed by wet granulating the hydroxyalkyl cellulose/butorphanol with water. In a particularly preferred embodiment of this process, the amount of water added during the wet granulation step is preferably between 1.5 and 5 times, especially between 1.75 and 3.5 times, the dry weight of the butorphanol.

In yet other alternative embodiments, a spheronizing agent, together with the active ingredient can be spheronized to form spheroids. Microcrystalline cellulose is preferred. A suitable microcrystalline cellulose is, for example, the material sold as Avicel® PH 101. In such embodiments, in addition to the active ingredient and spheronizing agent, the spheroids may also contain a binder. Suitable binders, such as low viscosity, water soluble polymers, will be well known to those skilled in the pharmaceutical art. However, water soluble hydroxy lower alkyl cellulose, such as hydroxy propyl cellulose, are preferred. Additionally (or alternatively) the spheroids may contain a water insoluble polymer, especially an acrylic polymer, an acrylic copolymer, such as a methacrylic acid-ethyl acrylate co-polymer, or ethyl cellulose. In such embodiments, the sustained-release coating will generally include a water insoluble material such as (a) a wax, either alone or in admixture with a fatty alcohol; or (b) shellac or zein.

Spheroids of the present invention comprise a matrix formulation as described above or bead formulation as described hereinafter having a diameter of between 0.1 mm and 2.5 mm, especially between 0.5 mm and 2 mm.

The spheroids are preferably film coated with a controlled release material that permits release of the butorphanol (or salt) at a controlled rate in an aqueous medium. The film coat is chosen so as to achieve, in combination with the other stated properties, the in-vitro release rate outlined above (e.g., at least about 12.5% released after 1 hour). The controlled-release coating formulations of the present invention preferably produce a strong, continuous film that is smooth and elegant, capable of supporting pigments and other coating additives, non-toxic, inert, and tack-free.

Preparation of Coated Bead Formulations

In certain preferred embodiments of the present invention the oral solid controlled release dosage form of the present invention comprises a plurality of coated substrates, e.g., inert pharmaceutical beads such as nu pariel 18/20 beads. An aqueous dispersion of hydrophobic material is used to coat the beads to provide for the controlled release of the butorphanol. In certain preferred embodiments a plurality of the resultant stabilized solid controlled-release beads may be placed in a gelatin capsule in an amount sufficient to provide an effective controlled-release dose when ingested and contacted by an environmental fluid, e.g., gastric fluid or dissolution media.

The stabilized controlled-release bead formulations of the present invention slowly release the butorphanol, e.g., when ingested and exposed to gastric fluids, and then to intestinal fluids. The controlled-release profile of the formulations of the invention can be altered, for example, by varying the amount of overcoating with the aqueous dispersion of hydrophobic controlled release material, altering the manner in which the plasticizer is added to the aqueous dispersion of hydrophobic controlled release material, by varying the amount of plasticizer relative to hydrophobic controlled release material, by the inclusion of additional ingredients or excipients, by altering the method of manufacture, etc. The dissolution profile of the ultimate product may also be modified, for example, by increasing or decreasing the thickness of the controlled release coating.

Substrates coated with a therapeutically active agent are prepared, e.g. by dissolving the therapeutically active agent in water and then spraying the solution onto a substrate, for example, nu pariel 18/20 beads, using a Wuster insert. Optionally, additional ingredients are also added prior to coating the beads in order to assist the binding of the butorphanol to the beads, and/or to color the solution, etc. For example, a product which includes hydroxypropyl methylcellulose, etc. with or without colorant (e.g., Opadry®) may be added to the solution and the solution mixed (e.g., for about 1 hour) prior to application of the same onto the substrate. The resultant coated substrate may then be optionally overcoated with a barrier agent, to separate the therapeutically active agent from the hydrophobic controlled-release coating.

An example of a suitable barrier agent is one which comprises hydroxypropyl methylcellulose. However, any film-former known in the art may be used. It is preferred that the barrier agent does not affect the dissolution rate of the final product.

The substrates may then be overcoated with an aqueous dispersion of the hydrophobic controlled release material as described herein. The aqueous dispersion of hydrophobic controlled release material preferably further includes an effective amount of plasticizer, e.g. triethyl citrate. Pre-formulated aqueous dispersions of ethylcellulose, such as Aquacoat® or Surelease®, may be used. If Surelease® is used, it is not necessary to separately add a plasticizer. Alternatively, pre-formulated aqueous dispersions of acrylic polymers such as Eudragit® can be used.

The coating solutions of the present invention preferably contain, in addition to the film-former, plasticizer, and solvent system (i.e., water), a colorant to provide elegance and product distinction. Color may be added to the solution of the therapeutically active agent instead, or in addition to the aqueous dispersion of hydrophobic material. For example, color can be added to Aquacoat® via the use of alcohol or propylene glycol based color dispersions, milled aluminum lakes and opacifiers such as titanium dioxide by adding color with shear to water soluble polymer solution and then using low shear to the plasticized Aquacoat®. Alternatively, any suitable method of providing color to dioxide and color pigments, such as iron oxide pigments. The incorporation of pigments, may, however, increase the retard effect of the coating.

The plasticized aqueous dispersion of hydrophobic controlled release material may be applied onto the substrate comprising the therapeutically active agent by spraying using any suitable spray equipment known in the art. In a preferred method, a Wurster fluidized-bed system is used in which an air jet, injected from underneath, fluidizes the core material and effects drying while the acrylic polymer coating is sprayed on. A sufficient amount of the aqueous dispersion of hydrophobic material to obtain a predetermined controlled-release of said therapeutically active agent when said coated substrate is exposed to aqueous solutions, e.g. gastric fluid, is preferably applied, taking into account the physical characteristics of the therapeutically active agent, the manner of incorporation of the plasticizer, etc. After coating with the hydrophobic controlled release material, a further overcoat of a film-former, such as Opadry®, is optionally applied to the beads. This overcoat is provided, if at all, in order to substantially reduce agglomeration of the beads.

Another method of producing controlled release bead formulations suitable for about 24-hour administration is via powder layering. The powder-layered beads are prepared by spraying an aqueous binder solution onto inert beads to provide a tacky surface, and subsequently spraying a powder that is a homogenous mixture of the butorphanol and hydrous lactose impalpable onto the tacky beads. The beads are then dried and coated with a hydrophobic material such as those described hereinabove to obtain the desired release of drug when the final formulation is exposed to environmental fluids. An appropriate amount of the controlled release beads are then, e.g. encapsulated to provide a final dosage form which provides effective plasma concentrations for the intended duration of effect or dosing frequency.

Controlled Release Osmotic Dosage

In another embodiment, the modified release formulations of the present invention are provided as osmotic pump dosage forms. In an osmotic pump dosage form, a core containing the butorphanol and optionally one or more osmotic excipients is typically encased by a selectively permeable membrane having at least one orifice. The selectively permeable membrane is generally permeable to water, but impermeable to the drug. When the system is exposed to GI fluids, water penetrates through the selectively permeable membrane into the core containing the drug and optional osmotic excipients. The osmotic pressure increases within the dosage form. Consequently, the drug is released through the orifice in an attempt to equalize the osmotic pressure across the selectively permeable membrane. In more complex pumps, the dosage form may contain two internal compartments in the core. The first compartment contains the drug and the second compartment may contain a polymer, which swells on contact with aqueous fluid. After ingestion, this polymer swells into the drug-containing compartment, diminishing the volume occupied by the drug, thereby delivering the drug from the device at a controlled rate over an extended period of time. Such dosage forms are often used when a zero order release profile is desired.

Osmotic pumps are well known in the art. The osmotic pumps useful in accordance with the present invention may be formed by compressing a tablet of an osmotically active drug, or an osmotically inactive drug in combination with an osmotically active agent, and then coating the tablet with a selectively permeable membrane which is permeable to an exterior aqueous-based fluid but impermeable to the drug and/or osmotic agent.

One or more delivery orifices may be drilled through the selectively permeable membrane wall. Alternatively, one or more orifices in the wall may be formed by incorporating leachable pore-forming materials in the wall. In operation, the exterior aqueous-based fluid is imbibed through the selectively permeable membrane wall and contacts the drug to form a solution or suspension of the drug. The drug solution or suspension is then pumped out through the orifice as fresh fluid is imbibed through the selectively permeable membrane.

Typical materials for the selectively permeable membrane include selectively permeable polymers known in the art to be useful in osmosis and reverse osmosis membranes, such as cellulose acylate, cellulose diacylate, cellulose triacylate, cellulose acetate, cellulose diacetate, cellulose triacetate, agar acetate, amylose triacetate, beta glucan acetate, acetaldehyde dimethyl acetate, cellulose acetate ethyl carbamate, polyamides, polyurethanes, sulfonated polystyrenes, cellulose acetate phthalate, cellulose acetate methyl carbamate, cellulose acetate succinate, cellulose acetate dimethyl aminoacetate, cellulose acetate ethyl carbamate, cellulose acetate chloroacetate, cellulose dipalmitate, cellulose dioctanoate, cellulose dicaprylate, cellulose dipentanlate, cellulose acetate valerate, cellulose acetate succinate, cellulose propionate succinate, methyl cellulose, cellulose acetate p-toluene sulfonate, cellulose acetate butyrate, lightly cross-linked polystyrene derivatives, cross-linked poly(sodium styrene sulfonate), poly(vinylbenzyltrimethyl ammonium chloride), cellulose acetate, cellulose diacetate, cellulose triacetate, and/or mixtures thereof.

The osmotic agents that can be used in the pump are typically soluble in the fluid that enters the device following administration, resulting in an osmotic pressure gradient across the selectively permeable wall against the exterior fluid. Suitable osmotic agents include, but are not limited to, magnesium sulfate, calcium sulfate, magnesium chloride, sodium chloride, lithium chloride, potassium sulfate, sodium carbonate, sodium sulfite, lithium sulfate, potassium chloride, sodium sulfate, d-mannitol, urea, sorbitol, inositol, raffinose, sucrose, glucose, hydrophilic polymers such as cellulose polymers, and/or mixtures thereof.

The osmotic pump dosage form may contain a second compartment containing a swellable polymer. Suitable swellable polymers typically interact with water and/or aqueous biological fluids, which causes them to swell or expand to an equilibrium state. Acceptable polymers exhibit the ability to swell in water and/or aqueous biological fluids, retaining a significant portion of such imbibed fluids within their polymeric structure, so as into increase the hydrostatic pressure within the dosage form. The polymers may swell or expand to a very high degree, usually exhibiting a 2- to 40-fold volume increase. The polymers can be non-cross-linked or cross-linked. In one embodiment, the swellable polymers are hydrophilic polymers. Suitable polymers include, but are not limited to, poly(hydroxy alkyl methacrylate) having a molecular weight of from 30,000 to 5,000,000; kappa-carrageenan; polyvinylpyrrolidone having a molecular weight of from 10,000 to 360,000; anionic and cationic hydrogels; polyelectrolyte complexes; poly(vinyl alcohol) having low amounts of acetate, cross-linked with glyoxal, formaldehyde, or glutaraldehyde, and having a degree of polymerization from 200 to 30,000; a mixture including methyl cellulose, cross-linked agar and carboxymethyl cellulose; a water-insoluble, water-swellable copolymer produced by forming a dispersion of finely divided maleic anhydride with styrene, ethylene, propylene, butylene or isobutylene; water-swellable polymers of N-vinyl lactams; and/or mixtures of any of the foregoing.

The term "orifice" as used herein comprises means and methods suitable for releasing the drug from the dosage form. The expression includes one or more apertures orifices that have been bored through the selectively permeable membrane by mechanical procedures. Alternatively, an orifice may be formed by incorporating an erodible element, such as a gelatin plug, in the selectively permeable membrane. In such cases, the pores of the selectively permeable membrane form a "passageway" for the passage of the drug. Such passageway formulations are described in the art.

The osmotic pumps useful in accordance with this invention may be manufactured by techniques known in the art. For example, the drug and other ingredients may be milled together and pressed into a solid having the desired dimensions (e.g., corresponding to the first compartment). The swellable polymer is then formed, placed in contact with the drug, and both are surrounded with the selectively permeable agent. If desired, the drug component and polymer component may be pressed together before applying the selectively permeable membrane. The selectively permeable membrane may be applied by any suitable method, for example, by molding, spraying, or dipping.

Controlled release dosage forms according to the present invention may also be prepared as osmotic dosage formulations. The osmotic dosage forms preferably include a bilayer core comprising a drug layer and a delivery or push layer, wherein the bilayer core is surrounded by a semipermeable wall and optionally having at least one passageway disposed therein. In certain embodiments, the bilayer core comprises a drug layer with the butorphanol or a salt thereof and a displacement or push layer. In certain preferred embodiments the drug layer may also comprise at least one polymer hydrogel. The polymer hydrogel may have an average molecular weight of between about 500 and about 6,000,000. Examples of polymer hydrogels include but are not limited to a maltodextrin polymer comprising the formula $(C_6H_{12}O_5)_n \cdot H2O$, wherein n is 3 to 7,500, and the maltodextrin polymer comprises a 500 to 1,250,000 number-average molecular weight; a poly(alkylene oxide) represented by, e.g., a poly(ethylene oxide) and a poly(propylene oxide) having a 50,000 to 750,000 weight-average molecular weight, and more specifically represented by a poly (ethylene oxide) of at least one of 100,000, 200,000, 300,000 or 400,000 weight-average molecular weights; an alkali carboxyalkylcellulose, wherein the alkali is sodium or potassium, the alkyl is methyl, ethyl, propyl, or butyl of 10,000 to 175,000 weight-average molecular weight; and a copolymer of ethylene-acrylic acid, including methacrylic and ethacrylic acid of 10,000 to 500,000 number-average molecular weight.

In certain preferred embodiments of the present invention, the delivery or push layer comprises an osmopolymer. Examples of an osmopolymer include but are not limited to a member selected from the group consisting of a polyalkylene oxide and a carboxyalkylcellulose. The polyalkylene oxide possesses a 1,000,000 to 10,000,000 weight-average molecular weight. The polyalkylene oxide may be a member selected from the group consisting of polymethylene oxide, polyethylene oxide, polypropylene oxide, polyethylene oxide having a 1,000,000 average molecular weight, polyethylene oxide comprising a 5,000,000 average molecular weight, polyethylene oxide comprising a 7,000,000 average molecular weight, cross-linked polymethylene oxide possessing a 1,000,000 average molecular weight, and polypropylene oxide of 1,200,000 average molecular weight. Typical osmopolymer carboxyalkylcellulose comprises a member selected from the group consisting of alkali carboxyalkylcellulose, sodium car boxymethylcellulose, potassium carboxymethylcellulose, sodium carboxyethylcellulose, lithium carboxymethylcellulose, sodium carboxyethylcellulose, carboxyalkylhydroxyalkylcellulose, carboxymethylhydroxyethyl cellulose, carboxyethylhydroxyethylcellulose and carboxymethylhydroxypropylcellulose. The osmopolymers used for the displacement layer exhibit an osmotic pressure gradient across the semipermeable wall. The osmopolymers imbibe fluid into dosage form, thereby swelling and expanding as an osmotic hydrogel (also known as osmogel), whereby they push the butorphanol or pharmaceutically acceptable salt thereof from the osmotic dosage form.

The push layer may also include one or more osmotically effective compounds also known as osmagents and as osmotically effective solutes. They imbibe an environmental fluid, for example, from the gastrointestinal tract, into dosage form and contribute to the delivery kinetics of the displacement layer. Examples of osmotically active compounds comprise a member selected from the group consisting of osmotic salts and osmotic carbohydrates. Examples of specific osmagents include but are not limited to sodium chloride, potassium chloride, magnesium sulfate, lithium phosphate, lithium chloride, sodium phosphate, potassium sulfate, sodium sulfate, potassium phosphate, glucose, fructose and maltose.

The push layer may optionally include a hydroxypropylalkylcellulose represented by a member selected from the group consisting of hydroxypropylmethylcellulose, hydroxypropylethylcellulose, hydroxypropyl isopropylcellulose, hydroxypropylbutylcellulose, and hydroxypropyl pentylcellulose.

The push layer optionally may comprise a nontoxic colorant or dye. Examples of colorants or dyes include but are not limited to Food and Drug Administration Colorant (FD&C), such as FD&C No. 1 blue dye, FD&C No. 4 red dye, red ferric oxide, yellow ferric oxide, titanium dioxide, carbon black, and indigo.

The push layer which is devoid of butorphanol may also optionally comprise an antioxidant to inhibit the oxidation of the excipients of the push layer. Some examples of antioxidants include but are not limited to a member selected from the group consisting of ascorbic acid, ascorbyl palmitate, butylated hydroxyanisole, a mixture of 2 and 3 tertiary-butyl-4-hydroxyanisole, butylated hydroxytoluene, sodium isoascorbate, dihydroguaretic acid, potassium sorbate, sodium bisulfate, sodium metabisulfate, sorbic acid, potassium ascorbate, vitamin E, 4-chloro-2,6-ditertiarybutylphenol, alphatocopherol, and propylgallate.

In certain alternative embodiments, the dosage form comprises an homogenous core comprising the butorphanol or a pharmaceutically acceptable salt thereof, a pharmaceutically acceptable polymer (e.g., polyethylene oxide), optionally a disintegrant (e.g., polyvinylpyrrolidone), optionally an absorption enhancer (e.g., a fatty acid, a surfactant, a chelating agent, a bile salt, etc.). The homogenous core is surrounded by a semipermeable wall having a passageway (as defined above) for the release of the butorphanol or pharmaceutically acceptable salt thereof.

In certain embodiments, the semipermeable wall comprises a member selected from the group consisting of a cellulose ester polymer, a cellulose ether polymer and a cellulose ester-ether polymer. Representative wall polymers comprise a member selected from the group consisting of cellulose acylate, cellulose diacylate, cellulose triacylate, cellulose acetate, cellulose diacetate, cellulose triacetate, mono-, di- and tricellulose alkenylates, and mono-, di- and tricellulose alkenylates. The poly(cellulose) used for the present invention comprises a number-average molecular weight of 20,000 to 7,500,000.

Additional semipermeable polymers for the purpose of this invention comprise acetaldehyde dimethycellulose acetate, cellulose acetate ethylcarbamate, cellulose acetate methylcarbamate, cellulose diacetate, propylcarbamate, cellulose acetate diethylaminoacetate; semipermeable polyamide; semipermeable polyurethane; semipermeable sulfonated polystyrene; semipermeable cross-linked polymer formed by the coprecipitation of a polyanion and a polycation as disclosed in U.S. Pat. Nos. 3,173,876; 3,276,586; 3,541,005; 3,541,006 and 3,546,876; semipermeable polymers as disclosed by Loeb and Sourirajan in U.S. Pat. No. 3,133,132; semipermeable crosslinked polystyrenes; semipermeable cross-linked poly(sodium styrene sulfonate); semipermeable crosslinked poly(vinylbenzyltrimethyl ammonium chloride); and semipermeable polymers possessing a fluid permeability of $2.5 \times 10^{-8}$ to $2.5 \times 10^{-2}$ (cm$^2$/hr·atm) expressed per atmosphere of hydrostatic or osmotic pressure difference across the semipermeable wall. Other polymers useful in the present invention are known in the art in U.S. Pat. Nos. 3,845,770; 3,916,899 and 4,160,020; and in Handbook of Common Polymers, Scott, J. R. and W. J. Roff, 1971, CRC Press, Cleveland, Ohio.

In certain embodiments, preferably the semipermeable wall is nontoxic, inert, and it maintains its physical and chemical integrity during the dispensing life of the drug. In certain embodiments, the dosage form comprises a binder as described above.

In certain embodiments, the dosage form comprises a lubricant, which may be used during the manufacture of the dosage form to prevent sticking to die wall or punch faces. Examples of lubricants include but are not limited to magnesium stearate, sodium stearate, stearic acid, calcium stearate, magnesium oleate, oleic acid, potassium oleate, caprylic acid, sodium stearyl fumarate, and magnesium palmitate.

Coatings

The dosage forms of the present invention may optionally be coated with one or more coatings suitable for the regulation of release or for the protection of the formulation. In one embodiment, coatings are provided to permit either pH-dependent or pH-independent release, e.g., when exposed to gastrointestinal fluid. When a pH-independent coating is desired, the coating is designed to achieve optimal release regardless of pH-changes in the environmental fluid, e.g., the GI tract. Other preferred embodiments include a pH-dependent coating that releases the butorphanol in desired areas of the gastrointestinal (GI) tract, e.g., the stomach or small intestine, such that an absorption profile is provided which is capable of providing at least about twelve hour and preferably up to twenty-four hour analgesia to a patient. It is also possible to formulate compositions which release a portion of the dose in one desired area of the GI tract, e.g., the stomach, and release the remainder of the dose in another area of the GI tract, e.g., the small intestine.

Formulations according to the invention that utilize pH-dependent coatings may also impart a repeat-action effect whereby unprotected drug is coated over an enteric coat and is released in the stomach, while the remainder, being protected by the enteric coating, is released further down the gastrointestinal tract. Coatings which are pH-dependent may be used in accordance with the present invention include a controlled release material such as, e.g., shellac, cellulose acetate phthalate (CAP), polyvinyl acetate phthalate (PVAP), hydroxypropyl methylcellulose phthalate, and methacrylic acid ester copolymers, zein, and the like.

In another preferred embodiment, the present invention is related to a stabilized solid controlled dosage form comprising the butorphanol coated with a hydrophobic controlled release material selected from (i) an alkylcellulose; (ii) an acrylic polymer; or (iii) mixtures thereof. The coating may be applied in the form of an organic or aqueous solution or dispersion.

In certain preferred embodiments, the controlled release coating is derived from an aqueous dispersion of the hydrophobic controlled release material. The coated substrate containing the butorphanol (e.g., a tablet core or inert pharmaceutical beads or spheroids) is then cured until an endpoint is reached at which the substrate provides a stable dissolution. The curing endpoint may be determined by comparing the dissolution profile (curve) of the dosage form immediately after curing to the dissolution profile (curve) of the dosage form after exposure to accelerated storage conditions of, e.g., at least one month at a temperature of 40° C. and a relative humidity of 75%.

In preferred embodiments, the controlled release coatings include a plasticizer such as those described herein.

In certain embodiments, it is necessary to overcoat the substrate comprising the butorphanol with a sufficient amount of the aqueous dispersion of e.g., alkylcellulose or acrylic polymer, to obtain a weight gain level from about 2 to about 50%, e.g., about 2 to about 25% in order to obtain a controlled-release formulation. The overcoat may be lesser or greater depending upon the physical properties of the therapeutically active agent and the desired release rate, the inclusion of plasticizer in the aqueous dispersion and the manner of incorporation of the same, for example.

Alkylcellulose Polymers

Cellulosic materials and polymers, including alkylcelluloses are controlled release materials well suited for coating the substrates, e.g., beads, tablets, etc. according to the invention. Simply by way of example, one preferred alkylcellulose polymer is ethylcellulose, although the artisan will appreciate that other cellulose and/or alkylcellulose polymers may be readily employed, singly or on any combination, as all or part of a hydrophobic coating according to the invention.

One commercially-available aqueous dispersion of ethylcellulose is Aquacoat®. Aquacoat® is prepared by dissolving the ethylcellulose in a water-immiscible organic solvent and then emulsifying the same in water in the presence of a surfactant and a stabilizer. After homogenization to generate submicron droplets, the organic solvent is evaporated under vacuum to form a pseudolatex. The plasticizer is not incorporated in the pseudolatex during the manufacturing phase. Thus, prior to using the same as a coating, it is necessary to intimately mix the Aquacoat® with a suitable plasticizer prior to use.

Another aqueous dispersion of ethylcellulose is commercially available as Surelease®. This product is prepared by incorporating plasticizer into the dispersion during the manufacturing process. A hot melt of a polymer, plasticizer (dibutyl sebacate), and stabilizer (oleic acid) is prepared as a homogeneous mixture, which is then diluted with an alkaline solution to obtain an aqueous dispersion which can be applied directly onto substrates.

Acrylic Polymers

In other preferred embodiments of the present invention, the controlled release material comprising the controlled-release coating is a pharmaceutically acceptable acrylic polymer, including but not limited to acrylic acid and methacrylic acid copolymers, methyl methacrylate copolymers, ethoxyethyl methacrylates, cynaoethyl methacrylate, poly(acrylic acid), poly(methacrylic acid), methacrylic acid alkylamide copolymer, poly(methyl methacrylate), polymethacrylate, poly(methyl methacrylate) copolymer, polyacrylamide, aminoalkyl methacrylate copolymer, poly(methacrylic acid anhydride), and glycidyl methacrylate copolymers.

In certain preferred embodiments, the acrylic polymer is comprised of one or more ammonio methacrylate copolymers Ammonio methacrylate copolymers are well known in the art, and are described in NF XVII as fully polymerized copolymers of acrylic and methacrylic acid esters with a low content of quaternary ammonium groups.

In order to obtain a desirable dissolution profile, it may be necessary to incorporate two or more ammonio methacrylate copolymers having differing physical properties, such as different molar ratios of the quaternary ammonium groups to the neutral (meth)acrylic esters.

Certain methacrylic acid ester-type polymers are useful for preparing pH-dependent coatings which may be used in accordance with the present invention. For example, there are a family of copolymers synthesized from diethylaminoethyl methacrylate and other neutral methacrylic esters, also known as methacrylic acid copolymer or polymeric methacrylates, commercially available as Eudragit®. There are several different types of Eudragit®. For example, Eudragit® E is an example of a methacrylic acid copolymer which swells and dissolves in acidic media. Eudragit® L is a methacrylic acid copolymer which does not swell at about pH<5.7 and is soluble at about pH>6. Eudragit® S does not swell at about pH<6.5 and is soluble at about pH>7. Eudragit® RL and Eudragit® RS are water swellable, and the amount of water absorbed by these polymers is pH-dependent, however, dosage forms coated with Eudragit® RL and RS are pH-independent.

In certain preferred embodiments, the acrylic coating comprises a mixture of two acrylic resin lacquers commercially available as Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. The code designations RL (high permeability) and RS (low permeability) refer to the permeability properties of these agents. Eudragit® RL/RS mixtures are insoluble in water and in digestive fluids. However, coatings formed from the same are swellable and permeable in aqueous solutions and digestive fluids.

The Eudragit® RL/RS dispersions of the present invention may be mixed together in any desired ratio in order to ultimately obtain a controlled-release formulation having a desirable dissolution profile. Desirable controlled-release formulations may be obtained, for instance, from a retardant coating derived from 100% Eudragit® RL, 50% Eudragit® RL and 50% Eudragit® RS, and 10% Eudragit® RL:Eudragit® 90% RS. Of course, one skilled in the art will recognize that other acrylic polymers may also be used, such as, for example, Eudragit® L.

Plasticizers

In embodiments of the present invention where the coating comprises an aqueous dispersion of a hydrophobic controlled release material, the inclusion of an effective amount of a plasticizer in the aqueous dispersion of hydrophobic material will further improve the physical properties of the controlled-release coating. For example, because ethylcellulose has a relatively high glass transition temperature and does not form flexible films under normal coating conditions, it is preferable to incorporate a plasticizer into an ethylcellulose coating containing controlled-release coating before using the same as a coating material. Generally, the amount of plasticizer included in a coating solution is based on the concentration of the film-former, e.g., most often from about 1 to about 50 percent by weight of the film-former. Concentration of the plasticizer, however, can only be properly determined after careful experimentation with the particular coating solution and method of application.

Examples of suitable plasticizers for ethylcellulose include water insoluble plasticizers such as dibutyl sebacate, diethyl phthalate, triethyl citrate, tibutyl citrate, and triacetin, although it is possible that other water-insoluble plasticizers (such as acetylated monoglycerides, phthalate esters, castor oil, etc.) may be used. Triethyl citrate is an especially preferred plasticizer for the aqueous dispersions of ethyl cellulose of the present invention.

Examples of suitable plasticizers for the acrylic polymers of the present invention include, but are not limited to citric acid esters such as triethyl citrate NF XVI, tributyl citrate, dibutyl phthalate, and possibly 1,2-propylene glycol. Other plasticizers which have proved to be suitable for enhancing the elasticity of the films formed from acrylic films such as Eudragit® RL/RS lacquer solutions include polyethylene glycols, propylene glycol, diethyl phthalate, castor oil, and triacetin. Triethyl citrate is an especially preferred plasticizer for the aqueous dispersions of ethyl cellulose of the present invention.

In certain embodiments, the addition of a small amount of talc to the controlled release coating reduces the tendency of the aqueous dispersion to stick during processing, and acts as a polishing agent.

The release of the therapeutically active agent from the controlled-release formulation of the present invention can be further influenced, i.e., adjusted to a desired rate, by the addition of one or more release-modifying agents, or by providing one or more passageways through the coating. The ratio of hydrophobic controlled release material to water soluble material is determined by, among other factors, the release rate required and the solubility characteristics of the materials selected.

The release-modifying agents which function as pore-formers may be organic or inorganic, and include materials that can be dissolved, extracted or leached from the coating in the environment of use. The pore-formers may comprise one or more hydrophilic materials such as hydroxypropylmethylcellulose.

The controlled-release coatings of the present invention can also include erosion-promoting agents such as starch and gums.

The controlled-release coatings of the present invention can also include materials useful for making microporous lamina in the environment of use, such as polycarbonates comprised of linear polyesters of carbonic acid in which carbonate groups reoccur in the polymer chain.

The release-modifying agent may also comprise a semi-permeable polymer. In certain preferred embodiments, the release-modifying agent is selected from hydroxypropylmethylcellulose, lactose, metal stearates, and mixtures of any of the foregoing.

The controlled-release coatings of the present invention may also include an exit means comprising at least one passageway, orifice, or the like. The passageway may be formed by such methods as those disclosed in U.S. Pat. Nos. 3,845,770; 3,916,889; 4,063,064; and 4,088,864, all of which are hereby incorporated by reference. The passageway can have any shape such as round, triangular, square, elliptical, irregular, etc.

These and other embodiments of the present invention will readily occur to those of ordinary skill in the art in view of the disclosure herein.

A wide variety of materials can be used for preparing the dosage form according to this invention. This invention therefore contemplates the use of materials other than those specifically disclosed herein, including those which may hereafter become known to the art to be capable of performing the necessary functions.

DETAILED DESCRIPTION OF THE PREFERRED EMBODIMENTS

The following examples illustrate various aspects of the present invention. They are not to be construed to limit the claims in any manner whatsoever. A wide variety of methods known in the art for the preparation of oral immediate release and oral controlled release dosage forms may be incorporated into the invention. Other suitable dosage forms may also be prepared by modification of the examples herein and by use of material other than those specifically disclosed herein, including those which may hereafter become known to the art to be capable of performing the necessary functions. Other suitable modifications and adaptations of the variety of conditions and parameters normally encountered and obvious to those skilled in the art are within the spirit and scope of the invention.

The percent loading of the butorphanol onto the dosage form may be varied depending on the physiochemical and pharmaceutical properties of immediate release and controlled release material, excipients, the selected salt of butorphanol and the desired release profile and duration of actions.

The ingredients used for the preparation of the butorphanol dosage form agent may be modified depending on the selection, dose and desired duration of effect. In some embodiments, a change in the dose or amount butorphanol will not require a significant change in amount of other ingredients. In other embodiments, a proportional change in the amount of other ingredients is required to maintain the desired properties. In yet other embodiments, a change in the dose or amount butorphanol necessitates a change in the nature and/or amount of ingredients to provide the required characteristics of the butorphanol (e.g., duration of effect, rate and extent of absorption, therapeutic concentrations and effect, etc.).

A wide variety of formulations of modified release butorphanol have been prepared and evaluated by the applicant.

EXAMPLES

Example 1

Tablet Composition of Extended Release Butorphanol Tartrate

| Ingredients | Qty./Unit |
| --- | --- |
| 1. Butorphanol Tartrate | 20 mg |
| 2. HPMC 2208, USP | 150 mg |
| 3. Carnauba wax | 30 mg |
| 4. HPMC 2910, USP | 15 mg |
| 5. Magnesium Stearate | 2 mg |
| 6. Stearic acid | 8 mg |
| 7. Talc | 3 mg |

Place the ingredients 1, 2 and 3 in the granulator and mix for 15 minutes. Dissolve ingredient 4 in water (mix in hot water, then cool down) and spray into the fluidized mixture. Dry to approximately 5% moisture. Sequentially add ingredient 5, 6 and 7, with mixing steps between each addition. Compress using capsule shaped tooling.

Example 2

Tablet Composition of Extended Release Butorphanol Tartrate

| Ingredients | Qty./Unit |
| --- | --- |
| 1. Butorphanol Tartrate | 100 mg |
| 2. HPMC 2208, USP | 250 mg |
| 3. Carnauba wax | 50 mg |
| 4. HPMC 2910, USP | 25 mg |
| 5. Magnesium Stearate | 4 mg |
| 6. Stearic acid | 14 mg |
| 7. Talc | 5 mg |

Place the ingredients 1, 2 and 3 in the granulator and mix for 15 minutes. Dissolve ingredient 4 in water (mix in hot water, then cool down) and spray into the fluidized mixture. Dry to approximately 5% moisture. Sequentially add ingredient 5, 6 and 7, with mixing steps between each addition. Compress using capsule shaped tooling.

Example 3

Tablet Composition of Extended Release Butorphanol Tartrate

| Ingredients | Qty./Unit |
| --- | --- |
| 1. Butorphanol Tartrate | 500 mg |
| 2. HPMC 2208, USP | 250 mg |
| 3. Carnauba wax | 50 mg |
| 4. HPMC 2910, USP | 25 mg |
| 5. Magnesium Stearate | 4 mg |
| 6. Stearic acid | 14 mg |
| 7. Talc | 5 mg |

Place the ingredients 1, 2 and 3 in the granulator and mix for 15 minutes. Dissolve ingredient 4 in water (mix in hot water, then cool down) and spray into the fluidized mixture. Dry to approximately 5% moisture. Sequentially add ingredient 5, 6 and 7, with mixing steps between each addition. Compress using capsule shaped tooling.

Example 4

Tablet Composition of Extended Release Butorphanol Base

| Ingredients | Amt/Unit (mg) |
| --- | --- |
| Butorphanol Base | 20 |
| Spray Dried Lactose | 60 |
| Povidone | 5 |
| Eudragit RS30D (solids) | 10 |
| Triacetin | 2 |
| Stearyl Alcohol | 25 |
| Talc | 2.5 |
| Magnesium Stearate | 1.25 |
| Opadry Pink Y-S-14518A | 4.0 |

1. Granulation: Spray the Eudragit/Triacetin dispersion onto the Butorphanol, Spray Dried Lactose and Povidone using a fluid bed granulator. 2. Milling: Discharge the granulation and pass through a mill. 3. Waxing: Melt the stearyl alcohol and add to the milled granulation using a mixer. Allow to cool. 4. Milling: Pass the cooled granulation through a mill. 5. Lubrication: Lubricate the granulation with talc and magnesium stearate using a mixer. 6. Compression: Compress the granulation into tablets using a tablet press. 7. Film coating: Apply an aqueous film coat to the tablets.

Example 5

Tablet Composition of Extended Release Butorphanol Tartrate

| Ingredients | Amt/Unit (mg) |
| --- | --- |
| Butorphanol Tartrate | 30 |
| Spray Dried Lactose | 60 |
| Povidone | 5 |
| Eudragit RS30D (solids) | 10 |
| Triacetin | 2 |
| Stearyl Alcohol | 25 |
| Talc | 2.5 |
| Magnesium Stearate | 1.25 |
| Opadry Pink Y-S-14518A | 4.0 |

1. Granulation: Spray the Eudragit/Triacetin dispersion onto the Butorphanol, Spray Dried Lactose and Povidone using a fluid bed granulator. 2. Milling: Discharge the granulation and pass through a mill. 3. Waxing: Melt the stearyl alcohol and add to the milled granulation using a mixer. Allow to cool. 4. Milling: Pass the cooled granulation through a mill. 5. Lubrication: Lubricate the granulation with talc and magnesium stearate using a mixer. 6. Compression: Compress the granulation into tablets using a tablet press. 7. Film coating: Apply an aqueous film coat to the tablets.

Example 6

Capsule Composition of Extended Release Butorphanol Base

| Ingredients | Amt/Unit (mg) |
| --- | --- |
| Butorphanol Base | 20 |
| Eudragit RSPO | 76 |
| Eudragit RLPO | 4 |
| Stearyl Alcohol | 25 |

1. Blend milled Stearyl Alcohol, Eudragit RLPO, Butorphanol, and Eudragit RSPO using a Hobart Mixer. 2. Extrude the granulation using a Powder Feeder, Melt Extruder (equipped with the 6×1 mm die head), Conveyor, Lasermike, and Pelletizer. Powder feed rate—40 g/min; vacuum—about 980 mBar; Conveyor, such that diameter of extrudate is 1 mm, Pelletizer, such that pellets are cut to 1 mm in length. Screen pellets using #16 mesh and #20 mesh screens. Collect material that passes through the #16 mesh screen and is retained on the #20 mesh screen. 4. Fill capsules with the pellets.

Example 7

Capsule Composition of Extended Release Butorphanol Base

| Ingredients | Amt/Unit (mg) |
| --- | --- |
| Butorphanol Base | 200 |
| Eudragit RSPO | 150 |
| Eudragit RLPO | 10 |
| Stearyl Alcohol | 40 |

1. Blend milled Stearyl Alcohol, Eudragit RLPO, Butorphanol, and Eudragit RSPO using a Hobart Mixer. 2. Extrude the granulation using a Powder Feeder, Melt Extruder (equipped with the 6×1 mm die head), Conveyor, Lasermike, and Pelletizer. Powder feed rate—40 g/min; vacuum—about 980 mBar; Conveyor, such that diameter of extrudate is 1 mm, Pelletizer, such that pellets are cut to 1 mm in length. Screen pellets using #16 mesh and #20 mesh screens. Collect material that passes through the #16 mesh screen and is retained on the #20 mesh screen. 4. Fill capsules with the pellets.

Example 8

Capsule Composition of Extended Release Butorphanol Base

| Ingredients | Amt/Unit (mg) |
| --- | --- |
| Butorphanol Base | 15 |
| Eudragit RSPO | 77 |
| Ethocel | 4.5 |
| Stearic acid | 27 |

Blend milled Stearic acid, Ethocel, Butorphanol Base, and Eudragit RSPO using a V-blender. 2. Extrude the mixture using a Powder Feeder, Melt Extruder (equipped with the 6×1 mm die head), Conveyor, Lasermike, and Pelletizer. Powder feed rate, 1.2 kg/hr; vacuum, about 980 mBar; Conveyor, such that diameter of extrudate is 1 mm; Pelletizer, such that pellets are cut to 1 mm in length. 3. Screen pellets using #16 mesh and #20 mesh screens. Collect material that passes through the #16 mesh screen and is retained on the #20 mesh screen. Fill pellets in capsules.

Example 9

Capsule Composition of Extended Release Butorphanol Tartrate

| Steps | Ingredients | Amt/unit (mg) |
| --- | --- | --- |
| 1 | Butorphanol Tartrate | 12 |
|   | Non-pareil beads (30/35 mesh) | 45 |
|   | Opadry Clear | 2.5 |
| 2 | Eudragit RS3-D (dry) | 7.2 |
|   | Eudragit RL30D (dry) | 0.4 |
|   | Triethyl citrate | 1.5 |
|   | Cabosil | 0.4 |
| 3 | Opadry Clear (HPMC) | 1.9 |
|   | Cabosil | 0.28 |

1. Dissolve Butorphanol Tartrate and Opadry (HPMC) in water. Spray the drug solution onto nonpareil beads in a fluid bed coater with Wurster insert. 2. Disperse Eudragit RS, Eudragit RL, triethyl citrate, and Cabosil in water. Spray the dispersion onto the beads in the fluid bed coater. 3. Dissolve Opadry in water. Spray the solution onto the beads in the fluid bed coater. 4. Cure the beads at 60° C. for 24 hours.

Example 10

Tablet Composition of Extended Release Butorphanol Tartrate

| Ingredient | Amt/unit (mg) |
| --- | --- |
| Butorphanol Tartrate | 75 |
| Anhydrous Dicalcium Phosphate (Powdered) | 60 |
|  | 80 |
| Microcrystalline Cellulose | 80 |
| Glyceryl Behenate | 40 |
| Magnesium Stearate | 4 |
| Opadry Red | 17 |
| Purified Water | 900* |

*Remains in product as residual moisture only.

1. Pass the Stearyl Alcohol flakes through an oscillating mill. 2. Mix the Butorphanol Tartrate, milled Stearyl Alcohol, Anhydrous Dicalcium Phosphate, Microcrystalline Cellulose, and Glyceryl Behenate in a twin shell blender. 3.

Continuously feed the blended material into a twin screw extruder and collect the resultant heated material on a conveyor. 4. Allow the extrudate to cool on the conveyor. 5. Mill the cooled extrudate using an oscillating mill 6 Blend the milled extrudate and Magnesium Stearate. 7. Compress the resultant granulation using a tablet press, preferably into a caplet. 8. Prepare a film coating solution by dispersing the Opadry in Purified Water and applying it to the tablet.

Example 11

Capsule Composition of Extended Release Butorphanol Tartrate

| Ingredient | Amt/unit (mg) |
|---|---|
| Butorphanol Tartrate | 20 |
| Eudragit RSPO | 76.5 |
| Ethylcellulose | 4.5 |
| Stearyl Alcohol | 27 |

1. Pass Stearyl Alcohol flakes through an impact mill. 2. Mix the Butorphanol Tartrate, Eudragit, Ethylcellulose and milled Stearyl Alcohol in a twin shell blender. 3. Continuously feed the blended material into a twin screw extruder and collect the resultant strands on a conveyor. 4. Allow the strands to cool on the conveyor. 5. Cut the cooled strands into pellets using a Pelletizer. 6. Screen the pellets and collect desired sieve portion. 7. Fill the extruded pellets into capsules.

Example 12 to 23 may be prepared as follows: (i) Dispense the specified hydrophobic controlled release material (e.g., hydrogenated Type I vegetable oil, hydrogenated Type II vegetable oil, polyoxyethylene stearates, polyoxyethylene distearates, glycerol monostearate, poorly water soluble, or high melting point waxes) into a mixer; (ii) Heat until fully melted; (iii) dispense the hydroxypropyl methyl cellulose (HPMC) into the mixer; (iv) Mix until dispersed; (v) Dispense the Aerosil into the same vessel; (vi) Mix until dispersed; (vii) Dispense the butorphanol into the same vessel; (viii) Stir thoroughly with a high shear mixer; (ix) Transfer the mix into a liquid filling machine; (x) Fill into hard gelatin (or HPMC) capsule; (xi) Optionally, transfer the capsules to a banding machine and band the capsules.

Example 12

Capsule Composition of Extended Release Butorphanol Tartrate

| Ingredients | Quantity (mg)/Dose |
|---|---|
| Sterotex ® NF | 200 |
| Fractionated coconut oil | 70 |
| Methocel ® K 15M | 81 |
| Aerosil ® COK 84 | 4 |
| Butorphanol Tartrate | 50 |

Example 13

Capsule Composition of Extended Release Butorphanol Tartrate

| Ingredients | Quantity (mg)/Dose |
|---|---|
| Beeswax | 200 |
| HPMC, K15M | 80 |
| Aerosil COK 84 | 8 |
| Butorphanol Tartrate | 40 |

Example 14

Capsule Composition of Extended Release Butorphanol Base

| Ingredients | Quantity (mg)/Dose |
|---|---|
| Sterotex NF | 150 |
| HPMC, K15M | 75 |
| Coconut oil | 75 |
| Aerosil COK 84 | 5 |
| Butorphanol | 100 |

Example 15

Capsule Composition of Extended Release Butorphanol Base

| Ingredients | Quantity (mg)/Dose |
|---|---|
| Cithrol GMS | 275 |
| HPMC, K100M | 40 |
| Aerosil COK 84 | 10 |
| Butorphanol | 75 |

Example 16

Capsule Composition of Extended Release Butorphanol Tartrate

| Ingredients | Quantity (mg)/Dose |
|---|---|
| Hydrokote 112 | 250 |
| HPMC, K15M | 60 |
| Aerosil COK 84 | 10 |
| Butorphanol Tartrate | 150 |

Example 17

Capsule Composition of Extended Release Butorphanol Base

| Ingredients | Quantity (mg)/Dose |
|---|---|
| Beeswax | 200 |
| HPMC, Pharmacoat 606 | 62.5 |
| Aerosil COK 84 | 7.5 |
| Butorphanol Base | 200 |

Example 18

Capsule Composition of Extended Release Butorphanol Base

| Ingredients | Quantity (mg)/Dose |
|---|---|
| Gelucire 50/02 | 190 |
| Methocel K 100M | 35 |
| Aerosil COK 84 | 10 |
| Butorphanol Base | 250 |

Example 19

Capsule Composition of Extended Release Butorphanol Base

| Ingredients | Quantity (mg)/Dose |
|---|---|
| Cetyl alcohol | 280 |
| Methocel K 100M | 50 |
| Aerosil COK 84 | 10 |
| Butorphanol Base | 100 |

Example 20

Capsule Composition of Extended Release Butorphanol

| Ingredients | Quantity (mg)/Dose |
|---|---|
| Sterotex NF | 320 |
| Methocel K 15M | 60 |
| Aerosil COK 84 | 10 |
| Butorphanol Tartrate | 300 |

Example 21

Capsule Composition of Extended Release Butorphanol Tartrate

| Ingredients | Quantity (mg)/Dose |
|---|---|
| Cithrol GMS | 320 |
| Methocel K 100M | 55 |
| Aerosil COK 84 | 15 |
| Butorphanol Tartrate | 150 |

Example 22

Capsule Composition of Extended Release Butorphanol Tartrate

| Ingredients | Quantity (mg)/Dose |
|---|---|
| Sterotex ® NF | 100 |
| Fractionated coconut oil | 70 |
| Beeswax | 100 |
| Methocel ® K 15M | 81 |
| Aerosil ® COK 84 | 4 |
| Butorphanol Tartrate | 200 |

Example 23

Capsule Composition of Extended Release Butorphanol Tartrate

| Ingredients | Quantity (mg)/Dose |
|---|---|
| Glyceryl behenate | 135 |
| Fractionated coconut oil | 50 |
| Methocel ® K 15M | 60 |
| Aerosil ® COK 84 | 3 |
| Butorphanol Tartrate | 50 |

Example 24

Tablet Composition of Extended Release Butorphanol Tartrate

| Ingredients | Quantity (mg)/Dose |
|---|---|
| Lactose (spray dried) | 230 |
| Eudragit ® RS PM | 60 |
| Purified water | q.s.* |
| Stearyl Alcohol | 90 |
| Talc | 8 |
| Magnesium Stearate | 4 |
| Butorphanol Tartrate | 300 |

*Remains in product as residual moisture only.

In Example 24, the required quantities of Butorphanol Tartrate, spray-dried lactose, and Eudragit® RS PM are transferred into an appropriate-size mixer, and mixed for approximately 5 minutes. While the powders are mixing, the mixture is granulated with enough water to produce a moist granular mass. The granules are then dried in a fluid bed dryer at 60° C., and then passed through an 8-mesh screen. Thereafter, the granules are re-dried and pushed through a 12-mesh screen. The required quantity of stearyl alcohol is melted at approximately 60 to 70° C., and while the granules are mixing, the melted stearyl alcohol is added. The warm granules are returned to the mixer. The coated granules are removed from the mixer and allowed to cool. The granules are then passed through a 12-mesh screen. The granulate is then lubricated by mixing the required quantity of talc and magnesium stearate in a suitable blender. Tablets are compressed on a suitable tableting machine.

In some embodiments, oral immediate release compressed tablets of butorphanol can be formulated using conventional wet granulation procedures and equipment.

Example 25

| Immediate Release Tablet Composition of Butorphanol Tartrate | |
|---|---|
| Ingredients | Qty./Unit |
| 1. Butorphanol Tartrate | 100 mg |
| 2. Polyvinylpyrrolidine | 7.5 mg |
| 3. Lactose | 30 mg |
| 4. Alcohol SD3A-2 proof | 3 mL mg |
| 5. Stearic acid | 5 mg |
| 6. Talc | 7.5 mg |
| 7. Cornstarch | 20 mg |

Example 26

| Immediate Release Tablet Composition of Butorphanol Tartrate | |
|---|---|
| Ingredients | Qty./Unit |
| 1. Butorphanol Tartrate | 50 mg |
| 2. Polyvinylpyrrolidine | 7.5 mg |
| 3. Lactose | 30 mg |
| 4. Alcohol SD3A-2 proof | 3 mL mg |
| 5. Stearic acid | 5 mg |
| 6. Talc | 7.5 mg |
| 7. Cornstarch | 20 mg |

Example 27

| Immediate Release Tablet Composition of Butorphanol Tartrate | |
|---|---|
| Ingredients | Qty./Unit |
| 1. Butorphanol Tartrate | 75 mg |
| 2. Polyvinylpyrrolidine | 7.5 mg |
| 3. Lactose | 30 mg |
| 4. Alcohol SD3A-2 proof | 3 mL mg |
| 5. Stearic acid | 5 mg |
| 6. Talc | 7.5 mg |
| 7. Cornstarch | 20 mg |

In Example 25 to 27, blend 1, 2 and 3 together; pass through a 40-mesh screen. Add 4 slowly and knead well. Screen wet mass through a 4-mesh screen. Dry the granulation at 50° C. overnight. Screen the dried granulation through a 20-mesh screen. Bolt 5, 6 and 7 through a 60-mesh screen prior to mixing by tumbling with granulation. Compress using a concave punch.

In some embodiments, oral immediate release compressed tablets of butorphanol can be formulated using conventional dry granulation procedures and equipment.

Example 28

| Tablet Composition of Butorphanol Tartrate | |
|---|---|
| Ingredients | Qty./Unit |
| 1 Butorphanol Tartrate | 20 mg |
| 2 Lactose (granular, 12-mesh) | 25 mg |
| 3 Starch | 20 mg |
| 4 Talc | 20 mg |
| 5 Magnesium Stearate | 0.3 mg |

In Example 28, mix ingredients 1 to 5 thoroughly. Compress into slugs. Grind and screen to 14- to 16-mesh granules. Recompress into tablets using a concave punch.

In some embodiments, oral sustained release compressed tablets of butorphanol can be formulated using conventional fluid-bed granulation procedures and equipment.

Example 29

| Tablet Composition of Butorphanol Tartrate | |
|---|---|
| Ingredients | Qty./Unit |
| 1. Butorphanol Tartrate | 50 mg |
| 2. HPMC 2208, USP | 150 mg |
| 3. Carnauba wax | 30 mg |
| 4. HPMC 2910, USP | 15 mg |
| 5. Magnesium Stearate | 2 mg |
| 6. Stearic acid | 8 mg |
| 7. Talc | 3 mg |

In Example 29, place the ingredients 1, 2 and 3 in the granulator and mix for 15 minutes. Dissolve ingredient 4 in water (mix in how water, then cool down) and spay into the fluidized mixture. Dry to approximately 5% moisture. Sequentially add ingredient 5, 6 and 7, with mixing steps between each addition. Compress using capsule shaped tooling.

In some embodiments, oral butorphanol for duodenal delivery, jejunal delivery, ileal delivery, ileo-colonic delivery or colonic delivery formulated as modified release dosage forms that provide: (i) rapid release of butorphanol from the dosage form in the appropriate GI environment; or (ii) extended or sustained release of butorphanol from the dosage form in the appropriate gastrointestinal environment. In some embodiments, the appropriate environment is defined by the anatomic location within the GI tract, pH at the point of release, osmotic pressure in the dosage form, osmotic pressure in the GI lumen at the point of release, level of hydration and/or the time after ingestion.

In some embodiments, an (otherwise) immediate release or a controlled release tablet dosage form may be overcoated with one or more polymers to provide butorphanol release in the appropriate gastrointestinal environment.

In some embodiments, oral modified release capsules of butorphanol for ileal delivery, ileal release, ileo-colonic delivery, ileo-colonic release and/or colonic delivery and colonic release for rapid release in the appropriate GI environment can be formulated using conventional wet granulation technique.

Examples 30 to 31 are capsule formulations of oral modified release capsules of butorphanol for rapid release in the ileum or ileo-colonic region. They are formulated using conventional wet granulation procedures and equipment

Example 30

| Rapid Release Butorphanol Tartrate Capsules for Ileal or Ileo-colonic Delivery | |
|---|---|
| Ingredients | Qty./Unit |
| 1. Butorphanol Tartrate | 4 mg |
| 2. Polyvinylpyrrolidine | 7.5 mg |
| 3. Lactose | 30 mg |
| 4. Alcohol SD3A-2 proof | 3 mL mg |
| 5. Stearic acid | 5 mg |
| 6. Talc | 7.5 mg |
| 7. Cornstarch | 20 mg |

Example 31

| Rapid Release Butorphanol Tartrate Capsules for Ileal or Ileo-colonic Delivery | |
|---|---|
| Ingredients | Qty./Unit |
| 1. Butorphanol Tartrate | 10 mg |
| 2. Polyvinylpyrrolidine | 7.5 mg |
| 3. Lactose | 30 mg |
| 4. Alcohol SD3A-2 proof | 3 mL mg |
| 5. Stearic acid | 5 mg |
| 6. Talc | 7.5 mg |
| 7. Cornstarch | 20 mg |

Example 32

| Rapid Release Butorphanol Base Capsules for Ileal or Ileo-colonic Delivery | |
|---|---|
| Ingredients | Qty./Unit |
| 1. Butorphanol Base | 5 mg |
| 2. Polyvinylpyrrolidine | 7.5 mg |
| 3. Lactose | 35 mg |
| 4. Alcohol SD3A-2 proof | 3 mL mg |
| 5. Stearic acid | 5 mg |
| 6. Talc | 7.5 mg |
| 7. Cornstarch | 20 g |

In Example 30 to 32, blend 1, 2 and 3 together; pass through a 40-mesh screen. Add 4 slowly and knead well. Screen wet mass through a 4-mesh screen. Dry the granulation at 50° C. overnight. Screen the dried granulation through a 20-mesh screen. Bolt 5, 6 and 7 through a 60-mesh screen prior to mixing by tumbling with granulation. Encapsulate in an HPMC capsule.

Prepare a composition of aqueous Eudragit® 1.30D-55 dispersion to coat 1.3 kg HPMC capsules: Eudragit L30D-55 1509 g (solids, 453 g), Triethyl citrate 91 g (solids 91 g), Tween 80 (33%) 20 g (solids 7 g) and Distilled Water 1130 g. Spray the dispersion onto the HPMC capsules using an Accela-Cota 10. The temperature of the capsule bed during the coating process is maintained between 26 and 32° C. The mean amounts of polymer applied ranges from 5 mg/cm$^2$ to 20 mg/cm$^2$, preferably 5 mg/cm$^2$ to 10 mg/2 cm$^2$.

The in vitro performance of the capsules can be tested using methods know in the art and described herein. When the capsules are tested using the USP Paddle Method in 0.1N HCl (pH 1.2) for two hours, the capsules will remain intact and substantially non-releasing. Following a switch to phosphate buffer pH 6.8, the capsule dissolution is rapid and complete.

Examples 33 to 35 are capsule formulations of oral modified release capsules of butorphanol for rapid release in the ileo-colonic or colonic region. They are formulated using conventional wet granulation procedures and equipment

Example 33

| Rapid Release Butorphanol Tartrate Capsules for Ileo-colonic or Colonic Delivery | |
|---|---|
| Ingredients | Qty./Unit |
| 1. Butorphanol Tartrate | 2 mg |
| 2. Polyvinylpyrrolidine | 7.5 mg |
| 3. Lactose | 30 mg |
| 4. Alcohol SD3A-2 proof | 3 mL mg |
| 5. Stearic acid | 5 mg |
| 6. Talc | 7.5 mg |
| 7. Cornstarch | 20 mg |

Example 34

| Rapid Release Butorphanol Tartrate Capsules for Ileo-colonic or Colonic Delivery | |
|---|---|
| Ingredients | Qty./Unit |
| 1. Butorphanol Tartrate | 10 mg |
| 2. Polyvinylpyrrolidine | 7.5 mg |
| 3. Lactose | 30 mg |
| 4. Alcohol SD3A-2 proof | 3 mL mg |
| 5. Stearic acid | 5 mg |
| 6. Talc | 7.5 mg |
| 7. Cornstarch | 20 mg |

Example 35

| Rapid Release Butorphanol Tartrate Capsules for Ileo-colonic or Colonic Delivery | |
|---|---|
| Ingredients | Qty./Unit |
| 1. Butorphanol Tartrate | 6 mg |
| 2. Polyvinylpyrrolidine | 7.5 mg |
| 3. Lactose | 30 mg |
| 4. Alcohol SD3A-2 proof | 3 mL mg |
| 5. Stearic acid | 5 mg |
| 6. Talc | 7.5 mg |
| 7. Cornstarch | 20 g |

In Example 33 to 35, blend 1, 2 and 3 together; pass through a 40-mesh screen. Add 4 slowly and knead well. Screen wet mass through a 4-mesh screen. Dry the granulation at 50° C. overnight. Screen the dried granulation through a 20-mesh screen. Bolt 5, 6 and 7 through a 60-mesh screen prior to mixing by tumbling with granulation. Encapsulate in an HPMC capsule.

Prepare a composition of aqueous Eudragit® FS30D dispersion to coat 1.3 kg HPMC capsules: Eudragit FS30D 1207 g (solids, 362 g), Triethyl citrate 18 g (solids 18 g), Glyceryl monostearate 11 g (solids 11 g), Tween 80 (33%) 13 g (solids 4 g) and Distilled Water 728 g. Spray the dispersion onto the HPMC capsules using an Accela-Cota 10. The temperature of the capsule bed during the coating process is maintained between 26 and 32° C. The mean amounts of polymer applied ranges from 5 mg/cm$^2$ to 20 mg/cm$^2$, preferably 6 mg/cm$^2$ to 10 mg/cm$^2$.

The in vitro performance of the capsules can be tested using methods know in the art and described herein. When the capsules are tested using the USP Paddle Method in 0.1N HCl (pH 1.2) for two hours, followed by a switch to phosphate buffer pH 6.8 for one to two hours and then again, a switch to phosphate buffer pH 7.4, the capsules will remain intact and substantially non-releasing at pH 1.2 and pH 6.8 and will provide rapid and complete dissolution upon switch to pH 7.4.

In some embodiments, oral modified release capsules of butorphanol for ileal release, ileo-colonic release and/or colonic release can be formulated using conventional dry granulation procedures and equipment.

Example 36 is a capsule formulation of oral modified release butorphanol for rapid release in the ileo-colonic or colonic region. It is formulated using conventional dry granulation procedures and equipment.

Example 36

Rapid Release Butorphanol Tartrate Capsules for Ileo-colonic or Colonic Delivery

| Ingredients | Qty./Unit |
|---|---|
| 1 Butorphanol Tartrate | 5 mg |
| 2 Lactose (granular, 12-mesh) | 25 mg |
| 3 Starch | 20 mg |
| 4 Talc | 20 mg |
| 5 Magnesium Stearate | 0.3 mg |

In Example 36, mix ingredients 1 to 5 thoroughly. (Optionally, compress into slugs and then grind and screen to 14- to 16-mesh granules). Fill into HPMC capsules to provide the desired dose.

Prepare a composition of aqueous Eudragit® FS30D dispersion to coat 1.3 kg HPMC capsules: Eudragit FS30D 1207 g (solids, 362 g), Triethyl citrate 18 g (solids 18 g), Glyceryl monostearate 11 g (solids 11 g), Tween 80 (33%) 13 g (solids 4 g) and Distilled Water 728 g. Spray the dispersion onto the HPMC capsules using an Accela-Cota 10. The temperature of the capsule bed during the coating process is maintained between 26 and 32° C. The mean amounts of polymer applied ranges from 5 mg/cm$^2$ to 20 mg/cm$^2$, preferably 6 mg/cm$^2$ to 10 mg/cm$^2$.

The in vitro performance of the capsules can be tested using methods know in the art and described herein. When the capsules are tested using the USP Paddle Method in 0.1N HCl (pH 1.2) for two hours, followed by a switch to phosphate buffer pH 6.8 for one to two hours and then again, a switch to phosphate buffer pH 7.4, the capsules will remain intact and substantially non-releasing at pH 1.2 and pH 6.8 and provide rapid and complete dissolution at pH 7.4.

In some embodiments, oral modified release tablets or capsule of butorphanol for ileal release, ileo-colonic release and/or colonic release can be formulated using conventional fluid-bed granulation procedures and equipment.

Example 37 is a capsule (or optionally tablet) formulation of oral butorphanol for ileo-colonic and colonic delivery.

Example 37

Modified Release Butorphanol Tartrate Capsules for Ileo-colonic or Colonic Delivery

| Ingredients | Qty./Unit |
|---|---|
| 1. Butorphanol Tartrate | 12 mg |
| 2. HPMC 2208, USP | 150 mg |
| 3. Carnauba wax | 30 mg |
| 4. HPMC 2910, USP | 15 mg |
| 5. Magnesium Stearate | 2 mg |
| 6. Stearic acid | 8 mg |
| 7. Talc | 3 mg |

In Example 37, place the ingredients 1, 2 and 3 in the granulator and mix for 15 minutes. Dissolve ingredient 4 in water (mix in how water, then cool down) and spray into the fluidized mixture. Dry to approximately 5% moisture. Sequentially add ingredient 5, 6 and 7, with mixing steps between each addition. Encapsulate the dosage form in HPMC or other suitable capsules or compress into a tablet.

For the capsule formulation, prepare a composition of aqueous Eudragit® FS30D dispersion to coat 1.3 kg HPMC capsules: Eudragit FS30D 1207 g (solids, 362 g), Triethyl citrate 18 g (solids 18 g), Glyceryl monostearate 11 g (solids 11 g), Tween 80 (33%) 13 g (solids 4 g) and Distilled Water 728 g. Spray the dispersion onto the HPMC capsules using an Accela-Cota 10. The temperature of the capsule bed during the coating process is maintained between 26 and 32° C. The mean amounts of polymer applied ranges from 5 mg/cm$^2$ to 20 mg/cm$^2$, preferably 6 mg/cm$^2$ to 10 mg/cm$^2$.

For the tablet formulation, the composition of aqueous Eudragit® FS30D dispersion described above may be applied with a typical coating thicknesses of 10 to 30 mg polymer per cm$^2$ of tablet surface, preferably, 10 to 18 mg polymer per cm$^2$ capsule surface.

The in vitro performance of the dosage form can be tested using methods know in the art and described herein. When the capsules are tested using the USP Paddle Method in 0.1N HCl (pH 12) for two hours, followed by a switch to phosphate buffer pH 6.8 for one to two hours and then again, a switch to phosphate buffer pH 7.4, the capsules will remain intact and substantially non-releasing at pH 1.2 and pH 6.8 and provide substantial release at pH 7.4.

In some embodiments, oral modified release capsule of butorphanol for ileo-colonic and colonic delivery in sustained release form can be made, as shown in Example 9 to 21.

Example 38 to 51 may be prepared as follows: (i) Dispense the specified hydrophobic controlled release material (e.g., hydrogenated Type I vegetable oil, hydrogenated Type II vegetable oil, polyoxyethylene stearates, polyoxyethylene distearates, glycerol monostearate, poorly water soluble, or high melting point waxes) into a mixer; (ii) Heat until fully melted; (iii) dispense the hydroxypropyl methyl cellulose (HPMC) into the mixer; (iv) Mix until dispersed; (v) Dispense the Aerosil into the same vessel; (vi) Mix until dispersed; (vii) Dispense the butorphanol into the same vessel; (viii) Stir thoroughly with a high shear mixer; (ix) Transfer the mix into a liquid filling machine; (x) Fill into hard gelatin (or HPMC) capsule; (xi) Optionally, transfer the capsules to a banding machine and band the capsules.

Optionally, cure the capsules by setting them at room temperature for a period of 1 to 7 days.

For Example 38 to 51, prepare a composition of aqueous Eudragit® FS30D dispersion to coat 1.3 kg HPMC capsules: Eudragit FS30D 1207 g (solids, 362 g), Triethyl citrate 18 g (solids 18 g), Glyceryl monostearate 11 g (solids 11 g), Tween 80 (33%) 13 g (solids 4 g) and Distilled Water 728 g. Spray the dispersion onto the HPMC capsules using an Accela-Cota 10. The temperature of the capsule bed during the coating process is maintained between 26 and 32° C. The mean amounts of polymer applied ranges from 5 mg/cm$^2$ to 20 mg/cm$^2$, preferably 6 mg/cm$^2$ to 15 mg/cm$^2$.

The in vitro performance of the dosage form can be tested using methods know in the art and described herein. When the capsules are tested using the USP Paddle Method in 0.1N HCl (pH 1.2) for two hours, followed by a switch to phosphate buffer pH 6.8 for one to two hours and then again, a switch to phosphate buffer pH 7.4, the capsules will remain intact and substantially non-releasing at pH 1.2 and pH 6.8, and they will release the butorphanol at pH 7.4 over a prolonged period (e.g., over 12 to 48 hours).

Example 38

| Modified Release Butorphanol Tartrate Capsules for Slow Ileo-colonic or Colonic Release | |
| --- | --- |
| Ingredients | Quantity (mg)/Dose |
| Sterotex ® NF | 200 |
| Fractionated coconut oil | 70 |
| Methocel ® K 15M | 81 |
| Aerosil ® COK 84 | 4 |
| Butorphanol Tartrate | 20 |

Example 39

| Modified Release Butorphanol Tartrate Capsules for Slow Ileo-colonic or Colonic Release | |
| --- | --- |
| Ingredients | Quantity (mg)/Dose |
| Beeswax | 200 |
| HPMC, K15M | 80 |
| Aerosil COK 84 | 8 |
| Butorphanol Tartrate | 10 |

Example 40

| Modified Release Butorphanol Tartrate Capsules for Slow Ileo-colonic or Colonic Release | |
| --- | --- |
| Ingredients | Quantity (mg)/Dose |
| Sterotex NF | 150 |
| HPMC, K15M | 75 |
| Coconut oil | 75 |
| Aerosil COK 84 | 5 |
| Butorphanol Tartrate | 12 |

Example 41

| Modified Release Butorphanol Tartrate Capsules for Slow Ileo-colonic or Colonic Release | |
| --- | --- |
| Ingredients | Quantity (mg)/Dose |
| Cithrol GMS | 275 |
| HPMC, K100M | 40 |
| Aerosil COK 84 | 10 |
| Butorphanol Tartrate | 20 |

Example 42

| Modified Release Butorphanol Tartrate Capsules for Slow Ileo-colonicor Colonic Release | |
| --- | --- |
| Ingredients | Quantity (mg)/Dose |
| Hydrokote 112 | 250 |
| HPMC, K15M | 60 |
| Aerosil COK 84 | 10 |
| Butorphanol Tartrate | 5 |

Example 43

| Modified Release Butorphanol Tartrate Capsules for Slow Ileo-colonicor Colonic Release | |
| --- | --- |
| Ingredients | Quantity (mg)/Dose |
| Beeswax | 200 |
| HPMC, Pharmacoat 606 | 62.5 |
| Aerosil COK 84 | 7.5 |
| Butorphanol Tartrate | 25 |

Example 44

| Modified Release Butorphanol Tartrate Capsules for Slow Ileo-colonicor Colonic Release | |
| --- | --- |
| Ingredients | Quantity (mg)/Dose |
| Gelucire 50/02 | 190 |
| Methocel K 100M | 35 |
| Aerosil COK 84 | 10 |
| Butorphanol Tartrate | 10 |

Example 45

| Modified Release Butorphanol Tartrate Capsules for Slow Ileo-colonicor Colonic Release | |
| --- | --- |
| Ingredients | Quantity (mg)/Dose |
| Cetyl alcohol | 280 |
| Methocel K 100M | 50 |
| Aerosil COK 84 | 10 |
| Butorphanol Tartrate | 40 |

Example 46

Modified Release Butorphanol Tartrate Capsules for Slow
Ileo-colonicor Colonic Release

| Ingredients | Quantity (mg)/Dose |
|---|---|
| Sterotex NF | 320 |
| Methocel K 15M | 60 |
| Aerosil COK 84 | 10 |
| Butorphanol Tartrate | 15 |

Example 47

Modified Release Butorphanol Tartrate Capsules for Slow
Ileo-colonicor Colonic Release

| Ingredients | Quantity (mg)/Dose |
|---|---|
| Cithrol GMS | 320 |
| Methocel K 100M | 55 |
| Aerosil COK 84 | 15 |
| Butorphanol Tartrate | 15 |

Example 48

Modified Release Butorphanol Tartrate Capsules for Slow
Ileo-colonicor Colonic Release

| Ingredients | Quantity (mg)/Dose |
|---|---|
| Sterotex ® NF | 100 |
| Fractionated coconut oil | 70 |
| Beeswax | 100 |
| Methocel ® K 15M | 81 |
| Aerosil ® COK 84 | 4 |
| Butorphanol Tartrate | 30 |

Example 49

Modified Release Butorphanol Tartrate Capsules for Slow
Ileo-colonicor Colonic Release

| Ingredients | Quantity (mg)/Dose |
|---|---|
| Cetyl alcohol | 270 |
| Methocel K 100M | 50 |
| Aerosil COK 84 | 10 |
| Butorphanol Tartrate | 40 |

Example 50

Modified Release Butorphanol Tartrate Capsules for Slow
Ileo-colonicor Colonic Release

| Ingredients | Quantity (mg)/Dose |
|---|---|
| Sterotex NF | 293 |
| Methocel K 15M | 45 |
| Aerosil COK 84 | 10 |
| Butorphanol Tartrate | 10 |

Example 51

Modified Release Butorphanol Tartrate Capsules for Slow
Ileo-colonic or Colonic Release

| Ingredients | Quantity (mg)/Dose |
|---|---|
| Cithrol GMS | 325 |
| Methocel K 100M | 55 |
| Aerosil COK 84 | 15 |
| Butorphanol Tartrate | 20 |

Examples 52 and 53 are oral modified release tablets of butorphanol for ileo-colonic and colonic delivery in sustained release.

The core tablet of butorphanol is prepared using the composition shown in the Tables for Examples 52 and 53 using the following procedure: (i) Mix 1, 2, (and 3), and 5 and pass through #20 mesh; (ii) Dissolve 4 in 7; (iii) Granulate the powder from (i) using a fluid bed granulator and then dry; (iv) Pass the dry granules through #20 mesh; (v) Mix the granules with 6; (vi) Compress to tablet using plain/plain tooling.

Prepare a coating solution comprising: (a) Ethylcellulose (Ethocel PR100), 9.0 to 15 mg per tablet; (b) Polyvinylpyrrolidone (Kollidon 90F), 3.0 to 7.0 mg per tablet; (c) Dibutyl Sebacate, 2.0 to 4.0 mg per tablet; (d) Denatured Alcohol 150 to 300 mg per tablet (evaporates during process). Spray coating solution using coating pan until desired in vitro release is achieved as described herein. Adjust coating solution composition or coating weight/thickness as required. The coating weight is usually approximately 5 to 40% w/w.

For the initial trial, prepare one coating comprising: (a) Ethylcellulose (Ethocel PR100), 9.2 mg per tablet; (b) Polyvinylpyrrolidone (Kollidon 90F), 4.15 mg per tablet; (c) Dibutyl Sebacate, 2.70 mg per tablet; (d) Denatured Alcohol 170 mg per tablet (evaporates during process). Prepare another coating comprising: (a) Ethylcellulose (Ethocel PR100), 14.15 mg per tablet; (b) Polyvinylpyrrolidone (Kollidon 90F), 5.1 mg per tablet; (c) Dibutyl Sebacate, 3.85 mg per tablet; (d) Denatured Alcohol 245 mg per tablet (evaporates during process).

Example 52

Modified Release Butorphanol Tartrate Tablets for Slow
Ileo-colonic or Colonic Release

| Ingredients | Quantity (mg) |
|---|---|
| 1. Butorphanol Tartrate | 40.00 |
| 2. Microcrystalline Cellulose | 90.00 |

Modified Release Butorphanol Tartrate Tablets for Slow Ileo-colonic or Colonic Release -continued

| Ingredients | Quantity (mg) |
|---|---|
| 3. HPMC (low viscosity grade) | 46.00 |
| 4. Polyvinyl Alcohol | 2.00 |
| 5. Colloidal Silicon Dioxide | 1.00 |
| 6. Sodium Stearyl Fumarate | 1.00 |
| 7. Purified Water * | As needed to form granules |

\* Evaporated during process

Example 53

Modified Release Butorphanol Tartrate Tablets for Slow Ileo-colonic or Colonic Release

| Ingredient | Quantity (mg) |
|---|---|
| 1. Butorphanol Tartrate | 10.00 |
| 2. Microcrystalline Cellulose | 90.00 |
| 3. HPMC (low viscosity grade) | |
| 4. Polyvinyl Alcohol | 2.00 |
| 5. Colloidal Silicon Dioxide | 1.00 |
| 6. Sodium Stearyl Fumarate | 1.00 |
| 7. Purified Water * | 41.60 (to form granules) |

\* Evaporated during process

Alternatively, Examples 52 and 53 may be coated with a suitable amount of Eudragit® S 100, or Eudragit® S 12.5, or Eudragit® FS 30D

Example 54

Example 54 provides a method for manually sealing the overlapping region of the HPMC capsule body and cap using a process called banding. The banding solution is prepared as follows: (i) prepare the banding solution with 18 g of 4.5 cps HPMC along with 33 g of water and heated to 80° C. in a beaker; (ii) stir the mixture until the HPMC is well dispersed in the water; (iii) to completely solubilize the HPMC, add 50 mL of absolute alcohol and sonicate for 10 minutes; (iv) seal capsules using equipment such as the Lab band sealing machine (LBS 100) or the Qualicaps® Lab-Top Capsule Band-Sealer (S-1); (v) apply banding solution uniformly to the external edge of the gap of the capsule to be sealed to form a liquid ring around the circumference of the capsule and remove excess sealing liquid from the exterior of the capsule; (vi) dry the capsules by applying thermal energy, such as hot air and a controlled temperature oven. For larger scale banding, automated equipment such as the Qualicaps S-40 or S-100 capsule band-sealing machine or the Hermetica® is a capsule banding machine may be used to seal filled, two-piece capsules with a single or double band of substances such as gelatin or hypromellose at the joined portion of the cap and body.

Example 55

Example 55 provides an alternative method of coating small batches of capsules to provide ileo-colonic or colonic deliver of the oral butorphanol dosage form for rapid release or slow release (depending on the dosage form used). This method can be used in place of other described enteric coating methods. The method can be readily modified by those skilled in the art to coat tablet dosage forms. In this example, coating is carried out using 45% suspension of Eudragit® FS30D. Coating solution is prepared by homogenizing talc and triethyl citrate in water for 10 minutes. This suspension is poured into Eudragit FS 30 D dispersion under stirring. This spray suspension is transferred through 0.5 mm sieve. Coating suspension is spread by spray gun on a moving capsule bed. The process is carried out in conventional coating pan (see Table below). The coating solution may be further modified to achieve targeted GI delivery or release in or distal to the duodenum, jejunum, ileum, ileo-cecal junction, ileo-colonic region or colon, using methods known in the art and those described herein.

Composition of Coating Solution

| Ingredients | Enteric coating |
|---|---|
| Eudragit FS 30 D | 150 g |
| Talc | 22.5 g |
| Triethyl citrate | 2.5 g |
| Water | 175 g |

The coating process parameters like the coating pan, baffles, inlet air temperature, product temperature, exhaust and spray air pressure are shown in Table below.

Coating Process Parameters

| | |
|---|---|
| Coating pan | 12 inch |
| Baffles | Present |
| Silicone tube od/id | 2 mm |
| Inlet air temperature | 40° C. |
| Product Temperature | 30° C. |
| Exhaust | ON |
| Blower | ON |
| Spray air pressure | 2 bar |

Example 56

Example 56 provides an alternative method of coating small batches of capsules to provide ileo-colonic or colonic delivery of the oral butorphanol dosage form for rapid release or slow release (depending on the dosage form used). This method can be used in place of other described enteric coating methods. The method can be readily modified by those skilled in the art to coat tablet dosage forms. The coating solution may be further modified to achieve targeted GI delivery or release in or distal to the duodenum, jejunum, ileum, ileo-cecal junction, ileo-colonic region or colon, using methods known in the art and those described herein. An initial coating solution is provided in the Table below. This can be modified further to achieve the desired delivery profile:

| S. No. | Ingredients | % w/w |
|---|---|---|
| 1 | Eudragit S 100 | 6.1 |
| 2 | Triethyl citrate | 0.9 |
| 3 | Talc | 3.0 |
| 4 | Isopropyl alcohol | 85.0 |
| 5 | Water | 5.0 |

The procedure for preparation of the above coating solution is: (a) dissolve Eudragit in 70% of total IPA and 100% of water; (b) homogenize talc and triethyl citrate in 30% of remaining IPA; (c) add talc and triethyl citrate dispersion to Eudragit solution and stir gently. Apply the coat by dip coating using the ProCoater® (Torpac, N.J.), with the method recommended by the manufacturer or preferably described by described by Dodds and Podczeck (Tablets & Capsules, January 2008, CSC Publishing Inc). Once dry, check weight gain. Additional coating may be applied to provide further weight gain. Batches with polymer target weight gains of about 10 mg/cm$^2$ to about 20 mg/cm$^2$ are prepared (for example, 10 mg/cm$^2$ or 15 mg/cm$^2$ and 20 mg/cm$^2$). The approximate surface area of Capsule Size 00, 0, 1 and 2 are 6.16 cm$^2$, 5.07 cm2, 4.06 cm2, and 3.43 cm2, respectively (see Jones, Tablets & Capsules, January 2009 and April 2009, CSC Publishing Inc). This provides a target weight gain range shown below:

| Capsule | | Total Capsule Weight Gain | | |
|---|---|---|---|---|
| Size | Surface Area | 10 mg/cm$^2$ | 15 mg/cm$^2$ | 20 mg/cm$^2$ |
| 00 | 6.16 cm$^2$ | 60 mg | 90 mg | 120 mg |
| 0 | 5.07 cm$^2$ | 50 mg | 75 mg | 100 mg |
| 1 | 4.06 cm$^2$ | 40 mg | 60 mg | 80 mg |
| 2 | 3.43 cm$^2$ | 35 mg | 50 mg | 70 mg |

To determine if the desired target delivery or release has been achieved, a disintegration tester is used (e.g. manually with the ERWEKA® ZT 120, ZT 120, ZT 220, or ZT 320, or using the automated ZT 850). Alternatively, an orbital shaker or a beaker with an agitator (or magnetic stirrer at moderate or high speed) is used, first in 0.1N HCl for two hours, then with a change in media to water at pH >7 (or other suitable pH). The capsules shell remains intact in 0.1 N HCL (pH 1.2) for two hours and disintegrates or ruptures at the desired pH (e.g., pH 7) usually after 5 to 90 minutes (the higher the weight gain, the longer they stay intact at pH 7). For modified release dosage forms intended to provide targeted GI delivery (e.g., ileo-colonic or colonic delivery) for subsequent slow or sustained release, the capsule shell will rupture, disintegrate, or dissolve but the contents may remain intact (depending on the dosage form used).

A more specific and reliable method to determine coating integrity and attainment of target GI delivery (which does not rely on visual inspection of capsules) for both modified release forms which rapidly release drug and those which slowly release (sustained release) drug in the target GI environment is the use of a dissolution methods where the drug release is quantified. When such the capsules are tested using the USP Paddle Method in 0.1N HCl (pH 1.2) for 2 hours at 37° C., the capsules (or tablets) remain intact and substantially non-releasing. Following a switch to the USP Basket or Paddle Method at 100 rpm in 900 mL distilled water (time=0 hour begins here) at 37° C. at the target pH, the dosage form begins to provide rapid or slow release of the drug usually after 5 to 90 minutes.

The optimal coating solution composition, weight gain and process parameters to achieve the desired target delivery or release is achieved by simultaneously testing the coated dosage form dosage form at various pH using the USP Paddle Method in 0.1N HCl (pH 1.2) for 2 hours at 37° C., followed by a switch to the USP Basket or Paddle Method at 100 rpm in 900 mL distilled water (time=0 hour begins here) at 37° C. at the target pH (e.g., pH 6.5, pH 6.8, pH 7.0, pH 7.5). For modified release dosage forms intended to provide targeted GI delivery for rapid release of butorphanol, less than 10% of drug should be released at pH 1.2.

Various alternative small and large scale methods of organic and aqueous coating of tablets and capsules have been described or referenced herein, or are known those skilled in the art. Enteric coatings may also be applied over tablet and capsule osmotic delivery dosage forms of oral butorphanol, including push pull osmotic pumps, monolithic osmotic delivery systems and controlled porosity osmotic pumps to provide targeted delivery in the GI tract.

Example 57

A matrix tablet formulation of oral modified release butorphanol was prepared using the method described here: (i) The Polyox and MCC were passed through a 44# sieve and then weighed; (ii) Butorphanol Tartrate was weighed and milled in mortar-pestle to make fine powder; (iii) The mixture of step (i) was mixed with step (ii) to provide a homogeneous mixture. Uniform mixture was achieved through sieving several times and mixing geometrically; (iv) The lubricants were added and passed through 25# sieve in above mixture by sieving them with step (iii); (v) The mixture was well mixed and sieved through a 25# sieve twice and homogenized in a polybag; (vi) tablets were compressed using a standard concave 9 mm punch on single punch compression machine.

| Modified Release Butorphanol Matrix Tablets | | | |
|---|---|---|---|
| | Drug Layer | mg/Tablet | % w/w |
| 1 | Butorphanol Tartrate | 10.0 | 5.0 |
| 2 | Polyox WSR 301 | 100.0 | 50.0 |
| 3 | MCC 101 | 80.0 | 40.0 |
| 4 | Talc | 3.0 | 1.5 |
| 5 | Mg. Stearate | 3.0 | 1.5 |
| 6 | SiO2 | 4.0 | 2 |

The tablet dissolution was evaluated in 250 mL of pH 1.2 for 2 hours, followed by a switch to pH 6.8 phosphate buffer using the USP paddle method at 50 rpm, and in 250 mL of pH 6.8 phosphate buffer using the USP paddle method at 100 rpm and. See Table below.

| Modified Release Butorphanol Matrix Tablet Dissolution | | |
|---|---|---|
| | Dissolution Rate ( % w/w) | |
| Time (hr) | pH 1.2 (2 hrs), then pH 6.8 50 RPM | Dissolution Rate (% w/w) pH 6.8, 100 RPM |
| 1 | 11.10 | 5.78 |
| 2 | 17.76 | 10.58 |
| 4 | 31.83 | 24.16 |
| 6 | 46.56 | 41.16 |
| 8 | 57.92 | 54.50 |
| 10 | 65.88 | 67.95 |
| 14 | 87.26 | 82.10 |
| 17 | 99.03 | 97.01 |
| 21 | 101.44 | 106.26 |
| 24 | 101.80 | |

Example 58

A matrix tablet formulation of oral modified release butorphanol was prepared using the method described here:

(i) The Polyox, HPMC K100M CR and MCC were passed through a 44# sieve and then weighed; (ii) Butorphanol Tartrate was weighed and passed through a 25# sieve; (iii) The mixture of step (i) was mixed with step (ii) to provide a homogeneous mixture. Uniform mixture was achieved through sieving several times and mixing geometrically; (iv) The lubricants were added and passed through 100# sieve in above mixture by sieving them with step (iii); (v) The mixture was well mixed and sieved through a 25# sieve twice and homogenized in a polybag; (vi) tablets were compressed using a standard concave 9 mm punch on single punch compression machine.

| Modified Release Butorphanol Matrix Tablets | | | |
|---|---|---|---|
| | Drug Layer | mg/Tablet | % w/w |
| 1 | Butorphanol Tartrate | 10.0 | 5.0 |
| 2 | Polyox WSR 301 | 50.0 | 25.0 |
| 3 | HPMC K100M CR | 50.0 | 25.0 |
| 4 | MCC 101 | 80.0 | 40.0 |
| 5 | Talc | 3.0 | 1.5 |
| 6 | Mg. Stearate | 3.0 | 1.5 |
| 7 | SiO2 | 4.0 | 2 |

The tablet dissolution was evaluated in 250 mL of pH 1.2 for 2 hours, followed by a switch to pH 6.8 phosphate buffer using the USP paddle method at 50 rpm, and in 250 mL of pH 6.8 phosphate buffer using the USP paddle method at 100 rpm and. See Table below.

| Modified Release Butorphanol Matrix Tablet Dissolution | |
|---|---|
| Time (hr) | Dissolution Rate (% w/w) pH 1.2 (2 hrs), then pH 6.8 50 RPM |
| 1 | 7.55 |
| 2 | 15.50 |
| 4 | 20.24 |
| 6 | 36.17 |
| 8 | 47.89 |
| 10 | 54.81 |
| 14 | 76.02 |
| 17 | 82.51 |
| 21 | 88.99 |
| 24 | 92.66 |

Example 59

A controlled porosity osmotic pump (CPOP) dosage form of oral butorphanol was prepared using the method described here.

Core Tablet: (i) Butorphanol tartrate was mixed with lactose and sodium chloride after passing through 40# sieve; (ii) The mixture of step (1) was added to PVP K 30 solution in IPA; (iii) The mass was well mixed to achieve a homogeneous mixture; (iv) The mass dried in a dryer at 50° C. for 10 minutes; (v) The mass was passed through a #18 sieve once for granulation; (vi) The granules were further dried; (vii) Magnesium stearate and talc were then added and mixed; (viii) The tablets were compress using a standard concave 9 mm punch on single punch compression machine.

Coating Solution: (i) Cellulose acetate was dissolved in acetone; (ii) D-sorbitol was dissolved in water half quantity; (iii) PEG was dissolved in rest of the one fourth of water; (iv) Step (ii) was mixed with step (1) with high stirring; (v) Mix step (iii) with the mixture of step (i) and step ii); (vi) Stir to homogenize the solution; (vii) Dip the tube of the coating solution dispenser into the product of step (vi).

| Modified Release Osmotic Dosage Form Core Tablet | | | |
|---|---|---|---|
| | Drug Layer | mg/Tablet | % w/w |
| 1 | Butorphanol Tartrate | 10.0 | 4.3 |
| 2 | Sodium Chloride | 100.0 | 43.5 |
| 3 | Lactose | 100.0 | 43.5 |
| 4 | PVP K 30 in IPA 3 ml | 12.0 | 5.2 |
| 5 | Mg. Stearate | 3.0 | 1.3 |
| 6 | Talc | 3.0 | 1.3 |
| 7 | Aerosil 200 | 2.0 | 0.87 |

| Modified Release Osmotic Dosage Form Coating Solution | | | |
|---|---|---|---|
| | Coating Formula | mg/Tablet | % w/w |
| 1 | Cellulose Acetate | 22.95 | 2.39 |
| 2 | D-Sorbitol | 4.05 | 0.42 |
| 3 | PEG-400 | 4.05 | 0.42 |
| 4 | Acetone | 855.00 | 88.97 |
| 5 | Water | 75.00 | 7.80 |

| Modified Release Osmotic Dosage Form Coating Process Parameters Coating Parameters | |
|---|---|
| Solvent | Acetone:Water (90:10) |
| Solids content (% w/w) | 4% (3.23%) |
| Weight gain (%) | 15% Target/13.71 Achieved |
| Inlet air temperature (° C.) | 50-55° C. (Set) 49° Actual |
| Out let air temperature (° C.) | 45-50° C. (Set) 40° Actual |
| Inlet air CFM | 32 |
| Outlet air CFM | 43 |
| Tablet surface bed temp (° C.) | 40-42° C. |
| Pre-warm tablet bed (° C.) | 41-43° C. |
| Load | 175 gm |
| Atomizing air pressure ( kg/cm$^2$) | 3.0 kg/cm$^2$ |
| Gun-to-bed distance (inches) | Three to Four inch |
| Spray rate (g/min) | 4.5 to 5.5 g\min |
| Baffles | 6 |
| Pan speed (rpm) | 3.0 RPM |
| Peristaltic Pump RPM | 10 RPM |
| Fluid nozzle (mm) | 1.5 |
| Spray equipment | Solace |
| Spray pan size | 12" |

The tablet dissolution was evaluated in 250 mL of pH 6.8 phosphate buffer using the USP paddle method at 50 rpm after application of coating in the following w/w % amounts: (i) 5.7%; (ii) 9.6%; and (13.7%). See Table below.

| Modified Release Osmotic Dosage Form Dissolution | | | |
|---|---|---|---|
| Time (hr) | Dissolution Rate (i) (% w/w) | Dissolution Rate (ii) (% w/w) | Dissolution Rate (iii) (% w/w) |
| 1 | 0.00 | 0.00 | 0.00 |
| 2 | 0.65 | 0.40 | 0.00 |
| 4 | 19.72 | 7.24 | 5.56 |
| 6 | 37.15 | 26.62 | 17.55 |
| 8 | 58.42 | 38.84 | 23.50 |
| 10 | 61.62 | 43.42 | 34.41 |
| 14 | 79.19 | 58.66 | 40.42 |
| 17 | 82.64 | 64.34 | 51.41 |
| 21 | 85.02 | 68.51 | 56.35 |
| 24 | 89.72 | 75.02 | 60.10 |

Example 59

Numerous robust matrix butorphanol tartrate tartrate formulations of the invention suitable for 24 hour dosing (QD dosing) were prepared and tested in 500 mL of 0.1 N HCl (at pH 1.2) at 37 C for 2 hours, followed by a switch to pH 6.8 phosphate buffer and also exclusively in pH 6.8 buffer under the same conditions. They provided the following dissolution release specifications: less than about 20% release at 1 hour, between about 15% and about 55% release at 4 hours, between 35% and 75% release at 8 hours and greater than 70% release at 24 hours. Using methods described herein, the matrix tablets may be further overcoated to provide ileo-colonic release, which when tested in 0.1 N HCl (at pH 1.2) or at pH 5 for 2 hours, followed by a switch to pH 6.8 phosphate buffer tested will provide the following dissolution release specifications: less than about 10% release at 2 hours, between about 15% and about 55% release at 6 hours, between 35% and 75% release at 10 hours and greater than 55% release at 24 hours.

Example 60

Numerous robust controlled porosity osmotic pump butorphanol tartrate dosage forms of the invention suitable for 24 hour dosing (QD dosing) were prepared and tested in 500 mL of pH 6.8 phosphate buffer at 37 C and in distilled water. They provided the following dissolution release specifications: less than about 20% at 3 hours, about 15% to 55% at 6 hours, about 35% and 75% at 10 hours and greater than 60% at 24 hours. Using methods described herein, the matrix tablets may be further overcoated to provide ileo-colonic release, which when tested in 0.1 N HCl (at pH 1.2) or at pH 5 for 2 hours, followed by a switch to pH 6.8 phosphate buffer tested will provide the following dissolution release specifications: less than about 10% release at 2 hours, less than about 30% at 5 hours, about 15% to 60% at 8 hours, about 30% and 85% at 10 hours and greater than 50% at 24 hours.

Example 61

A matrix tablet formulation of oral modified release butorphanol was prepared using the method described here: (i) The Polyox, HPMC K100M CR and MCC were passed through a 44# sieve and then weighed; (ii) Butorphanol Tartrate was weighed and passed through a 25# sieve; (iii) The mixture of step (i) was mixed with step (ii) to provide a homogeneous mixture. Uniform mixture was achieved through sieving several times and mixing geometrically; (iv) The lubricants were added and passed through 100# sieve in above mixture by sieving them with step (iii); (v) The mixture was well mixed and sieved through a 25# sieve twice and homogenized in a polybag; (vi) tablets were compressed using a standard concave 9 mm punch on single punch compression machine.

| | Modified Release Butorphanol Matrix Tablets | | |
|---|---|---|---|
| | Drug Layer | mg/Tablet | %w/w |
| 1 | Butorphanol Tartrate | 5.0 | 5.0 |
| 2 | Polyox WSR 301 | 50.0 | 25.0 |
| 3 | HPMC K100M CR | 50.0 | 25.0 |
| 4 | MCC 101 | 85.0 | 42.5 |
| 5 | Talc | 3.0 | 1.5 |
| 6 | Mg. Stearate | 3.0 | 1.5 |
| 7 | SiO2 | 4.0 | 2 |

The tablet dissolution was evaluated in 250 mL of pH 1.2 for 2 hours, followed by a switch to pH 6.8 phosphate buffer using the USP paddle method at 50 rpm, and in 250 mL of pH 6.8 phosphate buffer using the USP paddle method at 100 rpm and. See Table below.

| | Modified Release Butorphanol Matrix Tablet Dissolution | |
|---|---|---|
| Time (hr) | Dissolution Rate (% w/w) pH 1.2 (2 hrs), then pH 6.8 50 RPM | Range (% w/w) |
| 1 | 9 | <20 |
| 2 | 15 | |
| 4 | 29 | 15-55 |
| 6 | 37 | |
| 8 | 48 | 35-75 |
| 10 | 52 | |
| 24 | 52 | >70 |

Example 62

A matrix tablet formulation of oral modified release butorphanol was prepared using the method described previously.

| | Formula | | | |
|---|---|---|---|---|
| Excipient | mg/tab | % w/w | Range 1 | Range 2 |
| Butorphanol tartrate | 10.0 | 4.0 | | |
| Microcrystalline cellulose 101 | 100.0 | 40.0 | | |
| Hypromellose K100M | 87.5 | 35.0 | 25%-45% | 15%-55% |
| Ethyl cellulose N7 | 25.0 | 10.0 | 5%-20% | 0%-30% |
| Talc | 1.25 | 0.5 | | |
| Aerosil 200 | 1.25 | 0.5 | | |
| Carbopol 71G | 25.0 | 10.0 | | |
| Total | 250.0 | 100.0 | | |

The tablet dissolution was evaluated in 250 mL of pH 1.2 for 2 hours, followed by a switch to pH 6.8 phosphate buffer using the USP paddle method at 50 rpm. See Table below.

| Time (hr) | Avg | Range |
|---|---|---|
| 0 | 0 | |
| 1 | 13 | <20 |
| 2 | 20 | |
| 4 | 30 | 15-55 |
| 6 | 36 | |
| 8 | 42 | 35-75 |
| 24 | 74 | >70 |

A matrix tablet formulation of oral modified release butorphanol was prepared using the method described previously.

| Formula | | | | |
|---|---|---|---|---|
| Excipient | mg/tab | % w/w | Range 1 | Range 2 |
| Butorphanol tartrate | 10.0 | 5.0 | | |
| POLYOX WSR 301 | 50.0 | 25.0 | 15%-35% | 10%-40% |
| Hypromellose K4M | 50.0 | 25.0 | 15%-35% | 10%-40% |
| Microcrystalline cellulose 101 | 79.625 | 39.8125 | | |
| BTH EP | 0.375 | 0.1875 | | |
| Talc | 3.0 | 1.5 | | |
| Magnesium Stearate | 3.0 | 1.5 | | |
| Silicone dioxide | 4.0 | 2.0 | | |
| Total | 200.0 | 100.0 | | |

The tablet dissolution was evaluated in 250 mL of pH 6.8 phosphate buffer using the USP paddle method at 50 rpm. See Table below.

| Time (hr) | Avg. | Range |
|---|---|---|
| 1 | 5 | <20 |
| 2 | 15 | |
| 4 | 34 | 15-55 |
| 6 | 46 | |
| 8 | 57 | 35-75 |
| 10 | 64 | |
| 14 | 75 | |
| 17 | 82 | |
| 21 | 86 | |
| 24 | 86 | >70 |

Antinociceptive Effects of Oral Butorphanol

Radiant Heat Tail Flick Test

Background

The tail flick test was first described by D'Amour and Smith (1941), and remains essentially unchanged in application. (See generally D'Amour, F. E. and Smith, D. L., "A method for determining loss of pain sensation", *J. Pharmacol. Exp. Therap.*, 72:74-79(1941); Dewey, D. L. and Harris, L. S., The Tail-flick test. In: S. Ehrenpreis and A. Neidle (Eds.), Methods in Narcotic Research, Marcel Dekker, Inc., New York, 1975, pp. 101-109; and Dubner, R. and Ren, K., "Assessing transient and persistent pain in animals" In: P. D. Wall and R. Melzack (Eds.), Textbook of Pain, Churchill Livingstone, London, 1999, pp. 359-369). Quite simply, the tail of a rat or mouse is exposed to radiant heat, and the latency to withdraw is determined. The basal heat intensity is set so that naive rats withdraw their tails within 2 to 3 sec. A cut-off latency of 10 sec (i.e., 3 to 4 times basal control value) is commonly employed to prevent tissue damage. An alternative to using radiant heat is to dip the tail into a water bath maintained at a fixed temperature, usually in the moderately noxious range of about 52° C. or 55° C. One advantage of a water bath is that the temperature is kept constant.

The tail-flick test is considered to be very robust in that weak analgesic agents are not detected by this test. In contrast, it is considered highly selective. There is a high degree of correlation between drugs that are identified as antinociceptive in the tail-flick test and clinically active analgesic agents. Importantly, agents that are sedating and may produce a positive response in the writhing test or hot plate test do not show antinociceptive activity in the tail-flick test. It is even possible to perform the tail-flick test in lightly anesthetized animals.

Example 60

Aim

The aim of this study was to evaluate the analgesic effect of orally administered butorphanol following administration into different parts of the gastrointestinal tract in transiently ether anaesthetized rats, using the tail flick test of nociception. The primary measurements were made using the tail flick test designed to detect effects of the treatment(s) on nociception in rats.

Animals:

Wistar rats weighing 250±20 g were maintained on standard laboratory diet and having free access to tap water ad lib were employed in the present study. They were housed in the animal house and were exposed to 12 hr cycle of light and dark. The experiments were conducted in a semi-sound proof laboratory. Care of the animals was in accordance with guidelines for experimentation on animals.

Experimental Design:

Three groups were employed in the present study with each group comprising of 8 animals. Each animal was subjected to transient ether anesthesia followed by a minor incision in the abdominal cavity through which butorphanol 1 mg/kg was administered using a syringe into the stomach, ileum and colon. Tail flick test was performed 0, 30, 45 and 60 minutes after administration of the butorphanol. Area under the curve was calculated using a graph between % MPE and time. Area under the curve was employed as a quantitative measure of the analgesic effect of the treatments.

Measurement of Effect:

Nociceptive threshold was measured with the tail flick test (D'Amour and Smith, 1941). The tail flick latency was considered as the time between exposure of the tail to radiant heat and tail withdrawal. Electrically heated nichrome wire was used as a source of radiant heat in the analgesiometer. The intensity of radiant heat was regulated in order to obtain a pretreatment latency between 2 and 4 sec in the animals. A cut-off latency time was fixed at 10 sec. Tail flick latency is expressed as a percentage of the maximum possible effect (MPE):

$$MPE(\%) = \frac{(\text{Post treatment latency} - \text{pre treatment latency})}{(\text{Cut-off-time} - \text{pre treatment latency})} \times 100$$

Data Analysis:

The anti-nociceptive effect following intragastric, intra-ileal and intra-colonic administration was assessed in terms of area under the curve calculated from a graph having time (relative to dosing time point) on the x-axis and percent maximum possible effect (% MPE) on the y-axis. The results were expressed as mean±standard error of means (S.E.M.). Statistical analysis for was done using one-way ANOVA, followed by Tukey's multiple range tests as post-hoc analysis. A value of P<0.05 was considered to be statistically significant.

Figure 13:
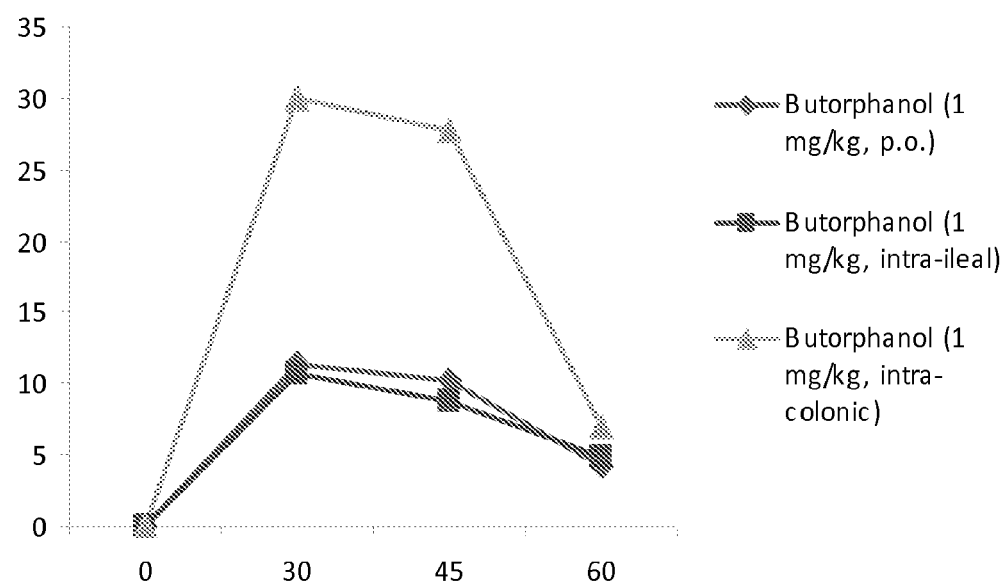
FIG. 13: Time-effect curves depicting antinociceptive effect of intra-gastric, intra-ileal and intra-colonic butorphanol in the tail flick test. The percent maximum possible effect (% MPE) is plotted versus time. Top curve (intra-colonic, triangle), second from top curve (intra-ileal, large square) and bottom curve (intra-gastric, diamond).

Results: Intra-gastric, intra-ileal, and intra-colonic administration of butorphanol each caused a significant increase in the tail flick latency in rats. However, intra-colonic administration of butorphanol produced a significantly greater antinociceptive effect that intra-gastric or intra-ileal (see FIG. 13).

Hot Plate Test

Background

Heat is often used as a noxious stimulus in models of pain. Typically, the latency of the rat's response to the thermal stimulus is recorded as the dependent variable. To determine whether a test compound has analgesic properties, the latency responses of treated and control rats are evaluated. A significant increase in the latency to respond to the thermal stimulus after a treatment relative to a control treatment is interpreted as an antinociceptive or analgesic response. The latency of response will vary depending on the type of heat stimulus used. In the hot-plate assay, the rat is placed on a heated surface and the latency for the rat to respond to the stimulus, by licking its paw or jumping, is recorded.

Example 61

Aim

The aim of this study was to evaluate the analgesic effect of orally administered butorphanol following administration into different parts of the gastrointestinal tract in transiently ether anaesthetized rats, using the hot plate test of nociception The primary measurements were made using the hot plate test designed to detect effects of the treatment(s) on nociception in rats.

Animals:

Wistar rats weighing 250±20 g were maintained on standard laboratory diet and having free access to tap water ad lib were employed in the present study. They were housed in the animal house and were exposed to 12 hr cycle of light and dark. The experiments were conducted in a semi-sound proof laboratory. Care of the animals was in accordance with guidelines for experimentation on animals.

Experimental Design:

Three groups were employed in the present study with each group comprising of 8 animals. Each animal was subjected to transient ether anesthesia followed by a minor incision in the abdominal cavity through which butorphanol 1 mg/kg was administered using a syringe into the stomach, ileum and colon. Hot plate latency was assessed at 0, 30, 45 and 60 minutes after administration of the butorphanol. Area under the curve was calculated using a graph between % MPE and time. Area under the curve was employed as a quantitative measure of the analgesic effect of the treatments.

Measurement of Effect:

Nociceptive threshold was measured with the Eddy's hot plate test. The reaction time was considered as the time between placing of the rat on the Eddy's hot plate heated to a temperature of 52.5° C. and the reaction of the animal in the form of a jump or fore paw licking reflex. A cut-off latency time was fixed at 10 sec. Reaction time is expressed as a percentage of the maximum possible effect (MPE):

$$MPE(\%) = \frac{(\text{Post treatment latency} - \text{pre treatment latency})}{(\text{Cut-off-time} - \text{pre treatment latency})} \times 100$$

Data Analysis:

The anti-nociceptive effect following intragastric, intra-ileal and intra-colonic administration was assessed in terms of area under the curve calculated from a graph having time (relative to dosing time point) on the x-axis and percent maximum possible effect (% MPE) on the y-axis. The results were expressed as mean±standard error of means (S.E.M.). Statistical analysis for was done using one-way ANOVA, followed by Tukey's multiple range tests as post-hoc analysis. A value of P<0.05 was considered to be statistically significant.

Figure 14:
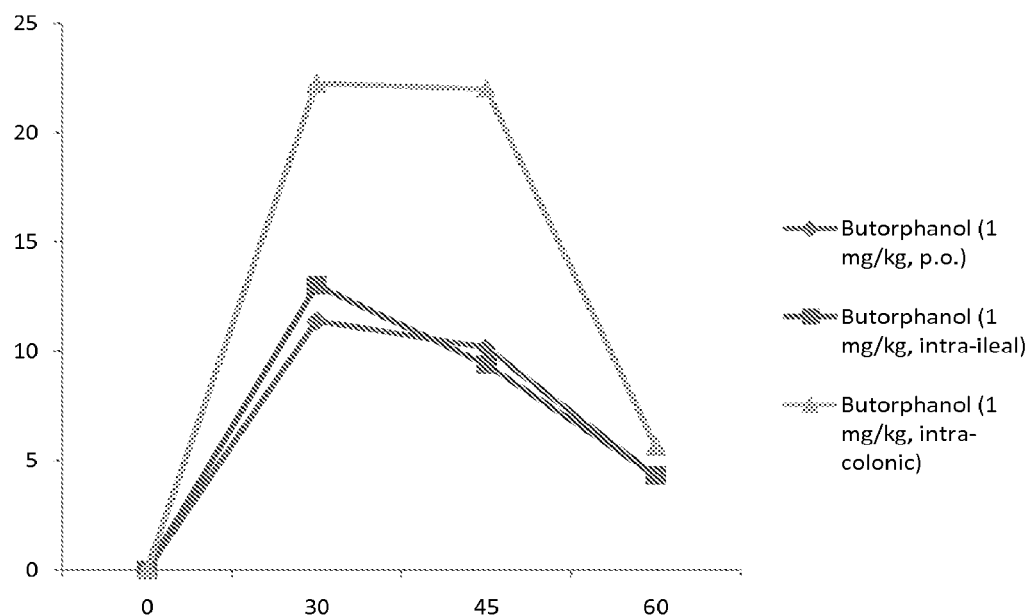
FIG. 14: Time-effect curves depicting antinociceptive effect of intra-gastric, intra-ileal and intra-colonic butorphanol in the tail flick test. The percent maximum possible effect (% MPE) is plotted versus time. Top curve (intra-colonic, triangle), second from top curve (intra-ileal, large square) and bottom curve (intra-gastric, diamond).

Results:

Intra-gastric, intra-ileal, and intra-colonic administration of butorphanol each caused a significant increase in the hot plate latency in rats. However, intra-colonic administration of butorphanol produced a significantly greater antinociceptive effect that intra-gastric or intra-ileal (see FIG. 14).

Chemotherapy Induced Peripheral Neuropathy

Example 62

Aim

The aim of this study was to evaluate the effect of oral administration of butorphanol in rats with vincristine induced painful neuropathy. The primary measurements were made mechanical and thermal allodynia designed to detect effects of the treatment(s) on neuropathic pain.

Animals:

Wistar rats weighing 250±20 g were maintained on standard laboratory diet and having free access to tap water ad lib were employed in the present study. They were housed in the animal house and were exposed to 12 hr cycle of light and dark. The experiments were conducted in a semi-sound proof laboratory. Care of the animals was in accordance with guidelines for experimentation on animals.

Experimental Design:

The vincristine model was adapted from Authier et al (1999). Rats were injected on five alternate days (day 4, 6, 8, 10 & 12) with vincristine (200 µg/kg i.p.) using an injection volume of 2 ml/kg. Thus, the cumulative dose of vincristine was computed to be 1 mg/kg. Tests took place three days after the last injection and continued over the next three weeks. Five groups were employed in the present study with each group comprising of 8 animals: Group 1: Vehicle control group 2 ml/kg, i.p.; Group II: Oral butorphanol 1 mg/kg; Group III: Oral butorphanol 3 mg/kg; Group IV: Oral butorphanol 10 mg/kg; Group V: Oral butorphanol 30 mg/kg.

Measurement of Effect

Assessment of Mechanical Allodynia

Mechano-allodynia was assessed using von Frey filaments. The filaments are nylon monofilaments of different diameters that exert defined levels of force to cause the hair to bend. Once a rat was calm, a series of von Frey filaments with roughly exponential incremental target force (0.008, 0.02, 0.04, 0.07, 0.16, 0.4, 0.6, 1, 1.4, 2, 4, 6, 8, 10, 15, 26, 60, 100, 180, 300 g) were applied to the bottom of the right paw, behind the front pads and lateral to the medial pads of the rat. The filament was presented perpendicular to the rat paw and applied with enough force so as to cause a slight bend. It was held steadily against the paw for a period of 5 s. A response was considered positive if, within the 5-s period, the rat withdrew from the stimulus or briskly withdrew immediately after the filament was removed. A negative response was the one in which the rat did not withdraw within the given time. Testing was initiated using middle filament (2 g). A negative response required the use of next filament with greater bending force. A positive response required the use of next filament with less bending force. Both hind paws were tested for allodynia and the average of the two was recorded as data. Results were expressed in grams and determined before and 30 and 60 min after the administration of the test drugs.

Assessment of Cold Allodynia

For the assessment of cold allodynia, which was stable for 3 weeks, the rats were placed on a wire mesh covered with a plastic dome and were allowed to habituate until the exploratory behavior diminished. Cold allodynia was measured as the number of foot withdrawal responses after application of stimuli to the plantar surface of the paw. A drop of acetone (10 µl) was gently applied to the heel of the animal with a micro-pipette. A brisk foot withdrawal response (shaking, tapping, or licking) after the spread of acetone over the plantar region of the paw was considered a sign of cold allodynia. Acetone was applied two times (once every 5 min) on the left paw, and the number of reactions (shaking, tapping, or licking) was counted during 30 sec. A cut-off number of reactions were fixed at 20 per trial (i.e. 40). The score was expressed as accumulated numbers of reactions over the trials and determined before and 30 and 60 min after administration of the test drugs. Each individual test was expressed as a percentage of maximum possible effect (% MPE):

$$MPE\ (\%) = \frac{(\text{Post treatment frequency} - \text{pre treatment frequency})}{(\text{Cut-off frequency} - \text{pre treatment frequency})} \times 100$$

The peak effect was seen at a time point 30 minutes after the drug administration. MPE (%) at 30 min time point was employed as a quantitative measure of the analgesic effect of the test drugs.

Data Analysis:

The anti-nociceptive effect was plotted assessed having time (relative to dosing time point) on the x-axis and percent maximum possible effect (% MPE) on the y-axis. The results were expressed as mean±standard error of means (S.E.M.). Statistical analysis for was done using one-way ANOVA, followed by Tukey's multiple range tests as post-hoc analysis. A value of P<0.05 was considered to be statistically significant.

Results

Response to Mechanical Allodynia

Figure 15:
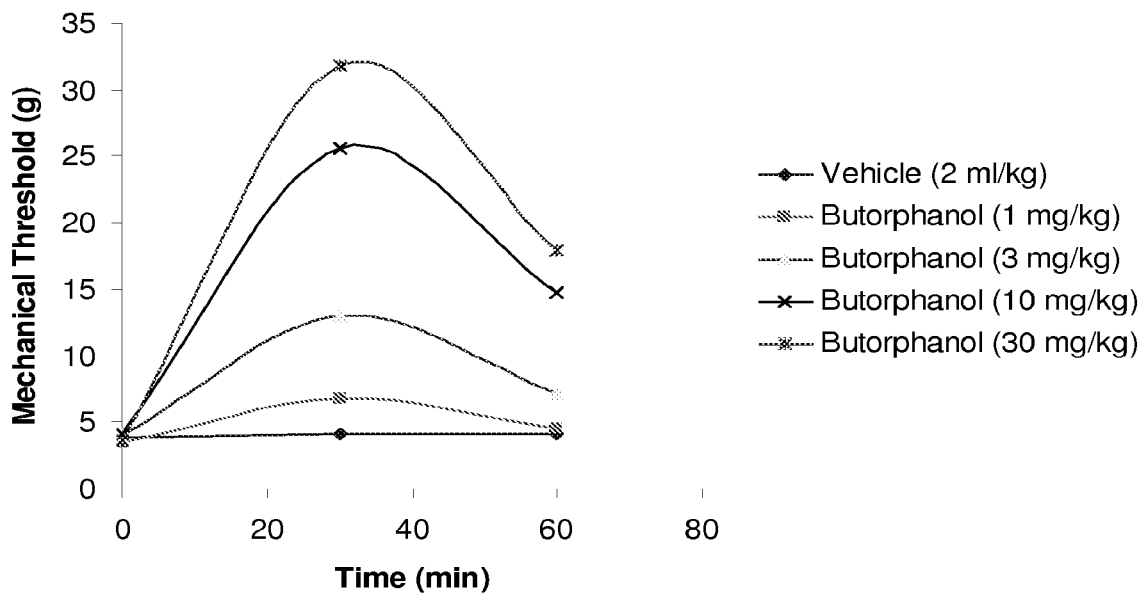
FIG. 15: Time-effect curves depicting the analgesic effect of the orally administered butorphanol in the von Frey hair test of mechanical threshold of pain in rats with vincristine induced peripheral neuropathy. The mechanical threshold of pain (g) are plotted versus time]

Baseline mean mechanical withdrawal threshold in the vincristine treatment induced neuropathic rat was observed to be 4.04±0.77 g. All animals included in the study had a mean threshold below five, thus conforming to the requirements of being considered neuropathic. Oral administration of butorphanol demonstrated a dose dependent increase in the mechanical withdrawal threshold that elicits pain in the neuropathic rats. Moreover, the effect of the butorphanol was dependent on the dose and the peak effect of drug was noted to be 30 min post-administration (FIG. 15).

Response to Cold Allodynia

Figure 16:
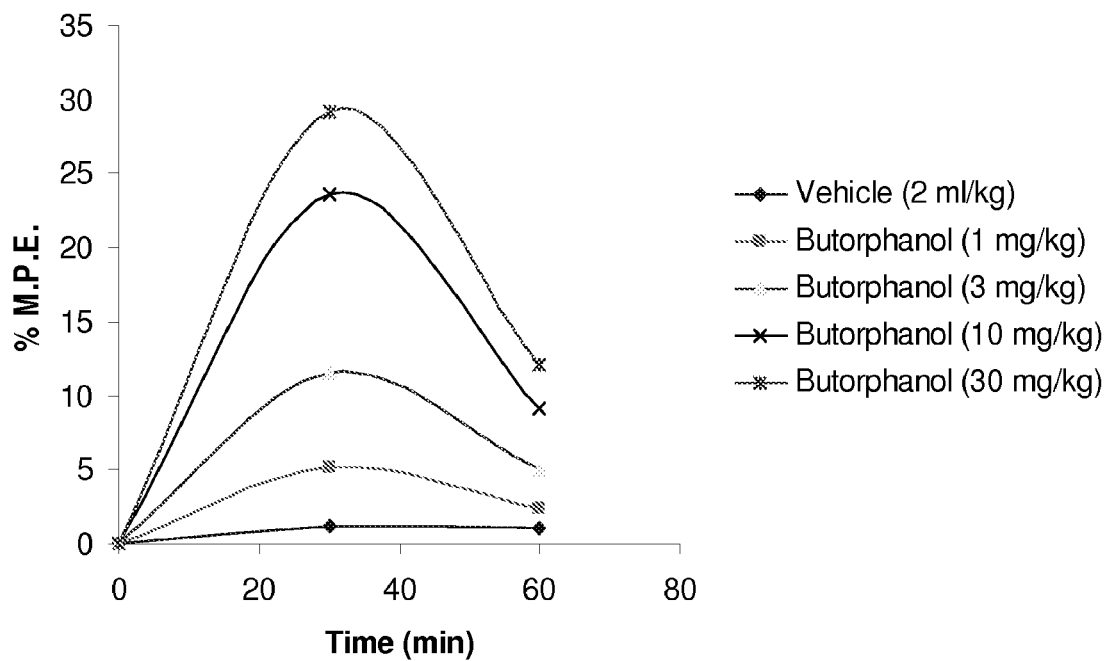
FIG. 16: Time-effect curves depicting the analgesic effect of the orally administered butorphanol in the acetone drop test of thermal allodynia as assessed in rats with vincristine induced peripheral neuropathy. The percent maximum possible effect (% MPE) is plotted versus time.

Baseline of cold allodynia score was determined using the acetone drop test in the vincristine treatment induced neuropathic rats. Moreover, effect of the drug was dependent on the dose and the peak effect of drug was noted to be 30 min post-administration. Furthermore, the oral administration of butorphanol demonstrated a dose dependent decrease in the cold allodynia score in the neuropathic rats (FIG. 16).

Conclusion:

Oral administration of butorphanol caused a significant increase in the mechanical allodynia withdrawal threshold and cold allodynia withdrawal threshold in rats with neuropathic pain in comparison to the control readings. This effect of butorphanol was observed to be dependent of the dose. Thus, butorphanol demonstrated a marked dose dependent effect in rats with vincristine induced neuropathy.

Example 63

Aim

The aim of this study was to evaluate the effect of oral administration of butorphanol in rats with paclitaxel induced painful neuropathy. The primary measurements were made mechanical and thermal allodynia designed to detect effects of the treatment(s) on neuropathic pain.

Animals:

Wistar rats weighing 250±20 g were maintained on standard laboratory diet and having free access to tap water ad lib were employed in the present study. They were housed in the animal house and were exposed to 12 hr cycle of light and dark. The experiments were conducted in a semi-sound proof laboratory. Care of the animals was in accordance with guidelines for experimentation on animals.

Experimental Design:

Rats were injected on five alternate days (day 4, 6, 8, 10 & 12) with paclitaxel (2 mg/kg i.p.) using an injection volume of 2 ml/kg. Thus, the cumulative dose of paclitaxel was computed to be 10 mg/kg. Tests took place ten days after the last injection and continued over the next three weeks. Five groups were employed in the present study with each group comprising of 8 animals: Group I (Vehicle control group): Vehicle (2 ml/kg, i.p) administration was followed by the pain assessment; Group II (Oral butorphanol treatment group-I): Butorphanol (0.01 mg/kg, p.o.) administration was followed by the pain assessment; Group III (Oral butorphanol treatment group-II): Butorphanol (0.03 mg/kg, p.o) administration was followed by the pain assessment; Group IV (Oral butorphanol treatment group-III): Butorphanol (0.1 mg/kg, p.o) administration was followed by the pain assessment; Group V (Oral butorphanol treatment group-IV): Butorphanol (0.3 mg/kg, p.o) administration was followed by the pain assessment.

Measurement of Effect

Assessment of Mechanical Allodynia

Mechano-allodynia was assessed using von Frey filaments. The filaments are nylon monofilaments of different diameters that exert defined levels of force to cause the hair to bend. Once a rat was calm, a series of von Frey filaments with roughly exponential incremental target force (0.008, 0.02, 0.04, 0.07, 0.16, 0.4, 0.6, 1, 1.4, 2, 4, 6, 8, 10, 15, 26, 60, 100, 180, 300 g) were applied to the bottom of the right paw, behind the front pads and lateral to the medial pads of the rat. The filament was presented perpendicular to the rat paw and applied with enough force so as to cause a slight bend. It was held steadily against the paw for a period of 5 s. A response was considered positive if, within the 5-s period, the rat withdrew from the stimulus or briskly withdrew immediately after the filament was removed. A negative response was the one in which the rat did not withdraw within the given time. Testing was initiated using middle filament (2 g). A negative response required the use of next filament with greater bending force. A positive response required the use of next filament with less bending force. Both hind paws were tested for allodynia and the average of the two was recorded as data. Results were expressed in grams and determined before and 30 and 60 min after the administration of the test drugs.

Assessment of Cold Allodynia

For the assessment of cold allodynia, which was stable for 3 weeks, the rats were placed on a wire mesh covered with a plastic dome and were allowed to habituate until the exploratory behavior diminished. Cold allodynia was measured as the number of foot withdrawal responses after application of stimuli to the plantar surface of the paw. A drop of acetone (10 µl) was gently applied to the heel of the animal with a micro-pipette. A brisk foot withdrawal response (shaking, tapping, or licking) after the spread of acetone over the plantar region of the paw was considered a sign of cold allodynia. Acetone was applied two times (once every 5 min) on the left paw, and the number of reactions (shaking, tapping, or licking) was counted during 30 sec. A cut-off number of reactions were fixed at 20 per trial (i.e. 40). The score was expressed as accumulated numbers of reactions over the trials and determined before and 30 and 60 min after administration of the test drugs. Each individual test was expressed as a percentage of maximum possible effect (% MPE):

$$MPE\,(\%) = \frac{(\text{Post treatment frequency} - \text{pre treatment frequency})}{(\text{Cut-off frequency} - \text{pre treatment frequency})} \times 100$$

The peak effect was seen at a time point 30 minutes after the drug administration. MPE (%) at 30 min time point was employed as a quantitative measure of the analgesic effect of the test drugs.

Data Analysis:

The anti-nociceptive effect was plotted assessed having time (relative to dosing time point) on the x-axis and percent maximum possible effect (% MPE) on the y-axis. The results were expressed as mean±standard error of means (S.E.M.). Statistical analysis for was done using one-way ANOVA, followed by Tukey's multiple range tests as post-hoc analysis. A value of P<0.05 was considered to be statistically significant.

Results

Response to Mechanical Allodynia

Figure 17:
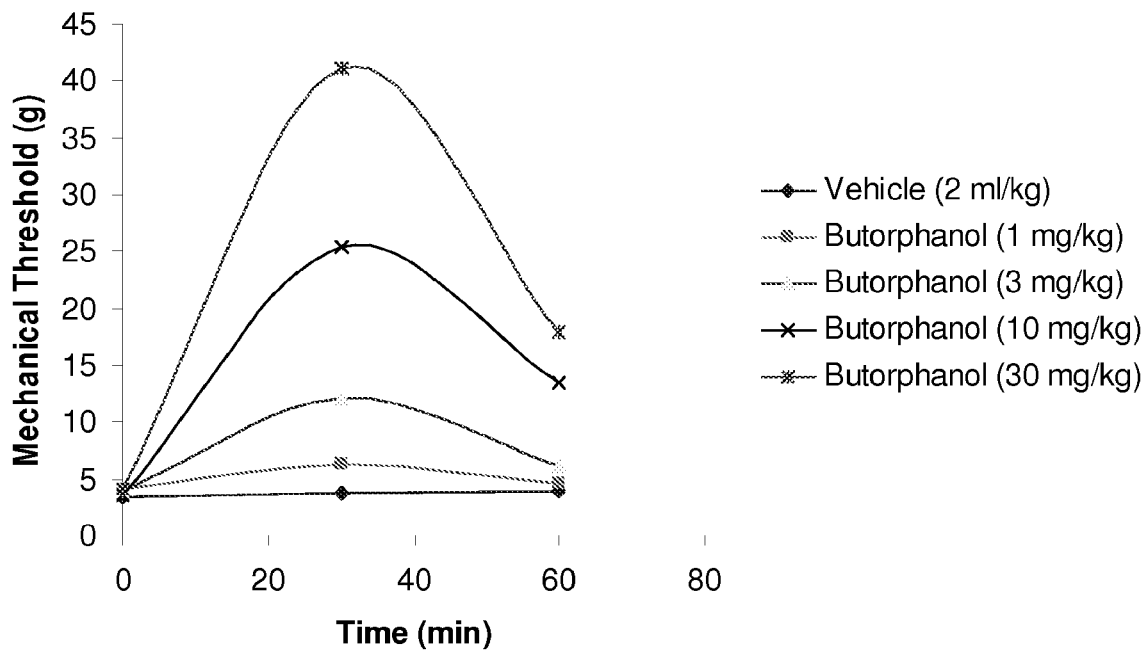
FIG. 17: Time-effect curves depicting the analgesic effect of the orally administered butorphanol in the von Frey hair test of mechanical threshold of pain in rats with paclitaxel induced peripheral neuropathy. The mechanical threshold of pain (g) are plotted versus time]

Baseline mean mechanical withdrawal threshold in the paclitaxel treatment induced neuropathic rat was observed to be 4.23±0.42 g. All animals included in the study had a mean threshold below five, thus conforming to the requirements of being considered neuropathic. Oral administration of butorphanol demonstrated a dose dependent increase in the mechanical withdrawal threshold that elicits pain in the neuropathic rats. Moreover, the effect of the butorphanol was dependent on the dose and the peak effect of drug was noted to be 30 min post-administration (FIG. 17).

Response to Cold Allodynia

Figure 18:
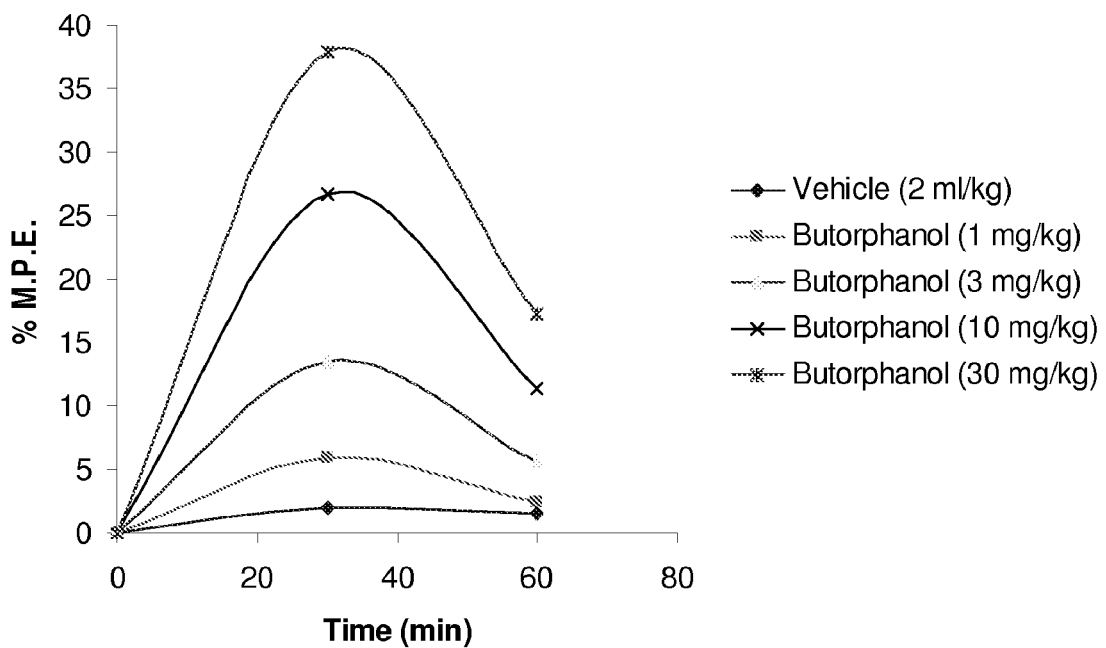
FIG. 18: Time-effect curves depicting the analgesic effect of the orally administered butorphanol in the acetone drop test of thermal allodynia as assessed in rats with paclitaxel induced peripheral neuropathy. The percent maximum possible effect (% MPE) is plotted versus time.

Baseline of cold allodynia score was determined using the acetone drop test in the paclitaxel treatment induced neuropathic rats. Moreover, effect of the drug was dependent on the dose and the peak effect of drug was noted to be 30 min post-administration. Furthermore, the oral administration of butorphanol demonstrated a dose dependent decrease in the cold allodynia score in the neuropathic rats (FIG. 18).

Conclusion:

Oral administration of butorphanol caused a significant increase in the mechanical allodynia withdrawal threshold and cold allodynia withdrawal threshold in rats with neuropathic pain in comparison to the control readings. This effect of butorphanol was observed to be dependent of the dose. Thus, butorphanol demonstrated a marked dose dependent effect in rats with paclitaxel induced neuropathy.

Streptozotocin Induced Diabetic Neuropathy

Example 64

Aim

The aim of this study was to evaluate the effect of oral administration of butorphanol in rats with streptozotocin (STZ) induced diabetes neuropathy. A single injection of streptozotocin (STZ) (40-70 mg/kg, i.p.) was used to induce diabetes in rats. The primary measurements were made mechanical and thermal allodynia designed to detect effects of the treatment(s) on neuropathic pain.

Animals:

Wistar rats weighing 250±20 g were maintained on standard laboratory diet and having free access to tap water ad lib were employed in the present study. They were housed in the animal house and were exposed to 12 hr cycle of light and dark. The experiments were conducted in a semi-sound proof laboratory. Care of the animals was in accordance with guidelines for experimentation on animals.

Experimental Design:

The STZ-induced diabetes model was adapted from Arison et al (1967).

On the experimental day 1 all rats were fasted 6-8 hrs prior to STZ treatment Immediately prior to the injection, STZ was dissolved in 50 Mm sodium citrate buffer (pH 4.5) to a final concentration of 10 mg/ml. Using an insulin syringe and a 26 G needle, STZ solution was injected intraperitoneally at a dose level of 40-70 mg/kg. The animals were then shifted individually to their home cage and were provided normal food and 10% sucrose water. On experimental day 2 the sucrose water was switched to regular water. On experimental day 21 all rats were fasted for 6-8 hrs the blood glucose level was tested from a tail vein sample using a spectrophotometeric method in order to check hyperglycemia. Blood glucose levels ranging from 250-600 mg/dL confirmed diabetes in the STZ injected rats. Neuropathy assessment tests were performed after the completion of 8 weeks after STZ treatment. Tests continued over the next four weeks. Five groups were employed in the present study with each group comprising of 8 animals: Group I: Vehicle control group, 2 ml/kg, i.p.; Group II: Oral butorphanol, 1 mg/kg; Group III: Oral butorphanol 3 mg/kg; Group IV: Oral butorphanol 10 mg/kg; Group V: Oral butorphanol 30 mg/kg.

Measurement of Effect

Assessment of Mechanical Allodynia:

Mechano-allodynia was assessed using von Frey filaments. The filaments are nylon monofilaments of different diameters that exert defined levels of force to cause the hair to bend. Once a rat was calm, a series of von Frey filaments with roughly exponential incremental target force (0.008, 0.02, 0.04, 0.07, 0.16, 0.4, 0.6, 1, 1.4, 2, 4, 6, 8, 10, 15, 26, 60, 100, 180, 300 g) were applied to the bottom of the right paw, behind the front pads and lateral to the medial pads of the rat. The filament was presented perpendicular to the rat paw and applied with enough force so as to cause a slight bend. It was held steadily against the paw for a period of 5 s. A response was considered positive if, within the 5-s period, the rat withdrew from the stimulus or briskly withdrew immediately after the filament was removed. A negative response was the one in which the rat did not withdraw within the given time. Testing was initiated using middle filament (2 g). A negative response required the use of next filament with greater bending force. A positive response required the use of next filament with less bending force. Both hind paws were tested for allodynia and the average of the two was recorded. Results were expressed in grams and determined before and 30 and 60 min after the administration of the test drugs.

Assessment of Cold Allodynia

For the assessment of cold allodynia, which was stable for 3 weeks, the rats were placed on a wire mesh covered with a plastic dome and were allowed to habituate until the exploratory behavior diminished. Cold allodynia was measured as the number of foot withdrawal responses after application of stimuli to the plantar surface of the paw. A drop of acetone (10 µl) was gently applied to the heel of the animal with a micro-pipette. A brisk foot withdrawal response (shaking, tapping, or licking) after the spread of acetone over the plantar region of the paw was considered a sign of cold allodynia. Acetone was applied two times (once every 5 min) on the left paw, and the number of reactions (shaking, tapping, or licking) was counted during 30 sec. A cut-off number of reactions were fixed at 20 per trial (i.e. 40). The score was expressed as accumulated numbers of reactions over the trials and determined before and 30 and 60 min after administration of the test drugs. Each individual test was expressed as a percentage of maximum possible effect (% MPE):

$$MPE\,(\%) = \frac{(\text{Post treatment frequency} - \text{pre treatment frequency})}{(\text{Cut-off frequency} - \text{pre treatment frequency})} \times 100$$

The peak effect was seen at a time point 30 minutes after the drug administration. MPE (%) at 30 min time point was employed as a quantitative measure of the analgesic effect of the test drugs.

Data Analysis:

The anti-nociceptive effect was plotted assessed having time (relative to dosing time point) on the x-axis and percent maximum possible effect (% MPE) on the y-axis. The results were expressed as mean±standard error of means (S.E.M.). Statistical analysis for was done using one-way ANOVA, followed by Tukey's multiple range tests as post-hoc analysis. A value of $P<0.05$ was considered to be statistically significant.

Results

Response to Mechanical Allodynia

Figure 19:
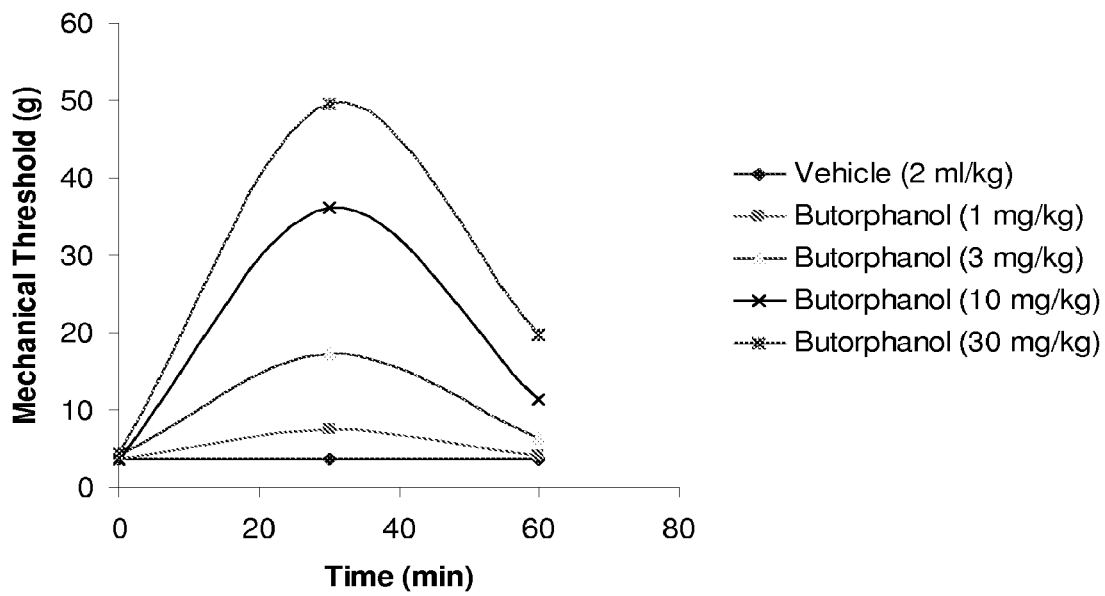
FIG. 19: Time-effect curves depicting the analgesic effect of the orally administered butorphanol in the von Frey hair test of mechanical threshold of pain in rats with streptozotocin (STZ) induced diabetes neuropathy. The mechanical threshold of pain (g) are plotted versus time]

Baseline mean mechanical withdrawal threshold in the diabetes induced neuropathy in rats was observed to be 2.91±0.23 g. All animals included in the study had a mean threshold below five, thus conforming to the requirements of being considered neuropathic. Oral administration of butorphanol demonstrated a dose dependent increase in the mechanical withdrawal threshold that elicits pain in the neuropathic rats. Moreover, the effect of the butorphanol was dependent on the dose and the peak effect of drug was noted to be 30 min post-administration (FIG. 19).

Response to Cold Allodynia

Figure 20:
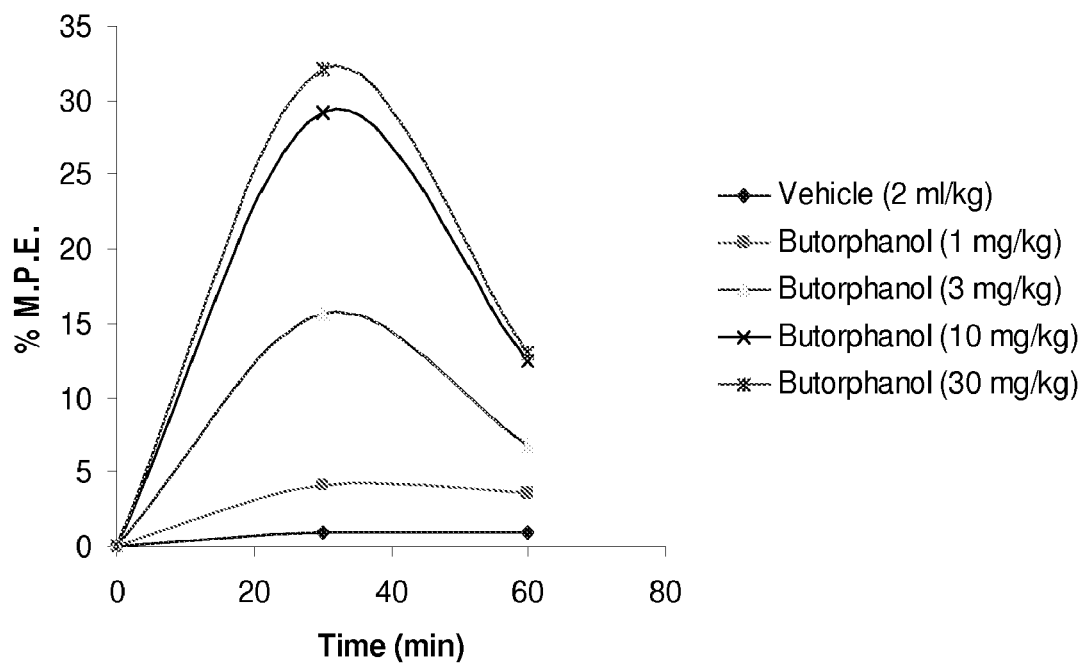
FIG. 20: Time-effect curves depicting the analgesic effect of the orally administered butorphanol in the acetone drop test of thermal allodynia as assessed in rats with streptozotocin (STZ) induced diabetes neuropathy. The percent maximum possible effect (% MPE) is plotted versus time.

Baseline of cold allodynia score was determined using the acetone drop test in the SNL induced neuropathic rats. Moreover, effect of the drug was dependent on the dose and the peak effect of drug was noted to be 30 min post-administration. Furthermore, the oral administration of butorphanol demonstrated a dose dependent decrease in the cold allodynia score in the neuropathic rats (FIG. 20).

Conclusion:

Oral administration of butorphanol caused a significant increase in the mechanical allodynia and cold allodynia withdrawal thresholds in rats with STZ induced diabetic neuropathic pain in comparison to the control readings. This effect of butorphanol was observed to be dependent of the dose. Thus, butorphanol demonstrated a marked dose dependent effect in rats with STZ induced diabetic neuropathic pain.

Clinical Response to Modified Release Butorphanol

Example 65

The therapeutic effect of single dose oral butorphanol was evaluated in patients with chronic pain. Oral butorphanol intended for delayed onset, rapid release was prepared by encapsulating butorphanol tartrate 6 mg diluted with 94 mg of lactose) into a capsule.

Following encapsulation, the dosage form was coated using the coated with polymers using the method described herein to provide release at a pH >7. Release of capsule contents at the desired pH was confirmed by in vitro testing, using a dye. Five subjects each with chronic low back pain and osteoarthritis, all with moderate to severe pain received a single dose of oral delayed onset, rapid release butorphanol early in the morning. The onset of pain and magnitude of pain relief was recorded using a categorical scale ((My relief from starting pain is: 0=None, 1=A little, 2=Some, 3=A lot, and 4=Complete). After a delay of approximately 2 to 5 hours, 3 of 5 patients with back pain and 4 of 5 patients with osteoarthritis reported some a lot of relief or complete relief. One patient with osteoarthritis reported some relief. One patient with low back pain reported a lot relief after one hour and a further one patient reported little relief. Two patients each experienced mild nausea and mild drowsiness at the time of their pain relief Example 66

The therapeutic effect of repeated dose oral butorphanol was evaluated in patients with chronic pain by comparing oral immediate release butorphanol with oral modified release butorphanol intended for delayed onset, rapid release butorphanol. Oral immediate release butorphanol was prepared by encapsulating butorphanol tartrate 4 mg diluted with 96 mg of lactose) into a capsule. Oral butorphanol intended for delayed onset, rapid release was prepared by coating the above capsules with polymers, using the method described herein to provide release at a pH ≥7. Release of capsule contents at the desired pH was confirmed by in vitro testing, using a dye at pH 5.5 and at pH 7. Oral butorphanol intended for immediate release liberated the dye at pH 5.5 in less than 10 minutes, while oral butorphanol intended for delayed onset, rapid release did not liberate its dye at pH 5.5 for at least 2 hours, but liberated its dye at pH 7 in less than 10 minutes. Five patients each with chronic low back pain and osteoarthritis, all with moderate to severe pain received oral immediate release butorphanol or delayed onset, rapid release butorphanol for one week (5 to 7 days). Patients were instructed to take the first dose of medication at bedtime. Pain was assessed in the clinic before initiating therapy and upon the return clinic visit one week later using an 11-point Likert Numeric Rating Scale (NRS). Side effects were recorded at the return clinic visit using a non-directed questionnaire. Both oral immediate release butorphanol and delayed onset, rapid release butorphanol provided pain relief. However, the pain relief in the overall treatment group receiving delayed onset, rapid release was greater (Baseline Score: 7.6, Post-treatment Score 3.0) than after oral immediate release butorphanol (Baseline Score: 7.2, Post-treatment Score 4.6). Nausea and drowsiness were almost twice as common in the immediate release butorphanol than in the delayed onset, rapid release butorphanol group. In addition, the intensity of both nausea and drowsiness was higher in the immediate release butorphanol than in the delayed onset, rapid release butorphanol group.

These and other embodiments of the present invention will readily occur to those of ordinary skill in the art in view of the disclosure herein.

The included examples are illustrative but not limiting of the methods and composition of the present invention. Other suitable modifications and adaptations of the variety of conditions and parameters normally encountered and obvious to those skilled in the art are within the spirit and scope of the invention.

A wide variety of materials can be used for preparing the dosage form according to this invention. This invention therefore contemplates the use of materials other than those specifically disclosed herein, including those which may hereafter become known to the art to be capable of performing the necessary functions. In all instances wherein prophetic examples are provided, these compositions are intended to be exemplary and it should be understood that the specific procedures, constituents, amounts thereof and the like can be varied in order to obtain a composition possessing desired properties.

Having now fully described the invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:

1. An oral dosage form comprising: (i) a therapeutically effective amount of butorphanol, a pharmaceutically acceptable salt thereof, or a mixture thereof, and (ii) controlled release material to release the butorphanol from the dosage form substantially only into one or more lower segments of the gastrointestinal tract following oral administration of the dosage form.

2. The oral dosage form of claim 1, wherein the dosage form gradually releases substantially all of the butorphanol from the dosage form during a period of at least about 5 hours after the dosage form is distal to the stomach following oral administration of the dosage form.

3. The oral dosage form of claim 1, wherein the dosage form gradually releases substantially all of the butorphanol from the dosage form during a period of from about 5 to 30 hours after the dosage form is distal to the stomach following oral administration of the dosage form.

4. The oral dosage form of claim 1, wherein the dosage form gradually releases substantially all of the butorphanol from the dosage form during a period of from about 5 to 30 hours after the dosage form is distal to the duodenum following oral administration of the dosage form.

5. The oral dosage form of claim 1, wherein the dosage form gradually releases substantially all of the butorphanol from the dosage form over a period of from about 5 to 30 hours after the dosage form is distal to the jejunum following oral administration of the dosage form.

6. The oral dosage form of claim 1, wherein the dosage form gradually releases substantially all of the butorphanol from the dosage form over a period of from about 5 to 30 hours after the dosage form is distal to the ileum following oral administration of the dosage form.

7. The oral dosage form of claim 1, comprising a coating that substantially prevents release of butorphanol therefrom in the stomach.

8. The oral dosage form of claim 7, the coating overcoats a matrix in which the butorphanol is combined with the controlled release material.

9. The oral dosage form of claim 8, wherein the dosage form releases substantially all of the butorphanol from the dosage form after the dosage form is distal to the stomach following oral administration of the dosage form.

10. The oral dosage form of claim 8, wherein the dosage form gradually releases substantially all of the butorphanol from the dosage form during a period of from about 5 to 30 hours after the dosage form is distal to the stomach following oral administration of the dosage form.

11. The oral dosage form of claim 8, wherein the coating dissolves substantially only at a pH greater than about 5.

12. The oral dosage form of claim 11, wherein the coating dissolves substantially only at a pH greater than about 7.

13. The oral dosage form of claim 11, wherein a second coating overcoats the coating, the second coating substantially resists dissolution at a pH greater than about 5.

14. A method of administering butorphanol to a human, the method comprising orally administering to the human the dosage form of claim 1.

15. In a method of administering butorphanol to a human to treat a butorphanol responsive medical condition, the improvement comprising orally administering the butorphanol to the human in the oral dosage form of claim 1.

16. The oral dosage form of claim 1, where each of the one or more lower segments of the gastrointestinal tract is selected from the group consisting of the duodenum, the jejunum the ileum, and the colon.

* * * * *

UNITED STATES PATENT AND TRADEMARK OFFICE
CERTIFICATE OF CORRECTION

PATENT NO. : 10,624,887 B2
APPLICATION NO. : 15/135985
DATED : April 21, 2020
INVENTOR(S) : Najib Babul It is certified that error appears in the above-identified patent and that said Letters Patent is hereby corrected as shown below:

In the Drawings

Page 2, Figure 1, "TRANVSVER COLON" should be --TRANSVERSE COLON--.

Figure 5:
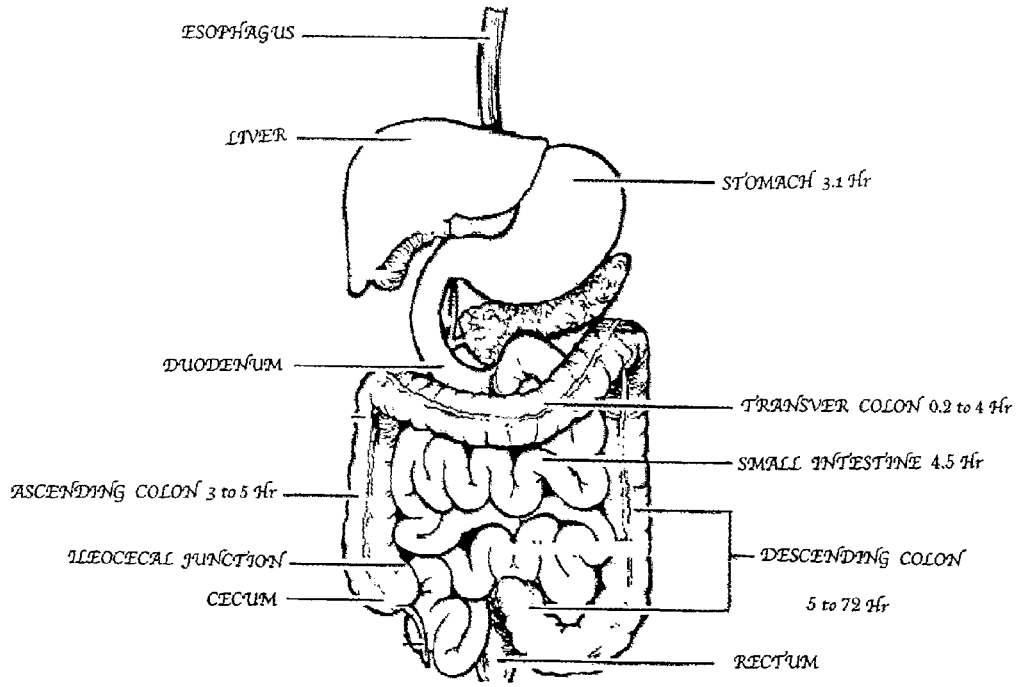
FIG. 5: Illustrates the average gastrointestinal transit times for various segments of the gastrointestinal tract.
Figure 6:
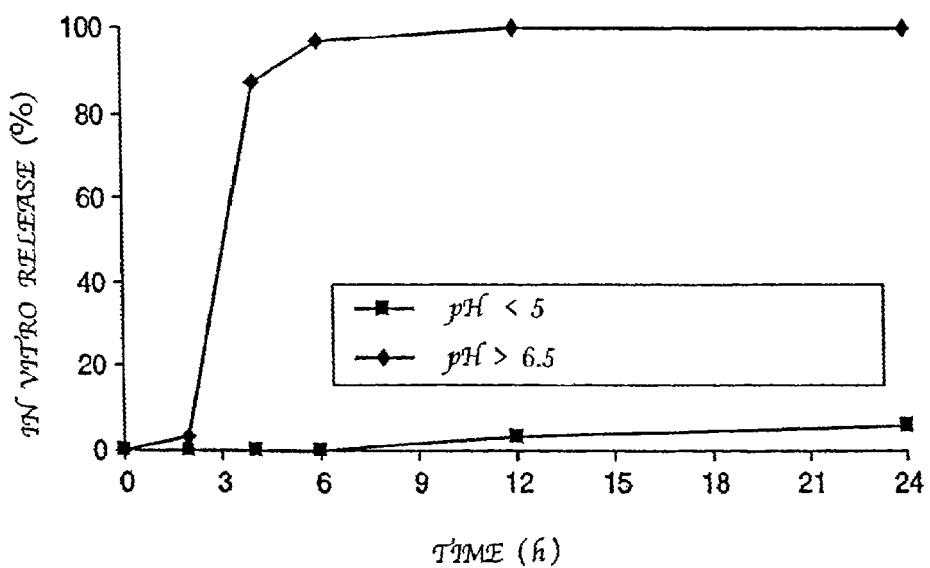
FIG. 6: Illustrates the in vivo release of a delayed onset, rapid release dosage form of oral butorphanol containing an ileo-colonic pH sensitive polymer. The dosage form resists release of the butorphanol at pH less than 5 for a prolonged period of time and releases the contents of the dosage form at a pH greater than 6.5.
Figure 7:
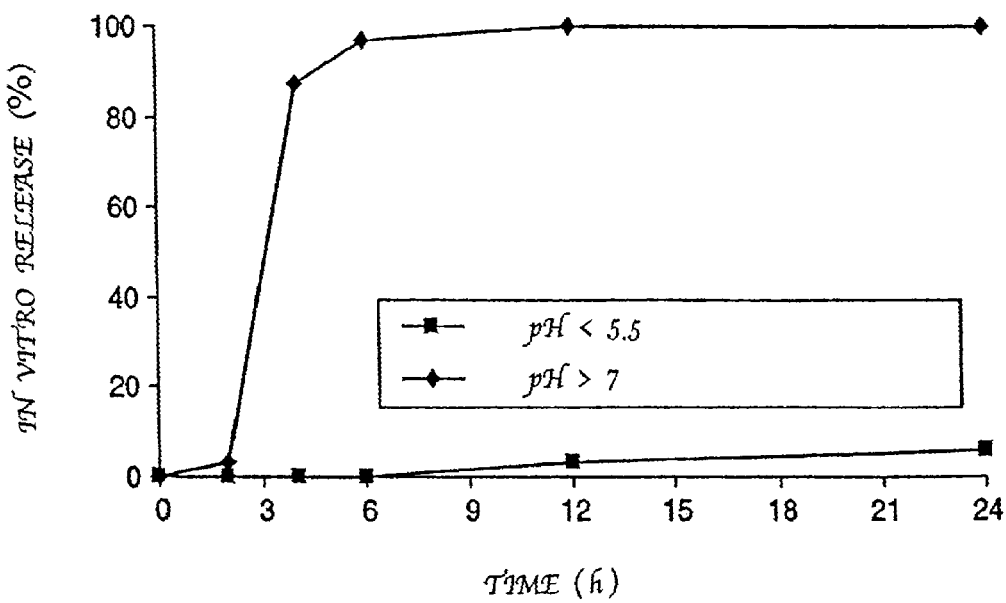
FIG. 7: Illustrates the in vivo release of a delayed onset, rapid release dosage form of oral butorphanol containing an ileo-colonic pH sensitive polymer. The dosage form resists release of the butorphanol at pH less than 5.5 for a prolonged period of time and releases the contents of the dosage form at a pH greater than 7.
Figure 8:
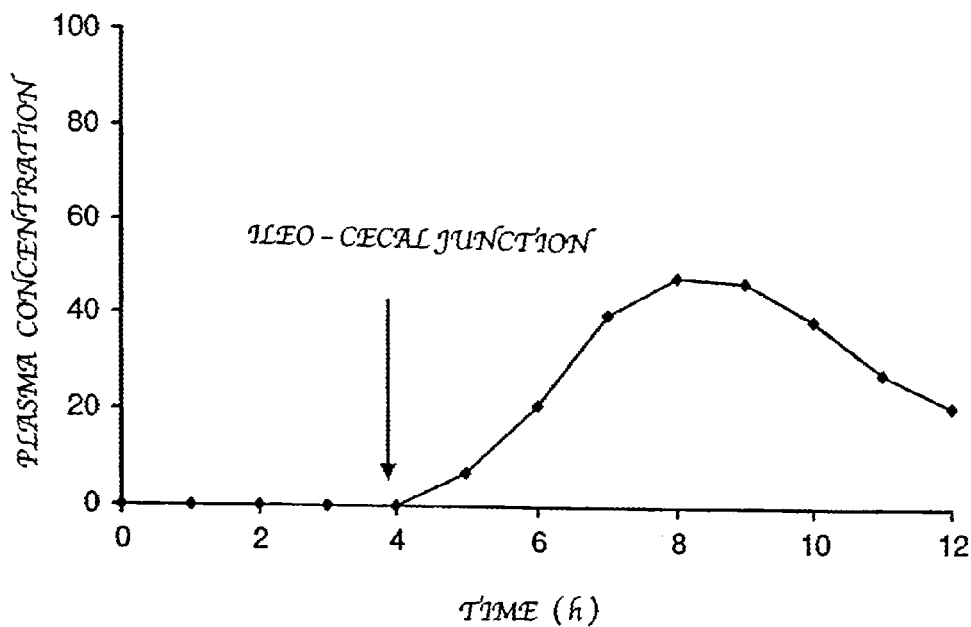
FIG. 8: Illustrates the in vivo release of a delayed onset, extended release dosage form of oral butorphanol upon reaching or traversing the ileo-cecal junction and transiting into the colon.
Figure 9:
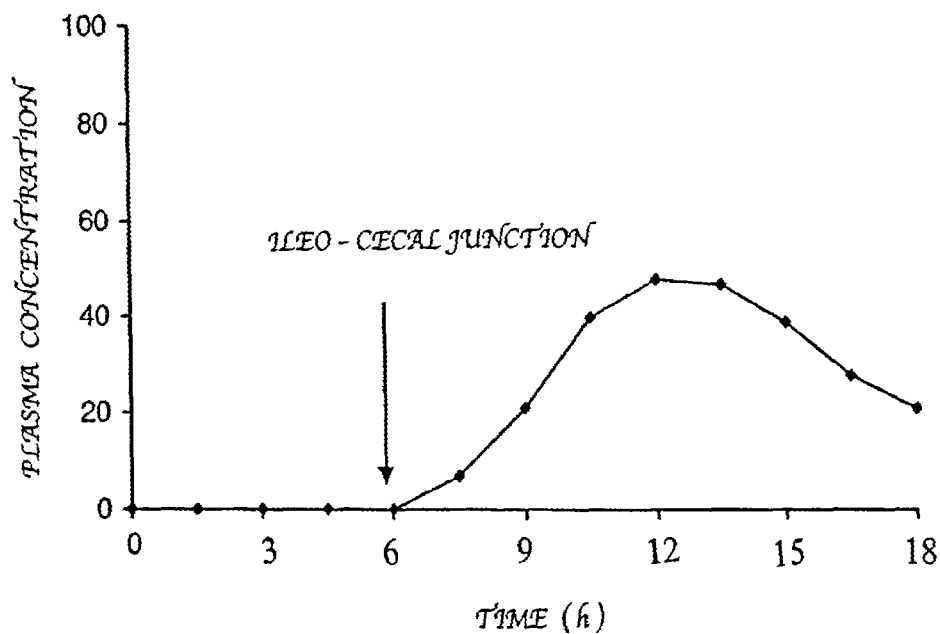
FIG. 9: Illustrates the in vivo release of a delayed onset, extended release dosage form of oral butorphanol upon reaching or traversing the ileo-cecal junction and transiting into the colon.
Figure 10:
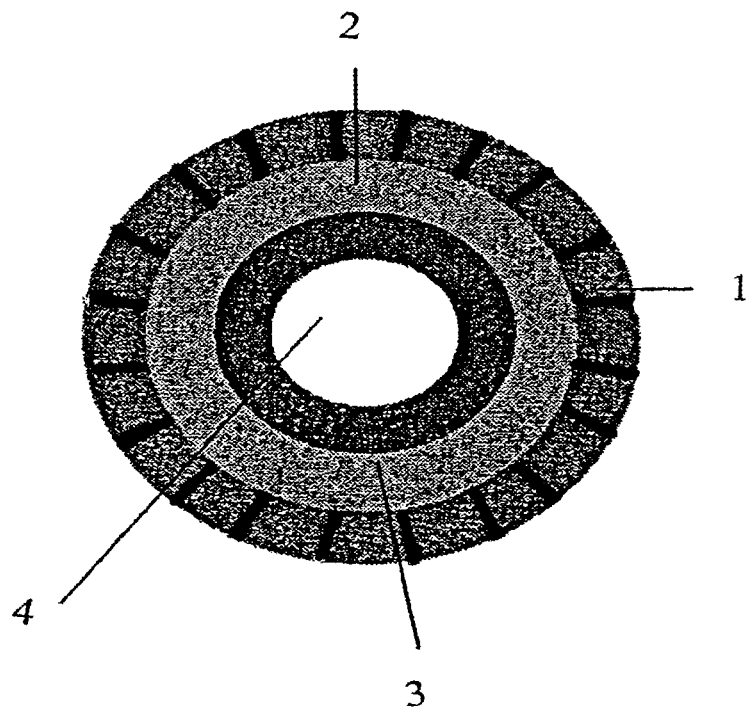
FIG. 10: Illustrates a dosage form for colonic release: (1) the outer layer which dissolves at a pH of about 7; (2) a sustained release polymer coating; (3) the butorphanol which has been coated onto a nonpareil core or bead (4).
Figure 11:
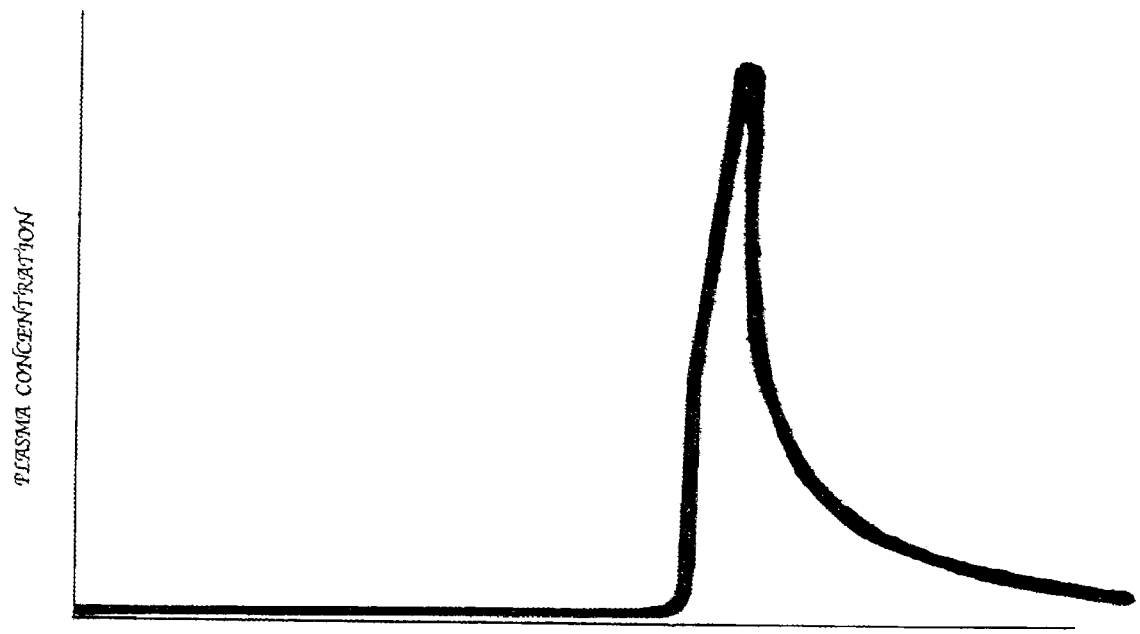
FIG. 11: Illustrates a delayed onset, rapid release dosage form for ileo-colonic or colonic release. Following a lag period during which no butorphanol or very little no butorphanol is released in vivo, the dosage form upon reaching a certain GI environment (e.g., desired pH, pressure, enzymes, microbial flora) or time, or a combination of variables, releases the dosage form in a rapid (albeit) pulse or burst.
Figure 12:
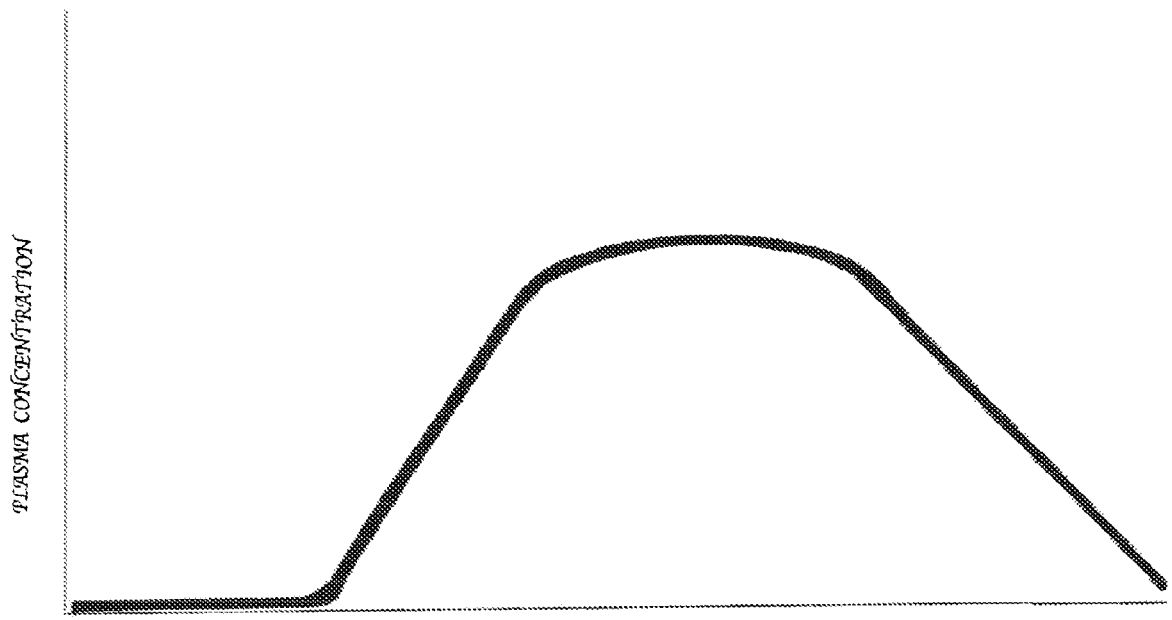
FIG. 12: Illustrates a delayed onset, extended release dosage form for ileo-colonic or colonic release. Following a lag period during which no butorphanol or very little butorphanol is released in vivo, the dosage form upon reaching a certain GI environment (e.g., desired pH, pressure, enzymes, microbial flora) or time, or a combination of variables, releases the dosage form in an extended release form.

Page 4, Figure 5, "TRANVSVER COLON" should be --TRANSVERSE COLON--.

In the Specification

Column 1, Line 18, "it" should be --its--.

Column 1, Line 41, "lack of a consistent," should be --lack of consistent,--.

Column 1, Lines 45-46, "(for example due to GI obstruction, nausea, vomiting, GI obstruction, obtundation" should be --(for example due to GI obstruction, nausea, vomiting, obtundation--.

Column 3, Lines 5-6, "release release form has heretofore not been not been tested" should be --release form has heretofore not been tested--.

Column 3, Line 10, "have been has heretofore been developed" should be --have heretofore been developed--.

Column 3, Lines 13-14, "have been has heretofore been developed" should be --have heretofore been developed--.

Column 3, Lines 15-17, "that that butorphanol deposited, delivered or made bioavailable distal to stomach," should be --that butorphanol deposited, delivered or made bioavailable distal to the stomach,--.

Signed and Sealed this
Seventeenth Day of November, 2020

Andrei Iancu
*Director of the United States Patent and Trademark Office*

Column 3, Lines 23-25, "that that butorphanol deposited, delivered or made bioavailable distal to stomach," should be --that butorphanol deposited, delivered or made bioavailable distal to the stomach,--.

Column 3, Lines 31-33, "that that butorphanol deposited, delivered or made bioavailable distal to stomach," should be --that butorphanol deposited, delivered or made bioavailable distal to the stomach,--.

Column 3, Lines 39-41, "that that butorphanol deposited, delivered or made bioavailable distal to stomach," should be --that butorphanol deposited, delivered or made bioavailable distal to the stomach,--.

Column 4, Line 32, "There is a need oral" should be --There is a need for oral--.

Column 4, Line 36, "ilcal" should be --ileal--.

Column 4, Line 43, "that that" should be --that--.

Column 5, Line 12, "physician visits, etc)." should be --physician visits, etc.).--.

Column 5, Lines 23-24, "was also than 2 hours" should be --was also less than 2 hours--.

Column 5, Line 51, "reduced fed fasted" should be --reduced fed or fasted--.

Column 5, Line 53, "is its potential" should be --is their potential--.

Column 6, Line 14, "applicants" should be --applicant's--.

Column 6, Line 52, "for the treatment for patients" should be --for the treatment of patients--.

Column 7, Line 4, "on" should be --or--.

Column 7, Line 21, "is" should be --are--.

Column 7, Line 27, "where in" should be --wherein--.

Column 10, Lines 20-21, "to provide an oral butorphanol formulation which are delayed onset," should be --to provide oral butorphanol formulations which are delayed onset,--.

Column 10, Lines 30-31, "for up to for up to" should be --for up to--.

Column 10, Lines 57-58, "comprises pharmaceutical composition" should be --comprises a pharmaceutical composition--.

Column 11, Line 9, "etc)." should be --etc.).--.

CERTIFICATE OF CORRECTION (continued)
U.S. Pat. No. 10,624,887 B2

Column 11, Line 28, "greater that" should be --greater than--.

Column 11, Line 36, "means" should be --mean--.

Column 12, Line 20, "mood alerting" should be --mood altering--.

Column 12, Line 33, "mood alerting" should be --mood altering--.

Column 13, Lines 31-32, "mood alerting" should be --mood altering--.

Column 13, Line 43, "mood alerting" should be --mood altering--.

Column 14, Line 3, "mood alerting effects, the term" should be --mood altering effects, the terms--.

Column 14, Line 17, "mood alerting" should be --mood altering--.

Column 14, Line 21, ""mood alerting" should be --mood altering--.

Column 14, Line 57, "hound" should be --bound--.

Column 15, Line 14, "diffusion-controlled pH-controlled," should be --diffusion-controlled, pH-controlled,--.

Column 16, Line approx. 24, "In the applicants view," should be --In the applicant's view,--.

Column 16, Lines approx. 51-52, "higher that the" should be --higher than the--.

Column 16, Line approx. 53, "donot deal with" should be --do not deal with the--.

Column 16, Line approx. 56-58, "generally an onset of euphoric or psychic within about 15 to about 180 minutes" should be --generally bring an onset of euphoric or psychic effects within about 15 to about 180 minutes--.

Column 16, Lines approx. 61-63, "reduces the intensity," should be --reduce the intensity,--.

Column 17, Line approx. 13, "dosage froms" should be --dosage forms--.

Column 17, Line approx. 63, "mood alerting" should be --mood altering--.

Column 18, Lines approx. 5-6, "mood alerting effects" should be --mood altering effects--.

Column 18, Line approx. 16, "mood alerting effects" should be --mood altering effects--.

Column 18, Line approx. 25, "mood alerting" should be --mood altering--.

Column 19, Line 6, "with the an oral immediate release" should be --with an oral immediate release--.

Column 20, Line approx. 19, "a mean a systemic" should be --a mean systemic--.

Column 20, Line approx. 53, "a mean a systemic" should be --a mean systemic--.

Column 21, Line approx. 4, "a mean a systemic" should be --a mean systemic--.

Column 21, Line approx. 24, "a mean a systemic" should be --a mean systemic--.

Column 21, Line approx. 57, "a mean a systemic" should be --a mean systemic--.

Column 22, Line approx. 7, "a mean a systemic" should be --a mean systemic--.

Column 22, Line approx. 26, "a mean a systemic" should be --a mean systemic--.

Column 22, Line approx. 60, "a mean a systemic" should be --a mean systemic--.

Column 23, Line approx. 11, "a mean a systemic" should be --a mean systemic--.

Column 23, Line approx. 31, "a mean a systemic" should be --a mean systemic--.

Column 23, Line approx. 64, "a mean a systemic" should be --a mean systemic--.

Column 24, Line approx. 14, "a mean a systemic" should be --a mean systemic--.

Column 24, Line approx. 33, "a mean a systemic" should be --a mean systemic--.

Column 24, Line 67, "a mean a systemic" should be --a mean systemic--.

Column 25, Line approx. 18, "a mean a systemic" should be --a mean systemic--.

Column 25, Line approx. 38, "a mean a systemic" should be --a mean systemic--.

Column 26, Line 4, "a mean a systemic" should be --a mean systemic--.

Column 26, Line approx. 21, "a mean a systemic" should be --a mean systemic--.

Column 26, Line approx. 41, "a mean a systemic" should be --a mean systemic--.

Column 27, Line approx. 10, "a mean a systemic" should be --a mean systemic--.

Column 27, Line approx. 29, "a mean a systemic" should be --a mean systemic--.

Column 27, Line approx. 50, "a mean a systemic" should be --a mean systemic--.

Column 28, Line approx. 19, "a mean a systemic" should be --a mean systemic--.

Column 28, Line approx. 37, "a mean a systemic" should be --a mean systemic--.

Column 28, Line approx. 57, "a mean a systemic" should be --a mean systemic--.

Column 29, Line approx. 26, "a mean a systemic" should be --a mean systemic--.

Column 29, Line approx. 45, "a mean a systemic" should be --a mean systemic--.

Column 29, Line approx. 66, "a mean a systemic" should be --a mean systemic--.

Column 30, Line approx. 34, "a mean a systemic" should be --a mean systemic--.

Column 30, Line approx. 52, "a mean a systemic" should be --a mean systemic--.

Column 31, Line 5, "a mean a systemic" should be --a mean systemic--.

Column 31, Line approx. 41, "a mean a systemic" should be --a mean systemic--.

Column 31, Line approx. 60, "a mean a systemic" should be --a mean systemic--.

Column 32, Line 14, "a mean a systemic" should be --a mean systemic--.

Column 32, Line approx. 49, "a mean a systemic" should be --a mean systemic--.

Column 32, Line 67, "a mean a systemic" should be --a mean systemic--.

Column 34, Line approx. 18-19, "the only potential "therapeutic gap" of relates to the delay with" should be --the only potential "therapeutic gap" relates to the delay with--.

Column 36, Line approx. 31, "dosage form demonstrate increased efficacy of at" should be --dosage form demonstrates increased efficacy of at--.

Column 36, Line approx. 36, "dosage form demonstrate reduced euphoria, drug" should be --dosage form demonstrates reduced euphoria--.

Column 36, Line approx. 43, "dosage form demonstrate reduced euphoria, drug" should be --dosage form demonstrates reduced euphoria--.

Column 36, Line approx. 62, "said delayed release" should be --Said delayed release--.

Column 41, Line approx. 9, "excdees" should be --exceeds--.

Column 41, Line approx. 28, "4 to 6 hours, preferably over for period of up to about 8" should be --4 to 6 hours, preferably over a period of up to about 8--.

Column 41, Line approx. 42-43, "preparations which release begin the first release" should be --preparations which begin the first release--.

Column 41, Line approx. 66, "rapidly releases" should be --rapidly release--.

Column 42, Line approx. 9, "rapidly releases" should be --rapidly release--.

Column 42, Line approx. 55-56, "controlled release dosage forms of ... releases butorphanol" should be --controlled release dosage forms of ... release butorphanol--.

Column 43, Line 7-12, "When applied to the present invention, present invention, ..., ..., ..., ..., and the like is a dosage form which is formulated to release" should be --When applied to the present invention, ..., ..., ..., ..., and the like refer to a dosage form which is formulated to release--.

Column 43, Line approx. 17-19, "contents, with no intention of delaying or prolonging the dissolution or absorption of the drug) Immediate release" should be --contents (with no intention of delaying or prolonging the dissolution or absorption of the drug). Immediate release--.

Column 44, Line approx. 19-20, ""jejunal release" and "jejunal delivery" are interchangeable, and refers to" should be --"jejunal release" and "jejunal delivery" are interchangeable, and refer to--.

Column 44, Line approx. 34-35, ""ileal release" and "ileal delivery" are interchangeable and refers to" should be --"ileal release" and "ileal delivery" are interchangeable and refer to--.

Column 44, Line approx. 49-51, ""ileo-colonic release" and "ileo-colonic delivery" are interchangeable and are interchangeable and refer to an in vivo release of all," should be --"ileo-colonic release" and "ileo-colonic delivery" are interchangeable and refer to an in vivo release of all,--.

Column 45, Line approx. 47, "upon reaching a the desired" should be --upon reaching the desired--.

Column 46, Line 1, "or 6.5, or 7.75, or 7, or 7.25," should be --or 6.5, or 6.75, or 7, or 7.25,--.

Column 46, Line 3, "11.25, or 1.5, or 11.75," should be --11.25, or 11.5, or 11.75,--.

Column 47, Line 1, "to dosage forms where is the coating is applied" should be --to dosage forms where the coating is applied--.

Column 47, Line approx. 16, "butorphanol Tmax" should be --butorphanol $T_{max}$--.

Column 47, Line 27, "Tmax ratio" should be --$T_{max}$ ratio--.

Column 47, Line approx. 34, "the butorphanol Cmax" should be --the butorphanol $C_{max}$--.

Column 47, Line approx. 44, "Cmax ratio of butorphanol given" should be --$C_{max}$ ratio of butorphanol given--.

CERTIFICATE OF CORRECTION (continued)
U.S. Pat. No. 10,624,887 B2

Column 47, Line approx. 47-48, "given orally is ≥1.1, or ≥1.2, or ≥1.3, or ≥1.5, or ≥1.5, or ≥1.6," should be --given orally is ≥1.1, or ≥1.2, or ≥1.3, or ≥1.4, or ≥1.5, or ≥1.6,--.

Column 47, Line approx. 56, "≥1.3, or ≥1.5, or ≥1.5, or ≥1.6, or" should be --≥1.3, or ≥1.4, or ≥1.5, or ≥1.6, or--.

Column 47, Line approx. 62, "≥1.1, or ≥1.2, or ≥1.3, or ≥1.5, or ≥1.5, or" should be --≥1.1, or ≥1.2, or ≥1.3, or ≥1.4, or ≥1.5, or--.

Column 48, Line 1, "≥1.1, or ≥1.2, or ≥1.3, or ≥1.5, or ≥1.5," should be --≥1.1, or ≥1.2, or ≥1.3, or ≥1.4, or ≥1.5,--.

Column 48, Line 7, "≥1.1, or ≥1.2, or ≥1.3, or ≥1.5, or ≥1.5," should be --≥1.1, or ≥1.2, or ≥1.3, or ≥1.4, or ≥1.5,--.

Column 48, Line 20-22, "the dosage form prior to reaching the ..., or descending colon, or colon" should be --the dosage form prior to reaching the ..., or descending colon, or colon.--.

Column 49, Line approx. 24, "including but limited to" should be --including but not limited to--.

Column 51, Line approx. 46, "pressure in the gastrointestinal tract, hydration, etc), said" should be --pressure in the gastrointestinal tract, hydration, etc.), said--.

Column 51, Line approx. 63-65, "the oral butorphanol is interdispersed and are not isolated from each other in two distinct layers." should be --the oral butorphanol is interdispersed and not isolated into two distinct layers.--.

Column 52, Line 4, "butorphanol is in the form of multiparticulates can be" should be --butorphanol is in the form of multiparticulates that can be--.

Column 52, Line approx. 7, "butorphanol is in the form of multiparticulates can be" should be --butorphanol is in the form of multiparticulates that can be--.

Column 52, Line approx. 16, "a liquid fill capsule." should be --a liquid filled capsule.--.

Column 52, Line approx. 52-53, "and (ii) a displacement layer ...; and (b) a" should be --and (ii) a displacement layer ...; and (iii) a--.

Column 52, Line approx. 59-60, "material suitable for extended release in a human patient of the dosage form comprises a matrix." should be --material suitable for extended release in a human patient where the dosage form comprises a matrix.--.

Column 53, Line approx. 23, "soluble liquids carbohydrate-based substances" should be --soluble liquids, carbohydrate-based substances--.

Column 53, Line approx. 31-32, "and (ii) a displacement layer ...; and (b) a" should be --and (ii) a displacement layer ...; and (iii) a--.

Column 53, Line approx. 38, "oral dosage form comprises a liquid fill capsule." should be --oral dosage form comprises a liquid filled capsule.--.

Column 55, Line approx. 57-58, "are limited to modified release butorphanol provide a psychic effect" should be --are limited to modified release butorphanol providing a psychic effect--.

Column 56, Line approx. 61-62, "release of butorphanol form the dosage form when" should be --release of butorphanol from the dosage form when--.

Column 58, Line approx. 27-28, "for treatment unresponsive to intranasal butorphanol." should be --for treatment of pain unresponsive to intranasal butorphanol."--.

Column 58, Line approx. 33-35, "said dosage form intended solely for treatment unresponsive to oral immediate release butorphanol." should be --said dosage form intended solely for treatment of pain unresponsive to oral immediate release butorphanol.--.

Column 62, Line approx. 43-44, "optionally; said dosage form" should be --optionally, said dosage form--.

Column 62, Line approx. 60, "about for about 1 to about 16 days, then about then about 3" should be --about 1 to about 16 days, then about 3--.

Column 62, Line approx. 62, "optionally thereafter; or a dose of about then about 2" should be --optionally thereafter; or a dose of about 2--.

Column 62, Line approx. 64, "then about then about 2.1" should be --then about 2.1--.

Column 63, Line approx. 14-18, "ng·hr/mL for about for about 1 to about 16 days, then about then about 3 ... for at least 1 day and optionally thereafter; or a dose of about then about 2 ... to about 4 ... for about 1 to about 16 days, then about then about 2.1" should be --ng·hr/mL for about 1 to about 16 days, then about 3 ... for at least 1 day and optionally thereafter; or a dose of about 2 ... to about 4 ... for about 1 to about 16 days, then about 2.1--.

Column 63, Line approx. 34-38, "about 0.1 ... to about 0.2 ... for about for about 1 to about 16 days, then about then about 0.3 ... to about 8 ... for at least 1 clay and optionally thereafter; or a close of about then about 0.2 ... to about 0.44 ... for about 1 to about 16 days, then about then about" should be --about 0.1 ... to about 0.2 ... for about 1 to 16 days, then about 0.3 ... to about 8 ... for at least 1 day and optionally thereafter; or a dose of about 0.2 ... to about 0.44 ... for about 1 to about 16 days, then about--.

Column 64, Line approx. 55, "butorphanol $C_4$/Cmax ratio" should be --butorphanol $C_4/C_{max}$ ratio--.

Column 65, Lines approx. 18-19, "butorphanol $C_4$/Cmax ratio" should be --butorphanol $C_4/C_{max}$

CERTIFICATE OF CORRECTION (continued)
U.S. Pat. No. 10,624,887 B2 ratio--.

Column 65, Line approx. 24, "oral pharmaceutical composition provides of butorphanol" should be --oral pharmaceutical composition provides a butorphanol--.

Column 65, Line approx. 52, "C$_8$/Cmax ratio of" should be --C$_8$/C$_{max}$ ratio of--.

Column 65, Line approx. 57, "pharmaceutical composition provides of butorphanol W$_{50}$ of" should be --pharmaceutical composition provides a butorphanol W$_{50}$ of--.

Column 66, Line 2, "said dosage from providing a C$_{max}$ of" should be --said dosage form providing a C$_{max}$ of--.

Column 66, Line approx. 22-23, "therapeutically effective amount of butorphanol; said dosage from" should be --therapeutically effective amount of butorphanol; said dosage form--.

Column 67, Line approx. 13, "for duration of treatment; or about 4 for 1 to 7 days, followed" should be --for duration of treatment; or about 4 mg for 1 to 7 days, followed--.

Column 67, Line approx. 43, "clays, followed by about" should be --days, followed by about--.

Column 67, Line approx. 65, "clays, followed by about" should be --days, followed by about--.

Column 68, Line approx. 48, there should be no extra spacing.

Column 68, Line approx. 61, "said dosage from" should be --said dosage form--.

Column 68, Line approx. 63, "ng/mL to about 20 ng/mL In other" should be --ng/mL to about 20 ng/mL. In other--.

Column 69, Line approx. 9-10, "said dosage from" should be --said dosage form--.

Column 75, Line approx. 63, "about 30 ng/mL In other preferred" should be --about 30 ng/mL. In other preferred--.

Column 79, Line 5, "a-clay ..., three times-a-clay" should be --a-day ..., three times-a-day--.

Column 79, Line approx. 25, "the specifications (e.g., AUC, Cmax)" should be --the specifications (e.g., AUC, C$_{max}$)--.

Column 81, Line 44-46, "ng·hr/mL, or about 2 ... to about 90 ..., or about 2 ... to about 8 ..., or about 2 ... to about 70 ..., or about 2... to about 60" should be --ng·hr/mL, or about 2 ... to about 90 ..., or about 2 ... to about 80 ..., or about 2 ... to about 70 ..., or about 2 ... to about 60--.

Column 87, Line approx. 30-31, "said dosage from providing a Cmax of butorphanol from about" should be --said dosage form providing a C$_{max}$ of butorphanol from about--.

CERTIFICATE OF CORRECTION (continued)
U.S. Pat. No. 10,624,887 B2

Column 87, Line approx. 35-36, "said dosage from providing a of butorphanol from about" should be --said dosage form providing a $C_{min}$ of butorphanol from about--.

Column 91, Line approx. 22-23, "In some preferred embodiments, the oral immediate release and oral extended release dosage forms provides a" should be --In some preferred embodiments, the oral immediate release and oral extended release dosage forms provide a--.

Column 91, Line approx. 47-50, "In some preferred embodiments, the ratio of the mean ratio of the extent of absorption ... of hydroxybutorphanol to butorphanol oral extended release butorphanol after" should be --In some preferred embodiments, the ratio of the mean extent of absorption ... of hydroxybutorphanol to butorphanol oral extended release butorphanol after--.

Column 93, Line approx. 61, ""street price" is based the price" should be --"street price" is based on the price--.

Column 94, Line approx. 7, ""street price" is based the price" should be --"street price" is based on the price--.

Column 96, Line approx. 14-17, "In some preferred embodiments, the foregoing drowsiness, dizziness score, nausea, ... and ... impairment is" should be --In some preferred embodiments, the foregoing drowsiness, dizziness score, nausea, ... and ... impairment are--.

Column 97, Line approx. 34, "where "street price" is based the price" should be --where "street price" is based on the price--.

Column 97, Line approx. 48, ""street price" is based the price" should be --"street price" is based on the price--.

Column 97, Line approx. 59-60, "each given to according to its intended route" should be --each given according to its intended route--.

Column 98, Line 3-4, "each given to according to its intended route of" should be --each given according to its intended route of--.

Column 98, Line approx. 32-33, "each given to according to its intended" should be --each given according to its intended--.

Column 98, Line approx. 50-51, "each given to according to its intended" should be --each given according to its intended--.

Column 99, Line approx. 15-16, "each given to according to its intended" should be --each given according to its intended--.

Column 99, Line approx. 38-39, "the dosage from maintains a plasma" should be --the dosage form maintains a plasma--.

CERTIFICATE OF CORRECTION (continued)
U.S. Pat. No. 10,624,887 B2

Column 99, Line approx. 51-52, "the dosage from maintains a plasma" should be --the dosage form maintains a plasma--.

Column 99, Line approx. 64-65, "the dosage from maintains a plasma" should be --the dosage form maintains a plasma--.

Column 100, Line approx. 14-15, "the dosage from maintains a plasma" should be --the dosage form maintains a plasma--.

Column 100, Line approx. 32-34, "the oral pharmaceutical composition of butorphanol or a pharmaceutically dosage from provides a" should be --the oral pharmaceutical composition of butorphanol or a pharmaceutical dosage form provides a--.

Column 100, Line approx. 47-49, "the oral pharmaceutical composition of butorphanol or a pharmaceutically dosage from provides a" should be --the oral pharmaceutical composition of butorphanol or a pharmaceutical dosage form provides a--.

Column 101, Line approx. 12-15, "the oral pharmaceutical composition of butorphanol or a pharmaceutically dosage from provides a" should be --the oral pharmaceutical composition of butorphanol or a pharmaceutical dosage form provides a--.

Column 101, Line approx. 28-30, "the oral pharmaceutical composition of butorphanol or a pharmaceutically dosage from provides a" should be --the oral pharmaceutical composition of butorphanol or a pharmaceutical dosage form provides a--.

Column 101, Line approx. 63, "mean in vivo extent of absorption from to 0 to 12 hours," should be --mean in vivo extent of absorption from 0 to 12 hours,--.

Column 102, Line 4, "mean in vivo extent of absorption from to 0 to 12 hours," should be --mean in vivo extent of absorption from 0 to 12 hours,--.

Column 102, Line approx. 13, "mean in vivo extent of absorption from to 0 to 12 hours," should be --mean in vivo extent of absorption from 0 to 12 hours,--.

Column 102, Line approx. 26, "1% of the mean in vivo extent of absorption from to 0 to 12" should be --1% of the mean in vivo extent of absorption from 0 to 12--.

Column 102, Line approx. 39, "absorption from to 0 to 12 hours." should be --absorption from 0 to 12 hours.--.

Column 102, Line approx. 45, "1% of the mean in vivo extent of absorption from to 0 to 24" should be --1% of the mean in vivo extent of absorption from 0 to 24--.

Column 102, Line approx. 58, "absorption from to 0 to 24 hours." should be --absorption from 0 to 24 hours.--.

CERTIFICATE OF CORRECTION (continued)
U.S. Pat. No. 10,624,887 B2

Column 103, Line approx. 9-10, "or ≤about 50% of the mean in vivo extent of absorption from to 0 to 24 hours." should be --or ≤about 50% of the mean in vivo extent of absorption from 0 to 24 hours.--.

Column 103, Line approx. 18, "1% of the mean in vivo extent of absorption from to 0 to 36" should be --1% of the mean in vivo extent of absorption from 0 to 36--.

Column 103, Line approx. 33-34, "in vivo extent of absorption from to 0 to 36 hours." should be --in vivo extent of absorption from 0 to 36 hours.--.

Column 104, Line approx. 13-14, "FDA noted that the manufacturer of "drinking alcohol while..."" should be --the FDA noted to the manufacturer that "drinking alcohol while..."--.

Column 104, Line approx. 32-33, "FDA the mandated a "Black Box" warning which states" should be --The FDA then mandated a "Black Box" warning which states--.

Column 106, Line approx. 19-20, "is its potential for" should be --is the potential for--.

Column 106, Line approx. 44, "Cmax shifting $t_{max}$ from" should be --$C_{max}$ shifting $t_{max}$ from--.

Column 108, Line approx. 8, "$AUC_{0\text{-}1}2$ of butorphanol" should be --$AUC_{0\text{-}12}$ of butorphanol--.

Column 109, Line approx. 16, "(i) is non-dissolving at pH" should be --(i) non-dissolving at pH--.

Column 109, Line approx. 25-26, "at pH<3 to 5 and dissolving at pH>7; or (ix) is non-dissolving at" should be --at pH<3 to 5 and dissolving at pH>7; or (ix) non-dissolving at--.

Column 109, Line 67, "or 10 of butorphanol in vitro" should be --or 10% of butorphanol in vitro--.

Column 110, Line approx. 43, "≥9.0, each when measured when by" should be --≥9.0, each when measured by--.

Column 110, Line approx. 65, "when measured when by USP" should be --when measured by USP--.

Column 112, Line 3, "or ≤5, or ≤5.5 and an amount released at a pH of or ≥5.8, or" should be --or ≤5, or ≤5.5 and an amount released at a pH of ≥5.8, or--.

Column 115, Line approx. 17, "≥50%, or ≥60%, or ≥70% or ≥80%, or ≥90%, or about 100." should be --≥50%, or ≥60%, or ≥70%, or ≥80%, or ≥90%, or about 100%.--.

Column 116, Line approx. 53, "between about 50% and about 100% hours at 24 hours" should be --between about 50% and about 100% at 24 hours--.

Column 120, Line approx. 49, "100% hours at 24 hours" should be --100% at 24 hours--.

Column 120, Line approx. 55, "between about 45% and about 100% hours at 24 hours" should be --between about 45% and about 100% at 24 hours--.

Column 120, Line approx. 61-62, "hours, between about 40% and about 100% hours at 24 hours and greater" should be --hours, between about 40% and about 100% at 24 hours and greater--.

Column 120, Line 67, "70% at 16 hours, between about 35% and about 100% hours" should be --70% at 16 hours, between about 35% and about 100%--.

Column 121, Line approx. 13, "100% hours at 24 hours" should be --100% at 24 hours--.

Column 121, Line approx. 19, "between about 55% and about 100% hours at 24 hours" should be --between about 55% and about 100% at 24 hours--.

Column 121, Line approx. 25-26, "100% at 16 hours, between about 60% and about 100% hours at 24 hours" should be --100% at 16 hours, between about 60% and about 100% at 24 hours--.

Column 121, Line approx. 32, "100% hours at 24 hours" should be --100% at 24 hours--.

Column 121, Line approx. 38, "between about 60% and about 100% hours at 24 hours" should be --between about 60% and about 100% at 24 hours--.

Column 121, Line approx. 44, "hours, between about 40% and about 100% hours at 24" should be --hours, between about 40% and about 100% at 24--.

Column 121, Line approx. 50, "80% at 16 hours, between about 40% and about 100% hours" should be --80% at 16 hours, between about 40% and about 100%--.

Column 121, Line approx. 57, "and about 100% hours at 24 hours" should be --and about 100% at 24 hours--.

Column 121, Line approx. 63, "between about 50% and about 100% hours at 24 hours" should be --between about 50% and about 100% at 24 hours--.

Column 122, Line 2-3, "at 16 hours, between about 45% and about 100% hours at 24 hours" should be --at 16 hours, between about 45% and about 100% at 24 hours--.

Column 122, Line approx. 9, "100% hours at 24 hours" should be --100% at 24 hours--.

Column 122, Line approx. 15, "100% hours at 24 hours" should be --100% at 24 hours--.

Column 122, Line approx. 21, "between about 60% and about 100% hours at 24 hours" should be --between about 60% and about 100% at 24 hours--.

Column 122, Line approx. 27-28, "between about 60% and about 100% hours at 24 hours" should be --between about 60% and about 100% at 24 hours--.

Column 122, Line approx. 34, "100% hours at 24 hours and greater" should be --100% at 24 hours and greater--.

Column 123, Line approx. 40, "the foregoing in-vitro release rate of" should be --the foregoing in vitro release rates of--.

Column 123, Line approx. 48, "the foregoing in-vitro release rate of" should be --the foregoing in vitro release rates of--.

Column 123, Line approx. 59, "the foregoing in-vitro release rate of" should be --the foregoing in vitro release rates of--.

Column 126, Line approx. 63, "objectives of the some" should be --objectives of some--.

Column 126, Line approx. 66-67, "dosage form in the proximal to the stomach, duodenum, or" should be --dosage form proximal to the stomach, duodenum, or--.

Column 127, Line approx. 25-26, "the dosage forms of the invention contains one or more" should be --the dosage forms of the invention contain one or more--.

Column 127, Line 57-58, "the oral dosage form is a controlled release material" should be --the oral dosage form of a controlled release material--.

Column 130, Line approx. 53, "average doe and/or" should be --average dose and/or--.

Column 131, Line approx. 66-67, "epidural, intra-atricular, intranasal, rectal or ocular routes." should be --epidural, intra-artricular, rectal or ocular routes.--.

Column 132, Line approx. 16, "respectively; (ii) "$AUC_{0-inf}$" (means" should be --respectively; (ii) "$AUC_{0-inf}$" means--.

Column 132, Line approx. 39, "concentration of drug are greater than" should be --concentration of drug is greater than--.

Column 133, Line approx. 5, "time point ("n")." should be --time point ("n").--.

Column 133, Line approx. 6-7, "parameters of the invention are be computed from single dose" should be --parameters of the invention can be computed from single dose--.

Column 133, Line approx. 10-11, "The AI and percent of steady state computations requires" should be --The AI and percent of steady state computations require--.

Column 133, Line approx. 27, "immediate release layer maybe coated onto the surface" should be --immediate release layer may be coated onto the surface--.

Column 133, Line approx. 64, "and Basket Method described, e.g., in specified in the United" should be --and Basket Method described, e.g., as specified in the United--.

Column 134, Line approx. 59-60, "the taste aversive agents (...) is coated on the oral dosage" should be --the taste aversive agents (...) are coated on the oral dosage--.

Column 135, Line approx. 4-5, "the taste aversive agents (...) is incorporated in the oral dosage" should be --the taste aversive agents (...) are incorporated in the oral dosage--.

Column 135, Line approx. 11-12, "the taste aversive agents (...) is incorporated into the" should be --the taste aversive agents (...) are incorporated into the--.

Column 135, Line approx. 61, "found in humans that serve as a" should be --found in humans that serves as a--.

Column 136, Line approx. 44, "any salt may be use." should be --any salt may be used.--.

Column 136, Line approx. 51-52, "different permeation enhancer in combination," should be --different permeation enhancers in combination,--.

Column 139, Line approx. 5, "L (eds)], which is" should be --L (ed), which is--.

Column 139, Line approx. 52, "(e.g., cervical thoracic, lumbosacral)," should be --(e.g., cervical, thoracic, lumbosacral),--.

Column 140, Line approx. 46-47, "limiting pain that subsides over time and usually lasting less that about 30 days" should be --limiting pain that subsides over time and usually lasting less than about 30 days--.

Column 141, Line approx. 38-40, "As used herein, "dosage forms" is interchangeable with "formulations", "compositions", "pharmaceutical compositions" or "formulations"." should be --As used herein, "dosage forms" is interchangeable with "formulations", "compositions", "pharmaceutical compositions" or "pharmaceutical formulations".--.

Column 142, Line 2, "extent of absorption or butorphanol" should be --extent of absorption of butorphanol--.

Column 142, Line approx. 60-62, "the term "aversive", "aversive agents", "aversion producing agents" and "aversive compounds" mean to compounds" should be --the terms "aversive", "aversive agents", "aversion producing agents" and "aversive compounds" refer to compounds--.

Column 143, Line approx. 53-55, "The term "abuse", "drug abuse", ... in the context of ... means," should be --The terms "abuse", "drug abuse", ... in the context of ... mean,--.

Column 144, Line approx. 11-14, "The term "abuse resistant", "abuse deterrent", ... are used interchangeably in the context" should be --The terms "abuse resistant", "abuse deterrent", ... are used interchangeably in the context--.

Column 144, Line approx. 54, "use covalently bound moieties" should be --use of covalently bound moieties--.

Column 144, Line approx. 62-63, "about 10 by weight" should be --about 10% by weight--.

Column 144, Line approx. 65-66, "or 1% or 10%, or 2% to 7%) depending" should be --or 1% to 10%, or 2% to 7%) depending--.

Column 145, Line approx. 26-27, "aversive effects, for example, e.g., nausea, emesis," should be --aversive effects (e.g., nausea, emesis,--.

Column 148, Line approx. 40-42, "In some embodiment, co-administered may be used to provide a different therapeutic effects" should be --In some embodiments, co-administered may be used to provide different therapeutic effects--.

Column 148, Line approx. 58, "Jameson J L (eds)]," should be --Jameson J L (eds),--.

Column 148, Line 67, "in need to butorphanol" should be --"in need of butorphanol",--.

Column 149, Line approx. 50, "layer maybe coated" should be --layer may be coated--.

Figure 4:
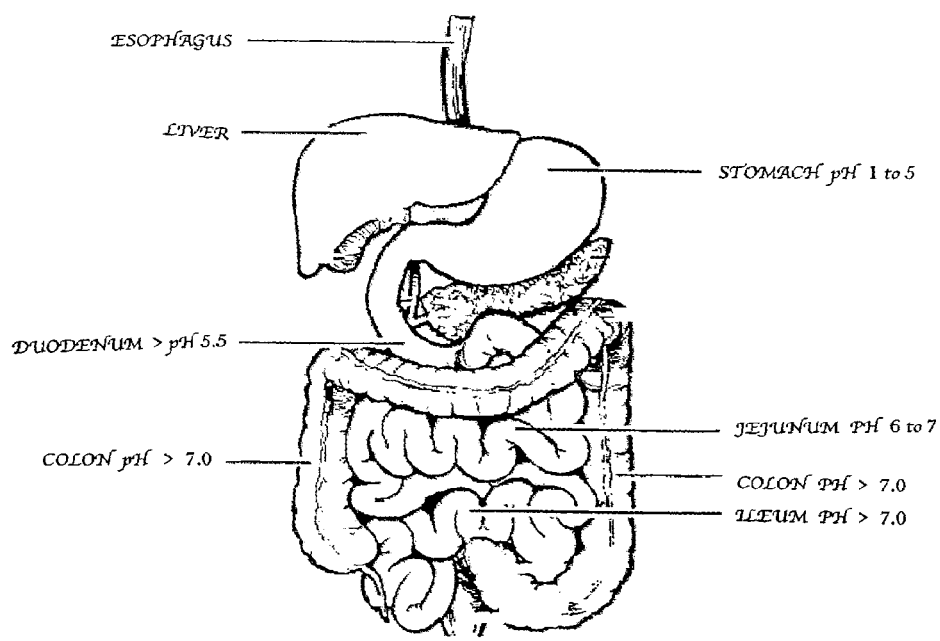
FIG. 4: Illustrates the average pH of for dissolution of many pH sensitive polymers in the various segments of the gastrointestinal tract.

Column 150, Line approx. 51, "FIG. 4: Illustrates the average pH of for dissolution of" should be --FIG. 4: Illustrates the average pH for dissolution of--.

Column 151, Line approx. 16-17, "period during which no butorphanol or very little no butorphanol" should be --period during which no butorphanol or very little to no butorphanol--.

Column 151, Line approx. 43-44, "The mechanical threshold of pain (g) are plotted versus time]" should be --The mechanical thresholds of pain (g) are plotted versus time.--.

Column 151, Line approx. 53-54, "The mechanical threshold of pain (g) are plotted versus time]" should be --The mechanical thresholds of pain (g) are plotted versus time.--.

Column 151, Line approx. 63-64, "The mechanical threshold of pain (g) are plotted versus time]" should be --The mechanical thresholds of pain (g) are plotted versus time.--.

Column 152, Line approx. 66, "(vii) Diluents such lactose, starch," should be --(vii) Diluents such as lactose, starch,--.

Column 153, Line approx. 53, "relief" should be --relief.--.

Column 153, Line approx. 66, "methacrylic acid and" should be --methacrylic acid) and--.

Column 154, Line approx. 13, "ileum or at a pH o >7.0," should be --ileum or at a pH of >7.0,--.

Column 154, Line approx. 48-49, "the butorphanol if formulated as an" should be --the butorphanol is formulated as an--.

Column 155, Line approx. 27, "and deal release," should be --and ileal release,--.

Column 157, Line approx. 48, "substantially prevent the absorption of in the stomach," should be --substantially prevent the absorption in the stomach,--.

Column 158, Line 3, "the dosage form of is a capsule" should be --the dosage form is a capsule--.

Column 158, Line approx. 24, "double-band sealing technique is used to ensure ensures that" should be --double-band sealing technique is used to ensure that--.

Column 159, Line approx. 11, "until it is reaches" should be --until it reaches--.

Column 159, Line approx. 43, "hydration, etc)" should be --hydration, etc.).--.

Column 161, Line approx. 13, "be prepared using methods described in the art achieve" should be --be prepared using methods described in the art to achieve--.

Column 161, Line approx. 19, "or jejum, or ileum," should be --or jejunum, or ileum,--.

Column 163, Line approx. 27, "in the art –see—$^{se}$e for example," should be --in the art -- see for example,--.

Column 164, Line approx. 44, "release is can be kept" should be --release can be kept--.

Column 165, Lines 34-38, duplicate of the preceding paragraph; please delete Lines 34-38.

Column 165, Line approx. 43, "Carbopol 710." should be --Carbopol 71G.--.

Column 165, Lines 49-53, duplicate of the preceding paragraph; please delete Lines 49-53.

Column 166, Lines 1-4, duplicate of the preceding paragraph; please delete Lines 1-4.

Column 166, Lines 35-40, duplicate of the preceding paragraph; please delete Lines 35-40.

Column 166, Lines 53-58, duplicate of the preceding paragraph; please delete Lines 53-58.

Column 167, Lines 9-14, duplicate of the preceding paragraph; please delete Lines 9-14.

Column 168, Line approx. 8, "such crospovidone," should be --such as crospovidone,--.

Column 168, Line approx. 28, "tablet cores, etc)." should be --tablet cores, etc.).--.

Column 168, Line approx. 59, "the invention include" should be --the invention includes--.

Column 169, Line approx. 48, "may incorporated." should be --may be incorporated.--.

Column 171, Line approx. 32, "glycol maybe," should be --glycol may be,--.

Column 175, Line approx. 41-43, "multiparticulates prepared ... provides" should be --multiparticulates prepared ... provide--.

Column 176, Line approx. 10-11, "However, water soluble hydroxy lower ..., such as ..., are preferred." should be --However, water soluble hydroxy lower ..., such as ..., is preferred.--.

Column 177, Line approx. 3-5, "However, water soluble hydroxy lower ..., such as ..., are preferred." should be --However, water soluble hydroxy lower ..., such as ..., is preferred.--.

Column 178, Line approx. 31-32, "Alternatively, any suitable method of providing color to dioxide and color pigments, such as iron oxide pigments." should be --Alternatively, any suitable method of providing color to dioxide and color pigments, such as by iron oxide pigments, may be used.--.

Column 180, Line approx. 14, "so as into increase" should be --so as to increase--.

Column 181, Line approx. 34, "sodium car boxymethylcellulose," should be --sodium carboxytheylcellulose,--.

Column 182, Line approx. 16-17, "comprises an homogenous core" should be --comprises a homogenous core--.

Column 184, Line approx. 41-42, "copolymers Ammonio" should be --copolymers. Ammonio--.

Column 189, Line approx. 2-3, remove the extra spaces after "Spray Dried" and before "Lactose".

Column 191, Line 4, "an oscillating mill 6 Blend" should be --an oscillating mill. 6. Blend--.

Column 195, Line approx. 61, "In Example 25 to 27," should be --In Examples 25 to 27,--.

Column 196, Line approx. 48, "delivery formulated" should be --delivery is formulated--.

Column 197, Line approx. 52, "In Example 30 to 32," should be --In Examples 30 to 32,--.

Column 197, Line approx. 66, "mean amounts of polymer" should be --mean amount of polymer--.

Column 198, Line approx. 59, "In Example 33 to 35," should be --In Examples 33 to 35,--.

Column 199, Line approx. 6-7, "mean amounts of polymer" should be --mean amount of polymer--.

Column 199, Line 53-54, "mean amounts of polymer" should be --mean amount of polymer--.

CERTIFICATE OF CORRECTION (continued)

U.S. Pat. No. 10,624,887 B2

Column 199, Line approx. 65, "capsule of butorphanol" should be --capsules of butorphanol--.

Column 200, Line approx. 21, "(mix in how water, then cool" should be --(mix in hot water, then cool--.

Column 200, Line approx. 23, "Sequentially add ingredient" should be --Sequentially add ingredients--.

Column 200, Line approx. 35, "amounts of polymer" should be --amount of polymer--.

Column 200, Line approx. 52-53, "Example 9 to 21." should be --Examples 9 to 21.--

Column 200, Line approx. 54, "Example 38 to 51" should be --Examples 38 to 51--.

Column 201, Line 3, "Example 38 to 51," should be --Examples 38 to 51,--.

Column 201, Line approx. 11, "amounts of polymer" should be --amount of polymer--.

Column 202, Example 42, Line approx. 19, "Ileo-colonicor" should be --Ileo-colonic or--.

Column 202, Example 43, Line approx. 32, "Ileo-colonicor" should be --Ileo-colonic or--.

Column 202, Example 44, Line approx. 46, "Ileo-colonicor" should be --Ileo-colonic or--.

Column 202, Example 45, Line approx. 59, "Ileo-colonicor" should be --Ileo-colonic or--.

Column 203, Example 46, Line approx. 6, "Ileo-colonicor" should be --Ileo-colonic or--.

Column 203, Example 47, Line approx. 19, "Ileo-colonicor" should be --Ileo-colonic or--.

Column 203, Example 48, Line approx. 33, "Ileo-colonicor" should be --Ileo-colonic or--.

Column 203, Example 49, Line 48, "Ileo-colonicor" should be --Ileo-colonic or--.

Column 203, Example 50, Line 62, "Ileo-colonicor" should be --Ileo-colonic or--.

Column 205, Line approx. 57, "hot air and a controlled" should be --hot air in a controlled--.

Column 207, Line approx. 52, "of a dissolution methods" should be --of dissolution methods--.

Column 207, Line 62-64, "parameter to achieve... or release is achieved by ... dosage form dosage form" should be --parameters to achieve ... or release are achieved by ... dosage form--.

Column 208, Line approx. 7-8, "known those skilled" should be --known to those skilled--.

Column 209, Line approx. 29, "rpm and. See Table below." should be --rpm. See Table below.--.

Column 209, Line approx. 55, "(ii) The mixture of step (1)" should be --(ii) The mixture of step (i)--.

Column 209, Line approx. 61, "tablets were compress" should be --tablets were compressed--.

Column 209, Line approx. 66-67, "(iv) Step (ii) was mixed with step (1) with high stirring; (v) Mix step (iii) with the mixture of step (i) and step ii);" should be --(iv) Step (ii) was mixed with step (i) with high stirring; (v) Mix step (iii) with the mixture of step (i) and step (ii);--.

Column 211, Line approx. 1-4, "butorphanol tartrate tartrate formulations of the invention suitable for... were prepared and tested in ... at 37 C" should be --butorphanol tartrate formulations of the invention suitable for... were prepared and tested in ... at 37° C--.

Column 211, Line approx. 31, "55% at 6 hours, about 35% and 75% at 10 hours" should be --55% at 6 hours, about 35% to 75% at 10 hours--.

Column 211, Line approx. 39, "8 hours, about 30% and 85% at 10 hours" should be --8 hours, about 30% to 85% at 10 hours--.

Column 212, Line approx. 15, "rpm and. See Table below." should be --rpm. See Table below.--.

Column 214, Line approx. 22, "each group comprising of 8 animals." should be --each group comprising 8 animals.--.

Column 214, Line approx. 56, "Statistical analysis for was done using" should be --Statistical analysis was done using--.

Column 214, Line approx. 64, "effect that intra-gastric" should be --effect than intra-gastric--.

Column 215, Line approx. 35, "each group comprising of 8 animals." should be --each group comprising 8 animals.--.

Column 215, Line approx. 67, "Statistical analysis for was done using" should be --Statistical analysis was done using--.

Column 216, Line approx. 9, "effect that intra-gastric" should be --effect than intra-gastric--.

Column 216, Line approx. 38, "comprising of 8 animals." should be --comprising 8 animals.--.

Column 217, Line approx. 15, "reactions were fixed at" should be --reactions was fixed at--.

Column 217, Line approx. 37, "Statistical analysis for was done using" should be --Statistical analysis was done using--.

Column 218, Line approx. 27, "comprising of 8 animals." should be --comprising 8 animals.--.

Column 219, Line approx. 11, "reactions were fixed at" should be --reactions was fixed at--.

CERTIFICATE OF CORRECTION (continued)
U.S. Pat. No. 10,624,887 B2

Column 219, Line approx. 34, "Statistical analysis for was done using" should be --Statistical analysis was done using--.

Column 220, Line approx. 25, "prior to STZ treatment Immediately prior to the injection," should be --prior to STZ treatment. Immediately prior to the injection,--.

Column 220, Line approx. 33-34, "all rats were fasted for 6-8 hrs the blood glucose level was tested" should be --all rats were fasted for 6-8 hrs and the blood glucose level was tested--.

Column 220, Line approx. 41, "comprising of 8 animals." should be --comprising 8 animals.--.

Column 221, Line approx. 18, "reactions were fixed at" should be --reactions was fixed at--.

Column 221, Line approx. 39, "Statistical analysis for was done using" should be --Statistical analysis was done using--.

Column 222, Line approx. 15-16, "the dosage form was coated using the coated with polymer using" should be --the dosage form was coated with polymer using--.

Column 222, Line approx. 22-23, "The onset of pain and magnitude of pain relief was recorded" should be --The onset of pain and magnitude of pain relief were recorded--.

Column 222, Line approx. 27, "osteoarthritis reported some a lot of relief or complete relief." should be --osteoarthritis reported some, a lot of relief or complete relief.--.

Column 222, Line approx. 29, "patient with low back pain reported a lot relief after one hour" should be --patient with low back pain reported a lot of relief after one hour--.

In the Claims

Column 224, Line 19, Claim 8, "The oral dosage form of claim 7, the coating overcoats" should be --The oral dosage form of claim 7, wherein the coating overcoats--.

Column 224, Line 48, Claim 16, "jejunum the ileum, and the colon." should be --jejunum, the ileum, and the colon.--.